US012570756B2

(12) United States Patent
Boitano et al.

(10) Patent No.: US 12,570,756 B2
(45) Date of Patent: Mar. 10, 2026

(54) METHODS OF USE OF ANTI-CD45 ANTIBODIES AND CONJUGATES THEREOF

(71) Applicant: Regeneron Pharmaceuticals, Inc., Tarrytown, NY (US)

(72) Inventors: Anthony Boitano, Newton, MA (US); Michael Cooke, Boston, MA (US); Charlotte Fenton McDonagh, Winchester, MA (US); Rahul Palchaudhuri, Somerville, MA (US); Rajiv Panwar, Acton, MA (US); Bradley Pearse, Somerville, MA (US); Paul Fredrick Widboom, Hanover, NH (US); Patricia Ann Cruite, Medford, MA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 765 days.

(21) Appl. No.: 17/452,028

(22) Filed: Oct. 22, 2021

(65) Prior Publication Data

US 2022/0267441 A1 Aug. 25, 2022

Related U.S. Application Data

(63) Continuation of application No. PCT/US2020/058373, filed on Oct. 30, 2020.

(60) Provisional application No. 63/084,903, filed on Sep. 29, 2020, provisional application No. 63/046,046, filed on Jun. 30, 2020, provisional application No. 63/046,164, filed on Jun. 30, 2020, provisional application No. 63/015,348, filed on Apr. 24, 2020, provisional application No. 62/978,147, filed on Feb. 18, 2020, provisional application No. 62/940,742, filed on Nov. 26, 2019, provisional application No. 62/929,137, filed on Nov. 1, 2019, provisional application No. 62/929,194, filed on Nov. 1, 2019, provisional application No. 62/929,207, filed on Nov. 1, 2019, provisional application No. 62/929,283, filed on Nov. 1, 2019, provisional application No. 62/929,288, filed on Nov. 1, 2019, provisional application No. 62/929,347, filed on Nov. 1, 2019, provisional application No. 62/929,601, filed on Nov. 1, 2019.

(51) Int. Cl.

| | |
|---|---|
| ***A61K 39/40*** | (2006.01) |
| ***A61K 35/28*** | (2015.01) |
| ***A61K 47/68*** | (2017.01) |
| ***A61P 35/02*** | (2006.01) |
| ***A61P 37/06*** | (2006.01) |
| ***C07K 16/28*** | (2006.01) |
| *A61K 35/12* | (2015.01) |
| *A61K 39/00* | (2006.01) |
| *C07K 16/00* | (2006.01) |

(52) U.S. Cl.

CPC ........... *C07K 16/289* (2013.01); *A61K 35/28* (2013.01); *A61K 47/6803* (2017.08); *A61K 47/68035* (2023.08); *A61K 47/6849* (2017.08); *A61P 35/02* (2018.01); *A61P 37/06* (2018.01); *A61K 2035/124* (2013.01); *A61K 2039/505* (2013.01); *C07K 2317/24* (2013.01); *C07K 2317/52* (2013.01); *C07K 2317/565* (2013.01); *C07K 2317/73* (2013.01); *C07K 2317/77* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 2007/0003554 | A1 | 1/2007 | Miller |
| 2007/0161081 | A1 | 7/2007 | Jin et al. |
| 2008/0124345 | A1 | 5/2008 | Rothe et al. |
| 2009/0117124 | A1 | 5/2009 | Liu et al. |
| 2012/0171223 | A1 | 7/2012 | Sass et al. |
| 2014/0106981 | A1 | 4/2014 | Hood et al. |
| 2014/0271617 | A1 | 9/2014 | Igawa et al. |
| 2015/0030600 | A1 | 1/2015 | Marks et al. |

(Continued)

FOREIGN PATENT DOCUMENTS

| | | | |
|---|---|---|---|
| CN | 104178454 | A | 12/2014 |
| WO | WO-2017091745 | A1 | 6/2017 |

(Continued)

OTHER PUBLICATIONS

Rheinlander et al. Immunology Letters, 2018, 196:22-32. (Year: 2018).*

(Continued)

*Primary Examiner* — Chun W Dahle

(74) *Attorney, Agent, or Firm* — Womble Bond Dickinson (US) LLP; Cristin Howley Cowles

(57) ABSTRACT

Disclosed are anti-CD45 antibodies, antigen binding fragments thereof, and antibody drug conjugates (ADCs) that specifically bind to human CD45. Such antibodies and ADCs are useful in therapeutic methods, including methods of depleting CD45+ cells from a patient. The compositions and methods described herein can be used to treat a disorder directly, for instance, by depleting a population of CD45+ cancer cells or autoimmune cells. The compositions and methods described herein can also be used to prepare a patient for hematopoietic stem cell transplant therapy, and to improve the engraftment of hematopoietic stem cell transplants, by selectively depleting endogenous CD45+ cells prior to the transplant procedure.

21 Claims, 46 Drawing Sheets

Specification includes a Sequence Listing.

(56) References Cited

U.S. PATENT DOCUMENTS

| | | | |
|---|---|---|---|
| 2018/0237521 A1 | 8/2018 | Finney et al. |
| 2020/0255523 A1 | 8/2020 | Palchaudhuri et al. |
| 2020/0376135 A1 | 12/2020 | Boitano et al. |
| 2022/0267441 A1 | 8/2022 | Boitano et al. |
| 2024/0075157 A1 | 3/2024 | Boitano et al. |

FOREIGN PATENT DOCUMENTS

| | | |
|---|---|---|
| WO | WO-2017155937 A1 | 9/2017 |
| WO | 2019010224 A1 | 1/2019 |
| WO | WO-2019129178 A1 | 7/2019 |
| WO | WO-2020092654 A1 | 5/2020 |
| WO | 2021168128 A1 | 8/2021 |

OTHER PUBLICATIONS

Sarsenova et al. International Journal of Molecular Sciences. 2021, 22, 11592:1-27. (Year: 2021).*

Archer, K.E. et al., "Synthesis of Highly Potent N-10 Amino-Linked DNA-Alkylating Indolinobenzodiazepine Antibody-Drug Conjugates (ADCs)", ACS Medicinal Chemistry Letters, Jul. 22, 2019, pp. 1211-1215, , vol. 10, No. 8, United States, ISSN: 1948-5875, DOI: 10.1021/acsmedchemlett.9b00254.

Atlas Antibodies AB, Anti-CD45 Product Datasheet Monoclonal Antibody, Product Datasheet (online), Dec. 2012, Retrieved from the Internet: [URL: https://atlasantibodies.com/products/AMAb90519]; p. 1.

Brenner, M.K. et al., Complement-Fixing CD45 Monoclonal Antibodies to Facilitate Stem Cell Transplantation in Mouse and Man, Annals of the New York Academy of Sciences, New York Academy of Sciences, Jan. 24, 2006, pp. 80-88, vol. 996, No. 1, XP071395992, ISSN: 0077-8923, DOI: 10.IIII/J.1749-6632.2003.TB03236.X.

EPO, Extended European Search Report for EP Application No. 20880619.0, dated Jan. 24, 2024, pp. 1-11.

Glatting, G. et al., "Anti-CD45 Monoclonal Antibody YAML568: A Promising Radioimmunoconjugate for Targeted Therapy of Acute Leukemia", The Journal of nuclear medicine (1978), Aug. 1, 2006, pp. 1335-1341, XP055865905, United States, Retrieved from the Internet: URL:https://jnm.snmjournals.org/content/jn umed/47/8/1335.full.pdf.

Jager, M.D. et al., "A Depleting Anti-CD45 Monoclonal Antibody as Isolated Conditioning for Bone Marrow Transplantation in the Rat", PLO SONE, May 3, 2016, p. 1-17, vol. 11, No. 5, XP055595236, DOI: 10.1371/journal.pone.0154682.

Lapin, M. et al., "MINDEC—An Enhanced Negative Depletion Strategy for Circulating Tumour Cell Enrichment", Scientific Reports, Jul. 19, 2016, pp. 1-10, vol. 6, No. 1, XP055622689, DOI: 10.1038/srep28929.

Pahl, A. et al., "Amanitins and their development as a payload for antibody-drug conjugates", Drug Discovery Today: Technologies, Elsevier, Amsterdam, NL, Sep. 24, 2018, pp. 85-89, vol. 30, XP085556178, ISSN: 1740-6749, DOI: 10.1016/J.DDTEC.2018.08.005.

Palchaudhuri, R. et al., "Non-Genotoxic Conditioning Using Amanitin Antibody-Drug Conjugates Targeting CD45 Effectively Deplete Human and Non-Human Primate Hematopoietic Stem Cells and Immune Cells", Biology of Blood and Marrow Transplantation, Jan. 31, 2019, p. S32, vol. 25, No. 3, XP085593847, ISSN: 1083-8791, DOI: 10.1016/J.BBMT.2018.12.104.

Saber, H. et al., "An FDA oncology analysis of toxicities associated with PBD-containing antibody-drug conjugates", Regulatory Toxicology and Pharmacology, Academic Press, New York, NY, US, Jul. 17, 2019, pp. 1-8, vol. 107, XP085787919, ISSN: 0273-2300, DOI: 10.1016/J.YRTPH.2019.104429.

Symons, A et al., Domain organization of the extracellular region of CD45, Protein Engineering, 1999, vol. 12, No. 10; pp. 885-892; DOI: 10.1093/protein/12.10.885.

WIPO, International Search Report for PCT Application No. PCT/US2020/058373, dated Apr. 22, 2021, pp. 1-5.

WIPO, International Preliminary Report on Patentability for PCT Application No. PCT/US2020/058373, dated May 3, 2022, pp. 1-13.

Matthews, Dana C. et al., "Phase I Study of 131I-Anti-CD45 Antibody Plus Cyclophosphamide and Total Body Irradiation for Advanced Acute Leukemia and Myelodysplastic Syndrome" (1999) vol. 94(4): 1237-1247.

* cited by examiner

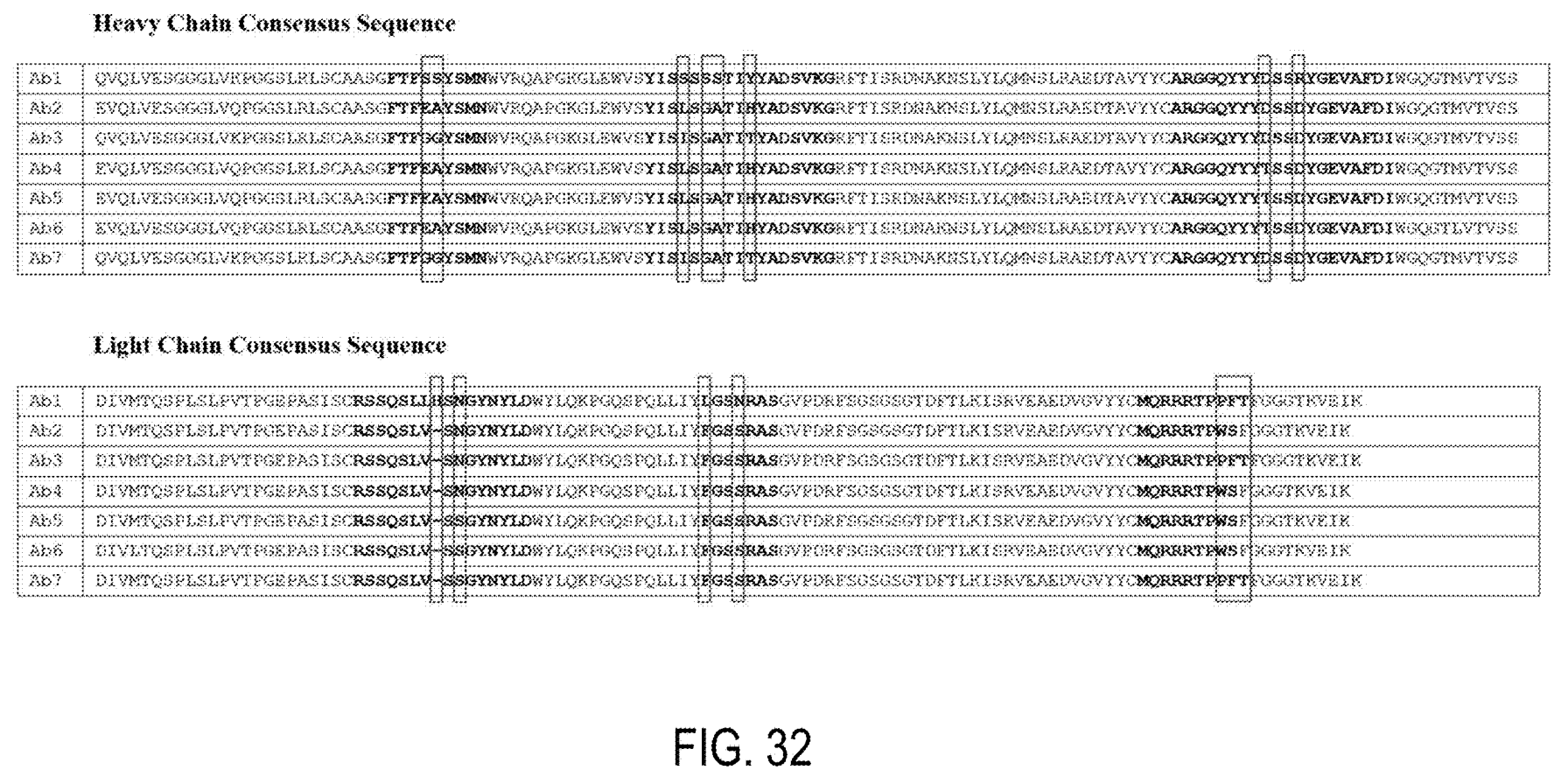

Heavy Chain Consensus Sequence

| | |
|---|---|
| Ab1 | QVQLVESGGGLVKPGGSLRLSCAASG**FTFSSYSMN**WVRQAPGKGLEWVS**YISSSSSTIYYADSVKG**RFTISRDNAKNSLYLQMNSLRAEDTAVYYC**ARGGQYYYDSSRYGEVAFDI**WGQGTMVTVSS |
| Ab2 | EVQLVESGGGLVQPGGSLRLSCAASG**FTFEAYSMN**WVRQAPGKGLEWVS**YISLSGATIHYADSVKG**RFTISRDNAKNSLYLQMNSLRAEDTAVYYC**ARGGQYYYDSSDYGEVAFDI**WGQGTMVTVSS |
| Ab3 | QVQLVESGGGLVKPGGSLRLSCAASG**FTFGGYSMN**WVRQAPGKGLEWVS**YISISGATITYADSVKG**RFTISRDNAKNSLYLQMNSLRAEDTAVYYC**ARGGQYYYISSDYGEVAFDI**WGQGTMVTVSS |
| Ab4 | EVQLVESGGGLVQPGGSLRLSCAASG**FTFEAYSMN**WVRQAPGKGLEWVS**YISLSGATIHYADSVKG**RFTISRDNAKNSLYLQMNSLRAEDTAVYYC**ARGGQYYYTSSDYGEVAFDI**WGQGTMVTVSS |
| Ab5 | EVQLVESGGGLVQPGGSLRLSCAASG**FTFEAYSMN**WVRQAPGKGLEWVS**YISLSGATIHYADSVKG**RFTISRDNAKNSLYLQMNSLRAEDTAVYYC**ARGGQYYYTSSDYGEVAFDI**WGQGTMVTVSS |
| Ab6 | EVQLVESGGGLVQPGGSLRLSCAASG**FTFEAYSMN**WVRQAPGKGLEWVS**YISLSGATIHYADSVKG**RFTISRDNAKNSLYLQMNSLRAEDTAVYYC**ARGGQYYYTSSDYGEVAFDI**WGQGTLVTVSS |
| Ab7 | QVQLVESGGGLVKPGGSLRLSCAASG**FTFGGYSMN**WVRQAPGKGLEWVS**YISISGATITYADSVKG**RFTISRDNAKNSLYLQMNSLRAEDTAVYYC**ARGGQYYYDSSDYGEVAFDI**WGQGTMVTVSS |

Light Chain Consensus Sequence

| | |
|---|---|
| Ab1 | DIVMTQSPLSLPVTPGEPASISC**RSSQSLLHSNGYNYLD**WYLQKPGQSPQLLIY**LGSNRAS**GVPDRFSGSGSGTDFTLKISRVEAEDVGVYYC**MQRRRTPPFT**FGGGTKVEIK |
| Ab2 | DIVMTQSPLSLPVTPGEPASISC**RSSQSLV-SNGYNYLD**WYLQKPGQSPQLLIY**FGSSRAS**GVPDRFSGSGSGTDFTLKISRVEAEDVGVYYC**MQRRRTPWS**FGGGTKVEIK |
| Ab3 | DIVMTQSPLSLPVTPGEPASISC**RSSQSLV-SNGYNYLD**WYLQKPGQSPQLLIY**FGSSRAS**GVPDRFSGSGSGTDFTLKISRVEAEDVGVYYC**MQRRRTPPFT**FGGGTKVEIK |
| Ab4 | DIVMTQSPLSLPVTPGEPASISC**RSSQSLV-SNGYNYLD**WYLQKPGQSPQLLIY**FGSSRAS**GVPDRFSGSGSGTDFTLKISRVEAEDVGVYYC**MQRRRTPWS**FGGGTKVEIK |
| Ab5 | DIVMTQSPLSLPVTPGEPASISC**RSSQSLV-SSGYNYLD**WYLQKPGQSPQLLIY**FGSSRAS**GVPDRFSGSGSGTDFTLKISRVEAEDVGVYYC**MQRRRTPWS**FGGGTKVEIK |
| Ab6 | DIVLTQSPLSLPVTPGEPASISC**RSSQSLV-SSGYNYLD**WYLQKPGQSPQLLIY**FGSSRAS**GVPDRFSGSGSGTDFTLKISRVEAEDVGVYYC**MQRRRTPWS**FGGGTKVEIK |
| Ab7 | DIVMTQSPLSLPVTPGEPASISC**RSSQSLV-SSGYNYLD**WYLQKPGQSPQLLIY**FGSSRAS**GVPDRFSGSGSGTDFTLKISRVEAEDVGVYYC**MQRRRTPPFT**FGGGTKVEIK |

FIG. 32

SEQUENCE LISTING

```
<160> NUMBER OF SEQ ID NOS: 161

<210> SEQ ID NO 1
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

```
Ala Arg Gly Gly Gln Tyr Tyr Tyr Asp Ser Ser Arg Tyr Gly Glu Val
            100                 105                 110

Ala Phe Asp Ile Trp Gly Gln Gly Thr Met Val Thr Val Ser Ser
        115                 120                 125


<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Thr Phe Ser Ser Tyr Ser Met Asn
1               5


<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Ile Ser Ser Ser Ser Ser Thr Ile Tyr Tyr Ala Asp Ser Val Lys
1               5                   10                  15

Gly


<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Arg Gly Gly Gln Tyr Tyr Tyr Asp Ser Ser Arg Tyr Gly Glu Val
1               5                   10                  15

Ala Phe Asp Ile
            20


<210> SEQ ID NO 5
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Met Gln Arg
85 90 95

Arg Arg Thr Pro Pro Phe Thr Phe Gly Gly Gly Thr Lys Val Glu Ile
100 105 110

Lys

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Arg Ser Ser Gln Ser Leu Leu His Ser Asn Gly Tyr Asn Tyr Leu Asp
1 5 10 15

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Leu Gly Ser Asn Arg Ala Ser
1 5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Met Gln Arg Arg Arg Thr Pro Pro Phe Thr
1 5 10

<210> SEQ ID NO 9
<211> LENGTH: 457
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Tyr Ile Ser Ser Ser Ser Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

```
Ala Arg Gly Gly Gln Tyr Tyr Tyr Asp Ser Ser Arg Tyr Gly Glu Val
            100                 105                 110

Ala Phe Asp Ile Trp Gly Gln Gly Thr Met Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Ala Ala Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Cys Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn Ala Tyr Thr Gln
        435                 440                 445

Lys Ser Leu Ser Leu Ser Pro Gly Lys
    450                 455
```

<210> SEQ ID NO 10
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Arg
                85                  90                  95

Arg Arg Thr Pro Pro Phe Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 11
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Glu Ala Tyr
            20                  25                  30

Ser Met Asn Trp Val Arg Gln Ala Pro Gly Lys Gly Leu Glu Trp Val
        35                  40                  45

Ser Tyr Ile Ser Leu Ser Gly Ala Thr Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Tyr Tyr Tyr Asp Ser Ser Asp Tyr Gly Glu Val
            100                 105                 110

Ala Phe Asp Ile Trp Gly Gln Gly Thr Met Val Thr Val Ser Ser
        115                 120                 125
```

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Phe Thr Phe Glu Ala Tyr Ser Met Asn
1               5

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Ile Ser Leu Ser Gly Ala Thr Ile His Tyr Ala Asp Ser Val Lys
1               5                   10                  15

Gly

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Arg Gly Gly Gln Tyr Tyr Tyr Asp Ser Ser Asp Tyr Gly Glu Val
1               5                   10                  15

Ala Phe Asp Ile
            20

<210> SEQ ID NO 15
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Asn
            20                  25                  30

Gly Tyr Asn Tyr Leu Asp Trp Tyr Leu Gln Lys Pro Gly Gln Ser Pro
        35                  40                  45

Gln Leu Leu Ile Tyr Phe Gly Ser Ser Arg Ala Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Met Gln Arg Arg
                85                  90                  95

Arg Thr Pro Trp Ser Phe Gly Gly Gly Thr Lys Val Glu Ile Lys
            100                 105                 110

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Ser Gln Ser Leu Val Ser Asn Gly Tyr Asn Tyr Leu Asp
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Phe Gly Ser Ser Arg Ala Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Gln Arg Arg Arg Thr Pro Trp Ser
1               5

<210> SEQ ID NO 19
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Glu Ala Tyr
            20                  25                  30

Ser Met Asn Trp Val Arg Gln Ala Pro Gly Lys Gly Leu Glu Trp Val
        35                  40                  45

Ser Tyr Ile Ser Leu Ser Gly Ala Thr Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Tyr Tyr Tyr Asp Ser Ser Asp Tyr Gly Glu Val
            100                 105                 110

Ala Phe Asp Ile Trp Gly Gln Gly Thr Met Val Thr Val Ser Ser Ala
        115                 120                 125

Ser Thr Lys Gly Pro Ser Val Phe Pro Leu Ala Pro Ser Ser Lys Ser
    130                 135                 140

```
Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Ala Ala Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Cys Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn Ala Tyr Thr Gln
        435                 440                 445

Lys Ser Leu Ser Leu Ser Pro Gly Lys
    450                 455


<210> SEQ ID NO 20
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Asn
            20                  25                  30

Gly Tyr Asn Tyr Leu Asp Trp Tyr Leu Gln Lys Pro Gly Gln Ser Pro
```

```
        35                  40                  45

Gln Leu Leu Ile Tyr Phe Gly Ser Ser Arg Ala Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Met Gln Arg Arg
                85                  90                  95

Arg Thr Pro Trp Ser Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 21
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Gly Tyr
            20                  25                  30

Ser Met Asn Trp Val Arg Gln Ala Pro Gly Lys Gly Leu Glu Trp Val
        35                  40                  45

Ser Tyr Ile Ser Ile Ser Gly Ala Thr Ile Thr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Tyr Tyr Tyr Asp Ser Ser Asp Tyr Gly Glu Val
            100                 105                 110

Ala Phe Asp Ile Trp Gly Gln Gly Thr Met Val Thr Val Ser Ser
        115                 120                 125


<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 22

Phe Thr Phe Gly Gly Tyr Ser Met Asn
1               5

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Tyr Ile Ser Ile Ser Gly Ala Thr Ile Thr Tyr Ala Asp Ser Val Lys
1               5                   10                  15

Gly

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Ala Arg Gly Gly Gln Tyr Tyr Tyr Asp Ser Ser Asp Tyr Gly Glu Val
1               5                   10                  15

Ala Phe Asp Ile
            20

<210> SEQ ID NO 25
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Asn
            20                  25                  30

Gly Tyr Asn Tyr Leu Asp Trp Tyr Leu Gln Lys Pro Gly Gln Ser Pro
        35                  40                  45

Gln Leu Leu Ile Tyr Phe Gly Ser Ser Arg Ala Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Met Gln Arg Arg
                85                  90                  95

Arg Thr Pro Pro Phe Thr Phe Gly Gly Gly Thr Lys Val Glu Ile Lys
            100                 105                 110

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Arg Ser Ser Gln Ser Leu Val Ser Asn Gly Tyr Asn Tyr Leu Asp
1 5 10 15

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Phe Gly Ser Ser Arg Ala Ser
1 5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Met Gln Arg Arg Arg Thr Pro Pro Phe Thr
1 5 10

<210> SEQ ID NO 29
<211> LENGTH: 457
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Gly Gly Tyr
20 25 30

Ser Met Asn Trp Val Arg Gln Ala Pro Gly Lys Gly Leu Glu Trp Val
35 40 45

Ser Tyr Ile Ser Ile Ser Gly Ala Thr Ile Thr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gly Gly Gln Tyr Tyr Tyr Asp Ser Ser Asp Tyr Gly Glu Val
100 105 110

Ala Phe Asp Ile Trp Gly Gln Gly Thr Met Val Thr Val Ser Ser Ala
115 120 125

Ser Thr Lys Gly Pro Ser Val Phe Pro Leu Ala Pro Ser Ser Lys Ser
130 135 140

Thr Ser Gly Gly Thr Ala Ala Leu Gly Cys Leu Val Lys Asp Tyr Phe
145 150 155 160

Pro Glu Pro Val Thr Val Ser Trp Asn Ser Gly Ala Leu Thr Ser Gly
165 170 175

Val His Thr Phe Pro Ala Val Leu Gln Ser Ser Gly Leu Tyr Ser Leu
180 185 190

Ser Ser Val Val Thr Val Pro Ser Ser Ser Leu Gly Thr Gln Thr Tyr
195 200 205

Ile Cys Asn Val Asn His Lys Pro Ser Asn Thr Lys Val Asp Lys Lys
210 215 220

Val Glu Pro Lys Ser Cys Asp Lys Thr His Thr Cys Pro Pro Cys Pro
225 230 235 240

Ala Pro Glu Ala Ala Gly Gly Pro Ser Val Phe Leu Phe Pro Pro Lys
245 250 255

Pro Lys Asp Thr Leu Met Ile Ser Arg Thr Pro Glu Val Thr Cys Val
260 265 270

Val Val Cys Val Ser His Glu Asp Pro Glu Val Lys Phe Asn Trp Tyr
275 280 285

Val Asp Gly Val Glu Val His Asn Ala Lys Thr Lys Pro Arg Glu Glu
290 295 300

Gln Tyr Asn Ser Thr Tyr Arg Val Val Ser Val Leu Thr Val Leu His
305 310 315 320

Gln Asp Trp Leu Asn Gly Lys Glu Tyr Lys Cys Lys Val Ser Asn Lys
325 330 335

Ala Leu Pro Ala Pro Ile Glu Lys Thr Ile Ser Lys Ala Lys Gly Gln
340 345 350

Pro Arg Glu Pro Gln Val Tyr Thr Leu Pro Pro Ser Arg Asp Glu Leu
355 360 365

Thr Lys Asn Gln Val Ser Leu Thr Cys Leu Val Lys Gly Phe Tyr Pro
370 375 380

Ser Asp Ile Ala Val Glu Trp Glu Ser Asn Gly Gln Pro Glu Asn Asn
385 390 395 400

Tyr Lys Thr Thr Pro Pro Val Leu Asp Ser Asp Gly Ser Phe Phe Leu
405 410 415

Tyr Ser Lys Leu Thr Val Asp Lys Ser Arg Trp Gln Gln Gly Asn Val
420 425 430

Phe Ser Cys Ser Val Met His Glu Ala Leu His Asn Ala Tyr Thr Gln
435 440 445

Lys Ser Leu Ser Leu Ser Pro Gly Lys
450 455

<210> SEQ ID NO 30
<211> LENGTH: 219
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 30

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Val Ser Asn
20 25 30

Gly Tyr Asn Tyr Leu Asp Trp Tyr Leu Gln Lys Pro Gly Gln Ser Pro
35 40 45

Gln Leu Leu Ile Tyr Phe Gly Ser Ser Arg Ala Ser Gly Val Pro Asp
50 55 60

Arg Phe Ser Gly Ser Gly Ser Gly Thr Asp Phe Thr Leu Lys Ile Ser
65 70 75 80

Arg Val Glu Ala Glu Asp Val Gly Val Tyr Tyr Cys Met Gln Arg Arg

-continued

```
                85                  90                  95

Arg Thr Pro Pro Phe Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 31
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Glu Ala Tyr
            20                  25                  30

Ser Met Asn Trp Val Arg Gln Ala Pro Gly Lys Gly Leu Glu Trp Val
        35                  40                  45

Ser Tyr Ile Ser Leu Ser Gly Ala Thr Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Tyr Tyr Tyr Thr Ser Ser Asp Tyr Gly Glu Val
            100                 105                 110

Ala Phe Asp Ile Trp Gly Gln Gly Thr Met Val Thr Val Ser Ser
        115                 120                 125


<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Thr Phe Glu Ala Tyr Ser Met Asn
1               5


<210> SEQ ID NO 33
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 33

Tyr Ile Ser Leu Ser Gly Ala Thr Ile His Tyr Ala Asp Ser Val Lys
1               5                   10                  15

Gly


<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Arg Gly Gly Gln Tyr Tyr Tyr Thr Ser Ser Asp Tyr Gly Glu Val
1               5                   10                  15

Ala Phe Asp Ile
            20


<210> SEQ ID NO 35
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Asn
            20                  25                  30

Gly Tyr Asn Tyr Leu Asp Trp Tyr Leu Gln Lys Pro Gly Gln Ser Pro
        35                  40                  45

Gln Leu Leu Ile Tyr Phe Gly Ser Ser Arg Ala Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Met Gln Arg Arg
                85                  90                  95

Arg Thr Pro Trp Ser Phe Gly Gly Gly Thr Lys Val Glu Ile Lys
            100                 105                 110


<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ser Ser Gln Ser Leu Val Ser Asn Gly Tyr Asn Tyr Leu Asp
1               5                   10                  15


<210> SEQ ID NO 37
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 37

Phe Gly Ser Ser Arg Ala Ser
1               5


<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Met Gln Arg Arg Arg Thr Pro Trp Ser
1               5


<210> SEQ ID NO 39
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Glu Ala Tyr
            20                  25                  30

Ser Met Asn Trp Val Arg Gln Ala Pro Gly Lys Gly Leu Glu Trp Val
        35                  40                  45

Ser Tyr Ile Ser Leu Ser Gly Ala Thr Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Tyr Tyr Tyr Thr Ser Ser Asp Tyr Gly Glu Val
            100                 105                 110

Ala Phe Asp Ile Trp Gly Gln Gly Thr Met Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240
```

Ala Pro Glu Ala Ala Gly Gly Pro Ser Val Phe Leu Phe Pro Pro Lys
245 250 255

Pro Lys Asp Thr Leu Met Ile Ser Arg Thr Pro Glu Val Thr Cys Val
260 265 270

Val Val Cys Val Ser His Glu Asp Pro Glu Val Lys Phe Asn Trp Tyr
275 280 285

Val Asp Gly Val Glu Val His Asn Ala Lys Thr Lys Pro Arg Glu Glu
290 295 300

Gln Tyr Asn Ser Thr Tyr Arg Val Val Ser Val Leu Thr Val Leu His
305 310 315 320

Gln Asp Trp Leu Asn Gly Lys Glu Tyr Lys Cys Lys Val Ser Asn Lys
325 330 335

Ala Leu Pro Ala Pro Ile Glu Lys Thr Ile Ser Lys Ala Lys Gly Gln
340 345 350

Pro Arg Glu Pro Gln Val Tyr Thr Leu Pro Pro Ser Arg Asp Glu Leu
355 360 365

Thr Lys Asn Gln Val Ser Leu Thr Cys Leu Val Lys Gly Phe Tyr Pro
370 375 380

Ser Asp Ile Ala Val Glu Trp Glu Ser Asn Gly Gln Pro Glu Asn Asn
385 390 395 400

Tyr Lys Thr Thr Pro Pro Val Leu Asp Ser Asp Gly Ser Phe Phe Leu
405 410 415

Tyr Ser Lys Leu Thr Val Asp Lys Ser Arg Trp Gln Gln Gly Asn Val
420 425 430

Phe Ser Cys Ser Val Met His Glu Ala Leu His Asn Ala Tyr Thr Gln
435 440 445

Lys Ser Leu Ser Leu Ser Pro Gly Lys
450 455

<210> SEQ ID NO 40
<211> LENGTH: 218
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 40

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Val Ser Asn
20 25 30

Gly Tyr Asn Tyr Leu Asp Trp Tyr Leu Gln Lys Pro Gly Gln Ser Pro
35 40 45

Gln Leu Leu Ile Tyr Phe Gly Ser Ser Arg Ala Ser Gly Val Pro Asp
50 55 60

Arg Phe Ser Gly Ser Gly Ser Gly Thr Asp Phe Thr Leu Lys Ile Ser
65 70 75 80

Arg Val Glu Ala Glu Asp Val Gly Val Tyr Tyr Cys Met Gln Arg Arg
85 90 95

Arg Thr Pro Trp Ser Phe Gly Gly Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr

```
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 41
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Glu Ala Tyr
            20                  25                  30

Ser Met Asn Trp Val Arg Gln Ala Pro Gly Lys Gly Leu Glu Trp Val
        35                  40                  45

Ser Tyr Ile Ser Leu Ser Gly Ala Thr Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Tyr Tyr Tyr Thr Ser Ser Asp Tyr Gly Glu Val
            100                 105                 110

Ala Phe Asp Ile Trp Gly Gln Gly Thr Met Val Thr Val Ser Ser
        115                 120                 125


<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Phe Thr Phe Glu Ala Tyr Ser Met Asn
1               5


<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Ile Ser Leu Ser Gly Ala Thr Ile His Tyr Ala Asp Ser Val Lys
1               5                   10                  15
```

Gly

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Ala Arg Gly Gly Gln Tyr Tyr Tyr Thr Ser Ser Asp Tyr Gly Glu Val
1               5                   10                  15

Ala Phe Asp Ile
            20
```

<210> SEQ ID NO 45
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Ser
            20                  25                  30

Gly Tyr Asn Tyr Leu Asp Trp Tyr Leu Gln Lys Pro Gly Gln Ser Pro
        35                  40                  45

Gln Leu Leu Ile Tyr Phe Gly Ser Ser Arg Ala Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Met Gln Arg Arg
                85                  90                  95

Arg Thr Pro Trp Ser Phe Gly Gly Gly Thr Lys Val Glu Ile Lys
            100                 105                 110
```

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Arg Ser Ser Gln Ser Leu Val Ser Ser Gly Tyr Asn Tyr Leu Asp
1               5                   10                  15
```

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

```
Phe Gly Ser Ser Arg Ala Ser
1               5
```

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Met Gln Arg Arg Arg Thr Pro Trp Ser
1 5

<210> SEQ ID NO 49
<211> LENGTH: 457
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Glu Ala Tyr
20 25 30

Ser Met Asn Trp Val Arg Gln Ala Pro Gly Lys Gly Leu Glu Trp Val
35 40 45

Ser Tyr Ile Ser Leu Ser Gly Ala Thr Ile His Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gly Gly Gln Tyr Tyr Tyr Thr Ser Ser Asp Tyr Gly Glu Val
100 105 110

Ala Phe Asp Ile Trp Gly Gln Gly Thr Met Val Thr Val Ser Ser Ala
115 120 125

Ser Thr Lys Gly Pro Ser Val Phe Pro Leu Ala Pro Ser Ser Lys Ser
130 135 140

Thr Ser Gly Gly Thr Ala Ala Leu Gly Cys Leu Val Lys Asp Tyr Phe
145 150 155 160

Pro Glu Pro Val Thr Val Ser Trp Asn Ser Gly Ala Leu Thr Ser Gly
165 170 175

Val His Thr Phe Pro Ala Val Leu Gln Ser Ser Gly Leu Tyr Ser Leu
180 185 190

Ser Ser Val Val Thr Val Pro Ser Ser Ser Leu Gly Thr Gln Thr Tyr
195 200 205

Ile Cys Asn Val Asn His Lys Pro Ser Asn Thr Lys Val Asp Lys Lys
210 215 220

Val Glu Pro Lys Ser Cys Asp Lys Thr His Thr Cys Pro Pro Cys Pro
225 230 235 240

Ala Pro Glu Ala Ala Gly Gly Pro Ser Val Phe Leu Phe Pro Pro Lys
245 250 255

Pro Lys Asp Thr Leu Met Ile Ser Arg Thr Pro Glu Val Thr Cys Val
260 265 270

Val Val Cys Val Ser His Glu Asp Pro Glu Val Lys Phe Asn Trp Tyr
275 280 285

```
Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn Ala Tyr Thr Gln
        435                 440                 445

Lys Ser Leu Ser Leu Ser Pro Gly Lys
    450                 455


<210> SEQ ID NO 50
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Ser
            20                  25                  30

Gly Tyr Asn Tyr Leu Asp Trp Tyr Leu Gln Lys Pro Gly Gln Ser Pro
        35                  40                  45

Gln Leu Leu Ile Tyr Phe Gly Ser Ser Arg Ala Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Met Gln Arg Arg
                85                  90                  95

Arg Thr Pro Trp Ser Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
```

```
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 51
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Glu Ala Tyr
            20                  25                  30

Ser Met Asn Trp Val Arg Gln Ala Pro Gly Lys Gly Leu Glu Trp Val
        35                  40                  45

Ser Tyr Ile Ser Leu Ser Gly Ala Thr Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Tyr Tyr Tyr Thr Ser Ser Asp Tyr Gly Glu Val
            100                 105                 110

Ala Phe Asp Ile Trp Gly Gln Gly Thr Leu Val Thr Val Ser Ser
        115                 120                 125


<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Phe Thr Phe Glu Ala Tyr Ser Met Asn
1               5


<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Tyr Ile Ser Leu Ser Gly Ala Thr Ile His Tyr Ala Asp Ser Val Lys
1               5                   10                  15

Gly


<210> SEQ ID NO 54
<211> LENGTH: 20
<212> TYPE: PRT
<213> ORGANISM: Artificial Sequence
<220> FEATURE:
```

<223> OTHER INFORMATION: Description of Artificial Sequence: Synthetic peptide

<400> SEQUENCE: 54

Ala Arg Gly Gly Gln Tyr Tyr Tyr Thr Ser Ser Asp Tyr Gly Glu Val
1 5 10 15

Ala Phe Asp Ile
20

<210> SEQ ID NO 55
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

Asp Ile Val Leu Thr Gln Ser Pro Leu Ser Leu Pro Val Thr Pro Gly
1 5 10 15

Glu Pro Ala Ser Ile Ser Cys Arg Ser Ser Gln Ser Leu Val Ser Ser
20 25 30

Gly Tyr Asn Tyr Leu Asp Trp Tyr Leu Gln Lys Pro Gly Gln Ser Pro
35 40 45

Gln Leu Leu Ile Tyr Phe Gly Ser Ser Arg Ala Ser Gly Val Pro Asp
50 55 60

Arg Phe Ser Gly Ser Gly Ser Gly Thr Asp Phe Thr Leu Lys Ile Ser
65 70 75 80

Arg Val Glu Ala Glu Asp Val Gly Val Tyr Tyr Cys Met Gln Arg Arg
85 90 95

Arg Thr Pro Trp Ser Phe Gly Gly Gly Thr Lys Val Glu Ile Lys
100 105 110

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Arg Ser Ser Gln Ser Leu Val Ser Ser Gly Tyr Asn Tyr Leu Asp
1 5 10 15

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Phe Gly Ser Ser Arg Ala Ser
1 5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 58

Met Gln Arg Arg Arg Thr Pro Trp Ser
1               5


<210> SEQ ID NO 59
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Glu Ala Tyr
            20                  25                  30

Ser Met Asn Trp Val Arg Gln Ala Pro Gly Lys Gly Leu Glu Trp Val
        35                  40                  45

Ser Tyr Ile Ser Leu Ser Gly Ala Thr Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Tyr Tyr Tyr Thr Ser Ser Asp Tyr Gly Glu Val
            100                 105                 110

Ala Phe Asp Ile Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Ala Ala Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Cys Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335
```

```
Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn Ala Tyr Thr Gln
        435                 440                 445

Lys Ser Leu Ser Leu Ser Pro Gly Lys
    450                 455


<210> SEQ ID NO 60
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Ser
            20                  25                  30

Gly Tyr Asn Tyr Leu Asp Trp Tyr Leu Gln Lys Pro Gly Gln Ser Pro
        35                  40                  45

Gln Leu Leu Ile Tyr Phe Gly Ser Ser Arg Ala Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Met Gln Arg Arg
                85                  90                  95

Arg Thr Pro Trp Ser Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 61
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Gly Tyr
            20                  25                  30

Ser Met Asn Trp Val Arg Gln Ala Pro Gly Lys Gly Leu Glu Trp Val
        35                  40                  45

Ser Tyr Ile Ser Ile Ser Gly Ala Thr Ile Thr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Tyr Tyr Tyr Asp Ser Ser Asp Tyr Gly Glu Val
            100                 105                 110

Ala Phe Asp Ile Trp Gly Gln Gly Thr Met Val Thr Val Ser Ser
        115                 120                 125
```

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Phe Thr Phe Gly Gly Tyr Ser Met Asn
1               5
```

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Tyr Ile Ser Ile Ser Gly Ala Thr Ile Thr Tyr Ala Asp Ser Val Lys
1               5                   10                  15

Gly
```

<210> SEQ ID NO 64
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Ala Arg Gly Gly Gln Tyr Tyr Tyr Asp Ser Ser Asp Tyr Gly Glu Val
1               5                   10                  15

Ala Phe Asp Ile
```

20

<210> SEQ ID NO 65
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 65

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Val Ser Ser
20 25 30

Gly Tyr Asn Tyr Leu Asp Trp Tyr Leu Gln Lys Pro Gly Gln Ser Pro
35 40 45

Gln Leu Leu Ile Tyr Phe Gly Ser Ser Arg Ala Ser Gly Val Pro Asp
50 55 60

Arg Phe Ser Gly Ser Gly Ser Gly Thr Asp Phe Thr Leu Lys Ile Ser
65 70 75 80

Arg Val Glu Ala Glu Asp Val Gly Val Tyr Tyr Cys Met Gln Arg Arg
85 90 95

Arg Thr Pro Pro Phe Thr Phe Gly Gly Gly Thr Lys Val Glu Ile Lys
100 105 110

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Arg Ser Ser Gln Ser Leu Val Ser Ser Gly Tyr Asn Tyr Leu Asp
1 5 10 15

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Phe Gly Ser Ser Arg Ala Ser
1 5

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Met Gln Arg Arg Arg Thr Pro Pro Phe Thr
1 5 10

<210> SEQ ID NO 69
<211> LENGTH: 457

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 69

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Gly Tyr
            20                  25                  30

Ser Met Asn Trp Val Arg Gln Ala Pro Gly Lys Gly Leu Glu Trp Val
        35                  40                  45

Ser Tyr Ile Ser Ile Ser Gly Ala Thr Ile Thr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Tyr Tyr Tyr Asp Ser Ser Asp Tyr Gly Glu Val
            100                 105                 110

Ala Phe Asp Ile Trp Gly Gln Gly Thr Met Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Ala Ala Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Cys Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380
```

Ser Asp Ile Ala Val Glu Trp Glu Ser Asn Gly Gln Pro Glu Asn Asn
385 390 395 400

Tyr Lys Thr Thr Pro Pro Val Leu Asp Ser Asp Gly Ser Phe Phe Leu
405 410 415

Tyr Ser Lys Leu Thr Val Asp Lys Ser Arg Trp Gln Gln Gly Asn Val
420 425 430

Phe Ser Cys Ser Val Met His Glu Ala Leu His Asn Ala Tyr Thr Gln
435 440 445

Lys Ser Leu Ser Leu Ser Pro Gly Lys
450 455

<210> SEQ ID NO 70
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Val Ser Ser
20 25 30

Gly Tyr Asn Tyr Leu Asp Trp Tyr Leu Gln Lys Pro Gly Gln Ser Pro
35 40 45

Gln Leu Leu Ile Tyr Phe Gly Ser Ser Arg Ala Ser Gly Val Pro Asp
50 55 60

Arg Phe Ser Gly Ser Gly Ser Gly Thr Asp Phe Thr Leu Lys Ile Ser
65 70 75 80

Arg Val Glu Ala Glu Asp Val Gly Val Tyr Tyr Cys Met Gln Arg Arg
85 90 95

Arg Thr Pro Pro Phe Thr Phe Gly Gly Gly Thr Lys Val Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 71
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Val Arg Gln Ala Pro Gly Lys Gly Leu Glu Trp Val
        35                  40                  45

Ser Ser Ile Ser Ser Ser Gly Gly Ser Ile Tyr Tyr Pro Asp Arg Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Arg Trp Ala Gly Ala Met Asp Ala Trp Gly Gln Gly
            100                 105                 110

Thr Thr Val Thr Val Ser Ser
        115
```

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

```
Phe Thr Phe Asn Asn Tyr Trp Met Thr
1               5
```

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

```
Ser Ile Ser Ser Ser Gly Gly Ser Ile Tyr Tyr Pro Asp Arg Val Lys
1               5                   10                  15

Gly
```

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

```
Ala Arg Asp Glu Arg Trp Ala Gly Ala Met Asp Ala
1               5                   10
```

<210> SEQ ID NO 75
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys Asn
            20                  25                  30

Leu Asp Trp Tyr Gln Gln Lys Pro Gly Lys Ala Pro Lys Leu Leu Ile
        35                  40                  45

Tyr Glu Thr Asn Asn Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Tyr Gln His Asn Ser Arg Phe Thr
                85                  90                  95

Phe Gly Gln Gly Thr Lys Leu Glu Ile Lys
            100                 105


<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys Ala Ser Gln Asn Ile Asn Lys Asn Leu Asp
1               5                   10


<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Thr Asn Asn Leu Gln Thr
1               5


<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Tyr Gln His Asn Ser Arg Phe Thr
1               5


<210> SEQ ID NO 79
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
```

-continued

```
            20                  25                  30

Trp Met Thr Trp Val Arg Gln Ala Pro Gly Lys Gly Leu Glu Trp Val
        35                  40                  45

Ser Ser Ile Ser Ser Ser Gly Gly Ser Ile Tyr Tyr Pro Asp Arg Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Arg Trp Ala Gly Ala Met Asp Ala Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Cys Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Ala Tyr Thr Gln Lys Ser Leu Ser Leu Ser Pro Gly
        435                 440                 445
```

Lys

<210> SEQ ID NO 80
<211> LENGTH: 213
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 80

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys Asn
            20                  25                  30

Leu Asp Trp Tyr Gln Gln Lys Pro Gly Lys Ala Pro Lys Leu Leu Ile
        35                  40                  45

Tyr Glu Thr Asn Asn Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Tyr Gln His Asn Ser Arg Phe Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 81
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 81

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Phe
            20                  25                  30

Trp Met Ala Trp Ile Arg Gln Ala Pro Gly Lys Gly Leu Glu Trp Val
        35                  40                  45

Ala Ser Ile Ser Ser Ser Gly Gly Ser Ile Tyr Tyr Pro Asp Ser Val
    50                  55                  60
```

Lys Asp Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Val Lys Phe His His Tyr Ser Gly Gly Gly Asp Ala Trp Gly Gln Gly
100 105 110

Thr Leu Val Thr Val Ser Ser
115

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

Phe Thr Phe Thr Asn Phe Trp Met Ala
1 5

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Ser Ile Ser Ser Ser Gly Gly Ser Ile Tyr Tyr Pro Asp Ser Val Lys
1 5 10 15

Asp

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Val Lys Phe His His Tyr Ser Gly Gly Gly Asp Ala
1 5 10

<210> SEQ ID NO 85
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Ile Asn Lys Tyr
20 25 30

Leu Asp Trp Tyr Gln Gln Lys Pro Gly Lys Ala Pro Lys Leu Leu Ile
35 40 45

His Tyr Thr Asn Asn Leu His Thr Gly Ile Pro Ser Arg Phe Ser Gly
50 55 60

```
Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln His Ser Ser Arg Trp Thr
                85                  90                  95

Phe Gly Gly Gly Thr Lys Val Glu Ile Lys
            100                 105


<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Lys Ala Ser Gln Asn Ile Asn Lys Tyr Leu Asp
1               5                   10


<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Tyr Thr Asn Asn Leu His Thr
1               5


<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Leu Gln His Ser Ser Arg Trp Thr
1               5


<210> SEQ ID NO 89
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Phe
            20                  25                  30

Trp Met Ala Trp Ile Arg Gln Ala Pro Gly Lys Gly Leu Glu Trp Val
        35                  40                  45

Ala Ser Ile Ser Ser Ser Gly Gly Ser Ile Tyr Tyr Pro Asp Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

```
Val Lys Phe His His Tyr Ser Gly Gly Gly Asp Ala Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Cys Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Ala Tyr Thr Gln Lys Ser Leu Ser Leu Ser Pro Gly
        435                 440                 445

Lys
```

<210> SEQ ID NO 90
<211> LENGTH: 213
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys Tyr
            20                  25                  30

Leu Asp Trp Tyr Gln Gln Lys Pro Gly Lys Ala Pro Lys Leu Leu Ile
        35                  40                  45

His Tyr Thr Asn Asn Leu His Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln His Ser Ser Arg Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 91
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Val Arg Gln Ala Pro Gly Lys Gly Leu Glu Trp Val
        35                  40                  45

Ser Ser Ile Ser Ser Ser Gly Gly Ser Ile Tyr Tyr Pro Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Met Ala Val Tyr Tyr Cys
                85                  90                  95

Ala Arg Leu Tyr Tyr Tyr Asp Gly Gly Gly Asp Ala Trp Gly Gln Gly
            100                 105                 110

Thr Leu Val Thr Val Ser Ser
        115
```

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

Phe Thr Phe Asn Asn Tyr Trp Met Thr
1               5

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Ser Ile Ser Ser Ser Gly Gly Ser Ile Tyr Tyr Pro Asp Ser Val Lys
1               5                   10                  15

Asp

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Ala Arg Leu Tyr Tyr Tyr Asp Gly Gly Gly Asp Ala
1               5                   10

<210> SEQ ID NO 95
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

Gly Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Leu Asp Trp Tyr Gln Gln Lys Pro Gly Lys Ala Pro Lys Leu Leu Ile
        35                  40                  45

Tyr Asn Thr Asn Asn Leu His Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln His Ile Ser Arg Trp Thr
                85                  90                  95

Phe Gly Gly Gly Thr Lys Val Glu Ile Lys
            100                 105

<210> SEQ ID NO 96
<211> LENGTH: 11
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 96

Lys Ala Ser Gln Asp Ile Asn Lys Tyr Leu Asp
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asn Thr Asn Asn Leu His Thr
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Leu Gln His Ile Ser Arg Trp Thr
1               5

<210> SEQ ID NO 99
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Val Arg Gln Ala Pro Gly Lys Gly Leu Glu Trp Val
        35                  40                  45

Ser Ser Ile Ser Ser Ser Gly Gly Ser Ile Tyr Tyr Pro Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Met Ala Val Tyr Tyr Cys
                85                  90                  95

Ala Arg Leu Tyr Tyr Tyr Asp Gly Gly Gly Asp Ala Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Cys Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Ala Tyr Thr Gln Lys Ser Leu Ser Leu Ser Pro Gly
        435                 440                 445

Lys


<210> SEQ ID NO 100
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gly Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Leu Asp Trp Tyr Gln Gln Lys Pro Gly Lys Ala Pro Lys Leu Leu Ile
        35                  40                  45

Tyr Asn Thr Asn Asn Leu His Thr Gly Ile Pro Ser Arg Phe Ser Gly
    50                  55                  60
```

Ser Gly Ser Gly Thr Asp Tyr Thr Leu Thr Ile Ser Ser Leu Gln Pro
65 70 75 80

Glu Asp Phe Ala Thr Tyr Tyr Cys Leu Gln His Ile Ser Arg Trp Thr
85 90 95

Phe Gly Gly Gly Thr Lys Val Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 101
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 101

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 102
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 103
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Cys Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 104
<211> LENGTH: 330
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 104

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys

```
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Cys Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 105
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

-continued

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Cys Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn Ala Tyr Thr
305 310 315 320

Gln Lys Ser Leu Ser Leu Ser Pro Gly Lys
325 330

<210> SEQ ID NO 106
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Ala Ala Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Cys Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn Ala Tyr Thr
305 310 315 320

Gln Lys Ser Leu Ser Leu Ser Pro Gly Lys
325 330

<210> SEQ ID NO 107
<211> LENGTH: 1211
<212> TYPE: PRT
<213> ORGANISM: Homo sapiens

<400> SEQUENCE: 107

Met Thr Met Tyr Leu Trp Leu Lys Leu Leu Ala Phe Gly Phe Ala Phe
1 5 10 15

Leu Asp Thr Glu Val Phe Val Thr Gly Gln Ser Pro Thr Pro Ser Pro
20 25 30

Thr Gly Leu Thr Thr Ala Lys Met Pro Ser Val Pro Leu Ser Ser Asp
35 40 45

Pro Leu Pro Thr His Thr Thr Ala Phe Ser Pro Ala Ser Thr Phe Glu
50 55 60

Arg Glu Asn Asp Phe Ser Glu Thr Thr Thr Ser Leu Ser Pro Asp Asn
65 70 75 80

Thr Ser Thr Gln Val Ser Pro Asp Ser Leu Asp Asn Ala Ser Ala Phe
85 90 95

Asn Thr Thr Asp Ala Tyr Leu Asn Ala Ser Glu Thr Thr Thr Leu Ser
100 105 110

Pro Ser Gly Ser Ala Val Ile Ser Thr Thr Thr Ile Ala Thr Thr Pro
115 120 125

Ser Lys Pro Thr Cys Asp Glu Lys Tyr Ala Asn Ile Thr Val Asp Tyr
130 135 140

Leu Tyr Asn Lys Glu Thr Lys Leu Phe Thr Ala Lys Leu Asn Val Asn
145 150 155 160

Glu Asn Val Glu Cys Gly Asn Asn Thr Cys Thr Asn Asn Glu Val His
165 170 175

Asn Leu Thr Glu Cys Lys Asn Ala Ser Val Ser Ile Ser His Asn Ser

```
            180                 185                 190

Cys Thr Ala Pro Asp Lys Thr Leu Ile Leu Asp Val Pro Pro Gly Val
        195                 200                 205

Glu Lys Phe Gln Leu His Asp Cys Thr Gln Val Glu Lys Ala Asp Thr
    210                 215                 220

Thr Ile Cys Leu Lys Trp Lys Asn Ile Glu Thr Phe Thr Cys Asp Thr
225                 230                 235                 240

Gln Asn Ile Thr Tyr Arg Phe Gln Cys Gly Asn Met Ile Phe Asp Asn
                245                 250                 255

Lys Glu Ile Lys Leu Glu Asn Leu Glu Pro Glu His Glu Tyr Lys Cys
            260                 265                 270

Asp Ser Glu Ile Leu Tyr Asn Asn His Lys Phe Thr Asn Ala Ser Lys
        275                 280                 285

Ile Ile Lys Thr Asp Phe Gly Ser Pro Gly Glu Pro Gln Ile Ile Phe
    290                 295                 300

Cys Arg Ser Glu Ala Ala His Gln Gly Val Ile Thr Trp Asn Pro Pro
305                 310                 315                 320

Gln Arg Ser Phe His Asn Phe Thr Leu Cys Tyr Ile Lys Glu Thr Glu
                325                 330                 335

Lys Asp Cys Leu Asn Leu Asp Lys Asn Leu Ile Lys Tyr Asp Leu Gln
            340                 345                 350

Asn Leu Lys Pro Tyr Thr Lys Tyr Val Leu Ser Leu His Ala Tyr Ile
        355                 360                 365

Ile Ala Lys Val Gln Arg Asn Gly Ser Ala Ala Met Cys His Phe Thr
    370                 375                 380

Thr Lys Ser Ala Pro Pro Ser Gln Val Trp Asn Met Thr Val Ser Met
385                 390                 395                 400

Thr Ser Asp Asn Ser Met His Val Lys Cys Arg Pro Pro Arg Asp Arg
                405                 410                 415

Asn Gly Pro His Glu Arg Tyr His Leu Glu Val Glu Ala Gly Asn Thr
            420                 425                 430

Leu Val Arg Asn Glu Ser His Lys Asn Cys Asp Phe Arg Val Lys Asp
        435                 440                 445

Leu Gln Tyr Ser Thr Asp Tyr Thr Phe Lys Ala Tyr Phe His Asn Gly
    450                 455                 460

Asp Tyr Pro Gly Glu Pro Phe Ile Leu His His Ser Thr Ser Tyr Asn
465                 470                 475                 480

Ser Lys Ala Leu Ile Ala Phe Leu Ala Phe Leu Ile Ile Val Thr Ser
                485                 490                 495

Ile Ala Leu Leu Val Val Leu Tyr Lys Ile Tyr Asp Leu His Lys Lys
            500                 505                 510

Arg Ser Cys Asn Leu Asp Glu Gln Gln Glu Leu Val Glu Arg Asp Asp
        515                 520                 525

Glu Lys Gln Leu Met Asn Val Glu Pro Ile His Ala Asp Ile Leu Leu
    530                 535                 540

Glu Thr Tyr Lys Arg Lys Ile Ala Asp Glu Gly Arg Leu Phe Leu Ala
545                 550                 555                 560

Glu Phe Gln Ser Ile Pro Arg Val Phe Ser Lys Phe Pro Ile Lys Glu
                565                 570                 575

Ala Arg Lys Pro Phe Asn Gln Asn Lys Asn Arg Tyr Val Asp Ile Leu
            580                 585                 590

Pro Tyr Asp Tyr Asn Arg Val Glu Leu Ser Glu Ile Asn Gly Asp Ala
        595                 600                 605
```

```
Gly Ser Asn Tyr Ile Asn Ala Ser Tyr Ile Asp Gly Phe Lys Glu Pro
    610                 615                 620

Arg Lys Tyr Ile Ala Ala Gln Gly Pro Arg Asp Glu Thr Val Asp Asp
625                 630                 635                 640

Phe Trp Arg Met Ile Trp Glu Gln Lys Ala Thr Val Ile Val Met Val
                645                 650                 655

Thr Arg Cys Glu Glu Gly Asn Arg Asn Lys Cys Ala Glu Tyr Trp Pro
            660                 665                 670

Ser Met Glu Glu Gly Thr Arg Ala Phe Gly Asp Val Val Val Lys Ile
        675                 680                 685

Asn Gln His Lys Arg Cys Pro Asp Tyr Ile Ile Gln Lys Leu Asn Ile
    690                 695                 700

Val Asn Lys Lys Glu Lys Ala Thr Gly Arg Glu Val Thr His Ile Gln
705                 710                 715                 720

Phe Thr Ser Trp Pro Asp His Gly Val Pro Glu Asp Pro His Leu Leu
                725                 730                 735

Leu Lys Leu Arg Arg Arg Val Asn Ala Phe Ser Asn Phe Phe Ser Gly
            740                 745                 750

Pro Ile Val Val His Cys Ser Ala Gly Val Gly Arg Thr Gly Thr Tyr
        755                 760                 765

Ile Gly Ile Asp Ala Met Leu Glu Gly Leu Glu Ala Glu Asn Lys Val
    770                 775                 780

Asp Val Tyr Gly Tyr Val Val Lys Leu Arg Arg Gln Arg Cys Leu Met
785                 790                 795                 800

Val Gln Val Glu Ala Gln Tyr Ile Leu Ile His Gln Ala Leu Val Glu
                805                 810                 815

Tyr Asn Gln Phe Gly Glu Thr Glu Val Asn Leu Ser Glu Leu His Pro
            820                 825                 830

Tyr Leu His Asn Met Lys Lys Arg Asp Pro Pro Ser Glu Pro Ser Pro
        835                 840                 845

Leu Glu Ala Glu Phe Gln Arg Leu Pro Ser Tyr Arg Ser Trp Arg Thr
    850                 855                 860

Gln His Ile Gly Asn Gln Glu Glu Asn Lys Ser Lys Asn Arg Asn Ser
865                 870                 875                 880

Asn Val Ile Pro Tyr Asp Tyr Asn Arg Val Pro Leu Lys His Glu Leu
                885                 890                 895

Glu Met Ser Lys Glu Ser Glu His Asp Ser Asp Glu Ser Ser Asp Asp
            900                 905                 910

Asp Ser Asp Ser Glu Glu Pro Ser Lys Tyr Ile Asn Ala Ser Phe Ile
        915                 920                 925

Met Ser Tyr Trp Lys Pro Glu Val Met Ile Ala Ala Gln Gly Pro Leu
    930                 935                 940

Lys Glu Thr Ile Gly Asp Phe Trp Gln Met Ile Phe Gln Arg Lys Val
945                 950                 955                 960

Lys Val Ile Val Met Leu Thr Glu Leu Lys His Gly Asp Gln Glu Ile
                965                 970                 975

Cys Ala Gln Tyr Trp Gly Glu Gly Lys Gln Thr Tyr Gly Asp Ile Glu
            980                 985                 990

Val Asp Leu Lys Asp Thr Asp Lys  Ser Ser Thr Tyr Thr  Leu Arg Val
        995                 1000                 1005

Phe Glu  Leu Arg His Ser Lys  Arg Lys Asp Ser Arg  Thr Val Tyr
    1010                 1015                 1020
```

```
Gln Tyr  Gln Tyr Thr Asn Trp  Ser Val Glu Gln Leu  Pro Ala Glu
    1025                 1030                 1035

Pro Lys  Glu Leu Ile Ser Met  Ile Gln Val Val Lys  Gln Lys Leu
    1040                 1045                 1050

Pro Gln  Lys Asn Ser Ser Glu  Gly Asn Lys His His  Lys Ser Thr
    1055                 1060                 1065

Pro Leu  Leu Ile His Cys Arg  Asp Gly Ser Gln Gln  Thr Gly Ile
    1070                 1075                 1080

Phe Cys  Ala Leu Leu Asn Leu  Leu Glu Ser Ala Glu  Thr Glu Glu
    1085                 1090                 1095

Val Val  Asp Ile Phe Gln Val  Val Lys Ala Leu Arg  Lys Ala Arg
    1100                 1105                 1110

Pro Gly  Met Val Ser Thr Phe  Glu Gln Tyr Gln Phe  Leu Tyr Asp
    1115                 1120                 1125

Val Ile  Ala Ser Thr Tyr Pro  Ala Gln Asn Gly Gln  Val Lys Lys
    1130                 1135                 1140

Asn Asn  His Gln Glu Asp Lys  Ile Glu Phe Asp Asn  Glu Val Asp
    1145                 1150                 1155

Lys Val  Lys Gln Asp Ala Asn  Cys Val Asn Pro Leu  Gly Ala Pro
    1160                 1165                 1170

Glu Lys  Leu Pro Glu Ala Lys  Glu Gln Ala Glu Gly  Ser Glu Pro
    1175                 1180                 1185

Thr Ser  Gly Thr Glu Gly Pro  Glu His Ser Val Asn  Gly Pro Ala
    1190                 1195                 1200

Ser Pro  Ala Leu Asn Gln Gly  Ser
    1205                 1210


<210> SEQ ID NO 108
<211> LENGTH: 1145
<212> TYPE: PRT
<213> ORGANISM: Homo sapiens

<400> SEQUENCE: 108

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Asp Ala Tyr Leu Asn Ala Ser Glu Thr Thr Thr Leu Ser Pro Ser
        35                  40                  45

Gly Ser Ala Val Ile Ser Thr Thr Thr Ile Ala Thr Thr Pro Ser Lys
    50                  55                  60

Pro Thr Cys Asp Glu Lys Tyr Ala Asn Ile Thr Val Asp Tyr Leu Tyr
65                  70                  75                  80

Asn Lys Glu Thr Lys Leu Phe Thr Ala Lys Leu Asn Val Asn Glu Asn
                85                  90                  95

Val Glu Cys Gly Asn Asn Thr Cys Thr Asn Asn Glu Val His Asn Leu
            100                 105                 110

Thr Glu Cys Lys Asn Ala Ser Val Ser Ile Ser His Asn Ser Cys Thr
        115                 120                 125

Ala Pro Asp Lys Thr Leu Ile Leu Asp Val Pro Pro Gly Val Glu Lys
    130                 135                 140

Phe Gln Leu His Asp Cys Thr Gln Val Glu Lys Ala Asp Thr Thr Ile
145                 150                 155                 160

Cys Leu Lys Trp Lys Asn Ile Glu Thr Phe Thr Cys Asp Thr Gln Asn
                165                 170                 175
```

-continued

```
Ile Thr Tyr Arg Phe Gln Cys Gly Asn Met Ile Phe Asp Asn Lys Glu
            180                 185                 190

Ile Lys Leu Glu Asn Leu Glu Pro Glu His Glu Tyr Lys Cys Asp Ser
        195                 200                 205

Glu Ile Leu Tyr Asn Asn His Lys Phe Thr Asn Ala Ser Lys Ile Ile
    210                 215                 220

Lys Thr Asp Phe Gly Ser Pro Gly Glu Pro Gln Ile Ile Phe Cys Arg
225                 230                 235                 240

Ser Glu Ala Ala His Gln Gly Val Ile Thr Trp Asn Pro Pro Gln Arg
                245                 250                 255

Ser Phe His Asn Phe Thr Leu Cys Tyr Ile Lys Glu Thr Glu Lys Asp
            260                 265                 270

Cys Leu Asn Leu Asp Lys Asn Leu Ile Lys Tyr Asp Leu Gln Asn Leu
        275                 280                 285

Lys Pro Tyr Thr Lys Tyr Val Leu Ser Leu His Ala Tyr Ile Ile Ala
    290                 295                 300

Lys Val Gln Arg Asn Gly Ser Ala Ala Met Cys His Phe Thr Thr Lys
305                 310                 315                 320

Ser Ala Pro Pro Ser Gln Val Trp Asn Met Thr Val Ser Met Thr Ser
                325                 330                 335

Asp Asn Ser Met His Val Lys Cys Arg Pro Pro Arg Asp Arg Asn Gly
            340                 345                 350

Pro His Glu Arg Tyr His Leu Glu Val Glu Ala Gly Asn Thr Leu Val
        355                 360                 365

Arg Asn Glu Ser His Lys Asn Cys Asp Phe Arg Val Lys Asp Leu Gln
    370                 375                 380

Tyr Ser Thr Asp Tyr Thr Phe Lys Ala Tyr Phe His Asn Gly Asp Tyr
385                 390                 395                 400

Pro Gly Glu Pro Phe Ile Leu His His Ser Thr Ser Tyr Asn Ser Lys
                405                 410                 415

Ala Leu Ile Ala Phe Leu Ala Phe Leu Ile Ile Val Thr Ser Ile Ala
            420                 425                 430

Leu Leu Val Val Leu Tyr Lys Ile Tyr Asp Leu His Lys Lys Arg Ser
        435                 440                 445

Cys Asn Leu Asp Glu Gln Gln Glu Leu Val Glu Arg Asp Asp Glu Lys
    450                 455                 460

Gln Leu Met Asn Val Glu Pro Ile His Ala Asp Ile Leu Leu Glu Thr
465                 470                 475                 480

Tyr Lys Arg Lys Ile Ala Asp Glu Gly Arg Leu Phe Leu Ala Glu Phe
                485                 490                 495

Gln Ser Ile Pro Arg Val Phe Ser Lys Phe Pro Ile Lys Glu Ala Arg
            500                 505                 510

Lys Pro Phe Asn Gln Asn Lys Asn Arg Tyr Val Asp Ile Leu Pro Tyr
        515                 520                 525

Asp Tyr Asn Arg Val Glu Leu Ser Glu Ile Asn Gly Asp Ala Gly Ser
    530                 535                 540

Asn Tyr Ile Asn Ala Ser Tyr Ile Asp Gly Phe Lys Glu Pro Arg Lys
545                 550                 555                 560

Tyr Ile Ala Ala Gln Gly Pro Arg Asp Glu Thr Val Asp Asp Phe Trp
                565                 570                 575

Arg Met Ile Trp Glu Gln Lys Ala Thr Val Ile Val Met Val Thr Arg
            580                 585                 590
```

-continued

```
Cys Glu Glu Gly Asn Arg Asn Lys Cys Ala Glu Tyr Trp Pro Ser Met
        595                 600                 605

Glu Glu Gly Thr Arg Ala Phe Gly Asp Val Val Val Lys Ile Asn Gln
    610                 615                 620

His Lys Arg Cys Pro Asp Tyr Ile Ile Gln Lys Leu Asn Ile Val Asn
625                 630                 635                 640

Lys Lys Glu Lys Ala Thr Gly Arg Glu Val Thr His Ile Gln Phe Thr
                645                 650                 655

Ser Trp Pro Asp His Gly Val Pro Glu Asp Pro His Leu Leu Leu Lys
            660                 665                 670

Leu Arg Arg Arg Val Asn Ala Phe Ser Asn Phe Phe Ser Gly Pro Ile
        675                 680                 685

Val Val His Cys Ser Ala Gly Val Gly Arg Thr Gly Thr Tyr Ile Gly
    690                 695                 700

Ile Asp Ala Met Leu Glu Gly Leu Glu Ala Glu Asn Lys Val Asp Val
705                 710                 715                 720

Tyr Gly Tyr Val Val Lys Leu Arg Arg Gln Arg Cys Leu Met Val Gln
                725                 730                 735

Val Glu Ala Gln Tyr Ile Leu Ile His Gln Ala Leu Val Glu Tyr Asn
            740                 745                 750

Gln Phe Gly Glu Thr Glu Val Asn Leu Ser Glu Leu His Pro Tyr Leu
        755                 760                 765

His Asn Met Lys Lys Arg Asp Pro Pro Ser Glu Pro Ser Pro Leu Glu
    770                 775                 780

Ala Glu Phe Gln Arg Leu Pro Ser Tyr Arg Ser Trp Arg Thr Gln His
785                 790                 795                 800

Ile Gly Asn Gln Glu Glu Asn Lys Ser Lys Asn Arg Asn Ser Asn Val
                805                 810                 815

Ile Pro Tyr Asp Tyr Asn Arg Val Pro Leu Lys His Glu Leu Glu Met
            820                 825                 830

Ser Lys Glu Ser Glu His Asp Ser Asp Glu Ser Ser Asp Asp Asp Ser
        835                 840                 845

Asp Ser Glu Glu Pro Ser Lys Tyr Ile Asn Ala Ser Phe Ile Met Ser
    850                 855                 860

Tyr Trp Lys Pro Glu Val Met Ile Ala Ala Gln Gly Pro Leu Lys Glu
865                 870                 875                 880

Thr Ile Gly Asp Phe Trp Gln Met Ile Phe Gln Arg Lys Val Lys Val
                885                 890                 895

Ile Val Met Leu Thr Glu Leu Lys His Gly Asp Gln Glu Ile Cys Ala
            900                 905                 910

Gln Tyr Trp Gly Glu Gly Lys Gln Thr Tyr Gly Asp Ile Glu Val Asp
        915                 920                 925

Leu Lys Asp Thr Asp Lys Ser Ser Thr Tyr Thr Leu Arg Val Phe Glu
    930                 935                 940

Leu Arg His Ser Lys Arg Lys Asp Ser Arg Thr Val Tyr Gln Tyr Gln
945                 950                 955                 960

Tyr Thr Asn Trp Ser Val Glu Gln Leu Pro Ala Glu Pro Lys Glu Leu
                965                 970                 975

Ile Ser Met Ile Gln Val Val Lys Gln Lys Leu Pro Gln Lys Asn Ser
            980                 985                 990

Ser Glu Gly Asn Lys His His Lys  Ser Thr Pro Leu Leu  Ile His Cys
        995                 1000                 1005

Arg Asp  Gly Ser Gln Gln Thr  Gly Ile Phe Cys Ala  Leu Leu Asn
```

```
    1010                1015                1020

Leu Leu  Glu Ser Ala Glu Thr  Glu Glu Val Val Asp  Ile Phe Gln
    1025                1030                1035

Val Val  Lys Ala Leu Arg Lys  Ala Arg Pro Gly Met  Val Ser Thr
    1040                1045                1050

Phe Glu  Gln Tyr Gln Phe Leu  Tyr Asp Val Ile Ala  Ser Thr Tyr
    1055                1060                1065

Pro Ala  Gln Asn Gly Gln Val  Lys Lys Asn Asn His  Gln Glu Asp
    1070                1075                1080

Lys Ile  Glu Phe Asp Asn Glu  Val Asp Lys Val Lys  Gln Asp Ala
    1085                1090                1095

Asn Cys  Val Asn Pro Leu Gly  Ala Pro Glu Lys Leu  Pro Glu Ala
    1100                1105                1110

Lys Glu  Gln Ala Glu Gly Ser  Glu Pro Thr Ser Gly  Thr Glu Gly
    1115                1120                1125

Pro Glu  His Ser Val Asn Gly  Pro Ala Ser Pro Ala  Leu Asn Gln
    1130                1135                1140

Gly Ser
    1145


<210> SEQ ID NO 109
<211> LENGTH: 1192
<212> TYPE: PRT
<213> ORGANISM: Homo sapiens

<400> SEQUENCE: 109

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Val Ser Ser Val Gln Thr Pro His Leu Pro Thr His Ala Asp
        35                  40                  45

Ser Gln Thr Pro Ser Ala Gly Thr Asp Thr Gln Thr Phe Ser Gly Ser
    50                  55                  60

Ala Ala Asn Ala Lys Leu Asn Pro Thr Pro Gly Ser Asn Ala Ile Ser
65                  70                  75                  80

Asp Ala Tyr Leu Asn Ala Ser Glu Thr Thr Thr Leu Ser Pro Ser Gly
                85                  90                  95

Ser Ala Val Ile Ser Thr Thr Thr Ile Ala Thr Thr Pro Ser Lys Pro
            100                 105                 110

Thr Cys Asp Glu Lys Tyr Ala Asn Ile Thr Val Asp Tyr Leu Tyr Asn
        115                 120                 125

Lys Glu Thr Lys Leu Phe Thr Ala Lys Leu Asn Val Asn Glu Asn Val
    130                 135                 140

Glu Cys Gly Asn Asn Thr Cys Thr Asn Asn Glu Val His Asn Leu Thr
145                 150                 155                 160

Glu Cys Lys Asn Ala Ser Val Ser Ile Ser His Asn Ser Cys Thr Ala
                165                 170                 175

Pro Asp Lys Thr Leu Ile Leu Asp Val Pro Pro Gly Val Glu Lys Phe
            180                 185                 190

Gln Leu His Asp Cys Thr Gln Val Glu Lys Ala Asp Thr Thr Ile Cys
        195                 200                 205

Leu Lys Trp Lys Asn Ile Glu Thr Phe Thr Cys Asp Thr Gln Asn Ile
    210                 215                 220
```

-continued

```
Thr Tyr Arg Phe Gln Cys Gly Asn Met Ile Phe Asp Asn Lys Glu Ile
225                 230                 235                 240

Lys Leu Glu Asn Leu Glu Pro Glu His Glu Tyr Lys Cys Asp Ser Glu
                245                 250                 255

Ile Leu Tyr Asn Asn His Lys Phe Thr Asn Ala Ser Lys Ile Ile Lys
            260                 265                 270

Thr Asp Phe Gly Ser Pro Gly Glu Pro Gln Ile Ile Phe Cys Arg Ser
        275                 280                 285

Glu Ala Ala His Gln Gly Val Ile Thr Trp Asn Pro Pro Gln Arg Ser
    290                 295                 300

Phe His Asn Phe Thr Leu Cys Tyr Ile Lys Glu Thr Glu Lys Asp Cys
305                 310                 315                 320

Leu Asn Leu Asp Lys Asn Leu Ile Lys Tyr Asp Leu Gln Asn Leu Lys
                325                 330                 335

Pro Tyr Thr Lys Tyr Val Leu Ser Leu His Ala Tyr Ile Ile Ala Lys
            340                 345                 350

Val Gln Arg Asn Gly Ser Ala Ala Met Cys His Phe Thr Thr Lys Ser
        355                 360                 365

Ala Pro Pro Ser Gln Val Trp Asn Met Thr Val Ser Met Thr Ser Asp
    370                 375                 380

Asn Ser Met His Val Lys Cys Arg Pro Pro Arg Asp Arg Asn Gly Pro
385                 390                 395                 400

His Glu Arg Tyr His Leu Glu Val Glu Ala Gly Asn Thr Leu Val Arg
                405                 410                 415

Asn Glu Ser His Lys Asn Cys Asp Phe Arg Val Lys Asp Leu Gln Tyr
            420                 425                 430

Ser Thr Asp Tyr Thr Phe Lys Ala Tyr Phe His Asn Gly Asp Tyr Pro
        435                 440                 445

Gly Glu Pro Phe Ile Leu His His Ser Thr Ser Tyr Asn Ser Lys Ala
    450                 455                 460

Leu Ile Ala Phe Leu Ala Phe Leu Ile Ile Val Thr Ser Ile Ala Leu
465                 470                 475                 480

Leu Val Val Leu Tyr Lys Ile Tyr Asp Leu His Lys Lys Arg Ser Cys
                485                 490                 495

Asn Leu Asp Glu Gln Gln Glu Leu Val Glu Arg Asp Asp Glu Lys Gln
            500                 505                 510

Leu Met Asn Val Glu Pro Ile His Ala Asp Ile Leu Leu Glu Thr Tyr
        515                 520                 525

Lys Arg Lys Ile Ala Asp Glu Gly Arg Leu Phe Leu Ala Glu Phe Gln
    530                 535                 540

Ser Ile Pro Arg Val Phe Ser Lys Phe Pro Ile Lys Glu Ala Arg Lys
545                 550                 555                 560

Pro Phe Asn Gln Asn Lys Asn Arg Tyr Val Asp Ile Leu Pro Tyr Asp
                565                 570                 575

Tyr Asn Arg Val Glu Leu Ser Glu Ile Asn Gly Asp Ala Gly Ser Asn
            580                 585                 590

Tyr Ile Asn Ala Ser Tyr Ile Asp Gly Phe Lys Glu Pro Arg Lys Tyr
        595                 600                 605

Ile Ala Ala Gln Gly Pro Arg Asp Glu Thr Val Asp Asp Phe Trp Arg
    610                 615                 620

Met Ile Trp Glu Gln Lys Ala Thr Val Ile Val Met Val Thr Arg Cys
625                 630                 635                 640

Glu Glu Gly Asn Arg Asn Lys Cys Ala Glu Tyr Trp Pro Ser Met Glu
```

-continued

```
                645                 650                 655

Glu Gly Thr Arg Ala Phe Gly Asp Val Val Lys Ile Asn Gln His
            660                 665                 670

Lys Arg Cys Pro Asp Tyr Ile Ile Gln Lys Leu Asn Ile Val Asn Lys
        675                 680                 685

Lys Glu Lys Ala Thr Gly Arg Glu Val Thr His Ile Gln Phe Thr Ser
    690                 695                 700

Trp Pro Asp His Gly Val Pro Glu Asp Pro His Leu Leu Leu Lys Leu
705                 710                 715                 720

Arg Arg Arg Val Asn Ala Phe Ser Asn Phe Phe Ser Gly Pro Ile Val
                725                 730                 735

Val His Cys Ser Ala Gly Val Gly Arg Thr Gly Thr Tyr Ile Gly Ile
            740                 745                 750

Asp Ala Met Leu Glu Gly Leu Glu Ala Glu Asn Lys Val Asp Val Tyr
        755                 760                 765

Gly Tyr Val Val Lys Leu Arg Arg Gln Arg Cys Leu Met Val Gln Val
    770                 775                 780

Glu Ala Gln Tyr Ile Leu Ile His Gln Ala Leu Val Glu Tyr Asn Gln
785                 790                 795                 800

Phe Gly Glu Thr Glu Val Asn Leu Ser Glu Leu His Pro Tyr Leu His
                805                 810                 815

Asn Met Lys Lys Arg Asp Pro Pro Ser Glu Pro Ser Pro Leu Glu Ala
            820                 825                 830

Glu Phe Gln Arg Leu Pro Ser Tyr Arg Ser Trp Arg Thr Gln His Ile
        835                 840                 845

Gly Asn Gln Glu Glu Asn Lys Ser Lys Asn Arg Asn Ser Asn Val Ile
    850                 855                 860

Pro Tyr Asp Tyr Asn Arg Val Pro Leu Lys His Glu Leu Glu Met Ser
865                 870                 875                 880

Lys Glu Ser Glu His Asp Ser Asp Glu Ser Ser Asp Asp Asp Ser Asp
                885                 890                 895

Ser Glu Glu Pro Ser Lys Tyr Ile Asn Ala Ser Phe Ile Met Ser Tyr
            900                 905                 910

Trp Lys Pro Glu Val Met Ile Ala Ala Gln Gly Pro Leu Lys Glu Thr
        915                 920                 925

Ile Gly Asp Phe Trp Gln Met Ile Phe Gln Arg Lys Val Lys Val Ile
    930                 935                 940

Val Met Leu Thr Glu Leu Lys His Gly Asp Gln Glu Ile Cys Ala Gln
945                 950                 955                 960

Tyr Trp Gly Glu Gly Lys Gln Thr Tyr Gly Asp Ile Glu Val Asp Leu
                965                 970                 975

Lys Asp Thr Asp Lys Ser Ser Thr Tyr Thr Leu Arg Val Phe Glu Leu
            980                 985                 990

Arg His Ser Lys Arg Lys Asp Ser  Arg Thr Val Tyr Gln  Tyr Gln Tyr
        995                 1000                1005

Thr Asn  Trp Ser Val Glu Gln  Leu Pro Ala Glu Pro  Lys Glu Leu
    1010                 1015                 1020

Ile Ser  Met Ile Gln Val Val  Lys Gln Lys Leu Pro  Gln Lys Asn
    1025                 1030                 1035

Ser Ser  Glu Gly Asn Lys His  His Lys Ser Thr Pro  Leu Leu Ile
    1040                 1045                 1050

His Cys  Arg Asp Gly Ser Gln  Gln Thr Gly Ile Phe  Cys Ala Leu
    1055                 1060                 1065
```

Leu Asn Leu Leu Glu Ser Ala Glu Thr Glu Glu Val Val Asp Ile
1070 1075 1080

Phe Gln Val Val Lys Ala Leu Arg Lys Ala Arg Pro Gly Met Val
1085 1090 1095

Ser Thr Phe Glu Gln Tyr Gln Phe Leu Tyr Asp Val Ile Ala Ser
1100 1105 1110

Thr Tyr Pro Ala Gln Asn Gly Gln Val Lys Lys Asn Asn His Gln
1115 1120 1125

Glu Asp Lys Ile Glu Phe Asp Asn Glu Val Asp Lys Val Lys Gln
1130 1135 1140

Asp Ala Asn Cys Val Asn Pro Leu Gly Ala Pro Glu Lys Leu Pro
1145 1150 1155

Glu Ala Lys Glu Gln Ala Glu Gly Ser Glu Pro Thr Ser Gly Thr
1160 1165 1170

Glu Gly Pro Glu His Ser Val Asn Gly Pro Ala Ser Pro Ala Leu
1175 1180 1185

Asn Gln Gly Ser
1190

<210> SEQ ID NO 110
<211> LENGTH: 1258
<212> TYPE: PRT
<213> ORGANISM: Homo sapiens

<400> SEQUENCE: 110

Met Thr Met Tyr Leu Trp Leu Lys Leu Leu Ala Phe Gly Phe Ala Phe
1 5 10 15

Leu Asp Thr Glu Val Phe Val Thr Gly Gln Ser Pro Thr Pro Ser Pro
20 25 30

Thr Gly Leu Thr Thr Ala Lys Met Pro Ser Val Pro Leu Ser Ser Asp
35 40 45

Pro Leu Pro Thr His Thr Thr Ala Phe Ser Pro Ala Ser Thr Phe Glu
50 55 60

Arg Glu Asn Asp Phe Ser Glu Thr Thr Thr Ser Leu Ser Pro Asp Asn
65 70 75 80

Thr Ser Thr Gln Val Ser Pro Asp Ser Leu Asp Asn Ala Ser Ala Phe
85 90 95

Asn Thr Thr Gly Val Ser Ser Val Gln Thr Pro His Leu Pro Thr His
100 105 110

Ala Asp Ser Gln Thr Pro Ser Ala Gly Thr Asp Thr Gln Thr Phe Ser
115 120 125

Gly Ser Ala Ala Asn Ala Lys Leu Asn Pro Thr Pro Gly Ser Asn Ala
130 135 140

Ile Ser Asp Ala Tyr Leu Asn Ala Ser Glu Thr Thr Thr Leu Ser Pro
145 150 155 160

Ser Gly Ser Ala Val Ile Ser Thr Thr Thr Ile Ala Thr Thr Pro Ser
165 170 175

Lys Pro Thr Cys Asp Glu Lys Tyr Ala Asn Ile Thr Val Asp Tyr Leu
180 185 190

Tyr Asn Lys Glu Thr Lys Leu Phe Thr Ala Lys Leu Asn Val Asn Glu
195 200 205

Asn Val Glu Cys Gly Asn Asn Thr Cys Thr Asn Asn Glu Val His Asn
210 215 220

Leu Thr Glu Cys Lys Asn Ala Ser Val Ser Ile Ser His Asn Ser Cys

-continued

```
225                 230                 235                 240

Thr Ala Pro Asp Lys Thr Leu Ile Leu Asp Val Pro Pro Gly Val Glu
                245                 250                 255

Lys Phe Gln Leu His Asp Cys Thr Gln Val Glu Lys Ala Asp Thr Thr
            260                 265                 270

Ile Cys Leu Lys Trp Lys Asn Ile Glu Thr Phe Thr Cys Asp Thr Gln
        275                 280                 285

Asn Ile Thr Tyr Arg Phe Gln Cys Gly Asn Met Ile Phe Asp Asn Lys
    290                 295                 300

Glu Ile Lys Leu Glu Asn Leu Glu Pro Glu His Glu Tyr Lys Cys Asp
305                 310                 315                 320

Ser Glu Ile Leu Tyr Asn Asn His Lys Phe Thr Asn Ala Ser Lys Ile
                325                 330                 335

Ile Lys Thr Asp Phe Gly Ser Pro Gly Glu Pro Gln Ile Ile Phe Cys
            340                 345                 350

Arg Ser Glu Ala Ala His Gln Gly Val Ile Thr Trp Asn Pro Pro Gln
        355                 360                 365

Arg Ser Phe His Asn Phe Thr Leu Cys Tyr Ile Lys Glu Thr Glu Lys
    370                 375                 380

Asp Cys Leu Asn Leu Asp Lys Asn Leu Ile Lys Tyr Asp Leu Gln Asn
385                 390                 395                 400

Leu Lys Pro Tyr Thr Lys Tyr Val Leu Ser Leu His Ala Tyr Ile Ile
                405                 410                 415

Ala Lys Val Gln Arg Asn Gly Ser Ala Ala Met Cys His Phe Thr Thr
            420                 425                 430

Lys Ser Ala Pro Pro Ser Gln Val Trp Asn Met Thr Val Ser Met Thr
        435                 440                 445

Ser Asp Asn Ser Met His Val Lys Cys Arg Pro Pro Arg Asp Arg Asn
    450                 455                 460

Gly Pro His Glu Arg Tyr His Leu Glu Val Glu Ala Gly Asn Thr Leu
465                 470                 475                 480

Val Arg Asn Glu Ser His Lys Asn Cys Asp Phe Arg Val Lys Asp Leu
                485                 490                 495

Gln Tyr Ser Thr Asp Tyr Thr Phe Lys Ala Tyr Phe His Asn Gly Asp
            500                 505                 510

Tyr Pro Gly Glu Pro Phe Ile Leu His His Ser Thr Ser Tyr Asn Ser
        515                 520                 525

Lys Ala Leu Ile Ala Phe Leu Ala Phe Leu Ile Ile Val Thr Ser Ile
    530                 535                 540

Ala Leu Leu Val Val Leu Tyr Lys Ile Tyr Asp Leu His Lys Lys Arg
545                 550                 555                 560

Ser Cys Asn Leu Asp Glu Gln Gln Glu Leu Val Glu Arg Asp Asp Glu
                565                 570                 575

Lys Gln Leu Met Asn Val Glu Pro Ile His Ala Asp Ile Leu Leu Glu
            580                 585                 590

Thr Tyr Lys Arg Lys Ile Ala Asp Glu Gly Arg Leu Phe Leu Ala Glu
        595                 600                 605

Phe Gln Ser Ile Pro Arg Val Phe Ser Lys Phe Pro Ile Lys Glu Ala
    610                 615                 620

Arg Lys Pro Phe Asn Gln Asn Lys Asn Arg Tyr Val Asp Ile Leu Pro
625                 630                 635                 640

Tyr Asp Tyr Asn Arg Val Glu Leu Ser Glu Ile Asn Gly Asp Ala Gly
                645                 650                 655
```

-continued

```
Ser Asn Tyr Ile Asn Ala Ser Tyr Ile Asp Gly Phe Lys Glu Pro Arg
            660                 665                 670

Lys Tyr Ile Ala Ala Gln Gly Pro Arg Asp Glu Thr Val Asp Asp Phe
        675                 680                 685

Trp Arg Met Ile Trp Glu Gln Lys Ala Thr Val Ile Val Met Val Thr
    690                 695                 700

Arg Cys Glu Glu Gly Asn Arg Asn Lys Cys Ala Glu Tyr Trp Pro Ser
705                 710                 715                 720

Met Glu Glu Gly Thr Arg Ala Phe Gly Asp Val Val Val Lys Ile Asn
                725                 730                 735

Gln His Lys Arg Cys Pro Asp Tyr Ile Ile Gln Lys Leu Asn Ile Val
            740                 745                 750

Asn Lys Lys Glu Lys Ala Thr Gly Arg Glu Val Thr His Ile Gln Phe
        755                 760                 765

Thr Ser Trp Pro Asp His Gly Val Pro Glu Asp Pro His Leu Leu Leu
    770                 775                 780

Lys Leu Arg Arg Arg Val Asn Ala Phe Ser Asn Phe Phe Ser Gly Pro
785                 790                 795                 800

Ile Val Val His Cys Ser Ala Gly Val Gly Arg Thr Gly Thr Tyr Ile
                805                 810                 815

Gly Ile Asp Ala Met Leu Glu Gly Leu Glu Ala Glu Asn Lys Val Asp
            820                 825                 830

Val Tyr Gly Tyr Val Val Lys Leu Arg Arg Gln Arg Cys Leu Met Val
        835                 840                 845

Gln Val Glu Ala Gln Tyr Ile Leu Ile His Gln Ala Leu Val Glu Tyr
    850                 855                 860

Asn Gln Phe Gly Glu Thr Glu Val Asn Leu Ser Glu Leu His Pro Tyr
865                 870                 875                 880

Leu His Asn Met Lys Lys Arg Asp Pro Pro Ser Glu Pro Ser Pro Leu
                885                 890                 895

Glu Ala Glu Phe Gln Arg Leu Pro Ser Tyr Arg Ser Trp Arg Thr Gln
            900                 905                 910

His Ile Gly Asn Gln Glu Glu Asn Lys Ser Lys Asn Arg Asn Ser Asn
        915                 920                 925

Val Ile Pro Tyr Asp Tyr Asn Arg Val Pro Leu Lys His Glu Leu Glu
    930                 935                 940

Met Ser Lys Glu Ser Glu His Asp Ser Asp Glu Ser Ser Asp Asp Asp
945                 950                 955                 960

Ser Asp Ser Glu Glu Pro Ser Lys Tyr Ile Asn Ala Ser Phe Ile Met
                965                 970                 975

Ser Tyr Trp Lys Pro Glu Val Met Ile Ala Ala Gln Gly Pro Leu Lys
            980                 985                 990

Glu Thr Ile Gly Asp Phe Trp Gln  Met Ile Phe Gln Arg  Lys Val Lys
        995                 1000                 1005

Val Ile  Val Met Leu Thr Glu  Leu Lys His Gly Asp  Gln Glu Ile
    1010                 1015                 1020

Cys Ala  Gln Tyr Trp Gly Glu  Gly Lys Gln Thr Tyr  Gly Asp Ile
    1025                 1030                 1035

Glu Val  Asp Leu Lys Asp Thr  Asp Lys Ser Ser Thr  Tyr Thr Leu
    1040                 1045                 1050

Arg Val  Phe Glu Leu Arg His  Ser Lys Arg Lys Asp  Ser Arg Thr
    1055                 1060                 1065
```

```
Val Tyr  Gln Tyr Gln Tyr Thr  Asn Trp Ser Val Glu  Gln Leu Pro
    1070                1075                1080

Ala Glu  Pro Lys Glu Leu Ile  Ser Met Ile Gln Val  Val Lys Gln
    1085                1090                1095

Lys Leu  Pro Gln Lys Asn Ser  Ser Glu Gly Asn Lys  His His Lys
    1100                1105                1110

Ser Thr  Pro Leu Leu Ile His  Cys Arg Asp Gly Ser  Gln Gln Thr
    1115                1120                1125

Gly Ile  Phe Cys Ala Leu Leu  Asn Leu Leu Glu Ser  Ala Glu Thr
    1130                1135                1140

Glu Glu  Val Val Asp Ile Phe  Gln Val Val Lys Ala  Leu Arg Lys
    1145                1150                1155

Ala Arg  Pro Gly Met Val Ser  Thr Phe Glu Gln Tyr  Gln Phe Leu
    1160                1165                1170

Tyr Asp  Val Ile Ala Ser Thr  Tyr Pro Ala Gln Asn  Gly Gln Val
    1175                1180                1185

Lys Lys  Asn Asn His Gln Glu  Asp Lys Ile Glu Phe  Asp Asn Glu
    1190                1195                1200

Val Asp  Lys Val Lys Gln Asp  Ala Asn Cys Val Asn  Pro Leu Gly
    1205                1210                1215

Ala Pro  Glu Lys Leu Pro Glu  Ala Lys Glu Gln Ala  Glu Gly Ser
    1220                1225                1230

Glu Pro  Thr Ser Gly Thr Glu  Gly Pro Glu His Ser  Val Asn Gly
    1235                1240                1245

Pro Ala  Ser Pro Ala Leu Asn  Gln Gly Ser
    1250                1255


<210> SEQ ID NO 111
<211> LENGTH: 1240
<212> TYPE: PRT
<213> ORGANISM: Homo sapiens

<400> SEQUENCE: 111

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Val Ser Ser Val Gln Thr Pro His Leu Pro Thr His Ala Asp
        35                  40                  45

Ser Gln Thr Pro Ser Ala Gly Thr Asp Thr Gln Thr Phe Ser Gly Ser
    50                  55                  60

Ala Ala Asn Ala Lys Leu Asn Pro Thr Pro Gly Ser Asn Ala Ile Ser
65                  70                  75                  80

Asp Val Pro Gly Glu Arg Ser Thr Ala Ser Thr Phe Pro Thr Asp Pro
                85                  90                  95

Val Ser Pro Leu Thr Thr Thr Leu Ser Leu Ala His His Ser Ser Ala
            100                 105                 110

Ala Leu Pro Ala Arg Thr Ser Asn Thr Thr Ile Thr Ala Asn Thr Ser
        115                 120                 125

Asp Ala Tyr Leu Asn Ala Ser Glu Thr Thr Thr Leu Ser Pro Ser Gly
    130                 135                 140

Ser Ala Val Ile Ser Thr Thr Thr Ile Ala Thr Thr Pro Ser Lys Pro
145                 150                 155                 160

Thr Cys Asp Glu Lys Tyr Ala Asn Ile Thr Val Asp Tyr Leu Tyr Asn
                165                 170                 175
```

```
Lys Glu Thr Lys Leu Phe Thr Ala Lys Leu Asn Val Asn Glu Asn Val
            180                 185                 190

Glu Cys Gly Asn Asn Thr Cys Thr Asn Asn Glu Val His Asn Leu Thr
        195                 200                 205

Glu Cys Lys Asn Ala Ser Val Ser Ile Ser His Asn Ser Cys Thr Ala
    210                 215                 220

Pro Asp Lys Thr Leu Ile Leu Asp Val Pro Pro Gly Val Glu Lys Phe
225                 230                 235                 240

Gln Leu His Asp Cys Thr Gln Val Glu Lys Ala Asp Thr Thr Ile Cys
                245                 250                 255

Leu Lys Trp Lys Asn Ile Glu Thr Phe Thr Cys Asp Thr Gln Asn Ile
            260                 265                 270

Thr Tyr Arg Phe Gln Cys Gly Asn Met Ile Phe Asp Asn Lys Glu Ile
        275                 280                 285

Lys Leu Glu Asn Leu Glu Pro Glu His Glu Tyr Lys Cys Asp Ser Glu
    290                 295                 300

Ile Leu Tyr Asn Asn His Lys Phe Thr Asn Ala Ser Lys Ile Ile Lys
305                 310                 315                 320

Thr Asp Phe Gly Ser Pro Gly Glu Pro Gln Ile Ile Phe Cys Arg Ser
                325                 330                 335

Glu Ala Ala His Gln Gly Val Ile Thr Trp Asn Pro Pro Gln Arg Ser
            340                 345                 350

Phe His Asn Phe Thr Leu Cys Tyr Ile Lys Glu Thr Glu Lys Asp Cys
        355                 360                 365

Leu Asn Leu Asp Lys Asn Leu Ile Lys Tyr Asp Leu Gln Asn Leu Lys
    370                 375                 380

Pro Tyr Thr Lys Tyr Val Leu Ser Leu His Ala Tyr Ile Ile Ala Lys
385                 390                 395                 400

Val Gln Arg Asn Gly Ser Ala Ala Met Cys His Phe Thr Thr Lys Ser
                405                 410                 415

Ala Pro Pro Ser Gln Val Trp Asn Met Thr Val Ser Met Thr Ser Asp
            420                 425                 430

Asn Ser Met His Val Lys Cys Arg Pro Pro Arg Asp Arg Asn Gly Pro
        435                 440                 445

His Glu Arg Tyr His Leu Glu Val Glu Ala Gly Asn Thr Leu Val Arg
    450                 455                 460

Asn Glu Ser His Lys Asn Cys Asp Phe Arg Val Lys Asp Leu Gln Tyr
465                 470                 475                 480

Ser Thr Asp Tyr Thr Phe Lys Ala Tyr Phe His Asn Gly Asp Tyr Pro
                485                 490                 495

Gly Glu Pro Phe Ile Leu His His Ser Thr Ser Tyr Asn Ser Lys Ala
            500                 505                 510

Leu Ile Ala Phe Leu Ala Phe Leu Ile Ile Val Thr Ser Ile Ala Leu
        515                 520                 525

Leu Val Val Leu Tyr Lys Ile Tyr Asp Leu His Lys Lys Arg Ser Cys
    530                 535                 540

Asn Leu Asp Glu Gln Gln Glu Leu Val Glu Arg Asp Asp Glu Lys Gln
545                 550                 555                 560

Leu Met Asn Val Glu Pro Ile His Ala Asp Ile Leu Leu Glu Thr Tyr
                565                 570                 575

Lys Arg Lys Ile Ala Asp Glu Gly Arg Leu Phe Leu Ala Glu Phe Gln
            580                 585                 590
```

-continued

```
Ser Ile Pro Arg Val Phe Ser Lys Phe Pro Ile Lys Glu Ala Arg Lys
        595                 600                 605

Pro Phe Asn Gln Asn Lys Asn Arg Tyr Val Asp Ile Leu Pro Tyr Asp
    610                 615                 620

Tyr Asn Arg Val Glu Leu Ser Glu Ile Asn Gly Asp Ala Gly Ser Asn
625                 630                 635                 640

Tyr Ile Asn Ala Ser Tyr Ile Asp Gly Phe Lys Glu Pro Arg Lys Tyr
                645                 650                 655

Ile Ala Ala Gln Gly Pro Arg Asp Glu Thr Val Asp Asp Phe Trp Arg
            660                 665                 670

Met Ile Trp Glu Gln Lys Ala Thr Val Ile Val Met Val Thr Arg Cys
        675                 680                 685

Glu Glu Gly Asn Arg Asn Lys Cys Ala Glu Tyr Trp Pro Ser Met Glu
    690                 695                 700

Glu Gly Thr Arg Ala Phe Gly Asp Val Val Val Lys Ile Asn Gln His
705                 710                 715                 720

Lys Arg Cys Pro Asp Tyr Ile Ile Gln Lys Leu Asn Ile Val Asn Lys
                725                 730                 735

Lys Glu Lys Ala Thr Gly Arg Glu Val Thr His Ile Gln Phe Thr Ser
            740                 745                 750

Trp Pro Asp His Gly Val Pro Glu Asp Pro His Leu Leu Leu Lys Leu
        755                 760                 765

Arg Arg Arg Val Asn Ala Phe Ser Asn Phe Phe Ser Gly Pro Ile Val
    770                 775                 780

Val His Cys Ser Ala Gly Val Gly Arg Thr Gly Thr Tyr Ile Gly Ile
785                 790                 795                 800

Asp Ala Met Leu Glu Gly Leu Glu Ala Glu Asn Lys Val Asp Val Tyr
                805                 810                 815

Gly Tyr Val Val Lys Leu Arg Arg Gln Arg Cys Leu Met Val Gln Val
            820                 825                 830

Glu Ala Gln Tyr Ile Leu Ile His Gln Ala Leu Val Glu Tyr Asn Gln
        835                 840                 845

Phe Gly Glu Thr Glu Val Asn Leu Ser Glu Leu His Pro Tyr Leu His
    850                 855                 860

Asn Met Lys Lys Arg Asp Pro Pro Ser Glu Pro Ser Pro Leu Glu Ala
865                 870                 875                 880

Glu Phe Gln Arg Leu Pro Ser Tyr Arg Ser Trp Arg Thr Gln His Ile
                885                 890                 895

Gly Asn Gln Glu Glu Asn Lys Ser Lys Asn Arg Asn Ser Asn Val Ile
            900                 905                 910

Pro Tyr Asp Tyr Asn Arg Val Pro Leu Lys His Glu Leu Glu Met Ser
        915                 920                 925

Lys Glu Ser Glu His Asp Ser Asp Glu Ser Ser Asp Asp Asp Ser Asp
    930                 935                 940

Ser Glu Glu Pro Ser Lys Tyr Ile Asn Ala Ser Phe Ile Met Ser Tyr
945                 950                 955                 960

Trp Lys Pro Glu Val Met Ile Ala Ala Gln Gly Pro Leu Lys Glu Thr
                965                 970                 975

Ile Gly Asp Phe Trp Gln Met Ile Phe Gln Arg Lys Val Lys Val Ile
            980                 985                 990

Val Met Leu Thr Glu Leu Lys His  Gly Asp Gln Glu Ile  Cys Ala Gln
        995                 1000                1005

Tyr Trp  Gly Glu Gly Lys Gln  Thr Tyr Gly Asp Ile  Glu Val Asp
```

```
    1010                1015                1020

Leu Lys  Asp Thr Asp Lys Ser  Ser Thr Tyr Thr Leu  Arg Val Phe
    1025                1030                1035

Glu Leu  Arg His Ser Lys Arg  Lys Asp Ser Arg Thr  Val Tyr Gln
    1040                1045                1050

Tyr Gln  Tyr Thr Asn Trp Ser  Val Glu Gln Leu Pro  Ala Glu Pro
    1055                1060                1065

Lys Glu  Leu Ile Ser Met Ile  Gln Val Val Lys Gln  Lys Leu Pro
    1070                1075                1080

Gln Lys  Asn Ser Ser Glu Gly  Asn Lys His His Lys  Ser Thr Pro
    1085                1090                1095

Leu Leu  Ile His Cys Arg Asp  Gly Ser Gln Gln Thr  Gly Ile Phe
    1100                1105                1110

Cys Ala  Leu Leu Asn Leu Leu  Glu Ser Ala Glu Thr  Glu Glu Val
    1115                1120                1125

Val Asp  Ile Phe Gln Val Val  Lys Ala Leu Arg Lys  Ala Arg Pro
    1130                1135                1140

Gly Met  Val Ser Thr Phe Glu  Gln Tyr Gln Phe Leu  Tyr Asp Val
    1145                1150                1155

Ile Ala  Ser Thr Tyr Pro Ala  Gln Asn Gly Gln Val  Lys Lys Asn
    1160                1165                1170

Asn His  Gln Glu Asp Lys Ile  Glu Phe Asp Asn Glu  Val Asp Lys
    1175                1180                1185

Val Lys  Gln Asp Ala Asn Cys  Val Asn Pro Leu Gly  Ala Pro Glu
    1190                1195                1200

Lys Leu  Pro Glu Ala Lys Glu  Gln Ala Glu Gly Ser  Glu Pro Thr
    1205                1210                1215

Ser Gly  Thr Glu Gly Pro Glu  His Ser Val Asn Gly  Pro Ala Ser
    1220                1225                1230

Pro Ala  Leu Asn Gln Gly Ser
    1235                1240


<210> SEQ ID NO 112
<211> LENGTH: 1306
<212> TYPE: PRT
<213> ORGANISM: Homo sapiens

<400> SEQUENCE: 112

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Leu Thr Thr Ala Lys Met Pro Ser Val Pro Leu Ser Ser Asp
        35                  40                  45

Pro Leu Pro Thr His Thr Thr Ala Phe Ser Pro Ala Ser Thr Phe Glu
    50                  55                  60

Arg Glu Asn Asp Phe Ser Glu Thr Thr Thr Ser Leu Ser Pro Asp Asn
65                  70                  75                  80

Thr Ser Thr Gln Val Ser Pro Asp Ser Leu Asp Asn Ala Ser Ala Phe
                85                  90                  95

Asn Thr Thr Gly Val Ser Ser Val Gln Thr Pro His Leu Pro Thr His
            100                 105                 110

Ala Asp Ser Gln Thr Pro Ser Ala Gly Thr Asp Thr Gln Thr Phe Ser
        115                 120                 125
```

```
Gly Ser Ala Ala Asn Ala Lys Leu Asn Pro Thr Pro Gly Ser Asn Ala
    130                 135                 140

Ile Ser Asp Val Pro Gly Glu Arg Ser Thr Ala Ser Thr Phe Pro Thr
145                 150                 155                 160

Asp Pro Val Ser Pro Leu Thr Thr Thr Leu Ser Leu Ala His His Ser
                165                 170                 175

Ser Ala Ala Leu Pro Ala Arg Thr Ser Asn Thr Thr Ile Thr Ala Asn
            180                 185                 190

Thr Ser Asp Ala Tyr Leu Asn Ala Ser Glu Thr Thr Thr Leu Ser Pro
        195                 200                 205

Ser Gly Ser Ala Val Ile Ser Thr Thr Thr Ile Ala Thr Thr Pro Ser
    210                 215                 220

Lys Pro Thr Cys Asp Glu Lys Tyr Ala Asn Ile Thr Val Asp Tyr Leu
225                 230                 235                 240

Tyr Asn Lys Glu Thr Lys Leu Phe Thr Ala Lys Leu Asn Val Asn Glu
                245                 250                 255

Asn Val Glu Cys Gly Asn Asn Thr Cys Thr Asn Asn Glu Val His Asn
            260                 265                 270

Leu Thr Glu Cys Lys Asn Ala Ser Val Ser Ile Ser His Asn Ser Cys
        275                 280                 285

Thr Ala Pro Asp Lys Thr Leu Ile Leu Asp Val Pro Pro Gly Val Glu
    290                 295                 300

Lys Phe Gln Leu His Asp Cys Thr Gln Val Glu Lys Ala Asp Thr Thr
305                 310                 315                 320

Ile Cys Leu Lys Trp Lys Asn Ile Glu Thr Phe Thr Cys Asp Thr Gln
                325                 330                 335

Asn Ile Thr Tyr Arg Phe Gln Cys Gly Asn Met Ile Phe Asp Asn Lys
            340                 345                 350

Glu Ile Lys Leu Glu Asn Leu Glu Pro Glu His Glu Tyr Lys Cys Asp
        355                 360                 365

Ser Glu Ile Leu Tyr Asn Asn His Lys Phe Thr Asn Ala Ser Lys Ile
    370                 375                 380

Ile Lys Thr Asp Phe Gly Ser Pro Gly Glu Pro Gln Ile Ile Phe Cys
385                 390                 395                 400

Arg Ser Glu Ala Ala His Gln Gly Val Ile Thr Trp Asn Pro Pro Gln
                405                 410                 415

Arg Ser Phe His Asn Phe Thr Leu Cys Tyr Ile Lys Glu Thr Glu Lys
            420                 425                 430

Asp Cys Leu Asn Leu Asp Lys Asn Leu Ile Lys Tyr Asp Leu Gln Asn
        435                 440                 445

Leu Lys Pro Tyr Thr Lys Tyr Val Leu Ser Leu His Ala Tyr Ile Ile
    450                 455                 460

Ala Lys Val Gln Arg Asn Gly Ser Ala Ala Met Cys His Phe Thr Thr
465                 470                 475                 480

Lys Ser Ala Pro Pro Ser Gln Val Trp Asn Met Thr Val Ser Met Thr
                485                 490                 495

Ser Asp Asn Ser Met His Val Lys Cys Arg Pro Pro Arg Asp Arg Asn
            500                 505                 510

Gly Pro His Glu Arg Tyr His Leu Glu Val Glu Ala Gly Asn Thr Leu
        515                 520                 525

Val Arg Asn Glu Ser His Lys Asn Cys Asp Phe Arg Val Lys Asp Leu
    530                 535                 540

Gln Tyr Ser Thr Asp Tyr Thr Phe Lys Ala Tyr Phe His Asn Gly Asp
```

```
545                 550                 555                 560

Tyr Pro Gly Glu Pro Phe Ile Leu His His Ser Thr Ser Tyr Asn Ser
                565                 570                 575

Lys Ala Leu Ile Ala Phe Leu Ala Phe Leu Ile Ile Val Thr Ser Ile
            580                 585                 590

Ala Leu Leu Val Val Leu Tyr Lys Ile Tyr Asp Leu His Lys Lys Arg
        595                 600                 605

Ser Cys Asn Leu Asp Glu Gln Gln Glu Leu Val Glu Arg Asp Asp Glu
    610                 615                 620

Lys Gln Leu Met Asn Val Glu Pro Ile His Ala Asp Ile Leu Leu Glu
625                 630                 635                 640

Thr Tyr Lys Arg Lys Ile Ala Asp Glu Gly Arg Leu Phe Leu Ala Glu
                645                 650                 655

Phe Gln Ser Ile Pro Arg Val Phe Ser Lys Phe Pro Ile Lys Glu Ala
            660                 665                 670

Arg Lys Pro Phe Asn Gln Asn Lys Asn Arg Tyr Val Asp Ile Leu Pro
        675                 680                 685

Tyr Asp Tyr Asn Arg Val Glu Leu Ser Glu Ile Asn Gly Asp Ala Gly
    690                 695                 700

Ser Asn Tyr Ile Asn Ala Ser Tyr Ile Asp Gly Phe Lys Glu Pro Arg
705                 710                 715                 720

Lys Tyr Ile Ala Ala Gln Gly Pro Arg Asp Glu Thr Val Asp Asp Phe
                725                 730                 735

Trp Arg Met Ile Trp Glu Gln Lys Ala Thr Val Ile Val Met Val Thr
            740                 745                 750

Arg Cys Glu Glu Gly Asn Arg Asn Lys Cys Ala Glu Tyr Trp Pro Ser
        755                 760                 765

Met Glu Glu Gly Thr Arg Ala Phe Gly Asp Val Val Val Lys Ile Asn
    770                 775                 780

Gln His Lys Arg Cys Pro Asp Tyr Ile Ile Gln Lys Leu Asn Ile Val
785                 790                 795                 800

Asn Lys Lys Glu Lys Ala Thr Gly Arg Glu Val Thr His Ile Gln Phe
                805                 810                 815

Thr Ser Trp Pro Asp His Gly Val Pro Glu Asp Pro His Leu Leu Leu
            820                 825                 830

Lys Leu Arg Arg Arg Val Asn Ala Phe Ser Asn Phe Phe Ser Gly Pro
        835                 840                 845

Ile Val Val His Cys Ser Ala Gly Val Gly Arg Thr Gly Thr Tyr Ile
    850                 855                 860

Gly Ile Asp Ala Met Leu Glu Gly Leu Glu Ala Glu Asn Lys Val Asp
865                 870                 875                 880

Val Tyr Gly Tyr Val Val Lys Leu Arg Arg Gln Arg Cys Leu Met Val
                885                 890                 895

Gln Val Glu Ala Gln Tyr Ile Leu Ile His Gln Ala Leu Val Glu Tyr
            900                 905                 910

Asn Gln Phe Gly Glu Thr Glu Val Asn Leu Ser Glu Leu His Pro Tyr
        915                 920                 925

Leu His Asn Met Lys Lys Arg Asp Pro Pro Ser Glu Pro Ser Pro Leu
    930                 935                 940

Glu Ala Glu Phe Gln Arg Leu Pro Ser Tyr Arg Ser Trp Arg Thr Gln
945                 950                 955                 960

His Ile Gly Asn Gln Glu Glu Asn Lys Ser Lys Asn Arg Asn Ser Asn
                965                 970                 975
```

Val Ile Pro Tyr Asp Tyr Asn Arg Val Pro Leu Lys His Glu Leu Glu
980 985 990

Met Ser Lys Glu Ser Glu His Asp Ser Asp Glu Ser Ser Asp Asp Asp
995 1000 1005

Ser Asp Ser Glu Glu Pro Ser Lys Tyr Ile Asn Ala Ser Phe Ile
1010 1015 1020

Met Ser Tyr Trp Lys Pro Glu Val Met Ile Ala Ala Gln Gly Pro
1025 1030 1035

Leu Lys Glu Thr Ile Gly Asp Phe Trp Gln Met Ile Phe Gln Arg
1040 1045 1050

Lys Val Lys Val Ile Val Met Leu Thr Glu Leu Lys His Gly Asp
1055 1060 1065

Gln Glu Ile Cys Ala Gln Tyr Trp Gly Glu Gly Lys Gln Thr Tyr
1070 1075 1080

Gly Asp Ile Glu Val Asp Leu Lys Asp Thr Asp Lys Ser Ser Thr
1085 1090 1095

Tyr Thr Leu Arg Val Phe Glu Leu Arg His Ser Lys Arg Lys Asp
1100 1105 1110

Ser Arg Thr Val Tyr Gln Tyr Gln Tyr Thr Asn Trp Ser Val Glu
1115 1120 1125

Gln Leu Pro Ala Glu Pro Lys Glu Leu Ile Ser Met Ile Gln Val
1130 1135 1140

Val Lys Gln Lys Leu Pro Gln Lys Asn Ser Ser Glu Gly Asn Lys
1145 1150 1155

His His Lys Ser Thr Pro Leu Leu Ile His Cys Arg Asp Gly Ser
1160 1165 1170

Gln Gln Thr Gly Ile Phe Cys Ala Leu Leu Asn Leu Leu Glu Ser
1175 1180 1185

Ala Glu Thr Glu Glu Val Val Asp Ile Phe Gln Val Val Lys Ala
1190 1195 1200

Leu Arg Lys Ala Arg Pro Gly Met Val Ser Thr Phe Glu Gln Tyr
1205 1210 1215

Gln Phe Leu Tyr Asp Val Ile Ala Ser Thr Tyr Pro Ala Gln Asn
1220 1225 1230

Gly Gln Val Lys Lys Asn Asn His Gln Glu Asp Lys Ile Glu Phe
1235 1240 1245

Asp Asn Glu Val Asp Lys Val Lys Gln Asp Ala Asn Cys Val Asn
1250 1255 1260

Pro Leu Gly Ala Pro Glu Lys Leu Pro Glu Ala Lys Glu Gln Ala
1265 1270 1275

Glu Gly Ser Glu Pro Thr Ser Gly Thr Glu Gly Pro Glu His Ser
1280 1285 1290

Val Asn Gly Pro Ala Ser Pro Ala Leu Asn Gln Gly Ser
1295 1300 1305

<210> SEQ ID NO 113
<211> LENGTH: 552
<212> TYPE: PRT
<213> ORGANISM: Homo sapiens

<400> SEQUENCE: 113

Gln Ser Pro Thr Pro Ser Pro Thr Gly Leu Thr Thr Ala Lys Met Pro
1 5 10 15

Ser Val Pro Leu Ser Ser Asp Pro Leu Pro Thr His Thr Thr Ala Phe

```
            20                  25                  30

Ser Pro Ala Ser Thr Phe Glu Arg Glu Asn Asp Phe Ser Glu Thr Thr
        35                  40                  45

Thr Ser Leu Ser Pro Asp Asn Thr Ser Thr Gln Val Ser Pro Asp Ser
    50                  55                  60

Leu Asp Asn Ala Ser Ala Phe Asn Thr Thr Gly Val Ser Ser Val Gln
65                  70                  75                  80

Thr Pro His Leu Pro Thr His Ala Asp Ser Gln Thr Pro Ser Ala Gly
                85                  90                  95

Thr Asp Thr Gln Thr Phe Ser Gly Ser Ala Ala Asn Ala Lys Leu Asn
            100                 105                 110

Pro Thr Pro Gly Ser Asn Ala Ile Ser Asp Val Pro Gly Glu Arg Ser
        115                 120                 125

Thr Ala Ser Thr Phe Pro Thr Asp Pro Val Ser Pro Leu Thr Thr Thr
    130                 135                 140

Leu Ser Leu Ala His His Ser Ser Ala Ala Leu Pro Ala Arg Thr Ser
145                 150                 155                 160

Asn Thr Thr Ile Thr Ala Asn Thr Ser Asp Ala Tyr Leu Asn Ala Ser
                165                 170                 175

Glu Thr Thr Thr Leu Ser Pro Ser Gly Ser Ala Val Ile Ser Thr Thr
            180                 185                 190

Thr Ile Ala Thr Thr Pro Ser Lys Pro Thr Cys Asp Glu Lys Tyr Ala
        195                 200                 205

Asn Ile Thr Val Asp Tyr Leu Tyr Asn Lys Glu Thr Lys Leu Phe Thr
    210                 215                 220

Ala Lys Leu Asn Val Asn Glu Asn Val Glu Cys Gly Asn Asn Thr Cys
225                 230                 235                 240

Thr Asn Asn Glu Val His Asn Leu Thr Glu Cys Lys Asn Ala Ser Val
                245                 250                 255

Ser Ile Ser His Asn Ser Cys Thr Ala Pro Asp Lys Thr Leu Ile Leu
            260                 265                 270

Asp Val Pro Pro Gly Val Glu Lys Phe Gln Leu His Asp Cys Thr Gln
        275                 280                 285

Val Glu Lys Ala Asp Thr Thr Ile Cys Leu Lys Trp Lys Asn Ile Glu
    290                 295                 300

Thr Phe Thr Cys Asp Thr Gln Asn Ile Thr Tyr Arg Phe Gln Cys Gly
305                 310                 315                 320

Asn Met Ile Phe Asp Asn Lys Glu Ile Lys Leu Glu Asn Leu Glu Pro
                325                 330                 335

Glu His Glu Tyr Lys Cys Asp Ser Glu Ile Leu Tyr Asn Asn His Lys
            340                 345                 350

Phe Thr Asn Ala Ser Lys Ile Ile Lys Thr Asp Phe Gly Ser Pro Gly
        355                 360                 365

Glu Pro Gln Ile Ile Phe Cys Arg Ser Glu Ala Ala His Gln Gly Val
    370                 375                 380

Ile Thr Trp Asn Pro Pro Gln Arg Ser Phe His Asn Phe Thr Leu Cys
385                 390                 395                 400

Tyr Ile Lys Glu Thr Glu Lys Asp Cys Leu Asn Leu Asp Lys Asn Leu
                405                 410                 415

Ile Lys Tyr Asp Leu Gln Asn Leu Lys Pro Tyr Thr Lys Tyr Val Leu
            420                 425                 430

Ser Leu His Ala Tyr Ile Ile Ala Lys Val Gln Arg Asn Gly Ser Ala
        435                 440                 445
```

Ala Met Cys His Phe Thr Thr Lys Ser Ala Pro Pro Ser Gln Val Trp
450 455 460

Asn Met Thr Val Ser Met Thr Ser Asp Asn Ser Met His Val Lys Cys
465 470 475 480

Arg Pro Pro Arg Asp Arg Asn Gly Pro His Glu Arg Tyr His Leu Glu
485 490 495

Val Glu Ala Gly Asn Thr Leu Val Arg Asn Glu Ser His Lys Asn Cys
500 505 510

Asp Phe Arg Val Lys Asp Leu Gln Tyr Ser Thr Asp Tyr Thr Phe Lys
515 520 525

Ala Tyr Phe His Asn Gly Asp Tyr Pro Gly Glu Pro Phe Ile Leu His
530 535 540

His Ser Thr Ser Tyr Asn Ser Lys
545 550

<210> SEQ ID NO 114
<211> LENGTH: 21
<212> TYPE: PRT
<213> ORGANISM: Homo sapiens

<400> SEQUENCE: 114

Thr Glu Lys Asp Cys Leu Asn Leu Asp Lys Asn Leu Ile Lys Tyr Asp
1 5 10 15

Leu Gln Asn Leu Lys
20

<210> SEQ ID NO 115
<211> LENGTH: 31
<212> TYPE: PRT
<213> ORGANISM: Homo sapiens

<400> SEQUENCE: 115

Cys Tyr Ile Lys Glu Thr Glu Lys Asp Cys Leu Asn Leu Asp Lys Asn
1 5 10 15

Leu Ile Lys Tyr Asp Leu Gln Asn Leu Lys Pro Tyr Thr Lys Tyr
20 25 30

<210> SEQ ID NO 116
<211> LENGTH: 29
<212> TYPE: PRT
<213> ORGANISM: Homo sapiens

<400> SEQUENCE: 116

Arg Pro Pro Arg Asp Arg Asn Gly Pro His Glu Arg Tyr His Leu Glu
1 5 10 15

Val Glu Ala Gly Asn Thr Leu Val Arg Asn Glu Ser His
20 25

<210> SEQ ID NO 117
<211> LENGTH: 31
<212> TYPE: PRT
<213> ORGANISM: Homo sapiens

<400> SEQUENCE: 117

Cys Arg Pro Pro Arg Asp Arg Asn Gly Pro His Glu Arg Tyr His Leu
1 5 10 15

Glu Val Glu Ala Gly Asn Thr Leu Val Arg Asn Glu Ser His Lys
20 25 30

<210> SEQ ID NO 118
<211> LENGTH: 17
<212> TYPE: PRT
<213> ORGANISM: Homo sapiens

<400> SEQUENCE: 118

Arg Asn Gly Pro His Glu Arg Tyr His Leu Glu Val Glu Ala Gly Asn
1 5 10 15

Thr

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: S, E or G
<220> FEATURE:
<221> NAME/KEY: MOD_RES
<222> LOCATION: (5)..(5)
<223> OTHER INFORMATION: S, A or G

<400> SEQUENCE: 119

Phe Thr Phe Xaa Xaa Tyr Ser Met Asn
1 5

<210> SEQ ID NO 120
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: S, L or I
<220> FEATURE:
<221> NAME/KEY: MOD_RES
<222> LOCATION: (6)..(6)
<223> OTHER INFORMATION: S or G
<220> FEATURE:
<221> NAME/KEY: MOD_RES
<222> LOCATION: (7)..(7)
<223> OTHER INFORMATION: S or A
<220> FEATURE:
<221> NAME/KEY: MOD_RES
<222> LOCATION: (10)..(10)
<223> OTHER INFORMATION: Y, H or T

<400> SEQUENCE: 120

Tyr Ile Ser Xaa Ser Xaa Xaa Thr Ile Xaa Tyr Tyr Ala Asp Ser Val
1 5 10 15

Lys Gly

<210> SEQ ID NO 121
<211> LENGTH: 20
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (9)..(9)
<223> OTHER INFORMATION: D or T
<220> FEATURE:

<221> NAME/KEY: MOD_RES
<222> LOCATION: (12)..(12)
<223> OTHER INFORMATION: R or D

<400> SEQUENCE: 121

Ala Arg Gly Gly Gln Tyr Tyr Tyr Xaa Ser Ser Xaa Tyr Gly Glu Val
1 5 10 15

Ala Phe Asp Ile
20

<210> SEQ ID NO 122
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: H or absent

<400> SEQUENCE: 122

Arg Ser Ser Gln Ser Leu Leu Xaa Ser Asn Gly Tyr Asn Tyr Leu Asp
1 5 10 15

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: L or F
<220> FEATURE:
<221> NAME/KEY: MOD_RES
<222> LOCATION: (4)..(4)
<223> OTHER INFORMATION: N or S

<400> SEQUENCE: 123

Xaa Gly Ser Xaa Arg Ala Ser
1 5

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: P or W
<220> FEATURE:
<221> NAME/KEY: MOD_RES
<222> LOCATION: (9)..(9)
<223> OTHER INFORMATION: F or S
<220> FEATURE:
<221> NAME/KEY: MOD_RES
<222> LOCATION: (10)..(10)
<223> OTHER INFORMATION: T or F

<400> SEQUENCE: 124

Met Gln Arg Arg Arg Thr Pro Xaa Xaa Xaa
1 5 10

<210> SEQ ID NO 125
<211> LENGTH: 381
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 125
caggtgcagc tggtggagtc tgggggaggc ttggtcaagc ctggagggtc cctgagactc 60
tcctgtgcag cctctggatt caccttcagt agctatagca tgaactgggt ccgccaggct 120
ccagggaagg ggctggagtg ggtttcatac attagtagta gtagtagtac catatactac 180
gcagactctg tgaagggccg attcaccatc tccagagaca atgccaagaa ctcactgtat 240
ctgcaaatga acagcctgag agctgaggac acggcggtgt actactgcgc cagaggtgga 300
caatactact acgacagcag cagatacggt gaggtagcat tcgacatatg gggtcagggt 360
acaatggtca ccgtctcctc a 381

<210> SEQ ID NO 126
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 126
gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcagagaag acgcactcct 300
cctttcactt ttggcggagg gaccaaggtt gagatcaaa 339

<210> SEQ ID NO 127
<211> LENGTH: 381
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 127
gaagtgcagc ttgtggagtc cggtggcgga ctggtccagc cgggcggatc tctgagactt 60
tcgtgtgccg cctcgggatt caccttcgaa gcgtattcca tgaactgggt cagacaggcc 120
cccggaaagg gcctggaatg ggtgtcgtac attagcctgt cgggggccac catccattac 180
gccgatagcg tgaagggccg gttcacaatc tcccgggaca acgccaagaa ctccctctac 240
ctccaaatga acagcctgcg cgctgaggac actgctgtgt actattgcgc gaggggtggc 300
cagtactact acgactcaag cgactacggc gaagtggcat tcgatatctg gggacagggg 360
accatggtca ccgtcagctc c 381

<210> SEQ ID NO 128
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128
gatatcgtga tgacacagtc ccctctgtcc ctccctgtga cccccggaga accagcctct 60
atttcctgcc ggtcctccca atccctggtg tccaacggtt ataactacct ggattggtac 120
ttgcaaaagc ccggacagag cccccagctg ctcatctact tcggaagctc acgcgcgagc 180
ggggtgccgg ataggttttc gggatccgga agcggcaccg acttcacgct gaagatctcg 240
agagtcgagg ccgaggacgt gggcgtgtac tactgtatgc agcggcggcg cacccccctgg 300 tccttcggcg gcggaactaa ggtcgagatc aag 333

<210> SEQ ID NO 129
<211> LENGTH: 381
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 129
caagtgcagc ttgtggagtc cggtggcgga ctggtcaagc cgggcggatc tctgagactt 60
tcgtgtgccg cctcgggatt caccttcggc ggatattcca tgaactgggt cagacaggcc 120
cccggaaagg gcctggaatg ggtgtcgtac attagcatct cgggggccac catcacttac 180
gccgatagcg tgaagggccg gttcacaatc tcccgggaca acgccaagaa ctccctctac 240
ctccaaatga acagcctgcg cgctgaggac actgctgtgt actattgcgc gaggggtggc 300
cagtactact acgactcaag cgactacggc gaagtggcat tcgatatctg gggacagggg 360
accatggtca ccgtcagctc c 381

<210> SEQ ID NO 130
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 130
gatatcgtga tgacacagtc ccctctgtcc ctccctgtga cccccggaga accagcctct 60
atttcctgcc ggtcctccca atccctggtg tccaacggtt ataactacct ggattggtac 120
ttgcaaaagc ccggacagag cccccagctg ctcatctact tcggaagctc acgcgcgagc 180
ggggtgccgg ataggttttc gggatccgga agcggcaccg acttcacgct gaagatctcg 240
agagtcgagg ccgaggacgt gggcgtgtac tactgtatgc agcggcggcg caccccgccc 300
ttcaccttcg gcggcggaac taaggtcgag atcaag 336

<210> SEQ ID NO 131
<211> LENGTH: 381
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 131
gaagtgcagc ttgtggagtc cggtggcgga ctggtccagc cgggcggatc tctgagactt 60
tcgtgtgccg cctcgggatt caccttcgaa gcgtattcca tgaactgggt cagacaggcc 120
cccggaaagg gcctggaatg ggtgtcgtac attagcctgt cgggggccac catccattac 180
gccgatagcg tgaagggccg gttcacaatc tcccgggaca acgccaagaa ctccctctac 240
ctccaaatga acagcctgcg cgctgaggac actgctgtgt actattgcgc gaggggtggc 300
cagtactact acacctcaag cgactacggc gaagtggcat tcgatatctg ggacagggg 360 accatggtca ccgtcagctc c 381

<210> SEQ ID NO 132
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 132
gatatcgtga tgacacagtc ccctctgtcc ctccctgtga cccccggaga accagcctct 60
atttcctgcc ggtcctccca atccctggtg tccaacggtt ataactacct ggattggtac 120
ttgcaaaagc ccggacagag cccccagctg ctcatctact tcggaagctc acgcgcgagc 180
ggggtgccgg ataggttttc gggatccgga agcggcaccg acttcacgct gaagatctcg 240
agagtcgagg ccgaggacgt gggcgtgtac tactgtatgc agcggcggcg cacccccctgg 300 tccttcggcg gcggaactaa ggtcgagatc aag 333

<210> SEQ ID NO 133
<211> LENGTH: 381
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 133
gaagtgcagc ttgtggagtc cggtggcgga ctggtccagc cgggcggatc tctgagactt 60
tcgtgtgccg cctcgggatt caccttcgaa gcgtattcca tgaactgggt cagacaggcc 120
cccggaaagg gcctggaatg ggtgtcgtac attagcctgt cgggggccac catccattac 180
gccgatagcg tgaagggccg gttcacaatc tcccgggaca acgccaagaa ctccctctac 240
ctccaaatga acagcctgcg cgctgaggac actgctgtgt actattgcgc gaggggtggc 300
cagtactact acacctcaag cgactacggc gaagtggcat tcgatatctg ggacagggg 360 accatggtca ccgtcagctc c 381

<210> SEQ ID NO 134
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 134
gatatcgtga tgacacagtc ccctctgtcc ctccctgtga cccccggaga accagcctct 60
atttcctgcc ggtcctccca atccctggtg tcctcgggtt ataactacct ggattggtac 120
ttgcaaaagc ccggacagag cccccagctg ctcatctact tcggaagctc acgcgcgagc 180
ggggtgccgg ataggttttc gggatccgga agcggcaccg acttcacgct gaagatctcg 240
agagtcgagg ccgaggacgt gggcgtgtac tactgtatgc agcggcggcg cacccccctgg 300 tccttcggcg gcggaactaa ggtcgagatc aag 333

<210> SEQ ID NO 135
<211> LENGTH: 381
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 135
gaggtgcagc tggtcgaaag cggaggaggg ctggtgcagc ctggaggatc cctgcggctc 60
tcatgtgccg cctccggctt taccttcgaa gcctactcca tgaactgggt cagacaggct 120
cccgggaagg gactggaatg ggtcagctac atttcgctgt ccggagccac catccactac 180
gctgactcag ttaagggacg cttcaccatc tcccgggata atgcaaagaa ctccctgtac 240
ctccaaatga attcactgag ggccgaggac actgccgtgt actactgcgc ccggggaggt 300
caatactatt acacctcctc cgactacggc gaagtggcct tcgatatctg gggccaagga 360
accctcgtga ctgtctcctc c 381

<210> SEQ ID NO 136
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 136
gacatcgtgc tgacccagtc accgctttcc ttgcccgtga ctcctgggga accggcctcc 60
atttcgtgcc ggtccagcca gtccctggtg tcctccggct acaattacct ggattggtac 120
ctccaaaagc ccggacagtc cccacaactg ctcatctact tcgggagctc aagggcctca 180
ggagtgccgg atcgcttctc gggttccgga agcgggactg acttcactct gaaaatcagc 240
cgcgtggaag cagaggacgt gggcgtgtac tactgcatgc agcgcaggag aaccccctgg 300
tcctttggcg gtggaacgaa ggtcgaaatc aag 333

<210> SEQ ID NO 137
<211> LENGTH: 381
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 137
caagtgcagc ttgtggagtc cggtggcgga ctggtcaagc cgggcggatc tctgagactt 60
tcgtgtgccg cctcgggatt caccttcggc ggatattcca tgaactgggt cagacaggcc 120
cccggaaagg gcctggaatg ggtgtcgtac attagcatct cgggggccac catcacttac 180
gccgatagcg tgaagggccg gttcacaatc tcccgggaca acgccaagaa ctccctctac 240
ctccaaatga acagcctgcg cgctgaggac actgctgtgt actattgcgc gaggggtggc 300
cagtactact acgactcaag cgactacggc gaagtggcat tcgatatctg gggacagggg 360
accatggtca ccgtcagctc c 381

<210> SEQ ID NO 138
<211> LENGTH: 336
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 138
gatatcgtga tgacacagtc ccctctgtcc ctccctgtga cccccggaga accagcctct 60
atttcctgcc ggtcctccca atccctggtg tcctccggtt ataactacct ggattggtac 120
ttgcaaaagc ccggacagag cccccagctg ctcatctact tcggaagctc acgcgcgagc 180
ggggtgccgg ataggttttc gggatccgga agcggcaccg acttcacgct gaagatctcg 240
agagtcgagg ccgaggacgt gggcgtgtac tactgtatgc agcggcggcg caccccgccc 300
ttcaccttcg gcggcggaac taaggtcgag atcaag 336

<210> SEQ ID NO 139
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 139
gaagtgcagc ttctggagtc cggtggcgga ctggtccagc cgggcggatc tctgagactt 60
tcgtgtgccg cctcgggatt caccttcaac aactattgga tgacctgggt cagacaggcc 120
cccggaaagg gcctggaatg ggtgtcgtca attagctcct cggggggatc catctactac 180
cctgatcgcg tgaagggccg gttcacaatc tcccgggaca acagcaagaa caccctctac 240
ctccaaatga acagcctgcg cgctgaggac actgctgtgt actattgcgc gagggacgag 300
agatgggccg gcgcaatgga tgcctgggga caggggacca ccgtcaccgt cagctcc 357

<210> SEQ ID NO 140
<211> LENGTH: 318
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 140
gatattcaga tgacccagtc cccatcatcc ctgtccgcct ccgtgggcga ccgcgtgacg 60
atcacttgca aagccagcca gaatatcaac aagaacctgg attggtacca acagaagccg 120
gggaaggccc ctaagctgct gatctacgaa accaacaact tgcaaactgg cgtgccgtca 180
aggttcagcg gttccgggtc gggcaccgac ttcaccctga ccatttcctc gctgcaaccc 240
gaggacttcg cgacctacta ctgctatcag cacaacagcc ggttcacctt cggacagggc 300
accaagctcg agatcaag 318

<210> SEQ ID NO 141
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 141
gaagtgcagc tcgtggagtc gggtggaggc cttgtgcaac cgggaggatc cctgcggctc 60
tcctgcgccg catcaggctt cacgttcacc aacttttgga tggcctggat tagacaggca 120
ccggggaagg gactggaatg ggtggcgtcc attagctcgt ccggaggatc catctactat 180
cctgactcag tgaaggacag gtttaccatc tcccgggaca acagcaagaa cactctgtac 240
ctccaaatga actcgctgcg cgccgaggac accgccgtgt actactgcgt gaagttccat 300
cactactccg gcggaggaga tgcctgggga cagggtactc tcgtgactgt gtcgtcc 357

<210> SEQ ID NO 142
<211> LENGTH: 318
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 142
gacatccaga tgacccagag cccctcctcc ctgtccgcgt ctgtgggcga ccgcgtgacc 60
attacgtgca aagcttccca gaacattaac aagtacctgg attggtacca gcagaagcct 120
ggaaaggccc ccaagctgtt gatccactac acaaacaacc tccacactgg tatcccgtcc 180
cggttctcgg ggtccggatc gggaactgac tacaccctga ccatcagcag cctgcagcct 240
gaagatttcg ccacctatta ctgcctgcaa cactcctcgc gctggacctt cggcgggggt 300
actaaggtcg agatcaag 318

<210> SEQ ID NO 143
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 143
gaagtgcagc tcgtggagtc gggtggaggc cttgtgcaac cgggaggatc cctgcggctc 60
tcctgcgccg catcaggctt cacgttcaac aactactgga tgacttgggt cagacaggca 120
ccggggaagg gactggaatg ggtgtccagc attagctcgt ccggaggatc catctactat 180
ccggactcag tgaaggacag gtttaccatc tcccgggaca acgcaaagaa ctccctgtac 240
ctccaaatga actcgctgcg cgccgaggac atggccgtgt actactgcgc gaggctgtac 300
tactacgatg gggggggcga tgcctgggga cagggaaccc tagtgactgt gtcgtcc 357

<210> SEQ ID NO 144
<211> LENGTH: 318
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 144
ggaatccaga tgacacagag cccgtctagc ctgtcagcat ccgtggggga cagggtcacc 60
atcacctgta aagccagcca ggatattaac aagtacctgg actggtacca gcagaagccc 120
gggaaggccc cgaagctcct gatctacaac accaacaact tgcacaccgg aattccgtcc 180
cgcttttcgg gatcgggatc cgggaccgat tacaccctga ctatctcctc cctgcaaccc 240
gaggacttcg ccacttacta ttgcctccaa cacatttccc ggtggacttt cggcggcggc 300
accaaggtcg agatcaag 318

<210> SEQ ID NO 145
<211> LENGTH: 1310
<212> TYPE: PRT
<213> ORGANISM: Macaca fascicularis

<400> SEQUENCE: 145

```
Met Thr Met Cys Leu Trp Leu Lys Leu Leu Ala Phe Val Phe Ala Phe
1               5                   10                  15

Leu Asp Thr Glu Val Phe Val Thr Gly Gln Gly Ser Thr Leu Ser Pro
            20                  25                  30

Thr Gly Arg Arg Thr Thr Lys Met Pro Ser Val Pro Leu Ser Ser Asp
        35                  40                  45

Pro Leu Pro Thr His Thr Thr Ala Phe Ser Pro Ala Ser Ile Ser Glu
    50                  55                  60

Arg Glu Asn Asp Phe Ser Glu Thr Thr Pro Ser Leu Ser Ser Asp Asn
65                  70                  75                  80

Thr Ser Thr Gln Val Ser Pro Asp Ser Leu Asp Asn Ala Ser Ala Phe
                85                  90                  95

Asn Thr Thr Gly Val Ser Ser Ala Leu Thr Pro His Leu Pro Thr His
            100                 105                 110

Ala Asp Ser Gln Thr Pro Ser Thr Gly Thr Asp Thr Gln Thr Pro Ser
        115                 120                 125

Gly Ser Ala Ala Asn Thr Thr Leu Ser Pro Thr Pro Arg Ser Asn Asp
    130                 135                 140

Ile Ser Asp Val Pro Gly Glu Arg Ser Thr Ala Ser Thr Phe Pro Thr
145                 150                 155                 160

Asp Pro Ile Ser Pro Leu Ala Thr Thr Leu Ile Pro Ala Arg Asn Ser
                165                 170                 175

Ser Ala Ala Leu Pro Ala Arg Thr Ser Asn Thr Thr Ile Thr Ala Asn
            180                 185                 190

Thr Ser Val Ser Tyr Leu Asn Ala Ser Glu Thr Thr Thr Pro Ser Pro
        195                 200                 205

Ser Gly Ser Thr Val Ile Ser Thr Pro Thr Ile Ala Thr Thr Thr Ser
    210                 215                 220

Lys Pro Thr Cys Ala Glu Lys Tyr Ala Thr Ile Pro Val Asp Tyr Leu
225                 230                 235                 240

Tyr Asn Asn Lys Thr Lys Leu Phe Thr Ala Lys Leu Asn Val Asn Glu
                245                 250                 255

Asn Val Glu Cys Thr Asn Asn Asn His Thr His Asn Ile Cys Thr Asn
            260                 265                 270

Asn Glu Val Leu Asn Leu Pro Glu Cys Lys Glu Met Asn Val Phe Val
        275                 280                 285

Ser His Asn Ser Cys Thr Asp Arg His Lys Glu Leu Lys Leu Asp Val
    290                 295                 300

Pro Pro Glu Val Glu Lys Phe Gln Leu Asp Asp Cys Thr Pro Asp Val
305                 310                 315                 320

Glu Ala Asn Thr Thr Ile Cys Leu Lys Trp Lys Ile Ile Glu Thr Phe
                325                 330                 335

Ala Cys Asp Lys Ser Lys Ile Thr Tyr Arg Phe Gln Cys Gly Asn Lys
            340                 345                 350

Thr Tyr Asn Lys Glu Gly Ile Tyr Leu Glu Asn Leu Glu Pro Glu Tyr
        355                 360                 365

Glu Tyr Lys Cys Asp Ser Glu Ile Leu Tyr Asn Asn His Lys Tyr Ile
    370                 375                 380
```

-continued

```
Asn Ile Thr Lys Leu Ile Lys Thr Asp Phe Gly Ile Pro Gly Gln Pro
385                 390                 395                 400

Gln Asn Val Val Cys Arg His Glu Asp Ala His Gln Gly Val Ile Thr
                405                 410                 415

Trp Asn Pro Pro Gln Arg Ser Phe His Asn Phe Thr Leu Cys Tyr Val
            420                 425                 430

Asn Lys Pro Ala Lys Lys Cys Leu Ile Leu Asp Lys His Leu Thr Thr
        435                 440                 445

Tyr His Leu Gln Asn Leu Lys Pro Tyr Thr Asn Tyr Ser Leu Ser Leu
    450                 455                 460

His Ala Tyr Ile Ile Ala Lys Val Gln Arg Asn Gly Thr Ala Ala Thr
465                 470                 475                 480

Cys Asn Phe Thr Thr Glu Ser Ala Pro Pro Ser Gln Val Gln Asn Met
                485                 490                 495

Ile Val Ser Thr Ser Asp Asn Ser Met His Val Lys Cys Glu Val Pro
            500                 505                 510

Arg Asp Val Asn Gly Pro Thr Gly Leu Tyr His Leu Glu Val Glu Ala
        515                 520                 525

Gly Asn Thr Leu Val Arg Asn Leu Ser Gln Ser Lys Cys Asp Phe Ser
    530                 535                 540

Val Asn Asn Leu Gln Tyr Ser Thr Tyr Tyr Asn Leu Lys Ala Tyr Tyr
545                 550                 555                 560

His Asn Gly Lys Tyr Ser Gly Glu Pro Val Ile Leu Arg Glu Ser Thr
                565                 570                 575

Ser Tyr Asn Ser Lys Ala Leu Ile Ala Phe Leu Ala Phe Leu Ile Ile
            580                 585                 590

Val Thr Ser Ile Ala Leu Leu Val Val Leu Tyr Lys Ile Tyr Asp Leu
        595                 600                 605

His Lys Lys Arg Ser Cys Asn Leu Asp Glu Gln Gln Glu Leu Val Glu
    610                 615                 620

Arg Asp Asp Glu Lys Gln Leu Met Asn Val Glu Pro Ile His Ala Asp
625                 630                 635                 640

Ile Leu Leu Glu Thr Tyr Lys Arg Lys Ile Ala Asp Glu Gly Arg Leu
                645                 650                 655

Phe Leu Ala Glu Phe Gln Ser Ile Pro Arg Val Phe Ser Lys Phe Pro
            660                 665                 670

Ile Lys Glu Ala Arg Lys Pro Phe Asn Gln Asn Lys Asn Arg Tyr Val
        675                 680                 685

Asp Ile Leu Pro Tyr Asp Tyr Asn Arg Val Glu Leu Ser Glu Ile Asn
    690                 695                 700

Gly Asp Ala Gly Ser Asn Tyr Ile Asn Ala Ser Tyr Ile Asp Gly Phe
705                 710                 715                 720

Lys Glu Pro Arg Lys Tyr Ile Ala Ala Gln Gly Pro Arg Asp Glu Thr
                725                 730                 735

Val Asp Asp Phe Trp Arg Met Ile Trp Glu Gln Lys Ala Thr Val Ile
            740                 745                 750

Val Met Val Thr Arg Cys Glu Glu Gly Asn Arg Asn Lys Cys Ala Glu
        755                 760                 765

Tyr Trp Pro Ser Met Glu Glu Gly Thr Arg Ala Phe Gly Asp Ile Val
    770                 775                 780

Val Lys Ile Asn Gln His Lys Arg Cys Pro Asp Tyr Ile Ile Gln Lys
785                 790                 795                 800

Leu Asn Ile Val Asn Lys Lys Glu Lys Ala Thr Gly Arg Glu Val Thr
```

-continued

```
                805                 810                 815

His Ile Gln Phe Thr Ser Trp Pro Asp His Gly Val Pro Glu Asp Pro
            820                 825                 830

His Leu Leu Leu Lys Leu Arg Arg Arg Val Asn Ala Phe Ser Asn Phe
        835                 840                 845

Phe Ser Gly Pro Ile Val Val His Cys Ser Ala Gly Val Gly Arg Thr
    850                 855                 860

Gly Thr Tyr Ile Gly Ile Asp Ala Met Leu Glu Gly Leu Glu Ala Glu
865                 870                 875                 880

Asn Lys Val Asp Val Tyr Gly Tyr Val Val Lys Leu Arg Arg Gln Arg
                885                 890                 895

Cys Leu Met Val Gln Val Glu Ala Gln Tyr Ile Leu Ile His Gln Ala
            900                 905                 910

Leu Val Glu Tyr Asn Gln Phe Gly Glu Thr Glu Val Asn Leu Ser Glu
        915                 920                 925

Leu His Pro Tyr Leu His Asn Met Lys Lys Arg Asp Pro Pro Ser Glu
    930                 935                 940

Pro Ser Pro Leu Glu Ala Glu Phe Gln Arg Leu Pro Ser Tyr Arg Ser
945                 950                 955                 960

Trp Arg Thr Gln His Ile Gly Asn Gln Glu Glu Asn Lys Asn Lys Asn
                965                 970                 975

Arg Asn Ser Asn Val Ile Pro Tyr Asp Tyr Asn Arg Val Pro Leu Lys
            980                 985                 990

His Glu Leu Glu Met Ser Lys Glu  Ser Asp His Asp Ser  Asp Glu Ser
        995                 1000                1005

Ser Asp  Asp Asp Ser Asp Ser  Glu Glu Pro Ser Lys  Tyr Ile Asn
    1010                1015                1020

Ala Ser  Phe Ile Met Ser Tyr  Trp Lys Pro Glu Val  Met Ile Ala
    1025                1030                1035

Ala Gln  Gly Pro Leu Lys Glu  Thr Ile Gly Asp Phe  Trp Gln Met
    1040                1045                1050

Ile Phe  Gln Arg Lys Val Lys  Val Ile Val Met Leu  Thr Glu Leu
    1055                1060                1065

Lys His  Gly Asp Gln Glu Ile  Cys Ala Gln Tyr Trp  Gly Glu Gly
    1070                1075                1080

Lys Gln  Thr Tyr Gly Asp Ile  Glu Val Asp Met Lys  Asp Thr Asn
    1085                1090                1095

Lys Ser  Ser Thr Tyr Thr Leu  Arg Val Phe Glu Leu  Arg His Ser
    1100                1105                1110

Lys Arg  Lys Asp Ser Arg Thr  Val Tyr Gln Tyr Gln  Tyr Thr Asn
    1115                1120                1125

Trp Ser  Val Glu Gln Leu Pro  Ala Glu Pro Lys Glu  Leu Val Ser
    1130                1135                1140

Leu Ile  Gln Val Leu Lys Glu  Lys Leu Pro Gln Lys  Asn Phe Ser
    1145                1150                1155

Glu Gly  Asn Lys His His Lys  Ser Thr Pro Leu Leu  Ile His Cys
    1160                1165                1170

Arg Asp  Gly Ser Gln Gln Thr  Gly Ile Phe Cys Ala  Leu Leu Asn
    1175                1180                1185

Leu Leu  Glu Ser Ala Glu Thr  Glu Glu Val Val Asp  Ile Phe Gln
    1190                1195                1200

Val Val  Lys Ala Leu Arg Lys  Ala Arg Pro Gly Met  Val Ser Thr
    1205                1210                1215
```

```
Phe Glu  Gln Tyr Gln Phe Leu  Tyr Asp Ile Ile Ala  Ser Thr Tyr
    1220                 1225                 1230

Pro Ala  Gln Asn Gly Gln Val  Lys Lys Asn Asn His  Gln Glu Asp
    1235                 1240                 1245

Lys Ile  Glu Phe Asp Asn Glu  Val Asp Lys Val Lys  Gln Asp Ala
    1250                 1255                 1260

Asn Cys  Val Asn Pro Leu Gly  Ala Thr Glu Lys Leu  Pro Glu Ala
    1265                 1270                 1275

Lys Glu  Gln Ala Thr Gly Ser  Glu Pro Thr Ser Gly  Thr Glu Gly
    1280                 1285                 1290

Pro Glu  His Ser Val Asn Gly  Pro Ala Ser Pro Ala  Leu Asn Gln
    1295                 1300                 1305

Gly Ser
    1310


<210> SEQ ID NO 146
<211> LENGTH: 1310
<212> TYPE: PRT
<213> ORGANISM: Macaca mulatta

<400> SEQUENCE: 146

Met Thr Met Cys Leu Trp Leu Lys Leu Leu Ala Phe Val Phe Ala Phe
1               5                   10                  15

Leu Asp Thr Glu Val Phe Val Thr Gly Gln Gly Ser Thr Leu Ser Pro
            20                  25                  30

Thr Gly Arg Arg Thr Thr Lys Met Pro Ser Val Pro Leu Ser Ser Asp
        35                  40                  45

Pro Leu Pro Thr His Thr Thr Ala Phe Ser Pro Ala Ser Ile Ser Glu
    50                  55                  60

Arg Glu Asn Asp Phe Ser Glu Thr Thr Pro Ser Leu Ser Ser Asp Asn
65                  70                  75                  80

Thr Ser Thr His Val Ser Pro Asp Ser Leu Asp Asn Ala Ser Ala Phe
                85                  90                  95

Asn Thr Thr Gly Val Ser Ser Ala Leu Thr Pro His Leu Pro Thr His
            100                 105                 110

Ala Asp Ser Gln Thr Pro Ser Thr Gly Thr Asp Thr Gln Thr Pro Ser
        115                 120                 125

Gly Ser Ala Ala Asn Thr Thr Leu Ser Pro Thr Pro Arg Ser Asn Asp
    130                 135                 140

Ile Ser Asp Val Pro Gly Glu Arg Ser Thr Ala Ser Thr Phe Pro Thr
145                 150                 155                 160

Asp Pro Ile Ser Pro Leu Ala Thr Thr Leu Ile Pro Ala Arg Asn Ser
                165                 170                 175

Ser Ala Ala Leu Pro Ala Arg Thr Ser Asn Thr Thr Ile Thr Ala Asn
            180                 185                 190

Thr Ser Val Ser Tyr Leu Asn Ala Ser Glu Thr Thr Thr Pro Ser Pro
        195                 200                 205

Ser Gly Ser Thr Val Ile Ser Thr Pro Thr Ile Ala Thr Thr Thr Ser
    210                 215                 220

Lys Pro Thr Cys Ala Glu Lys Tyr Ala Thr Ile Pro Val Asp Tyr Leu
225                 230                 235                 240

Tyr Asn Asn Lys Thr Lys Leu Phe Thr Ala Lys Leu Asn Val Asn Glu
                245                 250                 255

Asn Val Glu Cys Thr Asn Asn Asn His Thr His Asn Ile Cys Thr Asn
```

```
            260                 265                 270

Asn Glu Val Leu Asn Leu Pro Glu Cys Lys Glu Met Asn Val Phe Val
        275                 280                 285

Ser His Asn Ser Cys Thr Asp Arg His Lys Glu Leu Lys Leu Asp Val
    290                 295                 300

Pro Pro Glu Val Glu Lys Phe Gln Leu Asp Asp Cys Thr Pro Asp Val
305                 310                 315                 320

Glu Ala Asn Thr Thr Ile Cys Leu Lys Trp Lys Ile Ile Glu Thr Phe
                325                 330                 335

Ala Cys Asp Lys Ser Lys Ile Thr Tyr Arg Phe Gln Cys Gly Asn Lys
            340                 345                 350

Thr Tyr Asn Lys Glu Gly Ile Tyr Leu Glu Asn Leu Glu Pro Glu Tyr
        355                 360                 365

Glu Tyr Lys Cys Asp Ser Glu Ile Leu Tyr Asn Asn His Lys Tyr Ile
    370                 375                 380

Asn Ile Thr Lys Leu Ile Lys Thr Asp Phe Gly Ile Pro Gly Gln Pro
385                 390                 395                 400

Gln Asn Val Val Cys Arg His Glu Asp Ala His Gln Gly Val Ile Thr
                405                 410                 415

Trp Asn Pro Pro Gln Arg Ser Phe His Asn Phe Thr Leu Cys Tyr Val
            420                 425                 430

Ser Lys Thr Ala Lys Lys Cys Leu Ser Leu Asp Lys His Leu Thr Thr
        435                 440                 445

Tyr His Leu Gln Asn Leu Lys Pro Tyr Thr Asn Tyr Ser Leu Ser Leu
    450                 455                 460

His Ala Tyr Ile Ile Ala Lys Val Gln Arg Asn Gly Thr Ala Ala Thr
465                 470                 475                 480

Cys Asn Phe Thr Thr Glu Ser Ala Pro Pro Ser Gln Val Gln Asn Met
                485                 490                 495

Ile Val Ser Thr Ser Asp Asn Ser Met Arg Val Lys Cys Glu Ala Pro
            500                 505                 510

Arg Asp Val Asn Gly Pro Thr Glu Leu Tyr Leu Leu Glu Val Glu Ala
        515                 520                 525

Gly Asn Thr Leu Val Arg Asn Leu Ser Gln Ser Glu Cys Asp Phe Ser
    530                 535                 540

Val Asn Asn Leu Gln Tyr Ser Thr Tyr Tyr Asn Leu Lys Ala Tyr Tyr
545                 550                 555                 560

His Asn Gly Lys Tyr Ser Gly Glu Pro Val Ile Leu Arg Glu Ser Thr
                565                 570                 575

Ser Tyr Asn Ser Lys Ala Leu Ile Ala Phe Leu Ala Phe Leu Ile Ile
            580                 585                 590

Val Thr Ser Ile Ala Leu Leu Val Val Leu Tyr Lys Ile Tyr Asp Leu
        595                 600                 605

His Lys Lys Arg Ser Cys Asn Leu Asp Glu Gln Gln Glu Leu Val Glu
    610                 615                 620

Arg Asp Asp Glu Lys Gln Leu Met Asn Val Glu Pro Ile His Ala Asp
625                 630                 635                 640

Ile Leu Leu Glu Thr Tyr Lys Arg Lys Ile Ala Asp Glu Gly Arg Leu
                645                 650                 655

Phe Leu Ala Glu Phe Gln Ser Ile Pro Arg Val Phe Ser Lys Phe Pro
            660                 665                 670

Ile Lys Glu Ala Arg Lys Pro Phe Asn Gln Asn Lys Asn Arg Tyr Val
        675                 680                 685
```

-continued

Asp Ile Leu Pro Tyr Asp Tyr Asn Arg Val Glu Leu Ser Glu Ile Asn
690 695 700

Gly Asp Ala Gly Ser Asn Tyr Ile Asn Ala Ser Tyr Ile Asp Gly Phe
705 710 715 720

Lys Glu Pro Arg Lys Tyr Ile Ala Ala Gln Gly Pro Arg Asp Glu Thr
725 730 735

Val Asp Asp Phe Trp Arg Met Ile Trp Glu Gln Lys Ala Thr Val Ile
740 745 750

Val Met Val Thr Arg Cys Glu Glu Gly Asn Arg Asn Lys Cys Ala Glu
755 760 765

Tyr Trp Pro Ser Met Glu Glu Gly Thr Arg Ala Phe Gly Asp Val Val
770 775 780

Val Lys Ile Asn Gln His Lys Arg Cys Pro Asp Tyr Ile Ile Gln Lys
785 790 795 800

Leu Asn Ile Val Asn Lys Lys Glu Lys Ala Thr Gly Arg Glu Val Thr
805 810 815

His Ile Gln Phe Thr Ser Trp Pro Asp His Gly Val Pro Glu Asp Pro
820 825 830

His Leu Leu Leu Lys Leu Arg Arg Arg Val Asn Ala Phe Ser Asn Phe
835 840 845

Phe Ser Gly Pro Ile Val Val His Cys Ser Ala Gly Val Gly Arg Thr
850 855 860

Gly Thr Tyr Ile Gly Ile Asp Ala Met Leu Glu Gly Leu Glu Ala Glu
865 870 875 880

Asn Lys Val Asp Val Tyr Gly Tyr Val Val Lys Leu Arg Arg Gln Arg
885 890 895

Cys Leu Met Val Gln Val Glu Ala Gln Tyr Ile Leu Ile His Gln Ala
900 905 910

Leu Val Glu Tyr Asn Gln Phe Gly Glu Thr Glu Val Asn Leu Ser Glu
915 920 925

Leu His Pro Tyr Leu His Asn Met Lys Lys Arg Asp Pro Pro Ser Glu
930 935 940

Pro Ser Pro Leu Glu Ala Glu Phe Gln Arg Leu Pro Ser Tyr Arg Ser
945 950 955 960

Trp Arg Thr Gln His Ile Gly Asn Gln Glu Glu Asn Lys Asn Lys Asn
965 970 975

Arg Asn Ser Asn Val Ile Pro Tyr Asp Tyr Asn Arg Val Pro Leu Lys
980 985 990

His Glu Leu Glu Met Ser Lys Glu Ser Asp His Asp Ser Asp Glu Ser
995 1000 1005

Ser Asp Asp Asp Ser Asp Ser Glu Glu Pro Ser Lys Tyr Ile Asn
1010 1015 1020

Ala Ser Phe Ile Met Ser Tyr Trp Lys Pro Glu Val Met Ile Ala
1025 1030 1035

Ala Gln Gly Pro Leu Lys Glu Thr Ile Gly Asp Phe Trp Gln Met
1040 1045 1050

Ile Phe Gln Arg Lys Val Lys Val Ile Val Met Leu Thr Glu Leu
1055 1060 1065

Lys His Gly Asp Gln Glu Ile Cys Ala Gln Tyr Trp Gly Glu Gly
1070 1075 1080

Lys Gln Thr Tyr Gly Asp Ile Glu Val Asp Met Lys Asp Thr Asn
1085 1090 1095

```
Lys Ser  Ser Thr Tyr Thr Leu  Arg Val Phe Glu Leu  Arg His Ser
    1100                 1105                 1110

Lys Arg  Lys Asp Ser Arg Thr  Val Tyr Gln Tyr Gln  Tyr Thr Asn
    1115                 1120                 1125

Trp Ser  Val Glu Gln Leu Pro  Ala Glu Pro Lys Glu  Leu Val Ser
    1130                 1135                 1140

Leu Ile  Gln Val Leu Lys Glu  Lys Leu Pro Gln Lys  Asn Ser Ser
    1145                 1150                 1155

Glu Gly  Asn Lys His His Lys  Ser Thr Pro Leu Leu  Ile His Cys
    1160                 1165                 1170

Arg Asp  Gly Ser Gln Gln Thr  Gly Ile Phe Cys Ala  Leu Leu Asn
    1175                 1180                 1185

Leu Leu  Glu Ser Ala Glu Thr  Glu Glu Val Val Asp  Ile Phe Gln
    1190                 1195                 1200

Val Val  Lys Ala Leu Arg Lys  Ala Arg Pro Gly Met  Val Ser Thr
    1205                 1210                 1215

Phe Glu  Gln Tyr Gln Phe Leu  Tyr Asp Ile Ile Ala  Ser Thr Tyr
    1220                 1225                 1230

Pro Ala  Gln Asn Gly Gln Val  Lys Lys Asn Asn His  Gln Glu Asp
    1235                 1240                 1245

Lys Ile  Glu Phe Asp Asn Glu  Val Asp Lys Val Lys  Gln Asp Ala
    1250                 1255                 1260

Asn Cys  Val Asn Pro Leu Gly  Ala Thr Glu Lys Leu  Pro Glu Ala
    1265                 1270                 1275

Lys Glu  Gln Ala Thr Gly Ser  Glu Pro Thr Ser Gly  Thr Glu Gly
    1280                 1285                 1290

Pro Glu  His Ser Val Asn Gly  Pro Ala Ser Pro Ala  Leu Asn Gln
    1295                 1300                 1305

Gly Ser
    1310
```

<210> SEQ ID NO 147
<211> LENGTH: 293
<212> TYPE: PRT
<213> ORGANISM: Escherichia coli

<400> SEQUENCE: 147

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140
```

```
His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
            260                 265                 270

Asn Lys Ile Leu Trp Asp Ser Ser Thr Leu Gly Ala Ile Leu Met Arg
        275                 280                 285

Arg Thr Ile Ser Ser
    290


<210> SEQ ID NO 148
<211> LENGTH: 293
<212> TYPE: PRT
<213> ORGANISM: Shigella dysenteriae

<400> SEQUENCE: 148

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
```

```
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
            260                 265                 270

Asn Lys Ile Leu Trp Asp Ser Ser Thr Leu Gly Ala Ile Leu Met Arg
        275                 280                 285

Arg Thr Ile Ser Ser
    290


<210> SEQ ID NO 149
<211> LENGTH: 297
<212> TYPE: PRT
<213> ORGANISM: Escherichia coli

<400> SEQUENCE: 149

Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
            20                  25                  30

Gln Gly Gly Val Ser Val Ser Val Ile Asn His Val Leu Gly Gly Asn
        35                  40                  45

Tyr Ile Ser Leu Asn Val Arg Gly Leu Asp Pro Tyr Ser Glu Arg Phe
    50                  55                  60

Asn His Leu Arg Leu Ile Met Glu Arg Asn Asn Leu Tyr Val Ala Gly
65                  70                  75                  80

Phe Ile Asn Thr Glu Thr Asn Ile Phe Tyr Arg Phe Ser Asp Phe Ser
                85                  90                  95

His Ile Ser Val Pro Asp Val Ile Thr Val Ser Met Thr Thr Asp Ser
            100                 105                 110

Ser Tyr Ser Ser Leu Gln Arg Ile Ala Asp Leu Glu Arg Thr Gly Met
        115                 120                 125

Gln Ile Gly Arg His Ser Leu Val Gly Ser Tyr Leu Asp Leu Met Glu
    130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
        195                 200                 205

Leu Pro Glu Tyr Arg Gly Glu Glu Gly Val Arg Ile Gly Arg Ile Ser
    210                 215                 220

Phe Asn Ser Leu Ser Ala Ile Leu Gly Ser Val Ala Val Ile Leu Asn
225                 230                 235                 240

Cys His Ser Thr Gly Ser Tyr Ser Val Arg Ser Val Ser Gln Lys Gln
                245                 250                 255

Lys Thr Glu Cys Gln Ile Val Gly Asp Arg Ala Ala Ile Lys Val Asn
            260                 265                 270

Asn Val Leu Trp Glu Ala Asn Thr Ile Ala Ala Leu Leu Asn Arg Lys
        275                 280                 285
```

-continued

```
Pro Gln Asp Leu Thr Glu Pro Asn Gln
    290                 295


<210> SEQ ID NO 150
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150

gaggtgcagc tggtggagtc tgggggaggc ttggtacagc ctggggggtc cctgagactc     60

tcctgtgcag cctctggatt caccttcgaa gcatatagca tgaactgggt ccgccaggct    120

ccagggaagg ggctggagtg ggtttcatac attagtctca gtggtgccac catacactac    180

gcagactctg tgaagggccg attcaccatc tccagggaca acgccaagaa ctcactgtat    240

ctgcaaatga acagcctgag agccgaggac acggcggtgt attactgcgc cagaggtgga    300

caatactact acgacagcag tgattacggt gaggtagcat tcgacatatg ggtcagggt    360

acaatggtca ccgtctcctc a                                              381


<210> SEQ ID NO 151
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151

gatattgtga tgactcagtc tccactctcc ctgcccgtca cccctggaga gccggcctcc     60

atctcctgca ggtctagtca gagcctggtc agtaatggat acaactattt ggattggtac    120

ctgcagaagc cagggcagtc tccacagctc ctgatctatt tcggttcttc ccgggcctcc    180

ggggtccctg acaggttcag tggcagtgga tcaggcacag attttacact gaaaatcagc    240

agagtggagg ctgaggatgt tggggtttat tactgcatgc agagaagacg cactccttgg    300

tcttttggcg gagggaccaa ggttgagatc aaa                                 333


<210> SEQ ID NO 152
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152

caggtgcagc tggtggagtc tgggggaggc ttggtcaagc ctggagggtc cctgagactc     60

tcctgtgcag cctctggatt caccttcgga ggatatagca tgaactgggt ccgccaggct    120

ccagggaagg ggctggagtg ggtttcatac attagtatca gtggtgccac cataacctac    180

gcagactctg tgaagggccg attcaccatc tccagggaca acgccaagaa ctcactgtat    240

ctgcaaatga acagcctgag agccgaggac acggcggtgt actactgcgc cagaggtgga    300

caatactact acgacagcag cgattatggt gaggtagcat tcgacatatg ggtcagggt    360

acaatggtca ccgtctcctc a                                              381


<210> SEQ ID NO 153
<211> LENGTH: 336
```

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 153
gatattgtga tgactcagtc tccactctcc ctgcccgtca cccctggaga gccggcctcc 60
atctcctgca ggtctagtca gagcctggtc agtaatggat acaactattt ggattggtac 120
ctgcagaagc cagggcagtc tccacagctc ctgatctatt tcggttcttc ccgggcctcc 180
ggggtccctg acaggttcag tggcagtgga tcaggcacag attttacact gaaaatcagc 240
agagtggagg ctgaggatgt tggggtttat tactgcatgc agagaagacg cactcctcct 300
ttcacttttg gcggagggac caaggttgag atcaaa 336

<210> SEQ ID NO 154
<211> LENGTH: 381
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 154
gaggtgcagc tggtggagtc tgggggaggc ttggtacagc ctggggggtc cctgagactc 60
tcctgtgcag cctctggatt caccttcgaa gcatatagca tgaactgggt ccgccaggct 120
ccagggaagg ggctggagtg ggtttcatac attagtctca gtggtgccac catacactac 180
gcagactctg tgaagggccg attcaccatc tccagggaca acgccaagaa ctcactgtat 240
ctgcaaatga acagcctgag agccgaggac acggcggtgt attactgcgc cagaggtgga 300
caatactact acacgagcag tgattacggt gaggtagcat tcgacatatg ggtcagggt 360 acaatggtca ccgtctcctc a 381

<210> SEQ ID NO 155
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 155
gatattgtga tgactcagtc tccactctcc ctgcccgtca cccctggaga gccggcctcc 60
atctcctgca ggtctagtca gagcctggtc agtaatggat acaactattt ggattggtac 120
ctgcagaagc cagggcagtc tccacagctc ctgatctatt tcggttcttc ccgggcctcc 180
ggggtccctg acaggttcag tggcagtgga tcaggcacag attttacact gaaaatcagc 240
agagtggagg ctgaggatgt tggggtttat tactgcatgc agagaagacg cactccttgg 300
tcttttggcg gagggaccaa ggttgagatc aaa 333

<210> SEQ ID NO 156
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 156
gaggtgcagc tgttggagtc tgggggaggc ttggtacagc ctggcgggtc cctgagactc 60
tcctgtgcag cctctggatt cacctttaat aattattgga tgacatgggt ccgccaggct 120
ccagggaagg ggctggagtg ggtctcatct attagttcca gtggtggtag catttactac 180
cccgacaggg tgaagggccg gttcaccatc tccagagaca attccaagaa cacgctgtat 240
ctgcaaatga acagcctgag agccgaggac acggcggtgt actactgcgc aagagacgag 300
agatgggcag gtgctatgga tgcctggggg caagggacca cggtcaccgt ctcctca 357

<210> SEQ ID NO 157
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 157
gacatccaga tgacccagtc tccatcctcc ctgtctgcat ctgtaggaga cagagtcacc 60
atcacttgca aggcaagtca gaatattaac aagaatttag actggtatca gcagaaacca 120
gggaaagccc ctaagctcct gatctatgag acgaataact tgcaaacagg ggtcccatca 180
aggttcagtg gcagtggatc tgggacagat ttcactctca ccatcagcag tctgcaacct 240
gaagattttg caacttacta ctgttatcag cataattcta gatttacttt tggccagggg 300
accaagctgg agatcaaa 318

<210> SEQ ID NO 158
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 158
gaggtgcagc tggtggagtc tgggggaggc ttggtacagc ctggagggtc cctgagactc 60
tcctgtgcag cctctggatt cacctttacc aatttttgga tggcgtggat ccgccaggct 120
ccagggaagg ggctggagtg ggtcgcaagt attagttcaa gtggtggtag catctactac 180
cctgactccg tgaaggaccg gttcaccatc tccagagaca attccaagaa cacgctgtat 240
ctgcaaatga acagcctgag agccgaggac acggcggtgt actactgcgt caagtttcac 300
cactattcag gcggcggcga tgcttggggc caagggaccc tggtcaccgt ctcctca 357

<210> SEQ ID NO 159
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 159
gacatccaga tgacccagtc tccatcctcc ctgtctgcat ctgtaggaga cagagtcacc 60
atcacttgca aagcaagtca gaatattaac aagtatttag attggtatca gcagaaacca 120
gggaaagccc ctaagctcct gatccattac actaacaact tgcacaccgg gattccatca 180
aggttcagtg gcagtggatc tgggacagat tatactctca ccatcagcag tctgcaacct 240
gaagattttg caacttacta ctgtctgcag cacagttcca gatggacatt cggcggaggg 300

-continued

```
accaaggtgg agatcaaa                                                 318


<210> SEQ ID NO 160
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160

gaggtgcagc tggtggagtc tgggggaggc ttggtacagc ctggagggtc cctgagactc     60

tcctgtgcag cctctggatt caccttcaat aactattgga tgacgtgggt ccgccaggct    120

ccagggaagg ggctggagtg ggtttcatcc attagtagta gtggcggtag tatatactac    180

cctgactctg tgaaggatcg attcaccatc tccagagaca atgccaagaa ctcactgtat    240

ctgcaaatga acagcctgag agctgaggac atggcggtgt actactgcgc caggttgtac    300

tactacgacg ggggagggga tgcgtggggc caaggaaccc tggtcaccgt ctcctca       357


<210> SEQ ID NO 161
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161

ggcatccaga tgacccagtc tccatcctcc ctgtctgcat ctgtaggaga cagagtcacc     60

atcacttgca aggcgagtca ggacattaat aagtatttag attggtatca gcagaaacca    120

gggaaagccc ctaagctcct gatctacaat acaaacaatt tgcatacagg gatcccatca    180

aggttcagtg gaagtggatc tgggacagat tatactctta ccatcagcag cctgcagcct    240

gaagattttg caacatatta ctgtcttcaa cacatatcta gatggacgtt cggcggaggg    300

accaaggtgg agatcaaa                                                 318
```

METHODS OF USE OF ANTI-CD45 ANTIBODIES AND CONJUGATES THEREOF

RELATED APPLICATIONS

This application is a continuation of International Application No. PCT/US2020/058373, filed Oct. 30, 2020, which claims priority to U.S. Provisional Application No. 62/929,137, filed Nov. 1, 2019; U.S. Provisional Application No. 62/929,194, filed Nov. 1, 2019; U.S. Provisional Application No. 62/929,207, filed Nov. 1, 2019; U.S. Provisional Application No. 62/929,288, filed Nov. 1, 2019; U.S. Provisional Application No. 62/929,601, filed Nov. 1, 2019; U.S. Provisional Application No. 62/929,283, filed Nov. 1, 2019; U.S. Provisional Application No. 62/929,347, filed Nov. 1, 2019; U.S. Provisional Application No. 62/940,742, filed Nov. 26, 2019; U.S. Provisional Application No. 62/978,147, filed Feb. 18, 2020; U.S. Provisional Application No. 63/015,348, filed Apr. 24, 2020; U.S. Provisional Application No. 63/046,046, filed Jun. 30, 2020; U.S. Provisional Application No. 63/046,164, filed Jun. 30, 2020; and U.S. Provisional Application No. 63/084,903, filed Sep. 29, 2020. The entire contents of each of the foregoing priority applications is incorporated by reference herein.

SEQUENCE LISTING

The instant application contains a Sequence Listing which has been submitted electronically in ASCII format, and which is hereby incorporated by reference in its entirety. Said ASCII copy, created on Oct. 22, 2021, is named 17452028_1_1.txt and is 238692 bytes in size.

FIELD OF THE INVENTION

Described herein are anti-CD45 antibodies, antigen binding fragments thereof, and antibody drug conjugates thereof. Also described is the treatment of patients suffering from various pathologies, such as blood diseases, metabolic disorders, cancers, and autoimmune diseases, among others, by administration of an anti-CD45 antibody, antigen binding fragment thereof, or antibody drug conjugate (ADC) thereof, wherein the antibody, antigen binding fragment thereof, or ADC is capable of binding CD45 on a target cell (e.g., a hematopoietic stem cell, an immune cell, or other type of cell.

BACKGROUND OF THE INVENTION

CD45, also known as protein tyrosine phosphatase, receptor type C (PTPRC), is an enzyme that, in humans, is encoded by the PTPRC gene (Kaplan et al., PNAS 87:7000-7004 (1990)). CD45 is a member of the protein tyrosine phosphatase (PTP) family, which includes signaling molecules that regulate a variety of cellular processes including cell growth, differentiation, mitotic cycle, and oncogenic transformation. CD45 contains an extracellular domain, a single transmembrane segment, and two tandem intracytoplasmic catalytic domains, and thus belongs to the receptor type PTP family. CD45 is a type I transmembrane protein that is present in various isoforms on differentiated hematopoietic cells (except erythrocytes and plasma cells) (Holmes, Immunology 117:145-55 (2006)). CD45 has been shown to be a regulator of T- and B-cell antigen receptor signaling. It functions through either direct interaction with components of the antigen receptor complexes via its extracellular domain (a form of co-stimulation), or by activating various Src family kinases required for the antigen receptor signaling via its cytoplasmic domain. CD45 also suppresses JAK kinases, and thus functions as a negative regulator of cytokine receptor signaling.

CD45 is present on the surface of hematopoietic cells, including HSCs, leukocytes, and osteoclasts, which are of hematopoietic origin (Shivtiel et al., *J Exp Med* 205:2381 (2008)). Deletion mutations within CD45 in humans are associated with severe immunodeficiency. This is primarily due to the absence of CD45 on T cells, where it is typically abundant and required to modulate SFK activity during antigen responses. CD45-deficient ($CD45^{-/-}$) mouse bone marrow contains normal numbers of hematopoietic cells, but the most primitive HSCs are reduced in number, and their mobilization in response to G-CSF is impaired. In part, this defect is intrinsic to the HSC; without CD45-mediated downregulation of SFK activity, integrin-mediated adhesion is high and HSCs are more likely to remain in the stem cell niche. $CD45^{-/-}$ HSCs are also deficient in G-CSF-stimulated mobilization and homing to the chemokine CXCL12/SDF-1, which negatively affects cell engraftment following transplantation. These deficiencies can be restored by supplementation with SFK inhibitors, indicating that this role is usually performed by CD45. Likewise, $CD45^{-/-}$ recipients also show deficient engraftment and subsequent mobilization of normal HSCs, indicating a role for CD45 in the stem cell niche, as well as in the HSC (Shivtiel et al., *J Exp Med* 205:2381 (2008)).

Despite advances in the medicinal arts, there remains a demand for treating pathologies of the hematopoietic system, such as diseases of a particular blood cell, metabolic disorders, cancers, and autoimmune conditions, among others. While hematopoietic stem cells (HSCs) have significant therapeutic potential, a limitation that has hindered their use in the clinic has been the difficulty associated with ensuring engraftment of HSC transplants in a host. In particular, hematopoietic stem cell therapies involving antibodies that target cell surface antigens on endogenous HSCs can trigger unwanted immunostimulatory and effector functions that impede engraftment of an exogenous HSC transplant. As CD45 is expressed, for example, on HSCs and leukocytes, it presents a target for therapies including conditioning therapies, immune reset, and treatment of diseases.

SUMMARY OF THE INVENTION

Given the important role of CD45 in cell biology, there is a need for anti-CD45 antibodies, and fragments thereof. Described herein are anti-CD45 antibodies, antigen binding fragments thereof, and antibody drug conjugates (ADCs) thereof. The anti-CD45 antibodies, antigen binding fragments thereof, and antibody drug conjugates (ADCs) thereof may bind to hematopoietic stem cells (HSCs) and are useful, for example, as conditioning agents for HSC transplantation. In particular, the anti-CD45 antibodies, antigen binding fragments thereof, and ADCs thereof described herein can be used to specifically deplete, for example, host HSCs, immune cells (e.g., leukocytes), or disease-causing cells. Further, the anti-CD45 antibodies, antigen binding fragments thereof, and ADCs thereof described herein may be used to treat patients with a leukemia or a lymphoma, or to treat patients with autoimmune diseases such as multiple sclerosis and scleroderma. The anti-CD45 antibodies, antigen binding fragments thereof, and ADCs described herein satisfy a need for compositions and methods for promoting the engraftment of exogenous hematopoietic stem cell grafts such that the multi-potency and hematopoietic functionality of these cells is preserved following transplantation.

In a first aspect, the present invention provides an isolated anti-CD45 antibody, or antigen binding portion thereof, comprising: (a) a heavy chain variable region comprising a CDR1 domain comprising the amino acid sequence as set forth in SEQ ID NO:2, a CDR2 domain comprising the amino acid sequence as set forth in SEQ ID NO:3, and a CDR3 domain comprising the amino acid sequence as set forth in SEQ ID NO:4; and a light chain variable region comprising a CDR1 domain comprising the amino acid sequence as set forth in SEQ ID NO:6, a CDR2 domain comprising the amino acid sequence as set forth in SEQ ID NO:7; and a CDR3 domain comprising the amino acid sequence as set forth in SEQ ID NO:8; (b) a heavy chain variable region comprising a CDR1 domain comprising the amino acid sequence as set forth in SEQ ID NO:12, a CDR2 domain comprising the amino acid sequence as set forth in SEQ ID NO:13, and a CDR3 domain comprising the amino acid sequence as set forth in SEQ ID NO:14; and a light chain variable region comprising a CDR1 domain comprising the amino acid sequence as set forth in SEQ ID NO:16, a CDR2 domain comprising the amino acid sequence as set forth in SEQ ID NO:17; and a CDR3 domain comprising the amino acid sequence as set forth in SEQ ID NO:18; (c) a heavy chain variable region comprising a CDR1 domain comprising the amino acid sequence as set forth in SEQ ID NO:22, a CDR2 domain comprising the amino acid sequence as set forth in SEQ ID NO:23, and a CDR3 domain comprising the amino acid sequence as set forth in SEQ ID NO:24; and a light chain variable region comprising a CDR1 domain comprising the amino acid sequence as set forth in SEQ ID NO:26, a CDR2 domain comprising the amino acid sequence as set forth in SEQ ID NO:27; and a CDR3 domain comprising the amino acid sequence as set forth in SEQ ID NO:28; (d) a heavy chain variable region comprising a CDR1 domain comprising the amino acid sequence as set forth in SEQ ID NO:32, a CDR2 domain comprising the amino acid sequence as set forth in SEQ ID NO:33, and a CDR3 domain comprising the amino acid sequence as set forth in SEQ ID NO:34; and a light chain variable region comprising a CDR1 domain comprising the amino acid sequence as set forth in SEQ ID NO:36, a CDR2 domain comprising the amino acid sequence as set forth in SEQ ID NO:37; and a CDR3 domain comprising the amino acid sequence as set forth in SEQ ID NO:38; (e) a heavy chain variable region comprising a CDR1 domain comprising the amino acid sequence as set forth in SEQ ID NO:42, a CDR2 domain comprising the amino acid sequence as set forth in SEQ ID NO:43, and a CDR3 domain comprising the amino acid sequence as set forth in SEQ ID NO:44; and a light chain variable region comprising a CDR1 domain comprising the amino acid sequence as set forth in SEQ ID NO:46, a CDR2 domain comprising the amino acid sequence as set forth in SEQ ID NO:47; and a CDR3 domain comprising the amino acid sequence as set forth in SEQ ID NO:48; (f) a heavy chain variable region comprising a CDR1 domain comprising the amino acid sequence as set forth in SEQ ID NO:52, a CDR2 domain comprising the amino acid sequence as set forth in SEQ ID NO:53, and a CDR3 domain comprising the amino acid sequence as set forth in SEQ ID NO:54; and a light chain variable region comprising a CDR1 domain comprising the amino acid sequence as set forth in SEQ ID NO:56, a CDR2 domain comprising the amino acid sequence as set forth in SEQ ID NO:57; and a CDR3 domain comprising the amino acid sequence as set forth in SEQ ID NO:58; (g) a heavy chain variable region comprising a CDR1 domain comprising the amino acid sequence as set forth in SEQ ID NO:62, a CDR2 domain comprising the amino acid sequence as set forth in SEQ ID NO:63, and a CDR3 domain comprising the amino acid sequence as set forth in SEQ ID NO:64; and a light chain variable region comprising a CDR1 domain comprising the amino acid sequence as set forth in SEQ ID NO:66, a CDR2 domain comprising the amino acid sequence as set forth in SEQ ID NO:67; and a CDR3 domain comprising the amino acid sequence as set forth in SEQ ID NO:68; (h) a heavy chain variable region comprising a CDR1 domain comprising the amino acid sequence as set forth in SEQ ID NO:72, a CDR2 domain comprising the amino acid sequence as set forth in SEQ ID NO:73, and a CDR3 domain comprising the amino acid sequence as set forth in SEQ ID NO:74; and a light chain variable region comprising a CDR1 domain comprising the amino acid sequence as set forth in SEQ ID NO:76, a CDR2 domain comprising the amino acid sequence as set forth in SEQ ID NO:77; and a CDR3 domain comprising the amino acid sequence as set forth in SEQ ID NO:78; (i) a heavy chain variable region comprising a CDR1 domain comprising the amino acid sequence as set forth in SEQ ID NO:82, a CDR2 domain comprising the amino acid sequence as set forth in SEQ ID NO:83, and a CDR3 domain comprising the amino acid sequence as set forth in SEQ ID NO:84; and a light chain variable region comprising a CDR1 domain comprising the amino acid sequence as set forth in SEQ ID NO:86, a CDR2 domain comprising the amino acid sequence as set forth in SEQ ID NO:87; and a CDR3 domain comprising the amino acid sequence as set forth in SEQ ID NO:88; or (j) a heavy chain variable region comprising a CDR1 domain comprising the amino acid sequence as set forth in SEQ ID NO:92, a CDR2 domain comprising the amino acid sequence as set forth in SEQ ID NO:93, and a CDR3 domain comprising the amino acid sequence as set forth in SEQ ID NO:94; and a light chain variable region comprising a CDR1 domain comprising the amino acid sequence as set forth in SEQ ID NO:96, a CDR2 domain comprising the amino acid sequence as set forth in SEQ ID NO:97; and a CDR3 domain comprising the amino acid sequence as set forth in SEQ ID NO:98.

In another aspect, provided herein is an isolated anti-CD45 antibody, or antigen-binding portion thereof, comprising: a heavy chain variable region comprising a CDR1 domain comprising the amino acid sequence as set forth in SEQ ID NO:119, a CDR2 domain comprising the amino acid sequence as set forth in SEQ ID NO:120, and a CDR3 domain comprising the amino acid sequence as set forth in SEQ ID NO:121; and a light chain variable region comprising a CDR1 domain comprising the amino acid sequence as set forth in SEQ ID NO:122, a CDR2 domain comprising the amino acid sequence as set forth in SEQ ID NO:123; and a CDR3 domain comprising the amino acid sequence as set forth in SEQ ID NO:124.

In another aspect, the present invention provides an isolated anti-CD45 antibody, or antigen-binding portion thereof, comprising: (a) a heavy chain variable region comprising the amino acid sequence as set forth in SEQ ID NO:1, and a light chain variable region comprising the amino acid sequence as set forth in SEQ ID NO:5; (b) a heavy chain variable region comprising the amino acid sequence as set forth in SEQ ID NO: 11, and a light chain variable region comprising the amino acid sequence as set forth in SEQ ID NO:15; (c) a heavy chain variable region comprising the amino acid sequence as set forth in SEQ ID NO:21, and a light chain variable region comprising the amino acid sequence as set forth in SEQ ID NO:25; (d) a heavy chain variable region comprising the amino acid sequence as set forth in SEQ ID NO:31, and a light chain variable region comprising the amino acid sequence as set forth in SEQ ID NO:35; (e) a heavy chain variable region comprising the amino acid sequence as set forth in SEQ ID NO:41, and a light chain variable region comprising the amino acid sequence as set forth in SEQ ID NO:45; (f) a heavy chain variable region comprising the amino acid sequence as set forth in SEQ ID NO:51, and a light chain variable region comprising the amino acid sequence as set forth in SEQ ID NO:55; (g) a heavy chain variable region comprising the amino acid sequence as set forth in SEQ ID NO:61, and a light chain variable region comprising the amino acid sequence as set forth in SEQ ID NO:65; (h) a heavy chain variable region comprising the amino acid sequence as set forth in SEQ ID NO:71, and a light chain variable region comprising the amino acid sequence as set forth in SEQ ID NO:75; (i) a heavy chain variable region comprising the amino acid sequence as set forth in SEQ ID NO:81, and a light chain variable region comprising the amino acid sequence as set forth in SEQ ID NO:85; or (j) a heavy chain variable region comprising the amino acid sequence as set forth in SEQ ID NO:91, and a light chain variable region comprising the amino acid sequence as set forth in SEQ ID NO:95.

In some embodiments of the aforementioned aspects, the isolated anti-CD45 antibody, or antigen-binding portion thereof comprises an Fc region. In certain embodiments, the Fc region is a human IgG1 Fc region of a human IgG4 Fc region.

In some embodiments, the antibody is a monoclonal antibody.

In some embodiments, the antibody is an intact antibody comprising a constant region.

In some embodiments, the antibody is an IgG. In particular embodiments, the IgG is an IgG1 or an IgG4.

In some embodiments of the aforementioned aspects, the antibody comprises a constant region, wherein the constant region comprises at least one, at least two, at least three, at least four, or at least five amino acid substitutions selected from the group consisting of L234A, L235A, D265C, H310A, and H435A (numbering according to the EU index). In particular embodiments, the constant region comprises amino acid substitutions L234A, L235A and D265C (numbering according to the EU index).

In some embodiments, the isolated anti-CD45 antibody of the present disclosure comprises a constant region, wherein the constant region comprises (a) a heavy chain amino acid sequence as set forth in SEQ ID NO:102, SEQ ID NO:103, SEQ ID NO:104, SEQ ID NO:105, or SEQ ID NO:106; and (b) a light chain amino acid sequence as set forth in SEQ ID NO:101.

In another aspect, the present invention provides an isolated anti-CD45 antibody comprising: (a) a heavy chain amino acid sequence as set forth in SEQ ID NO:9, and a light chain amino acid sequence as set forth in SEQ ID NO:10; (b) a heavy chain amino acid sequence as set forth in SEQ ID NO:19, and a light chain amino acid sequence as set forth in SEQ ID NO:20; (c) a heavy chain amino acid sequence as set forth in SEQ ID NO:29, and a light chain amino acid sequence as set forth in SEQ ID NO:30; (d) a heavy chain amino acid sequence as set forth in SEQ ID NO:39, and a light chain amino acid sequence as set forth in SEQ ID NO:40; (e) a heavy chain amino acid sequence as set forth in SEQ ID NO:49, and a light chain amino acid sequence as set forth in SEQ ID NO:50; (f) a heavy chain amino acid sequence as set forth in SEQ ID NO:59, and a light chain amino acid sequence as set forth in SEQ ID NO:60; (g) a heavy chain amino acid sequence as set forth in SEQ ID NO:69, and a light chain amino acid sequence as set forth in SEQ ID NO:70; (h) a heavy chain amino acid sequence as set forth in SEQ ID NO:79, and a light chain amino acid sequence as set forth in SEQ ID NO:80; (i) a heavy chain amino acid sequence as set forth in SEQ ID NO:89, and a light chain amino acid sequence as set forth in SEQ ID NO:90; or (j) a heavy chain amino acid sequence as set forth in SEQ ID NO:99, and a light chain amino acid sequence as set forth in SEQ ID NO:100.

In another aspect, the present invention provides an isolated anti-CD45 antibody, or antigen-binding portion thereof, that specifically binds to human CD45 at an epitope located within CD45 Fragment 1 (SEQ ID NO:114), CD45 Fragment 2 (SEQ ID NO:115), CD45 Fragment 3 (SEQ ID NO:116), CD45 Fragment 4 (SEQ ID NO:117), and/or CD45 Fragment 5 (SEQ ID NO:118).

In some embodiments of the above aspect, the isolated anti-CD45 antibody, or antigen-binding portion thereof specifically binds to (a) an epitope of human CD45 located within CD45 Fragment 2, and an epitope of human CD45 located within Fragment 4; (b) an epitope of human CD45 located within CD45 Fragment 1, and an epitope of human CD45 located within CD45 Fragment 3; or (c) an epitope of human CD45 located within CD45 Fragment 5.

In some embodiments, the isolated anti-CD45 antibody, or antigen-binding portion thereof specifically binds to (a) one or more residues selected from the group consisting of 405T, 407K, 419Y, 425K, 481R, 505R, and 509H in human CD45 (numbered with reference to SEQ ID NO:113); or (b) one or more residues selected from the group consisting of 486R, 493Y, and 502T in human CD45 (numbered with reference to SEQ ID NO:113).

In some embodiments, the isolated anti-CD45 antibody, or antigen-binding portion of the present disclosure specifically binds human CD45, and cross-reacts with cynomolgus CD45.

In some embodiments, the isolated anti-CD45 antibody, or antigen-binding portion of the present disclosure binds to human CD45 with a dissociation rate ($K_{OFF}$) of $1\times10^{-2}$ to $1\times10^{-3}$, $1\times10^{-3}$ to $1\times10^{-4}$, $1\times10^{-4}$ to $1\times10^{-5}$, $1\times10^{-5}$ to $1\times10^{-6}$, $1\times10^{-6}$ to $1\times10^{-7}$, or $1\times10^{-7}$ to $1\times10^{-8}$, as measured by Bio-Layer Interferometry (BLI). In some embodiments, the isolated anti-CD45 antibody, or antigen-binding portion of the present disclosure binds to human CD45 with a $K_D$ of about 100 nM or less, about 90 nM or less, about 80 nM or less, about 70 nM or less, about 60 nM or less, about 50 nM or less, about 40 nM or less, about 30 nM or less, about 20 nM or less, about 10 nM or less, about 10 nM or less, or about 0.1 nM or less, as determined by Bio-Layer Interferometry (BLI).

In another aspect, provided herein is a pharmaceutical composition comprising the antibody, or antigen-binding portion thereof of the present invention and a pharmaceutically acceptable carrier.

In another aspect, provided herein is an isolated nucleic acid comprising a nucleic acid sequence encoding the antibody, or antigen binding portion thereof, of the present invention.

In another aspect, provided herein is a vector comprising the isolated nucleic acid of the present invention.

In another aspect, provided herein is a host cell comprising the isolated nucleic acid of the present invention, or the vector of the present invention. In some embodiments, the host cell is a Chinese Hamster Ovary (CHO) cell.

In another aspect, provided herein is a pharmaceutical composition comprising the antibody, or antigen-binding portion thereof, of any of the aforementioned aspects, for use in depleting a population of CD45+ cells in a human patient.

In another aspect, provided herein is a method of depleting a population of CD45+ cells in a human patient by administering the antibody, or antigen-binding portion thereof, of any of the aforementioned aspects, to the human patient. In some embodiments, the CD45+ cells are CD3+, CD19+, CD33+, CD34+, or CD45+/B2M+. In other embodiments, the CD45+ cells are hematopoietic stem cells (HSCs). In yet other embodiments, the CD45+ cells are HSCs, T cells, B cells, and/or myeloid cells.

In some embodiments of the above aspect, the CD45+ cells are depleted from the bone marrow of the patient and/or from the peripheral blood of the patient.

In some embodiments of the above aspect, the patient is in need of a hematopoietic stem cell transplant. In some embodiments of the above aspect, the method further comprises administering to the patient a transplant comprising hematopoietic stem cells. In certain embodiments, the transplant is allogeneic. In alternative embodiments, the transplant is autologous.

In another aspect, the present invention provides an antibody drug conjugate (ADC) comprising an anti-CD45 antibody, or an antigen-binding portion thereof, conjugated to a cytotoxin via a linker, wherein the anti-CD45 antibody, or antigen-binding portion thereof, is an antibody or antigen-binding portion thereof of any of the aforementioned aspects.

In some embodiments of the above aspect, the antibody is conjugated to the cytotoxin by way of a cysteine residue in the constant domain of the antibody. In certain embodiments, the cysteine residue is introduced by way of an amino acid substitution in the constant region of the antibody. In particular embodiments, the amino acid substitution is D265C and/or V205C (EU numbering).

In some embodiments of the above aspect, the ADC has a drug to antibody ratio (DAR) of 1, 2, 3, 4, 5, 6, 7, or 8.

In some embodiments of the above aspect, the cytotoxin is an RNA polymerase inhibitor, a DNA intercalating agent, a DNA alkylating agent, a DNA crosslinking agent, an agent that disrupts protein synthesis, an agent that disrupts microtubule dynamics, or an agent that disrupts the mitotic spindle.

In some embodiments of the above aspect, the cytotoxin is selected from the group consisting of an amatoxin, an anthracycline, an auristatin, a calicheamicin, deBouganin, diphtheria toxin, a duocarmycin, an indolinobenzodiazepine (IGN), an indolinobenzodiazepine dimer, irinotecan, maytansine, a maytansinoid, pseudomonas exotoxin A, a pyrrolobenzodiazepine (PBD), a pyrrolobenzodiazepine dimer, saporin, and SN-38. In certain embodiments, the cytotoxin is an RNA polymerase inhibitor. In certain embodiments, the RNA polymerase inhibitor is an amatoxin.

In some embodiments, the ADC is represented by the formula Ab-Z-L-Am, wherein Ab is an antibody, or antigen-binding portion thereof, L is a linker, Z is a chemical moiety, and Am is an amatoxin. In certain embodiments, Am-L-Z is represented by Formula (I):

(I)

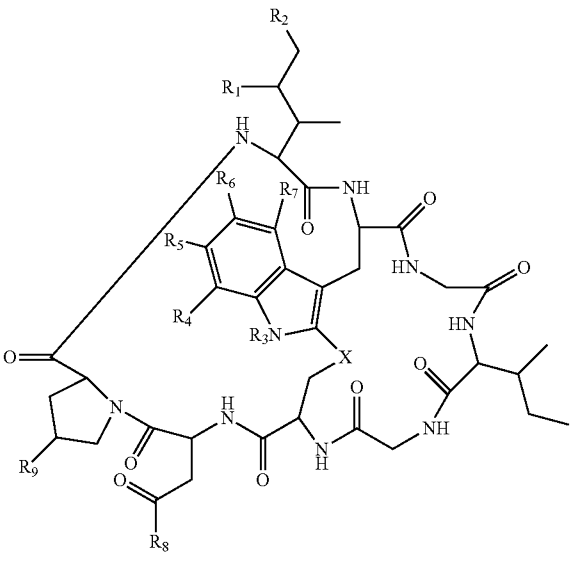

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$, $R_B$, $R_6$, and $R_7$ are each independently H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;

L is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, optionally substituted heteroarylene, a peptide, a dipeptide, —(C=O)—, a disulfide, a hydrazone, or a combination thereof; and Z is a chemical moiety formed from a coupling reaction between a reactive substituent present on L and a reactive substituent present within the antibody or antigen-binding fragment thereof, wherein Am comprises exactly one $R_C$ substituent.

In some embodiments, L-Z is
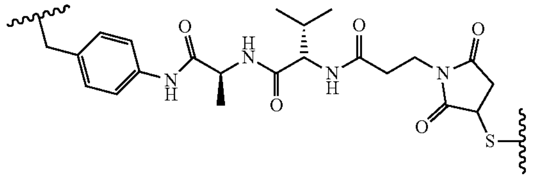
or
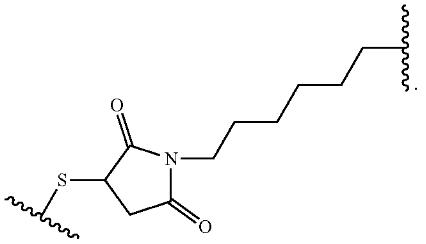
In some embodiments, the ADC is represented by one of:
(III)
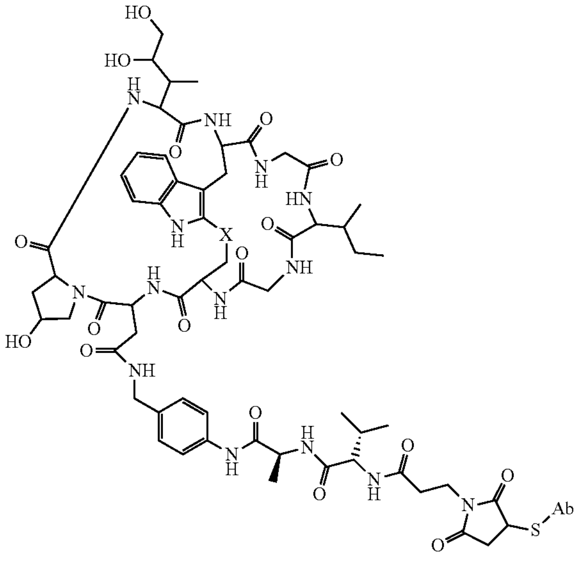
-continued
(IIIA)
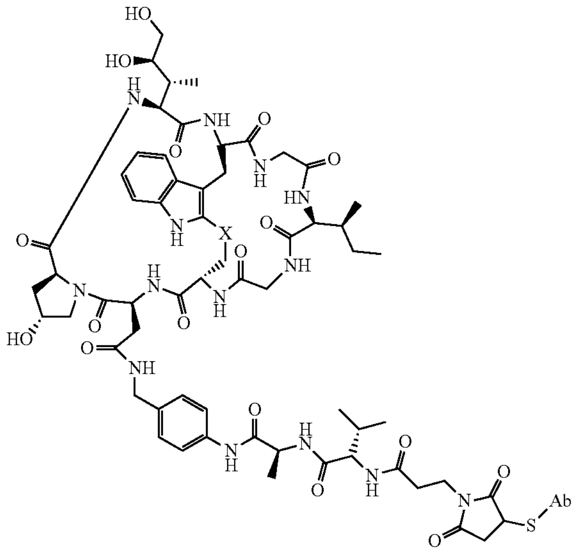
(IIIB)
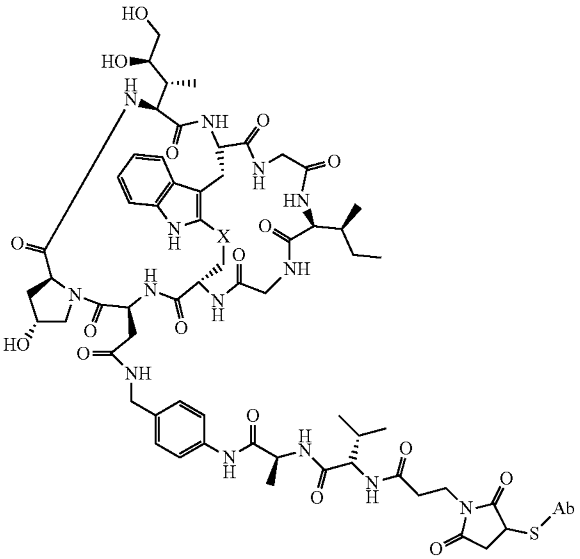
wherein X is —S—, —S(O)—, or —$SO_2$—.

In some embodiments, the ADC has a formula of

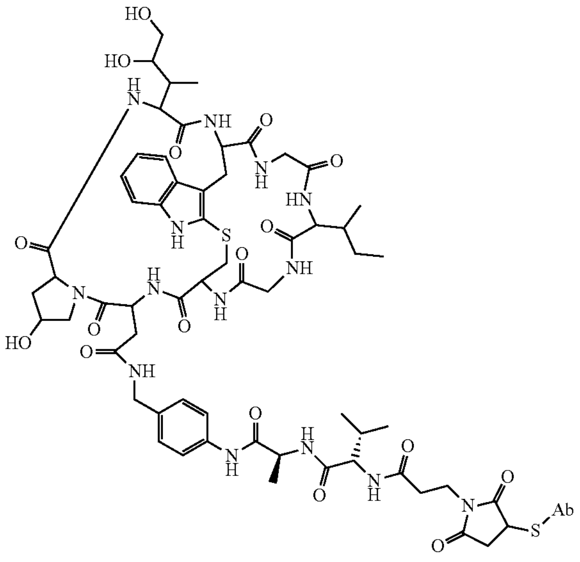

wherein Ab represents the point of attachment of the anti-CD45 antibody.

In other embodiments, the ADC has a formula of

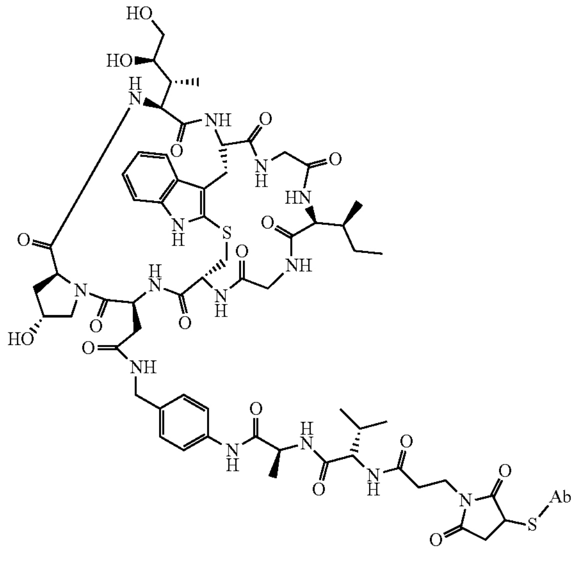

wherein Ab represents the point of attachment of the anti-CD45 antibody.

In alternative embodiments, the ADC has a formula of

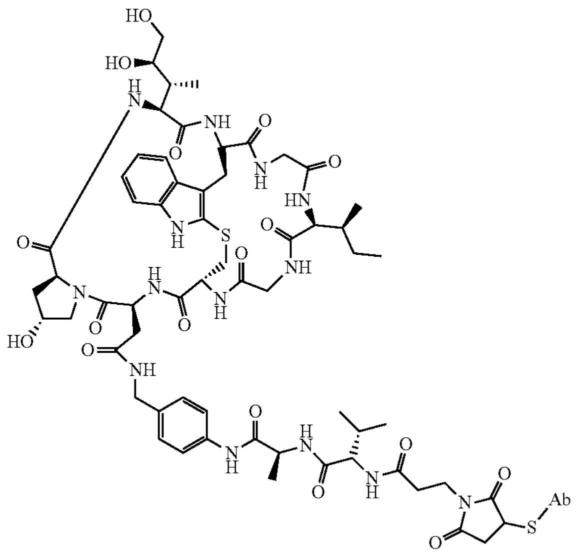

wherein Ab represents the point of attachment of the anti-CD45 antibody.

In other embodiments the ADC has a formula of

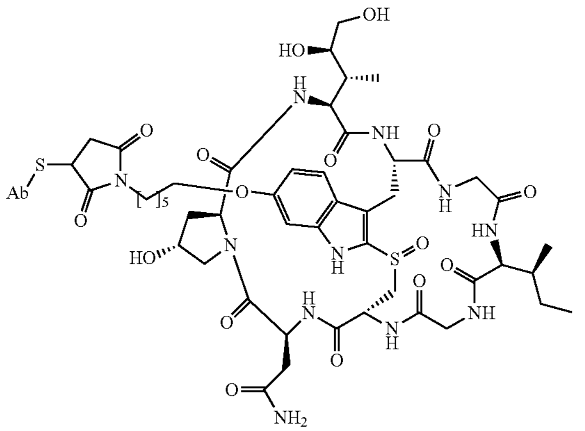

wherein Ab represents the point of attachment of the anti-CD45 antibody.

In yet other embodiments, the ADC has a formula of

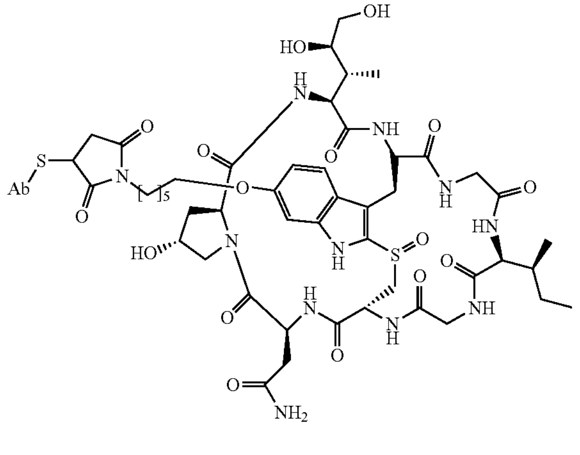

wherein Ab represents the point of attachment of the anti-CD45 antibody.

In some embodiments of an ADC disclosed herein, the cytotoxin is a pyrrolobenzodiazepine (PBD). In certain embodiments, the cytotoxin is a PBD dimer. In particular embodiments, the PBD dimer is represented by

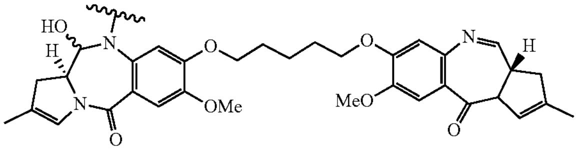

wherein the wavy line indicates the point of attachment to the linker of the ADC.

In some embodiments of an ADC disclosed herein, the linker comprises one or more of a peptide, oligosaccharide, $-(CH_2)_p-$, $-(CH_2CH_2O)_q-$, $-(C{=}O)(CH_2)_r-$, $-(C{=}O)(CH_2CH_2O)_t-$, $-(NHCH_2CH_2)_u-$, -PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB, wherein each of p, q, r, t, and u are integers from 1-12, selected independently for each occurrence.

In some embodiments of an ADC disclosed herein, the linker has the structure of

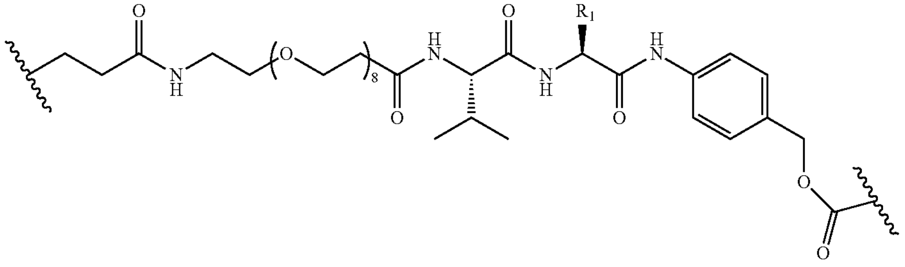

wherein $R_1$ is $CH_3$ (Ala) or $(CH_2)_3NH(CO)NH_2$ (Cit).

In some embodiments of an ADC disclosed herein, the linker, prior to conjugation to the anti-CD45 antibody and including the reactive substituent Z', taken together as L-Z', has the structure

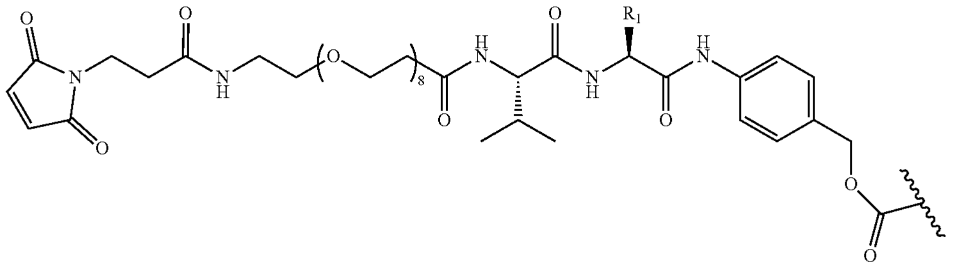

In certain embodiments, $R_1$ is $CH_3$.

In some embodiments of an ADC disclosed herein, the cytotoxin-linker conjugate, prior to conjugation to the anti-CD45 antibody and including the reactive substituent Z', taken together as Cy-L-Z', is tesirine, having the structure:

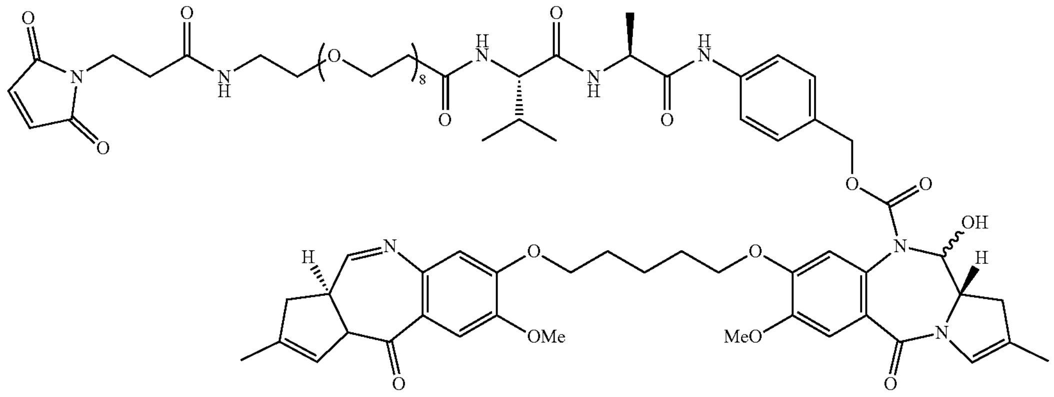

In some embodiments, the ADC disclosed herein has the structure

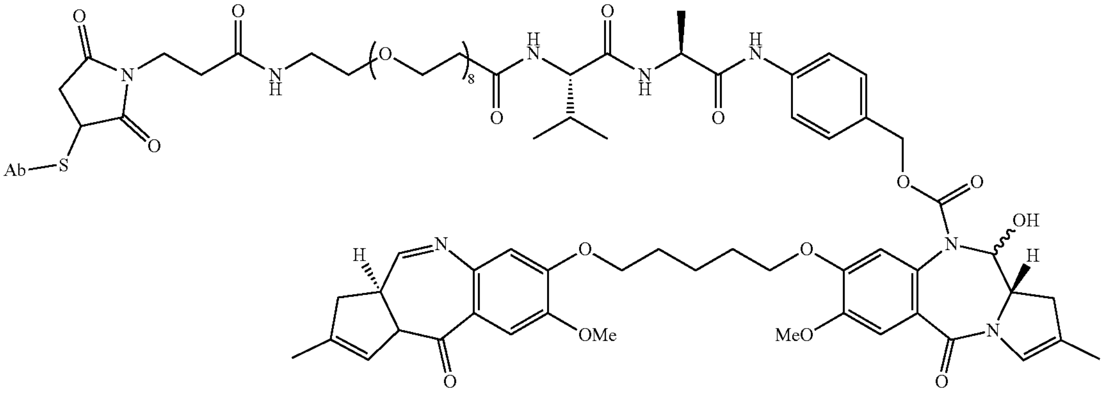

wherein Ab is the anti-CD45 antibody or antigen binding portion thereof, and S represents a sulfur atom present in or introduced into the anti-CD45 antibody or antigen binding portion thereof.

In some embodiments of an ADC disclosed herein, the cytotoxin is an indolinobenzodiazepine (IGN). In certain embodiments, the cytotoxin is an IGN dimer or an IGN pseudodimer.

In some embodiments, the cytotoxin is an IGN pseudodimer represented by:

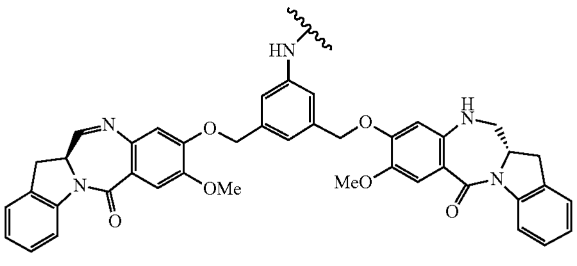 [SMILES: *Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

wherein the wavy line indicates the point of covalent attachment to the linker of the ADC.

In some embodiments, the linker comprises a dipeptide, a disulfide, C1-C12 alkyl, C═O, or combinations thereof.

In some embodiments, the linker comprises

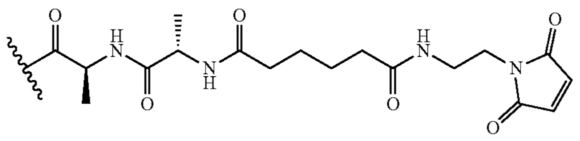

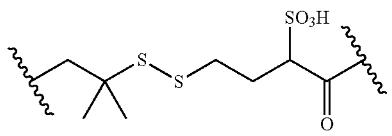

In some embodiments, the cytotoxin-linker conjugate, prior to conjugation to the anti-CD45 antibody or antigen binding portion thereof, and including the reactive substituent Z', taken together as Cy-L-Z', has a structure of:

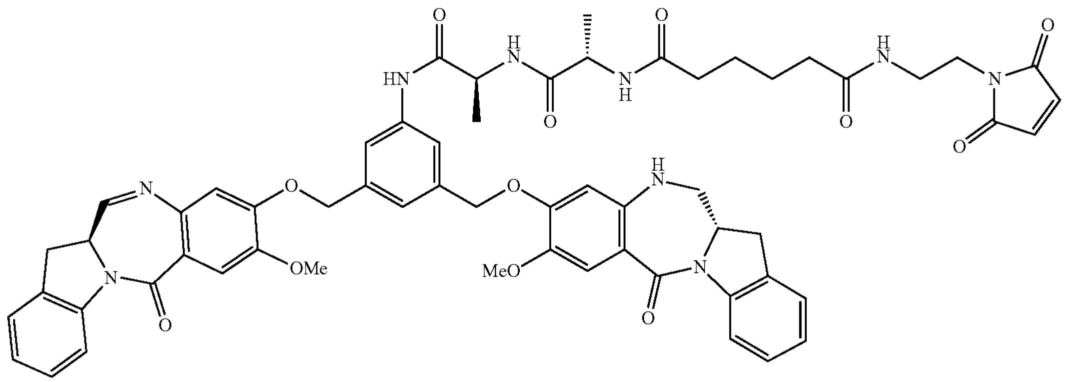 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O]

In another aspect, the present invention provides a pharmaceutical composition comprising an ADC described hereinabove, and a pharmaceutically acceptable carrier.

In another aspect, provided herein is a method of depleting a population of CD45+ cells in a human patient by administering to the patient an effective amount of an anti-CD45 ADC described hereinabove.

In some embodiments of the above aspect, the CD45+ cells are CD3+, CD19+, CD33+, CD34+, or CD45+/B2M+. In certain embodiments, the CD45+ cells are hematopoietic stem cells (HSCs). In other embodiments, the CD45+ cells are HSCs, T cells, B cells, and/or myeloid cells.

In some embodiments of the above aspect, the CD45+ cells are depleted from the bone marrow of the patient and/or from the peripheral blood of the patient.

In some embodiments of the above aspect, the patient is in need of a hematopoietic stem cell transplant.

In some embodiments of the above aspect, the method further comprises administering to the patient a transplant comprising hematopoietic stem cells.

In another aspect, the present invention provides a method of depleting a population of CD45+ cells in a human patient in need of a hematopoietic stem cell (HSC) transplant by administering to the patient an ADC described hereinabove prior to the patient receiving a transplant comprising hematopoietic stem cells.

In another aspect, the present invention provides a method comprising: (a) administering to a human patient an ADC described hereinabove, in an amount sufficient to deplete a population of CD45+ cells in the patient; and (b) subsequently administering to the patient a transplant comprising hematopoietic stem cells.

In some embodiments, the transplant is allogeneic. In other embodiments, the transplant is autologous.

In some embodiments, the transplant comprising hematopoietic stem cells is administered to the patient after the concentration of the ADC has substantially cleared from the blood of the patient.

In some embodiments, the hematopoietic stem cells or progeny thereof are capable of localizing to hematopoietic tissue and/or reestablishing hematopoiesis following transplantation of the hematopoietic stem cells into the patient.

In some embodiments, upon transplantation into the patient, the hematopoietic stem cells give rise to recovery of a population of cells selected from the group consisting of megakaryocytes, thrombocytes, platelets, erythrocytes, mast cells, myeloblasts, basophils, neutrophils, eosinophils, microglia, granulocytes, monocytes, osteoclasts, antigen-presenting cells, macrophages, dendritic cells, natural killer cells, T-lymphocytes, and B-lymphocytes.

In some embodiments, the patient has a blood disease, a metabolic disorder, cancer, or an autoimmune disorder, or severe combined immunodeficiency disease (SCID). In certain embodiments, the patient has cancer. In particular embodiments, the cancer is a hematological cancer. In specific embodiments, the hematological cancer is acute myeloid leukemia, acute lymphoid leukemia, chronic myeloid leukemia, chronic lymphoid leukemia, or multiple myeloma.

In certain embodiments, the patient has an autoimmune disorder. In particular embodiments, the autoimmune disorder is multiple sclerosis, Type 1 diabetes mellitus, or scleroderma. In other embodiments, the autoimmune disorder is selected from the group consisting of multiple sclerosis, human systemic lupus, rheumatoid arthritis, inflammatory bowel disease, treating psoriasis, Type 1 diabetes mellitus, acute disseminated encephalomyelitis, Addison's disease, alopecia universalis, ankylosing spondylitisis, antiphospholipid antibody syndrome, aplastic anemia, autoimmune hemolytic anemia, autoimmune hepatitis, autoimmune inner ear disease, autoimmune lymphoproliferative syndrome, autoimmune oophoritis, Balo disease, Behcet's disease, bullous pemphigoid, cardiomyopathy, Chagas' disease, chronic fatigue immune dysfunction syndrome, chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome, Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease, myasthenia gravis, neuromyotonia, opsoclonus myoclonus syndrome, optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis, ulcerative colitis, uveitis, vasculitis, vitiligo, vulvodynia, and Wegener's granulomatosis.

Additionally, the invention also comprises the following embodiments:

In one embodiment, the invention provides an isolated anti-CD45 antibody, or antigen binding portion thereof, comprising a heavy chain comprising a variable region comprising a CDR1 having the amino acid sequence as set forth in SEQ ID NO:2, a CDR2 having the amino acid sequence as set forth in SEQ ID NO:3, a CDR3 having the amino acid sequence as set forth in SEQ ID NO:4, and comprising a light chain comprising a variable region comprising a CDR1 having the amino acid sequence as set forth in SEQ ID NO:6, a CDR2 having the amino acid sequence as set forth in SEQ ID NO:7, a CDR3 having the amino acid sequence as set forth in SEQ ID NO:8.

In certain embodiments, the anti-CD45 antibody, or antigen binding portion thereof, comprises a heavy chain variable region comprising the amino acid sequence as set forth in SEQ ID NO:1.

In other embodiments, the anti-CD45 antibody, or antigen binding portion thereof, comprises a light chain variable region comprising the amino acid sequence as set forth in SEQ ID NO:5.

In certain embodiments, the anti-CD45 antibody, or antigen binding portion thereof, comprises a heavy chain variable region comprising the amino acid sequence as set forth in SEQ ID NO:1; and a light chain variable region comprising the amino acid sequence as set forth in SEQ ID NO:5.

In certain embodiments, the anti-CD45 antibody, or antigen binding portion thereof, comprises a heavy chain comprising the amino acid sequence as set forth in SEQ ID NO:9.

In certain embodiments, the anti-CD45 antibody, or antigen binding portion thereof, comprises a light chain comprising the amino acid sequence as set forth in SEQ ID NO:10.

In certain embodiments, the anti-CD45 antibody, or antigen binding portion thereof, comprises a heavy chain comprising the amino acid sequence as set forth in SEQ ID NO:9; and a light chain comprising the amino acid sequence as set forth in SEQ ID NO:10.

In one embodiment, the invention provides an isolated anti-CD45 antibody, or antigen binding portion thereof, comprising a heavy chain comprising a variable region comprising a CDR1 having the amino acid sequence as set forth in SEQ ID NO:12, a CDR2 having the amino acid sequence as set forth in SEQ ID NO:13, a CDR3 having the amino acid sequence as set forth in SEQ ID NO:14, and comprising a light chain comprising a variable region comprising a CDR1 having the amino acid sequence as set forth in SEQ ID NO:16, a CDR2 having the amino acid sequence as set forth in SEQ ID NO:17, a CDR3 having the amino acid sequence as set forth in SEQ ID NO:18.

In certain embodiments, the anti-CD45 antibody, or antigen binding portion thereof, comprises a heavy chain variable region comprising the amino acid sequence as set forth in SEQ ID NO:11.

In other embodiments, the anti-CD45 antibody, or antigen binding portion thereof, comprises a light chain variable region comprising the amino acid sequence as set forth in SEQ ID NO:15.

In certain embodiments, the anti-CD45 antibody, or antigen binding portion thereof, comprises a heavy chain variable region comprising the amino acid sequence as set forth in SEQ ID NO: 11; and a light chain variable region comprising the amino acid sequence as set forth in SEQ ID NO:15.

In certain embodiments, the anti-CD45 antibody, or antigen binding portion thereof, comprises a heavy chain comprising the amino acid sequence as set forth in SEQ ID NO:19.

In certain embodiments, the anti-CD45 antibody, or antigen binding portion thereof, comprises a light chain comprising the amino acid sequence as set forth in SEQ ID NO:20.

In certain embodiments, the anti-CD45 antibody, or antigen binding portion thereof, comprises a heavy chain comprising the amino acid sequence as set forth in SEQ ID NO:19; and a light chain comprising the amino acid sequence as set forth in SEQ ID NO:20.

In one embodiment, the invention provides an isolated anti-CD45 antibody, or antigen binding portion thereof, comprising a heavy chain comprising a variable region comprising a CDR1 having the amino acid sequence as set forth in SEQ ID NO:22, a CDR2 having the amino acid sequence as set forth in SEQ ID NO:23, a CDR3 having the amino acid sequence as set forth in SEQ ID NO:24, and comprising a light chain comprising a variable region comprising a CDR1 having the amino acid sequence as set forth in SEQ ID NO:26, a CDR2 having the amino acid sequence as set forth in SEQ ID NO:27, a CDR3 having the amino acid sequence as set forth in SEQ ID NO:28.

In certain embodiments, the anti-CD45 antibody, or antigen binding portion thereof, comprises a heavy chain variable region comprising the amino acid sequence as set forth in SEQ ID NO:21.

In other embodiments, the anti-CD45 antibody, or antigen binding portion thereof, comprises a light chain variable region comprising the amino acid sequence as set forth in SEQ ID NO:25.

In certain embodiments, the anti-CD45 antibody, or antigen binding portion thereof, comprises a heavy chain variable region comprising the amino acid sequence as set forth in SEQ ID NO:21; and a light chain variable region comprising the amino acid sequence as set forth in SEQ ID NO:25.

In certain embodiments, the anti-CD45 antibody, or antigen binding portion thereof, comprises a heavy chain comprising the amino acid sequence as set forth in SEQ ID NO:29.

In certain embodiments, the anti-CD45 antibody, or antigen binding portion thereof, comprises a light chain comprising the amino acid sequence as set forth in SEQ ID NO:30.

In certain embodiments, the anti-CD45 antibody, or antigen binding portion thereof, comprises a heavy chain comprising the amino acid sequence as set forth in SEQ ID NO:29; and a light chain comprising the amino acid sequence as set forth in SEQ ID NO:30.

In one embodiment, the invention provides an isolated anti-CD45 antibody, or antigen binding portion thereof, comprising a heavy chain comprising a variable region comprising a CDR1 having the amino acid sequence as set forth in SEQ ID NO:32, a CDR2 having the amino acid sequence as set forth in SEQ ID NO:33, a CDR3 having the amino acid sequence as set forth in SEQ ID NO:34, and comprising a light chain comprising a variable region comprising a CDR1 having the amino acid sequence as set forth in SEQ ID NO:36, a CDR2 having the amino acid sequence as set forth in SEQ ID NO:37, a CDR3 having the amino acid sequence as set forth in SEQ ID NO:38.

In certain embodiments, the anti-CD45 antibody, or antigen binding portion thereof, comprises a heavy chain variable region comprising the amino acid sequence as set forth in SEQ ID NO:31.

In other embodiments, the anti-CD45 antibody, or antigen binding portion thereof, comprises a light chain variable region comprising the amino acid sequence as set forth in SEQ ID NO:35.

In certain embodiments, the anti-CD45 antibody, or antigen binding portion thereof, comprises a heavy chain variable region comprising the amino acid sequence as set forth in SEQ ID NO:31; and a light chain variable region comprising the amino acid sequence as set forth in SEQ ID NO:35.

In certain embodiments, the anti-CD45 antibody, or antigen binding portion thereof, comprises a heavy chain comprising the amino acid sequence as set forth in SEQ ID NO:39.

In certain embodiments, the anti-CD45 antibody, or antigen binding portion thereof, comprises a light chain comprising the amino acid sequence as set forth in SEQ ID NO:40.

In certain embodiments, the anti-CD45 antibody, or antigen binding portion thereof, comprises a heavy chain comprising the amino acid sequence as set forth in SEQ ID NO:39; and a light chain comprising the amino acid sequence as set forth in SEQ ID NO:40.

In one embodiment, the invention provides an isolated anti-CD45 antibody, or antigen binding portion thereof, comprising a heavy chain comprising a variable region comprising a CDR1 having the amino acid sequence as set forth in SEQ ID NO:42, a CDR2 having the amino acid sequence as set forth in SEQ ID NO:43, a CDR3 having the amino acid sequence as set forth in SEQ ID NO:44, and comprising a light chain comprising a variable region comprising a CDR1 having the amino acid sequence as set forth in SEQ ID NO:46, a CDR2 having the amino acid sequence as set forth in SEQ ID NO:47, a CDR3 having the amino acid sequence as set forth in SEQ ID NO:48.

In certain embodiments, the anti-CD45 antibody, or antigen binding portion thereof, comprises a heavy chain variable region comprising the amino acid sequence as set forth in SEQ ID NO:41.

In other embodiments, the anti-CD45 antibody, or antigen binding portion thereof, comprises a light chain variable region comprising the amino acid sequence as set forth in SEQ ID NO:45.

In certain embodiments, the anti-CD45 antibody, or antigen binding portion thereof, comprises a heavy chain variable region comprising the amino acid sequence as set forth in SEQ ID NO:41; and a light chain variable region comprising the amino acid sequence as set forth in SEQ ID NO:45.

In certain embodiments, the anti-CD45 antibody, or antigen binding portion thereof, comprises a heavy chain comprising the amino acid sequence as set forth in SEQ ID NO:49.

In certain embodiments, the anti-CD45 antibody, or antigen binding portion thereof, comprises a light chain comprising the amino acid sequence as set forth in SEQ ID NO:50.

In certain embodiments, the anti-CD45 antibody, or antigen binding portion thereof, comprises a heavy chain comprising the amino acid sequence as set forth in SEQ ID NO:49; and a light chain comprising the amino acid sequence as set forth in SEQ ID NO:50.

In one embodiment, the invention provides an isolated anti-CD45 antibody, or antigen binding portion thereof, comprising a heavy chain comprising a variable region comprising a CDR1 having the amino acid sequence as set forth in SEQ ID NO:52, a CDR2 having the amino acid sequence as set forth in SEQ ID NO:53, a CDR3 having the amino acid sequence as set forth in SEQ ID NO:54, and comprising a light chain comprising a variable region comprising a CDR1 having the amino acid sequence as set forth in SEQ ID NO:56, a CDR2 having the amino acid sequence as set forth in SEQ ID NO:57, a CDR3 having the amino acid sequence as set forth in SEQ ID NO:58.

In certain embodiments, the anti-CD45 antibody, or antigen binding portion thereof, comprises a heavy chain variable region comprising the amino acid sequence as set forth in SEQ ID NO:51.

In other embodiments, the anti-CD45 antibody, or antigen binding portion thereof, comprises a light chain variable region comprising the amino acid sequence as set forth in SEQ ID NO:55.

In certain embodiments, the anti-CD45 antibody, or antigen binding portion thereof, comprises a heavy chain variable region comprising the amino acid sequence as set forth in SEQ ID NO:51; and a light chain variable region comprising the amino acid sequence as set forth in SEQ ID NO:55.

In certain embodiments, the anti-CD45 antibody, or antigen binding portion thereof, comprises a heavy chain comprising the amino acid sequence as set forth in SEQ ID NO:59.

In certain embodiments, the anti-CD45 antibody, or antigen binding portion thereof, comprises a light chain comprising the amino acid sequence as set forth in SEQ ID NO:60.

In certain embodiments, the anti-CD45 antibody, or antigen binding portion thereof, comprises a heavy chain comprising the amino acid sequence as set forth in SEQ ID NO:59; and a light chain comprising the amino acid sequence as set forth in SEQ ID NO:60.

In one embodiment, the invention provides an isolated anti-CD45 antibody, or antigen binding portion thereof, comprising a heavy chain comprising a variable region comprising a CDR1 having the amino acid sequence as set forth in SEQ ID NO:62, a CDR2 having the amino acid sequence as set forth in SEQ ID NO:63, a CDR3 having the amino acid sequence as set forth in SEQ ID NO:64, and comprising a light chain comprising a variable region comprising a CDR1 having the amino acid sequence as set forth in SEQ ID NO:66, a CDR2 having the amino acid sequence as set forth in SEQ ID NO:67, a CDR3 having the amino acid sequence as set forth in SEQ ID NO:68.

In certain embodiments, the anti-CD45 antibody, or antigen binding portion thereof, comprises a heavy chain variable region comprising the amino acid sequence as set forth in SEQ ID NO:61.

In other embodiments, the anti-CD45 antibody, or antigen binding portion thereof, comprises a light chain variable region comprising the amino acid sequence as set forth in SEQ ID NO:65.

In certain embodiments, the anti-CD45 antibody, or antigen binding portion thereof, comprises a heavy chain variable region comprising the amino acid sequence as set forth in SEQ ID NO:61; and a light chain variable region comprising the amino acid sequence as set forth in SEQ ID NO:65.

In certain embodiments, the anti-CD45 antibody, or antigen binding portion thereof, comprises a heavy chain comprising the amino acid sequence as set forth in SEQ ID NO:69.

In certain embodiments, the anti-CD45 antibody, or antigen binding portion thereof, comprises a light chain comprising the amino acid sequence as set forth in SEQ ID NO:70.

In certain embodiments, the anti-CD45 antibody, or antigen binding portion thereof, comprises a heavy chain comprising the amino acid sequence as set forth in SEQ ID NO:69; and a light chain comprising the amino acid sequence as set forth in SEQ ID NO:70.

In one embodiment, the invention provides an isolated anti-CD45 antibody, or antigen binding portion thereof, comprising a heavy chain comprising a variable region comprising a CDR1 having the amino acid sequence as set forth in SEQ ID NO:72, a CDR2 having the amino acid sequence as set forth in SEQ ID NO:73, a CDR3 having the amino acid sequence as set forth in SEQ ID NO:74, and comprising a light chain comprising a variable region comprising a CDR1 having the amino acid sequence as set forth in SEQ ID NO:76, a CDR2 having the amino acid sequence as set forth in SEQ ID NO:77, a CDR3 having the amino acid sequence as set forth in SEQ ID NO:78.

In certain embodiments, the anti-CD45 antibody, or antigen binding portion thereof, comprises a heavy chain variable region comprising the amino acid sequence as set forth in SEQ ID NO:71.

In other embodiments, the anti-CD45 antibody, or antigen binding portion thereof, comprises a light chain variable region comprising the amino acid sequence as set forth in SEQ ID NO:75.

In certain embodiments, the anti-CD45 antibody, or antigen binding portion thereof, comprises a heavy chain variable region comprising the amino acid sequence as set forth in SEQ ID NO:71; and a light chain variable region comprising the amino acid sequence as set forth in SEQ ID NO:75.

In certain embodiments, the anti-CD45 antibody, or antigen binding portion thereof, comprises a heavy chain comprising the amino acid sequence as set forth in SEQ ID NO:79.

In certain embodiments, the anti-CD45 antibody, or antigen binding portion thereof, comprises a light chain comprising the amino acid sequence as set forth in SEQ ID NO:80.

In certain embodiments, the anti-CD45 antibody, or antigen binding portion thereof, comprises a heavy chain comprising the amino acid sequence as set forth in SEQ ID NO:79; and a light chain comprising the amino acid sequence as set forth in SEQ ID NO:80.

In one embodiment, the invention provides an isolated anti-CD45 antibody, or antigen binding portion thereof, comprising a heavy chain comprising a variable region comprising a CDR1 having the amino acid sequence as set forth in SEQ ID NO:82, a CDR2 having the amino acid sequence as set forth in SEQ ID NO:83, a CDR3 having the amino acid sequence as set forth in SEQ ID NO:84, and comprising a light chain comprising a variable region comprising a CDR1 having the amino acid sequence as set forth in SEQ ID NO:86, a CDR2 having the amino acid sequence as set forth in SEQ ID NO:87, a CDR3 having the amino acid sequence as set forth in SEQ ID NO:88.

In certain embodiments, the anti-CD45 antibody, or antigen binding portion thereof, comprises a heavy chain variable region comprising the amino acid sequence as set forth in SEQ ID NO:81.

In other embodiments, the anti-CD45 antibody, or antigen binding portion thereof, comprises a light chain variable region comprising the amino acid sequence as set forth in SEQ ID NO:85.

In certain embodiments, the anti-CD45 antibody, or antigen binding portion thereof, comprises a heavy chain variable region comprising the amino acid sequence as set forth in SEQ ID NO:81; and a light chain variable region comprising the amino acid sequence as set forth in SEQ ID NO:85.

In certain embodiments, the anti-CD45 antibody, or antigen binding portion thereof, comprises a heavy chain comprising the amino acid sequence as set forth in SEQ ID NO:89.

In certain embodiments, the anti-CD45 antibody, or antigen binding portion thereof, comprises a light chain comprising the amino acid sequence as set forth in SEQ ID NO:90.

In certain embodiments, the anti-CD45 antibody, or antigen binding portion thereof, comprises a heavy chain comprising the amino acid sequence as set forth in SEQ ID NO:89; and a light chain comprising the amino acid sequence as set forth in SEQ ID NO:90.

In one embodiment, the invention provides an isolated anti-CD45 antibody, or antigen binding portion thereof, comprising a heavy chain comprising a variable region comprising a CDR1 having the amino acid sequence as set forth in SEQ ID NO:92, a CDR2 having the amino acid sequence as set forth in SEQ ID NO:93, a CDR3 having the amino acid sequence as set forth in SEQ ID NO:94, and comprising a light chain comprising a variable region comprising a CDR1 having the amino acid sequence as set forth in SEQ ID NO:96, a CDR2 having the amino acid sequence as set forth in SEQ ID NO:97, a CDR3 having the amino acid sequence as set forth in SEQ ID NO:98.

In certain embodiments, the anti-CD45 antibody, or antigen binding portion thereof, comprises a heavy chain variable region comprising the amino acid sequence as set forth in SEQ ID NO:91.

In other embodiments, the anti-CD45 antibody, or antigen binding portion thereof, comprises a light chain variable region comprising the amino acid sequence as set forth in SEQ ID NO:95.

In certain embodiments, the anti-CD45 antibody, or antigen binding portion thereof, comprises a heavy chain variable region comprising the amino acid sequence as set forth in SEQ ID NO:91; and a light chain variable region comprising the amino acid sequence as set forth in SEQ ID NO:95.

In certain embodiments, the anti-CD45 antibody, or antigen binding portion thereof, comprises a heavy chain comprising the amino acid sequence as set forth in SEQ ID NO:99.

In certain embodiments, the anti-CD45 antibody, or antigen binding portion thereof, comprises a light chain comprising the amino acid sequence as set forth in SEQ ID NO:100.

In certain embodiments, the anti-CD45 antibody, or antigen binding portion thereof, comprises a heavy chain comprising the amino acid sequence as set forth in SEQ ID NO:99; and a light chain comprising the amino acid sequence as set forth in SEQ ID NO:100.

In one embodiment, the anti-CD45 antibody described herein is intact.

In certain embodiments, the anti-CD45 antibody fragment is selected from the group consisting of a Fab, F(ab')2, and an scFv.

In other embodiments, the anti-CD45 antibody, or antigen binding portion thereof, is a human antibody, or binding fragment thereof.

In other embodiments, the anti-CD45 antibody, or antigen binding portion thereof, comprises an Fc region comprising at least one amino acid substitution is H435 or 1235/H310/H435 (EU numbering). In one embodiment, the Fc region comprises a H435 amino acid substitution is H435A (EU numbering). In other embodiment, the Fc region comprises 1235/H310/H435 amino acid substitutions as set forth as 1235A/H310A/H435A (EU numbering).

In certain embodiments, the anti-CD45 antibody, or antigen binding portion thereof, is an IgG, e.g., an IgG1 or an IgG4.

Also described herein are antibody drug conjugates (ADCs) comprising anti-CD45 antibodies (or antigen binding fragments), wherein the antibody (or CD45 binding fragment) is conjugated to a cytotoxin via a linker.

In one embodiment, an anti-CD45 ADC comprises an anti-CD45 antibody conjugated to a cytotoxin an RNA polymerase inhibitor. In one embodiment the RNA polymerase inhibitor is an amatoxin.

In one embodiment, an anti-CD45 ADC comprises a cytotoxin which is an amatoxin represented by Formula (IA)

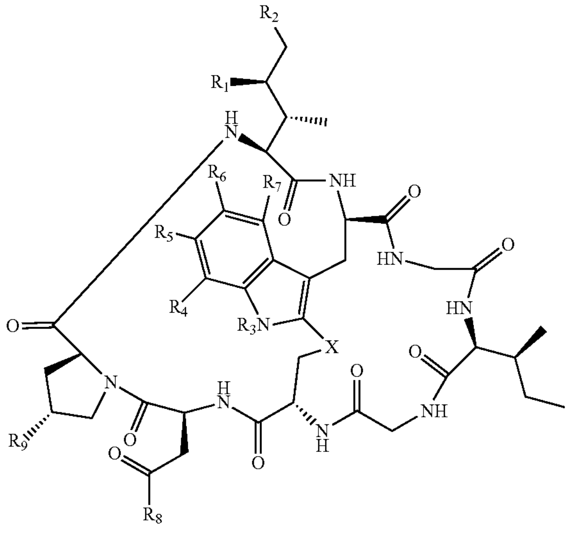

wherein $R_1$ is H, OH, $OR_A$, or $OR_C$;

$R_2$ is H, OH, $OR_B$, or $OR_C$;

$R_A$ and $R_B$, together with the oxygen atoms to which they are bound, combine to form an optionally substituted 5-membered heterocyclolalkyl group;

$R_3$ is H, $R_C$, or $R_D$;

$R_4$, $R_5$, $R_B$, and $R_7$ are each independently H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;

L is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, or optionally substituted heteroarylene; and Z is a chemical moiety formed from a coupling reaction between a reactive substituent present on L and a reactive substituent present within the antibody or antigen-binding fragment thereof, wherein Am comprises exactly one $R_C$ substituent.

In one embodiment, an anti-CD45 ADC has a formula of

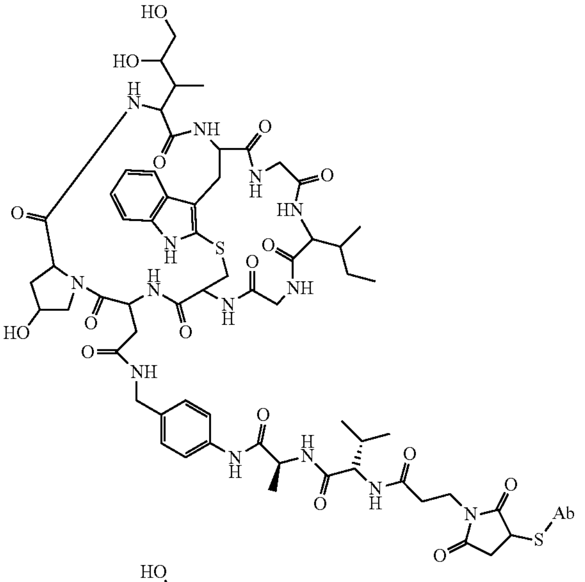

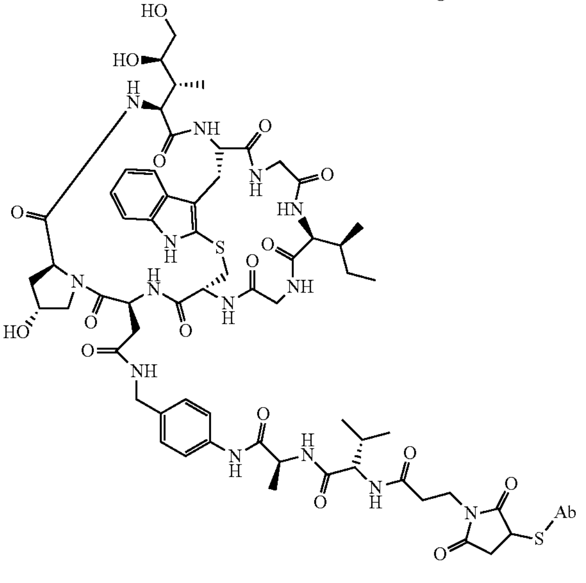

-continued

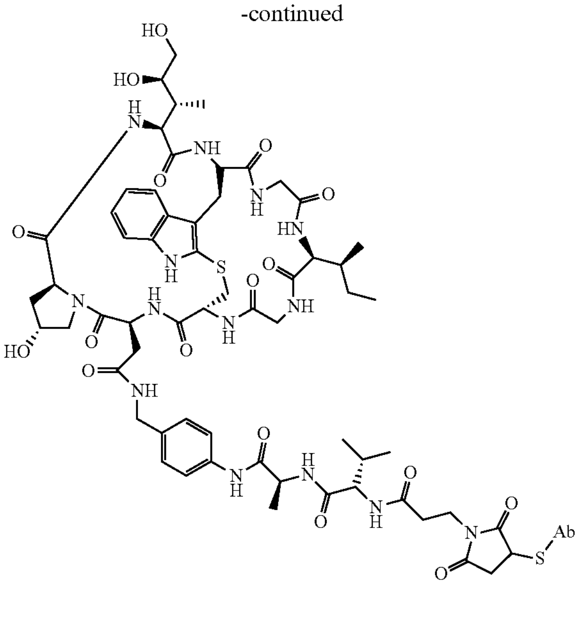

wherein Ab represents the point of attachment of the anti-CD45 antibody.

In one embodiment, an anti-CD45 ADC has a formula of

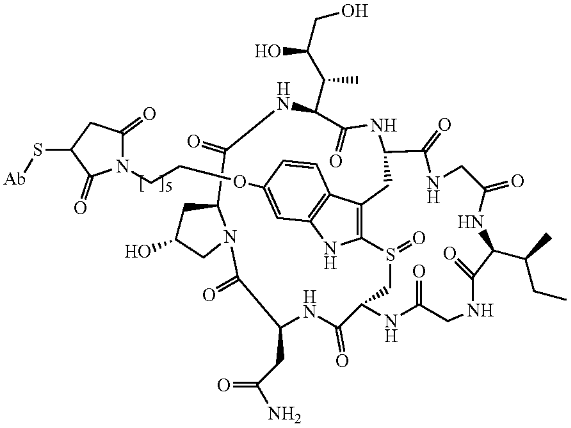

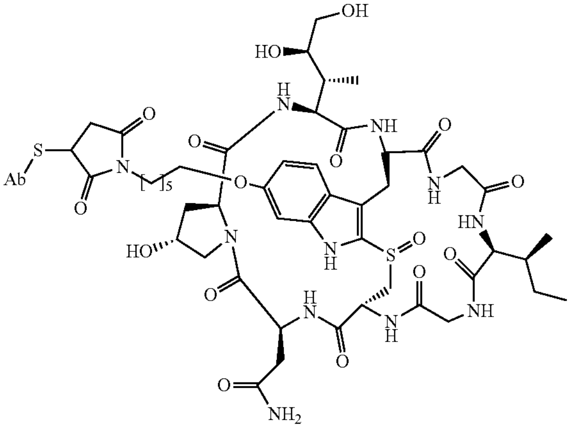

In one embodiment, an anti-CD45 ADC comprises a cytotoxin which is an amanitin, e.g., α-amanitin, β-amanitin, γ-amanitin, ε-amanitin, amanin, amaninamide, amanullin, amanullinic acid, and proamanullin.

In one embodiment, an anti-CD45 ADC comprises a cytotoxin selected from the group consisting of an pseudomonas exotoxin A, deBouganin, diphtheria toxin, saporin, maytansine, a maytansinoid, an auristatin (e.g., MMAE or MMAF), an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer.

In one embodiment, an anti-CD45 ADC comprises a cytotoxin that comprises a benzodiazepine moiety. In some embodiments, the anti-CD45 ADC comprises a pyrrolobenzodiazepine ("PBD"). In some embodiments, the anti-CD45 ADC comprises an indolinobenzodiazepine ("IGN").

In one embodiment, an anti-CD45 ADC comprises an anti-CD45 antibody conjugated to the toxin by way of a cysteine residue in the Fc domain of the antibody. In one embodiment, the cysteine residue is introduced by way of an amino acid substitution in the Fc domain of the antibody. In one embodiment, the amino acid substitution is D265C and/or V205C (EU numbering).

In certain embodiments, the anti-CD45 ADC has a drug to antibody ratio (DAR) of 1, 2, 3, 4, 5, 6, 7, or 8.

Also included in the invention is a pharmaceutical composition comprising an anti-CD45 antibody or ADC described herein, and a pharmaceutically acceptable carrier.

The anti-CD45 antibodies, fragments, and ADCs described herein can be used in a therapeutic method in a human patient, including, but not limited to, conditioning treatment prior to transplantation allogeneic or autologous).

In one embodiment, disclosed herein is a method of depleting a population of hematopoietic stem cells (HSC) in a human patient, the method comprising administering to the patient an effective amount of an anti-CD45 antibody, fragment, or ADC described herein. In certain embodiments, the method further comprises administering to the patient a transplant comprising hematopoietic stem cells.

In other embodiments, disclosed herein is a method comprising administering to a human patient a transplant (allogeneic or autologous) comprising hematopoietic stem cells, wherein the patient has been previously administered an anti-CD45 antibody, fragment, or ADC described herein in an amount sufficient to deplete a population of hematopoietic stem cells in the patient. In certain embodiments, the hematopoietic stem cell is a CD45+ cell.

In yet other embodiments, an anti-CD45 antibody, fragment, or ADC described herein is used to treat a human patient having a blood disease, a metabolic disorder, cancer, or an autoimmune disease, or severe combined immunodeficiency disease (SCID).

In one embodiment, an anti-CD45 antibody, fragment, or ADC described herein is administered to a human patient in order to treat leukemia in the human patient.

In other embodiments, disclosed herein is a method comprising administering to a human patient a transplant comprising hematopoietic stem cells, wherein the patient has been previously administered an anti-CD45 antibody, fragment, or ADC described herein in an amount sufficient to deplete a population of immune cells in the patient. In one embodiment, the immune cell is a CD137+, CD2+, or CD5+ cell. In other embodiments, the immune cell is a T cell.

BRIEF DESCRIPTION OF THE FIGURES

In FIG. 5A, SKNO1, Jurkat, REH (CD45+), or REH (CD45−/−) cell lines were cultured for seven days in the presence of Ab5-AM1 or a control, non-targeting isotype matched-ADC ("Isotype-AM1") and cell viability was measured by luminescence (y-axis) by Celltiter Glo as a function of antibody concentration (x-axis). In FIG. 5B, SKNO1, Jurkat, or REH (CD45+) cell lines were cultured for seven days in the presence of Ab4-AM2 or a control, non-targeting isotype matched-ADC ("Isotype-AM2") and cell viability was measured based on luminescence (y-axis) by Celltiter Glo as a function of antibody concentration (x-axis).

In FIG. 6A, human PBMCs were cultured for seven days in the presence of CD45-AM conjugate (Ab5-AM1) or a control, non-targeting isotype matched-ADC ("Isotype-AM1") and cell viability (y-axis) was measured by Celltiter Glo as a function of antibody concentration (x-axis). In FIG. 76B and FIG. 6C, primary human $CD34^+$ bone marrow cells were cultured for 5 days with an-anti-CD45-ADC (Ab5-AM1 in FIG. 6B; Ab2-AM2 or Ab4-AM2 in FIG. 6C) or Isotype-AM, and live CD34+CD90+ HSC counts (y-axis) were determined by flow cytometry as a function of antibody concentration (x-axis).

FIG. 10A shows the percentage of human CD3+ T-cells, CD19+ B-cells and CD33+ myeloid cells relative to baseline in mice 14 days post-administration of anti-CD45-ADCs (Ab2-AM2, Ab3-AM2, AbA-AM2). FIG. 10B shows the percentage of human CD45+ cells in peripheral blood 0, 7, and 14 days post-administration of anti-CD45-ADCs (Ab2-AM2 or Ab3-AM2). FIG. 10C shows the absolute number of human CD45 cells (left panel) and human HSCs (right panel) in the bone marrow of humanized NSG mice 14 days post-administration of anti-CD45-ADCs (Ab2-AM2 or Ab3-AM2). FIG. 10D graphically depicts the percentage and absolute number of HSCs (CD34+ cells, CD34+CD38−, and CD34+CD117+ cells) in the bone marrow of humanized NSG mice 14 days post-administration of anti-CD45 ADCs (Ab2-AM2 and Ab3-AM2). FIG. 10E graphically depicts the percentage of human CD45 cells in peripheral blood (relative to baseline), the absolute number of human CD45 cells in bone marrow, and the absolute number of HSCs (CD34+CD38− cells) in the bone marrow of humanized NSG mice 14 days post-administration of anti-CD45-ADCs (Ab5-AM1 or Ab7-AM1).

FIG. 11A graphically depicts the absolute number of lymphoid cells in the peripheral blood of cynomolgus monkeys at 72 hours post-administration of an anti-CD45 ADC (Ab5-AM1 or Ab7-AM1 at 0.5 mg/kg or 2 mg/kg). FIG. 11B graphically depicts the levels of white blood cells, HSCs, and lymphocytes in the bone marrow of cynomolgus monkeys on Day 7 post-administration of an anti-CD45 ADC (Ab4-AM1 at 1 mg/kg or Ab5-AM1 at 0.5 or 2 mg/kg).

FIG. 29A graphically depicts percent survival as a function of days post implant for mice in the indicated treatment groups. FIG. 29B graphically depicts the level of radiance (mean±SEM) in the REH-luciferase over the time course of the study in the indicated treatment groups. FIG. 29C are representative bioluminescence signal pseudo colored images captured on day 22-23 post-implantation for all treatment groups.

FIG. 30A graphically depicts percent survival as a function of days post implant for mice in the indicated treatment groups. FIG. 30B graphically depicts percent tumor burden (hCD45+) in peripheral blood as a function of days post implant for mice in each of the indicated treatment groups.

FIGS. 31A and 31B graphically depict percent survival as a function of days post implant for PDX model AML #1 mice (FIG. 31A) or PDX model AML #2 mice (FIG. 31B) in the indicated treatment groups. The inset in each of FIGS. 31A and 31B depicts a flow cytometry analysis of each AML PDX model to assess CD117 and CD45 cell surface expression on splenocytes from diseased mice. FIGS. 31C and 31D graphically depict percent tumor burden (hCD45+) in peripheral blood as a function of days post implant for PDX model AML #1 mice (FIG. 31C) and PDX model AML #2 mice (FIG. 31D) in each of the indicated treatment groups.

FIG. 32 depicts a multiple sequence alignment of the heavy chain variable regions and the light chain variable regions of anti-CD45 antibodies Ab1, Ab2, Ab3, Ab4, Ab5, Ab6, and Ab7. The CDRs of each variable region are indicated in bold type.

DETAILED DESCRIPTION

Figure 1:
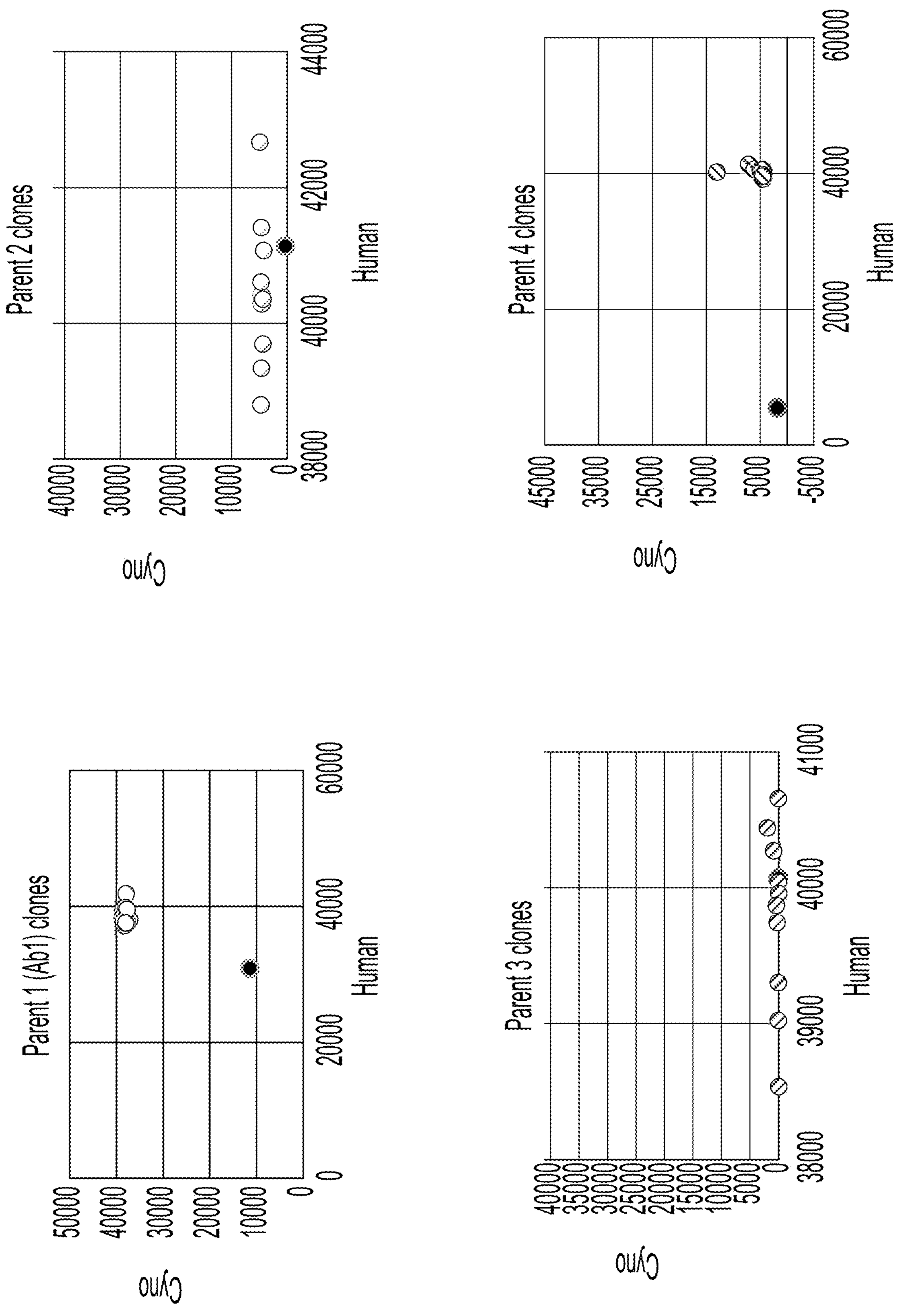
FIG. 1 graphically depicts the results of an in vitro binding assay, in which binding of affinity matured anti-CD45 antibodies and their corresponding parent antibodies (Parents 1-4) were assessed for binding to human CD45 or cynomolgus CD45. Parent 1 corresponds with Ab1 described herein. Binding was measured by Bio-Layer Interferometry (BLI) of the indicated purified IgG (sensor-associated) incubated with purified human CD45 or cynomolgus CD45 ectodomain.

Disclosed herein are novel anti-CD45 antibodies, antigen binding fragments thereof, and conjugates thereof (e.g., antibody drug conjugates; ADCs) that are useful, e.g., because they cross-react between human CD45 and non-human primate CD45. Further, anti-CD45 antibodies, and fragments thereof, described herein can be used as therapeutic agents. For example, anti-CD45 antibodies, fragments thereof, and anti-CD45 ADCs can be used to treat patients with conditions for which depletion of CD45+ cells is beneficial, including, but not limited to, leukemias and lymphomas, as well as patients with autoimmune diseases such as multiple sclerosis and scleroderma. In addition, the anti-hematopoietic cell antibodies (anti-CD45 antibodies) included hereincri are useful in hematopoietic stem cell therapies. For example, the antibodies or ADCs herein are useful in conditioning procedures, in which a patient is prepared for receipt of a transplant including hematopoietic stem cells. Such procedures promote the engraftment of a hematopoietic stem cell transplant. According to the methods described herein, a patient may be conditioned for hematopoietic stem cell transplant therapy by administration to the patient of an anti-CD45 ADC, antibody or antigen-binding fragment thereof capable of binding CD45 (e.g., CD45 expressed by hematopoietic cells (e.g., hematopoietic stem cells or mature immune cells (e.g., T cells)). As described herein, the anti-CD45 antibody may be covalently conjugated to a cytotoxin so as to form an antibody drug conjugate (ADC). Administration of an ADC capable of binding CD45 to a patient in need of hematopoietic stem cell transplant therapy can promote the engraftment of a hematopoietic stem cell graft, for example, by selectively depleting endogenous hematopoietic stem cells, thereby creating a vacancy filled by an exogenous hematopoietic stem cell transplant.

The sections that follow provide novel anti-CD45 antibodies, and fragments thereof, that have unique properties, e.g., cross reactivity with both human and non-human primate CD45. The sections that follow also provide a description of the anti-CD45 antibodies, or conjugates thereof, that can be administered to a patient, such as a patient suffering from a cancer or autoimmune disease, or a patient in need of hematopoietic stem cell transplant therapy in order to promote engraftment of hematopoietic stem cell grafts, as well as methods of administering such therapeutics to a patient (e.g., prior to hematopoietic stem cell transplantation).

Definitions

As used herein, the term "about" refers to a value that is within 5% above or below the value being described. For example, the term "about 100 nM" indicates a range of 95-105 nM.

As used herein, the term "allogeneic", in the context of transplantation, is used to define a transplant (e.g., cells, tissue or an organ transplant) that is transplanted from a donor to a recipient, wherein the recipient is a different individual of the same species, relative to the donor.

As used herein, the term "autologous", in the context of transplantation, refers to a transplant where the donor and recipient are the same individual, i.e., the same subject.

As used herein, the term "xenogeneic", in the context of transplantation, refers to a transplant where the donor and recipient are of different species.

As used herein, the term "immune cell" is intended to include, but is not limited to, a cell that is of hematopoietic origin and that plays a role in the immune response. Immune cells include, but are not limited to, T cells and natural killer (NK) cells. Natural killer cells are well known in the art. In one embodiment, natural killer cells include cell lines, such as NK-92 cells. Further examples of NK cell lines include NKG, YT, NK-YS, HANK-1, YTS cells, and NKL cells. An immune cell can be allogeneic or autologous.

As used herein, the term "antibody" refers to an immunoglobulin molecule that specifically binds to, or is immunologically reactive with, a particular antigen. An antibody includes, but is not limited to, monoclonal antibodies, polyclonal antibodies, multispecific antibodies (e.g., bispecific antibodies), and antibody fragments so long as they exhibit the desired antigen-binding activity.

Generally, antibodies comprise heavy and light chains containing antigen binding regions. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH, and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The term "antigen-binding fragment," or "antigen binding portion" of an antibody, as used herein, refers to one or more portions of an antibody that retain the ability to specifically bind to a target antigen. The antigen-binding function of an antibody can be performed by fragments of a full-length antibody. The antibody fragments can be, for example, a Fab, F(ab')2, scFv, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the VL, VH, CL, and CH1 domains; (ii) a F(ab')2 fragment, a bivalent fragment containing two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb including VH and VL domains; (vi) a dAb fragment that consists of a VH domain (see, e.g., Ward et al., Nature 341:544-546, 1989); (vii) a dAb which consists of a VH or a VL domain; (viii) an isolated complementarity determining region (CDR); and (ix) a combination of two or more (e.g., two, three, four, five, or six) isolated CDRs which may optionally be joined by a synthetic linker. Furthermore, although the two domains of the Fv fragment, VL and VH, are coded for by separate genes, they can be joined, using recombinant methods, by a linker that enables them to be made as a single protein chain in which the VL and VH regions pair to form monovalent molecules (known as single chain Fv (scFv); see, for example, Bird et al., Science 242:423-426, 1988 and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

An "intact" or "full length" antibody, as used herein, refers to an antibody having two heavy (H) chain polypeptides and two light (L) chain polypeptides interconnected by disulfide bonds. In certain embodiments, a toxin can be conjugated to an intact anti-CD45 antibody having heavy and/or light chain amino acid sequences described herein.

The term "monoclonal antibody" as used herein refers to an antibody that is derived from a single clone, including any eukaryotic, prokaryotic, or phage clone, by any means available or known in the art, and is not limited to antibodies produced through hybridoma technology. Monoclonal antibodies useful with the present disclosure can be prepared using a wide variety of techniques known in the art including the use of hybridoma, recombinant, and phage display technologies, or a combination thereof.

The terms "Fc region," "Fc domain," and "IgG Fc domain" as used herein refer to the portion of an immunoglobulin, e.g., an IgG molecule, that correlates to a crystallizable fragment obtained by papain digestion of an IgG molecule. The Fc region comprises the C-terminal half of two heavy chains of an IgG molecule that are linked by disulfide bonds. It has no antigen binding activity but contains the carbohydrate moiety and binding sites for complement and Fc receptors, including the FcRn receptor (see below). For example, an Fc domain contains the entire second constant domain CH2 (residues at EU positions 231-340 of IgG1) and the third constant domain CH3 (residues at EU positions 341-447 of human IgG1). As used herein, the Fc domain includes the "lower hinge region" (residues at EU positions 233-239 of IgG1).

Fc can refer to this region in isolation, or this region in the context of an antibody, antibody fragment, or Fc fusion protein. Polymorphisms have been observed at a number of positions in Fc domains, including but not limited to EU positions 270, 272, 312, 315, 356, and 358, and thus slight differences between the sequences presented in the instant application and sequences known in the art can exist. Thus, a "wild type IgG Fc domain" or "WT IgG Fc domain" refers to any naturally occurring IgG Fc region (i.e., any allele). The sequences of the heavy chains of human IgG1, IgG2, IgG3 and IgG4 can be found in a number of sequence databases, for example, at the Uniprot database (www.uniprot.org) under accession numbers P01857 (IGHG1_HUMAN), P01859 (IGHG2_HUMAN), P01860 (IGHG3_HUMAN), and P01861 (IGHG1_HUMAN), respectively.

The terms "modified Fc region" or "variant Fc region" as used herein refers to an IgG Fc domain comprising one or more amino acid substitutions, deletions, insertions or modifications introduced at any position within the Fc domain. In certain aspects a variant IgG Fc domain comprises one or more amino acid substitutions resulting in decreased or ablated binding affinity for an Fc gamma R and/or C1q as compared to the wild type Fc domain not comprising the one or more amino acid substitutions. Further, Fc binding interactions are essential for a variety of effector functions and downstream signaling events including, but not limited to, antibody dependent cell-mediated cytotoxicity (ADCC) and complement dependent cytotoxicity (CDC). Accordingly, in certain aspects, an antibody comprising a variant Fc domain (e.g., an antibody, fusion protein or conjugate) can exhibit altered binding affinity for at least one or more Fc ligands (e.g., Fc gamma Rs) relative to a corresponding antibody otherwise having the same amino acid sequence but not comprising the one or more amino acid substitution, deletion, insertion or modifications such as, for example, an unmodified Fc region containing naturally occurring amino acid residues at the corresponding position in the Fc region.

Variant Fc domains are defined according to the amino acid modifications that compose them. For all amino acid substitutions discussed herein in regard to the Fc region, numbering is always according to the EU index as in Kabat. Thus, for example, D265C is an Fc variant with the aspartic acid (D) at EU position 265 substituted with cysteine (C) relative to the parent Fc domain. It is noted that the order in which substitutions are provided is arbitrary.

The terms "Fc gamma receptor" or "Fc gamma R" as used herein refer to any member of the family of proteins that bind the IgG antibody Fc region and are encoded by the FcgammaR genes. In humans this family includes but is not limited to FcgammaRI (CD64), including isoforms FcgammaRIa, FcgammaRIb, and FcgammaRIc; FcgammaRII (CD32), including isoforms FcgammaRIIa (including allotypes H131 and R131), FcgammaRIIb (including FcgammaRIIb-1 and FcgammaRIIb-2), and FcgammaRIIc; and FcgammaRIII (CD16), including isoforms FcgammaRIIIa (including allotypes V158 and F158) and FcgammaRIIIb (including allotypes FcgammaRIIIb-NA1 and FcgammaRIIIb-NA2), as well as any undiscovered human FcgammaRs or FcgammaR isoforms or allotypes. An FcgammaR can be from any organism, including but not limited to humans, mice, rats, rabbits, and monkeys. Mouse FcgammaRs include but are not limited to FcgammaRI (CD64), FcgammaRII (CD32), FcgammaRIII (CD16), and FcgammaRIII-2 (CD16-2), as well as any undiscovered mouse FcgammaRs or FcgammaR isoforms or allotypes.

The term "effector function" as used herein refers to a biochemical event that results from the interaction of an Fc domain with an Fc receptor. Effector functions include but are not limited to ADCC, ADCP, and CDC. By "effector cell" as used herein is meant a cell of the immune system that expresses or one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and gamma-delta T cells, and can be from any organism included but not limited to humans, mice, rats, rabbits, and monkeys.

The term "silent", "silenced", or "silencing" as used herein refers to an antibody having a modified Fc region described herein that has decreased binding to an Fc gamma receptor (FcγR) relative to binding of an identical antibody comprising an unmodified Fc region to the FcγR (e.g., a decrease in binding to a FcγR by at least 70%, at least 80%, at least 90%, at least 95%, at least 98%, at least 99%, or 100% relative to binding of the identical antibody comprising an unmodified Fc region to the FcγR as measured by, e.g., BLI). In some embodiments, the Fc silenced antibody has no detectable binding to an FcγR. Binding of an antibody having a modified Fc region to an FcγR can be determined using a variety of techniques known in the art, for example but not limited to, equilibrium methods (e.g., enzyme-linked immunoabsorbent assay (ELISA); KinExA, Rathanaswami et al. Analytical Biochemistry, Vol. 373:52-60, 2008; or radioimmunoassay (RIA)), or by a surface plasmon resonance assay or other mechanism of kinetics-based assay (e.g., BIACORE® analysis or Octet™ analysis (forteBIO)), and other methods such as indirect binding assays, competitive binding assays fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions. One example of a competitive binding assay is a radioimmunoassay comprising the incubation of labeled antigen with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound in the presence of increasing amounts of an unlabeled second antibody.

As used herein, the term "identical antibody comprising an unmodified Fc region" refers to an antibody that lacks the recited amino acid substitutions (e.g., D265C,H435A), but otherwise has the same amino acid sequence as the Fc modified antibody to which it is being compared.

The terms "antibody-dependent cell-mediated cytotoxicity" or "ADCC" refer to a form of cytotoxicity in which a polypeptide comprising an Fc domain, e.g., an antibody, bound onto Fc receptors (FcRs) present on certain cytotoxic cells (e.g., primarily NK cells, neutrophils, and macrophages) and enables these cytotoxic effector cells to bind specifically to an antigen-bearing "target cell" and subsequently kill the target cell with cytotoxins. (Hogarth et al., Nature review Drug Discovery 2012, 11:313) It is contemplated that, in addition to antibodies and fragments thereof, other polypeptides comprising Fc domains, e.g., Fc fusion proteins and Fc conjugate proteins, having the capacity to bind specifically to an antigen-bearing target cell will be able to effect cell-mediated cytotoxicity.

For simplicity, the cell-mediated cytotoxicity resulting from the activity of a polypeptide comprising an Fc domain is also referred to herein as ADCC activity. The ability of any particular polypeptide of the present disclosure to mediate lysis of the target cell by ADCC can be assayed. To assess ADCC activity, a polypeptide of interest (e.g., an antibody) is added to target cells in combination with immune effector cells, resulting in cytolysis of the target cell. Cytolysis is generally detected by the release of label (e.g., radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Bruggemann et al., J. Exp. Med. 166:1351 (1987); Wilkinson et al., J. Immunol. Methods 258:183 (2001); Patel et al., J. Immunol. Methods 184:29 (1995). Alternatively, or additionally, ADCC activity of the antibody of interest can be assessed in vivo, e.g., in an animal model such as that disclosed in Clynes et al., Proc. Natl. Acad. Sci. USA 95:652 (1998).

As used herein, the terms "condition" and "conditioning" refer to processes by which a patient is prepared for receipt of a transplant, e.g., a transplant containing hematopoietic stem cells. Such procedures promote the engraftment of a hematopoietic stem cell transplant (for instance, as inferred from a sustained increase in the quantity of viable hematopoietic stem cells within a blood sample isolated from a patient following a conditioning procedure and subsequent hematopoietic stem cell transplantation. According to the methods described herein, a patient may be conditioned for hematopoietic stem cell transplant therapy by administration to the patient of an ADC, antibody or antigen-binding fragment thereof capable of binding CD45 expressed by hematopoietic stem cells. As described herein, the antibody may be covalently conjugated to a cytotoxin so as to form a drug-antibody conjugate. Administration of an antibody, antigen-binding fragment thereof, or ADC capable of binding the foregoing antigen to a patient in need of hematopoietic stem cell transplant therapy can promote the engraftment of a hematopoietic stem cell graft, for example, by selectively depleting endogenous hematopoietic stem cells, thereby creating a vacancy filled by an exogenous hematopoietic stem cell transplant.

As used herein, the term "effective amount" or "therapeutically effective amount" refers to an amount of a therapeutic agent, e.g., an anti-CD45 ADC, that is sufficient to achieve the desired result in the context of treating, preventing, ameliorating, or reducing the symptoms of a disease or disorder in a patient. For example, in some embodiments, a therapeutically effective amount of an anti-CD45 antibody or ADC is an amount sufficient to reduce or deplete a population of CD45+ cells in a patient. In other embodiments, a therapeutically effective amount of an anti-CD45 antibody or ADC is an amount sufficient to condition a patient for receipt of a hematopoietic stem cell transplant. In such embodiments, the therapeutically effective amount can be, for example, an amount sufficient to selectively deplete endogenous hematopoietic stem cells from the patient, and/or an amount sufficient to promote the engraftment of a hematopoietic stem cell transplant in the patient. In other embodiments, a therapeutically effective amount of an anti-CD45 antibody or ADC is an amount sufficient to have an effect on an autoimmune disease or cancer in a human patient.

As used herein, the term "half-life" refers to the time it takes for the plasma concentration of the antibody drug in the body to be reduced by one half or 50% in a subject, e.g., a human subject. This 50% reduction in serum concentration reflects the amount of drug circulating.

As used herein, the phrase "substantially cleared from the blood" refers to a point in time following administration of a therapeutic agent (such as an anti-CD45 antibody, or antigen-binding fragment thereof) to a patient when the concentration of the therapeutic agent in a blood sample isolated from the patient is such that the therapeutic agent is not detectable by conventional means (for instance, such that the therapeutic agent is not detectable above the noise threshold of the device or assay used to detect the therapeutic agent). A variety of techniques known in the art can be used to detect antibodies, or antibody fragments, such as ELISA-based detection assays known in the art or described herein. Additional assays that can be used to detect antibodies, or antibody fragments, include immunoprecipitation techniques and immunoblot assays, among others known in the art.

The terms "specific binding" or "specifically binding", as used herein, refers to the ability of an antibody to recognize and bind to a specific protein structure (epitope) rather than to proteins generally. If an antibody is specific for epitope "A", the presence of a molecule containing epitope A (or free, unlabeled A), in a reaction containing labeled "A" and the antibody, will reduce the amount of labeled A bound to the antibody. By way of example, an antibody "binds specifically" to a target if the antibody, when labeled, can be competed away from its target by the corresponding non-labeled antibody. In one embodiment, an antibody specifically binds to a target, e.g., CD45, if the antibody has a $K_D$ for the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, or less (less meaning a number that is less than $10^{-12}$, e.g. $10^{-13}$). In one embodiment, the term "specific binding to CD45" or "specifically binds to CD45," as used herein, refers to an antibody or that binds to CD45 and has a dissociation constant ($K_D$) of $1.0\times10^{-7}$ M or less, as determined by surface plasmon resonance. In one embodiment, $K_D$ (M) is determined according to standard bio-layer interferometery (BLI). In one embodiment, $K_{off}$ (1/s) is determined according to standard bio-layer interferometery (BLI). It shall be understood, however, that the antibody may be capable of specifically binding to two or more antigens which are related in sequence. For example, in one embodiment, an antibody can specifically bind to both human and a non-human (e.g., mouse, cynomolgus or non-human primate) orthologs of CD45. Thus, as used herein, an antibody that "specifically binds to human CD45" is intended to refer to an antibody that binds to human CD45 (and possibly CD45 from one or more non-human species, such as cynomolgus) but does not substantially bind to non-CD45 proteins. Preferably, the antibody binds to human CD45 with a $K_D$ of $1\times10^{-7}$ M or less, a $K_D$ of $5\times10^{-8}$ M or less, a $K_D$ of $3\times10^{-8}$ M or less, a $K_D$ of $1\times10^{-8}$ M or less, or a $K_D$ of $5\times10^{-9}$ M or less.

As used herein, the term "human antibody" is intended to include antibodies having variable regions derived from human germline immunoglobulin sequences. In embodiments in which a human antibody contains a constant region, the constant region can likewise be derived from human germline immunoglobulin sequences. A human antibody may include amino acid residues not encoded by human germline immunoglobulin sequences (e.g., mutations introduced by random or site-specific mutagenesis in vitro or during gene rearrangement or by somatic mutation in vivo). However, the term "human antibody", as used herein, is not intended to include antibodies in which CDR sequences derived from the germline of another mammalian species, such as a mouse, have been grafted onto human framework sequences. A human antibody can be produced in a human cell (for example, by recombinant expression) or by a non-human animal or a prokaryotic or eukaryotic cell that is capable of expressing functionally rearranged human immunoglobulin (such as heavy chain and/or light chain) genes. When a human antibody is a single chain antibody, it can include a linker peptide that is not found in native human antibodies. For example, an Fv can contain a linker peptide, such as two to about eight glycine or other amino acid residues, which connects the variable region of the heavy chain and the variable region of the light chain. Human antibodies can be made by a variety of methods known in the art including phage display methods or yeast display methods using antibody libraries derived from human immunoglobulin sequences. Human antibodies can also be produced using transgenic mice that are incapable of expressing functional endogenous immunoglobulins, but which can express human immunoglobulin genes (see, for example, PCT Publication Nos. WO 1998/24893; WO 1992/01047; WO 1996/34096; WO 1996/33735; U.S. Pat. Nos. 5,413,923; 5,625,126; 5,633,425; 5,569,825; 5,661,016; 5,545,806; 5,814,318; 5,885,793; 5,916,771; and 5,939,598).

The term "chimeric antibody" is intended to refer to antibodies in which the variable region sequences are derived from one species and the constant region sequences are derived from another species, such as an antibody in which the variable region sequences are derived from a rat antibody and the constant region sequences are derived from a human antibody.

"Humanized" forms of non-human (e.g., murine or rat) antibodies are immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise all or a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332.

Also provided are "conservative sequence modifications" of the sequences set forth in SEQ ID NOs described herein. Conservative sequence modifications include nucleotide and amino acid sequence modifications which do not abrogate the binding of an antibody or antigen binding portion thereof containing an amino acid sequence, encoded by a nucleotide sequence, provided herein to its cognate antigen (e.g., CD45). Such conservative sequence modifications include conservative nucleotide and amino acid substitutions, as well as, nucleotide and amino acid additions and deletions. For example, modifications can be introduced into SEQ ID NOs described herein by standard techniques known in the art, such as site-directed mutagenesis and PCR-mediated mutagenesis. Conservative sequence modifications include conservative amino acid substitutions, in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-CD73 antibody is preferably replaced with another amino acid residue from the same side chain family. Methods of identifying nucleotide and amino acid conservative substitutions that do not eliminate antigen binding are well-known in the art (see, e.g., Brummell et al., Biochem. 32:1180-1187 (1993); Kobayashi et al. Protein Eng. 12(10):879-884 (1999); and Burks et al. Proc. Natl. Acad. Sci. USA 94:412-417 (1997)).

As used herein, the term "engraftment potential" is used to refer to the ability of hematopoietic stem and progenitor cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s) into which stem cells have homed, colonized, or become engrafted; or by evaluation of the progress of a subject through disease progression, survival of hematopoietic stem and progenitor cells, or survival of a recipient. Engraftment can also be determined by measuring white blood cell counts in peripheral blood during a post-transplant period. Engraftment can also be assessed by measuring recovery of marrow cells by donor cells in a bone marrow aspirate sample.

As used herein, the term "hematopoietic stem cells" ("HSCs") refers to immature blood cells having the capacity to self-renew and to differentiate into mature blood cells comprising diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B cells and T cells). Such cells may include $CD34^+$ cells. $CD34^+$ cells are immature cells that express the CD34 cell surface marker. In humans, CD34+ cells are believed to include a subpopulation of cells with the stem cell properties defined above, whereas in mice, HSCs are CD34−. In addition, HSCs also refer to long term repopulating HSCs (LT-HSC) and short term repopulating HSCs (ST-HSC). LT-HSCs and ST-HSCs are differentiated, based on functional potential and on cell surface marker expression. For example, human HSCs are CD34+, CD38−, CD45RA−, CD90+, CD49F+, and lin− (negative for mature lineage markers including CD2, CD3, CD4, CD7, CD8, CD10, CD11B, CD19, CD20, CD56, CD235A). In mice, bone marrow LT-HSCs are CD34−, SCA-1+, C-kit+, CD135−, Slamfl/CD150+, CD48−, and lin− (negative for mature lineage markers including Ter119, CD11b, Gr1, CD3, CD4, CD8, B220, IL7ra), whereas ST-HSCs are CD34+, SCA-1+, C-kit+, CD135−, Slamfl/CD150+, and lin− (negative for mature lineage markers including Ter119, CD11 b, Gr1, CD3, CD4, CD8, B220, IL7ra). In addition, ST-HSCs are less quiescent and more proliferative than LT-HSCs under homeostatic conditions. However, LT-HSC have greater self-renewal potential (i.e., they survive throughout adulthood, and can be serially transplanted through successive recipients), whereas ST-HSCs have limited self-renewal (i.e., they survive for only a limited period of time, and do not possess serial transplantation potential). Any of these HSCs can be used in the methods described herein. ST-HSCs are particularly useful because they are highly proliferative and thus, can more quickly give rise to differentiated progeny.

As used herein, the term "hematopoietic stem cell functional potential" refers to the functional properties of hematopoietic stem cells which include 1) multi-potency (which refers to the ability to differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, T cells and B cells), 2) self-renewal (which refers to the ability of hematopoietic stem cells to give rise to daughter cells that have equivalent potential as the mother cell, and further that this ability can repeatedly occur throughout the lifetime of an individual without exhaustion), and 3) the ability of hematopoietic stem cells or progeny thereof to be reintroduced into a transplant recipient whereupon they home to the hematopoietic stem cell niche and re-establish productive and sustained hematopoiesis.

As used herein, the terms "subject" and "patient" refer to an organism, such as a human, that receives treatment for a particular disease or condition as described herein. In some embodiments, the subject or patient referenced in the methods provided herein is a human subject.

As used herein, the term "recipient" refers to a patient that receives a transplant, such as a transplant containing a population of hematopoietic stem cells. The transplanted cells administered to a recipient may be, e.g., autologous, syngeneic, or allogeneic cells.

As used herein "to treat" or "treatment", refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act. For example, treatment can refer to reducing the severity and/or frequency of disease symptoms, eliminating disease symptoms and/or the underlying cause of said symptoms, reducing the frequency or likelihood of disease symptoms and/or their underlying cause, and improving or remediating damage caused, directly or indirectly, by disease. Beneficial or desired clinical results include, but are not limited to, promoting the engraftment of exogenous hematopoietic cells in a patient following antibody conditioning therapy as described herein and subsequent hematopoietic stem cell transplant therapy Additional beneficial results include an increase in the cell count or relative concentration of hematopoietic stem cells in a patient in need of a hematopoietic stem cell transplant following conditioning therapy and subsequent administration of an exogenous hematopoietic stem cell graft to the patient. Beneficial results of therapy described herein may also include an increase in the cell count or relative concentration of one or more cells of hematopoietic lineage, such as a megakaryocyte, thrombocyte, platelet, erythrocyte, mast cell, myeloblast, basophil, neutrophil, eosinophil, microglial cell, granulocyte, monocyte, osteoclast, antigen-presenting cell, macrophage, dendritic cell, natural killer cell, T-lymphocyte, or B-lymphocyte, following conditioning therapy and subsequent hematopoietic stem cell transplant therapy. Additional beneficial results may include the reduction in quantity of a disease-causing cell population, such as a population of cancer cells (e.g., CD45+ leukemic cells) or autoimmune cells (e.g., CD45+ autoimmune lymphocytes, such as a CD45+ T-cell that expresses a T-cell receptor that cross-reacts with a self antigen). Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state is completely avoided.

As used herein, patients that are "in need of" a hematopoietic stem cell transplant include patients that exhibit a defect or deficiency in one or more blood cell types, as well as patients having a stem cell disorder, autoimmune disease, cancer, or other pathology described herein. Hematopoietic stem cells generally exhibit 1) multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal, and can thus give rise to daughter cells that have equivalent potential as the mother cell, and 3) the ability to be reintroduced into a transplant recipient whereupon they home to the hematopoietic stem cell niche and re-establish productive and sustained hematopoiesis. Hematopoietic stem cells can thus be administered to a patient defective or deficient in one or more cell types of the hematopoietic lineage in order to re-constitute the defective or deficient population of cells in vivo. For example, the patient may be suffering from cancer, and the deficiency may be caused by administration of a chemotherapeutic agent or other medicament that depletes, either selectively or non-specifically, the cancerous cell population. Additionally or alternatively, the patient may be suffering from a hemoglobinopathy (e.g., a non-malignant hemoglobinopathy), such as sickle cell anemia, thalassemia, Fanconi anemia, aplastic anemia, and Wiskott-Aldrich syndrome. The subject may be one that is suffering from adenosine deaminase severe combined immunodeficiency (ADA SCID), HIV/AIDS, metachromatic leukodystrophy, Diamond-Blackfan anemia, and Schwachman-Diamond syndrome. The subject may have or be affected by an inherited blood disorder (e.g., sickle cell anemia) or an autoimmune disorder. Additionally or alternatively, the subject may have or be affected by a malignancy, such as neuroblastoma or a hematologic cancer. For instance, the subject may have a leukemia, lymphoma, or myeloma. In some embodiments, the subject has acute myeloid leukemia, acute lymphoid leukemia, chronic myeloid leukemia, chronic lymphoid leukemia, multiple myeloma, diffuse large B-cell lymphoma, or non-Hodgkin's lymphoma. In some embodiments, the subject has myelodysplastic syndrome. In some embodiments, the subject has an autoimmune disease, such as scleroderma, multiple sclerosis, ulcerative colitis, Crohn's disease, Type 1 diabetes, or another autoimmune pathology described herein. In some embodiments, the subject is in need of chimeric antigen receptor T-cell (CART) therapy. In some embodiments, the subject has or is otherwise affected by a metabolic storage disorder. The subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy. Additionally or alternatively, a patient "in need of" a hematopoietic stem cell transplant may one that is or is not suffering from one of the foregoing pathologies, but nonetheless exhibits a reduced level (e.g., as compared to that of an otherwise healthy subject) of one or more endogenous cell types within the hematopoietic lineage, such as megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes. One of skill in the art can readily determine whether one's level of one or more of the foregoing cell types, or other blood cell type, is reduced with respect to an otherwise healthy subject, for instance, by way of flow cytometry and fluorescence activated cell sorting (FACS) methods, among other procedures, known in the art.

As used herein, the phrase "stem cell disorder" broadly refers to any disease, disorder, or condition that may be treated or cured by conditioning a subject's target tissues, and/or by ablating an endogenous stem cell population in a target tissue (e.g., ablating an endogenous hematopoietic stem or progenitor cell population from a subject's bone marrow tissue) and/or by engrafting or transplanting stem cells in a subject's target tissues. For example, Type I diabetes has been shown to be cured by hematopoietic stem cell transplant and may benefit from conditioning in accordance with the compositions and methods described herein. Additional disorders that can be treated using the compositions and methods described herein include, without limitation, sickle cell anemia, thalassemias, Fanconi anemia, aplastic anemia, Wiskott-Aldrich syndrome, ADA SCID, HIV/AIDS, metachromatic leukodystrophy, Diamond-Blackfan anemia, and Schwachman-Diamond syndrome. Additional diseases that may be treated using the patient conditioning and/or hematopoietic stem cell transplant methods described herein include inherited blood disorders (e.g., sickle cell anemia) and autoimmune disorders, such as scleroderma, multiple sclerosis, ulcerative colitis, and Crohn's disease. Additional diseases that may be treated using the conditioning and/or transplantation methods described herein include a malignancy, such as a neuroblastoma or a hematologic cancer, such as leukemia, lymphoma, and myeloma. For instance, the cancer may be acute myeloid leukemia, acute lymphoid leukemia, chronic myeloid leukemia, chronic lymphoid leukemia, multiple myeloma, diffuse large B-cell lymphoma, or non-Hodgkin's lymphoma. Additional diseases treatable using the conditioning and/or transplantation methods described herein include myelodysplastic syndrome. In some embodiments, the subject has or is otherwise affected by a metabolic storage disorder. For example, the subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy.

As used herein, the term "vector" includes a nucleic acid vector, such as a plasmid, a DNA vector, a plasmid, a RNA vector, virus, or other suitable replicon. Expression vectors described herein may contain a polynucleotide sequence as well as, for example, additional sequence elements used for the expression of proteins and/or the integration of these polynucleotide sequences into the genome of a mammalian cell. Certain vectors that can be used for the expression of antibodies and antibody fragments of the invention include plasmids that contain regulatory sequences, such as promoter and enhancer regions, which direct gene transcription. Other useful vectors for expression of antibodies and antibody fragments contain polynucleotide sequences that enhance the rate of translation of these genes or improve the stability or nuclear export of the mRNA that results from gene transcription. These sequence elements may include, for example, 5' and 3' untranslated regions and a polyadenylation signal site in order to direct efficient transcription of the gene carried on the expression vector. The expression vectors described herein may also contain a polynucleotide encoding a marker for selection of cells that contain such a vector. Examples of a suitable marker include genes that encode resistance to antibiotics, such as ampicillin, chloramphenicol, kanamycin, and nourseothricin.

As used herein, the term "conjugate" or "antibody drug conjugate" or "ADC" refers to an antibody which is linked to a cytotoxin or toxin, used interchangeably throughout. In one embodiment, an ADC is formed by the chemical bonding of a reactive functional group of one molecule, such as an antibody or antigen-binding fragment thereof, with an appropriately reactive functional group of another molecule, such as a cytotoxin described herein. Non-limiting examples of cytotoxins that can, in some embodiments, be used in a conjugate provided herein include a small organic molecule (e.g., MW 1500 Da or less), a biomolecule (e.g., a protein), a drug filled nanoparticle, or a radionucleide. Conjugates may include a linker between the two molecules bound to one another, e.g., between an antibody and a cytotoxin. Examples of linkers that can be used for the formation of a conjugate include peptide-containing linkers, such as those that contain naturally occurring or non-naturally occurring amino acids, such as D-amino acids. Linkers can be prepared using a variety of strategies described herein and known in the art. Depending on the reactive components therein, a linker may be cleaved, for example, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012).

The term "conjugate", "conjugate to" or "conjugate with", when used in the sense of at least two molecules being conjugated together, refers to one molecule, e.g., an antibody, being linked to or combined with a second molecule, e.g., a toxin. Anti-CD45 antibodies, and fragments thereof, can be conjugated to other molecules, including toxins, labelling agents (e.g., fluorescein or biotin), drug-loaded nanoparticles. Conjugated molecules may be conjugated via covalent or non-covalent interactions. In certain embodiments, an anti-CD45 antibody, or fragment thereof, is conjugated to a protein toxin to form a protein fusion, e.g., an scFv-toxin chimera. In some embodiments, the conjugated molecules can be coupled via the non-covalent interaction of a first interacting moiety (e.g., biotin) and a second interacting moiety (e.g., streptavidin) associated with the conjugated molecules.

As used herein, "drug-to-antibody ratio" or "DAR" refers to the number of drugs, e.g., amatoxin, attached to the antibody of a conjugate. The DAR of an ADC can range from 1 to 8, although higher loads are also possible depending on the number of linkage sites on an antibody. In certain embodiments, the conjugate has a DAR of 1, 2, 3, 4, 5, 6, 7, or 8.

As used herein, the term "microtubule-binding agent" refers to a compound which acts by disrupting the microtubular network that is essential for mitotic and interphase cellular function in a cell. Examples of microtubule-binding agents include, but are not limited to, maytasine, maytansinoids, and derivatives thereof, such as those described herein or known in the art, vinca alkaloids, such as vinblastine, vinblastine sulfate, vincristine, vincristine sulfate, vindesine, and vinorelbine, taxanes, such as docetaxel and paclitaxel, macrolides, such as discodermolides, cochicine, and epothilones, and derivatives thereof, such as epothilone B or a derivative thereof.

As used herein, the term "amatoxin" refers to a member of the amatoxin family of peptides produced by *Amanita phalloides* mushrooms, or derivative thereof, such as a variant or derivative thereof capable of inhibiting RNA polymerase II activity. Amatoxins useful in conjunction with the compositions and methods described herein include compounds described herein, e.g., α-amanitin, β-amanitin, γ-amanitin, ε-amanitin, amanin, amaninamide, amanullin, amanullinic acid, or proamanullin. As described herein, amatoxins may be conjugated to an antibody, or antigen-binding fragment thereof, for instance, by way of a linker moiety (L) (thus forming an ADC). Exemplary methods of amatoxin conjugation and linkers useful for such processes are described below. Exemplary linker-containing amatoxins useful for conjugation to an antibody, or antigen-binding fragment, in accordance with the compositions and methods are also described herein.

The term "acyl" as used herein refers to —C(═O)R, wherein R is hydrogen ("aldehyde"), C1-C12 alkyl, C2-C12 alkenyl, C2-C12 alkynyl, C3-C7 carbocyclyl, C6-C20 aryl, 5-10 membered heteroaryl, or 5-10 membered heterocyclyl, as defined herein. Non-limiting examples include formyl, acetyl, propanoyl, benzoyl, and acryloyl.

The term "C1-C12 alkyl" as used herein refers to a straight chain or branched, saturated hydrocarbon having from 1 to 12 carbon atoms. Representative C1-C12 alkyl groups include, but are not limited to, -methyl, -ethyl, -n-propyl, -n-butyl, -n-pentyl, and -n-hexyl; while branched C1-C12 alkyls include, but are not limited to, -isopropyl, -sec-butyl, -isobutyl, -tert-butyl, -isopentyl, and 2-methylbutyl. A C1-C12 alkyl group can be unsubstituted or substituted.

The term "alkenyl" as used herein refers to C2-C12 hydrocarbon containing normal, secondary, or tertiary carbon atoms with at least one site of unsaturation, i.e., a carbon-carbon, sp2 double bond. Examples include, but are not limited to: ethylene or vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, propenyl, isopropenyl, butenyl, tert-butylenyl, hexenyl and the like. An alkenyl group can be unsubstituted or substituted.

"Alkynyl" as used herein refers to a C2-C12 hydrocarbon containing normal, secondary, or tertiary carbon atoms with at least one site of unsaturation, i.e., a carbon-carbon, sp triple bond. Examples include, but are not limited to acetylenic and propargyl, butynyl, pentynyl, hexynyl, and the like. An alkynyl group can be unsubstituted or substituted.

"Aryl" as used herein refers to a C6-C20 carbocyclic aromatic group. Examples of aryl groups include, but are not limited to, phenyl, naphthyl and anthracenyl. An aryl group can be unsubstituted or substituted.

"Arylalkyl" as used herein refers to an acyclic alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms. An alkaryl group can be unsubstituted or substituted.

"Cycloalkyl" as used herein refers to a saturated carbocyclic radical, which may be mono- or bicyclic. Cycloalkyl groups include a ring having 3 to 7 carbon atoms as a monocycle or 7 to 12 carbon atoms as a bicycle. Examples of monocyclic cycloalkyl groups include cyclopropyl, cyclobutyl, cyclopentyl, cyclohexyl, cycloheptyl, and cyclooctyl. A cycloalkyl group can be unsubstituted or substituted.

"Cycloalkenyl" as used herein refers to an unsaturated carbocyclic radical, which may be mono- or bicyclic. Cycloalkenyl groups include a ring having 3 to 6 carbon atoms as a monocycle or 7 to 12 carbon atoms as a bicycle. Examples of monocyclic cycloalkenyl groups include 1-cyclopent-1-enyl, 1-cyclopent-2-enyl, 1-cyclopent-3-enyl, 1-cyclohex-1-enyl, 1-cyclohex-2-enyl, and 1-cyclohex-3-enyl. A cycloalkenyl group can be unsubstituted or substituted.

"Heteroaralkyl" as used herein refers to an acyclic alkyl radical in which one of the hydrogen atoms bonded to a carbon atom, typically a terminal or sp3 carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo[4,5], [5,5], [5,6], or [6,6] system.

"Heteroaryl" and "heterocycloalkyl" as used herein refer to an aromatic or non-aromatic ring system, respectively, in which one or more ring atoms is a heteroatom, e.g. nitrogen, oxygen, and sulfur. The heteroaryl or heterocycloalkyl radical comprises 2 to 20 carbon atoms and 1 to 3 heteroatoms selected from N, O, P, and S. A heteroaryl or heterocycloalkyl may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo[4,5], [5,5], [5,6], or [6,6] system. Heteroaryl and heterocycloalkyl can be unsubstituted or substituted.

Heteroaryl and heterocycloalkyl groups are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heteroaryl groups include by way of example and not limitation pyridyl, thiazolyl, tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, benzotriazolyl, benzisoxazolyl, and isatinoyl.

Examples of heterocycloalkyls include by way of example and not limitation dihydroypyridyl, tetrahydropyridyl (piperidyl), tetrahydrothiophenyl, piperidinyl, 4-piperidonyl, pyrrolidinyl, 2-pyrrolidonyl, tetrahydrofuranyl, tetrahydropyranyl, bis-tetrahydropyranyl, tetrahydroquinolinyl, tetrahydroisoquinolinyl, decahydroquinolinyl, octahydroisoquinolinyl, piperazinyl, quinuclidinyl, and morpholinyl.

By way of example and not limitation, carbon bonded heteroaryls and heterocycloalkyls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heteroaryls and heterocycloalkyls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or beta-carboline. Still more typically, nitrogen bonded heterocycles include 1-aziridyl, 1-azetedyl, 1-pyrrolyl, 1-imidazolyl, 1-pyrazolyl, and 1-piperidinyl.

"Substituted" as used herein and as applied to any of the above alkyl, alkenyl, alkynyl, aryl, arylalkyl, cycloalkyl, heteroaryl, heterocyclyl, and the like, means that one or more hydrogen atoms are each independently replaced with a substituent. Typical substituents include, but are not limited to, —X, —R, —OH, —OR, —SH, —SR, NH2, —NHR, —N(R)2, —N+(R)3, —CX3, —CN, —OCN, —SCN, —NCO, —NCS, —NO, —NO2, —N3, —NC(═O)H, —NC(═O)R, —C(═O)H, —C(═O)R, —C(═O)NH2, —C(═O)N(R)2, —SO3-, —SO3H, —S(═O)2R, —OS(═O)2OR, —S(═O)2NH2, —S(═O)2N(R)2, —S(═O)R, —OP(═O)(OH)2, —OP(═O)(OR)2, —P(═O)(OR)2, —PO3, —PO3H2, —C(═O)X, —C(═S)R, —CO2H, —CO2R, —CO2-, —C(═S)OR, —C(═O)SR, —C(═S)SR, —C(═O)NH2, —C(═O)N(R)2, —C(═S)NH2, —C(═S)N(R)2, —C(═NH)NH2, and —C(═NR)N(R)2; wherein each X is independently selected for each occasion from F, Cl, Br, and I; and each R is independently selected for each occasion from C1-C12 alkyl, C6-C20 aryl, C3-C14 heterocycloalkyl or heteroaryl, protecting group and prodrug moiety. Wherever a group is described as "optionally substituted," that group can be substituted with one or more of the above substituents, independently for each occasion.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as $—CH_2—$, $—CH_2CH_2—$, $—CH_2CH(CH_3)CH_2—$, and the like. Other radical naming conventions clearly indicate that the radical is a di-radical such as "alkylene," "alkenylene," "arylene," "heterocycloalkylene," and the like.

Wherever a substituent is depicted as a di-radical (i.e., has two points of attachment to the rest of the molecule), it is to be understood that the substituent can be attached in any directional configuration unless otherwise indicated.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers," or sometimes "optical isomers."

A carbon atom bonded to four non-identical substituents is termed a "chiral center." "Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116). A mixture containing equal amounts of individual enantiomeric forms of opposite chirality is termed a "racemic mixture."

The compounds disclosed in this description and in the claims may comprise one or more asymmetric centers, and different diastereomers and/or enantiomers of each of the compounds may exist. The description of any compound in this description and in the claims is meant to include all enantiomers, diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the disclosure of the present application is not limited to that specific enantiomer. Accordingly, enantiomers, optical isomers, and diastereomers of each of the structural formulae of the present disclosure are contemplated herein. In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. The compounds may occur in different tautomeric forms. The compounds according to the disclosure are meant to include all tautomeric forms, unless stated otherwise. When the structure of a compound is depicted as a specific tautomer, it is to be understood that the disclosure of the present application is not limited to that specific tautomer.

The compounds of any formula described herein include the compounds themselves, as well as their salts, and their solvates, if applicable. A salt, for example, can be formed between an anion and a positively charged group (e.g., amino) on a compound of the disclosure. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on a compound of the disclosure. Suitable cations include sodium ion, potassium ion, magnesium ion, calcium ion, and an ammonium cation such as tetramethylammonium ion. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. The compounds of the disclosure also include those salts containing quaternary nitrogen atoms. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Additionally, the compounds of the present disclosure, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc. "Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hydrate refers to, for example, a mono-hydrate, a di-hydrate, a tri-hydrate, etc.

In addition, a crystal polymorphism may be present for the compounds or salts thereof represented by the formulae disclosed herein. It is noted that any crystal form, crystal form mixture, or anhydride or hydrate thereof, is included in the scope of the present disclosure.

Anti-CD45 Antibodies

Contemplated herein are antibodies, or antigen-binding fragments thereof, capable of binding CD45, that can be used as therapeutic agents alone or as conjugates (ADCs) to, for example, (i) treat cancers and autoimmune diseases characterized by CD45+ cells and (ii) promote the engraftment of transplanted hematopoietic stem cells in a patient in need of transplant therapy. These therapeutic activities can be caused, for instance, by the binding of isolated anti-CD45 antibodies, antigen-binding fragments thereof, or ADCs that bind to CD45 expressed on the surface of a cell, such as a cancer cell, autoimmune cell, or hematopoietic stem cell and subsequently inducing cell death. The depletion of endogenous hematopoietic stem cells can provide a niche toward which transplanted hematopoietic stem cells can home, and subsequently establish productive hematopoiesis. In this way, transplanted hematopoietic stem cells may successfully engraft in a patient, such as human patient suffering from a stem cell disorder described herein. Additionally, depletion of leukocytes in a patient in need thereof in combination with HSC transplant can reset the patient's immune system, thereby, for example, curing the patient of an autoimmune disease.

CD45, also known as leukocyte common antigen and receptor-type tyrosine-protein phosphatase C, is a hematopoietic cell-specific transmembrane protein tyrosine phosphatase essential for T and B cell antigen receptor-mediated signaling. CD45 includes a large extracellular domain, and a phosphatase containing cytosolic domain. CD45 may act as both a positive and negative regulator depending on the nature of the stimulus and the cell type involved. Although there are a large number of permutations possible in the CD45 gene, only six isoforms are traditionally identified in humans. The isoforms are RA, RO, RB, RAB, RBC and RABC (Hermiston et al. 2003 "CD45: a critical regulator of signaling thresholds in immune cells." *Annu Rev Immunol.* 2:107-137.). CD45RA is expressed on naïve T cells, and CD45RO is expressed on activated and memory T cells, some B cell subsets, activated monocytes/macrophages, and granulocytes. CD45RB is expressed on peripheral B cells, naïve T cells, thymocytes, weakly on macrophages, and dendritic cells. An amino acid sequence of CD45RABC is provided herein as SEQ ID NO:112. An amino acid sequence of CD45RA is provided herein as SEQ ID NO:107. An amino acid sequence of CD45RO is provided herein as SEQ ID NO:108. An amino acid sequence of CD45RB is provided herein as SEQ ID NO:109. An amino acid sequence of CD45RAB is provided herein as SEQ ID NO:110. An amino acid sequence of SEQ ID NO:RBC is provided herein as SEQ ID NO:111.

As described below, in certain embodiments, novel anti-human CD45 (hCD45) antibodies were identified by screening a yeast display library that displays fully human antibodies. Seven human antibodies (designated Antibody 1 (Ab1), Antibody 2 (Ab2), Antibody 3 (Ab3), Antibody 4 (Ab4), Antibody 5 (Ab5), Antibody 6 (Ab6), and Antibody 7 (Ab7)) were identified in the screen, which bind to human CD45 (all isoforms), and which cross-react with CD45 from non-human primates (e.g., cynomolgus CD45 and/or rhesus CD45).

In other embodiments, humanized and affinity matured antibodies were prepared from three rat anti-CD45 antibodies. In this manner, three additional antibodies (designated Antibody A (AbA), Antibody B (AbB), and Antibody C (AbC) were identified, which bind to human CD45 (all isoforms), and which cross-react with CD45 from non-human primates (e.g., cynomolgus CD45 and/or rhesus CD45). The identified antibodies have diagnostic and therapeutic characteristics, as described herein.

Accordingly, provided herein are antibodies, or antigen-binding portions thereof, that specifically bind to human CD45, and which cross-react with CD45 from non-human primates.

In one embodiment, the invention provides an antibody, or antigen binding portion thereof, that binds to human CD45 (SEQ ID NO:112) and to cynomolgus CD45 (SEQ ID NO:145) and/or to rhesus CD45 (SEQ ID NO:146). In some embodiments, the antibody, of antigen-binding portion thereof, can bind to human CD45 with a $K_D$ of about 100 nM or less, e.g., about 100 nM or less, about 90 nM or less, about 80 nM or less, about 70 nM or less, about 60 nM or less, about 50 nM or less, about 40 nM or less, about 30 nM or less, about 20 nM or less, about 10 nM or less, about 10 nM or less, or about 0.1 nM or less, as determined by Bio-Layer Interferometry (BLI). In some embodiments, the antibody, of antigen-binding portion thereof, can bind to cynomolgus CD45 with a $K_D$ of about 100 nM or less, e.g., about 100 nM or less, about 90 nM or less, about 80 nM or less, about 70 nM or less, about 60 nM or less, about 50 nM or less, about 40 nM or less, about 30 nM or less, about 20 nM or less, about 10 nM or less, about 10 nM or less, or about 0.1 nM or less, as determined by Bio-Layer Interferometry (BLI). In some embodiments, the antibody, of antigen-binding portion thereof, can bind to rhesus CD45 with a $K_D$ of about 100 nM or less, e.g., about 100 nM or less, about 90 nM or less, about 80 nM or less, about 70 nM or less, about 60 nM or less, about 50 nM or less, about 40 nM or less, about 30 nM or less, about 20 nM or less, about 10 nM or less, about 10 nM or less, or about 0.1 nM or less, as determined by Bio-Layer Interferometry (BLI). In some embodiments, the antibody is a fully human antibody, or antigen-binding portion thereof. In other embodiments, the antibody is a humanized antibody, or antigen-binding portion thereof. In some embodiments, the antibody is a chimeric antibody, or antigen-binding portion thereof. In some embodiments, the antibody is a deimmunized antibody, or antigen-binding portion thereof.

The extracellular region of human CD45 includes a mucin-like domain, and four fibronectin-like domains (d1, d2, d3, and d4). Without wishing to be bound by any theory, it is believed that antibodies Ab1, Ab2, Ab3, Ab4, Ab5, Ab6, and Ab7 interact with residues of human CD45 located within the d3 and d4 fibronectin-like domains. In particular, these antibodies may interact with a fragment of human CD45 set forth in SEQ ID NO:115, and a fragment of human CD45 set forth in SEQ ID NO:117. Crosslinking studies described herein suggest that the antibodies can specifically interact with one or more CD45 amino acid residues, which are conserved between human CD45, cynomolgus CD45, and rhesus CD45. These residues include 405T, 407K, 419Y, 425K, and 505R (numbered with reference to the fragment of hCD45 set forth in SEQ ID NO:113). In addition, these antibodies may interact with residues 481R and/or 509H in human CD45 (numbered with reference to the fragment of hCD45 set forth in SEQ ID NO:113). Accordingly, in some embodiments, provided herein is an antibody, or antigen-binding portion thereof, that binds to human CD45 at an epitope located in the d3 and/or d4 fibronectin-like domains. In some embodiments, provided herein is an antibody, or antigen-binding portion thereof, that binds to CD45 at an epitope of human CD45 located within CD45 fragment 2 (SEQ ID NO:115 and/or CD45 fragment 4 (SEQ ID NO:117). In some embodiments, provided herein is an antibody, or antigen-binding portion thereof, that binds to CD45 at an epitope of human CD45 located within CD45 fragment 1 (SEQ ID NO:114 and/or CD45 fragment 3 (SEQ ID NO:116). In some embodiments, provided herein is an antibody, or antigen-binding portion thereof, that binds to CD45 at an epitope comprising at least one, at least two, at least three, at least four, or least five amino acid residues that are conserved among human CD45, cynomolgus CD45, and/or rhesus CD45. For example, in some embodiments, the antibody, or antigen-binding portion thereof, can bind to at least one, at least two, at least three, at least four, or all five of the following amino acid residues in human CD45: 405T, 407K, 419Y, 425K, and 505R (numbered with reference to the fragment of hCD45 set forth in SEQ ID NO:113). In some embodiments, the antibody, or antigen-binding portion thereof, can bind to one or more, two or more, three or more, four or more, five or more, six or more, or seven of the following amino acid residues in human CD45: 405T, 407K, 419Y, 425K, 481R, and 505R, 509H (numbered with reference to the fragment of hCD45 set forth in SEQ ID NO: 113). Also provided herein is an antibody, or antigen-binding portion thereof, that competes with Ab1, Ab2, Ab3, Ab4, Ab5, Ab6, and/or Ab7 for binding to human CD45 (SEQ ID NO:112). In some embodiments, the antibody, or antigen-binding portion thereof, can also compete with Ab1, Ab2, Ab3, Ab4, Ab5, Ab6, and/or Ab7 for binding to cynomolgus CD45 (SEQ ID NO:145), and/or rhesus CD45 (SEQ ID NO:146). In some embodiments, the antibody is a fully human antibody, or antigen-binding portion thereof. In other embodiments, the antibody is a humanized antibody, or antigen-binding portion thereof. In some embodiments, the antibody is a chimeric antibody, or antigen-binding portion thereof. In some embodiments, the antibody is a deimmunized antibody, or antigen-binding portion thereof.

Without wishing to be bound by any theory, it is believed that antibody AbA, described herein, also binds to the d4 fibronectin-like domain of CD45, but does not compete with any of Ab1-Ab7 for binding to CD45. Epitope mapping experiments described herein suggest that AbA binds to the d4 fibronectin-like domain at the opposite face of the molecule, relative to Ab1-Ab7. In particular, this antibody is believed to interact with a fragment of human CD45 set forth in SEQ ID NO: 118. Crosslinking studies described herein suggest that AbA can specifically interact with one or more CD45 amino acid residues, which are conserved between human CD45, cynomolgus CD45, and rhesus CD45. These residues include 493Y and 502T (numbered with reference to the fragment of hCD45 set forth in SEQ ID NO:113). In addition, this antibody may interact with residue 486R in human CD45 (numbered with reference to the fragment of hCD45 set forth in SEQ ID NO:113). Accordingly, in some embodiments, provided herein is an antibody, or antigen-binding portion thereof, that binds to human CD45 at an epitope located in the d4 fibronectin-like domain. In some embodiments, provided herein is an antibody, or antigen-binding portion thereof, that binds to CD45 at an epitope of human CD45 located within CD45 fragment 5 (SEQ ID NO:118). In some embodiments, provided herein is an antibody, or antigen-binding portion thereof, that binds to CD45 at an epitope comprising at least one or at least two amino acid residues that are conserved among human CD45, cynomolgus CD45, and/or rhesus CD45. For example, in some embodiments, the antibody, or antigen-binding portion thereof, can bind to one or both of the following amino acid residues in human CD45: 493Y and 502T (numbered with reference to the fragment of hCD45 set forth in SEQ ID NO:113). In some embodiments, the antibody, or antigen-binding portion thereof, can bind to one or more, two or more, or three of the following amino acid residues in human CD45: 486R, 493Y and 502T (numbered with reference to the fragment of hCD45 set forth in SEQ ID NO: 113). Also provided herein is an antibody, or antigen-binding portion thereof, that competes with AbA for binding to human CD45 (SEQ ID NO:112). In some embodiments, the antibody, or antigen-binding portion thereof, can also compete with AbA for binding to cynomolgus CD45 (SEQ ID NO:145), and/or rhesus CD45 (SEQ ID NO:146). In some embodiments, the antibody is a fully human antibody, or antigen-binding portion thereof. In other embodiments, the antibody is a humanized antibody, or antigen-binding portion thereof. In some embodiments, the antibody is a chimeric antibody, or antigen-binding portion thereof. In some embodiments, the antibody is a deimmunized antibody, or antigen-binding portion thereof.

In other embodiments, provided herein is an antibody, or antigen-binding portion thereof, that binds to the same epitope of human CD45 as AbB. In some embodiments, the antibody, or antigen-binding portion thereof, cross-reacts with cynomolgus CD45 and/or rhesus CD45. Also provided herein is an antibody, or antigen-binding portion thereof, that competes with AbB for binding to human CD45 (SEQ ID NO:112). In some embodiments, the antibody, or antigen-binding portion thereof, can also compete with AbB for binding to cynomolgus CD45 (SEQ ID NO:145), and/or rhesus CD45 (SEQ ID NO:146). In some embodiments, the antibody is a fully human antibody, or antigen-binding portion thereof. In other embodiments, the antibody is a humanized antibody, or antigen-binding portion thereof. In some embodiments, the antibody is a chimeric antibody, or antigen-binding portion thereof. In some embodiments, the antibody is a deimmunized antibody, or antigen-binding portion thereof.

In other embodiments, provided herein is an antibody, or antigen-binding portion thereof, that binds to the same epitope of human CD45 as AbC. In some embodiments, the antibody, or antigen-binding portion thereof, cross-reacts with cynomolgus CD45 and/or rhesus CD45. Also provided herein is an antibody, or antigen-binding portion thereof, that competes with AbC for binding to human CD45 (SEQ ID NO:112). In some embodiments, the antibody, or antigen-binding portion thereof, can also compete with AbC for binding to cynomolgus CD45 (SEQ ID NO:145), and/or rhesus CD45 (SEQ ID NO:146). In some embodiments, the antibody is a fully human antibody, or antigen-binding portion thereof. In other embodiments, the antibody is a humanized antibody, or antigen-binding portion thereof. In some embodiments, the antibody is a chimeric antibody, or antigen-binding portion thereof. In some embodiments, the antibody is a deimmunized antibody, or antigen-binding portion thereof.

The amino acid sequences of the various binding regions of anti-CD45 antibodies Ab1, Ab2, Ab3, Ab4, Ab5, Ab6, Ab7, AbA, AbB, and AbC are described in Table 27. In various aspect, the invention provides an antibody comprising the heavy chain and/or light chain CDR sequences of an antibody described in Table 27. In some aspects, the invention provides an antibody comprising the heavy chain variable region and/or the light chain variable region of an antibody described in Table 27. In some aspects, the invention provides an antibody comprising the heavy chain and/or the light chain of an antibody described in Table 27. Additional features of the antibodies, and antigen-binding portions thereof, provided herein are described below.

Ab1

Antibody 1 (Ab1) cross reacts with human CD45, cyno CD45 and rhesus CD45, and can bind the various isoforms of human CD45.

The amino acid sequences for the various binding regions of anti-CD45 Ab1 are described in Table 27. Included in the invention are anti-CD45 antibodies based on Ab1, e.g., that comprise the CDRs as set forth in Table 27.

In one embodiment, the invention provides an anti-CD45 antibody, or antigen-binding fragment thereof, comprising antigen binding regions, e.g., CDRs and/or variable regions, corresponding to those of Ab1. The heavy chain variable region (VH) amino acid sequence of Ab is set forth in SEQ ID NO:1 (see Table 27). The VH CDR domain amino acid sequences of Ab are set forth in SEQ ID NO:2 (VH CDR1); SEQ ID NO:3 (VH CDR2), and SEQ ID NO:4 (VH CDR3). The light chain variable region (VL) amino acid sequence of Ab is described in SEQ ID NO:5 (see Table 27). The VL CDR domain amino acid sequences of Ab are set forth in SEQ ID NO:6 (VL CDR1); SEQ ID NO:7 (VL CDR2), and SEQ ID NO:8 (VL CDR3).

Accordingly, in some embodiments, provided herein is an anti-CD45 antibody, or antigen-binding portion thereof, comprising a heavy chain variable region comprising a CDR1 domain comprising the amino acid sequence as set forth in SEQ ID NO:2, a CDR2 domain comprising the amino acid sequence as set forth in SEQ ID NO:3, and a CDR3 domain comprising the amino acid sequence as set forth in SEQ ID NO:4; and/or a light chain variable region comprising a CDR1 domain comprising the amino acid sequence as set forth in SEQ ID NO:6, a CDR2 domain comprising the amino acid sequence as set forth in SEQ ID NO:7; and a CDR3 domain comprising the amino acid sequence as set forth in SEQ ID NO:8. In certain embodiments, an anti-CD45 antibody comprises the CDRs described herein (SEQ ID Nos: 2 to 4 and 6 to 8) wherein the CDR comprises a conservative amino acid substitution (or 2, 3, 4, or 5 amino acid substitutions) while retaining the CD45 specificity of the antibody (i.e., specificity similar to Ab1).

In some embodiments, provided herein is an anti-CD45 antibody, or antigen-binding portion thereof, comprising a heavy chain variable region comprising the amino acid sequence as set forth in SEQ ID NO:1, and/or a light chain variable region comprising the amino acid sequence as set forth in SEQ ID NO:5. In certain embodiments, an antibody can comprise a modified heavy chain (HC) variable region comprising an HC variable domain comprising SEQ ID NO:1, or a variant of SEQ ID NO:1, which variant (i) differs from SEQ ID NO:1 in 1, 2, 3, 4 or 5 amino acids substitutions, additions or deletions; (ii) differs from SEQ ID NO:1 in at most 5, 4, 3, 2, or 1 amino acids substitutions, additions or deletions; (iii) differs from SEQ ID NO:1 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:1, wherein in any of (i)-(iv), an amino acid substitution may be a conservative amino acid substitution or a non-conservative amino acid substitution; and wherein the modified heavy chain variable region retains the CD45 specificity of the antibody (i.e., specificity similar to Ab1), or has an enhanced biological activity relative to that of another Ab1 heavy chain variable region. In certain embodiments, an antibody comprises a modified light chain (LC) variable region comprising an LC variable domain comprising SEQ ID NO:5, or a variant of SEQ ID NO:5, which variant (i) differs from SEQ ID NO:5 in 1, 2, 3, 4 or 5 amino acids substitutions, additions or deletions; (ii) differs from SEQ ID NO:5 in at most 5, 4, 3, 2, or 1 amino acids substitutions, additions or deletions; (iii) differs from SEQ ID NO:5 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:5, wherein in any of (i)-(iv), an amino acid substitution may be a conservative amino acid substitution or a non-conservative amino acid substitution; and wherein the modified light chain variable region retains the CD45 specificity of the antibody (i.e., specificity similar to Ab1), or has an enhanced biological activity relative to that of another Ab1 light chain variable region.

Antibodies comprising the CDR and/or variable region sequences of Ab can be in the form of full-length antibodies, bispecific antibodies, dual variable domain antibodies, multiple chain or single chain antibodies, and/or binding fragments that specifically bind human CD45, including but not limited to Fab, Fab', (Fab')2, Fv), scFv (single chain Fv), surrobodies (including surrogate light chain construct), single domain antibodies, camelized antibodies and the like. They also can be of, or derived from, any isotype, including, for example, IgA (e.g., IgA1 or IgA2), IgD, IgE, IgG (e.g. IgG1, IgG2, IgG3 or IgG4), or IgM. In some embodiments, the anti-45 antibody is an IgG (e.g. IgG1, IgG2, IgG3 or IgG4).

In some embodiments, an antibody comprising the CDR and/or variable region sequences of Ab can further comprise a heavy chain constant region and/or a light chain constant region. In some embodiments, the constant region is a human IgG1 constant region, a human IgG2 constant region, a human IgG3 constant region, or a human IgG4 constant region. In some embodiments, the heavy chain constant region can be a modified constant region. Exemplary constant regions substitutions and/or modifications are described herein, and include, but are not limited to, substitutions at one or more of the following positions: 234, 235, 265, and 435 (EU index according to Kabat). In some embodiments, an antibody comprising the CDR and/or variable region sequences of Ab can further comprise an IgG1 heavy chain constant region containing one or more of the following substitutions: L234A, L235A, D265C, and H435A (EU index according to Kabat). In some embodiments, an antibody comprising the CDR and/or variable region sequences of Ab can further comprise a heavy chain constant region set forth in SEQ ID NO:102, SEQ ID NO:103, SEQ ID NO:104, SEQ ID NO:105 or SEQ ID NO:106. In some embodiments the antibody comprises a light chain constant region set forth in SEQ ID NO:101.

In certain embodiments, the anti-CD45 antibody, or antigen binding portion thereof, comprises a heavy chain comprising the amino acid sequence as set forth in SEQ ID NO:9. In certain embodiments, an antibody comprises a modified heavy chain (HC) region comprising an HC domain comprising SEQ ID NO:9, or a variant of SEQ ID NO:9, which variant (i) differs from SEQ ID NO:9 in 1, 2, 3, 4 or 5 amino acids substitutions, additions or deletions; (ii) differs from SEQ ID NO:9 in at most 5, 4, 3, 2, or 1 amino acids substitutions, additions or deletions; (iii) differs from SEQ ID NO:9 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:9, wherein in any of (i)-(iv), an amino acid substitution may be a conservative amino acid substitution or a non-conservative amino acid substitution; and wherein the modified heavy chain region retains the CD45 specificity of the antibody (i.e., specificity similar to Ab1), or has an enhanced biological activity relative to that of another Ab1 heavy chain region.

In certain embodiments, the anti-CD45 antibody, or antigen binding portion thereof, comprises a light chain comprising the amino acid sequence as set forth in SEQ ID NO:10. In certain embodiments, an antibody comprises a modified light chain (LC) region comprising an LC domain comprising SEQ ID NO:10, or a variant of SEQ ID NO:10, which variant (i) differs from SEQ ID NO:10 in 1, 2, 3, 4 or 5 amino acids substitutions, additions or deletions; (ii) differs from SEQ ID NO:10 in at most 5, 4, 3, 2, or 1 amino acids substitutions, additions or deletions; (iii) differs from SEQ ID NO:10 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:10, wherein in any of (i)-(iv), an amino acid substitution may be a conservative amino acid substitution or a non-conservative amino acid substitution; and wherein the modified light chain region retains the CD45 specificity of the antibody (i.e., specificity similar to Ab1), or has an enhanced biological activity relative to that of another Ab1 light chain region.

In some embodiments, antibodies comprising the CDR regions and/or variable regions of Ab can be incorporated into antibody-drug conjugates, as described herein. In addition, antibodies comprising the CDR regions and/or variable regions of Ab can be used in the methods described herein, e.g., for depletion of CD45+ cells in a subject.

Ab2

Antibody 2 (Ab2) cross reacts with human CD45, cyno CD45 and rhesus CD45, and can bind the various isoforms of human CD45.

The amino acid sequences for the various binding regions of anti-CD45 Ab2 are described in Table 27. Included in the invention are anti-CD45 antibodies based on Ab2, e.g., that comprise the CDRs as set forth in Table 27.

In one embodiment, the invention provides an anti-CD45 antibody, or antigen-binding fragment thereof, comprising antigen binding regions, e.g., CDRs and/or variable regions, corresponding to those of Ab2. The heavy chain variable region (VH) amino acid sequence of Ab2 is set forth in SEQ ID NO:11 (see Table 27). The VH CDR domain amino acid sequences of Ab2 are set forth in SEQ ID NO:12 (VH CDR1); SEQ ID NO:13 (VH CDR2), and SEQ ID NO:14 (VH CDR3). The light chain variable region (VL) amino acid sequence of Ab2 is described in SEQ ID NO:15 (see Table 27). The VL CDR domain amino acid sequences of Ab2 are set forth in SEQ ID NO:16 (VL CDR1); SEQ ID NO:17 (VL CDR2), and SEQ ID NO:18 (VL CDR3).

Accordingly, in some embodiments, provided herein is an anti-CD45 antibody, or antigen-binding portion thereof, comprising a heavy chain variable region comprising a CDR1 domain comprising the amino acid sequence as set forth in SEQ ID NO:12, a CDR2 domain comprising the amino acid sequence as set forth in SEQ ID NO:13, and a CDR3 domain comprising the amino acid sequence as set forth in SEQ ID NO:14; and/or a light chain variable region comprising a CDR1 domain comprising the amino acid sequence as set forth in SEQ ID NO:16, a CDR2 domain comprising the amino acid sequence as set forth in SEQ ID NO:17; and a CDR3 domain comprising the amino acid sequence as set forth in SEQ ID NO:18. In certain embodiments, an anti-CD45 antibody comprises the CDRs described herein (SEQ ID NOs: 12 to 14 and 16 to 18) wherein the CDR comprises a conservative amino acid substitution (or 2, 3, 4, or 5 amino acid substitutions) while retaining the CD45 specificity of the antibody (i.e., specificity similar to Ab2).

In some embodiments, provided herein is an anti-CD45 antibody, or antigen-binding portion thereof, comprising a heavy chain variable region comprising the amino acid sequence as set forth in SEQ ID NO:11, and/or a light chain variable region comprising the amino acid sequence as set forth in SEQ ID NO:15. In certain embodiments, an antibody can comprise a modified heavy chain (HC) variable region comprising an HC variable domain comprising SEQ ID NO:11, or a variant of SEQ ID NO:11, which variant (i) differs from SEQ ID NO: 11 in 1, 2, 3, 4 or 5 amino acids substitutions, additions or deletions; (ii) differs from SEQ ID NO: 11 in at most 5, 4, 3, 2, or 1 amino acids substitutions, additions or deletions; (iii) differs from SEQ ID NO: 11 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:11, wherein in any of (i)-(iv), an amino acid substitution may be a conservative amino acid substitution or a non-conservative amino acid substitution; and wherein the modified heavy chain variable region retains the CD45 specificity of the antibody (i.e., specificity similar to Ab2), or has an enhanced biological activity relative to that of another Ab2 heavy chain variable region. In certain embodiments, an antibody comprises a modified light chain (LC) variable region comprising an LC variable domain comprising SEQ ID NO:15, or a variant of SEQ ID NO:15, which variant (i) differs from SEQ ID NO:15 in 1, 2, 3, 4 or 5 amino acids substitutions, additions or deletions; (ii) differs from SEQ ID NO:15 in at most 5, 4, 3, 2, or 1 amino acids substitutions, additions or deletions; (iii) differs from SEQ ID NO:15 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:15, wherein in any of (i)-(iv), an amino acid substitution may be a conservative amino acid substitution or a non-conservative amino acid substitution; and wherein the modified light chain variable region retains the CD45 specificity of the antibody (i.e., specificity similar to Ab2), or has an enhanced biological activity relative to that of another Ab2 light chain variable region.

Antibodies comprising the CDR and/or variable region sequences of Ab2 can be in the form of full-length antibodies, bispecific antibodies, dual variable domain antibodies, multiple chain or single chain antibodies, and/or binding fragments that specifically bind human CD45, including but not limited to Fab, Fab', (Fab')2, Fv), scFv (single chain Fv), surrobodies (including surrogate light chain construct), single domain antibodies, camelized antibodies and the like. They also can be of, or derived from, any isotype, including, for example, IgA (e.g., IgA1 or IgA2), IgD, IgE, IgG (e.g. IgG1, IgG2, IgG3 or IgG4), or IgM. In some embodiments, the anti-45 antibody is an IgG (e.g. IgG1, IgG2, IgG3 or IgG4).

In some embodiments, an antibody comprising the CDR and/or variable region sequences of Ab2 can further comprise a heavy chain constant region and/or a light chain constant region. In some embodiments, the constant region is a human IgG1 constant region, a human IgG2 constant region, a human IgG3 constant region, or a human IgG4 constant region. In some embodiments, the heavy chain constant region can be a modified constant region. Exemplary constant regions substitutions and/or modifications are described herein, and include, but are not limited to, substitutions at one or more of the following positions: 234, 235, 265, and 435 (EU index according to Kabat). In some embodiments, an antibody comprising the CDR and/or variable region sequences of Ab2 can further comprise an IgG1 heavy chain constant region containing one or more of the following substitutions: L234A, L235A, D265C, and H435A (EU index according to Kabat). In some embodiments, an antibody comprising the CDR and/or variable region sequences of Ab2 can further comprise a heavy chain constant region set forth in SEQ ID NO:102, SEQ ID NO:103, SEQ ID NO:104, SEQ ID NO:105 or SEQ ID NO:106. In some embodiments the antibody comprises a light chain constant region set forth in SEQ ID NO:101.

In certain embodiments, the anti-CD45 antibody, or antigen binding portion thereof, comprises a heavy chain comprising the amino acid sequence as set forth in SEQ ID NO:19. In certain embodiments, an antibody comprises a modified heavy chain (HC) region comprising an HC domain comprising SEQ ID NO:19, or a variant of SEQ ID NO:19, which variant (i) differs from SEQ ID NO:19 in 1, 2, 3, 4 or 5 amino acids substitutions, additions or deletions; (ii) differs from SEQ ID NO:19 in at most 5, 4, 3, 2, or 1 amino acids substitutions, additions or deletions; (iii) differs from SEQ ID NO:19 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:19, wherein in any of (i)-(iv), an amino acid substitution may be a conservative amino acid substitution or a non-conservative amino acid substitution; and wherein the modified heavy chain region retains the CD45 specificity of the antibody (i.e., specificity similar to Ab2), or has an enhanced biological activity relative to that of another Ab2 heavy chain region.

In certain embodiments, the anti-CD45 antibody, or antigen binding portion thereof, comprises a light chain comprising the amino acid sequence as set forth in SEQ ID NO:20. In certain embodiments, an antibody comprises a modified light chain (LC) region comprising an LC domain comprising SEQ ID NO:20, or a variant of SEQ ID NO:20, which variant (i) differs from SEQ ID NO:20 in 1, 2, 3, 4 or 5 amino acids substitutions, additions or deletions; (ii) differs from SEQ ID NO:20 in at most 5, 4, 3, 2, or 1 amino acids substitutions, additions or deletions; (iii) differs from SEQ ID NO:20 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:20, wherein in any of (i)-(iv), an amino acid substitution may be a conservative amino acid substitution or a non-conservative amino acid substitution; and wherein the modified light chain region retains the CD45 specificity of the antibody (i.e., specificity similar to Ab2), or has an enhanced biological activity relative to that of another Ab2 light chain region.

In some embodiments, antibodies comprising the CDR regions and/or variable regions of Ab2 can be incorporated into antibody-drug conjugates, as described herein. In addition, antibodies comprising the CDR regions and/or variable regions of Ab2 can be used in the methods described herein, e.g., for depletion of CD45+ cells in a subject.

Ab3

Antibody 3 (Ab3) cross reacts with human CD45, cyno CD45 and rhesus CD45, and can bind the various isoforms of human CD45.

The amino acid sequences for the various binding regions of anti-CD45 Ab3 are described in Table 27. Included in the invention are anti-CD45 antibodies based on Ab3, e.g., that comprise the CDRs as set forth in Table 27.

In one embodiment, the invention provides an anti-CD45 antibody, or antigen-binding fragment thereof, comprising antigen binding regions, e.g., CDRs and/or variable regions, corresponding to those of Ab3. The heavy chain variable region (VH) amino acid sequence of Ab3 is set forth in SEQ ID NO:21 (see Table 27). The VH CDR domain amino acid sequences of Ab3 are set forth in SEQ ID NO:22 (VH CDR1); SEQ ID NO:23 (VH CDR2), and SEQ ID NO:24 (VH CDR3). The light chain variable region (VL) amino acid sequence of Ab3 is described in SEQ ID NO:25 (see Table 27). The VL CDR domain amino acid sequences of Ab3 are set forth in SEQ ID NO:26 (VL CDR1); SEQ ID NO:27 (VL CDR2), and SEQ ID NO:28 (VL CDR3).

Accordingly, in some embodiments, provided herein is an anti-CD45 antibody, or antigen-binding portion thereof, comprising a heavy chain variable region comprising a CDR1 domain comprising the amino acid sequence as set forth in SEQ ID NO:22, a CDR2 domain comprising the amino acid sequence as set forth in SEQ ID NO:23, and a CDR3 domain comprising the amino acid sequence as set forth in SEQ ID NO:24; and/or a light chain variable region comprising a CDR1 domain comprising the amino acid sequence as set forth in SEQ ID NO:26, a CDR2 domain comprising the amino acid sequence as set forth in SEQ ID NO:27; and a CDR3 domain comprising the amino acid sequence as set forth in SEQ ID NO:28. In certain embodiments, an anti-CD45 antibody comprises the CDRs described herein (SEQ ID NOs: 22 to 24 and 26 to 28) wherein the CDR comprises a conservative amino acid substitution (or 2, 3, 4, or 5 amino acid substitutions) while retaining the CD45 specificity of the antibody (i.e., specificity similar to Ab3).

In some embodiments, provided herein is an anti-CD45 antibody, or antigen-binding portion thereof, comprising a heavy chain variable region comprising the amino acid sequence as set forth in SEQ ID NO:21, and/or a light chain variable region comprising the amino acid sequence as set forth in SEQ ID NO:25. In certain embodiments, an antibody can comprise a modified heavy chain (HC) variable region comprising an HC variable domain comprising SEQ ID NO:21, or a variant of SEQ ID NO:21, which variant (i) differs from SEQ ID NO:21 in 1, 2, 3, 4 or 5 amino acids substitutions, additions or deletions; (ii) differs from SEQ ID NO:21 in at most 5, 4, 3, 2, or 1 amino acids substitutions, additions or deletions; (iii) differs from SEQ ID NO:21 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:21, wherein in any of (i)-(iv), an amino acid substitution may be a conservative amino acid substitution or a non-conservative amino acid substitution; and wherein the modified heavy chain variable region retains the CD45 specificity of the antibody (i.e., specificity similar to Ab3), or has an enhanced biological activity relative to that of another Ab3 heavy chain variable region. In certain embodiments, an antibody comprises a modified light chain (LC) variable region comprising an LC variable domain comprising SEQ ID NO:25, or a variant of SEQ ID NO:25, which variant (i) differs from SEQ ID NO:25 in 1, 2, 3, 4 or 5 amino acids substitutions, additions or deletions; (ii) differs from SEQ ID NO:25 in at most 5, 4, 3, 2, or 1 amino acids substitutions, additions or deletions; (iii) differs from SEQ ID NO:25 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:25, wherein in any of (i)-(iv), an amino acid substitution may be a conservative amino acid substitution or a non-conservative amino acid substitution; and wherein the modified light chain variable region retains the CD45 specificity of the antibody (i.e., specificity similar to Ab3), or has an enhanced biological activity relative to that of another Ab3 light chain variable region.

Antibodies comprising the CDR and/or variable region sequences of Ab3 can be in the form of full-length antibodies, bispecific antibodies, dual variable domain antibodies, multiple chain or single chain antibodies, and/or binding fragments that specifically bind human CD45, including but not limited to Fab, Fab', (Fab')2, Fv), scFv (single chain Fv), surrobodies (including surrogate light chain construct), single domain antibodies, camelized antibodies and the like. They also can be of, or derived from, any isotype, including, for example, IgA (e.g., IgA1 or IgA2), IgD, IgE, IgG (e.g. IgG1, IgG2, IgG3 or IgG4), or IgM. In some embodiments, the anti-45 antibody is an IgG (e.g. IgG1, IgG2, IgG3 or IgG4).

In some embodiments, an antibody comprising the CDR and/or variable region sequences of Ab3 can further comprise a heavy chain constant region and/or a light chain constant region. In some embodiments, the constant region is a human IgG1 constant region, a human IgG2 constant region, a human IgG3 constant region, or a human IgG4 constant region. In some embodiments, the heavy chain constant region can be a modified constant region. Exemplary constant regions substitutions and/or modifications are described herein, and include, but are not limited to, substitutions at one or more of the following positions: 234, 235, 265, and 435 (EU index according to Kabat). In some embodiments, an antibody comprising the CDR and/or variable region sequences of Ab3 can further comprise an IgG1 heavy chain constant region containing one or more of the following substitutions: L234A, L235A, D265C, and H435A (EU index according to Kabat). In some embodiments, an antibody comprising the CDR and/or variable region sequences of Ab3 can further comprise a heavy chain constant region set forth in SEQ ID NO:102, SEQ ID NO:103, SEQ ID NO:104, SEQ ID NO:105 or SEQ ID NO:106. In some embodiments the antibody comprises a light chain constant region set forth in SEQ ID NO:101.

In certain embodiments, the anti-CD45 antibody, or antigen binding portion thereof, comprises a heavy chain comprising the amino acid sequence as set forth in SEQ ID NO:29. In certain embodiments, an antibody comprises a modified heavy chain (HC) region comprising an HC domain comprising SEQ ID NO:29, or a variant of SEQ ID NO:29, which variant (i) differs from SEQ ID NO:29 in 1, 2, 3, 4 or 5 amino acids substitutions, additions or deletions; (ii) differs from SEQ ID NO:29 in at most 5, 4, 3, 2, or 1 amino acids substitutions, additions or deletions; (iii) differs from SEQ ID NO:29 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:29, wherein in any of (i)-(iv), an amino acid substitution may be a conservative amino acid substitution or a non-conservative amino acid substitution; and wherein the modified heavy chain region retains the CD45 specificity of the antibody (i.e., specificity similar to Ab3), or has an enhanced biological activity relative to that of another Ab3 heavy chain region.

In certain embodiments, the anti-CD45 antibody, or antigen binding portion thereof, comprises a light chain comprising the amino acid sequence as set forth in SEQ ID NO:30. In certain embodiments, an antibody comprises a modified light chain (LC) region comprising an LC domain comprising SEQ ID NO:30, or a variant of SEQ ID NO:30, which variant (i) differs from SEQ ID NO:30 in 1, 2, 3, 4 or 5 amino acids substitutions, additions or deletions; (ii) differs from SEQ ID NO:30 in at most 5, 4, 3, 2, or 1 amino acids substitutions, additions or deletions; (iii) differs from SEQ ID NO:30 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:30, wherein in any of (i)-(iv), an amino acid substitution may be a conservative amino acid substitution or a non-conservative amino acid substitution; and wherein the modified light chain region retains the CD45 specificity of the antibody (i.e., specificity similar to Ab3), or has an enhanced biological activity relative to that of another Ab3 light chain region.

In some embodiments, antibodies comprising the CDR regions and/or variable regions of Ab3 can be incorporated into antibody-drug conjugates, as described herein. In addition, antibodies comprising the CDR regions and/or variable regions of Ab3 can be used in the methods described herein, e.g., for depletion of CD45+ cells in a subject.

Ab4

Antibody 4 (Ab4) cross reacts with human CD45, cyno CD45 and rhesus CD45, and can bind the various isoforms of human CD45.

The amino acid sequences for the various binding regions of anti-CD45 Ab4 are described in Table 27. Included in the invention are anti-CD45 antibodies based on Ab4, e.g., that comprise the CDRs as set forth in Table 27.

In one embodiment, the invention provides an anti-CD45 antibody, or antigen-binding fragment thereof, comprising antigen binding regions, e.g., CDRs and/or variable regions, corresponding to those of Ab4. The heavy chain variable region (VH) amino acid sequence of Ab4 is set forth in SEQ ID NO:31 (see Table 27). The VH CDR domain amino acid sequences of Ab4 are set forth in SEQ ID NO:32 (VH CDR1); SEQ ID NO:33 (VH CDR2), and SEQ ID NO:34 (VH CDR3). The light chain variable region (VL) amino acid sequence of Ab4 is described in SEQ ID NO:35 (see Table 27). The VL CDR domain amino acid sequences of Ab4 are set forth in SEQ ID NO:36 (VL CDR1); SEQ ID NO:37 (VL CDR2), and SEQ ID NO:38 (VL CDR3).

Accordingly, in some embodiments, provided herein is an anti-CD45 antibody, or antigen-binding portion thereof, comprising a heavy chain variable region comprising a CDR1 domain comprising the amino acid sequence as set forth in SEQ ID NO:32, a CDR2 domain comprising the amino acid sequence as set forth in SEQ ID NO:33, and a CDR3 domain comprising the amino acid sequence as set forth in SEQ ID NO:34; and/or a light chain variable region comprising a CDR1 domain comprising the amino acid sequence as set forth in SEQ ID NO:36, a CDR2 domain comprising the amino acid sequence as set forth in SEQ ID NO:37; and a CDR3 domain comprising the amino acid sequence as set forth in SEQ ID NO:38. In certain embodiments, an anti-CD45 antibody comprises the CDRs described herein (SEQ ID NOs: 32 to 34 and 36 to 38) wherein the CDR comprises a conservative amino acid substitution (or 2, 3, 4, or 5 amino acid substitutions) while retaining the CD45 specificity of the antibody (i.e., specificity similar to Ab4).

In some embodiments, provided herein is an anti-CD45 antibody, or antigen-binding portion thereof, comprising a heavy chain variable region comprising the amino acid sequence as set forth in SEQ ID NO:31, and/or a light chain variable region comprising the amino acid sequence as set forth in SEQ ID NO:35. In certain embodiments, an antibody can comprise a modified heavy chain (HC) variable region comprising an HC variable domain comprising SEQ ID NO:31, or a variant of SEQ ID NO:31, which variant (i) differs from SEQ ID NO:31 in 1, 2, 3, 4 or 5 amino acids substitutions, additions or deletions; (ii) differs from SEQ ID NO:31 in at most 5, 4, 3, 2, or 1 amino acids substitutions, additions or deletions; (iii) differs from SEQ ID NO:31 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:31, wherein in any of (i)-(iv), an amino acid substitution may be a conservative amino acid substitution or a non-conservative amino acid substitution; and wherein the modified heavy chain variable region retains the CD45 specificity of the antibody (i.e., specificity similar to Ab4), or has an enhanced biological activity relative to that of another Ab4 heavy chain variable region. In certain embodiments, an antibody comprises a modified light chain (LC) variable region comprising an LC variable domain comprising SEQ ID NO:35, or a variant of SEQ ID NO:35, which variant (i) differs from SEQ ID NO:35 in 1, 2, 3, 4 or 5 amino acids substitutions, additions or deletions; (ii) differs from SEQ ID NO:35 in at most 5, 4, 3, 2, or 1 amino acids substitutions, additions or deletions; (iii) differs from SEQ ID NO:35 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:35, wherein in any of (i)-(iv), an amino acid substitution may be a conservative amino acid substitution or a non-conservative amino acid substitution; and wherein the modified light chain variable region retains the CD45 specificity of the antibody (i.e., specificity similar to Ab4), or has an enhanced biological activity relative to that of another Ab4 light chain variable region.

Antibodies comprising the CDR and/or variable region sequences of Ab4 can be in the form of full-length antibodies, bispecific antibodies, dual variable domain antibodies, multiple chain or single chain antibodies, and/or binding fragments that specifically bind human CD45, including but not limited to Fab, Fab', (Fab')2, Fv), scFv (single chain Fv), surrobodies (including surrogate light chain construct), single domain antibodies, camelized antibodies and the like. They also can be of, or derived from, any isotype, including, for example, IgA (e.g., IgA1 or IgA2), IgD, IgE, IgG (e.g. IgG1, IgG2, IgG3 or IgG4), or IgM. In some embodiments, the anti-45 antibody is an IgG (e.g. IgG1, IgG2, IgG3 or IgG4).

In some embodiments, an antibody comprising the CDR and/or variable region sequences of Ab4 can further comprise a heavy chain constant region and/or a light chain constant region. In some embodiments, the constant region is a human IgG1 constant region, a human IgG2 constant region, a human IgG3 constant region, or a human IgG4 constant region. In some embodiments, the heavy chain constant region can be a modified constant region. Exemplary constant regions substitutions and/or modifications are described herein, and include, but are not limited to, substitutions at one or more of the following positions: 234, 235, 265, and 435 (EU index according to Kabat). In some embodiments, an antibody comprising the CDR and/or variable region sequences of Ab4 can further comprise an IgG1 heavy chain constant region containing one or more of the following substitutions: L234A, L235A, D265C, and H435A (EU index according to Kabat). In some embodiments, an antibody comprising the CDR and/or variable region sequences of Ab4 can further comprise a heavy chain constant region set forth in SEQ ID NO:102, SEQ ID NO:103, SEQ ID NO:104, SEQ ID NO:105 or SEQ ID NO:106. In some embodiments the antibody comprises a light chain constant region set forth in SEQ ID NO:101.

In certain embodiments, the anti-CD45 antibody, or antigen binding portion thereof, comprises a heavy chain comprising the amino acid sequence as set forth in SEQ ID NO:39. In certain embodiments, an antibody comprises a modified heavy chain (HC) region comprising an HC domain comprising SEQ ID NO:39, or a variant of SEQ ID NO:39, which variant (i) differs from SEQ ID NO:39 in 1, 2, 3, 4 or 5 amino acids substitutions, additions or deletions; (ii) differs from SEQ ID NO:39 in at most 5, 4, 3, 2, or 1 amino acids substitutions, additions or deletions; (iii) differs from SEQ ID NO:39 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:39, wherein in any of (i)-(iv), an amino acid substitution may be a conservative amino acid substitution or a non-conservative amino acid substitution; and wherein the modified heavy chain region retains the CD45 specificity of the antibody (i.e., specificity similar to Ab4), or has an enhanced biological activity relative to that of another Ab4 heavy chain region.

In certain embodiments, the anti-CD45 antibody, or antigen binding portion thereof, comprises a light chain comprising the amino acid sequence as set forth in SEQ ID NO:40. In certain embodiments, an antibody comprises a modified light chain (LC) region comprising an LC domain comprising SEQ ID NO:40, or a variant of SEQ ID NO:40, which variant (i) differs from SEQ ID NO:40 in 1, 2, 3, 4 or 5 amino acids substitutions, additions or deletions; (ii) differs from SEQ ID NO:40 in at most 5, 4, 3, 2, or 1 amino acids substitutions, additions or deletions; (iii) differs from SEQ ID NO:40 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:40, wherein in any of (i)-(iv), an amino acid substitution may be a conservative amino acid substitution or a non-conservative amino acid substitution; and wherein the modified light chain region retains the CD45 specificity of the antibody (i.e., specificity similar to Ab4), or has an enhanced biological activity relative to that of another Ab4 light chain region.

In some embodiments, antibodies comprising the CDR regions and/or variable regions of Ab4 can be incorporated into antibody-drug conjugates, as described herein. In addition, antibodies comprising the CDR regions and/or variable regions of Ab4 can be used in the methods described herein, e.g., for depletion of CD45+ cells in a subject.

Ab5

Antibody 5 (Ab5) cross reacts with human CD45, cyno CD45 and rhesus CD45, and can bind the various isoforms of human CD45.

The amino acid sequences for the various binding regions of anti-CD45 Ab5 are described in Table 27. Included in the invention are anti-CD45 antibodies based on Ab5, e.g., that comprise the CDRs as set forth in Table 27.

In one embodiment, the invention provides an anti-CD45 antibody, or antigen-binding fragment thereof, comprising antigen binding regions, e.g., CDRs and/or variable regions, corresponding to those of Ab5. The heavy chain variable region (VH) amino acid sequence of Ab5 is set forth in SEQ ID NO:41 (see Table 27). The VH CDR domain amino acid sequences of Ab5 are set forth in SEQ ID NO:42 (VH CDR1); SEQ ID NO:43 (VH CDR2), and SEQ ID NO:44 (VH CDR3). The light chain variable region (VL) amino acid sequence of Ab5 is described in SEQ ID NO:45 (see Table 27). The VL CDR domain amino acid sequences of Ab5 are set forth in SEQ ID NO:46 (VL CDR1); SEQ ID NO:47 (VL CDR2), and SEQ ID NO:48 (VL CDR3).

Accordingly, in some embodiments, provided herein is an anti-CD45 antibody, or antigen-binding portion thereof, comprising a heavy chain variable region comprising a CDR1 domain comprising the amino acid sequence as set forth in SEQ ID NO:42, a CDR2 domain comprising the amino acid sequence as set forth in SEQ ID NO:43, and a CDR3 domain comprising the amino acid sequence as set forth in SEQ ID NO:44; and/or a light chain variable region comprising a CDR1 domain comprising the amino acid sequence as set forth in SEQ ID NO:46, a CDR2 domain comprising the amino acid sequence as set forth in SEQ ID NO:47; and a CDR3 domain comprising the amino acid sequence as set forth in SEQ ID NO:48. In certain embodiments, an anti-CD45 antibody comprises the CDRs described herein (SEQ ID NOs: 42 to 44 and 46 to 48) wherein the CDR comprises a conservative amino acid substitution (or 2, 3, 4, or 5 amino acid substitutions) while retaining the CD45 specificity of the antibody (i.e., specificity similar to Ab5).

In some embodiments, provided herein is an anti-CD45 antibody, or antigen-binding portion thereof, comprising a heavy chain variable region comprising the amino acid sequence as set forth in SEQ ID NO:41, and/or a light chain variable region comprising the amino acid sequence as set forth in SEQ ID NO:45. In certain embodiments, an antibody can comprise a modified heavy chain (HC) variable region comprising an HC variable domain comprising SEQ ID NO:41, or a variant of SEQ ID NO:41, which variant (i) differs from SEQ ID NO:41 in 1, 2, 3, 4 or 5 amino acids substitutions, additions or deletions; (ii) differs from SEQ ID NO:41 in at most 5, 4, 3, 2, or 1 amino acids substitutions, additions or deletions; (iii) differs from SEQ ID NO:41 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:41, wherein in any of (i)-(iv), an amino acid substitution may be a conservative amino acid substitution or a non-conservative amino acid substitution; and wherein the modified heavy chain variable region retains the CD45 specificity of the antibody (i.e., specificity similar to Ab5), or has an enhanced biological activity relative to that of another Ab5 heavy chain variable region. In certain embodiments, an antibody comprises a modified light chain (LC) variable region comprising an LC variable domain comprising SEQ ID NO:45, or a variant of SEQ ID NO:45, which variant (i) differs from SEQ ID NO:45 in 1, 2, 3, 4 or 5 amino acids substitutions, additions or deletions; (ii) differs from SEQ ID NO:45 in at most 5, 4, 3, 2, or 1 amino acids substitutions, additions or deletions; (iii) differs from SEQ ID NO:45 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:45, wherein in any of (i)-(iv), an amino acid substitution may be a conservative amino acid substitution or a non-conservative amino acid substitution; and wherein the modified light chain variable region retains the CD45 specificity of the antibody (i.e., specificity similar to Ab5), or has an enhanced biological activity relative to that of another Ab5 light chain variable region.

Antibodies comprising the CDR and/or variable region sequences of Ab5 can be in the form of full-length antibodies, bispecific antibodies, dual variable domain antibodies, multiple chain or single chain antibodies, and/or binding fragments that specifically bind human CD45, including but not limited to Fab, Fab', (Fab')2, Fv), scFv (single chain Fv), surrobodies (including surrogate light chain construct), single domain antibodies, camelized antibodies and the like. They also can be of, or derived from, any isotype, including, for example, IgA (e.g., IgA1 or IgA2), IgD, IgE, IgG (e.g. IgG1, IgG2, IgG3 or IgG4), or IgM. In some embodiments, the anti-45 antibody is an IgG (e.g. IgG1, IgG2, IgG3 or IgG4).

In some embodiments, an antibody comprising the CDR and/or variable region sequences of Ab5 can further comprise a heavy chain constant region and/or a light chain constant region. In some embodiments, the constant region is a human IgG1 constant region, a human IgG2 constant region, a human IgG3 constant region, or a human IgG4 constant region. In some embodiments, the heavy chain constant region can be a modified constant region. Exemplary constant regions substitutions and/or modifications are described herein, and include, but are not limited to, substitutions at one or more of the following positions: 234, 235, 265, and 435 (EU index according to Kabat). In some embodiments, an antibody comprising the CDR and/or variable region sequences of Ab5 can further comprise an IgG1 heavy chain constant region containing one or more of the following substitutions: L234A, L235A, D265C, and H435A (EU index according to Kabat). In some embodiments, an antibody comprising the CDR and/or variable region sequences of Ab5 can further comprise a heavy chain constant region set forth in SEQ ID NO:102, SEQ ID NO:103, SEQ ID NO:104, SEQ ID NO:105 or SEQ ID NO:106. In some embodiments the antibody comprises a light chain constant region set forth in SEQ ID NO:101.

In certain embodiments, the anti-CD45 antibody, or antigen binding portion thereof, comprises a heavy chain comprising the amino acid sequence as set forth in SEQ ID NO:49. In certain embodiments, an antibody comprises a modified heavy chain (HC) region comprising an HC domain comprising SEQ ID NO:49, or a variant of SEQ ID NO:9, which variant (i) differs from SEQ ID NO:49 in 1, 2, 3, 4 or 5 amino acids substitutions, additions or deletions; (ii) differs from SEQ ID NO:49 in at most 5, 4, 3, 2, or 1 amino acids substitutions, additions or deletions; (iii) differs from SEQ ID NO:49 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:49, wherein in any of (i)-(iv), an amino acid substitution may be a conservative amino acid substitution or a non-conservative amino acid substitution; and wherein the modified heavy chain region retains the CD45 specificity of the antibody (i.e., specificity similar to Ab5), or has an enhanced biological activity relative to that of another Ab5 heavy chain region.

In certain embodiments, the anti-CD45 antibody, or antigen binding portion thereof, comprises a light chain comprising the amino acid sequence as set forth in SEQ ID NO:50. In certain embodiments, an antibody comprises a modified light chain (LC) region comprising an LC domain comprising SEQ ID NO:50, or a variant of SEQ ID NO:50, which variant (i) differs from SEQ ID NO:50 in 1, 2, 3, 4 or 5 amino acids substitutions, additions or deletions; (ii) differs from SEQ ID NO:50 in at most 5, 4, 3, 2, or 1 amino acids substitutions, additions or deletions; (iii) differs from SEQ ID NO:50 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:50, wherein in any of (i)-(iv), an amino acid substitution may be a conservative amino acid substitution or a non-conservative amino acid substitution; and wherein the modified light chain region retains the CD45 specificity of the antibody (i.e., specificity similar to Ab5), or has an enhanced biological activity relative to that of another Ab5 light chain region.

In some embodiments, antibodies comprising the CDR regions and/or variable regions of Ab5 can be incorporated into antibody-drug conjugates, as described herein. In addition, antibodies comprising the CDR regions and/or variable regions of Ab5 can be used in the methods described herein, e.g., for depletion of CD45+ cells in a subject.

Ab6

Antibody 6 (Ab6) cross reacts with human CD45, cyno CD45 and rhesus CD45, and can bind the various isoforms of human CD45.

The amino acid sequences for the various binding regions of anti-CD45 Ab6 are described in Table 27. Included in the invention are anti-CD45 antibodies based on Ab6, e.g., that comprise the CDRs as set forth in Table 27.

In one embodiment, the invention provides an anti-CD45 antibody, or antigen-binding fragment thereof, comprising antigen binding regions, e.g., CDRs and/or variable regions, corresponding to those of Ab6. The heavy chain variable region (VH) amino acid sequence of Ab6 is set forth in SEQ ID NO:51 (see Table 27). The VH CDR domain amino acid sequences of Ab6 are set forth in SEQ ID NO:52 (VH CDR1); SEQ ID NO:53 (VH CDR2), and SEQ ID NO:54 (VH CDR3). The light chain variable region (VL) amino acid sequence of Ab6 is described in SEQ ID NO:55 (see Table 27). The VL CDR domain amino acid sequences of Ab6 are set forth in SEQ ID NO:56 (VL CDR1); SEQ ID NO:57 (VL CDR2), and SEQ ID NO:58 (VL CDR3).

Accordingly, in some embodiments, provided herein is an anti-CD45 antibody, or antigen-binding portion thereof, comprising a heavy chain variable region comprising a CDR1 domain comprising the amino acid sequence as set forth in SEQ ID NO:52, a CDR2 domain comprising the amino acid sequence as set forth in SEQ ID NO:53, and a CDR3 domain comprising the amino acid sequence as set forth in SEQ ID NO:54; and/or a light chain variable region comprising a CDR1 domain comprising the amino acid sequence as set forth in SEQ ID NO:56, a CDR2 domain comprising the amino acid sequence as set forth in SEQ ID NO:57; and a CDR3 domain comprising the amino acid sequence as set forth in SEQ ID NO:58. In certain embodiments, an anti-CD45 antibody comprises the CDRs described herein (SEQ ID NOs: 52 to 54 and 56 to 58) wherein the CDR comprises a conservative amino acid substitution (or 2, 3, 4, or 5 amino acid substitutions) while retaining the CD45 specificity of the antibody (i.e., specificity similar to Ab6).

In some embodiments, provided herein is an anti-CD45 antibody, or antigen-binding portion thereof, comprising a heavy chain variable region comprising the amino acid sequence as set forth in SEQ ID NO:51, and/or a light chain variable region comprising the amino acid sequence as set forth in SEQ ID NO:55. In certain embodiments, an antibody can comprise a modified heavy chain (HC) variable region comprising an HC variable domain comprising SEQ ID NO:51, or a variant of SEQ ID NO:51, which variant (i) differs from SEQ ID NO:51 in 1, 2, 3, 4 or 5 amino acids substitutions, additions or deletions; (ii) differs from SEQ ID NO:51 in at most 5, 4, 3, 2, or 1 amino acids substitutions, additions or deletions; (iii) differs from SEQ ID NO:51 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:51, wherein in any of (i)-(iv), an amino acid substitution may be a conservative amino acid substitution or a non-conservative amino acid substitution; and wherein the modified heavy chain variable region retains the CD45 specificity of the antibody (i.e., specificity similar to Ab6), or has an enhanced biological activity relative to that of another Ab6 heavy chain variable region. In certain embodiments, an antibody comprises a modified light chain (LC) variable region comprising an LC variable domain comprising SEQ ID NO:55, or a variant of SEQ ID NO:55, which variant (i) differs from SEQ ID NO:55 in 1, 2, 3, 4 or 5 amino acids substitutions, additions or deletions; (ii) differs from SEQ ID NO:55 in at most 5, 4, 3, 2, or 1 amino acids substitutions, additions or deletions; (iii) differs from SEQ ID NO:55 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:55, wherein in any of (i)-(iv), an amino acid substitution may be a conservative amino acid substitution or a non-conservative amino acid substitution; and wherein the modified light chain variable region retains the CD45 specificity of the antibody (i.e., specificity similar to Ab6), or has an enhanced biological activity relative to that of another Ab6 light chain variable region.

Antibodies comprising the CDR and/or variable region sequences of Ab6 can be in the form of full-length antibodies, bispecific antibodies, dual variable domain antibodies, multiple chain or single chain antibodies, and/or binding fragments that specifically bind human CD45, including but not limited to Fab, Fab', (Fab')2, Fv), scFv (single chain Fv), surrobodies (including surrogate light chain construct), single domain antibodies, camelized antibodies and the like. They also can be of, or derived from, any isotype, including, for example, IgA (e.g., IgA1 or IgA2), IgD, IgE, IgG (e.g.

IgG1, IgG2, IgG3 or IgG4), or IgM. In some embodiments, the anti-45 antibody is an IgG (e.g. IgG1, IgG2, IgG3 or IgG4).

In some embodiments, an antibody comprising the CDR and/or variable region sequences of Ab6 can further comprise a heavy chain constant region and/or a light chain constant region. In some embodiments, the constant region is a human IgG1 constant region, a human IgG2 constant region, a human IgG3 constant region, or a human IgG4 constant region. In some embodiments, the heavy chain constant region can be a modified constant region. Exemplary constant regions substitutions and/or modifications are described herein, and include, but are not limited to, substitutions at one or more of the following positions: 234, 235, 265, and 435 (EU index according to Kabat). In some embodiments, an antibody comprising the CDR and/or variable region sequences of Ab6 can further comprise an IgG1 heavy chain constant region containing one or more of the following substitutions: L234A, L235A, D265C, and H435A (EU index according to Kabat). In some embodiments, an antibody comprising the CDR and/or variable region sequences of Ab6 can further comprise a heavy chain constant region set forth in SEQ ID NO:102, SEQ ID NO:103, SEQ ID NO:104, SEQ ID NO:105 or SEQ ID NO:106. In some embodiments the antibody comprises a light chain constant region set forth in SEQ ID NO:101.

In certain embodiments, the anti-CD45 antibody, or antigen binding portion thereof, comprises a heavy chain comprising the amino acid sequence as set forth in SEQ ID NO:59. In certain embodiments, an antibody comprises a modified heavy chain (HC) region comprising an HC domain comprising SEQ ID NO:59, or a variant of SEQ ID NO:59, which variant (i) differs from SEQ ID NO:59 in 1, 2, 3, 4 or 5 amino acids substitutions, additions or deletions; (ii) differs from SEQ ID NO:59 in at most 5, 4, 3, 2, or 1 amino acids substitutions, additions or deletions; (iii) differs from SEQ ID NO:59 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:59, wherein in any of (i)-(iv), an amino acid substitution may be a conservative amino acid substitution or a non-conservative amino acid substitution; and wherein the modified heavy chain region retains the CD45 specificity of the antibody (i.e., specificity similar to Ab6), or has an enhanced biological activity relative to that of another Ab6 heavy chain region.

In certain embodiments, the anti-CD45 antibody, or antigen binding portion thereof, comprises a light chain comprising the amino acid sequence as set forth in SEQ ID NO:60. In certain embodiments, an antibody comprises a modified light chain (LC) region comprising an LC domain comprising SEQ ID NO:60, or a variant of SEQ ID NO:60, which variant (i) differs from SEQ ID NO:60 in 1, 2, 3, 4 or 5 amino acids substitutions, additions or deletions; (ii) differs from SEQ ID NO:60 in at most 5, 4, 3, 2, or 1 amino acids substitutions, additions or deletions; (iii) differs from SEQ ID NO:60 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:60, wherein in any of (i)-(iv), an amino acid substitution may be a conservative amino acid substitution or a non-conservative amino acid substitution; and wherein the modified light chain region retains the CD45 specificity of the antibody (i.e., specificity similar to Ab6), or has an enhanced biological activity relative to that of another Ab6 light chain region.

In some embodiments, antibodies comprising the CDR regions and/or variable regions of Ab6 can be incorporated into antibody-drug conjugates, as described herein. In addition, antibodies comprising the CDR regions and/or variable regions of Ab6 can be used in the methods described herein, e.g., for depletion of CD45+ cells in a subject.

Ab7

Antibody 7 (Ab7) cross reacts with human CD45, cyno CD45 and rhesus CD45, and can bind the various isoforms of human CD45.

The amino acid sequences for the various binding regions of anti-CD45 Ab7 are described in Table 27. Included in the invention are anti-CD45 antibodies based on Ab7, e.g., that comprise the CDRs as set forth in Table 27.

In one embodiment, the invention provides an anti-CD45 antibody, or antigen-binding fragment thereof, comprising antigen binding regions, e.g., CDRs and/or variable regions, corresponding to those of Ab7. The heavy chain variable region (VH) amino acid sequence of Ab7 is set forth in SEQ ID NO:61 (see Table 27). The VH CDR domain amino acid sequences of Ab7 are set forth in SEQ ID NO:62 (VH CDR1); SEQ ID NO:63 (VH CDR2), and SEQ ID NO:64 (VH CDR3). The light chain variable region (VL) amino acid sequence of Ab7 is described in SEQ ID NO:65 (see Table 27). The VL CDR domain amino acid sequences of Ab7 are set forth in SEQ ID NO:66 (VL CDR1); SEQ ID NO:67 (VL CDR2), and SEQ ID NO:68 (VL CDR3).

Accordingly, in some embodiments, provided herein is an anti-CD45 antibody, or antigen-binding portion thereof, comprising a heavy chain variable region comprising a CDR1 domain comprising the amino acid sequence as set forth in SEQ ID NO:62, a CDR2 domain comprising the amino acid sequence as set forth in SEQ ID NO:63, and a CDR3 domain comprising the amino acid sequence as set forth in SEQ ID NO:64; and/or a light chain variable region comprising a CDR1 domain comprising the amino acid sequence as set forth in SEQ ID NO:66, a CDR2 domain comprising the amino acid sequence as set forth in SEQ ID NO:67; and a CDR3 domain comprising the amino acid sequence as set forth in SEQ ID NO:68. In certain embodiments, an anti-CD45 antibody comprises the CDRs described herein (SEQ ID NOs: 62 to 64 and 66 to 68) wherein the CDR comprises a conservative amino acid substitution (or 2, 3, 4, or 5 amino acid substitutions) while retaining the CD45 specificity of the antibody (i.e., specificity similar to Ab7).

In some embodiments, provided herein is an anti-CD45 antibody, or antigen-binding portion thereof, comprising a heavy chain variable region comprising the amino acid sequence as set forth in SEQ ID NO:61, and/or a light chain variable region comprising the amino acid sequence as set forth in SEQ ID NO:65. In certain embodiments, an antibody can comprise a modified heavy chain (HC) variable region comprising an HC variable domain comprising SEQ ID NO:61, or a variant of SEQ ID NO:61, which variant (i) differs from SEQ ID NO:61 in 1, 2, 3, 4 or 5 amino acids substitutions, additions or deletions; (ii) differs from SEQ ID NO:61 in at most 5, 4, 3, 2, or 1 amino acids substitutions, additions or deletions; (iii) differs from SEQ ID NO:61 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:61, wherein in any of (i)-(iv), an amino acid substitution may be a conservative amino acid substitution or a non-conservative amino acid substitution; and wherein the modified heavy chain variable region retains the CD45 specificity of the antibody (i.e., specificity similar to Ab7), or has an enhanced biological activity relative to that of another Ab7 heavy chain variable region. In certain embodiments, an antibody comprises a modified light chain (LC) variable region comprising an LC variable domain comprising SEQ ID NO:65, or a variant of SEQ ID NO:65, which variant (i) differs from SEQ ID NO:65 in 1, 2, 3, 4 or 5 amino acids substitutions, additions or deletions; (ii) differs from SEQ ID NO:65 in at most 5, 4, 3, 2, or 1 amino acids substitutions, additions or deletions; (iii) differs from SEQ ID NO:65 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:65, wherein in any of (i)-(iv), an amino acid substitution may be a conservative amino acid substitution or a non-conservative amino acid substitution; and wherein the modified light chain variable region retains the CD45 specificity of the antibody (i.e., specificity similar to Ab7), or has an enhanced biological activity relative to that of another Ab7 light chain variable region.

Antibodies comprising the CDR and/or variable region sequences of Ab7 can be in the form of full-length antibodies, bispecific antibodies, dual variable domain antibodies, multiple chain or single chain antibodies, and/or binding fragments that specifically bind human CD45, including but not limited to Fab, Fab', (Fab')2, Fv), scFv (single chain Fv), surrobodies (including surrogate light chain construct), single domain antibodies, camelized antibodies and the like. They also can be of, or derived from, any isotype, including, for example, IgA (e.g., IgA1 or IgA2), IgD, IgE, IgG (e.g. IgG1, IgG2, IgG3 or IgG4), or IgM. In some embodiments, the anti-45 antibody is an IgG (e.g. IgG1, IgG2, IgG3 or IgG4).

In some embodiments, an antibody comprising the CDR and/or variable region sequences of Ab7 can further comprise a heavy chain constant region and/or a light chain constant region. In some embodiments, the constant region is a human IgG1 constant region, a human IgG2 constant region, a human IgG3 constant region, or a human IgG4 constant region. In some embodiments, the heavy chain constant region can be a modified constant region. Exemplary constant regions substitutions and/or modifications are described herein, and include, but are not limited to, substitutions at one or more of the following positions: 234, 235, 265, and 435 (EU index according to Kabat). In some embodiments, an antibody comprising the CDR and/or variable region sequences of Ab7 can further comprise an IgG1 heavy chain constant region containing one or more of the following substitutions: L234A, L235A, D265C, and H435A (EU index according to Kabat). In some embodiments, an antibody comprising the CDR and/or variable region sequences of Ab7 can further comprise a heavy chain constant region set forth in SEQ ID NO:102, SEQ ID NO:103, SEQ ID NO:104, SEQ ID NO:105 or SEQ ID NO:106. In some embodiments the antibody comprises a light chain constant region set forth in SEQ ID NO:101.

In certain embodiments, the anti-CD45 antibody, or antigen binding portion thereof, comprises a heavy chain comprising the amino acid sequence as set forth in SEQ ID NO:69. In certain embodiments, an antibody comprises a modified heavy chain (HC) region comprising an HC domain comprising SEQ ID NO:69, or a variant of SEQ ID NO:69, which variant (i) differs from SEQ ID NO:9 in 1, 2, 3, 4 or 5 amino acids substitutions, additions or deletions; (ii) differs from SEQ ID NO:69 in at most 5, 4, 3, 2, or 1 amino acids substitutions, additions or deletions; (iii) differs from SEQ ID NO:69 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:69, wherein in any of (i)-(iv), an amino acid substitution may be a conservative amino acid substitution or a non-conservative amino acid substitution; and wherein the modified heavy chain region retains the CD45 specificity of the antibody (i.e., specificity similar to Ab7), or has an enhanced biological activity relative to that of another Ab7 heavy chain region.

In certain embodiments, the anti-CD45 antibody, or antigen binding portion thereof, comprises a light chain comprising the amino acid sequence as set forth in SEQ ID NO:70. In certain embodiments, an antibody comprises a modified light chain (LC) region comprising an LC domain comprising SEQ ID NO:70, or a variant of SEQ ID NO:70, which variant (i) differs from SEQ ID NO:70 in 1, 2, 3, 4 or 5 amino acids substitutions, additions or deletions; (ii) differs from SEQ ID NO:70 in at most 5, 4, 3, 2, or 1 amino acids substitutions, additions or deletions; (iii) differs from SEQ ID NO:70 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:70, wherein in any of (i)-(iv), an amino acid substitution may be a conservative amino acid substitution or a non-conservative amino acid substitution; and wherein the modified light chain region retains the CD45 specificity of the antibody (i.e., specificity similar to Ab7), or has an enhanced biological activity relative to that of another Ab7 light chain region.

In some embodiments, antibodies comprising the CDR regions and/or variable regions of Ab7 can be incorporated into antibody-drug conjugates, as described herein. In addition, antibodies comprising the CDR regions and/or variable regions of Ab7 can be used in the methods described herein, e.g., for depletion of CD45+ cells in a subject.

AbA

Antibody A (AbA) cross reacts with human CD45, cyno CD45 and rhesus CD45, and can bind the various isoforms of human CD45.

The amino acid sequences for the various binding regions of anti-CD45 AbA are described in Table 27. Included in the invention are anti-CD45 antibodies based on AbA, e.g., that comprise the CDRs as set forth in Table 27.

In one embodiment, the invention provides an anti-CD45 antibody, or antigen-binding fragment thereof, comprising antigen binding regions, e.g., CDRs and/or variable regions, corresponding to those of AbA. The heavy chain variable region (VH) amino acid sequence of AbA is set forth in SEQ ID NO:71 (see Table 27). The VH CDR domain amino acid sequences of AbA are set forth in SEQ ID NO:72 (VH CDR1); SEQ ID NO:73 (VH CDR2), and SEQ ID NO:74 (VH CDR3). The light chain variable region (VL) amino acid sequence of AbA is described in SEQ ID NO:75 (see Table 27). The VL CDR domain amino acid sequences of AbA are set forth in SEQ ID NO:76 (VL CDR1); SEQ ID NO:77 (VL CDR2), and SEQ ID NO:78 (VL CDR3).

Accordingly, in some embodiments, provided herein is an anti-CD45 antibody, or antigen-binding portion thereof, comprising a heavy chain variable region comprising a CDR1 domain comprising the amino acid sequence as set forth in SEQ ID NO:72, a CDR2 domain comprising the amino acid sequence as set forth in SEQ ID NO:73, and a CDR3 domain comprising the amino acid sequence as set forth in SEQ ID NO:74; and/or a light chain variable region comprising a CDR1 domain comprising the amino acid sequence as set forth in SEQ ID NO:76, a CDR2 domain comprising the amino acid sequence as set forth in SEQ ID NO:77; and a CDR3 domain comprising the amino acid sequence as set forth in SEQ ID NO:78. In certain embodiments, an anti-CD45 antibody comprises the CDRs described herein (SEQ ID NOs: 72 to 74 and 76 to 78) wherein the CDR comprises a conservative amino acid substitution (or 2, 3, 4, or 5 amino acid substitutions) while retaining the CD45 specificity of the antibody (i.e., specificity similar to AbA).

In some embodiments, provided herein is an anti-CD45 antibody, or antigen-binding portion thereof, comprising a heavy chain variable region comprising the amino acid sequence as set forth in SEQ ID NO:71, and/or a light chain variable region comprising the amino acid sequence as set forth in SEQ ID NO:75. In certain embodiments, an antibody can comprise a modified heavy chain (HC) variable region comprising an HC variable domain comprising SEQ ID NO:71, or a variant of SEQ ID NO:71, which variant (i) differs from SEQ ID NO:71 in 1, 2, 3, 4 or 5 amino acids substitutions, additions or deletions; (ii) differs from SEQ ID NO:71 in at most 5, 4, 3, 2, or 1 amino acids substitutions, additions or deletions; (iii) differs from SEQ ID NO:71 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:71, wherein in any of (i)-(iv), an amino acid substitution may be a conservative amino acid substitution or a non-conservative amino acid substitution; and wherein the modified heavy chain variable region retains the CD45 specificity of the antibody (i.e., specificity similar to AbA), or has an enhanced biological activity relative to that of another AbA heavy chain variable region. In certain embodiments, an antibody comprises a modified light chain (LC) variable region comprising an LC variable domain comprising SEQ ID NO:75, or a variant of SEQ ID NO:75, which variant (i) differs from SEQ ID NO:75 in 1, 2, 3, 4 or 5 amino acids substitutions, additions or deletions; (ii) differs from SEQ ID NO:75 in at most 5, 4, 3, 2, or 1 amino acids substitutions, additions or deletions; (iii) differs from SEQ ID NO:75 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:75, wherein in any of (i)-(iv), an amino acid substitution may be a conservative amino acid substitution or a non-conservative amino acid substitution; and wherein the modified light chain variable region retains the CD45 specificity of the antibody (i.e., specificity similar to AbA), or has an enhanced biological activity relative to that of another AbA light chain variable region.

Antibodies comprising the CDR and/or variable region sequences of AbA can be in the form of full-length antibodies, bispecific antibodies, dual variable domain antibodies, multiple chain or single chain antibodies, and/or binding fragments that specifically bind human CD45, including but not limited to Fab, Fab', (Fab')2, Fv), scFv (single chain Fv), surrobodies (including surrogate light chain construct), single domain antibodies, camelized antibodies and the like. They also can be of, or derived from, any isotype, including, for example, IgA (e.g., IgA1 or IgA2), IgD, IgE, IgG (e.g. IgG1, IgG2, IgG3 or IgG4), or IgM. In some embodiments, the anti-45 antibody is an IgG (e.g. IgG1, IgG2, IgG3 or IgG4).

In some embodiments, an antibody comprising the CDR and/or variable region sequences of AbA can further comprise a heavy chain constant region and/or a light chain constant region. In some embodiments, the constant region is a human IgG1 constant region, a human IgG2 constant region, a human IgG3 constant region, or a human IgG4 constant region. In some embodiments, the heavy chain constant region can be a modified constant region. Exemplary constant regions substitutions and/or modifications are described herein, and include, but are not limited to, substitutions at one or more of the following positions: 234, 235, 265, and 435 (EU index according to Kabat). In some embodiments, an antibody comprising the CDR and/or variable region sequences of AbA can further comprise an IgG1 heavy chain constant region containing one or more of the following substitutions: L234A, L235A, D265C, and H435A (EU index according to Kabat). In some embodiments, an antibody comprising the CDR and/or variable region sequences of AbA can further comprise a heavy chain constant region set forth in SEQ ID NO:102, SEQ ID NO:103, SEQ ID NO:104, SEQ ID NO:105 or SEQ ID NO:106. In some embodiments the antibody comprises a light chain constant region set forth in SEQ ID NO:101.

In certain embodiments, the anti-CD45 antibody, or antigen binding portion thereof, comprises a heavy chain comprising the amino acid sequence as set forth in SEQ ID NO:79. In certain embodiments, an antibody comprises a modified heavy chain (HC) region comprising an HC domain comprising SEQ ID NO:79, or a variant of SEQ ID NO:79, which variant (i) differs from SEQ ID NO:79 in 1, 2, 3, 4 or 5 amino acids substitutions, additions or deletions; (ii) differs from SEQ ID NO:79 in at most 5, 4, 3, 2, or 1 amino acids substitutions, additions or deletions; (iii) differs from SEQ ID NO:79 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:79, wherein in any of (i)-(iv), an amino acid substitution may be a conservative amino acid substitution or a non-conservative amino acid substitution; and wherein the modified heavy chain region retains the CD45 specificity of the antibody (i.e., specificity similar to AbA), or has an enhanced biological activity relative to that of another AbA heavy chain region.

In certain embodiments, the anti-CD45 antibody, or antigen binding portion thereof, comprises a light chain comprising the amino acid sequence as set forth in SEQ ID NO:80. In certain embodiments, an antibody comprises a modified light chain (LC) region comprising an LC domain comprising SEQ ID NO:80, or a variant of SEQ ID NO:80, which variant (i) differs from SEQ ID NO:80 in 1, 2, 3, 4 or 5 amino acids substitutions, additions or deletions; (ii) differs from SEQ ID NO:80 in at most 5, 4, 3, 2, or 1 amino acids substitutions, additions or deletions; (iii) differs from SEQ ID NO:80 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:80, wherein in any of (i)-(iv), an amino acid substitution may be a conservative amino acid substitution or a non-conservative amino acid substitution; and wherein the modified light chain region retains the CD45 specificity of the antibody (i.e., specificity similar to AbA), or has an enhanced biological activity relative to that of another AbA light chain region.

In some embodiments, antibodies comprising the CDR regions and/or variable regions of AbA can be incorporated into antibody-drug conjugates, as described herein. In addition, antibodies comprising the CDR regions and/or variable regions of AbA can be used in the methods described herein, e.g., for depletion of CD45+ cells in a subject.

AbB

Antibody B (AbB) cross reacts with human CD45, cyno CD45 and rhesus CD45, and can bind the various isoforms of human CD45.

The amino acid sequences for the various binding regions of anti-CD45 AbB are described in Table 27. Included in the invention are anti-CD45 antibodies based on AbB, e.g., that comprise the CDRs as set forth in Table 27.

In one embodiment, the invention provides an anti-CD45 antibody, or antigen-binding fragment thereof, comprising antigen binding regions, e.g., CDRs and/or variable regions, corresponding to those of AbB. The heavy chain variable region (VH) amino acid sequence of AbB is set forth in SEQ ID NO:81 (see Table 27). The VH CDR domain amino acid sequences of AbB are set forth in SEQ ID NO:82 (VH CDR1); SEQ ID NO:83 (VH CDR2), and SEQ ID NO:84 (VH CDR3). The light chain variable region (VL) amino acid sequence of AbB is described in SEQ ID NO:85 (see Table 27). The VL CDR domain amino acid sequences of AbB are set forth in SEQ ID NO:86 (VL CDR1); SEQ ID NO:87 (VL CDR2), and SEQ ID NO:88 (VL CDR3).

Accordingly, in some embodiments, provided herein is an anti-CD45 antibody, or antigen-binding portion thereof, comprising a heavy chain variable region comprising a CDR1 domain comprising the amino acid sequence as set forth in SEQ ID NO:82, a CDR2 domain comprising the amino acid sequence as set forth in SEQ ID NO:83, and a CDR3 domain comprising the amino acid sequence as set forth in SEQ ID NO:84; and/or a light chain variable region comprising a CDR1 domain comprising the amino acid sequence as set forth in SEQ ID NO:86, a CDR2 domain comprising the amino acid sequence as set forth in SEQ ID NO:87; and a CDR3 domain comprising the amino acid sequence as set forth in SEQ ID NO:88. In certain embodiments, an anti-CD45 antibody comprises the CDRs described herein (SEQ ID NOs: 82 to 84 and 86 to 88) wherein the CDR comprises a conservative amino acid substitution (or 2, 3, 4, or 5 amino acid substitutions) while retaining the CD45 specificity of the antibody (i.e., specificity similar to AbB).

In some embodiments, provided herein is an anti-CD45 antibody, or antigen-binding portion thereof, comprising a heavy chain variable region comprising the amino acid sequence as set forth in SEQ ID NO:81, and/or a light chain variable region comprising the amino acid sequence as set forth in SEQ ID NO:85. In certain embodiments, an antibody can comprise a modified heavy chain (HC) variable region comprising an HC variable domain comprising SEQ ID NO:81, or a variant of SEQ ID NO:81, which variant (i) differs from SEQ ID NO:81 in 1, 2, 3, 4 or 5 amino acids substitutions, additions or deletions; (ii) differs from SEQ ID NO:81 in at most 5, 4, 3, 2, or 1 amino acids substitutions, additions or deletions; (iii) differs from SEQ ID NO:81 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:81, wherein in any of (i)-(iv), an amino acid substitution may be a conservative amino acid substitution or a non-conservative amino acid substitution; and wherein the modified heavy chain variable region retains the CD45 specificity of the antibody (i.e., specificity similar to AbB), or has an enhanced biological activity relative to that of another AbB heavy chain variable region. In certain embodiments, an antibody comprises a modified light chain (LC) variable region comprising an LC variable domain comprising SEQ ID NO:85, or a variant of SEQ ID NO:85, which variant (i) differs from SEQ ID NO:85 in 1, 2, 3, 4 or 5 amino acids substitutions, additions or deletions; (ii) differs from SEQ ID NO:85 in at most 5, 4, 3, 2, or 1 amino acids substitutions, additions or deletions; (iii) differs from SEQ ID NO:85 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:85, wherein in any of (i)-(iv), an amino acid substitution may be a conservative amino acid substitution or a non-conservative amino acid substitution; and wherein the modified light chain variable region retains the CD45 specificity of the antibody (i.e., specificity similar to AbB), or has an enhanced biological activity relative to that of another AbB light chain variable region.

Antibodies comprising the CDR and/or variable region sequences of AbB can be in the form of full-length antibodies, bispecific antibodies, dual variable domain antibodies, multiple chain or single chain antibodies, and/or binding fragments that specifically bind human CD45, including but not limited to Fab, Fab', (Fab')2, Fv), scFv (single chain Fv), surrobodies (including surrogate light chain construct), single domain antibodies, camelized antibodies and the like. They also can be of, or derived from, any isotype, including, for example, IgA (e.g., IgA1 or IgA2), IgD, IgE, IgG (e.g. IgG1, IgG2, IgG3 or IgG4), or IgM. In some embodiments, the anti-45 antibody is an IgG (e.g. IgG1, IgG2, IgG3 or IgG4).

In some embodiments, an antibody comprising the CDR and/or variable region sequences of AbB can further comprise a heavy chain constant region and/or a light chain constant region. In some embodiments, the constant region is a human IgG1 constant region, a human IgG2 constant region, a human IgG3 constant region, or a human IgG4 constant region. In some embodiments, the heavy chain constant region can be a modified constant region. Exemplary constant regions substitutions and/or modifications are described herein, and include, but are not limited to, substitutions at one or more of the following positions: 234, 235, 265, and 435 (EU index according to Kabat). In some embodiments, an antibody comprising the CDR and/or variable region sequences of AbB can further comprise an IgG1 heavy chain constant region containing one or more of the following substitutions: L234A, L235A, D265C, and H435A (EU index according to Kabat). In some embodiments, an antibody comprising the CDR and/or variable region sequences of AbB can further comprise a heavy chain constant region set forth in SEQ ID NO:102, SEQ ID NO:103, SEQ ID NO:104, SEQ ID NO:105 or SEQ ID NO:106. In some embodiments the antibody comprises a light chain constant region set forth in SEQ ID NO:101.

In certain embodiments, the anti-CD45 antibody, or antigen binding portion thereof, comprises a heavy chain comprising the amino acid sequence as set forth in SEQ ID NO:89. In certain embodiments, an antibody comprises a modified heavy chain (HC) region comprising an HC domain comprising SEQ ID NO:89, or a variant of SEQ ID NO:89, which variant (i) differs from SEQ ID NO:89 in 1, 2, 3, 4 or 5 amino acids substitutions, additions or deletions; (ii) differs from SEQ ID NO:89 in at most 5, 4, 3, 2, or 1 amino acids substitutions, additions or deletions; (iii) differs from SEQ ID NO:89 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:89, wherein in any of (i)-(iv), an amino acid substitution may be a conservative amino acid substitution or a non-conservative amino acid substitution; and wherein the modified heavy chain region retains the CD45 specificity of the antibody (i.e., specificity similar to AbB), or has an enhanced biological activity relative to that of another AbB heavy chain region.

In certain embodiments, the anti-CD45 antibody, or antigen binding portion thereof, comprises a light chain comprising the amino acid sequence as set forth in SEQ ID NO:90. In certain embodiments, an antibody comprises a modified light chain (LC) region comprising an LC domain comprising SEQ ID NO:90, or a variant of SEQ ID NO:90, which variant (i) differs from SEQ ID NO:90 in 1, 2, 3, 4 or 5 amino acids substitutions, additions or deletions; (ii) differs from SEQ ID NO:90 in at most 5, 4, 3, 2, or 1 amino acids substitutions, additions or deletions; (iii) differs from SEQ ID NO:90 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:90, wherein in any of (i)-(iv), an amino acid substitution may be a conservative amino acid substitution or a non-conservative amino acid substitution; and wherein the modified light chain region retains the CD45 specificity of the antibody (i.e., specificity similar to AbB), or has an enhanced biological activity relative to that of another AbB light chain region.

In some embodiments, antibodies comprising the CDR regions and/or variable regions of AbB can be incorporated into antibody-drug conjugates, as described herein. In addition, antibodies comprising the CDR regions and/or variable regions of AbB can be used in the methods described herein, e.g., for depletion of CD45+ cells in a subject.

AbC

Antibody C (AbC) cross reacts with human CD45, cyno CD45 and rhesus CD45, and can bind the various isoforms of human CD45.

The amino acid sequences for the various binding regions of anti-CD45 AbC are described in Table 27. Included in the invention are anti-CD45 antibodies based on AbC, e.g., that comprise the CDRs as set forth in Table 27.

In one embodiment, the invention provides an anti-CD45 antibody, or antigen-binding fragment thereof, comprising antigen binding regions, e.g., CDRs and/or variable regions, corresponding to those of AbC. The heavy chain variable region (VH) amino acid sequence of AbC is set forth in SEQ ID NO:91 (see Table 27). The VH CDR domain amino acid sequences of AbC are set forth in SEQ ID NO:92 (VH CDR1); SEQ ID NO:93 (VH CDR2), and SEQ ID NO:94 (VH CDR3). The light chain variable region (VL) amino acid sequence of AbC is described in SEQ ID NO:95 (see Table 27). The VL CDR domain amino acid sequences of AbC are set forth in SEQ ID NO:96 (VL CDR1); SEQ ID NO:97 (VL CDR2), and SEQ ID NO:98 (VL CDR3).

Accordingly, in some embodiments, provided herein is an anti-CD45 antibody, or antigen-binding portion thereof, comprising a heavy chain variable region comprising a CDR1 domain comprising the amino acid sequence as set forth in SEQ ID NO:92, a CDR2 domain comprising the amino acid sequence as set forth in SEQ ID NO:93, and a CDR3 domain comprising the amino acid sequence as set forth in SEQ ID NO:94; and/or a light chain variable region comprising a CDR1 domain comprising the amino acid sequence as set forth in SEQ ID NO:96, a CDR2 domain comprising the amino acid sequence as set forth in SEQ ID NO:97; and a CDR3 domain comprising the amino acid sequence as set forth in SEQ ID NO:98. In certain embodiments, an anti-CD45 antibody comprises the CDRs described herein (SEQ ID NOs: 92 to 94 and 96 to 98) wherein the CDR comprises a conservative amino acid substitution (or 2, 3, 4, or 5 amino acid substitutions) while retaining the CD45 specificity of the antibody (i.e., specificity similar to AbC).

In some embodiments, provided herein is an anti-CD45 antibody, or antigen-binding portion thereof, comprising a heavy chain variable region comprising the amino acid sequence as set forth in SEQ ID NO:991, and/or a light chain variable region comprising the amino acid sequence as set forth in SEQ ID NO:95. In certain embodiments, an antibody can comprise a modified heavy chain (HC) variable region comprising an HC variable domain comprising SEQ ID NO:91, or a variant of SEQ ID NO:91, which variant (i) differs from SEQ ID NO:91 in 1, 2, 3, 4 or 5 amino acids substitutions, additions or deletions; (ii) differs from SEQ ID NO:91 in at most 5, 4, 3, 2, or 1 amino acids substitutions, additions or deletions; (iii) differs from SEQ ID NO:91 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:91, wherein in any of (i)-(iv), an amino acid substitution may be a conservative amino acid substitution or a non-conservative amino acid substitution; and wherein the modified heavy chain variable region retains the CD45 specificity of the antibody (i.e., specificity similar to AbC), or has an enhanced biological activity relative to that of another AbC heavy chain variable region. In certain embodiments, an antibody comprises a modified light chain (LC) variable region comprising an LC variable domain comprising SEQ ID NO:95, or a variant of SEQ ID NO:95, which variant (i) differs from SEQ ID NO:95 in 1, 2, 3, 4 or 5 amino acids substitutions, additions or deletions; (ii) differs from SEQ ID NO:95 in at most 5, 4, 3, 2, or 1 amino acids substitutions, additions or deletions; (iii) differs from SEQ ID NO:95 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:95, wherein in any of (i)-(iv), an amino acid substitution may be a conservative amino acid substitution or a non-conservative amino acid substitution; and wherein the modified light chain variable region retains the CD45 specificity of the antibody (i.e., specificity similar to AbC), or has an enhanced biological activity relative to that of another AbC light chain variable region.

Antibodies comprising the CDR and/or variable region sequences of AbC can be in the form of full-length antibodies, bispecific antibodies, dual variable domain antibodies, multiple chain or single chain antibodies, and/or binding fragments that specifically bind human CD45, including but not limited to Fab, Fab', (Fab')2, Fv), scFv (single chain Fv), surrobodies (including surrogate light chain construct), single domain antibodies, camelized antibodies and the like. They also can be of, or derived from, any isotype, including, for example, IgA (e.g., IgA1 or IgA2), IgD, IgE, IgG (e.g. IgG1, IgG2, IgG3 or IgG4), or IgM. In some embodiments, the anti-45 antibody is an IgG (e.g. IgG1, IgG2, IgG3 or IgG4).

In some embodiments, an antibody comprising the CDR and/or variable region sequences of AbC can further comprise a heavy chain constant region and/or a light chain constant region. In some embodiments, the constant region is a human IgG1 constant region, a human IgG2 constant region, a human IgG3 constant region, or a human IgG4 constant region. In some embodiments, the heavy chain constant region can be a modified constant region. Exemplary constant regions substitutions and/or modifications are described herein, and include, but are not limited to, substitutions at one or more of the following positions: 234, 235, 265, and 435 (EU index according to Kabat). In some embodiments, an antibody comprising the CDR and/or variable region sequences of AbC can further comprise an IgG1 heavy chain constant region containing one or more of the following substitutions: L234A, L235A, D265C, and H435A (EU index according to Kabat). In some embodiments, an antibody comprising the CDR and/or variable region sequences of AbC can further comprise a heavy chain constant region set forth in SEQ ID NO:102, SEQ ID NO:103, SEQ ID NO:104, SEQ ID NO:105 or SEQ ID NO:106. In some embodiments the antibody comprises a light chain constant region set forth in SEQ ID NO:101.

In certain embodiments, the anti-CD45 antibody, or antigen binding portion thereof, comprises a heavy chain comprising the amino acid sequence as set forth in SEQ ID NO:99. In certain embodiments, an antibody comprises a modified heavy chain (HC) region comprising an HC domain comprising SEQ ID NO:99, or a variant of SEQ ID NO:99, which variant (i) differs from SEQ ID NO:99 in 1, 2, 3, 4 or 5 amino acids substitutions, additions or deletions; (ii) differs from SEQ ID NO:99 in at most 5, 4, 3, 2, or 1 amino acids substitutions, additions or deletions; (iii) differs from SEQ ID NO:99 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:99, wherein in any of (i)-(iv), an amino acid substitution may be a conservative amino acid substitution or a non-conservative amino acid substitution; and wherein the modified heavy chain region retains the CD45 specificity of the antibody (i.e., specificity similar to AbC), or has an enhanced biological activity relative to that of another AbC heavy chain region.

In certain embodiments, the anti-CD45 antibody, or antigen binding portion thereof, comprises a light chain comprising the amino acid sequence as set forth in SEQ ID NO:100. In certain embodiments, an antibody comprises a modified light chain (LC) region comprising an LC domain comprising SEQ ID NO:100, or a variant of SEQ ID NO:100, which variant (i) differs from SEQ ID NO:100 in 1, 2, 3, 4 or 5 amino acids substitutions, additions or deletions; (ii) differs from SEQ ID NO:100 in at most 5, 4, 3, 2, or 1 amino acids substitutions, additions or deletions; (iii) differs from SEQ ID NO:100 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO:100, wherein in any of (i)-(iv), an amino acid substitution may be a conservative amino acid substitution or a non-conservative amino acid substitution; and wherein the modified light chain region retains the CD45 specificity of the antibody (i.e., specificity similar to AbC), or has an enhanced biological activity relative to that of another AbC light chain region.

In some embodiments, antibodies comprising the CDR regions and/or variable regions of AbC can be incorporated into antibody-drug conjugates, as described herein. In addition, antibodies comprising the CDR regions and/or variable regions of AbC can be used in the methods described herein, e.g., for depletion of CD45+ cells in a subject.

Consensus CDRs

A comparison of the amino acid sequences of the CDRs of Ab1, Ab2, Ab3, Ab4, Ab5, Ab6, and Ab7 is provided as FIG. 32. These antibodies bind to the same epitope on human CD45, and share certain consensus residues in their CDR regions. Consensus heavy chain amino acid CDR sequences are presented in SEQ ID NO:119, SEQ ID NO:120, and SEQ ID NO:121; and consensus light chain amino acid CDR sequences are presented in SEQ ID NO:122, SEQ ID NO:123, and SEQ ID NO:124.

Accordingly, in some embodiments, the invention provides an isolated anti-CD45 antibody, or antigen-binding portion thereof, comprising a heavy chain variable region comprising a CDR1 domain comprising the amino acid sequence as set forth in SEQ ID NO:119, a CDR2 domain comprising the amino acid sequence as set forth in SEQ ID NO:120, and a CDR3 domain comprising the amino acid sequence as set forth in SEQ ID NO:121; and a light chain variable region comprising a CDR1 domain comprising the amino acid sequence as set forth in SEQ ID NO:122, a CDR2 domain comprising the amino acid sequence as set forth in SEQ ID NO:123; and a CDR3 domain comprising the amino acid sequence as set forth in SEQ ID NO:124. The foregoing antibody can, in some embodiments, further comprise a heavy chain constant region and/or a light chain constant region. For example, in some embodiments, the foregoing antibody can further comprise a heavy chain constant region selected from that set forth in any one of SEQ ID NO:102, SEQ ID NO:103, SEQ ID NO:104, SEQ ID NO:105, or SEQ ID NO:106, and/or a light chain constant region set forth in SEQ ID NO:101.

Fc-Modified Antibodies

Contemplated herein are antibodies, or antigen-binding fragments thereof, capable of binding CD45 and having Fc modifications that allow Fc silencing, where such antibodies, or antigen-binding fragments thereof, can be used as therapeutic agents alone or as ADCs to deplete cells expressing CD45 in a patient in need thereof. For example, in some embodiments, such antibodies, or antigen-binding fragments thereof, contemplated herein may be used to deplete certain cell types, including HSCs and leukocytes. Thus, in certain embodiments, the antibodies, or antigen-binding fragments thereof, contemplated herein may be used to condition a patient for HSC transplant. In some embodiments, the antibodies, or antigen-binding fragments thereof, contemplated herein may be used to reset the immune system of a patient by, for example, depleting HSCs and leukocytes in the patient and administering an HSC transplant to the patient. In some embodiments, the antibodies, or antigen-binding fragments thereof, contemplated herein may be used to treat a disease associated with CD45 positive cells, including but not limited to cancer and autoimmune disease, by eliminating disease-causing CD45+ cells from the patient.

For example, contemplated herein are antibodies, or antigen-binding fragments thereof, capable of binding an antigen expressed by hematopoietic stem cells, such as CD45, and having Fc modifications that allow Fc silencing, where such antibodies, or antigen-binding fragments thereof, can be used as therapeutic agents alone or as ADCs to (i) treat cancers and autoimmune diseases characterized by CD45+ hematopoietic stem cells; and (ii) promote the engraftment of transplanted hematopoietic stem cells in a patient in need of transplant therapy. These therapeutic activities can be caused, for instance, by the binding of an anti-CD45 antibody, or antigen-binding fragment thereof, that binds to expressed by a hematopoietic cell (e.g., hematopoietic stem cell or mature immune cell (e.g., T cell)), such as a cancer cell, autoimmune cell, or hematopoietic stem cell and subsequently inducing cell death. The depletion of endogenous hematopoietic stem cells can provide a niche toward which transplanted hematopoietic stem cells can home, and subsequently establish productive hematopoiesis. In this way, transplanted hematopoietic stem cells may successfully engraft in a patient, such as human patient suffering from a stem cell disorder described herein. The Fc-modified antibodies and ADCs contemplated herein not only allow for selective depletion of endogenous hematopoietic stem cells but also have reduced cytotoxic effects on the exogenous hematopoietic stem cell transplant, thereby further promoting engraftment of the hematopoietic stem cell graft.

The antibodies or binding fragments described herein may also include modifications and/or mutations that alter the properties of the antibodies and/or fragments, such as those that increase or decrease half-life, or increase or decrease ADCC. In one embodiment, antibodies comprising one or more radiolabeled amino acids are provided. A radiolabeled antibody may be used for both diagnostic and therapeutic purposes (conjugation to radiolabeled molecules is another possible feature). Non-limiting examples of labels for polypeptides include, but are not limited to 3H, 14C, 15N, 35S, 90Y, 99Tc, and 125I, 131I, and 186Re. Methods for preparing radiolabeled amino acids and related peptide derivatives are known in the art (see for instance Junghans et al., in Cancer Chemotherapy and Biotherapy 655-686 (2d edition, Chafner and Longo, eds., Lippincott Raven (1996)) and U.S. Pat. Nos. 4,681,581, 4,735,210, 5,101,827, 5,102,990 (U.S. RE35,500), U.S. Pat. Nos. 5,648,471 and 5,697,902. For example, a radioisotope may be conjugated by a chloramine T method.

In one embodiment, the anti-CD45 antibody, or binding fragment thereof, comprises a modified Fc region, wherein said modified Fc region comprises at least one amino acid modification relative to a wild-type Fc region, such that said molecule has an altered affinity for or binding to an FcgammaR (FcγR). Certain amino acid positions within the Fc region are known through crystallography studies to make a direct contact with FcγR. Specifically amino acids 234-239 (hinge region), amino acids 265-269 (B/C loop), amino acids 297-299 (C'/E loop), and amino acids 327-332 (F/G) loop. (see Sondermann et al., 2000 Nature, 406: 267-273). The antibodies described herein may comprise variant Fc regions comprising modification of at least one residue that makes a direct contact with an FcγR based on structural and crystallographic analysis. In one embodiment, the Fc region of the anti-CD45 antibody (or fragment thereof) comprises an amino acid substitution at amino acid 265 according to the EU index as in Kabat et al., *Sequences of Proteins of Immunological Interest,* 5th Ed. Public Health Service, NH1, MD (1991), expressly incorporated herein by references. The "EU index as in Kabat" refers to the numbering of the human IgG1 EU antibody. In one embodiment, the Fc region comprises a D265A mutation. In one embodiment, the Fc region comprises a D265C mutation. In some embodiments, the Fc region of the antibody (or fragment thereof) comprises an amino acid substitution at amino acid 234 according to the EU index as in Kabat.

In one embodiment, the Fc region comprises a mutation at an amino acid position of D265, V205, H435, 1253, and/or H310. For example, specific mutations at these positions include D265C, V205C, H435A, 1253A, and/or H310A.

In one embodiment, the Fc region comprises a L234A mutation. In some embodiments, the Fc region of the anti-CD45 antibody (or fragment thereof) comprises an amino acid substitution at amino acid 235 according to the EU index as in Kabat. In one embodiment, the Fc region comprises a L235A mutation. In yet another embodiment, the Fc region comprises a L234A and L235A mutation. In a further embodiment, the Fc region comprises a D265C, L234A, and L235A mutation. In yet a further embodiment, the Fc region comprises a D265C, L234A, L235A, and H435A mutation. In a further embodiment, the Fc region comprises a D265C and H435A mutation.

In some embodiments, the anti-CD45 antibody herein comprises an Fc region comprising one of the following modifications or combinations of modifications: D265A, D265C, D265C/H435A, D265C/LALA, D265C/LALA/H435A, D265C/N297G, D265C/N297G/H435A, D265C (IgG2*), D265C (IgG2)/H435A, D265C/N297Q/H435A, D265C/N297Q, EPLVLAdelG/H435A, N297A, N297G, or N297Q (EU index according to Kabat).

Binding or affinity between a modified Fc region and a Fc gamma receptor can be determined using a variety of techniques known in the art, for example but not limited to, equilibrium methods (e.g., enzyme-linked immunoabsorbent assay (ELISA); KinExA, Rathanaswami et al. Analytical Biochemistry, Vol. 373:52-60, 2008; or radioimmunoassay (RIA)), or by a surface plasmon resonance assay or other mechanism of kinetics-based assay (e.g., BIACORE® analysis or Octet™ analysis (forteBIO)), and other methods such as indirect binding assays, competitive binding assays fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions. One example of a competitive binding assay is a radioimmuno assay comprising the incubation of labeled antigen with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound in the presence of increasing amounts of an unlabeled second antibody.

In one embodiment, an antibody having the Fc modifications described herein (e.g., D265C, L234A, L235A, and/or H435A) has at least a 70% decrease, at least a 80% decrease, at least a 90% decrease, at least a 95% decrease, at least a 98% decrease, at least a 99% decrease, or about a 100% decrease in binding to a Fc gamma receptor relative to binding of the identical antibody comprising an unmodified Fc region to the Fc gamma receptor (e.g., as assessed by biolayer interferometry (BLI)).

Fc region binding interactions with a Fc gamma receptor are essential for a variety of effector functions and downstream signaling events including, but not limited to, antibody dependent cell-mediated cytotoxicity (ADCC) and complement dependent cytotoxicity (CDC). Accordingly, in certain aspects, an antibody comprising a modified Fc region (e.g., comprising a L234A, L235A, and/or a D265C mutation) has substantially reduced or abolished effector functions. Effector functions can be assayed using a variety of methods known in the art, e.g., by measuring cellular responses (e.g., mast cell degranulation or cytokine release) in response to the antibody of interest. For example, using standard methods in the art, the Fc-modified antibodies can be assayed for their ability to trigger mast cell degranulation in or for their ability to trigger cytokine release, e.g. by human peripheral blood mononuclear cells.

Thus, in one embodiment, the Fc region comprises a mutation resulting in a decrease in half life (e.g., relative to an antibody having an unmodified Fc region). An antibody having a short half life may be advantageous in certain instances where the antibody is expected to function as a short-lived therapeutic, e.g., the conditioning step described herein where the antibody is administered followed by HSCs. Typically, the antibody would be substantially cleared prior to delivery of the HSCs, which also generally express a target antigen (e.g., CD45) but are not the target of the anti-CD45 antibody unlike the endogenous stem cells. In one embodiment, the Fc regions comprises a mutation at position 435 (EU index according to Kabat). In one embodiment, the mutation is an H435A mutation.

In one embodiment, the anti-CD45 antibody described herein has a half-life (e.g., in humans) equal to or less than 24 hours, equal to or less than 23 hours, equal to or less than 22 hours, equal to or less than 21 hours, equal to or less than 20 hours, equal to or less than 19 hours, equal to or less than 18 hours, equal to or less than 17 hours, equal to or less than 16 hours, equal to or less than 15 hours, equal to or less than 14 hours, equal to or less than 13 hours, equal to or less than 12 hours, or equal to or less than 11 hours.

In one embodiment, the anti-CD45 antibody described herein has a half-life (e.g., in humans) of about about 1-2 hours, about 1-3 hours, about 1-5 hours, about 1-10 hours, about 5-10 hours, about 5-15 hours, about $10^{-15}$ hours, about $10^{-20}$ hours, about 15-20 hours, about 15-25 hours, or about 20-25 hours.

In some aspects, the Fc region comprises two or more mutations that confer reduced half-life and reduce an effector function of the antibody. In some embodiments, the Fc region comprises a mutation resulting in a decrease in half-life and a mutation of at least one residue that can make direct contact with an FcγR (e.g., as based on structural and crystallographic analysis). In one embodiment, the Fc region comprises a H435A mutation, a L234A mutation, and a L235A mutation. In one embodiment, the Fc region comprises a H435A mutation and a D265C mutation. In one embodiment, the Fc region comprises a H435A mutation, a L234A mutation, a L235A mutation, and a D265C mutation.

In some embodiments, the antibody or antigen-binding fragment thereof is conjugated to a cytotoxin (e.g., amatoxin) by way of a cysteine residue in the Fc domain of the antibody or antigen-binding fragment thereof. In some embodiments, the cysteine residue is introduced by way of a mutation in the Fc domain of the antibody or antigen-binding fragment thereof. For instance, the cysteine residue may be selected from the group consisting of Cys118, Cys239, and Cys265. In one embodiment, the Fc region of the anti-CD45 antibody (or fragment thereof) comprises an amino acid substitution at amino acid 265 according to the EU index as in Kabat. In one embodiment, the Fc region comprises a D265C mutation. In one embodiment, the Fc region comprises a D265C and H435A mutation. In one embodiment, the Fc region comprises a D265C, a L234A, and a L235A mutation. In one embodiment, the Fc region comprises a D265C, a L234A, a L235A, and a H435A mutation.

Notably, Fc amino acid positions are in reference to the EU numbering index unless otherwise indicated.

The disclosures of each of the foregoing publications are incorporated herein by reference as they pertain to anti-CD45 antibody. Antibodies and antigen-binding fragments that may be used in conjunction with the compositions and methods described herein include the above-described antibodies and antigen-binding fragments thereof, as well as variants of those non-human antibodies and antigen-binding fragments described above and antibodies or antigen-binding fragments that bind the same epitope as those described above, as assessed, for instance, by way of a competitive antigen binding assay.

Methods of engineering antibodies to include any of the Fc modifications herein are well known in the art. These methods include, but are not limited to, preparation by site-directed (or oligonucleotide-mediated) mutagenesis, PCR mutagenesis, and cassette mutagenesis of a prepared DNA molecule encoding the antibody or at least the constant region of the antibody. Site-directed mutagenesis is well known in the art (see, e.g., Carter et al., Nucleic Acids Res., 13:4431-4443 (1985) and Kunkel et al., Proc. Natl. Acad. Sci. USA, 82:488 (1987)). PCR mutagenesis is also suitable for making amino acid sequence variants of the starting polypeptide. See Higuchi, in PCR Protocols, pp. 177-183 (Academic Press, 1990); and Vallette et al., Nuc. Acids Res. 17:723-733 (1989). Another method for preparing sequence variants, cassette mutagenesis, is based on the technique described by Wells et al., Gene, 34:315-323 (1985).

In certain embodiments, an anti-CD45 antibody, or binding-fragment thereof, described herein may be conjugated to a label. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, 3-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Nucleic Acids, Vectors, and Host Cells

Also provided herein are nucleic acid molecules (e.g., DNA or mRNA) that comprise a nucleic acid sequence which encodes an anti-CD45 antibody described herein, or an antigen binding portion thereof.

Accordingly, in some embodiments, provided herein is an isolated nucleic acid molecule that encodes a heavy chain variable region comprising heavy chain CDR1, CDR2, and CDR3 of Ab1, Ab2, Ab3, Ab4, Ab5, Ab6, Ab7, AbA, AbB, or AbC. In other embodiments, provided herein is an isolated nucleic acid molecule that encodes a heavy chain variable region of Ab1, Ab2, Ab3, Ab4, Ab5, Ab6, Ab7, AbA, AbB, or AbC. In other embodiments, provided herein is an isolated nucleic acid molecule that encodes a heavy chain of Ab1, Ab2, Ab3, Ab4, Ab5, Ab6, Ab7, AbA, AbB, or AbC.

In some embodiments, provided herein is an isolated nucleic acid molecule that encodes a light chain variable region comprising light chain CDR1, CDR2, and CDR3 of Ab1, Ab2, Ab3, Ab4, Ab5, Ab6, Ab7, AbA, AbB, or AbC. In other embodiments, provided herein is an isolated nucleic acid molecule that encodes a light chain variable region of Ab1, Ab2, Ab3, Ab4, Ab5, Ab6, Ab7, AbA, AbB, or AbC. In other embodiments, provided herein is an isolated nucleic acid molecule that encodes a light chain of Ab1, Ab2, Ab3, Ab4, Ab5, Ab6, Ab7, AbA, AbB, or AbC.

In some embodiments, provided herein is an isolated nucleic acid molecule that encodes a heavy chain variable region comprising heavy chain CDR1, CDR2, and CDR3, and a light chain variable region comprising light chain CDR1, CDR2, and CDR3 of Ab1, Ab2, Ab3, Ab4, Ab5, Ab6, Ab7, AbA, AbB, or AbC. In other embodiments, provided herein is an isolated nucleic acid molecule that encodes a heavy chain variable region and a light chain variable region of Ab1, Ab2, Ab3, Ab4, Ab5, Ab6, Ab7, AbA, AbB, or AbC. In other embodiments, provided herein is an isolated nucleic acid molecule that encodes a heavy chain and a light chain of Ab1, Ab2, Ab3, Ab4, Ab5, Ab6, Ab7, AbA, AbB, or AbC.

A nucleic acid encoding an antibody heavy chain, or a portion thereof, may be present in the same nucleic acid molecule (e.g., expression vector) as a nucleic acid encoding an antibody light chain, or a portion thereof. Alternatively, the heavy and light chain sequences may be present on separate nucleic acid molecules (e.g., separate expression vectors).

In one embodiment, the invention provides an isolated nucleic acid molecule comprising:

(a) a nucleic acid sequence set forth in SEQ ID NO:125;
(b) a nucleic acid sequence set forth in SEQ ID NO:126;
(c) a nucleic acid sequence set forth in SEQ ID NO:127;
(d) a nucleic acid sequence set forth in SEQ ID NO:128;
(e) a nucleic acid sequence set forth in SEQ ID NO:129;
(f) a nucleic acid sequence set forth in SEQ ID NO:130;
(g) a nucleic acid sequence set forth in SEQ ID NO:131;
(h) a nucleic acid sequence set forth in SEQ ID NO:132;
(i) a nucleic acid sequence set forth in SEQ ID NO:133;
(j) a nucleic acid sequence set forth in SEQ ID NO:134;
(k) a nucleic acid sequence set forth in SEQ ID NO:135;
(l) a nucleic acid sequence set forth in SEQ ID NO:136;
(m) a nucleic acid sequence set forth in SEQ ID NO:137;
(n) a nucleic acid sequence set forth in SEQ ID NO:138;
(o) a nucleic acid sequence set forth in SEQ ID NO:139;
(p) a nucleic acid sequence set forth in SEQ ID NO:140;
(q) a nucleic acid sequence set forth in SEQ ID NO:141;
(r) a nucleic acid sequence set forth in SEQ ID NO:142;
(s) a nucleic acid sequence set forth in SEQ ID NO:143; and/or
(t) a nucleic acid sequence set forth in SEQ ID NO:144;

wherein the isolated nucleic acid encodes an anti-CD45 antibody, or a portion thereof.

In another embodiment, the invention provides an isolated nucleic acid molecule comprising:

(a) a nucleic acid sequence set forth in SEQ ID NO:150;
(b) a nucleic acid sequence set forth in SEQ ID NO:151;
(c) a nucleic acid sequence set forth in SEQ ID NO:152;
(d) a nucleic acid sequence set forth in SEQ ID NO:153;
(e) a nucleic acid sequence set forth in SEQ ID NO:154;
(f) a nucleic acid sequence set forth in SEQ ID NO:155;
(g) a nucleic acid sequence set forth in SEQ ID NO:156;
(h) a nucleic acid sequence set forth in SEQ ID NO:157;
(i) a nucleic acid sequence set forth in SEQ ID NO:158;
(j) a nucleic acid sequence set forth in SEQ ID NO:159;
(k) a nucleic acid sequence set forth in SEQ ID NO:160; and/or
(l) a nucleic acid sequence set forth in SEQ ID NO:161;

wherein the isolated nucleic acid encodes an anti-CD45 antibody, or a portion thereof.

Antibodies may be produced using recombinant methods and compositions, e.g., as described in U.S. Pat. No. 4,816,567. In one embodiment, isolated nucleic acid encoding an anti-CD45 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CLL-1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD45 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

In one embodiment, the anti-CD45 antibody, or antigen binding fragment thereof, comprises variable regions having an amino acid sequence that is at least 95%, 96%, 97% or 99% identical to the SEQ ID Nos disclosed herein. Alternatively, the anti-CD45 antibody, or antigen binding fragment thereof, comprises CDRs comprising the SEQ ID Nos disclosed herein with framework regions of the variable regions described herein having an amino acid sequence that is at least 95%, 96%, 97% or 99% identical to the SEQ ID Nos disclosed herein.

In one embodiment, the anti-CD45 antibody, or antigen binding fragment thereof, comprises a heavy chain variable region and a heavy chain constant region having an amino acid sequence that is disclosed herein. In another embodiment, the anti-CD45 antibody, or antigen binding fragment thereof, comprises a light chain variable region and a light chain constant region having an amino acid sequence that is disclosed herein. In yet another embodiment, the anti-CD45 antibody, or antigen binding fragment thereof, comprises a heavy chain variable region, a light chain variable region, a heavy chain constant region and a light chain constant region having an amino acid sequence that is disclosed herein.

Methods of Identifying Antibodies

Provided herein are novel anti-CD45 antibodies that may be used, for example, to deplete CD45+ cells in a patient. These antibodies can be useful, e.g., in conditioning methods for stem cell transplantation. In view of the disclosure provided herein, other anti-CD45 antibodies can be identified.

Methods for high throughput screening of antibody, or antibody fragment libraries capable of binding CD45 expressed by hematopoietic stem can be used to identify anti-CD45 antibodies useful for treating cancers, autoimmune diseases, and conditioning a patient (e.g., a human patient) in need of hematopoietic stem cell therapy as described herein. Such methods can be used to identify improved versions of the anti-CD45 antibodies described herein. Such methods include in vitro display techniques known in the art, such as phage display, bacterial display, yeast display, mammalian cell display, ribosome display, mRNA display, and cDNA display, among others.

The use of phage display to isolate antibodies, or antigen-binding fragments, that bind biologically relevant molecules has been reviewed, for example, in Felici et al., Biotechnol. Annual Rev. 1:149-183, 1995; Katz, Annual Rev. Biophys. Biomol. Struct. 26:27-45, 1997; and Hoogenboom et al., Immunotechnology 4:1-20, 1998, the disclosures of each of which are incorporated herein by reference as they pertain to in vitro display techniques. Randomized combinatorial peptide libraries have been constructed to select for polypeptides that bind cell surface antigens as described in Kay, Perspect. Drug Discovery Des. 2:251-268, 1995 and Kay et al., Mol. Divers. 1:139-140, 1996, the disclosures of each of which are incorporated herein by reference as they pertain to the discovery of antigen-binding molecules. Proteins, such as multimeric proteins, have been successfully phage-displayed as functional molecules (see, for example, EP 0349578; EP 4527839; and EP 0589877, as well as Chiswell and McCafferty, Trends Biotechnol. 10:80-84 1992, the disclosures of each of which are incorporated herein by reference as they pertain to the use of in vitro display techniques for the discovery of antigen-binding molecules. In addition, functional antibody fragments, such as Fab and scFv fragments, have been expressed in in vitro display formats (see, for example, McCafferty et al., Nature 348: 552-554, 1990; Barbas et al., Proc. Natl. Acad. Sci. USA 88:7978-7982, 1991; and Clackson et al., *Nature* 352:624-628, 1991, the disclosures of each of which are incorporated herein by reference as they pertain to in vitro display platforms for the discovery of antigen-binding molecules). Human anti-CD45 antibodies can also be generated, for example, in the HuMAb-Mouse® or XenoMouse™. These techniques, among others, can be used to identify and improve the affinity of antibodies, antibody or fragments, capable of binding CD45 expressed by hematopoietic stem cells in turn be used to deplete endogenous hematopoietic stem cells in a patient (e.g., a human patient) in need of hematopoietic stem cell transplant therapy.

In addition to in vitro display techniques, computational modeling techniques can be used to design and identify antibodies capable of binding an antigen (e.g., CD45) expressed by hematopoietic stem cells. For example, using computational modeling techniques, one of skill in the art can screen libraries of antibodies, or antibody fragments, in silico for molecules capable of binding specific epitopes on an antigen expressed by hematopoietic stem cells (e.g., CD45), such as extracellular epitopes of the antigen.

Additional techniques can be used to identify antibodies, or antibody fragments, capable of binding CD45 expressed by hematopoietic stem cells and that are internalized by the cell, for instance, by receptor-mediated endocytosis. For example, the in vitro display techniques described above can be adapted to screen for antibodies, or antibody fragments, that bind CD45 and that are subsequently internalized. Phage display represents one such technique that can be used in conjunction with this screening paradigm. To identify an anti-CD45 antibody, or antibody fragment, that can be internalized by hematopoietic stem cells, one of skill in the art can use the phage display techniques described in Williams et al., *Leukemia* 19:1432-1438, 2005, the disclosure of which is incorporated herein by reference in its entirety. For example, using mutagenesis methods known in the art, recombinant phage libraries can be produced that encode antibodies, antibody fragments, such as scFv fragments, Fab fragments, diabodies, triabodies, and $^{10}$Fn3 domains, among others, or ligands that contain randomized amino acid cassettes (e.g., in one or more, or all, of the CDRs or equivalent regions thereof or an antibody or antibody fragment). The framework regions, hinge, Fc domain, and other regions of the antibodies or antibody fragments may be designed such that they are non-immunogenic in humans, for instance, by virtue of having human germline antibody sequences or sequences that exhibit only minor variations relative to human germline antibodies.

Using phage display techniques described herein or known in the art, phage libraries containing randomized antibodies, or antibody fragments, covalently bound to the phage particles can be incubated with CD45 for instance, by first incubating the phage library with blocking agents (such as, for instance, milk protein, bovine serum albumin, and/or IgG so as to remove phage encoding antibodies, or antibody fragments, that exhibit non-specific protein binding and phage that encode antibodies or fragments thereof that bind Fc domains, and then incubating the phage library with a population of cells, e.g., hematopoietic stem cells, which express CD45. The phage library can be incubated with the hematopoietic stem cells for a time sufficient to allow anti-CD45 antibodies, or antibody fragments, to bind the cognate cell-surface antigen and to subsequently be internalized by the hematopoietic stem cells (e.g., from 30 minutes to 6 hours at 4° C., such as 1 hour at 4° C.). Phage containing antibodies, or antibody fragments, that do not exhibit sufficient affinity for the CD45 so as to permit binding to, and internalization by, hematopoietic stem cells can subsequently be removed by washing the cells, for instance, with cold (4° C.) 0.1 M glycine buffer at pH 2.8. Phage bound to antibodies, or antibody fragments, that have been internalized by the hematopoietic stem cells can be identified, for instance, by lysing the cells and recovering internalized phage from the cell culture medium. The phage can then be amplified in bacterial cells, for example, by incubating bacterial cells with recovered phage in 2×YT medium using methods known in the art. Phage recovered from this medium can then be characterized, for instance, by determining the nucleic acid sequence of the gene(s) encoding the antibodies, or antibody fragments, inserted within the phage genome. The encoded antibodies, or antibody fragments, can subsequently be prepared de novo by chemical synthesis (for instance, of antibody fragments, such as scFv fragments) or by recombinant expression (for instance, of full-length antibodies).

The internalizing capacity of the prepared antibodies, or antibody fragments, can be assessed, for instance, using radionuclide internalization assays known in the art. For example, anti-CD45 antibodies, or antibody fragments, identified using in vitro display techniques described herein or known in the art can be functionalized by incorporation of a radioactive isotope, such as $^{18}$F, $^{75}$Br, $^{77}$Br, $^{122}$I, $^{123}$I, $^{124}$I, $^{125}$I, $^{129}$I, $^{131}$I, $^{211}$At, $^{67}$Ga, $^{111}$In, $^{99}$Tc, $^{169}$Yb, $^{186}$Re, $^{64}$CU, $^{67}$CU, $^{177}$Lu, $^{77}$As, $^{72}$As, $^{86}$Y, $^{90}$Y, $^{89}$Zr, $^{212}$Bi, $^{213}$Bi, or $^{225}$Ac. For instance, radioactive halogens, such as $^{18}$F, $^{75}$Br, $^{77}$Br, $^{122}$I, $^{123}$I, $^{124}$I, $^{125}$I, $^{129}$I, $^{131}$I, $^{211}$At, can be incorporated into antibodies, or antibody fragments, using beads, such as polystyrene beads, containing electrophilic halogen reagents (e.g., Iodination Beads, Thermo Fisher Scientific, Inc., Cambridge, Mass.). Radiolabeled antibodies, fragments thereof, or ADCs, can be incubated with hematopoietic stem cells for a time sufficient to permit internalization (e.g., from 30 minutes to 6 hours at 4° C., such as 1 hour at 4° C.). The cells can then be washed to remove non-internalized antibodies or fragments thereof, (e.g., using cold (4° C.) 0.1 M glycine buffer at pH 2.8). Internalized antibodies, or antibody fragments, can be identified by detecting the emitted radiation (e.g., γ-radiation) of the resulting hematopoietic stem cells in comparison with the emitted radiation (e.g., γ-radiation) of the recovered wash buffer. The foregoing internalization assays can also be used to characterize ADCs.

Antibodies may be produced using recombinant methods and compositions, e.g., as described in U.S. Pat. No. 4,816,567. In one embodiment, isolated nucleic acid encoding an anti-CD45 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CLL-1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD45 antibody, a nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003). In one embodiment, the host cell is eukaryotic, e.g. a Chinese Hamster Ovary (CHO) cell or lymphoid cell (e.g., Y0, NS0, Sp20 cell).

Antibody Drug Conjugates (ADCs)

Anti-CD45 antibodies, or antigen-binding fragments thereof, described herein can be conjugated (linked) to a cytotoxin via a linker. In some embodiments, the cytotoxic molecule is conjugated to a cell internalizing antibody, or antigen-binding fragment thereof as disclosed herein such that following the cellular uptake of the antibody, or fragment thereof, the cytotoxin may access its intracellular target and mediate hematopoietic cell death. In certain embodiments, an anti-CD45 scFv comprising VH and VL variable regions described herein (or variable regions comprising light chain and heavy chain CDR sets described herein) are conjugated to a toxin to form an scFv toxin.

Cytotoxins

Various cytotoxins can be conjugated to an anti-CD45 antibody via a linker for use in the therapies described herein. In particular, the anti-CD45 ADCs include an anti-CD45 antibody (or an antigen-binding fragment thereof) conjugated (i.e., covalently attached by a linker) to a cytotoxic moiety (or cytotoxin). In various embodiments, the cytotoxic moiety exhibits reduced or no cytotoxicity when bound in a conjugate, but resumes cytotoxicity after cleavage from the linker. In various embodiments, the cytotoxic moiety maintains cytotoxicity without cleavage from the linker. In some embodiments, the cytotoxic molecule is conjugated to a cell internalizing antibody, or antigen-binding fragment thereof as disclosed herein, such that following the cellular uptake of the antibody, or fragment thereof, the cytotoxin may access its intracellular target and, e.g., mediate T cell death.

ADCs of the present invention therefore may be of the general formula $$Ab\text{-}(Z\text{-}L\text{-}D)_n$$

wherein an antibody or antigen-binding fragment thereof (Ab) is conjugated (covalently linked) to linker (L), through a chemical moiety (Z), to a cytotoxic moiety ("drug," D, or "Cy").

Accordingly, the anti-CD45 antibody or antigen-binding fragment thereof may be conjugated to a number of drug moieties as indicated by integer n, which represents the average number of cytotoxins per antibody, which may range, e.g., from about 1 to about 20. In some embodiments, n is from 1 to 4. In some embodiments, n is 1. The average number of drug moieties per antibody in preparations of ADC from conjugation reactions may be characterized by conventional means such as mass spectroscopy, ELISA assay, and HPLC. The quantitative distribution of ADC in terms of n may also be determined. In some instances, separation, purification, and characterization of homogeneous ADC where n is a certain value from ADC with other drug loadings may be achieved by means such as reverse phase HPLC or electrophoresis.

For some anti-CD45 ADCs, they may be limited by the number of attachment sites on the antibody. For example, where the attachment is a cysteine thiol, an antibody may have only one or several cysteine thiol groups, or may have only one or several sufficiently reactive thiol groups through which a linker may be attached. Generally, antibodies do not contain many free and reactive cysteine thiol groups which may be linked to a drug moiety; primarily, cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, higher drug loading (DAR), e.g. n>5, may cause aggregation, insolubility, toxicity, or loss of cellular permeability of certain antibody-drug conjugates.

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Only the most reactive lysine groups may react with an amine-reactive linker reagent. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments.

Cytotoxins suitable for use with the compositions and methods described herein include DNA-intercalating agents, (e.g., anthracyclines), agents capable of disrupting the mitotic spindle apparatus (e.g., vinca alkaloids, maytansine, maytansinoids, and derivatives thereof), RNA polymerase inhibitors (e.g., an amatoxin, such as α-amanitin, and derivatives thereof), and agents capable of disrupting protein biosynthesis (e.g., agents that exhibit rRNA N-glycosidase activity, such as saporin and ricin A-chain), among others known in the art.

In some embodiments, the cytotoxin is a microtubule-binding agent (for instance, maytansine or a maytansinoid), an amatoxin, pseudomonas exotoxin A, deBouganin, diphtheria toxin, saporin, an auristatin, an anthracycline, a calicheamicin, irinotecan, SN-38, a duocarmycin, a pyrrolobenzodiazepine, a pyrrolobenzodiazepine dimer, an indolinobenzodiazepine, an indolinobenzodiazepine dimer, or a variant thereof, or another cytotoxic compound described herein or known in the art.

In some embodiments, the cytotoxin of the antibody-drug conjugate is an RNA polymerase inhibitor. In some embodiments, the RNA polymerase inhibitor is an amatoxin or derivative thereof. In some embodiments, the cytotoxin of the antibody-drug conjugate as disclosed herein is an amatoxin or derivative thereof, such as an α-amanitin, β-amanitin, γ-amanitin, ε-amanitin, amanin, amaninamide, amanullin, amanullinic acid, proamanullin or a derivative thereof.

Additional details regarding cytotoxins that can be used in the anti-CD45 ADCs useful in the compositions and methods of the invention are described below.

Amatoxins

In some embodiments, the cytotoxin of the antibody-drug conjugate is an amatoxin, or a derivative thereof, which is an RNA polymerase inhibitor. In some embodiments, the cytotoxin of the antibody-drug conjugate as disclosed herein is an amatoxin or derivative thereof, such as an α-amanitin, β-amanitin, γ-amanitin, ε-amanitin, amanin, amaninamide, amanullin, amanullinic acid, proamanullin or a derivative thereof.

The structure of an exemplary amatoxins represented by Formula IV below; examples are also disclosed in, e.g., Zanotti et al., Int. J. Peptide Protein Res. 30, 1987, 450-459.

(IV)

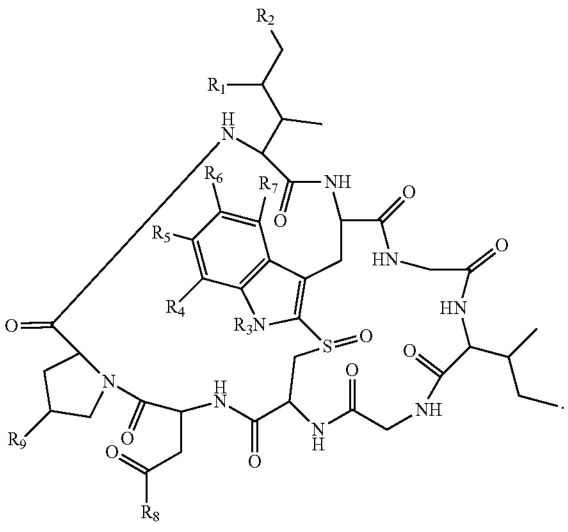

The below table provides additional amatoxin structures:

| Name | $R_1$ | $R_2$ | $R_3$, $R_4$ | $R_5$ | $R_6$, $R_7$ | $R_8$ | $R_9$ |
|---|---|---|---|---|---|---|---|
| α-amanitin | OH | OH | H | OH | H | $NH_2$ | OH |
| β-amanitin | OH | OH | H | OH | H | OH | OH |
| γ-amanitin | OH | H | H | OH | H | $NH_2$ | OH |
| ε-amanitin | OH | H | H | OH | H | OH | OH |
| Amanin | OH | OH | H | H | H | OH | OH |
| Amaninamide | OH | OH | H | H | H | $NH_2$ | OH |
| Amanullin | H | H | H | OH | H | $NH_2$ | OH |
| Amanullinic acid | H | H | H | OH | H | OH | OH |
| Proamanullin | H | H | H | OH | H | $NH_2$ | H |

Amatoxins useful in conjunction with the compositions, e.g., anti-CD45 ADCs, and methods described herein include compounds according to, but are not limited to, Formula (V), (V)

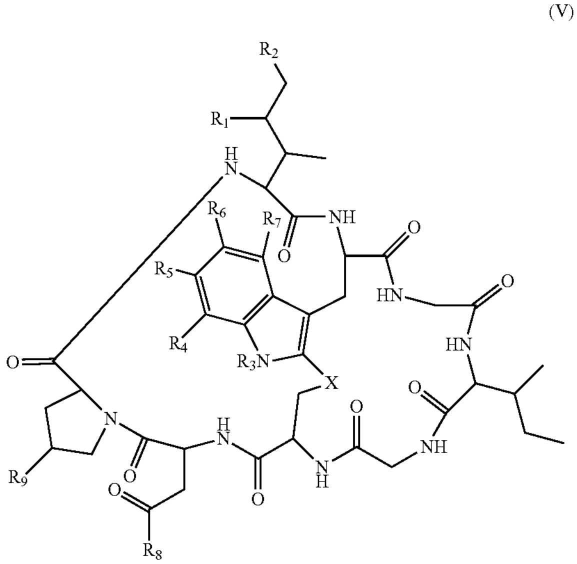

wherein:

$R_1$ is H, OH, or $OR_A$;

$R_2$ is H, OH, or $OR_B$;

$R_A$ and $R_B$, when present, together with the oxygen atoms to which they are bound, combine to form an optionally substituted 5-membered heterocycloalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_D$, or $R_D$;

$R_8$ is OH, $NH_2$, or $OR_D$;

$R_9$ is H, OH, or $OR_D$;

X is —S—, —S(O)—, or —$SO_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

For instance, in one embodiment, amatoxins useful in conjunction with the compositions and methods described herein include compounds according to Formula (VA)

(VA)

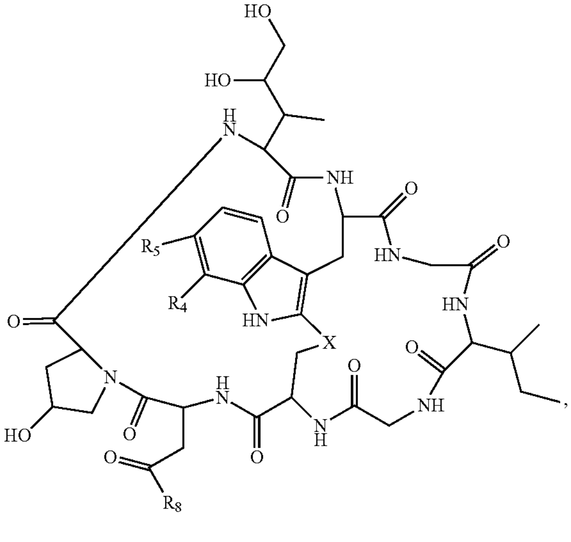

wherein $R_4$, $R_5$, X, and $R_8$ are each as defined above.

For instance, in one embodiment, amatoxins useful in conjunction with the compositions and methods described herein include compounds according to Formula (VB), below:

(VB)

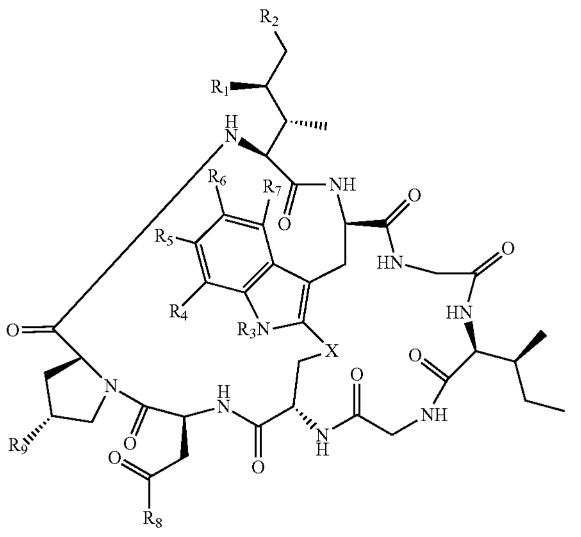

wherein:

$R_1$ is H, OH, or $OR_A$;

$R_2$ is H, OH, or $OR_B$;

$R_A$ and $R_B$, when present, together with the oxygen atoms to which they are bound, combine to form an optionally substituted 5-membered heterocycloalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_D$, or $R_D$;

$R_8$ is OH, $NH_2$, or $OR_D$;

$R_9$ is H, OH, or $OR_D$;

X is —S—, —S(O)—, or —$SO_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

In one embodiment, amatoxins useful in conjunction with the compositions and methods described herein also include compounds according to Formula (VC), below:

(VC)

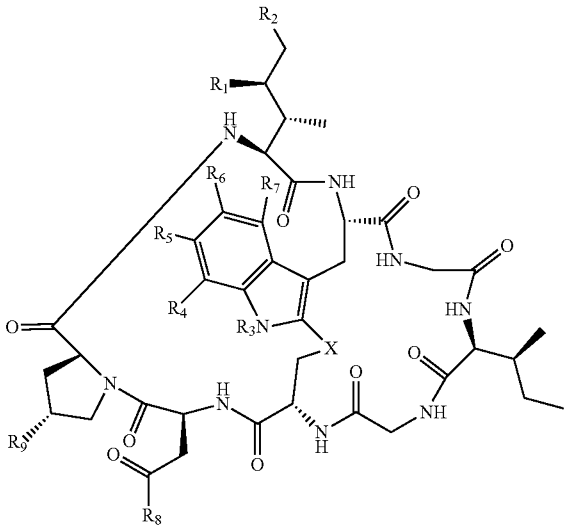

wherein:

$R_1$ is H, OH, or $OR_A$;

$R_2$ is H, OH, or $OR_B$;

$R_A$ and $R_B$, when present, together with the oxygen atoms to which they are bound, combine to form an optionally substituted 5-membered heterocycloalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_D$, or $R_D$;

$R_8$ is OH, $NH_2$, or $OR_D$;

$R_9$ is H, OH, or $OR_D$;

X is —S—, —S(O)—, or —$SO_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

Additional examples of amatoxins that may be used in the conjugates described herein include those described in WO 2020/216927, the contents of which are incorporated by reference herein. In one embodiment, an anti-CD45 antibody, or antigen-binding fragment thereof, is conjugated to an amatoxin via a linker, where the ADC has the structure of formula (VI)

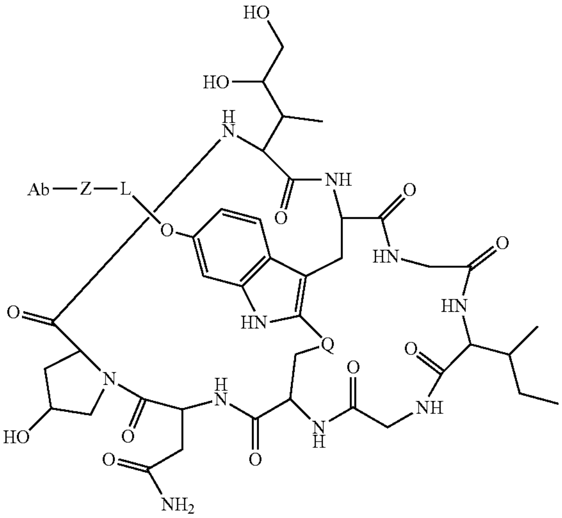

or a stereoisomer thereof;
wherein:
Q is S;
L is a linker;
Z is a chemical moiety formed by a coupling reaction between a reactive substituent present on L and a reactive substituent present within the antibody, or antigen-binding fragment thereof; and
Ab is the anti-CD45 antibody, or the antigen binding fragment thereof. In one embodiment, the linker is a cleavable linker. In another embodiment, the linker is a non-cleavable linker. In one embodiment, wherein L comprises a $-(CH_2)_n-$ unit, where n is an integer from 2-6. In one embodiment, L is $-(CH_2)_n-$, where n is 6. In one embodiment, Ab, Z, and L, taken together as Ab-Z-L, is represented by the formula:

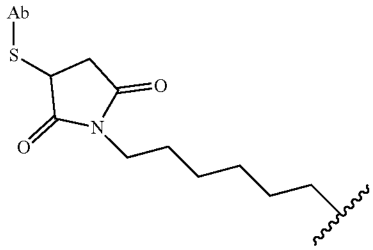

wherein S is the sulfur atom of a cysteine residue present in the anti-CD45 antibody, or the antigen-binding fragment thereof.

In one embodiment, an ADC comprises an anti-CD45 antibody conjugated to an amatoxin, the ADC having a structure according to formula (VII):

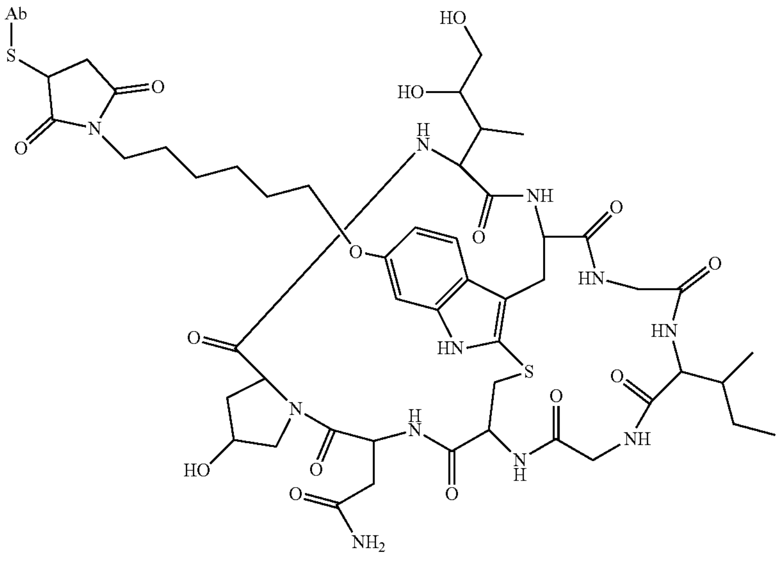

or a stereoisomer thereof.

In one embodiment, an ADC comprises an anti-CD45 antibody conjugated to an amatoxin, the ADC having a structure according to formula (VIIA):

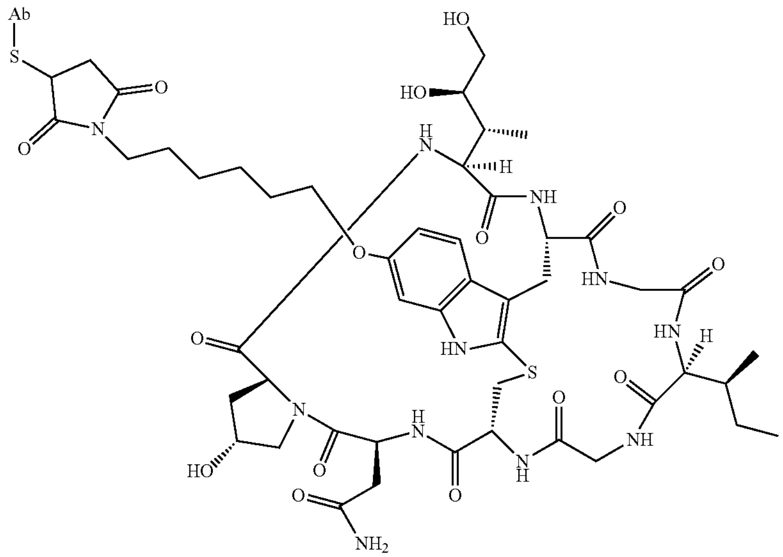

In one embodiment, an ADC comprises an anti-CD45 antibody conjugated to an amatoxin, the ADC having a structure according to formula (VIIB):

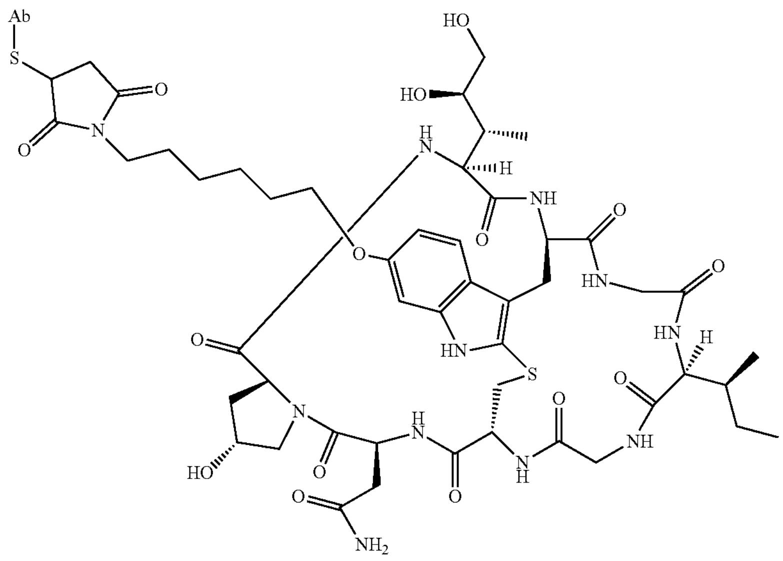

Synthetic methods of making amatoxin are described in U.S. Pat. No. 9,676,702, which is incorporated by reference herein.

In other embodiments, an anti-CD45 antibody, or antigen-binding fragment thereof, described herein may be bound to an amatoxin so as to form a conjugate represented by the formula Ab-Z-L-Am, wherein Ab is the anti-CD45 antibody, or antigen-binding fragment thereof, L is a linker, Z is a chemical moiety and Am is an amatoxin. Many positions on amatoxins or derivatives thereof can serve as the position to covalently bond the linking moiety L, and, hence the antibodies or antigen-binding fragments thereof. In some embodiments, Am-L-Z is represented by Formula (I)

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a peptide, a dipeptide, —(C═O)—, a disulfide, a hydrazone, or a combination thereof; and
Z is a chemical moiety formed from a coupling reaction between a reactive substituent present on L and a reactive substituent present within an antibody, or antigen-binding fragment thereof, that binds a target antigen (e.g., CD45).

In some embodiments, Am contains exactly one $R_C$ substituent.

In some embodiments, L-Z is

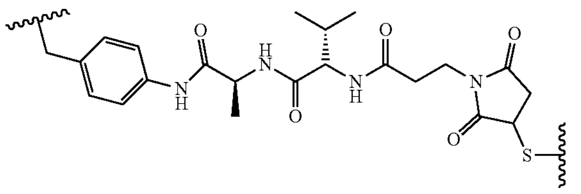

where S is a sulfur atom which represents the reactive substituent present within an antibody, or antigen-binding fragment thereof, that binds a target antigen (e.g., from the —SH group of a cysteine residue).

In some embodiments, the conjugate is represented by one of Formulas IIII, IIIA, or IIIIB:

(III)

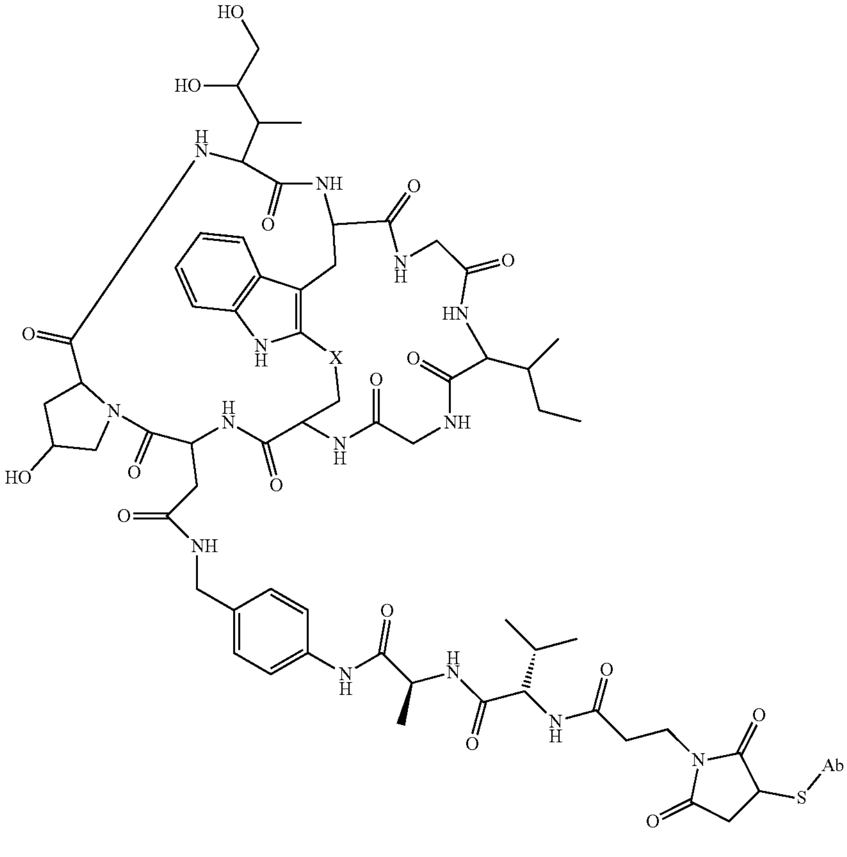

-continued
(IIIA)
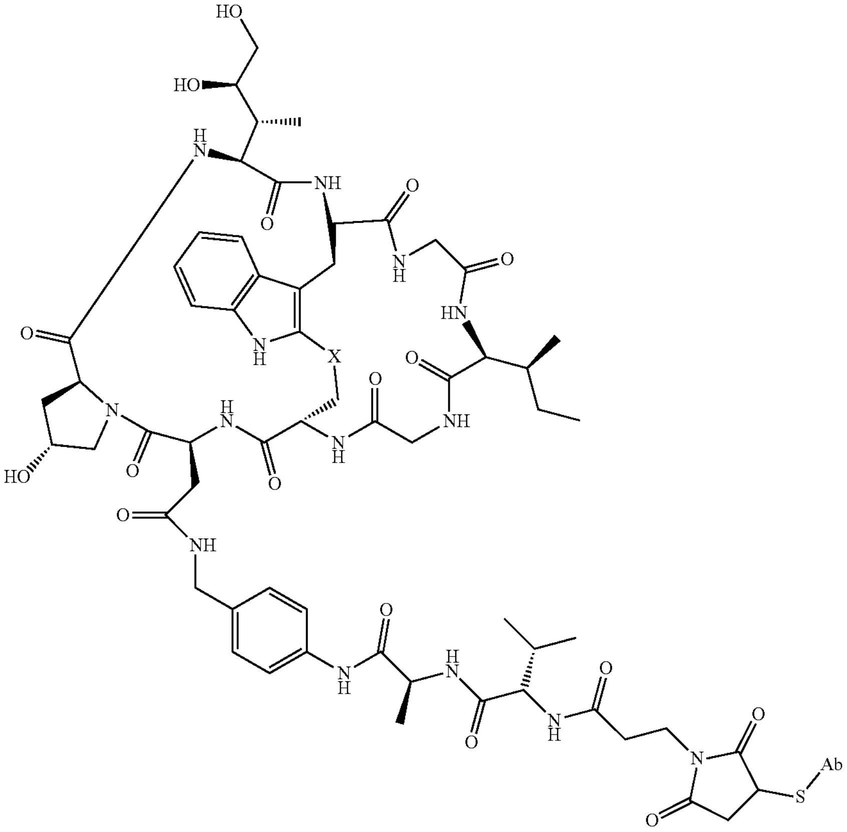
(IIIB)
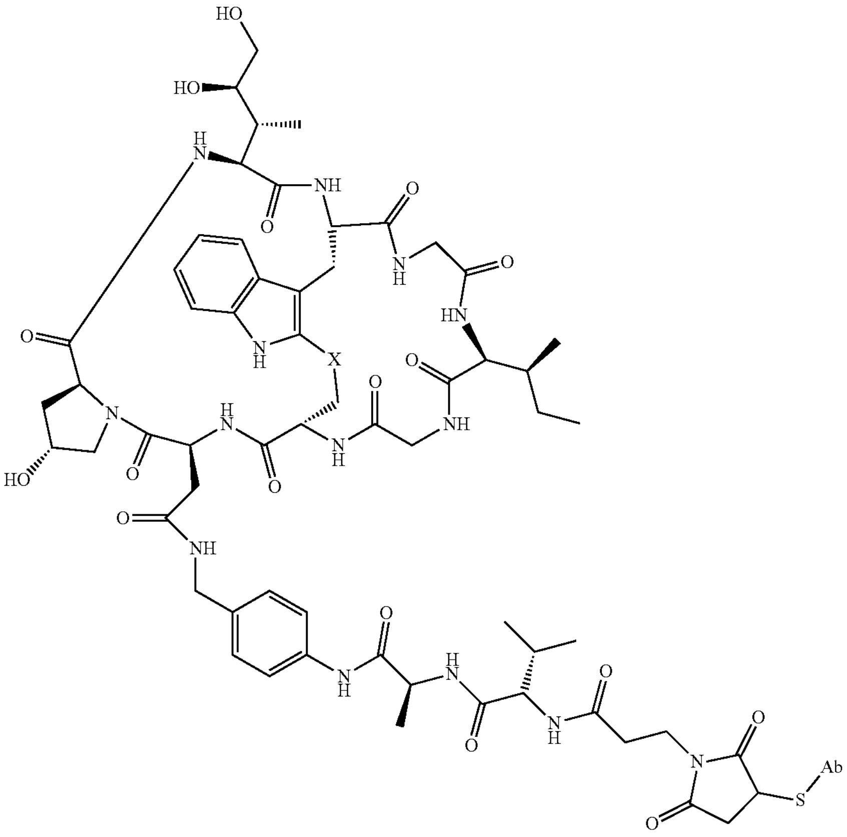

where X is S, SO or $SO_2$, and the Ab is shown to indicate the point of Ab attachment.
In some embodiments, Am-L-Z-Ab is
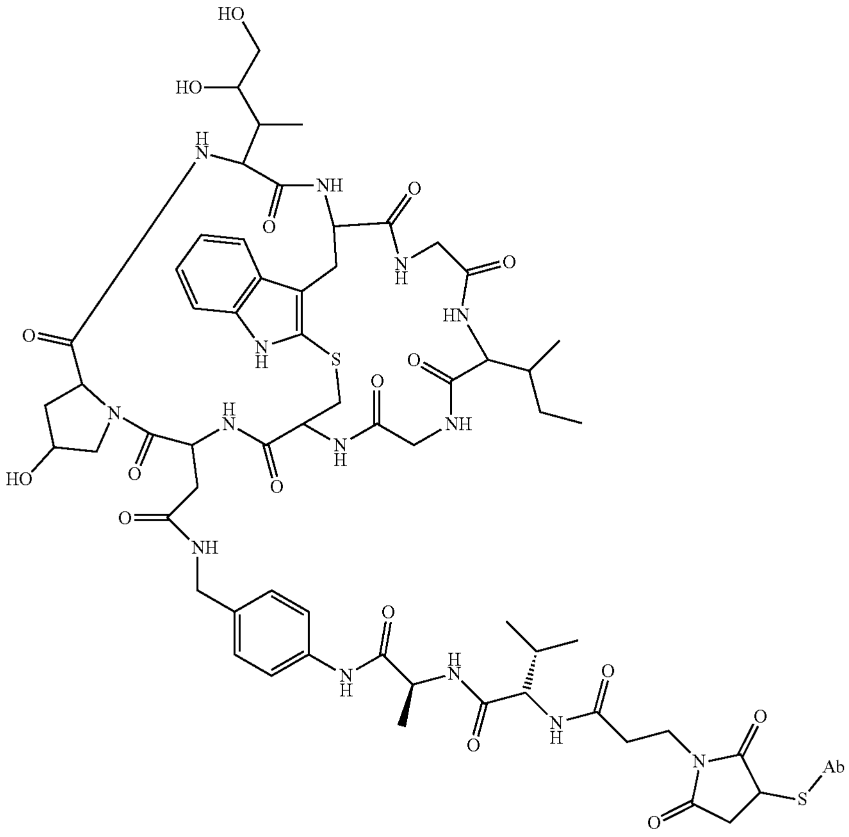

In some embodiments, Am-L-Z-Ab is
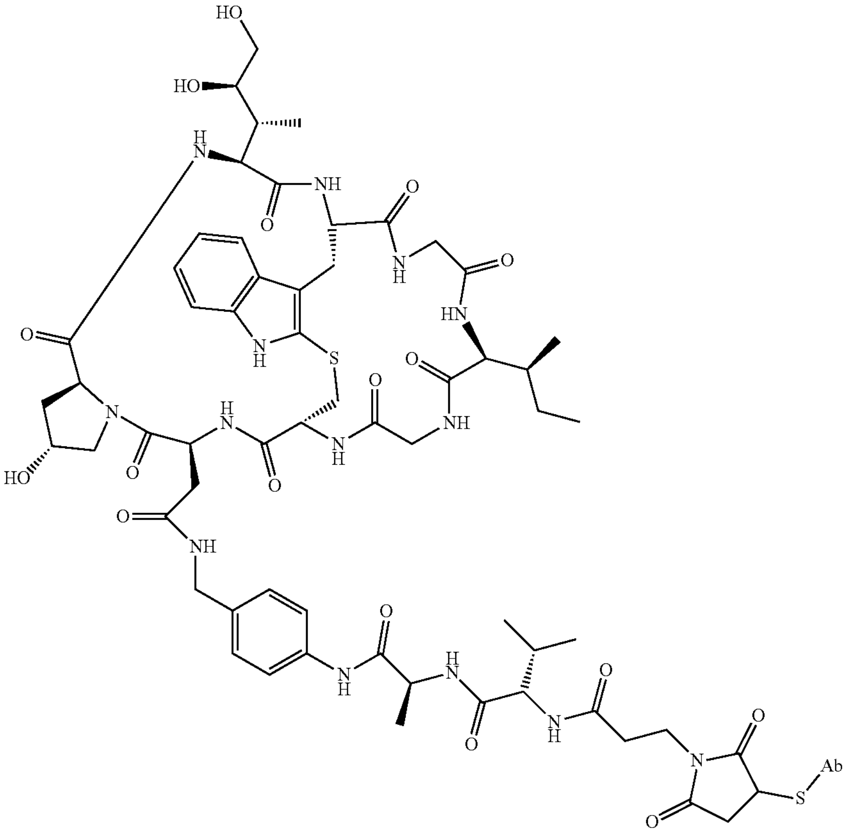
where Ab is shown to indicate the point of Ab attachment.

In some embodiments, Am-L-Z-Ab is
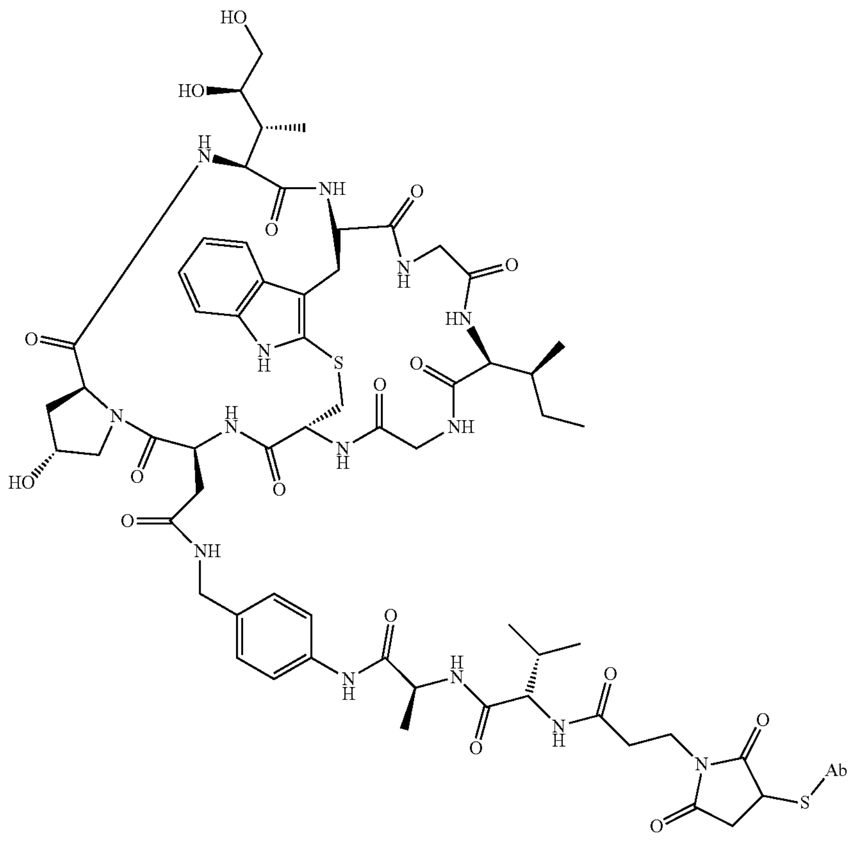
where Ab is shown to indicate the point of Ab attachment.
In some embodiments, the Am-L-Z-Ab precursor, Am-L-Z', is
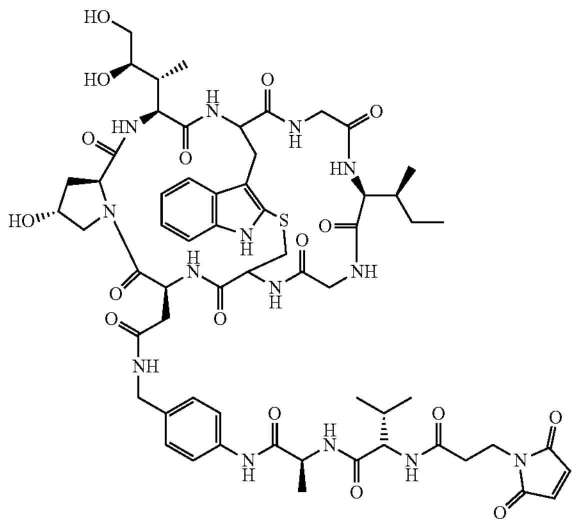
wherein the maleimide reacts with a thiol group found on a cysteine in the antibody.
In some embodiments, the Am-L-Z-Ab precursor, Am-L-Z', is
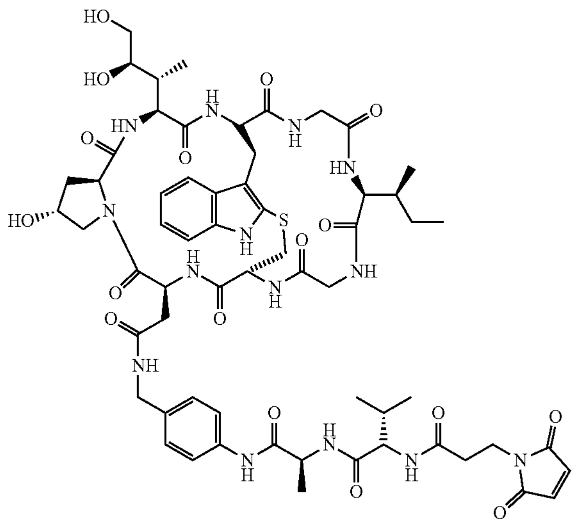
wherein the maleimide reacts with a thiol group found on a cysteine in the antibody.

In some embodiments, Am-L-Z is represented by Formula (IA)

(IA)

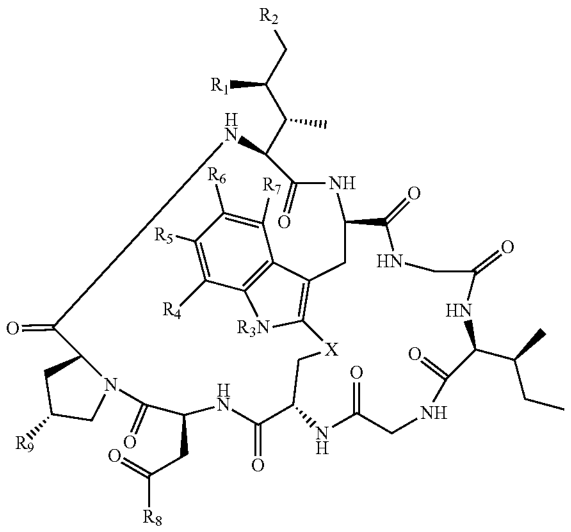

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$ $R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a peptide, a dipeptide, —(C═O)—, a disulfide, a hydrazone, or a combination thereof;

Z is a chemical moiety formed from a coupling reaction between a reactive substituent present on L and a reactive substituent present within an antibody, or antigen-binding fragment thereof, that binds CD45; and wherein Am contains exactly one $R_C$ substituent.

In some embodiments L-Z is

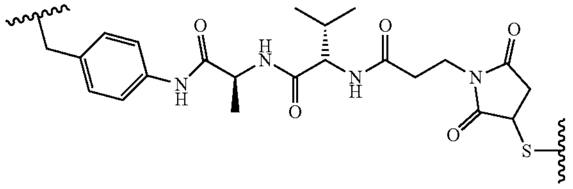

In some embodiments, Am-L-Z is represented by Formula (IB)

(IB)

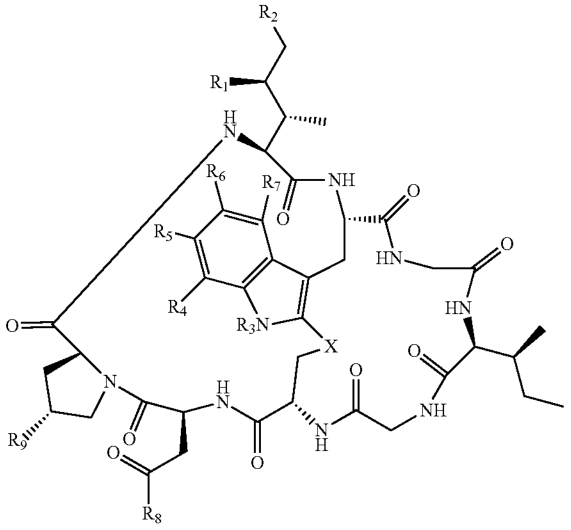

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a peptide, a dipeptide, —(C═O)—, a disulfide, a hydrazone, or a combination thereof;

Z is a chemical moiety formed from a coupling reaction between a reactive substituent present on L and a reactive substituent present within an antibody, or antigen-binding fragment thereof, that binds CD45; and wherein Am contains exactly one $R_C$ substituent.

In some embodiments, L-Z is

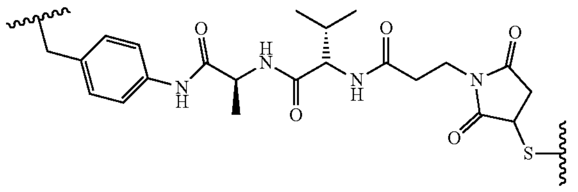

In some embodiments, $R_A$ and $R_B$, when present, together with the oxygen atoms to which they are bound, combine to form a 5-membered heterocycloalkyl group of formula:

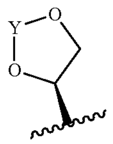

wherein Y is —(C═O)—, —(C═S)—, —(C═$NR_E$)—, or —($CR_ER_{E'}$)—; and $R_E$ and $R_{E'}$ are each independently optionally substituted $C_1$-$C_6$ alkylene-$R_C$, optionally substituted $C_1$-$C_6$ heteroalkylene-$R_C$, optionally substituted $C_2$-$C_6$ alkenylene-$R_C$, optionally substituted $C_2$-$C_6$ heteroalkenylene-$R_C$, optionally substituted $C_2$-$C_6$ alkynylene-$R_C$, optionally substituted $C_2$-$C_6$ heteroalkynylene-$R_C$, optionally substituted cycloalkylene-$R_C$, optionally substituted heterocycloalkylene-$R_C$, optionally substituted arylene-$R_C$, or optionally substituted heteroarylene-$R_C$.

In some embodiments, Am-L-Z is represented by Formula (IA) or Formula (IB), wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form:

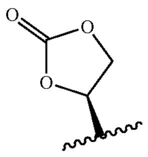 [SMILES: *[C@@H]1COC(=O)O1]

$R_3$ is H or $R_C$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, or $NHR_C$;

$R_9$ is H or OH;

X is —S—, —S(O)—, or —$SO_2$—; and wherein $R_C$ and $R_D$ are each as defined above.

In some embodiments, Am-L-Z is represented by Formula (IA) or Formula (IB), wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form:

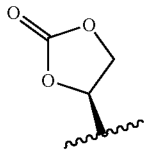 [SMILES: *[C@@H]1COC(=O)O1]

$R_3$ is H or $R_C$;

$R_4$ and $R_5$ are each independently H, OH, $OR_C$, $R_C$, or $OR_D$;

$R_6$ and $R_7$ are each H;

$R_8$ is OH, $NH_2$, $OR_C$, or $NHR_C$;

$R_9$ is H or OH;

X is —S—, —S(O)—, or —$SO_2$—; and wherein $R_C$ is as defined above.

In some embodiments, Am-L-Z is represented by formula (IA) or formula (IB), wherein $R_1$ is H, OH, or $OR_A$;

$R_2$ is H, OH, or $OR_B$;

$R_A$ and $R_B$, when present, together with the oxygen atoms to which they are bound, combine to form:

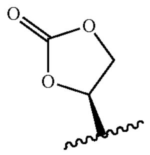 [SMILES: *[C@@H]1COC(=O)O1]

$R_3$, $R_4$, $R_6$, and $R_7$ are each H;

$R_5$ is $OR_C$;

$R_8$ is OH or $NH_2$;

$R_9$ is H or OH;

X is —S—, —S(O)—, or —$SO_2$—; and wherein $R_C$ is as defined above. Such amatoxin conjugates are described, for example, in US Patent Application Publication No. 2016/0002298, the disclosure of which is incorporated herein by reference in its entirety.

In some embodiments, Am-L-Z is represented by Formula (IA) or Formula (IB), wherein $R_1$ and $R_2$ are each independently H or OH;

$R_3$ is $R_C$;

$R_4$, $R_6$, and $R_7$ are each H;

$R_5$ is H, OH, or $OC_1$-$C_6$ alkyl;

$R_8$ is OH or $NH_2$;

$R_9$ is H or OH;

X is —S—, —S(O)—, or —$SO_2$—; and wherein $R_C$ is as defined above. Such amatoxin conjugates are described, for example, in US Patent Application Publication No. 2014/0294865, the disclosure of which is incorporated herein by reference in its entirety.

In some embodiments, Am-L-Z is represented by Formula (IA) or Formula (IB), wherein $R_1$ and $R_2$ are each independently H or OH;

$R_3$, $R_6$, and $R_7$ are each H;

$R_4$ and $R_5$ are each independently H, OH, $OR_C$, or $R_C$;

$R_8$ is OH or $NH_2$;

$R_9$ is H or OH;

X is —S—, —S(O)—, or —$SO_2$—; and wherein $R_C$ is as defined above. Such amatoxin conjugates are described, for example, in US Patent Application Publication No. 2015/0218220, the disclosure of which is incorporated herein by reference in its entirety.

In some embodiments, Am-L-Z is represented by Formula (IA) or Formula (IB), wherein $R_1$ and $R_2$ are each independently H or OH;

$R_3$, $R_6$, and $R_7$ are each H;

$R_4$ and $R_5$ are each independently H or OH;

$R_8$ is OH, $NH_2$, $OR_C$, or $NHR_C$;

$R_9$ is H or OH;

X is —S—, —S(O)—, or —$SO_2$—; and wherein $R_C$ is as defined above. Such amatoxin conjugates are described, for example, in U.S. Pat. Nos. 9,233,173 and 9,399,681, as well as in US 2016/0089450, the disclosures of each of which are incorporated herein by reference in their entirety.

In some embodiments, the Am-L-Z-Ab precursor Am-L-Z' is

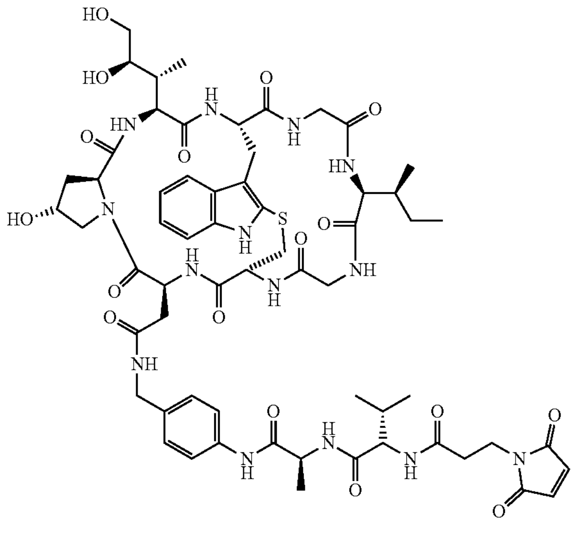

Additional amatoxins that may be used for conjugation to an antibody, or antigen-binding fragment thereof, in accordance with the compositions and methods described herein are described, for example, in WO 2016/142049; WO 2016/071856; WO 2017/149077; WO 2018/115466; and WO 2017/046658, the disclosures of which are incorporated herein by reference in their entirety.

In some embodiments, Am-L-Z is represented by Formula (II), Formula (IIA), or Formula (IIB)

(II)

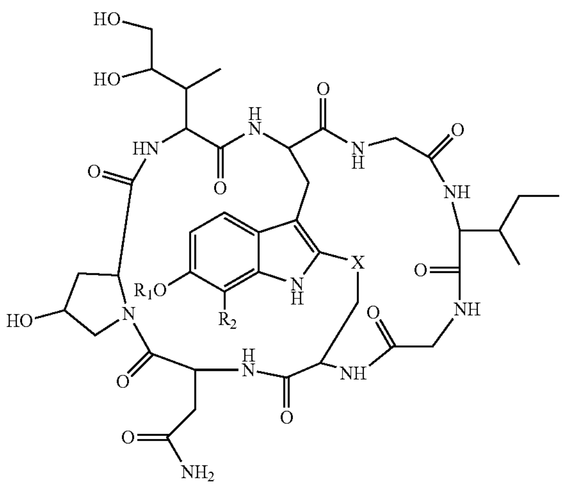

(IIA)

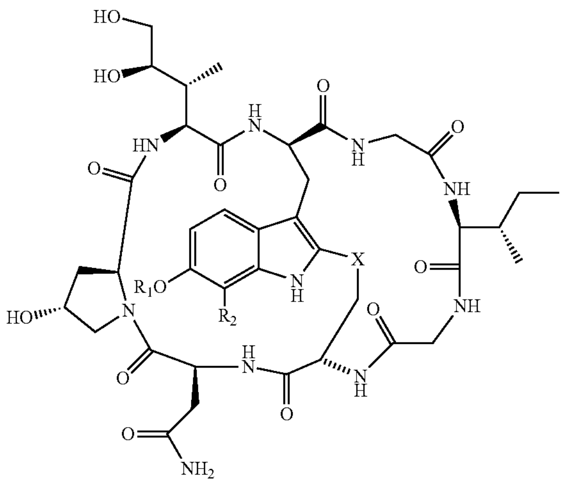

(IIB)

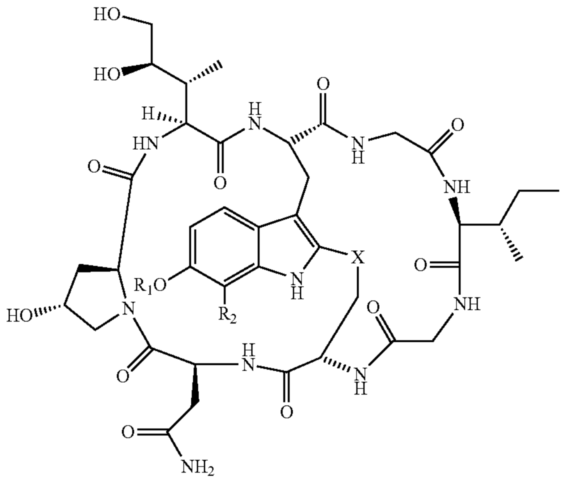

wherein X is S, SO, or $SO_2$; R, is H or a linker covalently bound to the antibody or antigen-binding fragment thereof through a chemical moiety Z, formed from a coupling reaction between a reactive substituent Z' present on the linker and a reactive substituent present within an antibody, or antigen-binding fragment thereof; and $R_2$ is H or a linker covalently bound to the antibody or antigen-binding fragment thereof through a chemical moiety Z, formed from a coupling reaction between a reactive substituent Z' present on the linker and a reactive substituent present within an antibody, or antigen-binding fragment thereof; wherein when $R_1$ is H, $R_2$ is the linker, and when $R_2$ is H, $R_1$ is the linker.

In some embodiments, $R_1$ is the linker and $R_2$ is H, and the linker and chemical moiety, together as L-Z, is

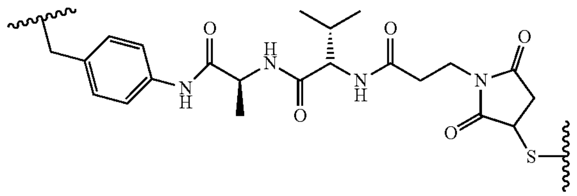

In some embodiments, $R_1$ is the linker and $R_2$ is H, and the linker and chemical moiety, together as L-Z, is

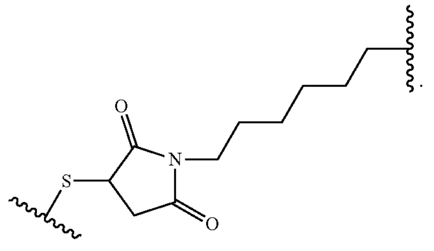 [SMILES: *CCCCCCN1C(=O)CC(S*)C1=O]

In one embodiment, Am-L-Z-Ab is:

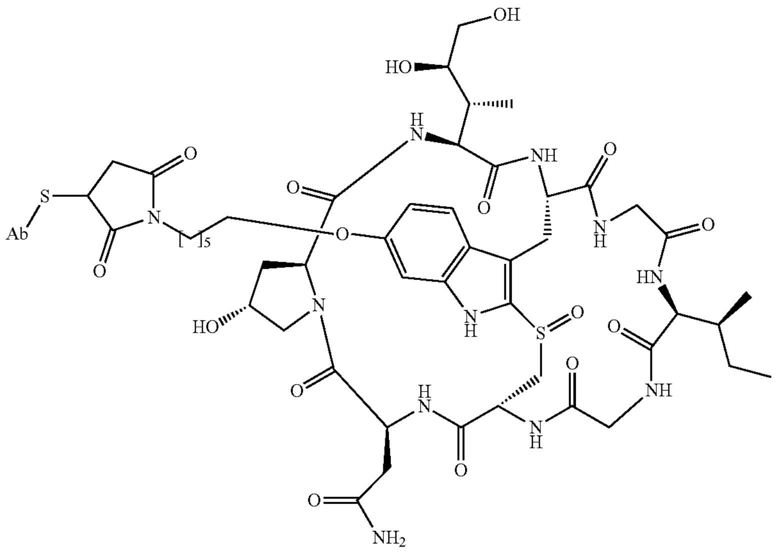

In one embodiment, Am-L-Z-Ab is:

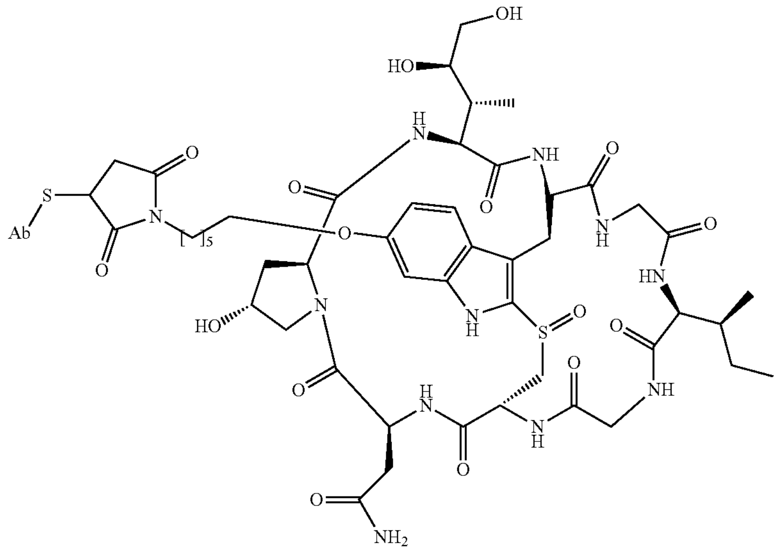

In some embodiments, the Am-L-Z-Ab precursor Am-L-Z' is one of:

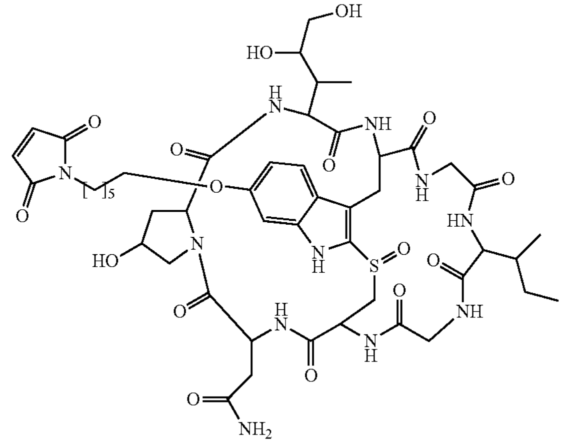

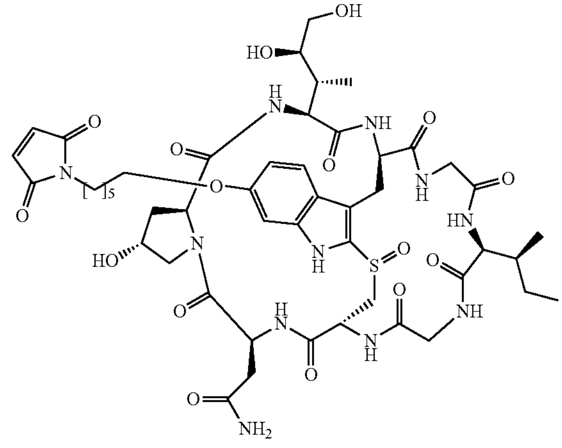

-continued

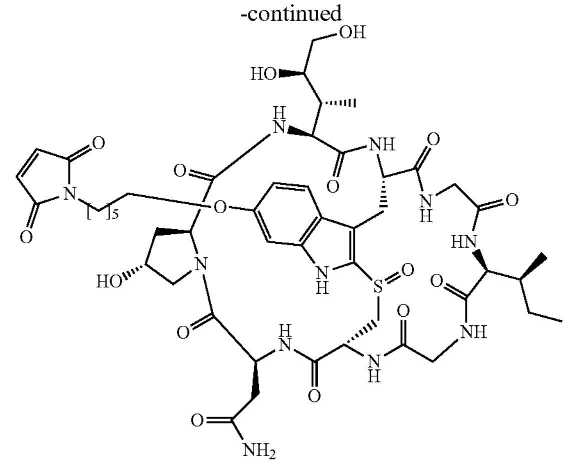

wherein the maleimide reacts with a thiol group found on a cysteine in the antibody to form the conjugate Am-L-Z-Ab.

In some embodiments, the cytotoxin is an α-amanitin. In some embodiments, the α-amanitin is attached to an anti-CD45 antibody via a linker L. In some embodiments, the α-amanitin is a compound of Formula V. The linker L may be attached to the α-amanitin of Formula V at any one of several possible positions (e.g., any of $R^1$-$R^9$) to provide an α-amanitin-linker conjugate of Formula I, IA, IB, II, IIA, or IIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a $-((C{=}O)(CH_2)_n-$ unit, wherein n is an integer from 1-6.

In some embodiments, the linker includes a $-(CH_2)_n-$ unit, where n is an integer from 2-6. In some embodiments, the linker is $-PAB-Cit-Val-(C{=}O)(CH_2)_n-$. In some embodiments, the linker is -PAB-Ala-Val-(C═O)$(CH_2)_n$—. In some embodiments, the linker L and the chemical moiety Z, taken together as L-Z, is

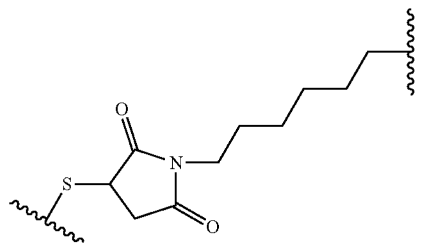

or

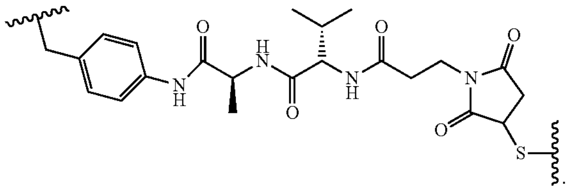

In some embodiments, the cytotoxin is a β-amanitin. In some embodiments, the β-amanitin is attached to an anti-CD45 antibody via a linker L. In some embodiments, the β-amanitin is a compound of formula V. The linker L may be attached to the β-amanitin of Formula V at any one of several possible positions (e.g., any of $R^1$-$R^9$) to provide an β-amanitin-linker conjugate of Formula I, IA, IB, II, IIA, or IIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —(C═O)$(CH_2)_n$— unit, wherein n is an integer from 1-6.

In some embodiments, the linker includes a —$(CH_2)_n$— unit, where n is an integer from 2-6. In some embodiments, the linker is -PAB-Cit-Val-(C═O)$(CH_2)_n$—. In some embodiments, the linker is -PAB-Ala-Val-(C═O)$(CH_2)_n$—. In some embodiments, the linker L and the chemical moiety Z, taken together as L-Z, is

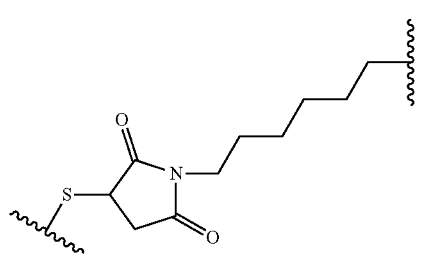

or

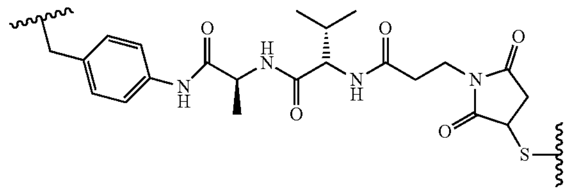

In some embodiments, the cytotoxin is a γ-amanitin. In some embodiments, the γ-amanitin is attached to an anti-CD45 antibody via a linker L. In some embodiments, the γ-amanitin is a compound of Formula V. The linker L may be attached to the γ-amanitin of Formula V at any one of several possible positions (e.g., any of $R^1$-$R^9$) to provide an γ-amanitin-linker conjugate of Formula I, IA, IB, II, IIA, or IIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —(C═O)$(CH_2)_n$— unit, wherein n is an integer from 1-6.

In some embodiments, the linker includes a —$(CH_2)_n$— unit, where n is an integer from 2-6. In some embodiments, the linker is -PAB-Cit-Val-(C═O)$(CH_2)_n$—. In some embodiments, the linker is -PAB-Ala-Val-((C═O)$(CH_2)_n$—. In some embodiments, the linker L and the chemical moiety Z, taken together as L-Z, is

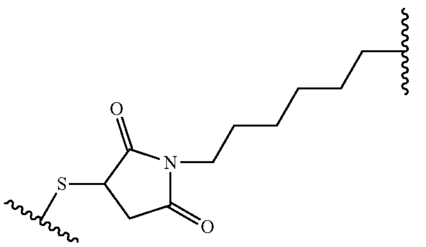

or

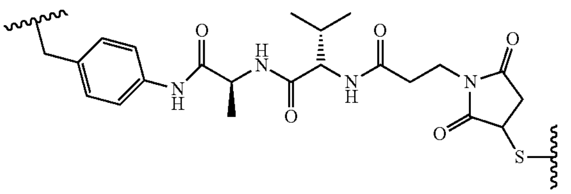

In some embodiments, the cytotoxin is a ε-amanitin. In some embodiments, the ε-amanitin is attached to an anti-CD45 antibody via a linker L. In some embodiments, the ε-amanitin is a compound of Formula V. The linker L may be attached to the ε-amanitin of Formula V at any one of several possible positions (e.g., any of $R^1$-$R^9$) to provide an ε-amanitin-linker conjugate of Formula I, IA, IB, II, IIA, or IIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —(C═O)$(CH_2)_n$— unit, wherein n is an integer from 1-6.

In some embodiments, the linker includes a —$(CH_2)_n$— unit, where n is an integer from 2-6. In some embodiments, the linker is -PAB-Cit-Val-(C═O)$(CH_2)_n$—. In some embodiments, the linker is -PAB-Ala-Val-((C═O)$(CH_2)_n$—. In some embodiments, the linker L and the chemical moiety Z, taken together as L-Z, is

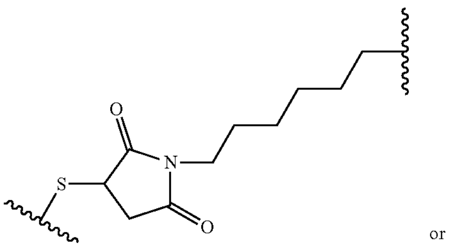

or

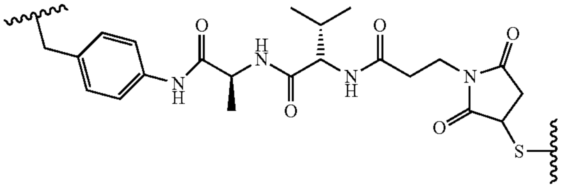

In some embodiments, the cytotoxin is an amanin. In some embodiments, the amanin is attached to an anti-CD45 antibody via a linker L. In some embodiments, the amanin is a compound of Formula V. The linker L may be attached to the amanin of Formula V at any one of several possible positions (e.g., any of $R^1$-$R^9$) to provide an amanin-linker conjugate of Formula I, IA, IB, II, IIA, or IIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a $-(C{=}O)(CH_2)_n-$ unit, wherein n is an integer from 1-6.

In some embodiments, the linker includes a $-(CH_2)_n-$ unit, where n is an integer from 2-6. In some embodiments, the linker is -PAB-Cit-Val-$(C{=}O)(CH_2)_n$—. In some embodiments, the linker is -PAB-Ala-Val-$(C{=}O)(CH_2)_n$—. In some embodiments, the linker L and the chemical moiety Z, taken together as L-Z, is

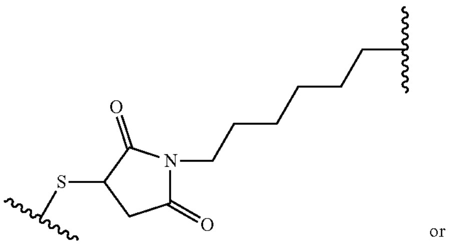

or

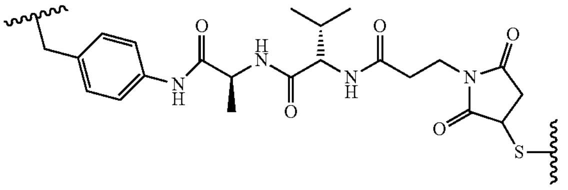

In some embodiments, the cytotoxin is an amaninamide. In some embodiments, the amaninamide is attached to an anti-CD45 antibody via a linker L. In some embodiments, the amaninamide is a compound of Formula V. The linker L may be attached to the amaninamide of Formula V at any one of several possible position. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a $-(C{=}O)(CH_2)_n-$ unit, wherein n is an integer from 1-6.

In some embodiments, the linker includes a $-(CH_2)_n-$ unit, where n is an integer from 2-6. In some embodiments, the linker is -PAB-Cit-Val-$(C{=}O)(CH_2)_n$—. In some embodiments, the linker is -PAB-Ala-Val-$(C{=}O)(CH_2)_n$—. In some embodiments, the linker L and the chemical moiety Z, taken together as L-Z, is

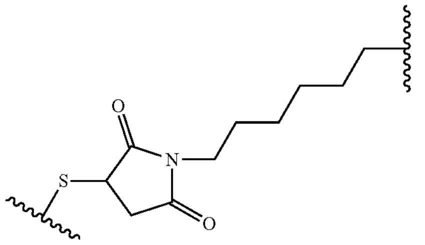

or

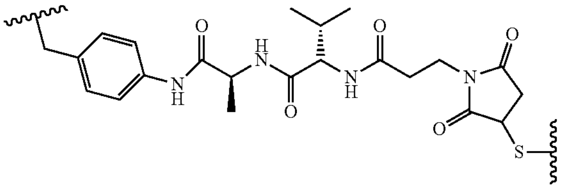

In some embodiments, the cytotoxin is an amanullin. In some embodiments, the amanullin is attached to an anti-CD45 antibody via a linker L. In some embodiments, the amanullin is a compound of formula V. The linker L may be attached to the amanullin of Formula V at any one of several possible positions (e.g., any of $R^1$-$R^9$) to provide an amanullin-linker conjugate of Formula I, IA, IB, II, IIA, or IIIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a $-(C{=}O)(CH_2)_n-$ unit, wherein n is an integer from 1-6.

In some embodiments, the linker includes a $-(CH_2)_n-$ unit, where n is an integer from 2-6. In some embodiments, the linker is -PAB-Cit-Val-$(C{=}O)(CH_2)_n$—. In some embodiments, the linker is -PAB-Ala-Val-$(C{=}O)(CH_2)_n$—. In some embodiments, the linker L and the chemical moiety Z, taken together as L-Z, is

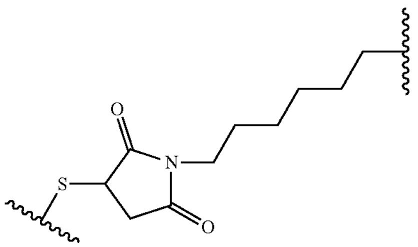

or

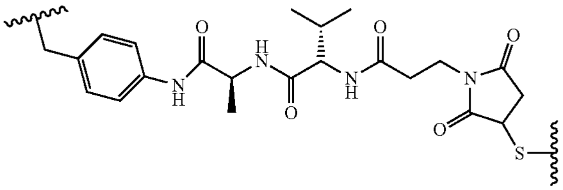

In some embodiments, the cytotoxin is an amanullinic acid. In some embodiments, the amanullinic acid is attached to an anti-CD45 antibody via a linker L. In some embodiments, the amanullinic acid is a compound of formula V. The linker L may be attached to the amanullinic acid of Formula V at any one of several possible positions (e.g., any of $R^1$-$R^9$) to provide an amanullinic acid-linker conjugate of Formula I, IA, IB, II, IIA, or IIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a $—(C{=}O)(CH_2)_n—$ unit, wherein n is an integer from 1-6.

In some embodiments, the linker includes a $—(CH_2)_n—$ unit, where n is an integer from 2-6. In some embodiments, the linker is -PAB-Cit-Val-$(C{=}O)(CH_2)_n$—. In some embodiments, the linker is -PAB-Ala-Val-$(C{=}O)(CH_2)_n$—. In some embodiments, the linker L and the chemical moiety Z, taken together as L-Z, is

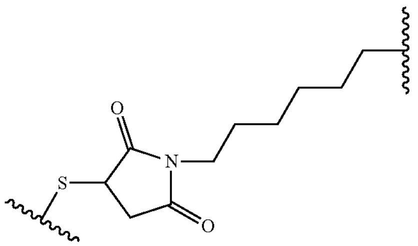

or

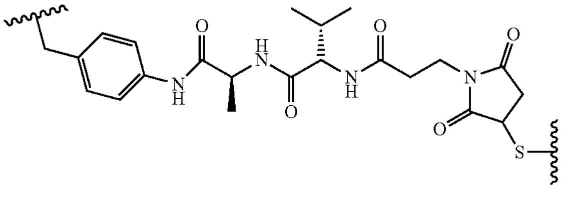

In some embodiments, the cytotoxin is a proamanullin. In some embodiments, the proamanullin is attached to an anti-CD45 antibody via a linker L. In some embodiments, the proamanullin is a compound of Formula V. The linker L may be attached to the proamanullin of formula V at any one of several possible positions (e.g., any of $R^1$-$R^9$) to provide an proamanullin-linker conjugate of Formula I, IA, IB, II, IIA, or IIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a $—(C{=}O)(CH_2)_n$ — unit, wherein n is an integer from 1-6.

In some embodiments, the linker includes a $—(CH_2)_n—$ unit, where n is an integer from 2-6. In some embodiments, the linker is -PAB-Cit-Val-$(C{=}O)(CH_2)_n$—. In some embodiments, the linker is -PAB-Ala-Val-$(C{=}O)(CH_2)_n$—. In some embodiments, the linker L and the chemical moiety Z, taken together as L-Z, is

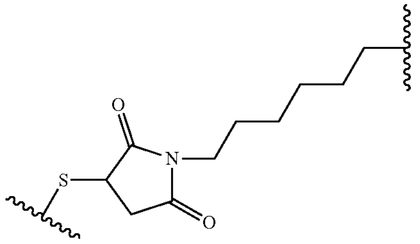

or

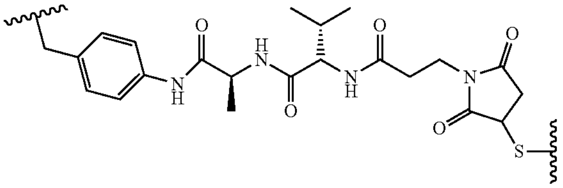

Synthetic methods of making amatoxins are described in U.S. Pat. No. 9,676,702, which is incorporated by reference herein.

Antibodies, and antigen-binding fragments, for use with the compositions and methods described herein can be conjugated to an amatoxin, such as an α-amanitin or a variant thereof, using conjugation techniques known in the art or described herein. For instance, antibodies, and antigen-binding fragments thereof, that recognize and bind a target antigen (an anti-CD45 antibody can be conjugated to an amatoxin, such as α-amanitin or a variant thereof, as described in US 2015/0218220, the disclosure of which is incorporated herein by reference as it pertains, for example, to amatoxins, such as α-amanitin and variants thereof, as well as covalent linkers that can be used for covalent conjugation.

Auristatins

An anti-CD45 antibody or antigen-binding fragment thereof, described herein can be conjugated to a cytotoxin that is an auristatin (U.S. Pat. Nos. 5,635,483; 5,780,588). Auristatins are anti-mitotic agents that interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). (U.S. Pat. Nos. 5,635,483; 5,780,588). The auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in Senter et al, Proceedings of the American Association for Cancer Research, Volume 45, Abstract Number 623, presented Mar. 28, 2004, the disclosure of which is expressly incorporated by reference in its entirety.

An exemplary auristatin embodiment is MMAE, wherein the wavy line indicates the point of covalent attachment to the linker of an antibody-linker conjugate (-L-Z-Ab or -L-Z', as described herein).

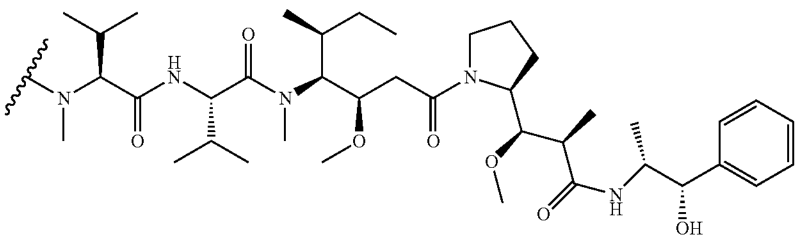 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

Another exemplary auristatin embodiment is MMAF, wherein the wavy line indicates the point of covalent attachment to the linker of an antibody-linker conjugate (-L-Z-Ab or -L-Z', as described herein), as disclosed in US 2005/0238649:

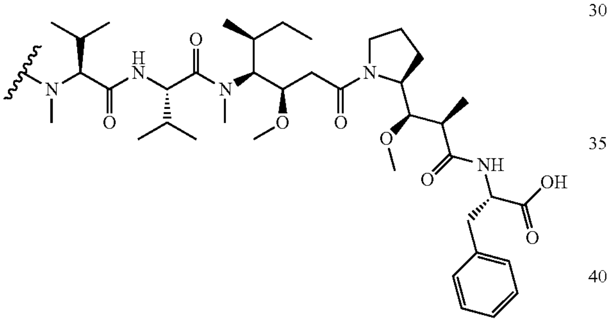

Auristatins may be prepared according to the methods of: U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 15:859-863; and Doronina (2003) Nat. Biotechnol. 21(7):778-784.

Maytansinoids

Antibodies and antigen-binding fragments thereof described herein can be conjugated to a cytotoxin that is a microtubule binding agent. In some embodiments, the microtubule binding agent is a maytansine, a maytansinoid or a maytansinoid analog. Maytansinoids are mitotic inhibitors which bind microtubules and act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533. Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Examples of suitable maytansinoids include esters of maytansinol, synthetic maytansinol, and maytansinol analogs and derivatives. Included herein are any cytotoxins that inhibit microtubule formation and that are highly toxic to mammalian cells, as are maytansinoids, maytansinol, and maytansinol analogs, and derivatives.

Examples of suitable maytansinol esters include those having a modified aromatic ring and those having modifications at other positions. Such suitable maytansinoids are disclosed in U.S. Pat. Nos. 4,137,230; 4,151,042; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,362,663; 4,364,866; 4,424,219; 4,450,254; 4,322,348; 4,362,663; 4,371,533; 5,208,020; 5,416,064; 5,475,092; 5,585,499; 5,846,545; 6,333,410; 7,276,497; and 7,473,796, the disclosures of each of which are incorporated herein by reference as they pertain to maytansinoids and derivatives thereof.

In some embodiments, the antibody-drug conjugates (ADCs) of the present disclosure utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula:

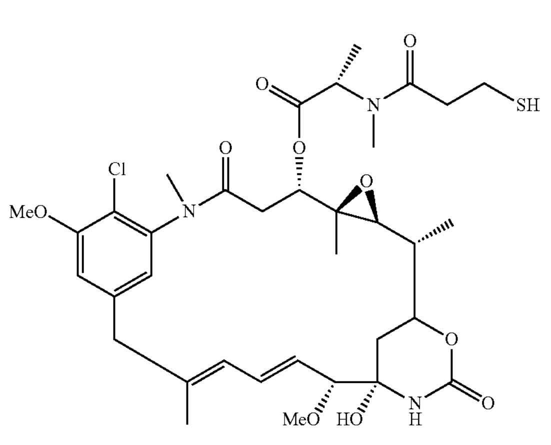 [SMILES: COc1cc2cc(c1Cl)N(C)C(=O)C[C@H](OC(=O)[C@H](C)N(C)C(=O)CCS)[C@]1(C)O[C@H]1[C@H](C)C1C[C@@](O)(NC(=O)O1)[C@H](OC)/C=C/C=C(\C)C2]

In another embodiment, the conjugates of the present invention utilize the thiol-containing maytansinoid $N^{2'}$-deacetyl-$N^{2'}$(4-methyl-4-mercapto-1-oxopentyl)-maytansine (e.g., DM4) as the cytotoxic agent. DM4 is represented by the following structural formula:

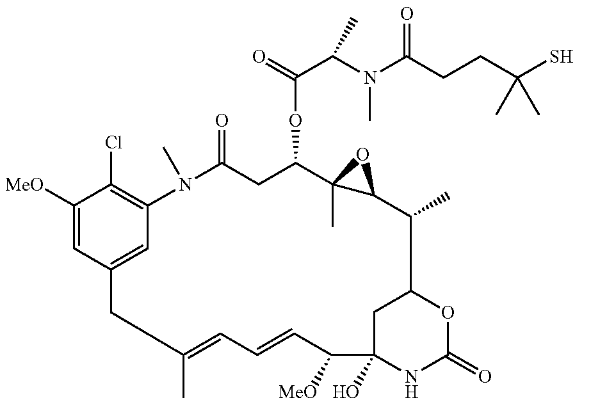 [SMILES: COc1cc2cc(c1Cl)N(C)C(=O)C[C@H](OC(=O)[C@H](C)N(C)C(=O)CCC(C)(C)S)[C@]1(C)O[C@H]1[C@H](C)C1C[C@@](O)(NC(=O)O1)[C@H](OC)/C=C/C=C(\C)C2]

Another maytansinoid comprising a side chain that contains a sterically hindered thiol bond is N[2']-deacetyl-N-[2'](4-mercapto-1-oxopentyl)-maytansine (termed DM3), represented by the following structural formula:

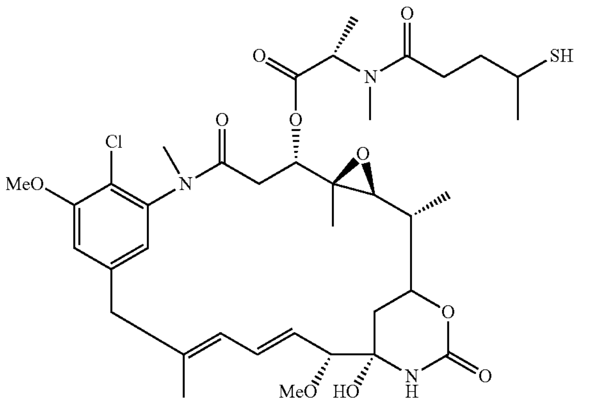 [SMILES: COc1cc2cc(c1Cl)N(C)C(=O)C[C@H](OC(=O)[C@H](C)N(C)C(=O)CCC(C)S)[C@]1(C)O[C@H]1[C@H](C)C1C[C@@](O)(NC(=O)O1)[C@H](OC)/C=C/C=C(\C)C2]

Each of the maytansinoids taught in U.S. Pat. Nos. 5,208,020 and 7,276,497, can also be used in the conjugates of the present disclosure. In this regard, the entire disclosure of U.S. Pat. Nos. 5,208,020 and 7,276,697 is incorporated herein by reference.

Many positions on maytansinoids can serve as the position to covalently bond the linking moiety and, hence the antibodies or antigen-binding fragments thereof (-L-Z-Ab or -L-Z', as described herein). For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to covalently bond the linker moiety, and in some particular embodiments, the C-3 position of maytansinol serves as the position to covalently bond the linking moiety. There are many linking groups known in the art for making antibody-maytansinoid conjugates, including, for example, those disclosed in U.S. Pat. Nos. 5,208,020, 6,441,163, and EP Patent No. 0425235 B1; Chari et al., Cancer Research 52:127-131 (1992); and U.S. 2005/0169933 A1, the disclosures of which are hereby expressly incorporated by reference. Additional linking groups are described and exemplified herein.

The present invention also includes various isomers and mixtures of maytansinoids and conjugates. Certain compounds and conjugates of the present invention may exist in various stereoisomeric, enantiomeric, and diastereomeric forms. Several descriptions for producing such antibody-maytansinoid conjugates are provided in U.S. Pat. Nos. 5,208,020; 5,416,064; 6,333,410; 6,441,163; 6,716,821; and 7,368,565, each of which is incorporated herein in its entirety.

Anthracyclines

In other embodiments, the antibodies and antigen-binding fragments thereof described herein can be conjugated to a cytotoxin that is an anthracycline molecule. Anthracyclines are antibiotic compounds that exhibit cytotoxic activity. Studies have indicated that anthracyclines may operate to kill cells by a number of different mechanisms including: 1) intercalation of the drug molecules into the DNA of the cell thereby inhibiting DNA-dependent nucleic acid synthesis; 2) production by the drug of free radicals which then react with cellular macromolecules to cause damage to the cells or 3) interactions of the drug molecules with the cell membrane [see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102]. Because of their cytotoxic potential anthracyclines have been used in the treatment of numerous cancers such as leukemia, breast carcinoma, lung carcinoma, ovarian adenocarcinoma and sarcomas [see e.g., P. H-Wiernik, in *Anthracycline: Current Status And New Development*s p 11]. Commonly used anthracyclines include doxorubicin, epirubicin, idarubicin and daunomycin. In some embodiments, the cytotoxin is an anthracycline selected from the group consisting of daunorubicin, doxorubicin, epirubicin, and idarubicin. Representative examples of anthracyclines include, but are not limited to daunorubicin (Cerubidine; Bedford Laboratories), doxorubicin (Adriamycin; Bedford Laboratories; also referred to as doxorubicin hydrochloride, hydroxy-daunorubicin, and Rubex), epirubicin (Ellence; Pfizer), and idarubicin (Idamycin; Pfizer Inc.)

The anthracycline analog, doxorubicin (ADRIAMYCIN) is thought to interact with DNA by intercalation and inhibition of the progression of the enzyme topoisomerase II, which unwinds DNA for transcription. Doxorubicin stabilizes the topoisomerase II complex after it has broken the DNA chain for replication, preventing the DNA double helix from being resealed and thereby stopping the process of replication. Doxorubicin and daunorubicin (DAUNOMYCIN) are prototype cytotoxic natural product anthracycline chemotherapeutics (Sessa et al., (2007) Cardiovasc. Toxicol. 7:75-79).

One non-limiting example of a suitable anthracycline for use herein is PNU-159682 ("PNU"). PNU exhibits greater than 3000-fold cytotoxicity relative to the parent nemorubicin (Quintieri et al., Clinical Cancer Research 2005, 11, 1608-1617). PNU is represented by structural formula:

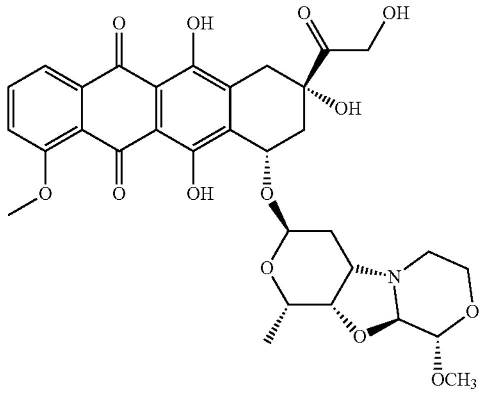

Multiple positions on anthracyclines such as PNU can serve as the position to covalently bond the linking moiety and, hence the anti-CD45 antibodies or antigen-binding fragments thereof as described herein. For example, linkers may be introduced through modifications to the hydroxymethyl ketone side chain.

In some embodiments, the cytotoxin is a PNU derivative represented by structural formula:

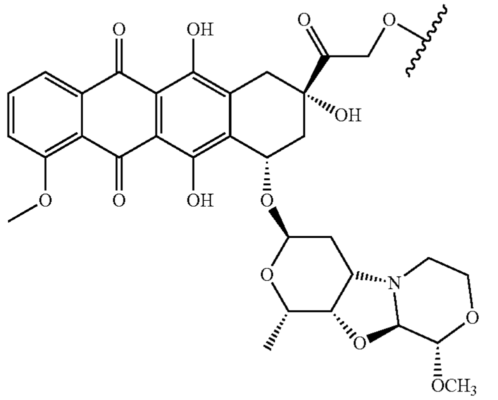

wherein the wavy line indicates the point of covalent attachment to the linker of the ADC as described herein.

In some embodiments, the cytotoxin is a PNU derivative represented by structural formula:

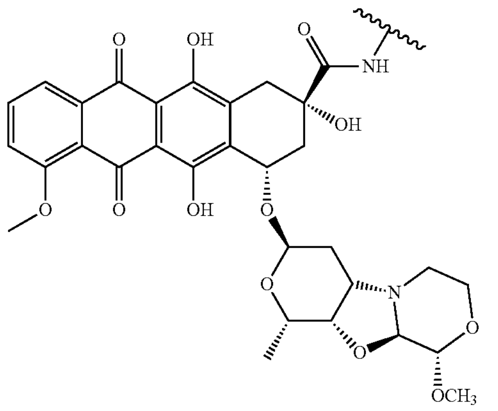

wherein the wavy line indicates the point of covalent attachment to the linker of the ADC as described herein.

Benzodiazepines

In other embodiments, the anti-CD45 antibodies, or antigen-binding fragments thereof, described herein can be conjugated to a cytotoxin that comprises a benzodiazepine moiety, such as a PBD or an IGN, as described herein.

Pyrrolobenzodiazepines (PBDs)

In some embodiments, the antibodies, or antigen-binding fragments thereof, that bind CD45 as described herein can be conjugated to a cytotoxin that is a pyrrolobenzodiazepine ("PBD") or a cytotoxin that comprises a PBD. PBDs are natural products produced by certain actinomycetes and have been shown to be sequence selective DNA alkylating compounds. PBD cytotoxins include, but are not limited to, anthramycin, dimeric PBDs, and those disclosed in, for example, Hartley, J A (2011). "The development of pyrrolobenzodiazepines as antitumor agents" Expert Opin. Inv. Drug, 20(6), 733-744; and Antonow, D. and Thurston, D. E. (2011) "Synthesis of DNA-interactive pyrrolo[2,1-c][1,4] benzodiazepines (PBDs)". Chem. Rev. 111: 2815-2864.

PBDs are of the general structure:

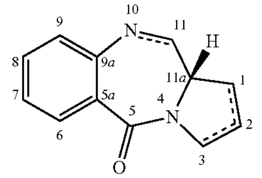

They differ in the number, type and position of substituents, in both their aromatic ("A") rings and pyrrolo ("C") rings, and in the degree of saturation of the C ring. In the diazepine B-ring there is either an imine (N═C), a carbinolamine (NH—CH(OH)), or a carbinolamine methyl ether (NH—CH(OMe)) at the N10-C11 position. This position is the electrophilic moiety responsible for DNA alkylation. All of the known natural product PBDs have an (S)-configuration at the chiral C11a position which provides them with a right-handed twist when viewed from the C ring towards the A ring. This provides the appropriate three-dimensional shape for isohelicity with the minor groove of B-form DNA, leading to a tight fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). The ability of PBDs to form adducts in the minor groove enables them to interfere with DNA processing, resulting in anti-tumor activity.

It has been previously disclosed that the biological activity of these molecules can be potentiated by joining two PBD units together through their C8-hydroxyl functionalities via a flexible alkylene linker (Bose, D. S., et al., *J. Am. Chem. Soc.*, 114, 4939-4941 (1992); Thurston, D. E., et al., *J. Org. Chem.*, 61, 8141-8147 (1996)). The PBD dimers are thought to form sequence-selective DNA lesions, such as the palindromic 5'-Pu-GATC-Py-3' inter-strand cross-link (Smellie, M., et al., *Biochemistry*, 42, 8232-8239 (2003); Martin, C., et al., *Biochemistry*, 44, 4135-4147) which is thought to be mainly responsible for their biological activity. An advantageous dimeric pyrrolobenzodiazepine compound has been described by Gregson et al. (*Chem. Commun.* 1999, 797-798; "compound 1", and by Gregson et al. (*J. Med.*

*Chem.* 2001, 44, 1161-1174; "compound 4a"). This compound, also known as SG2000, is of the structural formula:

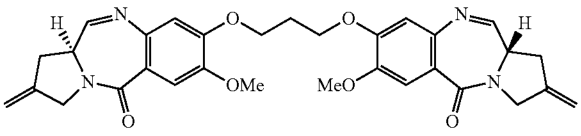

Generally, modifications to the pyrrolidine alkene moiety provide the handle with which to covalently bond the linking moiety and, hence the antibodies or antigen-binding fragments thereof (-L-Z' and -L-Z-Ab, respectively, as described herein). Alternatively, a linker may be attached at position N10.

In some embodiments, the cytotoxin is a pyrrolobenzodiazepine dimer represented by the structural formula:

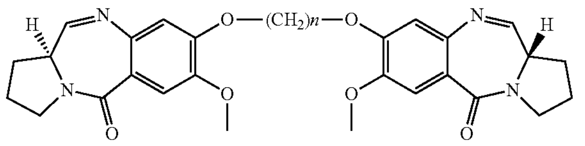

wherein n is an integer from 2 to 5. The compound of this formula wherein n is 3 is known as DSB-120 (Bose et al., J. Am. Chem. Soc. 1992, 114, 4939-4941).

In some embodiments, the cytotoxin is a pyrrolobenzodiazepine dimer represented by the structural formula:

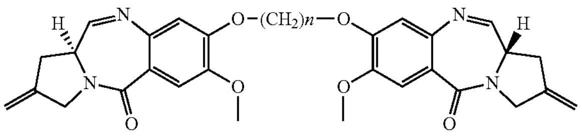

wherein n is an integer from 2 to 5. The compound of this formula wherein n is 3 is known as SJG-136 (Gregson et al., J. Med. Chem. 2001, 44, 737-748). The compound of this formula wherein n is 5 is known as DRG-16 (Gregson et al., Med. Chem. 2004; 47:1161-1174).

In some embodiments, the cytotoxin is a pyrrolobenzodiazepine dimer represented by the structural formula:

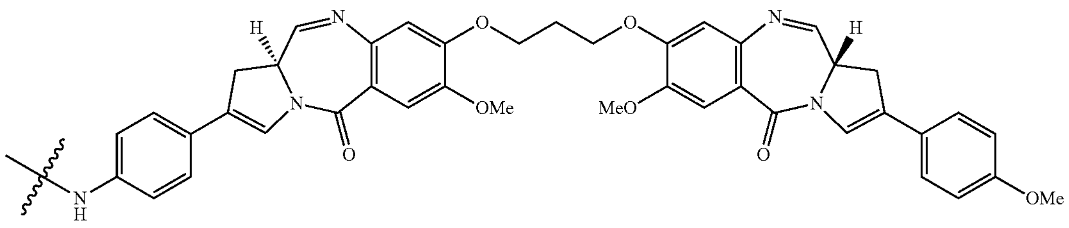 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

wherein the wavy line indicates the point of covalent attachment to the linker of the ADC as described herein. ADCs based on this PBD are disclosed in, for example, Sutherland et al., Blood 2013 122:1455-1463, which is incorporated by reference herein in its entirety.

In some embodiments, the cytotoxin is a PBD dimer represented by the structural formula:

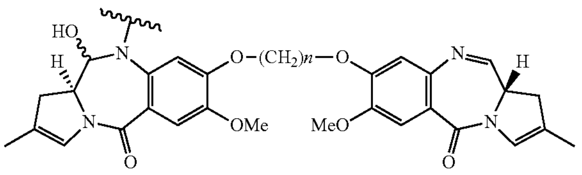

wherein n is 3 or 5, and wherein the wavy line indicates the point of covalent attachment the linker of the ADC as described herein.

In some embodiments, the cytotoxin is a PBD dimer represented by the structural formula:

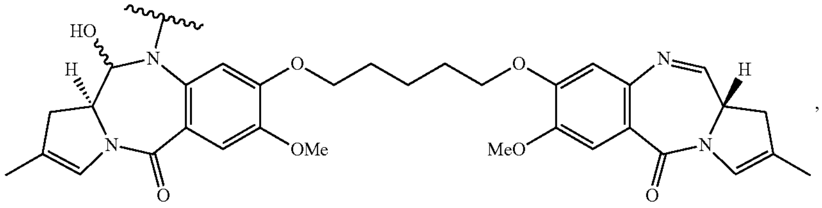
, wherein the wavy line indicates the point of covalent attachment to the linker of the ADC as described herein.

In a specific embodiment, the cytotoxin may be a PBD dimer, which, when taken together with a linker and a reactive moiety Z', each as described herein, may be represented by the structure:

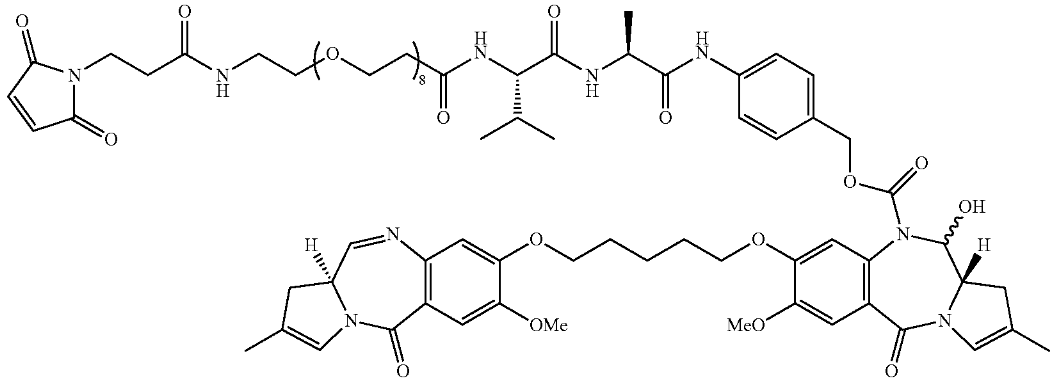

This particular cytotoxin-linker conjugate is known as tesirine (SG3249), and has been described in, for example, Howard et al., ACS Med. Chem. Lett. 2016, 7(11), 983-987, the disclosure of which is incorporated by reference herein in its entirety.

In some embodiments, the cytotoxin-linker conjugate, prior to conjugation to the antibody and including the reactive substituent Z', taken together as Cy-L-Z', has the structure:

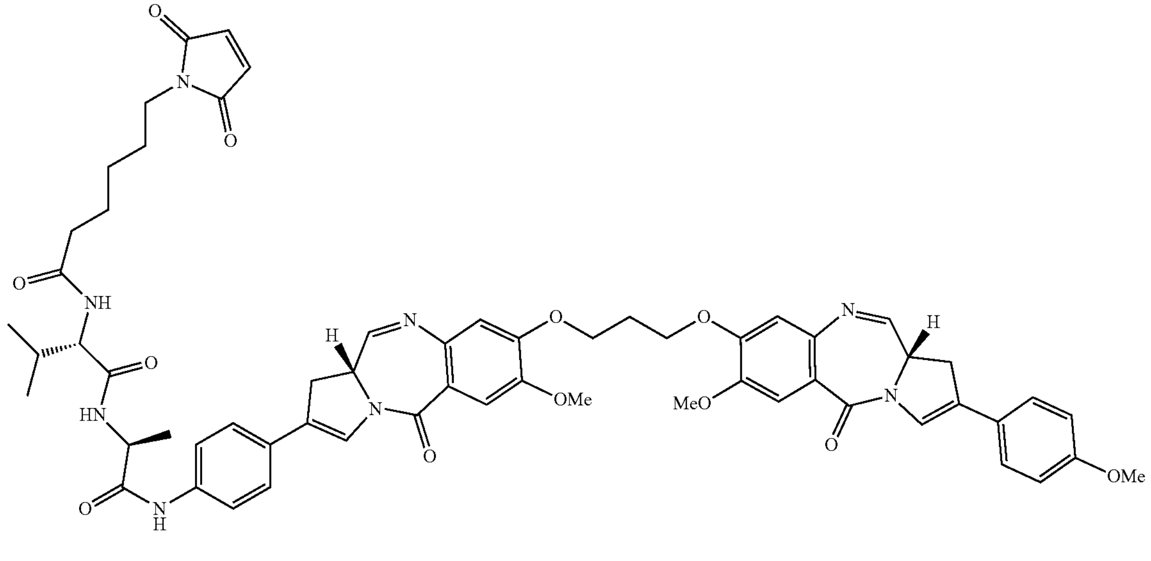 [SMILES: COc1ccc(C2=CN3C(=O)c4cc(OC)c(OCCCOc5cc6c(cc5OC)C(=O)N5C=C(c7ccc(NC(=O)[C@H](C)NC(=O)[C@@H](NC(=O)CCCCCN8C(=O)C=CC8=O)C(C)C)cc7)C[C@@H]5C=N6)cc4N=C[C@@H]3C2)cc1]

This particular cytotoxin-linker conjugate is known as talirine, and has been described, for example, in connection with the ADC Vadastuximab talirine (SGN-CD33A), Mantaj et al., Angewandte Chemie International Edition English 2017, 56, 462-488, the disclosure of which is incorporated by reference herein in its entirety.

Indolinobenzodiazepines (IGNs)

In some embodiments, the antibodies, or antigen-binding fragments thereof, that bind CD45 as described herein can be conjugated to a cytotoxin that is an indolinobenzodiazepine ("IGN") or a cytotoxin that comprises an IGN. In some embodiments, the IGN cytotoxin is an indolinobenzodiazepine dimer or an indolinobenzodiazepine pseudodimer.

Indolinobenzodiazepine dimers represent a relatively new chemical class of cytotoxins with high in vitro potency (low pM range $IC_{50}$ values) towards cancer cells. Similar to the PBD dimer SJG-136, IGN dimers bind to the minor groove of DNA, and covalently bind to guanine residues via the two imine functionalities in the dimer, resulting in crosslinking of the DNA. An IGN dimer (IGN 6; replacing the methylene groups of the PBD moiety with phenyl rings) demonstrated ~10-fold higher potency in vitro as compared to SJG-136, possibly due to faster rate of adduct formation with DNA IGN (see, e.g., Miller et al., "A New Class of Antibody-Drug Conjugates with Potent DNA Alkylating Activity" Mol. Cancer Ther. 2016, 15(8), 1870-1878). In contrast, IGN pseudodimers comprise a single reactive indolinobenzodiazepine imine; the second indolinobenzodiazepine in the dimeric cytotoxin is present in reduced (amine) form. Accordingly, IGN pseudodimers alkylate DNA through the single imine moiety present in the dimer, and do not cross-link DNA.

In some embodiments, the cytotoxin is an IGN pseudodimer having a structure of formula:

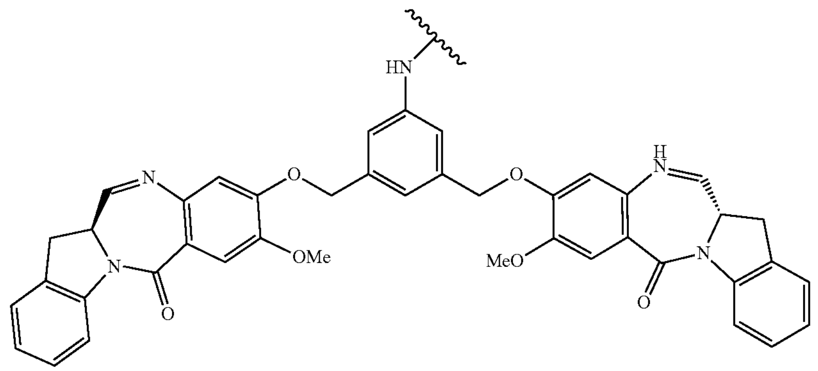

wherein the wavy line indicates the attachment point of the linker.

In some embodiments, the cytotoxin-linker conjugate, prior to conjugation to the antibody and including the reactive substituent Z', taken together as Cy-L-Z', has the structure:

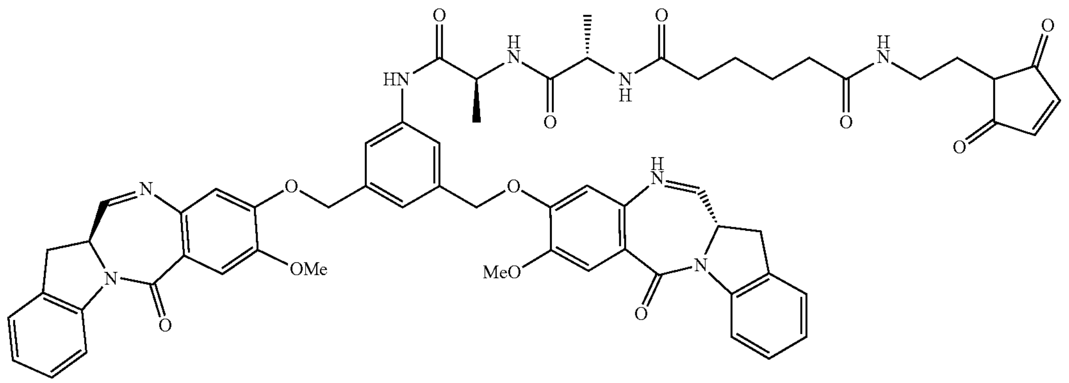

This cytotoxin-linker conjugate is referred to herein as DGN549, and is present in the ADC IMGN632, both of which are disclosed in, for example, International Patent Application Publication No. WO2017004026, which is incorporated by reference herein.

In some embodiments, the cytotoxin is an indolinobenzodiazepine pseudodimer having a structure of formula:

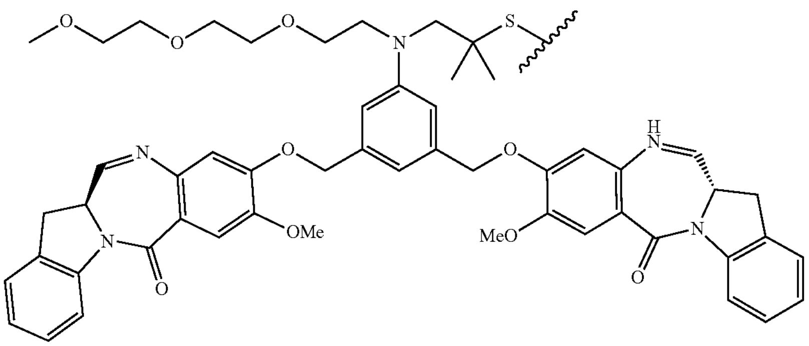

wherein the wavy line indicates the attachment point of the linker. This IGN pseudodimer cytotoxin is referred to herein as DGN462, disclosed in, for example, U.S. Patent Application Publication No. 20170080102, which is incorporated by reference herein.

In some embodiments, the cytotoxin-linker conjugate, prior to conjugation to the antibody and including the chemical moiety Z, taken together as Cy-L-Z, has the structure:

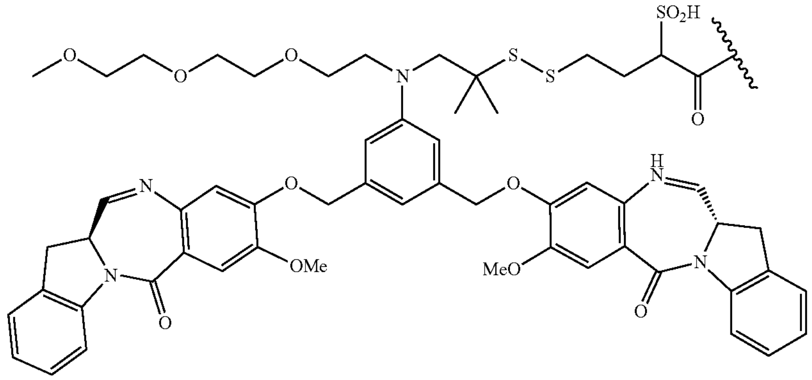

wherein the wavy line indicates the point of attachment to the antibody (e.g., an anti-CD45 antibody or fragment thereof). This cytotoxin-linker conjugate is present in the ADC IMGN779, disclosed in, for example, U.S. Patent Application Publication No. 20170080102, previously incorporated by reference herein.

Calicheamicin

In other embodiments, the antibodies and antigen-binding fragments thereof described herein can be conjugated to a cytotoxin that is an enediyne antitumor antibiotic (e.g., calicheamicins, ozogamicin). The calicheamicin family of antibiotics are capable of producing double-stranded DNA breaks at sub-picomolar concentrations. For the preparation of conjugates of the calicheamicin family, see U.S. Pat. Nos. 5,712,374; 5,714,586; 5,739,116; 5,767,285; 5,770,701; 5,770,710; 5,773,001; and 5,877,296 (all to American Cyanamid Company). Structural analogues of calicheamicin which may be used include, but are not limited to, those disclosed in, for example, Hinman et al., Cancer Research 53:3336-3342 (1993), Lode et al., Cancer Research 58:2925-2928 (1998), and the aforementioned U.S. patents to American Cyanamid.

An exemplary calicheamicin is designated $\gamma_1$, which is herein referenced simply as gamma, and has the structural formula:

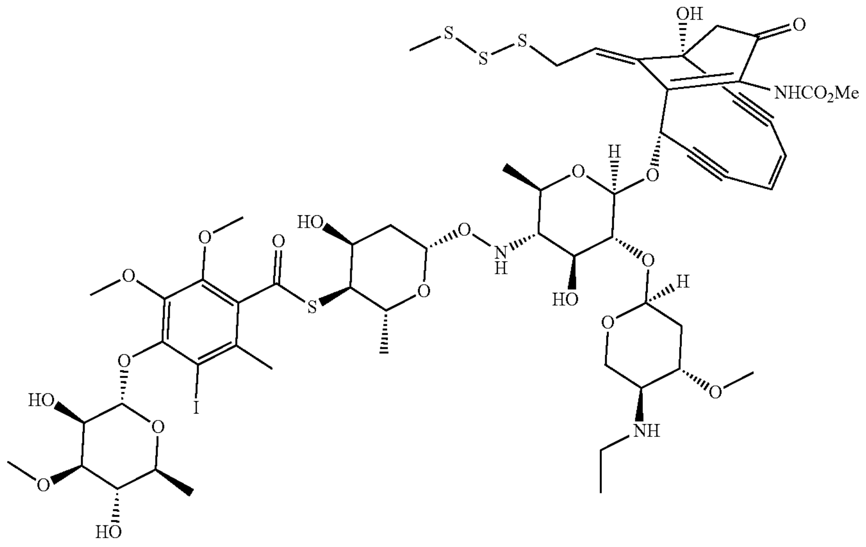

In some embodiments, the calicheamicin is a gamma-calicheamicin derivative or an N-acetyl gamma-calicheamicin derivative. Structural analogues of calicheamicin which may be used include, but are not limited to, those disclosed in, for example, Hinman et al., Cancer Research 53:3336-3342 (1993), Lode et al., Cancer Research 58:2925-2928 (1998), and the aforementioned U.S. patents. Calicheamicins contain a methyltrisulfide moiety that can be reacted with appropriate thiols to form disulfides, at the same time introducing a functional group that is useful in attaching a calicheamicin derivative to an anti-CD45 antibody or antigen-binding fragment thereof as described herein, via a linker. For the preparation of conjugates of the calicheamicin family, see U.S. Pat. Nos. 5,712,374; 5,714,586; 5,739,116; 5,767,285; 5,770,701; 5,770,710; 5,773,001; and 5,877,296 (all to American Cyanamid Company). Structural analogues of calicheamicin which may be used include, but are not limited to, those disclosed in, for example, Hinman et al., Cancer Research 53:3336-3342 (1993), Lode et al., Cancer Research 58:2925-2928 (1998), and the aforementioned U.S. patents to American Cyanamid.

In one embodiment, the cytotoxin of the ADC as disclosed herein is a calicheamicin disulfide derivative represented by the formula:

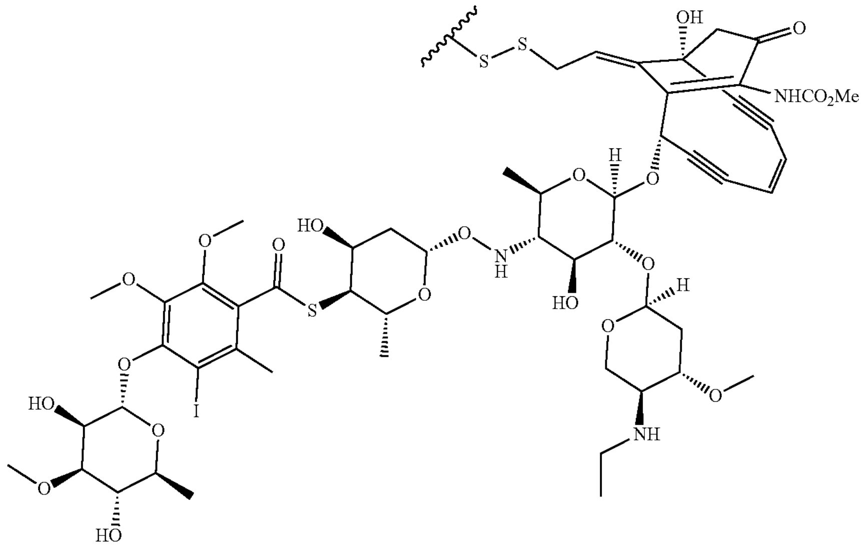

wherein the wavy line indicates the attachment point of the linker.

Ribosome Inactivating Proteins (RIPs)

In some embodiments, the cytotoxin conjugated to an anti-CD45 antibody, or fragment thereof, described herein, is a ribosome-inactivating protein (RIP). Ribosome inactivating proteins are protein synthesis inhibitors that act on ribosomes, usually irreversibly. RIPs are found in plants, as well as bacteria. Examples of RIPs include, but are not limited to, saporin, ricin, abrin, gelonin, Pseudomonas exotoxin (or exotoxin A), trichosanthin, luffin, agglutinin and the diphtheria toxin.

Another example of an RIP that may be used in the anti-CD45 antibody conjugates and methods disclosed herein are a Shiga toxin (Stx) or a Shiga-like toxins (SLT). Shiga toxin (Stx) is a potent bacterial toxin found in *Shigella dysenteriae* 1 and in some serogroups (including serotypes O157:H7, and O104:H4) of *Escherichia coli* (called Stx1 in *E. coli*). In addition to Stx1, some *E. coli* strains produce a second type of Stx (Stx2) that has the same mode of action as Stx/Stx1 but is antigenically distinct. SLT is a historical term for similar or identical toxins produced by *Escherichia coli*. Because subtypes of each toxin have been identified, the prototype toxin for each group is now designated Stx1a or Stx2a. Stx1a and Stx2a exhibit differences in cytotoxicity to various cell types, bind dissimilarly to receptor analogs or mimics, induce differential chemokine responses, and have several distinctive structural characteristics.

A member of the Shiga toxin family refers to any member of a family of naturally occurring protein toxins which are structurally and functionally related, notably, toxins isolated from *S. dysenteriae* and *E. coli* (Johannes L, Romer W, Nat Rev Microbiol 8: 105-16 (2010)). For example, the Shiga toxin family encompasses true Shiga toxin (Stx) isolated from *S. dysenteriae* serotype 1, Shiga-like toxin 1 variants (SLT1 or Stx1 or SLT-1 or Sit-I) isolated from serotypes of enterohemorrhagic *E. coli*, and Shiga-like toxin 2 variants (SLT2 or Stx2 or SLT-2) isolated from serotypes of enterohemorrhagic *E. coli*. SLT1 differs by only one residue from Stx, and both have been referred to as Verocytotoxins or Verotoxins (VTs) (O'Brien A et al., Curr Top Microbiol Immunol 180: 65-94 (1992)). Although SLT1 and SLT2 variants are reported to be only about 53-60% similar to each other at the amino acid sequence level, they share mechanisms of enzymatic activity and cytotoxicity common to the members of the Shiga toxin family (Johannes, Nat Rev Microbiol 8: 105-16 (2010)).

Members of the Shiga toxin family generally have two subunits; A subunit and a B subunit. The B subunit of the toxin binds to a component of the cell membrane known as glycolipid globotriaosylceramide (Gb3). Binding of the subunit B to Gb3 causes induction of narrow tubular membrane invaginations, which drives formation of inward membrane tubules for the bacterial uptake into the cell. The Shiga toxin (a non-pore forming toxin) is transferred to the cytosol via Golgi network and ER. From the Golgi toxin is trafficked to the ER. Shiga toxins act to inhibit protein synthesis within target cells by a mechanism similar to that of ricin (Sandvig and van Deurs (2000) *EMBO J* 19(220:5943). After entering a cell the A subunit of the toxin cleaves a specific adenine nucleobase from the 28S RNA of the 60S subunit of the ribosome, thereby halting protein synthesis (Donohue-Rolfe et al. (2010) Reviews of Infectious Diseases 13 Suppl. 4(7): S293-297).

As used herein, reference to Shiga family toxin refers to any member of the Shiga toxin family of naturally occurring protein toxins (e.g., toxins isolated from *S. dysenteriae* and *E. coli*) which are structurally and functionally related. For example, the Shiga toxin family encompasses true Shiga toxin (Stx) isolated from *S. dysenteriae* serotype 1, Shiga-like toxin 1 variants (SLT1 or Stx1 or SLT-1 or SIt-I) isolated from serotypes of enterohemorrhagic *E. coli*, and Shiga-like toxin 2 variants (SLT2 or Stx2 or SLT-2) isolated from serotypes of enterohemorrhagic *E. coli*. As used herein, "subunit A from a Shiga family toxin" or "Shiga family toxin subunit A" refers to a subunit A from any member of the Shiga toxin family, including Shiga toxins or Shiga-like toxins.

In one embodiment, an anti-CD45 ADC comprises an anti-CD45 antibody conjugated to a Shiga family toxin subunit A, or a portion of a Shiga family toxin subunit A having cytotoxic activity, i.e., ribosome inhibiting activity. Shiga toxin subunit A cytotoxic activities include, for example, ribosome inactivation, protein synthesis inhibition, N-glycosidase activity, polynucleotide:adenosine glycosidase activity, RNAse activity, and DNAse activity. Non-limiting examples of assays for Shiga toxin effector activity measure protein synthesis inhibitory activity, depurination activity, inhibition of cell growth, cytotoxicity, supercoiled DNA relaxation activity, and nuclease activity.

In certain embodiments, an anti-CD45 antibody, or an antigen binding fragment thereof, is conjugated to Shiga family toxin A subunit, or a fragment thereof having ribosome inhibiting activity. An example of a Shiga family toxin subunit A is Shiga-like toxin 1 subunit A (SLT-1A), the amino acid sequence of which is provided below

```
                                          (SEQ ID NO: 147)
KEFTLDFSTAKTYVDSLNVIRSAIGTPLQTISSGGTSLLMIDSGSGDNLF

AVDVRGIDPEEGRFNNLRLIVERNNLYVTGFVNRTNNVFYRFADFSHVTF
```

-continued

```
PGTTAVTLSGDSSYTTLQRVAGISRTGMQINRHSLTTSYLDLMSHSGTSL

TQSVARAMLRFVTVTAEALRFRQIQRGFRTTLDDLSGRSYVMTAEDVDLT

LNWGRLSSVLPDYHGQDSVRVGRISFGSINAILGSVALILNCHHHASRVA

RMASDEFPSMCPADGRVRGITHNKILWDSSTLGAILMRRTISS.
```

Another example of a Shiga family toxin subunit A is Shiga toxin subunit A (StxA), the amino acid sequence of which is provided below

```
                                          (SEQ ID NO: 148)
KEFTLDFSTAKTYVDSLNVIRSAIGTPLQTISSGGTSLLMIDSGTGDNLF

AVDVRGIDPEEGRFNNLRLIVERNNLYVTGFVNRTNNVFYRFADFSHVTF

PGTTAVTLSGDSSYTTLQRVAGISRTGMQINRHSLTTSYLDLMSHSGTSL

TQSVARAMLRFVTVTAEALRFRQIQRGFRTTLDDLSGRSYVMTAEDVDLT

LNWGRLSSVLPDYHGQDSVRVGRISFGSINAILGSVALILNCHHHASRVA

RMASDEFPSMCPADGRVRGITHNKILWDSSTLGAILMRRTISS.
```

Another example of a Shiga family toxin subunit A is Shiga-like toxin 2 subunit A (SLT-2A), the amino acid sequence of which is provided below

```
                                          (SEQ ID NO: 149)
DEFTVDFSSQKSYVDSLNSIRSAISTPLGNISQGGVSVSVINHVLGGNYI

SLNVRGLDPYSERFNHLRLIMERNNLYVAGFINTETNIFYRFSDFSHISV

PDVITVSMTTDSSYSSLQRIADLERTGMQIGRHSLVGSYLDLMEFRGRSM

TRASSRAMLRFVTVIAEALRFRQIQRGFRPALSEASPLYTMTAQDVDLTL

NWGRISNVLPEYRGEEGVRIGRISFNSLSAILGSVAVILNCHSTGSYSVR

SVSQKQKTECQIVGDRAAIKVNNVLWEANTIAALLNRKPQDLTEPNQ.
```

In certain circumstances, naturally occurring Shiga family toxin subunits A may comprise precursor forms containing signal sequences of about 22 amino acids at their amino-terminals which are removed to produce mature Shiga family toxin A subunits and are recognizable to the skilled worker. Cytotoxic fragments or truncated versions of Shiga family toxin subunit A may also be used in the ADCs and methods disclosed herein.

In certain embodiments, a Shiga family toxin subunit A differs from a naturally occurring Shiga toxin A subunit by up to 1, 2, 3, 4, 5, 6, 7, 8, 9, 10, 15, 20, 25, 30, 35, 40 or more amino acid residues (but by no more than that which retains at least 85%, 90%, 95%, 99%, or more amino acid sequence identity). In some embodiments, the Shiga family toxin subunit A differs from a naturally occurring Shiga family toxin A subunit by up to 1, 2, 3, 4, 5, 6, 7, 8, 9, 10, 15, 20, 25, 30, 35, 40 or more amino acid residues (but by no more than that which retains at least 85%, 90%, 95%, 99% or more amino acid sequence identity). Thus, a polypeptide region derived from an A Subunit of a member of the Shiga toxin family may comprise additions, deletions, truncations, or other alterations from the original sequence as long as at least 85%, 90%, 95%, 99% or more amino acid sequence identity is maintained to a naturally occurring Shiga family toxin subunit A.

Accordingly, in certain embodiments, the Shiga family toxin subunit A comprises or consists essentially of amino acid sequences having at least 55%, 60%, 65%, 70%, 75%, 80%, 85%, 90%, 95%, 97%, 98%, 99%, 99.5% or 99.7% overall sequence identity to a naturally occurring Shiga family toxin subunit A, such as SLT-1A (SEQ ID NO: 147), StxA (SEQ ID NO:148), and/or SLT-2A (SEQ ID NO:149).

Suitable Shiga toxins and RIPs suitable as cytotoxins are disclosed in, for example, US20180057544, which is incorporated by reference herein in its entirety.

In certain embodiments, an anti-CD45 scFv comprising VH and VL variable regions described herein (or variable regions comprising light chain and heavy chain CDR sets described herein) are conjugated to a toxin to form an scFv toxin. Such an example of a toxin is a Shiga toxin, as described above.

Additional Cytotoxins

In other embodiments, the antibodies and antigen-binding fragments thereof described herein can be conjugated to a cytotoxin other than or in addition to those cytotoxins disclosed herein above. Additional cytotoxins suitable for use with the compositions and methods described herein include, without limitation, 5-ethynyluracil, abiraterone, acylfulvene, adecypenol, adozelesin, aldesleukin, altretamine, ambamustine, amidox, amifostine, aminolevulinic acid, amrubicin, amsacrine, anagrelide, anastrozole, andrographolide, angiogenesis inhibitors, antarelix, anti-dorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitors, bicalutamide, bisantrene, bisaziridinylspermine, bisnafide, bistratene A, bizelesin, breflate, bleomycin A2, bleomycin B2, bropirimine, budotitane, buthionine sulfoximine, calcipotriol, calphostin C, camptothecin derivatives (e.g., 10-hydroxy-camptothecin), capecitabine, carboxamide-amino-triazole, carboxyamidotriazole, carzelesin, casein kinase inhibitors, castanospermine, cecropin B, cetrorelix, chlorins, chloroquinoxaline sulfonamide, cicaprost, cis-porphyrin, cladribine, clomifene and analogues thereof, clotrimazole, collismycin A, collismycin B, combretastatin A4, combretastatin analogues, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, 2'deoxycoformycin (DCF), deslorelin, dexifosfamide, dexrazoxane, dexverapamil, diaziquone, didemnin B, didox, diethylnorspermine, dihydro-5-azacytidine, dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epothilones, epithilones, epristeride, estramustine and analogues thereof, etoposide, etoposide 4'-phosphate (also referred to as etopofos), exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, homoharringtonine (HHT), hypericin, ibandronic acid, idoxifene, idramantone, ilmofosine, ilomastat, imidazoacridones, imiquimod, immunostimulant peptides, iobenguane, iododoxorubicin, ipomeanol, irinotecan, iroplact, irsogladine, isobengazole, jasplakinolide, kahalalide F, lamellarin-N triacetate, lanreotide, leinamycin, lenograstim, lentinan sulfate, leptolstatin, letrozole, lipophilic platinum compounds, lissoclinamide 7, lobaplatin, lometrexol, lonidamine, losoxantrone, loxoribine, lurtotecan, lutetium texaphyrin, lysofylline, masoprocol, maspin, matrix metalloproteinase inhibitors, menogaril, rnerbarone, meterelin, methioninase, metoclopramide, MIF inhibitor, ifepristone, miltefosine, mirimostim, mithracin, mitoguazone, mitolactol, mitomycin and analogues thereof, mitonafide, mitoxantrone, mofarotene, molgramostim, mycaperoxide B, myriaporone, N-acetyldinaline, N-substituted benzamides, nafarelin, nagrestip, napavin, naphterpin, nartograstim, nedaplatin, nemorubicin, neridronic acid, nilutamide, nisamycin, nitrullyn, octreotide, okicenone, onapristone, ondansetron, oracin, ormaplatin, oxaliplatin, oxaunomycin, paclitaxel and analogues thereof, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, phenazinomycin, picibanil, pirarubicin, piritrexim, podophyllotoxin, porfiromycin, purine nucleoside phosphorylase inhibitors, raltitrexed, rhizoxin, rogletimide, rohitukine, rubiginone B1, ruboxyl, safingol, saintopin, sarcophytol A, sargramostim, sobuzoxane, sonermin, sparfosic acid, spicamycin D, spiromustine, stipiamide, sulfinosine, tallimustine, tegafur, temozolomide, teniposide, thaliblastine, thiocoraline, tirapazamine, topotecan, topsentin, triciribine, trimetrexate, veramine, vinorelbine, vinxaltine, vorozole, zeniplatin, and zilascorb, among others.

Linkers

The term "Linker" as used herein means a divalent chemical moiety comprising a covalent bond or a chain of atoms that covalently attaches an anti-CD45 antibody to a cytotoxin to form an anti-CD45 antibody drug conjugate (ADC), each as described herein. Suitable linkers have two reactive termini, one for conjugation to an antibody and the other for conjugation to a cytotoxin. The antibody conjugation reactive terminus of the linker (reactive moiety, Z') is typically a site that is capable of conjugation to the antibody through a cysteine thiol or lysine amine group on the antibody, and so is typically a thiol-reactive group such as a double bond (as in maleimide) or a leaving group such as a chloro, bromo, iodo, or an R-sulfanyl group, or an amine-reactive group such as a carboxyl group; while the antibody conjugation reactive terminus of the linker is typically a site that is capable of conjugation to the cytotoxin through formation of an amide bond with a basic amine or carboxyl group on the cytotoxin, and so is typically a carboxyl or basic amine group. When the term "linker" is used in describing the linker in conjugated form, one or both of the reactive termini will be absent (such as reactive moiety Z', having been converted to chemical moiety Z) or incomplete (such as being only the carbonyl of the carboxylic acid) because of the formation of the bonds between the linker and/or the cytotoxin, and between the linker and/or the antibody or antigen-binding fragment thereof. Such conjugation reactions are described further herein below.

A variety of linkers can be used to conjugate the antibodies, or antibody fragments, described to a cytotoxic molecule. In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation. The linkers useful for the present ADCs are preferably stable extracellularly, prevent aggregation of ADC molecules and keep the ADC freely soluble in aqueous media and in a monomeric state. Before transport or delivery into a cell, the ADC is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the cytotoxic moiety. Stability of the ADC may be measured by standard analytical techniques such as mass spectroscopy, HPLC, and the separation/analysis technique LC/MS. Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p. 234-242).

Suitable cleavable linkers include those that may be cleaved, for instance, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012, the disclosure of which is incorporated herein by reference as it pertains to linkers suitable for covalent conjugation). Suitable cleavable linkers may include, for example, chemical moieties such as a hydrazine, a disulfide, a thioether or a dipeptide.

Linkers hydrolyzable under acidic conditions include, for example, hydrazones, semicarbazones, thiosemicarbazones, cis-aconitic amides, orthoesters, acetals, ketals, or the like. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661, the disclosure of each of which is incorporated herein by reference in its entirety as it pertains to linkers suitable for covalent conjugation. Such linkers are relatively stable under neutral pH conditions, such as those in the blood, but are unstable at below pH 5.5 or 5.0, the approximate pH of the lysosome.

Linkers cleavable under reducing conditions include, for example, a disulfide. A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935, the disclosure of each of which is incorporated herein by reference in its entirety as it pertains to linkers suitable for covalent conjugation.

Linkers susceptible to enzymatic hydrolysis can be, e.g., a peptide-containing linker that is cleaved by an intracellular peptidase or protease enzyme, including, but not limited to, a lysosomal or endosomal protease. One advantage of using intracellular proteolytic release of the therapeutic agent is that the agent is typically attenuated when conjugated and the serum stabilities of the conjugates are typically high. In some embodiments, the peptidyl linker is at least two amino acids long or at least three amino acids long. Exemplary amino acid linkers include a dipeptide, a tripeptide, a tetrapeptide or a pentapeptide. Examples of suitable peptides include those containing amino acids such as Valine, Alanine, Citrulline (Cit), Phenylalanine, Lysine, Leucine, and Glycine. Amino acid residues which comprise an amino acid linker component include those occurring naturally, as well as minor amino acids and non-naturally occurring amino acid analogs, such as citrulline. Exemplary dipeptides include valine-citrulline (vc or val-cit) and alanine-phenylalanine (af or ala-phe). Exemplary tripeptides include glycine-valine-citrulline (gly-val-cit) and glycine-glycine-glycine (gly-gly-gly). In some embodiments, the linker includes a dipeptide such as Val-Cit, Ala-Val, or Phe-Lys, Val-Lys, Ala-Lys, Phe-Cit, Leu-Cit, Ile-Cit, Phe-Arg, or Trp-Cit. Linkers containing dipeptides such as Val-Cit or Phe-Lys are disclosed in, for example, U.S. Pat. No. 6,214,345, the disclosure of which is incorporated herein by reference in its entirety as it pertains to linkers suitable for covalent conjugation. In some embodiments, the linker includes a dipeptide selected from Val-Ala and Val-Cit.

Linkers suitable for conjugating the antibodies, or antibody fragments, described herein to a cytotoxic molecule include those capable of releasing a cytotoxin by a 1,6-elimination process. Chemical moieties capable of this elimination process include the p-aminobenzyl (PAB) group, 6-maleimidohexanoic acid, pH-sensitive carbonates, and other reagents as described in Jain et al., Pharm. Res. 32:3526-3540, 2015, the disclosure of which is incorporated herein by reference in its entirety as it pertains to linkers suitable for covalent conjugation.

In some embodiments, the linker includes a "self-immolative" group such as the afore-mentioned PAB or PABC (para-aminobenzyloxycarbonyl), which are disclosed in, for example, Carl et al., J. Med. Chem. (1981) 24:479-480; Chakravarty et al (1983) J. Med. Chem. 26:638-644; U.S. Pat. No. 6,214,345; US20030130189; US20030096743; U.S. Pat. No. 6,759,509; US20040052793; U.S. Pat. Nos. 6,218,519; 6,835,807; 6,268,488; US20040018194; WO98/13059; US20040052793; U.S. Pat. Nos. 6,677,435; 5,621,002; US20040121940; WO2004/032828). Other such chemical moieties capable of this process ("self-immolative linkers") include methylene carbamates and heteroaryl groups such as aminothiazoles, aminoimidazoles, aminopyrimidines, and the like. Linkers containing such heterocyclic self-immolative groups are disclosed in, for example, U.S. Patent Publication Nos. 20160303254 and 20150079114, and U.S. Pat. No. 7,754,681; Hay et al. (1999) Bioorg. Med. Chem. Lett. 9:2237; US 2005/0256030; de Groot et al (2001) J. Org. Chem. 66:8815-8830; and U.S. Pat. No. 7,223,837. In some embodiments, a dipeptide is used in combination with a self-immolative linker.

Linkers suitable for use herein further may include one or more groups selected from $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, heteroarylene, and combinations thereof, each of which may be optionally substituted. Non-limiting examples of such groups include $(CH_2)_p$, $(CH_2CH_2O)_p$, and $-(C{=}O)(CH_2)_p-$ units, wherein p is an integer from 1-6, independently selected for each occasion.

Suitable linkers may contain groups having solubility enhancing properties. Linkers including the $(CH_2CH_2O)_p$ unit (polyethylene glycol, PEG), for example, can enhance solubility, as can alkyl chains substituted with amino, sulfonic acid, phosphonic acid or phosphoric acid residues. Linkers including such moieties are disclosed in, for example, U.S. Pat. Nos. 8,236,319 and 9,504,756, the disclosure of each of which is incorporated herein by reference in its entirety as it pertains to linkers suitable for covalent conjugation. Further solubility enhancing groups include, for example, acyl and carbamoyl sulfamide groups, having the structure:

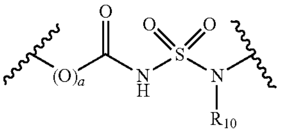

wherein a is 0 or 1; and $R^{10}$ is selected from the group consisting of hydrogen, $C_1$-$C_{24}$ alkyl groups, $C_3$-$C_{24}$ cycloalkyl groups, $C_1$-$C_{24}$ (hetero)aryl groups, $C_1$-$C_{24}$ alkyl(hetero)aryl groups and $C_1$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, each of which may be optionally substituted and/or optionally interrupted by one or more heteroatoms selected from O, S and $NR^{11}R^{12}$, wherein $R^{11}$ and $R^{12}$ are independently selected from the group consisting of hydrogen and $C_1$-$C_4$ alkyl groups; or $R^{10}$ is a cytotoxin, wherein the cytotoxin is optionally connected to N via a spacer moiety. Linkers containing such groups are described, for example, in U.S. Pat. No. 9,636,421 and U.S. Patent Application Publication No. 2017/0298145, the disclosures of which are incorporated herein by reference in their entirety as they pertain to linkers suitable for covalent conjugation to cytotoxins and antibodies or antigen-binding fragments thereof.

In some embodiments, the linker may include one or more of a hydrazine, a disulfide, a thioether, a dipeptide, a p-aminobenzyl (PAB) group, a heterocyclic self-immolative group, an optionally substituted $C_1$-$C_6$ alkyl, an optionally substituted $C_1$-$C_6$ heteroalkyl, an optionally substituted $C_2$-$C_6$ alkenyl, an optionally substituted $C_2$-$C_6$ heteroalkenyl, an optionally substituted $C_2$-$C_6$ alkynyl, an optionally substituted $C_2$-$C_6$ heteroalkynyl, an optionally substituted $C_3$—C cycloalkyl, an optionally substituted heterocycloalkyl, an optionally substituted aryl, an optionally substituted heteroaryl, a solubility enhancing group, acyl, —(C=O)—, or $-(CH_2CH_2O)_p-$ group, wherein p is an integer from 1-6. One of skill in the art will recognize that one or more of the groups listed may be present in the form of a bivalent (diradical) species, e.g., $C_1$-$C_6$ alkylene and the like.

In some embodiments, the linker L comprises the moiety *-$L_1L_2$-**, wherein:

$L_1$ is absent or is $-(CH_2)_mNR^{13}C(=O)-$, $-(CH_2)_mNR^{13}-$, $-(CH_2)_mX_3(CH_2)_m-$,

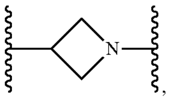,
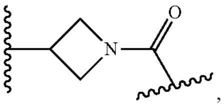,

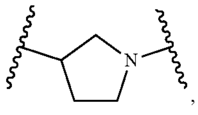,
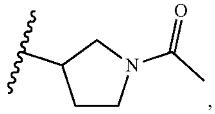,

-continued

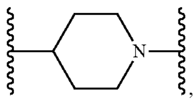,
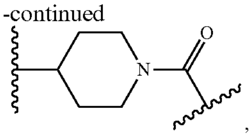, or

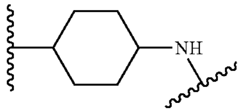

$L_2$ is absent or is $-(CH_2)_m-$, $-NR^{13}(CH_2)_m-$, $-(CH_2)_mNR^{13}C(=O)(CH_2)_m-$, $-X_4$, $-(CH_2)_mNR^{13}C(=O)X_4$, $-(CH_2)_mNR^{13}C(=O)-$, $-((CH_2)_mO)_n(CH_2)_m-$, $-((CH_2)_mO)_n(CH_2)_mX_3(CH_2)_m-$, $-NR^{13}((CH_2)_mO)_nX_3(CH_2)_m-$, $-NR^{13}((CH_2)_mO)_n(CH_2)_mX_3(CH_2)_m-$, $-X_1X_2C(=O)(CH_2)_m-$, $-(CH_2)_m(O(CH_2)_m)_n-$, $-(CH_2)_mNR^{13}(CH_2)_m-$, $-(CH_2)_mNR^{13}C(=O)(CH_2)_mX_3(CH_2)_m-$, $-(CH_2)_mC(=O)NR^{13}(CH_2)_mNR^{13}C(=O)(CH_2)_m-$, $-(CH_2)_mC(=O)-$, $-(CH_2)_mNR^{13}(CH_2)_mC(=O)X_2\times_1C(=O)-$, $-(CH_2)_mX_3(CH_2)_mC(=O)X_2X_1C(=O)-$, $-(CH_2)_mC(=O)NR^{13}(CH_2)_m-$, $-(CH_2)_mC(=O)NR^{13}(CH_2)_mX_3(CH_2)_m-$, $-(CH_2)_mX_3(CH_2)_mNR^{13}C(=O)(CH_2)_m-$, $-(CH_2)_mX_3(CH_2)_mC(=O)NR^{13}(CH_2)_m-$, $-(CH_2)_mO)_n(CH_2)_mNR^{13}C(=O)(CH_2)_m-$, $-(CH_2)_mC(=O)NR^{13}(CH_2)_m(O(CH_2)_m)_n-$, $-(CH_2)_m(O(CH_2)_m)_nC(=O)-$, $-(CH_2)_mNR^{13}(CH_2)_m\ C(=O)-$, $-(CH_2)_mC(=O)NR^{13}(CH_2)_mNR^{13}C(=O)-$, $-(CH_2)_m(O(CH_2)_m)_nX_3(CH_2)_m-$, $-(CH_2)_mX_3((CH_2)_mO)_n(CH_2)_m-$, $-(CH_2)_mX_3(CH_2)_m\ C(=O)-$, $-(CH_2)_mC(=O)NR^{13}(CH_2)_mO)_n(CH_2)_mX_3(CH_2)_m-$, $-(CH_2)_mX_3(CH_2)_m(O(CH_2)_m)_nNR^{13}C(=O)(CH_2)_m-$, $-(CH_2)_mX_3(CH_2)_m(O(CH_2)_m)_nC(=O)-$, $-(CH_2)_mX_3(CH_2)_m(O(CH_2)_m)_n-$, $-(CH_2)_mC(=O)NR^{13}(CH_2)_mC(=O)-$, $-(CH_2)_m\ C(=O)NR^{13}(CH_2)_m(O(CH_2)_m)_nC(=O)-$, $-((CH_2)_mO)_n(CH_2)_mNR^{13}C(=O)(CH_2)_m-$, $-(CH_2)_m\ C(=O)NR^{13}(CH_2)_mC(=O)NR^{13}(CH_2)_m-$, $-(CH_2)_mNR^{13}C(=O)(CH_2)_mNR^{13}C(=O)(CH_2)-(CH_2)_mX_3(CH_2)_mC(=O)NR^{13}-$, $-(CH_2)_mC(=O)NR^{13}-$, $-(CH_2)_mX_3-$, $-C(R^{13})_2(CH_2)_m-$, $-(CH_2)_mC(R^{13})_2NR^{13}-$, $-(CH_2)_mC(=O)NR^{13}(CH_2)_mNR^{13}-$, $-(CH_2)_mC(=O)NR^{13}(CH_2)_mNR^{13}C(=O)NR^{13}-$, $-(CH_2)_mC(=O)X_2X_1C(=O)-$, $-C(R^{13})_2(CH_2)_mNR^{13}C(=O)(CH_2)_m-$, $-(CH_2)_mC(=O)NR^{13}(CH_2)_mC(R^{13})_2NR^{13}-$, $-C(R^{13})_2(CH_2)_mX_3(CH_2)_m-$, $-(CH_2)_mX_3(CH_2)_mC(R^{13})_2NR^{13}-$, $-C(R^{13})_2(CH_2)_mOC(=O)NR^{13}(CH_2)_m-$, $-(CH_2)_mNR^{13}C(=O)O(CH_2)_mC(R^{13})_2NR^{13}-$, $-(CH_2)_mX_3(CH_2)_mNR^{13}-$, $-(CH_2)_mX_3(CH_2)_m(O(CH_2)_m)_nNR^{13}-$, $-(CH_2)_mNR^{13}-$, $-(CH_2)_mC(=O)NR^{13}(CH_2)_m(O(CH_2)_m)_nNR^{13}-$, $-(CH_2)_m(O(CH_2)_m)_nNR^{13}$, $-(CH_2CH_2O)_n(CH_2)_m-$, $-(CH_2)_m(OCH_2CH_2)_n$, $-(CH_2)_mO(CH_2)_m-$, $-(CH_2)_mS(=O)_2-$, $-(CH_2)_mC(=O)NR^{13}(CH_2)_mS(=O)_2-$, $-(CH_2)_mX_3(CH_2)_mS(=O)_2-$, $-(CH_2)_mX_2X_1C(=O)-$, $-(CH_2)_m(O(CH_2)_m)_nC(=O)X_2X_1C(=O)-$, $-(CH_2)_m(O(CH_2)_m)_nX_2X_1C(=O)-$, $-(CH_2)_mX_3(CH_2)_mX_2X_1C(=O)-$, $-(CH_2)_mX_3(CH_2)_m(O(CH_2)_m)_nX_2X_1C(=O)-$, $-(CH_2)_mX_3(CH_2)_mC(=O)NR^{13}(CH_2)_mNR^{13}C(=O)-$, $-(CH_2)_mX_3(CH_2)_mC(=O)NR^{13}(CH_2)_mC(=O)-$, $-(CH_2)_mX_3(CH_2)_mC(=O)NR^{13}(CH_2)_m(O(CH_2)_m)_nC(=O)-$, $-(CH_2)_mC(=O)X_2X_1C(=O)NR^{13}(CH_2)_m-$, $-(CH_2)_mX_3(O(CH_2)_m)_nC(=O)-$, $-(CH_2)_mNR^{13}C(=O)((CH_2)_mO)_n(CH_2)_m-$, $-(CH_2)_m(O(CH_2)_m)_nC$ (=O)$NR^{13}(CH_2)_m$—, —$(CH_2)_mNR^{13}C$(=O)$NR^{13}(CH_2)_m$— or —$(CH_2)_mX_3(CH_2)_mNR^{13}C$(=O)—;

wherein $X_1$ is

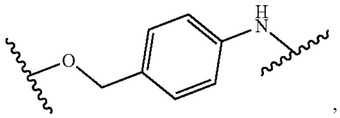

,

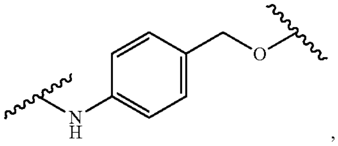

,

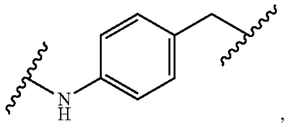

,

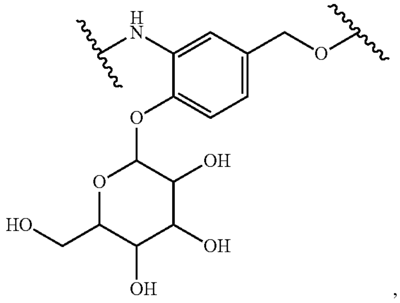

, or

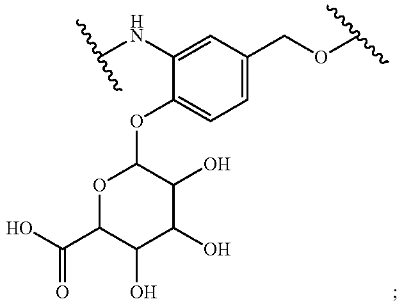

;

$X_2$ is

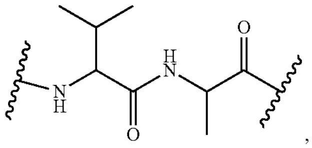

,

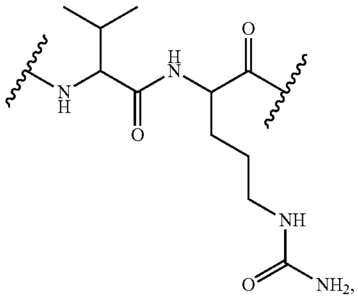

-continued

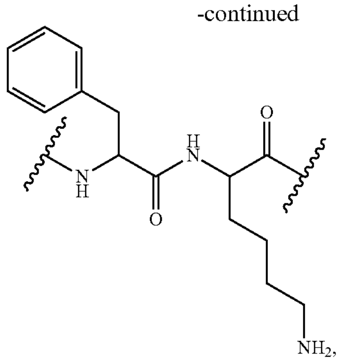

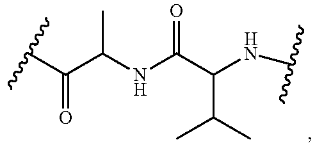

, or

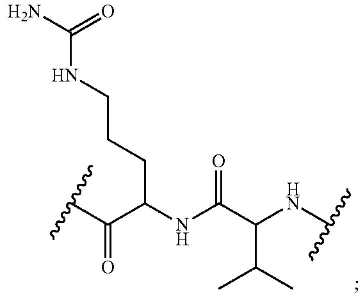

;

$X_3$ is

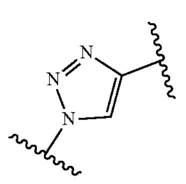

or

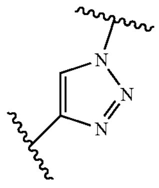

$X_4$ is

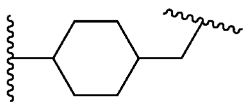

wherein $R^{13}$ is independently selected for each occasion from H and $C_1$-$C_6$ alkyl;

m is independently selected for each occasion from 1, 2, 3, 4, 5, 6, 7, 8, 9 and 10;

n is independently selected for each occasion from 1, 2, 3, 4, 5, 6, 7, 8, 9, 10, 11, 12, 13 and 14; and wherein the single asterisk (*) indicates the attachment point to the cytotoxin (e.g., an amatoxin), and the double asterisk (**) indicates the attachment point to the reactive substituent Z' or chemical moiety Z, with the proviso that L1 and $L_2$ are not both absent.

In some embodiments, the linker includes a p-aminobenzyl group (PAB). In one embodiment, the p-aminobenzyl group is disposed between the cytotoxic drug and a protease cleavage site in the linker. In one embodiment, the p-aminobenzyl group is part of a p-aminobenzyloxycarbonyl unit. In one embodiment, the p-aminobenzyl group is part of a p-aminobenzylamido unit.

In some embodiments, the linker comprises PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a combination of one or more of a peptide, oligosaccharide, $—(CH_2)_p—$, $—(CH_2CH_2O)_p—$, PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker includes $—((CH_2)_n$ where n is 6. In some embodiments, L-Z is

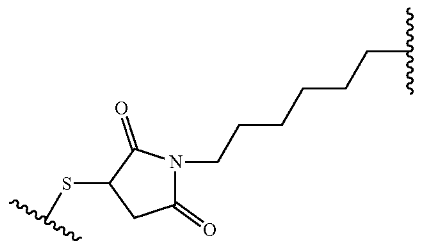

where S is a sulfur atom which represents the reactive substituent present within an antibody, or antigen-binding fragment thereof, In some embodiments, the linker comprises a $—(C{=}O)(CH_2)_p—$ unit, wherein p is an integer from 1-6.

In one specific embodiment, the linker comprises the structure

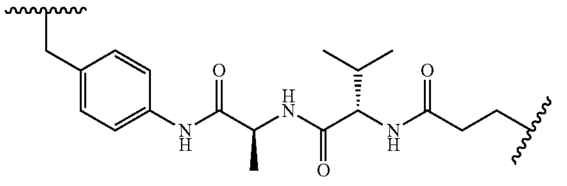 [SMILES: *CCC(=O)N[C@H](C(=O)N[C@@H](C)C(=O)Nc1ccc(C*)cc1)C(C)C]

wherein the wavy lines indicate attachment points to the cytotoxin and the reactive moiety Z'. In another specific embodiment, the linker comprises the structure

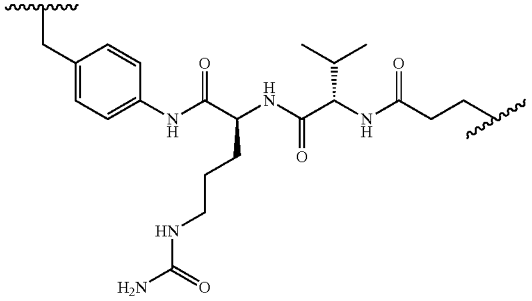 [SMILES: *CCC(=O)N[C@H](C(=O)N[C@@H](CCCNC(N)=O)C(=O)Nc1ccc(C*)cc1)C(C)C]

wherein the wavy lines indicate attachment points to the cytotoxin and the reactive moiety Z'. Such PAB-dipeptide-propionyl linkers are disclosed in, e.g., Patent Application Publication No. WO2017/149077, which is incorporated by reference herein in its entirety. Further, the cytotoxins disclosed in WO2017/149077 are incorporated by reference herein.

In certain embodiments, the linker of the ADC is maleimidocaproyl-Val-Ala-para-aminobenzyl (mc-Val-Ala-PAB).

In certain embodiments, the linker of the ADC is maleimidocaproyl-Val-Cit-para-aminobenzyl (mc-vc-PAB).

In some embodiments, the linker comprises

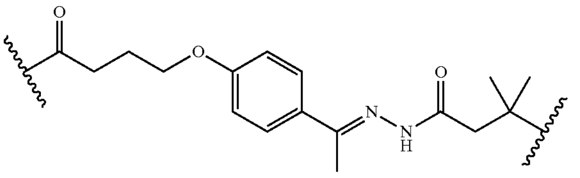 [SMILES: *C(=O)CCCOc1ccc(/C(C)=N/NC(=O)CC(*)(C)C)cc1]

In some embodiments, the linker comprises MCC (4-[N-maleimidomethyl]cyclohexane-1-carboxylate).

In some embodiments, the linker comprises a $((CH_2)_mO)_n(CH_2)_m—$ group where n and m are each independently selected from 1, 2, 3, 4, 5, 6, 7, 8, 9, and 10; and a heteroaryl group, wherein the heteroaryl group is a triazole. In some embodiments, the $((CH_2)_mO)_n(CH_2)_m—$ group and triazole together comprise

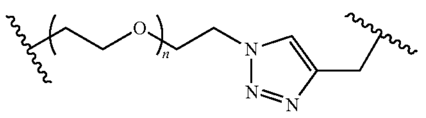

where n is from 1 to 10, and the wavy lines indicate attachment points to additional linker components, the chemical moiety Z, or the amatoxin. Other linkers that may be used in the methods and compositions described herein are described in US 2019/0144504, which is incorporated by reference herein.

It will be recognized by one of skill in the art that any one or more of the chemical groups, moieties and features disclosed herein may be combined in multiple ways to form linkers useful for conjugation of the antibodies and cytotoxins as disclosed herein. Further linkers useful in conjunction with the compositions and methods described herein, are described, for example, in U.S. Patent Application Publication No. 2015/0218220, the disclosure of which is incorporated herein by reference in its entirety.

In certain embodiments, an intermediate, which is the precursor of the linker, is reacted with the drug moiety under appropriate conditions. In certain embodiments, reactive groups are used on the drug and/or the intermediate or linker. The product of the reaction between the drug and the intermediate, or the derivatized drug, is subsequently reacted with the antibody or antigen-binding fragment under appropriate conditions. Alternatively, the linker or intermediate may first be reacted with the antibody or a derivatized antibody, and then reacted with the drug or derivatized drug. Such conjugation reactions will now be described more fully.

A number of different reactions are available for covalent attachment of linkers or drug-linker conjugates to the antibody or antigen-binding fragment thereof. Suitable attachment points on the antibody molecule include the amine groups of lysine, the free carboxylic acid groups of glutamic acid and aspartic acid, the sulfhydryl groups of cysteine, and the various moieties of the aromatic amino acids. For instance, non-specific covalent attachment may be undertaken using a carbodiimide reaction to link a carboxy (or amino) group on a compound to an amino (or carboxy) group on an antibody moiety. Additionally, bifunctional agents such as dialdehydes or imidoesters may also be used to link the amino group on a compound to an amino group on an antibody moiety. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates may also be used as coupling agents for covalently attaching drugs to binding agents. Other techniques are known to the skilled artisan and within the scope of the present disclosure.

Linkers useful in for conjugation to the antibodies or antigen-binding fragments as described herein include, without limitation, linkers containing chemical moieties Z formed by coupling reactions as depicted in Table 1, below. Curved lines designate points of attachment to the antibody or antigen-binding fragment, and the cytotoxic molecule, respectively.

TABLE 1

Exemplary chemical moieties Z formed by coupling reactions in the formation of antibody-drug conjugates

| Exemplary Coupling Reactions | Chemical Moiety Z Formed by Coupling Reactions |
|---|---|
| [3 + 2] Cycloaddition | 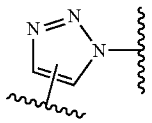 |
| [3 + 2] Cycloaddition | 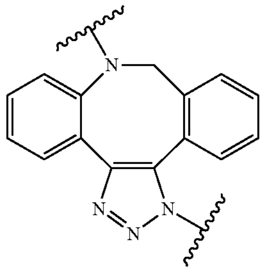 [SMILES: *N1Cc2ccccc2-c2c(nnn2*)-c2ccccc21] |
| [3 + 2] Cycloaddition, Esterification | 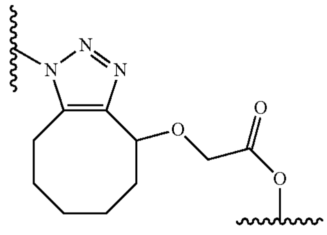 [SMILES: *OC(=O)COC1CCCCCc2c1nnn2*] |
| [3 + 2] Cycloaddition, Esterification | 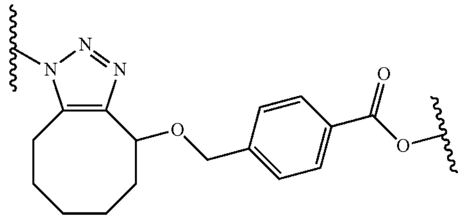 [SMILES: *OC(=O)c1ccc(COC2CCCCCc3c2nnn3*)cc1] |
| [3 + 2] Cycloaddition, Esterification | 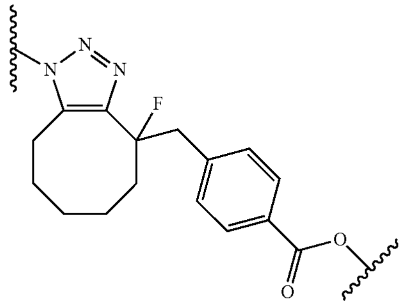 |

TABLE 1-continued

Exemplary chemical moieties Z formed by coupling reactions in the formation of antibody-drug conjugates

| Exemplary Coupling Reactions | Chemical Moiety Z Formed by Coupling Reactions |
| --- | --- |
| [3 + 2] Cycloaddition, Esterification | 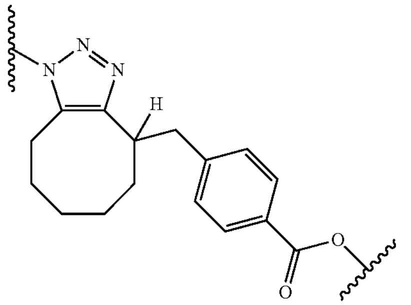 [SMILES: *OC(=O)c1ccc(CC2(F)CCCCCc3c2nnn3*)cc1] |
| [3+ 2] Cycloaddition, Esterification | 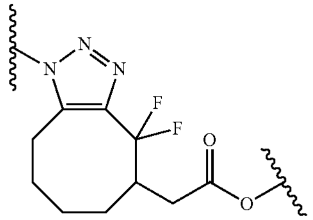 [SMILES: *OC(=O)CC1CCCCc2c(nnn2*)C1(F)F] |
| [3 + 2] Cycloaddition, Esterification | 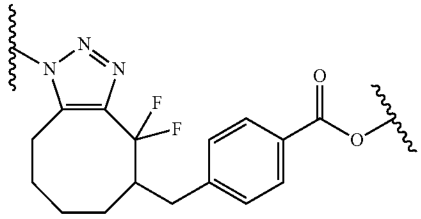 [SMILES: *OC(=O)c1ccc(CC2CCCCc3c(nnn3*)C2(F)F)cc1] |
| [3 + 2] Cycloaddition, Esterification | 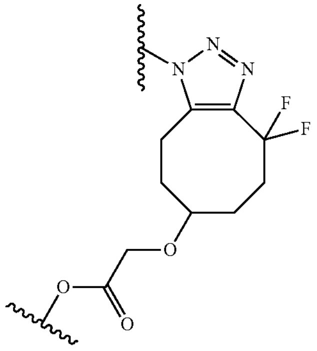 [SMILES: *OC(=O)COC1CCc2c(nnn2*)C(F)(F)CC1] |
| [3 + 2] Cycloaddition, Esterification | 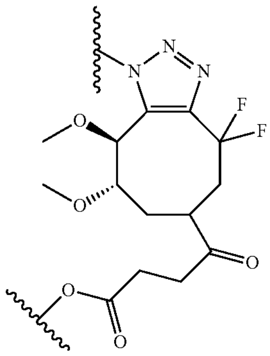 [SMILES: *OC(=O)CCC(=O)C1C[C@H](OC)[C@@H](OC)c2c(nnn2*)C(F)(F)C1] |

TABLE 1-continued
| Exemplary chemical moieties Z formed by coupling reactions in the formation of antibody-drug conjugates | |
|---|---|
| Exemplary Coupling Reactions | Chemical Moiety Z Formed by Coupling Reactions |
| [3 + 2] Cycloaddition, Esterification | 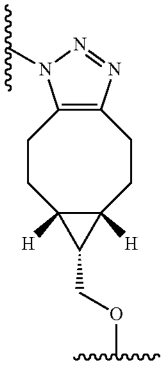 [SMILES: *OC[C@@H]1[C@@H]2CCc3c(nnn3*)CC[C@@H]21] |
| [3 + 2] Cycloaddition, Esterification | 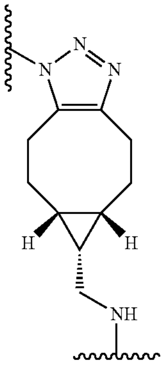 [SMILES: *NC[C@@H]1[C@@H]2CCc3c(nnn3*)CC[C@@H]21] |
| [3 + 2] Cycloaddition, Esterification | 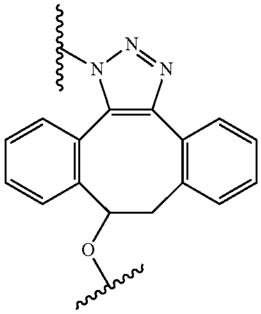 [SMILES: *OC1Cc2ccccc2-c2nnn(*)c2-c2ccccc21] |
| [3 + 2] Cycloaddition, Etherification | 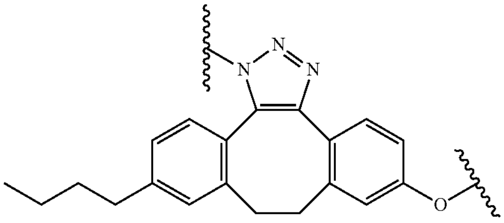 [SMILES: *Oc1ccc2c(c1)CCc1cc(CCCC)ccc1-c1c-2nnn1*] |

TABLE 1-continued

Exemplary chemical moieties Z formed by coupling reactions in the formation of antibody-drug conjugates

| Exemplary Coupling Reactions | Chemical Moiety Z Formed by Coupling Reactions |
| --- | --- |
| [3 + 2] Cycloaddition | 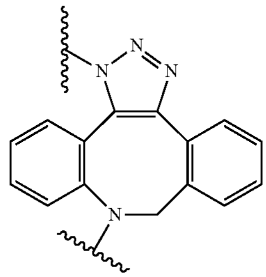 [SMILES: *N1Cc2ccccc2-c2nnn(*)c2-c2ccccc21] |
| Michael addition | 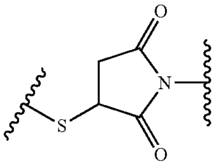 [SMILES: *SC1CC(=O)N(*)C1=O] |
| Michael addition | 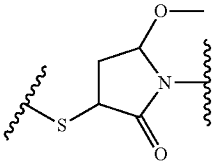 [SMILES: *SC1CC(OC)N(*)C1=O] |
| Imine condensation, Amidation | 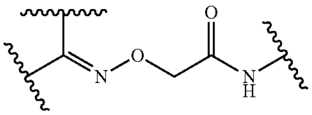 [SMILES: *NC(=O)CON=C(*)*] |
| Imine condensation | 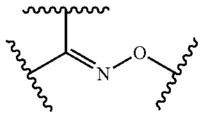 [SMILES: *ON=C(*)*] |
| Disulfide formation | 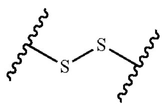 [SMILES: *SS*] |
| Thiol alkylation | 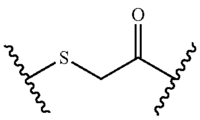 [SMILES: *SCC(*)=O] |
| Condensation, Michael addition | 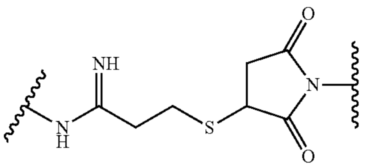 [SMILES: *NC(=N)CCSC1CC(=O)N(*)C1=O] |

One of skill in the art will recognize that a reactive substituent Z'attached to the linker and a reactive substituent on the antibody or antigen-binding fragment thereof, are engaged in the covalent coupling reaction to produce the chemical moiety Z, and will recognize the reactive moiety Z'. Therefore, antibody-drug conjugates useful in conjunction with the methods described herein may be formed by the reaction of an antibody, or antigen-binding fragment thereof, with a linker or cytotoxin-linker conjugate, as described herein, the linker or cytotoxin-linker conjugate including a reactive substituent Z', suitable for reaction with a reactive substituent on the antibody, or antigen-binding fragment thereof, to form the chemical moiety Z.

In some embodiments, Z' is $—NR^{13}C(═O)CH═CH_2$, $—N_3$, —SH, $—S(═O)_2(CH═CH_2)$, $—(CH_2)_2S(═O)_2(CH═CH_2)$, $—NR^{13}S(═O)_2(CH═CH_2)$, $—NR^{13}C(═O)CH_2R^{14}$, $—NR^{13}C(═O)CH_2Br$, $—NR^{13}C(═O)CH_2I$, $—NHC(═O)CH_2Br$, $—NHC(═O)CH_2I$, $—ONH_2$, $—C(O)NHNH_2$, $—CO_2H$, $—NH_2$, —NH(C═O), —NC(═S),
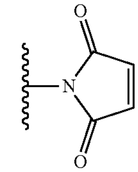,
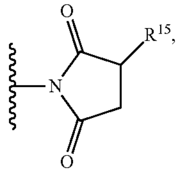
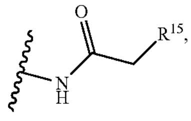
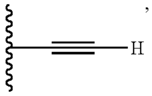,
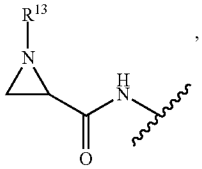,
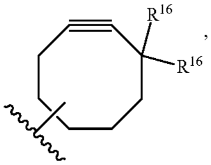,
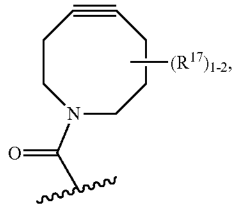
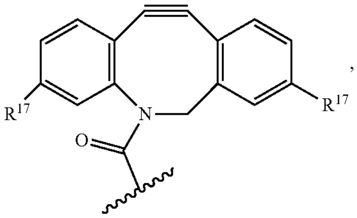,
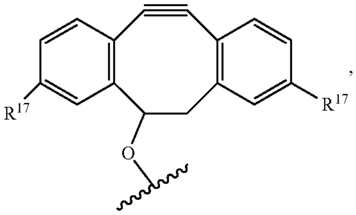,
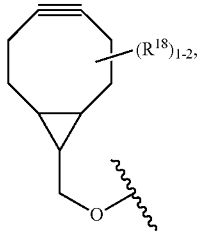
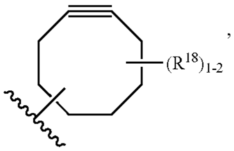,
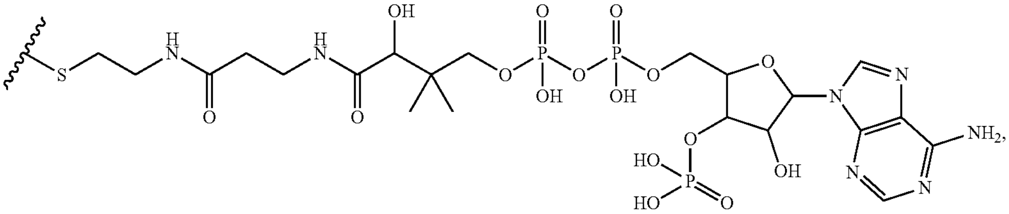
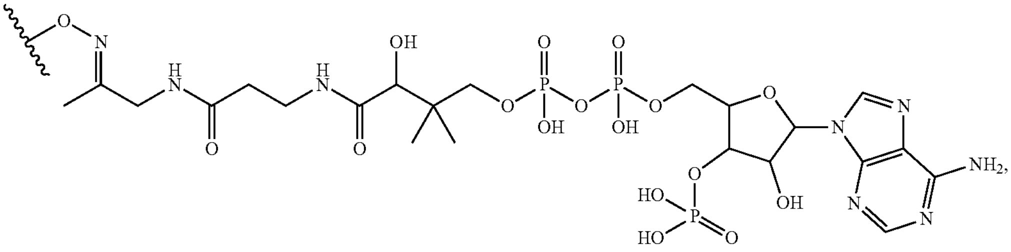
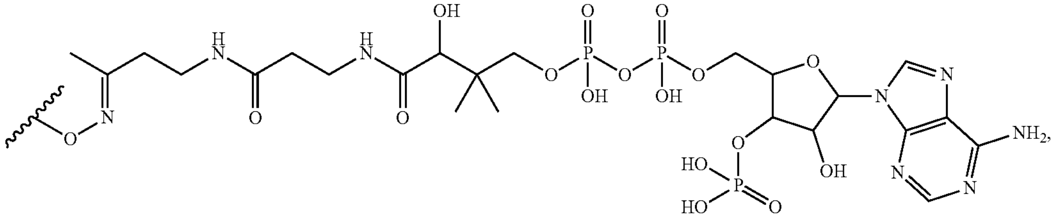
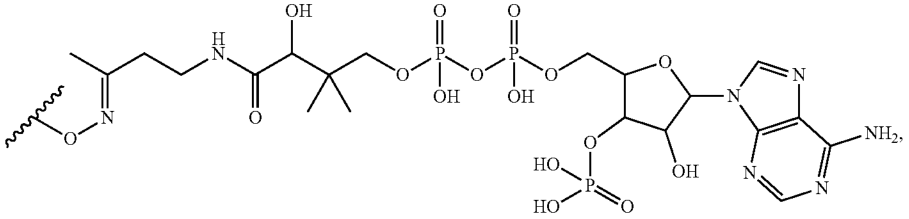

-continued

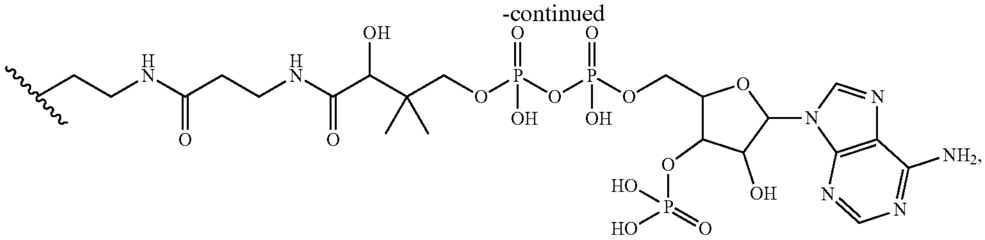

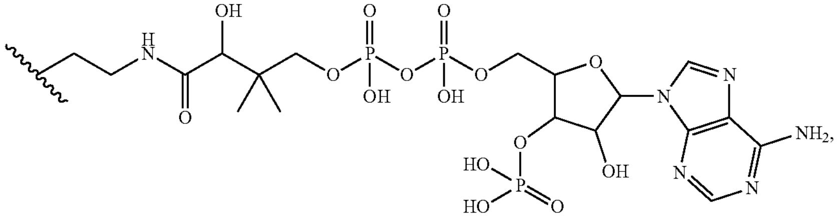

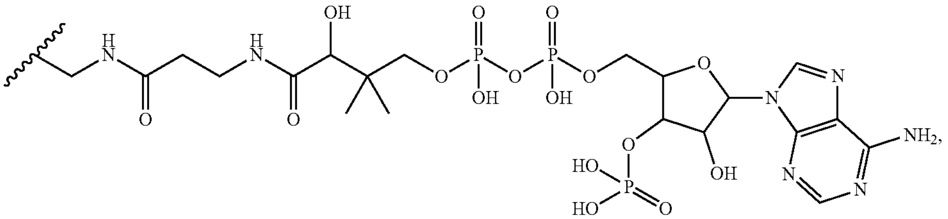

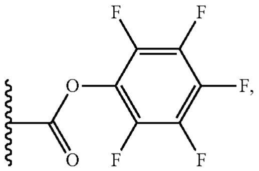

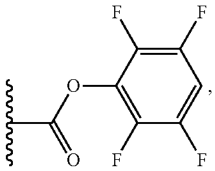
,
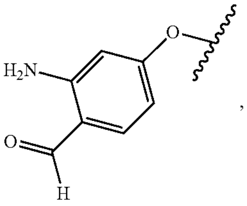
,
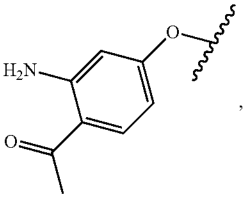
,
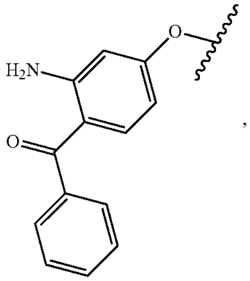
,
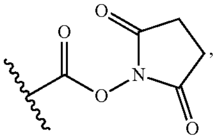
, or
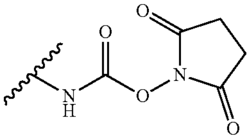

wherein $R^{13}$ is independently selected for each occasion from H and $C_1$-$C_6$ alkyl;

$R^{14}$ is —$S(CH_2)_nCHR^{15}NHC({=}O)R^{13}$;

$R^{15}$ is $R^{13}$ or —$C({=}O)OR^{13}$;

$R^{16}$ is independently selected for each occasion from H, $C_1$-$C_6$ alkyl, F, Cl, and —OH;

$R^{17}$ is independently selected for each occasion from H, $C_1$-$C_6$ alkyl, F, $C_1$, —$NH_2$, —$OCH_3$, —$OCH_2CH_3$, —$N(CH_3)_2$, —CN, —$NO_2$ and —OH; and $R^{18}$ is independently selected for each occasion from H, $C_1$-$C_6$ alkyl, F, benzyloxy substituted with —C(═O)OH, benzyl substituted with —C(═O)OH, $C_1$-$C_4$ alkoxy substituted with —C(═O)OH, and $C_1$-$C_4$ alkyl substituted with —C(═O)OH.

Examples of suitably reactive substituents on the linker and antibody or antigen-binding fragment thereof include a nucleophile/electrophile pair (e.g., a thiol/haloalkyl pair, an amine/carbonyl pair, or a thiol/α,β-unsaturated carbonyl pair, and the like), a diene/dienophile pair (e.g., an azide/alkyne pair, or a diene/α,β-unsaturated carbonyl pair, among others), and the like. Coupling reactions between the reactive substituents to form the chemical moiety Z include, without limitation, thiol alkylation, hydroxyl alkylation, amine alkylation, amine or hydroxylamine condensation, hydrazine formation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein. Preferably, the linker contains an electrophilic functional group for reaction with a nucleophilic functional group on the antibody, or antigen-binding fragment thereof.

Reactive substituents that may be present within an antibody, or antigen-binding fragment thereof, as disclosed herein include, without limitation, nucleophilic groups such as (i)N-terminal amine groups, (ii) side chain amine groups, e.g. lysine, (iii) side chain thiol groups, e.g. cysteine, and (iv) sugar hydroxyl or amino groups where the antibody is glycosylated. Reactive substituents that may be present within an antibody, or antigen-binding fragment thereof, as disclosed herein include, without limitation, hydroxyl moieties of serine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids. In some embodiments, the reactive substituents present within an antibody, or antigen-binding fragment thereof as disclosed herein include, are amine or thiol moieties. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

In some embodiments, the reactive moiety Z'attached to the linker is a nucleophilic group which is reactive with an electrophilic group present on an antibody. Useful electrophilic groups on an antibody include, but are not limited to, aldehyde and ketone carbonyl groups. The heteroatom of a nucleophilic group can react with an electrophilic group on an antibody and form a covalent bond to the antibody. Useful nucleophilic groups include, but are not limited to, hydrazide, oxime, amino, hydroxyl, hydrazine, thiosemicarbazone, hydrazine carboxylate, and arylhydrazide.

In some embodiments, Z is the product of a reaction between reactive nucleophilic substituents present within the antibodies, or antigen-binding fragments thereof, such as amine and thiol moieties, and a reactive electrophilic substituent Z'. For instance, Z' may be a Michael acceptor (e.g., maleimide), activated ester, electron-deficient carbonyl compound, and aldehyde, among others.

For instance, linkers suitable for the synthesis of ADCs include, without limitation, reactive substituents Z' such as maleimide or haloalkyl groups. These may be attached to the linker by reagents such as succinimidyl 4-(N-maleimidomethyl)-cyclohexane-L-carboxylate (SMCC), N-succinimidyl iodoacetate (SIA), sulfo-SMCC, m-maleimidobenzoyl-N-hydroxysuccinimidyl ester (MBS), sulfo-MBS, and succinimidyl iodoacetate, among others described, in for instance, Liu et al., 18:690-697, 1979, the disclosure of which is incorporated herein by reference as it pertains to linkers for chemical conjugation.

In some embodiments, the reactive substituent Z'attached to linker L is a maleimide, azide, or alkyne. An example of a maleimide-containing linker is the non-cleavable maleimidocaproyl-based linker, which is particularly useful for the conjugation of microtubule-disrupting agents such as auristatins. Such linkers are described by Doronina et al., Bioconjugate Chem. 17:14-24, 2006, the disclosure of which is incorporated herein by reference as it pertains to linkers for chemical conjugation.

In some embodiments, the reactive substituent Z' is —(C═O)— or —NH(C═O)—, such that the linker may be joined to the antibody, or antigen-binding fragment thereof, by an amide or urea moiety, respectively, resulting from reaction of the —(C═O)— or —NH(C═O)— group with an amino group of the antibody or antigen-binding fragment thereof.

In some embodiments, the reactive substituent is an N-maleimidyl group, halogenated N-alkylamido group, sulfonyloxy N-alkylamido group, carbonate group, sulfonyl halide group, thiol group or derivative thereof, alkynyl group comprising an internal carbon-carbon triple bond, (het-ero)cycloalkynyl group, bicyclo[6.1.0]non-4-yn-9-yl group, alkenyl group comprising an internal carbon-carbon double bond, cycloalkenyl group, tetrazinyl group, azido group, phosphine group, nitrile oxide group, nitrone group, nitrile imine group, diazo group, ketone group, (O-alkyl) hydroxylamino group, hydrazine group, halogenated N-maleimidyl group, 1,1-bis (sulfonylmethyl)methylcarbonyl group or elimination derivatives thereof, carbonyl halide group, or an allenamide group, each of which may be optionally substituted. In some embodiments, the reactive substituent comprises a cycloalkene group, a cycloalkyne group, or an optionally substituted (hetero)cycloalkynyl group.

Non-limiting examples of amatoxin-linker conjugates containing a reactive substituent Z'suitable for reaction with a reactive residue on the antibody or antigen-binding fragment thereof include, without limitation, 7'C-(4-(6-(maleimido)hexanoyl)piperazin-1-yl)-amatoxin; 7'C-(4-(6-(maleimido)hexanamido)piperidin-1-yl)-amatoxin; 7'C-(4-(6-(6-(maleimido)hexanamido)hexanoyl)piperazin-1-yl)-amatoxin; 7'C-(4-(4-((maleimido)methyl)cyclohexanecarbonyl)piperazin-1-yl)-amatoxin; 7'C-(4-(6-(4-((maleimido)methyl)cyclohexanecarboxamido)hexanoyl)piperazin-1-yl)-amatoxin; 7'C-(4-(2-(6-(maleimido)hexanamido)ethyl)piperidin-1-yl)-amatoxin; 7'C-(4-(2-(6-(6-(maleimido)hexanamido)hexanamido)ethyl)piperidin-1-yl)-amatoxin; 7'C-(4-(2-(4-((maleimido)methyl)cyclohexanecarboxamido)ethyl)piperidin-1-yl)-amatoxin; 7'C-(4-(2-(6-(4-((maleimido)methyl)cyclohexanecarboxamido)hexanamido)ethyl)piperidin-1-yl)-amatoxin; 7'C-(4-(2-(3-carboxypropanamido)ethyl)piperidin-1-yl)-amatoxin; 7'C-(4-(2-(2-bromoacetamido)ethyl)piperidin-1-yl)-amatoxin; 7'C-(4-(2-(3-(pyridin-2-yldisulfanyl)propanamido)ethyl)piperidin-1-yl)-amatoxin; 7'C-(4-(2-(4-(maleimido)butanamido)ethyl)piperidin-1-yl)-amatoxin; 7'C-(4-(2-(maleimido)acetyl)piperazin-1-yl)-amatoxin; 7'C-(4-(3-(maleimido)propanoyl)piperazin-1-yl)-amatoxin; 7'C-(4-(4-(maleimido)butanoyl)piperazin-1-yl)-amatoxin; 7'C-(4-(2-(6-(4-((maleimido)methyl)cyclohexanecarboxamido)hexanamido)ethyl)piperidin-1-yl)-amatoxin; 7'C-(3-((6-(maleimido)hexanamido)methyl)pyrrolidin-1-yl)-amatoxin; 7'C-(3-((6-(6-(maleimido)hexanamido)hexanamido)methyl)pyrrolidin-1-yl)-amatoxin; 7'C-(3-((4-((maleimido)methyl)cyclohexanecarboxamido)methyl)pyrrolidin-1-yl)-amatoxin; 7'C-(3-((6-((4-(maleimido)methyl)cyclohexanecarboxamido)hexanamido)methyl)pyrrolidin-1-yl)-amatoxin; 7'C-(4-(2-(6-(2-(aminooxy)acetamido)hexanamido)ethyl)piperidin-1-yl)-amatoxin; 7'C-(4-(2-(4-(2-(aminooxy)acetamido)butanamido)ethyl)piperidin-1-yl)-amatoxin; 7'C-(4-(4-(2-(aminooxy)acetamido)butanoyl)piperazin-1-yl)-amatoxin; 7'C-(4-(6-(2-(aminooxy)acetamido)hexanoyl)piperazin-1-yl)-amatoxin; 7'C-((4-(6-(maleimido)hexanamido)piperidin-1-yl)methyl)-amatoxin; 7'C-((4-(2-(6-(maleimido)hexanamido)ethyl)piperidin-1-yl)methyl)-amatoxin; 7'C-((4-(6-(maleimido)hexanoyl)piperazin-1-yl)methyl)-amatoxin; (R)-7'C-((3-((6-(maleimido)hexanamido)methyl)pyrrolidin-1-yl)methyl)-amatoxin; (S)-7'C-((3-((6-(maleimido)hexanamido)methyl)pyrrolidin-1- yl)methyl)-amatoxin; 7'C-((4-(2-(6-(6-(maleimido)hexanamido)hexanamido)ethyl)piperidin-1-yl)methyl)-amatoxin; 7'C-((4-(2-(4-((maleimido)methyl)cyclohexanecarboxamido)ethyl)piperidin-1-yl)methyl)-amatoxin; 7'C-((4-(2-(6-(4-((maleimido)methyl)cyclohexanecarboxamido)hexanamido)ethyl)piperidin-1-yl)methyl)-amatoxin; 7'C-((4-(2-(6-(maleimido)hexanamido)ethyl)piperazin-1-yl)methyl)-amatoxin; 7'C-((4-(2-(6-(6-(maleimido)hexanamido)hexanamido)ethyl)piperazin-1-yl)methyl)-amatoxin; 7'C-((4-(2-(4-((maleimido)methyl)cyclohexanecarboxamido)ethyl)piperazin-1-yl)methyl)-amatoxin; 7'C-((4-(2-(6-(4-((maleimido)methyl)cyclohexanecarboxamido)hexanamido)ethyl)piperazin-1-yl)methyl)-amatoxin; 7'C-((3-((6-(6-(maleimido)hexanamido)hexanamido)-S-methyl)pyrrolidin-1-yl)methyl)-amatoxin; 7'C-((3-((6-(6-(maleimido)hexanamido)hexanamido)-R-methyl)pyrrolidin-1-yl)methyl)-amatoxin; 7'C-((3-((4-((maleimido)methyl)cyclohexanecarboxamido)-S-methyl)pyrrolidin-1-yl)methyl)-amatoxin; 7'C-((3-((4-((maleimido)methyl)cyclohexanecarboxamido)-R-methyl)pyrrolidin-1-yl)methyl)-amatoxin; 7'C-((3-((6-(4-((maleimido)methyl)cyclohexanecarboxamido)hexanamido)methyl)pyrrolidin-1-yl)methyl)-amatoxin; 7'C-((4-(2-(3-carboxypropanamido)ethyl)piperazin-1-yl)methyl)-amatoxin; 7'C-((4-(6-(6-(maleimido)hexanamido)hexanoyl)piperazin-1-yl)methyl)-amatoxin; 7'C-((4-(6-(4-((maleimido)methyl)cyclohexanecarboxamido)hexanoyl)piperazin-1-yl)methyl)-amatoxin; 7'C-((4-(2-(maleimido)acetyl)piperazin-1-yl)methyl)-amatoxin; 7'C-((4-(3-(maleimido)propanoyl)piperazin-1-yl)methyl)-amatoxin; 7'C-((4-(4-(maleimido)butanoyl)piperazin-1-yl)methyl)-amatoxin; 7'C-((4-(2-(2-(maleimido)acetamido)ethyl)piperidin-1-yl)methyl)-amatoxin; 7'C-((4-(2-(4-(maleimido)butanamido)ethyl)piperidin-1-yl)methyl)-amatoxin; 7'C-((4-(2-(6-(4-((maleimido)methyl)cyclohexanecarboxamido)hexanamido)ethyl)piperidin-1-yl)methyl)-amatoxin; 7'C-((3-((6-(maleimido)hexanamido)methyl)azetidin-1-yl)methyl)-amatoxin; 7'C-((3-(2-(6-(maleimido)hexanamido)ethyl)azetidin-1-yl)methyl)-amatoxin; 7'C-((3-((4-((maleimido)methyl)cyclohexanecarboxamido)methyl)azetidin-1-yl)methyl)-amatoxin; 7'C-((3-(2-(4-((maleimido)methyl)cyclohexanecarboxamido)ethyl)azetidin-1-yl)methyl)-amatoxin; 7'C-((3-(2-(6-(4-((maleimido)methyl)cyclohexanecarboxamido)hexanamido)ethyl)azetidin-1-yl)methyl)-amatoxin; 7'C-(((2-(6-(maleimido)-N-methylhexanamido)ethyl)(methyl)amino)methyl)-amatoxin; 7'C-(((4-(6-(maleimido)-N-methylhexanamido)butyl(methyl)amino)methyl)-amatoxin; 7'C-((2-(2-(6-(maleimido)hexanamido)ethyl)aziridin-1-yl)methyl)-amatoxin; 7'C-((2-(2-(6-(4-((maleimido)methyl)cyclohexanecarboxamido)hexanamido)ethyl)aziridin-1-yl)methyl)-amatoxin; 7'C-((4-(6-(6-(2-(aminooxy)acetamido)hexanamido)hexanoyl)piperazin-1-yl)methyl)-amatoxin; 7'C-((4-(1-(aminooxy)-2-oxo-6,9,12,15-tetraoxa-3-azaheptadecan-17-oyl)piperazin-1-yl)methyl)-amatoxin; 7'C-((4-(2-(2-(aminooxy)acetamido)acetyl)piperazin-1-yl)methyl)-amatoxin; 7'C-((4-(3-(2-(aminooxy)acetamido)propanoyl)piperazin-1-yl)methyl)-amatoxin; 7'C-((4-(4-(2-(aminooxy)acetamido)butanoyl)piperazin-1-yl)methyl)-amatoxin; 7'C-((4-(2-(6-(2-(aminooxy)acetamido)hexanamido)ethyl)piperidin-1-yl)methyl)-amatoxin; 7'C-((4-(2-(2-(2-(aminooxy)acetamido)acetamido)ethyl)piperidin-1-yl)methyl)-amatoxin; 7'C-((4-(2-(4-(2-(aminooxy)acetamido)butanamido)ethyl)piperidin-1-yl)methyl)-amatoxin; 7'C-((4-(20-(aminooxy)-4,19-dioxo-6,9,12,15-tetraoxa-3,18-diazaicosyl)piperidin-1-yl)methyl)-amatoxin; 7'C-(((2-(6-(2-(aminooxy)acetamido)-N-methylhexanamido)ethyl)(methyl)amino)methyl)-amatoxin; 7'C-(((4-(6-(2-(aminooxy)acetamido)-N-methylhexanamido)butyl)(methyl)amino)methyl)-amatoxin; 7'C-((3-((6-(4-((maleimido)methyl)cyclohexanecarboxamido)hexanamido)methyl)pyrrolidin-1-yl)-S-methyl)-amatoxin; 7'C-((3-((6-(4-((maleimido)methyl)cyclohexanecarboxamido)hexanamido)-R-methyl)pyrrolidin-1-yl)methyl)-amatoxin; 7'C-((4-(2-(2-bromoacetamido)ethyl)piperazin-1-yl)methyl)-amatoxin; 7'C-((4-(2-(2-bromoacetamido)ethyl)piperidin-1-yl)methyl)-amatoxin; 7'C-((4-(2-(3-(pyridine-2-yldisulfanyl)propanamido)ethyl)piperidin-1-yl)methyl)-amatoxin; 6'O-(6-(6-(maleimido)hexanamido)hexyl)-amatoxin; 6'O-(5-(4-((maleimido)methyl)cyclohexanecarboxamido)pentyl)-amatoxin; 6'O-(2-((6-(maleimido)hexyl)oxy)-2-oxoethyl)-amatoxin; 6'O-((6-(maleimido)hexyl)carbamoyl)-amatoxin; 6'O-((6-(4-((maleimido)methyl)cyclohexanecarboxamido)hexyl)carbamoyl)-amatoxin; 6'O-(6-(2-bromoacetamido)hexyl)-amatoxin; 7'C-(4-(6-(azido)hexanamido)piperidin-1-yl)-amatoxin; 7'C-(4-(hex-5-ynoylamino)piperidin-1-yl)-amatoxin; 7'C-(4-(2-(6-(maleimido)hexanamido)ethyl)piperazin-1-yl)-amatoxin; 7'C-(4-(2-(6-(6-(maleimido)hexanamido)hexanamido)ethyl)piperazin-1-yl)-amatoxin; 6'O-(6-(6-(11,12-didehydro-5,6-dihydro-dibenz[b,f]azocin-5-yl)-6-oxohexanamido)hexyl)-amatoxin; 6'O-(6-(hex-5-ynoylamino)hexyl)-amatoxin; 6'O-(6-(2-(aminooxy)acetylamido)hexyl)-amatoxin; 6'O-((6-aminooxy)hexyl)-amatoxin; and 6'O-(6-(2-iodoacetamido)hexyl)-amatoxin.

In some embodiments, the chemical moiety Z is selected from Table 1. In some embodiments, the chemical moiety Z is

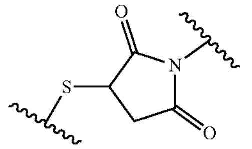

where S is a sulfur atom which represents the reactive substituent present within an antibody, or antigen-binding fragment thereof, that binds CD45 (e.g., from the —SH group of a cysteine residue).

In some embodiments, the linker-reactive substituent group structure L-Z', prior to conjugation with the antibody or antigen binding fragment thereof, is:

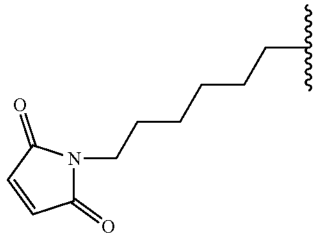

or

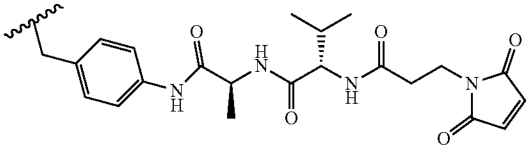

In some embodiments, an amatoxin as disclosed herein is conjugated to a linker-reactive moiety -L-Z'having the following formula:

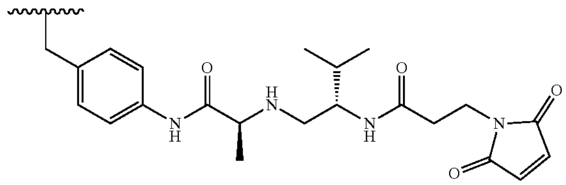 [SMILES: *Cc1ccc(NC(=O)[C@H](C)NC[C@@H](NC(=O)CCN2C(=O)C=CC2=O)C(C)C)cc1]

In some embodiments, an amatoxin as disclosed herein is conjugated to a linker-reactive moiety -L-Z'having the following formula:

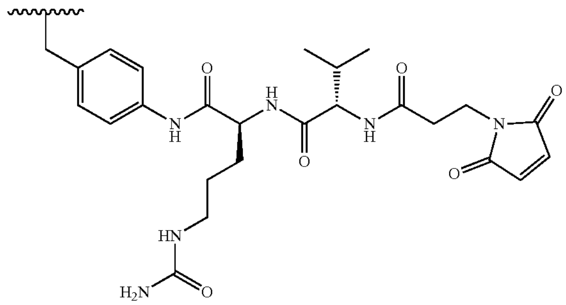 [SMILES: *Cc1ccc(NC(=O)[C@H](CCCNC(N)=O)NC(=O)[C@@H](NC(=O)CCN2C(=O)C=CC2=O)C(C)C)cc1]

The foregoing linker moieties and amatoxin-linker conjugates, among others useful in conjunction with the compositions and methods described herein, are described, for example, in U.S. Patent Application Publication No. 2015/0218220 and Patent Application Publication No. WO2017/149077, the disclosure of each of which is incorporated herein by reference in its entirety.

Preparation of Antibody-Drug Conjugates

In the ADCs as disclosed herein, an anti-CD45 antibody, or antigen binding fragment thereof, is conjugated to one or more cytotoxic drug moieties (D), e.g. about 1 to about 20 drug moieties per antibody, through a linker L and a chemical moiety Z as disclosed herein. The ADCs of the present disclosure may be prepared by several routes, employing organic chemistry reactions, conditions, and reagents known to those skilled in the art, including: (1) reaction of a reactive substituent of an antibody or antigen binding fragment thereof with a bivalent linker reagent to form Ab-Z-L as described herein above, followed by reaction with a drug moiety D; or (2) reaction of a reactive substituent of a drug moiety with a bivalent linker reagent to form D-L-Z', followed by reaction with a reactive substituent of an antibody or antigen binding fragment thereof as described herein above. Additional methods for preparing ADC are described herein.

In another aspect, the anti-CD45 antibody, or antigen binding fragment thereof, has one or more lysine residues that can be chemically modified to introduce one or more sulfhydryl groups. The ADC is then formed by conjugation through the sulfhydryl group's sulfur atom as described herein above. The reagents that can be used to modify lysine include, but are not limited to, N-succinimidyl S-acetylthioacetate (SATA) and 2-Iminothiolane hydrochloride (Traut's Reagent).

In another aspect, the anti-CD45 antibody, or antigen binding fragment thereof, can have one or more carbohydrate groups that can be chemically modified to have one or more sulfhydryl groups. The ADC is then formed by conjugation through the sulfhydryl group's sulfur atom as described herein above.

In yet another aspect, the anti-CD45 antibody can have one or more carbohydrate groups that can be oxidized to provide an aldehyde (—CHO) group (see, for e.g., Laguzza, et al., J. Med. Chem. 1989, 32(3), 548-55). The ADC is then formed by conjugation through the corresponding aldehyde as described herein above. Other protocols for the modification of proteins for the attachment or association of cytotoxins are described in Coligan et al., Current Protocols in Protein Science, vol. 2, John Wiley & Sons (2002), incorporated herein by reference.

Methods for the conjugation of linker-drug moieties to cell-targeted proteins such as antibodies, immunoglobulins or fragments thereof are found, for example, in U.S. Pat. Nos. 5,208,020; 6,441,163; WO2005037992; WO2005081711; and WO2006/034488, all of which are hereby expressly incorporated by reference in their entirety.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

ADCs described herein can be administered to a patient (e.g., a human patient suffering from an immune disease or cancer) in a variety of dosage forms. For instance, ADCs described herein can be administered to a patient suffering from an immune disease or cancer in the form of an aqueous solution, such as an aqueous solution containing one or more pharmaceutically acceptable excipients. Suitable pharmaceutically acceptable excipients for use with the compositions and methods described herein include viscosity-modifying agents. The aqueous solution may be sterilized using techniques known in the art.

Pharmaceutical formulations comprising anti-CD45 ADCs as described herein are prepared by mixing such ADC with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Therapeutic Uses

CD45 is an important cell surface molecule broadly expressed throughout the hematopoietic and immune systems. Described herein are anti-CD45 antibodies and anti-CD45 ADCs that can be used to treat patients with conditions for which depletion of CD45+ cells is beneficial, including, but not limited to, leukemias and lymphomas, as well as patients with autoimmune diseases such as multiple sclerosis and scleroderma. Further, there is currently a need for compositions and methods for promoting the engraftment of exogenous hematopoietic stem cell grafts such that the multi-potency and hematopoietic functionality of these cells is preserved following transplantation. The compositions and methods disclosed herein further provide a solution to this challenging problem.

By targeting CD45 with anti-CD45 antibodies, binding fragments thereof, and ADCs described herein, generally both hematopoietic stem cells (HSCs) and leukocytes can be depleted (CD45 is a pan leukocyte marker). Thus, in certain embodiments, provided herein is a method for providing an immune reset in a subject in need thereof. For example, by administering an anti-CD45 antibody or ADC described herein to a patient having a disease associated with disease causing leukocytes, e.g., an autoimmune disease, the disease causing leukocytes can be eliminated (along with the HSCs) and the patient can then build a new immune system from subsequently transplanted HSCs.

An additional benefit of the CD45 specific antibodies and ADCs described herein is that, as opposed to the non-targeted highly toxic chemotherapies, red blood cells should be unaffected in the patient given that red blood cells do not generally express CD45.

Thus, disclosed herein are methods of treating a variety of disorders, such as diseases of a cell type in the hematopoietic lineage, cancers, autoimmune diseases, metabolic disorders, and stem cell disorders, among others. The compositions and methods described herein may (i) directly deplete a population of cells that give rise to a pathology, such as a population of cancer cells (e.g., leukemia cells) and autoimmune cells (e.g., autoreactive T-cells), and/or (ii) deplete a population of endogenous hematopoietic stem cells so as to promote the engraftment of transplanted hematopoietic stem cells by providing a niche to which the transplanted cells may home. The foregoing activities can be achieved by administration of an anti-CD45 ADC, antibody, or antigen-binding fragment thereof, capable of binding an endogenous disease-causing cell or a hematopoietic stem cell. In the case of direct treatment of a disease, this administration can cause a reduction in the quantity of the cells that give rise to the pathology of interest. In the case of preparing a patient for hematopoietic stem cell transplant therapy, this administration can cause the selective depletion of a population of endogenous hematopoietic stem cells, thereby creating a vacancy in the hematopoietic tissue, such as the bone marrow, that can subsequently be filled by transplanted, exogenous hematopoietic stem cells. The ADCs, antibodies, or antigen-binding fragments thereof described herein, capable of binding CD45 can be administered to a patient to effect both of the above activities. ADCs, antibodies, or antigen-binding fragments thereof, that bind CD45 antigen expressed by immune cells, e.g., hematopoietic stem cells, can be administered to a patient suffering from a cancer or autoimmune disease to directly deplete a population of cancerous cells or autoimmune cells, and can also be administered to a patient in need of hematopoietic stem cell transplant therapy in order to promote the survival and engraftment potential of transplanted hematopoietic stem cells.

As described herein, hematopoietic stem cell transplant therapy can be administered to a subject in need of treatment so as to populate or re-populate one or more blood cell types. Hematopoietic stem cells generally exhibit multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Hematopoietic stem cells are additionally capable of self-renewal, and can thus give rise to daughter cells that have equivalent potential as the mother cell, and also feature the capacity to be reintroduced into a transplant recipient whereupon they home to the hematopoietic stem cell niche and re-establish productive and sustained hematopoiesis.

Hematopoietic stem cells can thus be administered to a patient defective or deficient in one or more cell types of the hematopoietic lineage in order to re-constitute the defective or deficient population of cells in vivo, thereby treating the pathology associated with the defect or depletion in the endogenous blood cell population. The compositions and methods described herein can thus be used to treat a non-malignant hemoglobinopathy (e.g., a hemoglobinopathy selected from the group consisting of sickle cell anemia, thalassemia, Fanconi anemia, aplastic anemia, and Wiskott-Aldrich syndrome). Additionally or alternatively, the compositions and methods described herein can be used to treat an immunodeficiency, such as a congenital immunodeficiency. Additionally or alternatively, the compositions and methods described herein can be used to treat an acquired immunodeficiency (e.g., an acquired immunodeficiency selected from the group consisting of HIV and AIDS). The compositions and methods described herein can be used to treat a metabolic disorder (e.g., a metabolic disorder selected from the group consisting of glycogen storage diseases, mucopolysaccharidoses, Gaucher's Disease, Hurlers Disease, sphingolipidoses, and metachromatic leukodystrophy).

Additionally or alternatively, the compositions and methods described herein can be used to treat a malignancy or proliferative disorder, such as a hematologic cancer, myeloproliferative disease. In the case of cancer treatment, the compositions and methods described herein may be administered to a patient so as to deplete a population of endogenous hematopoietic stem cells prior to hematopoietic stem cell transplantation therapy, in which case the transplanted cells can home to a niche created by the endogenous cell depletion step and establish productive hematopoiesis. This, in turn, can re-constitute a population of cells depleted during cancer cell eradication, such as during systemic chemotherapy. Exemplary hematological cancers that can be treated using the compositions and methods described herein include, without limitation, acute myeloid leukemia, acute lymphoid leukemia, chronic myeloid leukemia, chronic lymphoid leukemia, multiple myeloma, diffuse large B-cell lymphoma, and non-Hodgkin's lymphoma, as well as other cancerous conditions, including neuroblastoma.

Additional diseases that can be treated with the compositions and methods described herein include, without limitation, adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, multiple sclerosis, and juvenile rheumatoid arthritis.

The antibodies, or antigen-binding fragments thereof, and conjugates described herein may be used to induce solid organ transplant tolerance. For instance, the compositions and methods described herein may be used to deplete or ablate a population of cells from a target tissue (e.g., to deplete hematopoietic stem cells from the bone marrow stem cell niche). Following such depletion of cells from the target tissues, a population of stem or progenitor cells from an organ donor (e.g., hematopoietic stem cells from the organ donor) may be administered to the transplant recipient, and following the engraftment of such stem or progenitor cells, a temporary or stable mixed chimerism may be achieved, thereby enabling long-term transplant organ tolerance without the need for further immunosuppressive agents. For example, the compositions and methods described herein may be used to induce transplant tolerance in a solid organ transplant recipient (e.g., a kidney transplant, lung transplant, liver transplant, and heart transplant, among others). The compositions and methods described herein are well-suited for use in connection the induction of solid organ transplant tolerance, for instance, because a low percentage temporary or stable donor engraftment is sufficient to induce long-term tolerance of the transplanted organ.

In addition, the compositions and methods described herein can be used to treat cancers directly, such as cancers characterized by cells that are CD45+. For instance, the compositions and methods described herein can be used to treat leukemia, such as in patients that exhibit CD45+ leukemic cells. By depleting CD45+ cancerous cells, such as leukemic cells, the compositions and methods described herein can be used to treat various cancers directly.

Exemplary cancers that may be treated in this fashion include hematological cancers, such as acute myeloid leukemia, acute lymphoid leukemia, chronic myeloid leukemia, chronic lymphoid leukemia, multiple myeloma, diffuse large B-cell lymphoma, and non-Hodgkin's lymphoma, In addition, the compositions and methods described herein can be used to treat autoimmune disorders. For instance, an antibody, or antigen-binding fragment thereof, can be administered to a subject, such as a human patient suffering from an autoimmune disorder, so as to kill a CD45+ immune cell. For example, a CD45+ immune cell may be an autoreactive lymphocyte, such as a T-cell that expresses a T-cell receptor that specifically binds, and mounts an immune response against, a self antigen. By depleting self-reactive, CD45+, the compositions and methods described herein can be used to treat autoimmune pathologies, such as those described below. Additionally or alternatively, the compositions and methods described herein can be used to treat an autoimmune disease by depleting a population of endogenous hematopoietic stem cells prior to hematopoietic stem cell transplantation therapy, in which case the transplanted cells can home to a niche created by the endogenous cell depletion step and establish productive hematopoiesis. This, in turn, can reconstitute a population of cells depleted during autoimmune cell eradication.

Autoimmune diseases that can be treated using the compositions and methods described herein include, without limitation, psoriasis, psoriatic arthritis, Type 1 diabetes mellitus (Type 1 diabetes), rheumatoid arthritis (RA), human systemic lupus (SLE), multiple sclerosis (MS), inflammatory bowel disease (IBD), lymphocytic colitis, acute disseminated encephalomyelitis (ADEM), Addison's disease, alopecia universalis, ankylosing spondylitisis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, collagenous colitis, uveitis, vasculitis, vitiligo, vulvodynia ("vulvar vestibulitis"), and Wegener's granulomatosis.

In some embodiments, the transplant is allogeneic. In some embodiments, the transplant is autologous.

In some embodiments, the transplant is a bone marrow transplant, a peripheral blood transplant, or a cord blood transplant.

In some embodiments, the transplant includes hematopoietic cells (e.g., hematopoietic stem cells).

In any of the embodiments described herein, the transplant may be any solid organ or skin transplant. In some embodiments, the transplant is selected from the group consisting of kidney transplant, heart transplant, liver transplant, pancreas transplant, lung transplant, intestine transplant and skin transplant.

Antibodies, antigen-binding fragments thereof, or ADCs described herein can be administered to a patient (e.g., a human patient suffering from cancer, an autoimmune disease, or in need of hematopoietic stem cell transplant therapy) in a variety of dosage forms. For instance, antibodies, antigen-binding fragments thereof, or ADCs described herein can be administered to a patient suffering from cancer, an autoimmune disease, or in need of hematopoietic stem cell transplant therapy in the form of an aqueous solution, such as an aqueous solution containing one or more pharmaceutically acceptable excipients. Pharmaceutically acceptable excipients for use with the compositions and methods described herein include viscosity-modifying agents. The aqueous solution may be sterilized using techniques known in the art.

Pharmaceutical formulations comprising an anti-CD45 antibody, or conjugates thereof (e.g., ADCs as described herein) are prepared by mixing such antibody or ADC with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

The antibodies, antigen-binding fragments, or ADCs described herein may be administered by a variety of routes, such as orally, transdermally, subcutaneously, intranasally, intravenously, intramuscularly, intraocularly, or parenterally. The most suitable route for administration in any given case will depend on the particular antibody, or antigen-binding fragment, administered, the patient, pharmaceutical formulation methods, administration methods (e.g., administration time and administration route), the patient's age, body weight, sex, severity of the diseases being treated, the patient's diet, and the patient's excretion rate.

The effective dose of an antibody, or antigen-binding fragment thereof, described herein can range, for example from about 0.001 to about 100 mg/kg of body weight per single (e.g., bolus) administration, multiple administrations, or continuous administration, or to achieve an optimal serum concentration (e.g., a serum concentration of 0.0001-5000 μg/mL) of the antibody, or antigen-binding fragment thereof. The dose may be administered one or more times (e.g., 2-10 times) per day, week, or month to a subject (e.g., a human) suffering from cancer, an autoimmune disease, or undergoing conditioning therapy in preparation for receipt of a hematopoietic stem cell transplant. In the case of a conditioning procedure prior to hematopoietic stem cell transplantation, the antibody, or antigen-binding fragment thereof can be administered to the patient at a time that optimally promotes engraftment of the exogenous hematopoietic stem cells, for instance, from 1 hour to 1 week (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, or 7 days) or more prior to administration of the exogenous hematopoietic stem cell transplant.

Using the methods disclosed herein, a physician of skill in the art can administer to a human patient in need of hematopoietic stem cell transplant therapy an ADC, an antibody or an antigen-binding fragment thereof capable of binding CD45 expressed by hematopoietic stem cells. In this fashion, a population of endogenous hematopoietic stem cells can be depleted prior to administration of an exogenous hematopoietic stem cell graft so as to promote engraftment of the hematopoietic stem cell graft. The antibody may be covalently conjugated to a toxin, such as a cytotoxic molecule described herein or known in the art. For instance, an anti-CD45 antibody or antigen-binding fragment thereof can be covalently conjugated to a cytotoxin, such as pseudomonas exotoxin A, deBouganin, diphtheria toxin, an amatoxin, such as γ-amanitin, α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, an indolinobenzodiazepine dimer, or a variant thereof. This conjugation can be performed using covalent bond-forming techniques described herein or known in the art. The antibody, antigen-binding fragment thereof, or drug-antibody conjugate can subsequently be administered to the patient, for example, by intravenous administration, prior to transplantation of exogenous hematopoietic stem cells (such as autologous, syngeneic, or allogeneic hematopoietic stem cells) to the patient.

The anti-CD45 antibody, antigen-binding fragment thereof, or ADC can be administered in an amount sufficient to reduce the quantity of the target CD45 expressing cells. For example, the anti-CD45 antibody, antigen-binding fragment thereof, or ADC can be administered in an amount sufficient to reduce the quantity of endogenous CD45+ cells in the bone marrow and/or in the peripheral blood by, for example, about 10%, 20%, 30%, 40%, 50%, 60%, 70%, 80%, 90%, 95%, or more. In some embodiments, the anti-CD45 antibody, antigen-binding fragment thereof, or ADC can be administered in an amount sufficient to reduce the quantity of endogenous hematopoietic stem cells, for example, by 10%, 20%, 30%, 40%, 50%, 60%, 70%, 80%, 90%, 95%, or more prior to hematopoietic stem cell transplant therapy. The reduction in hematopoietic stem cell count can be monitored using conventional techniques known in the art, such as by FACS analysis of cells expressing characteristic hematopoietic stem cell surface antigens in a blood sample withdrawn from the patient at varying intervals during conditioning therapy. For instance, a physician of skill in the art can withdraw a blood sample from the patient at various time points during conditioning therapy and determine the extent of endogenous hematopoietic stem cell reduction by conducting a FACS analysis to elucidate the relative concentrations of hematopoietic stem cells in the sample using antibodies that bind to hematopoietic stem cell marker antigens. According to some embodiments, when the concentration of hematopoietic stem cells has reached a minimum value in response to conditioning therapy with an anti-CD45 antibody, antigen-binding fragment thereof, or ADC, the physician may conclude the conditioning therapy, and may begin preparing the patient for hematopoietic stem cell transplant therapy.

The anti-CD45 antibody, antigen-binding fragment thereof, or ADC can be administered to the patient in an aqueous solution containing one or more pharmaceutically acceptable excipients, such as a viscosity-modifying agent. The aqueous solution may be sterilized using techniques described herein or known in the art. The antibody, antigen-binding fragment thereof, or drug-antibody conjugate can be administered to the patient at a dosage of, for example, from 0.001 mg/kg to 100 mg/kg prior to administration of a hematopoietic stem cell graft to the patient. In one embodiment, the antibody, antigen-binding fragment thereof, or drug-antibody conjugate can be administered to the patient at a dosage of about 0.1 mg/kg to about 0.3 mg/kg. In one embodiment, the antibody, antigen-binding fragment thereof, or drug-antibody conjugate can be administered to the patient at a dosage of about 0.15 mg/kg to about 0.3 mg/kg. In one embodiment, the antibody, antigen-binding fragment thereof, or drug-antibody conjugate can be administered to the patient at a dosage of about 0.15 mg/kg to about 0.25 mg/kg. In one embodiment, the antibody, antigen-binding fragment thereof, or drug-antibody conjugate can be administered to the patient at a dosage of about 0.2 mg/kg to about 0.3 mg/kg. In one embodiment, the antibody, antigen-binding fragment thereof, or drug-antibody conjugate can be administered to the patient at a dosage of about 0.25 mg/kg to about 0.3 mg/kg. In some embodiments, the antibody, antigen-binding fragment thereof, or drug-antibody conjugate can be administered to the patient at a dosage of about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, or 1.0 mg/kg.

In other embodiments, the antibody, antigen-binding fragment thereof, or drug-antibody conjugate can be administered to the patient at a dosage of about 0.001 mg/kg to about 10 mg/kg, about 0.01 mg/kg to about 9.5 mg/kg, about 0.1 mg/kg to about 9 mg/kg, about 0.1 mg/kg to about 8.5 mg/kg, about 0.1 mg/kg to about 8 mg/kg, about 0.1 mg/kg to about 7.5 mg/kg, about 0.1 mg/kg to about 7 mg/kg, about 0.1 mg/kg to about 6.5 mg/kg, about 0.1 mg/kg to about 6 mg/kg, about 0.1 mg/kg to about 5.5 mg/kg, about 0.1 mg/kg to about 5 mg/kg, about 0.1 mg/kg to about 4.5 mg/kg, about 0.1 mg/kg to about 4 mg/kg, about 0.5 mg/kg to about 3.5 mg/kg, about 0.5 mg/kg to about 3 mg/kg, about 1 mg/kg to about 10 mg/kg, about 1 mg/kg to about 9 mg/kg, about 1 mg/kg to about 8 mg/kg, about 1 mg/kg to about 7 mg/kg, about 1 mg/kg to about 6 mg/kg, about 1 mg/kg to about 5 mg/kg, about 1 mg/kg to about 4 mg/kg, or about 1 mg/kg to about 3 mg/kg.

In certain embodiments, an anti-CD45 antibody, antigen-binding fragment thereof, or ADC described herein can be administered to the patient at a time that optimally promotes engraftment of the exogenous hematopoietic stem cells, for instance, from about 1 hour to about 1 week (e.g., about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, or 7 days) or more prior to administration of the exogenous hematopoietic stem cell transplant.

Following the conclusion of conditioning therapy, the patient may then receive an infusion (e.g., an intravenous infusion) of exogenous hematopoietic stem cells, such as from the same physician that performed the conditioning therapy or from a different physician. The physician may administer the patient an infusion of autologous, syngeneic, or allogeneic hematopoietic stem cells, for instance, at a dosage of from about $1\times10^3$ to about $1\times10^9$ hematopoietic stem cells/kg. The physician may monitor the engraftment of the hematopoietic stem cell transplant, for example, by withdrawing a blood sample from the patient and determining the increase in concentration of hematopoietic stem cells or cells of the hematopoietic lineage (such as megakaryocytes, thrombocytes, platelets, erythrocytes, mast cells, myeloblasts, basophils, neutrophils, eosinophils, microglia, granulocytes, monocytes, osteoclasts, antigen-presenting cells, macrophages, dendritic cells, natural killer cells, T-lymphocytes, and B-lymphocytes) following administration of the transplant. This analysis may be conducted, for example, from about 1 hour to about 6 months, or more, following hematopoietic stem cell transplant therapy (e.g., about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, or more). A finding that the concentration of hematopoietic stem cells or cells of the hematopoietic lineage has increased (e.g., by about 1%, 2%, 3%, 4%, 5%, 6%, 7%, 8%, 9%, 10%, 20%, 30%, 40%, 50%, 60%, 70%, 80%, 90%, 100%, 200%, 500%, or more) following the transplant therapy relative to the concentration of the corresponding cell type prior to transplant therapy provides one indication that treatment with the anti-CD45 antibody, or antigen-binding fragment thereof, or ADC has successfully promoted engraftment of the transplanted hematopoietic stem cell graft. The foregoing may also be used in therapies relating to CD45 cell; depletion, e.g., HSC and immune cell depletion for treatment of an autoimmune disease, or for treatment of a hematological cancer.

Engraftment of hematopoietic stem cell transplants due to the administration of an anti-CD45 antibody, antigen-binding fragments thereof, or ADCs, can manifest in a variety of empirical measurements. For instance, engraftment of transplanted hematopoietic stem cells can be evaluated by assessing the quantity of competitive repopulating units (CRU) present within the bone marrow of a patient following administration of an anti-CD45 antibody or antigen-binding fragment thereof, and subsequent administration of a hematopoietic stem cell transplant. Additionally, one can observe engraftment of a hematopoietic stem cell transplant by incorporating a reporter gene, such as an enzyme that catalyzes a chemical reaction yielding a fluorescent, chromophoric, or luminescent product, into a vector with which the donor hematopoietic stem cells have been transfected and subsequently monitoring the corresponding signal in a tissue into which the hematopoietic stem cells have homed, such as the bone marrow. One can also observe hematopoietic stem cell engraftment by evaluation of the quantity and survival of hematopoietic stem and progenitor cells, for instance, as determined by fluorescence activated cell sorting (FACS) analysis methods known in the art. Engraftment can also be determined by measuring white blood cell counts in peripheral blood during a post-transplant period, and/or by measuring recovery of marrow cells by donor cells in a bone marrow aspirate sample.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1. Identification of Anti-CD45 Antibodies Ab1-Ab7

A fully human library was screened and an anti-human CD45 antibodies Ab1, Ab2, Ab3, Ab4, Ab5, Ab6, and Ab7 were identified. Each of the foregoing antibodies were able to internalize on CD45 expressing cells. Additional detail on the library screen and resulting antibodies is provided in the examples that follow.

Yeast Display

A yeast display library that displays fully human antibodies (either natural or synthetic) was screened for binding to the ectodomain of human CD45 (Isoform CD45RABC; Uniprot: P08575-3) and non-human primate (NHP) CD45. Yeast cells that encoded antibodies that bound to recombinant CD45 antigen were selected. Nucleic acid sequences representing the antibodies from the selected yeast cells were isolated according to techniques known in the art.

In particular, the screen was performed to identify human and NHP cross-reactive anti-CD45 antibodies. The first screen yielded approximately 55 antibodies, but these only bound to human CD45 and were not cross-reactive to NHP CD45 antigen. The second screen successfully yielded 82 human reactive clones, 17 of which were reactive to human and rhesus CD45, of which 8 were triple cross-reactive to human, rhesus and cynomolgus CD45 recombinant antigens.

From the eight triple cross-reactive (human, rhesus, cynomolgus CD45 reactive) antibodies, four human IgG antibodies with distinct CDR3 heavy chain sequences were selected for several rounds of affinity maturation for further improvement of affinity by way of diversifying sequences in CDR1, CDR2, CDR3 in the heavy and light chains and selecting for improved affinity according to methods known in the art. A total of 55 human IgG antibodies with improved affinity and variant sequences were subsequently identified following affinity maturation of the four input antibodies. From the four parent antibodies input into the affinity maturation process, only one antibody generated daughter variants that were verified to be true cross-reactive clones on live cells by binding assays performed on human and cynomolgus peripheral mononuclear cells (PBMCs) (see FIG. 1).

As shown in FIG. 1, the daughter variants derived from Ab1 had improved binding to human CD45, relative to the parent antibody, as evaluated by an Octet binding assay. In addition, the affinity matured daughter variants derived from Ab1 showed interspecies cross-reactivity with human CD45 and cynomolgus CD45 (FIG. 1). In contrast, the antibodies derived from the other three parent antibodies were poorly cross-reactive (FIG. 1).

Selected daughter variants derived from Ab1 were expressed and the resulting antibodies were further screened to identify anti-CD45 antibodies that were able to internalize on CD45 expressing cells. Exemplary methods and reagents amenable for use in generating and screening antibody display libraries can be found in, for example, Boder E. T. and Wittrup K. D., Yeast surface display for directed evolution of protein expression, affinity, and stability, Methods Enzymol, 328:430-44 (2000) and Boder E. T. and Wittrup K. D., Yeast surface display for screening combinatorial polypeptide libraries, Nat Biotechnol. 15(6):553-7 (June 1997).

From the foregoing screening process, five human IgG antibodies were selected based on desired antigen and live-cell binding properties, including one antibody identified prior to affinity maturation (Ab1), and four following affinity maturation (Ab2, Ab3, Ab4, and Ab6). Subsequent site-specific substitutions were introduced in Ab4, to generate Ab5. Similarly, site-specific substitutions were introduced in Ab3, to generate Ab7. The amino acid sequences of the variable regions and CDR regions of the heavy and light chains of the seven selected antibodies are provided in Table 27. The seven antibodies include the following: antibody 1 (Ab1), Antibody 2 (Ab2), Antibody 3 (Ab3), Antibody 4 (Ab4), Antibody 5 (Ab5), Antibody 6 (Ab6), and Antibody 7 (Ab7).

Further characterization of Ab1-7 is provided in Examples 2 to 14.

Example 2. In Vitro Stability Analysis of Anti-CD45 Antibodies

The stability of the antibodies identified in Example 1 was assessed under various stress conditions. These studies identified VH/VL framework and CDR amino acids that may be susceptible to the formation of post-translational modifications that could affect antibody heterogeneity and/or binding.

A two-week stability assay was performed by incubating Ab3 and Ab4 at 4° C., 25° C., and 40° C. for 15 days, after which the antibodies were analyzed by hydrophilic interaction chromatography (HIC). Briefly, 25 micrograms of the indicated antibody were injected onto a Tosoh TSKgel Phenyl-5PW 7.5 mm ID×7.5 cm 10-micron column (Catalog #07573) on a Waters ARC HPLC/UPLC system. The HIC elution profiles of the antibodies exhibited a relatively hydrophilic pre-peak that increased as a function of thermal stress. This hydrophilic pre-peak was indicative of a potential site of post-translational modification (e.g., oxidation or deamidation). Peptide mapping was subsequently performed to identify which amino acids were modified in each antibody upon exposure to stress (high pH, low pH, and oxidative stress). The peptide mapping analysis identified a potential site of deamidation at an asparagine in CDR-L1 (N30 position) in response to high pH conditions (e.g., pH 8 or greater).

Comparison of other clones identified following affinity maturation suggested that a serine may be tolerated at the N30 position of CDR-L1. Accordingly, variants of Ab3 and Ab4 were generated in which the asparagine in CDR-L1 (e.g., at position 30B) was substituted with a serine. The resulting antibodies were named Ab7 and Ab5 respectively. The pre-peak corresponding to deamidated species was not observed in the HIC profile of Ab5 following exposure to high pH treatment, confirming that this substitution removes this potential site of deamidation.

Example 3. In Vitro Binding Analysis of Anti-CD45 Antibodies

The antibodies described in Examples 1 and 2 were studied to determine their binding characteristics with respect to human CD45, and to evaluate their ability to cross react with rhesus and cynomolgus CD45.

Antibody binding studies were performed at 25° C. in 1×PBS supplemented with 0.1% w/v bovine serum albumin with a Pall ForteBio Octet Red96 using biolayer interferometry (BLI). Each purified human antibody was immobilized onto anti-human Fc biosensors (AHQ; Pall ForteBio 18-5001) and incubated with 50 nM of purified human, rhesus or cynomolgus CD45 ectodomain for affinity matured clones Ab2-Ab7, and 100 nM human CD45 and 300 nM of rhesus or cynomolgus CD45 for parent clone Ab1.

The apparent monovalent affinity ($K_D$), apparent association rate ($K_{ON}$), and apparent dissociation rate ($K_{OFF}$) were determined by local full fitting with a 1:1 binding model as calculated by ForteBio data analysis software version 10 of each IgG to purified human, cynomolgus or rhesus CD45 ectodomain. $K_D$, $K_{ON}$, and $K_{dis}$ of each antibody are shown in Table 2. The affinity matured daughter clones (Ab 2-Ab 7) displayed improved binding to human CD45 relative to the parent clone Ab1. Further, these results indicate that the N_30_S substitution of Ab5 and Ab7 did not alter CD45 binding. Notably each of the selected antibodies Ab2-Ab7 were able to cross react with human, cynomolgus and rhesus CD45. Binding was confirmed using

TABLE 2

Monovalent affinity ($K_D$), apparent association rate ($K_{ON}$), and apparent dissociation rate ($K_{OFF}$ or $K_{dis}$) of the indicated IgG to human CD45 ectodomain, cynomolgus CD45 ectodomain or rhesus CD45 ectodomain

| | Human CD45 | | | Cynomolgus CD45 | | | Rhesus CD45 | | |
|---|---|---|---|---|---|---|---|---|---|
| | Kd (M) | Kon(1/Ms) | Kdis(1/s) | Kd (M) | Kon(1/Ms) | Kdis(1/s) | Kd (M) | Kon(1/Ms) | Kdis(1/s) |
| Ab1 | 1.09E−07 | 4.58E+05 | 4.99E−02 | No Binding | | | No Binding | | |
| Ab2 | 1.15E−10 | 2.45E+05 | 2.80E−05 | 1.08E−09 | 1.19E+05 | 1.29E−04 | 1.42E−09 | 1.35E+05 | 1.92E−04 |
| Ab4 | 1.39E−11 | 2.36E+05 | 3.28E−06 | 7.21E−10 | 1.10E+05 | 7.89E−05 | 8.67E−10 | 1.18E+05 | 1.02E−04 |
| Ab5* | 1.44E−10 | 2.33E+05 | 3.36E−05 | 1.40E−09 | 1.17E+05 | 1.64E−04 | 1.71E−09 | 1.13E+05 | 1.93E−04 |
| Ab6* | 7.16E−11 | 2.42E+05 | 1.73E−05 | 1.30E−09 | 1.18E+05 | 1.54E−04 | 1.44E−09 | 1.22E+05 | 1.75E−04 |
| Ab3 | 8.66E−10 | 2.60E+05 | 2.25E−04 | 1.61E−09 | 1.20E+05 | 1.92E−04 | 1.65E−09 | 1.35E+05 | 2.22E−04 |
| Ab7* | 2.33E−09 | 2.64E+05 | 6.15E−04 | 4.24E−09 | 1.27E+05 | 5.37E−04 | 4.39E−09 | 1.24E+05 | 5.44E−04 |

*Clones with N_S amino acid substitution

Example 4. In Vitro REH and PBMC Cell Binding Activity of Anti-CD45 Antibodies In vitro REH and PBMC cell binding of select anti-CD45 antibodies identified in Examples 1 and 2 (Ab5 and Ab7) was assessed in this Example. The Fc region of each antibody was modified with the amino acid substitutions D265C LALA H435A.

REH-1 (B cell non-Hodgkin's lymphoma cell line, ATCC No. CRL-3004) cells or primary human or cynomolgus peripheral blood mononuclear cells (PBMCs) in cell culture media were incubated with titrated doses of Ab5 and Ab7 overnight at 37° C. Bound anti-CD45 antibody was detected with fluorescently labeled AF488 anti-human IgG secondary antibody using flow cytometry. IC50s were determined by fitting the data using GraphPad Prism.

Figure 2:
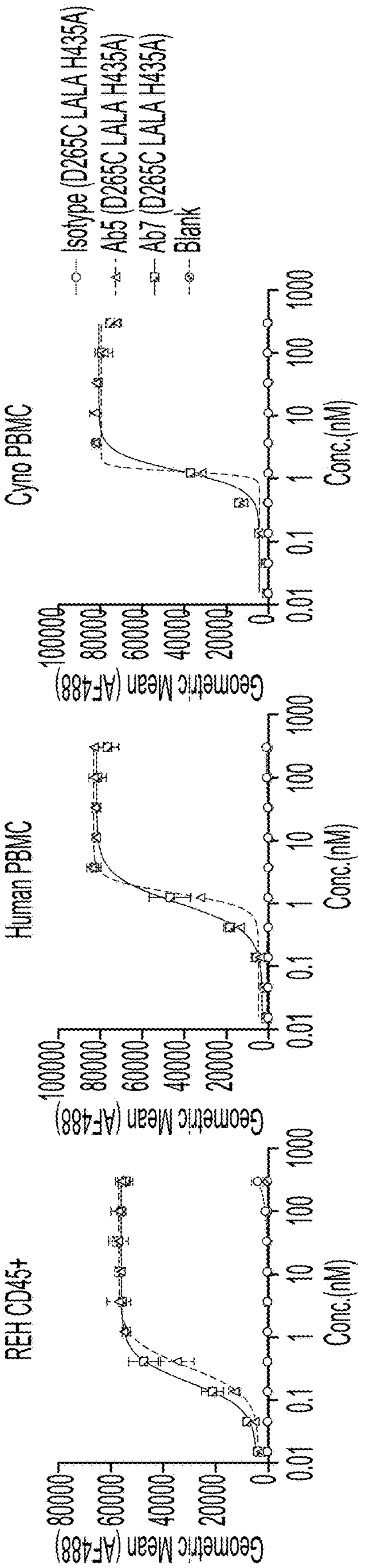
FIG. 2 graphically depicts the results of an in vitro cell binding assay to assess binding of the indicated anti-CD45 antibodies (Ab5 and Ab7) to REH cells, human PBMC cells, and cynomolgus ("cyno") PBMC cells. Ab5_D265C_LALA_H435A and A7_D265C_LALA_H435A, Fc variants of Ab5 and Ab7, were used in this study. A non-targeting isotype IgG having a Fc-modified region (D265C LALA H435A) was assessed as a control.

As shown in Table 3 and FIG. 2, Ab5 and Ab7 showed similar IC50s between human and cynomolgus PBMCs, demonstrating cross-reactive binding to human and cynomolgus CD45 on live cells. The antibodies also showed potent binding to the REH-1 cell line expressing human CD45.

TABLE 3

| | EC50s (nM) | | |
|---|---|---|---|
| Antibody | REH | Human | Cyno |
| Ab5 (D265C LALA H435A) | 0.3 | 1.4 | 1.3 |
| Ab7 (D265C LALA H435A) | 0.2 | 1.0 | 1.3 |

Example 5. Epitope Mapping

The epitope bound by an anti-CD45 antibody identified in Examples 1 and 2 (Ab5) was mapped using crosslinking mass spectrometry. The cross-linking experiments allow the direct analysis of non-covalent interaction by High-Mass MALDI mass spectrometry. By mixing a protein sample containing non-covalent interactions with a specially developed cross-linking mixture (Bich, C et al. Anal. Chem., 2010, 82 (1), pp 172-179), it is possible to specifically detect a non-covalent complex with high sensitivity. The covalent binding generated by crosslinking allows the interacting species to survive the sample preparation process and the MALDI ionization. A special High-Mass detection system allows characterization of the interaction in the High-Mass range.

In order to determine the epitope of Ab5 with high resolution, a protein complex was incubated with deuterated cross-linkers and subjected to multi-enzymatic cleavage. The protein complex was an Ab5 variant antibody (having the same epitope as Ab5) bound to human CD45. After enrichment of the cross-linked peptides, the samples were analyzed by high resolution mass spectrometry (nLC-LTQ-Orbitrap MS) and the data generated were analyzed using XQuest and Stavrox software.

Figure 3:
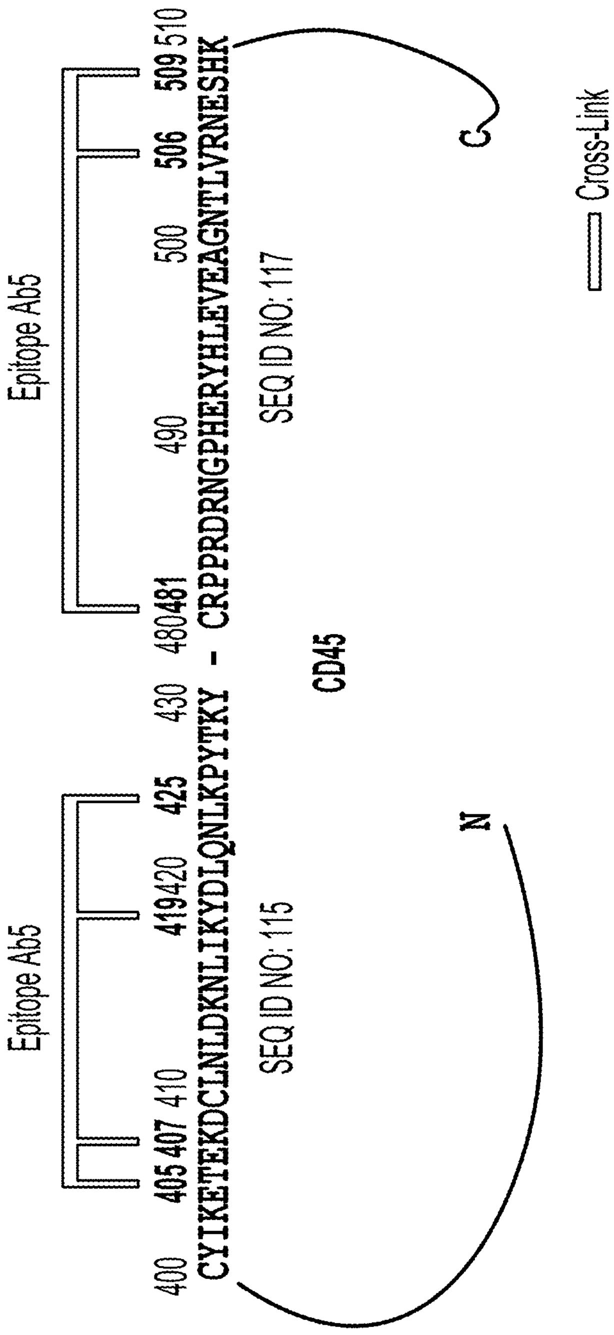
FIG. 3 depicts the results of an CD45 epitope mapping study with the anti-CD45 antibody Ab5. Depicted is a schematic of the Ab5 interaction site on CD45, with the amino acid sequences (SEQ ID NO:115 and SEQ ID NO:117) surrounding the Ab5-epitope notated. Contact residues are highlighted as 405T, 407K, 419Y, 425K, 481R, 505R, and 509H, with the residue numbering referring to the human CD45 fragment represented by SEQ ID NO:113.

After Trypsin, Chymotrypsin, ASP-N, Elastase and Thermolysin proteolysis of the protein complex CD45/Ab5 with deuterated d0d12, the nLC-orbitrap MS/MS analysis indicated that the Ab5 epitope includes residues in the peptides TEKDCLNLDKNLIKYDLQNLK (SEQ ID NO:114) and RPPRDRNGPHERYHLEVEAGNTLVRNESH (SEQ ID NO:116) and, in particular, interacts with amino acids on human CD45 corresponding to 405T, 407K, 419Y, 425K, 481R, 505R, and 509H of SEQ ID NO:113 (fragment of CD45 isoform corresponding to NP_002829.3). These results are illustrated in FIG. 3, showing the CD45 amino acid fragments corresponding to SEQ ID NOs: 115 and 117 that encompass the epitope of Ab5 (e.g., the epitope as described in SEQ ID NO:114 and SEQ ID NO:116), and the specific sites of interaction.

CD45 includes a mucin-like domain, d1-d4 fibronectin-like domain, and transmembrane and phosphatase domains. Based on the present results, Ab5 appears to interact with d3 and d4 of the fibronectin-like domain of CD45. Residues 405T, 407K, 419Y, 425K, and 505R of the Ab5 epitope are conserved across human, cynomolgus, and rhesus CD45, consistent with the ability of Ab5 (and clones derived from Ab1) to bind to human, rhesus, and cynomolgus CD45.

Example 6. Cell Internalization of Anti-CD45 Antibody Conjugate

For this study, an anti-CD45 antibody identified in Examples 1 and 2 (Ab5) was assessed in an in vitro internalization assay in human bone marrow cells. Ab5 having a modified Fc region (D265C LALA H435A) was conjugated to an amatoxin (amatoxin 1 (AM1)) to form an antibody drug conjugate (Ab5-AM1). AM1, as used throughout unless otherwise specified, is represented by Formula VI described herein.

The anti-CD45 ADC was conjugated to a pHAb dye that is water soluble, bright, photo-sensitive, and pH-reactive. Upon internalization, conjugated antibody can move to the acidic endosome/lysosome, where pHAb dye emits at 563 nM and can be detected by flow cytometry. Using this method, internalization of Ab5-AM1 ADC was assessed in CD34+ human bone marrow cells.

Figure 4:
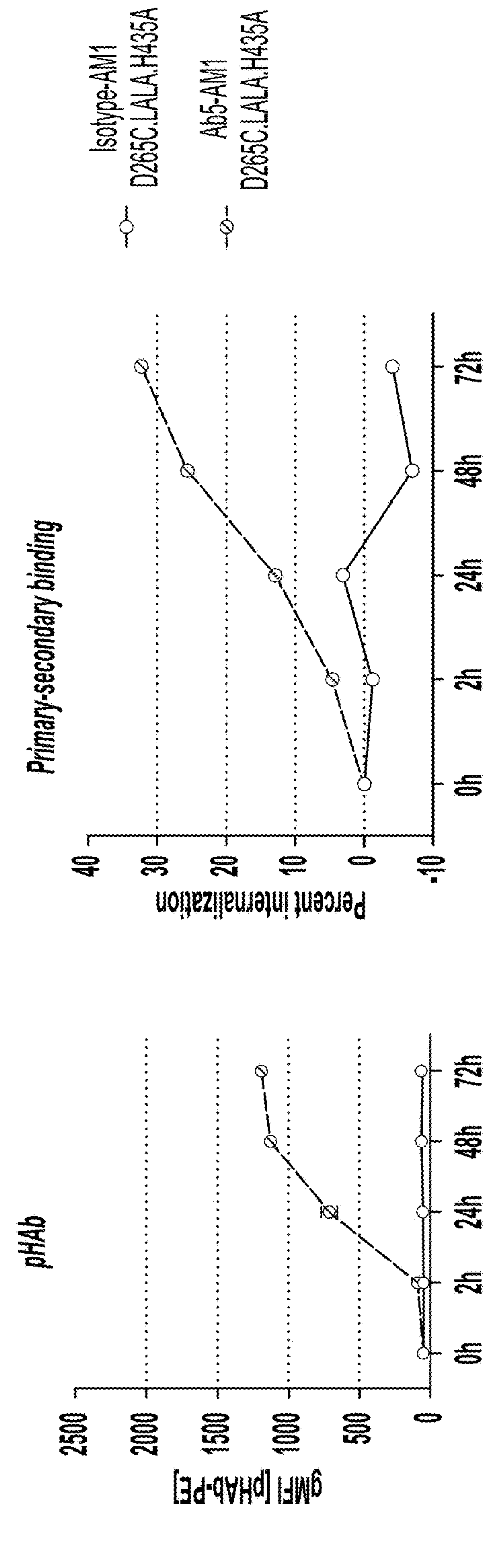
FIG. 4 graphically depicts the results of an in vitro internalization assay assessing internalization of an anti-CD45 antibody-drug conjugate (ADC) constructed from Ab5 in human CD34+ bone marrow cells. Ab5 D265C.LALA.H435A, an Fc variant of Ab5, was conjugated to an amatoxin (amatoxin 1 (AM1)) to form Ab5-AM1 D265C.LALA.H435A. The anti-CD45 ADC was conjugated to a pHAb dye that is water soluble, bright, photosensitive, and pH-reactive. Upon internalization, conjugated antibody can move to the acidic endosome/lysosome, where pHAb dye emits at 563 nM and can be detected by flow cytometry. Human bone marrow CD34+ cells were incubated on ice for two hours with a saturating concentration of ADC for 0, 2, 24, 48, or 72 hours. The left panel graphically depicts the level of pHAb over time. A fluorophore-labeled anti-IgG molecule was used to assess bound surface hIgG1 by flow cytometry, from which the percent of surface IgG was calculated overtime, as depicted in the right panel.

This assay was performed by incubating CD34+ human bone marrow cells on ice for two hours with a saturating concentration of ADC for 0, 2, 24, 48, or 72 hours. The levels of pHAb (as measured by gMFI) was assessed overtime (FIG. 4; left panel). At the end of the time course, a fluorophore-labeled anti-IgG molecule was used to assess bound surface hIgG1 by flow cytometry. An Isotype IgG conjugated to amatoxin 1 (Isotype-AM1), which does not bind human CD34+ cells, was included as a non-internalizing control. As the 0 h time point represents saturated binding of CD45, percent internalized ADC was calculated by comparing the geometric mean fluorescence intensity (gMFI) of the bound surface IgG at each time point to the gMFI of the same ADC at 0 hours (FIG. 4; right panel).

As shown in FIG. 4, the level of detected pHAb in the cells increased overtime (FIG. 4, left panel), which corresponded to an increase in the percentage of ADC internalization over time (FIG. 4, right panel). The percent internalization of Ab5-AM1 was markedly higher compared to that of the Isotype-AM1, indicating that Ab5-AM1 was internalized by human CD34+ bone marrow cells, while the isotype control was not internalized. These results indicate that Ab5-AM1 was internalized by human CD34+ bone marrow cells.

Example 7. Analysis of Anti-CD45 Antibody Conjugates Using an In Vitro Cell Line Killing Assays Antibody-drug conjugates (ADCs) of anti-CD45 antibodies identified in Examples 1 and 2 (Ab2-Ab7) were assessed for in vitro killing of Jurkat (acute T cell leukemia cell line, ATCC No. TIB-152), SKNO-1 (acute myeloid leukemia cell line JCRB1170), and REH-1 (B cell non-Hodgkin's lymphoma cell line, ATCC No. CRL-3004) cell lines, and a REH CD45−/− knockout cell line. The anti-CD45 antibodies, which had a modified Fc region (D265C LALA H435A or D265C.LALA.H435A-SG3249), were each conjugated to one of two amatoxins (amatoxin 1 (AM1) or amatoxin 2 (AM2)) or PBD (tesirine) to form an ADC. AM2, as used throughout unless otherwise indicated, is represented by Formula III, wherein X is S.

For in vitro killing assays using cell lines, the cells were grown according to ATCC guidelines. More specifically, cells were cultured for seven days in the presence of CD45-ADC or the Isotype control-ADC. Cell viability was then measured by a Cell-titer Glo assay that measures adenosine triphosphate (ATP) content correlating to live cells. Following the cell line killing assay, the level of cytotoxicity was quantified and IC50s were calculated using GraphPad Prism.

Figure 5A:
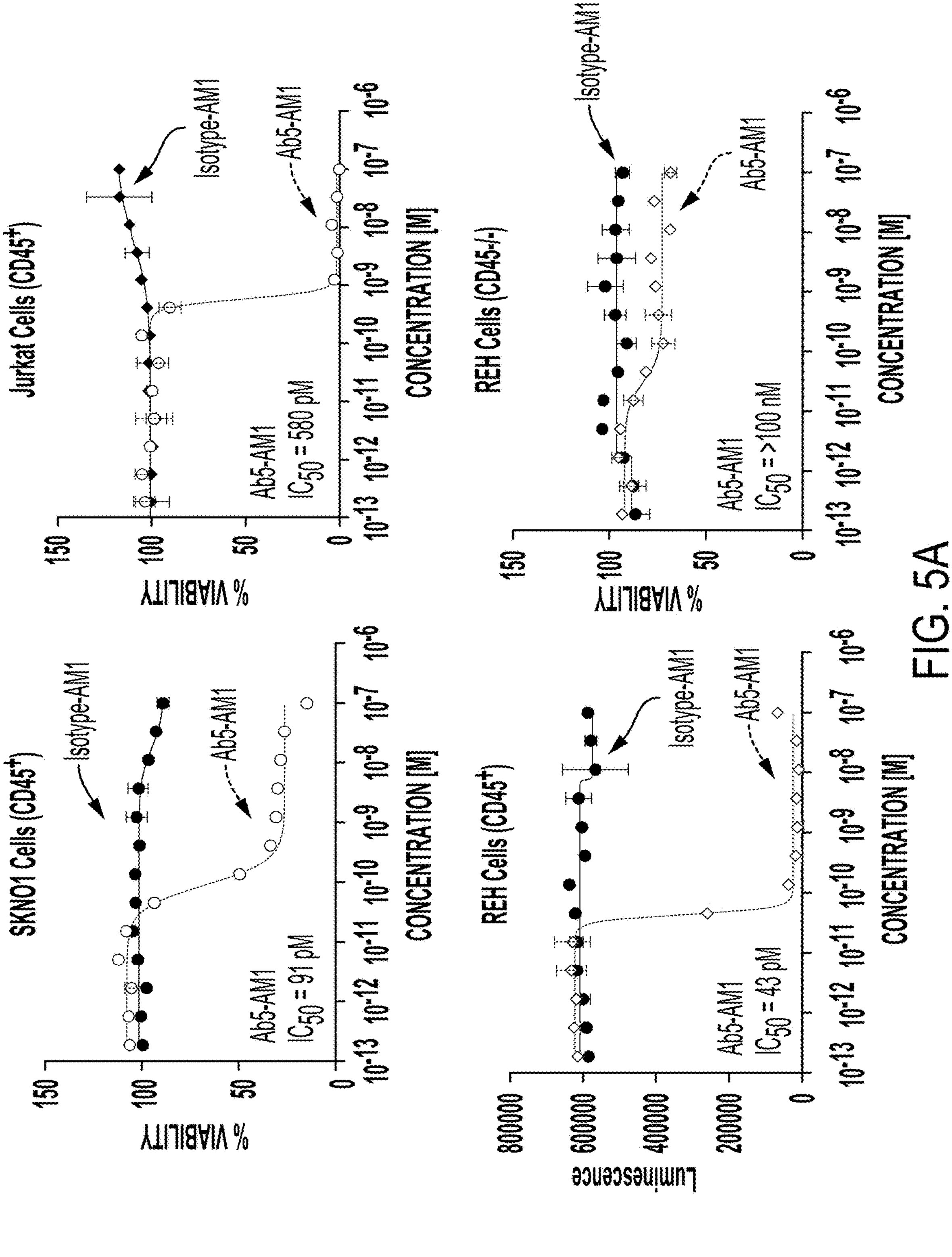
FIGS. 5A and 5B graphically depicts the results of in vitro cell line killing assays showing that anti-CD45 ADCs constructed from Ab4 and Ab5 were effective at killing CD45+ cell lines in vitro (Jurkat (acute T cell leukemia cell line, ATCC No. TIB-152), SKNO-1 (acute myeloid leukemia cell line JCRB1170), and REH-1 (B cell non-Hodgkin's lymphoma cell line, ATCC No. CRL-3004)). Ab4 D265C.LALA.H435A and Ab5 D265C.LALA.H435A, Fc variants of Ab4 and Ab5, were conjugated to an amatoxin (amatoxin 1 (AM1) or amatoxin 2 (AM2)) to form Ab4-AM2 D265C.LALA.H435A ("Ab4-AM2") and Ab5-AM1 D265C.LALA.H435A ("Ab5-AM1").
Figure 5B:
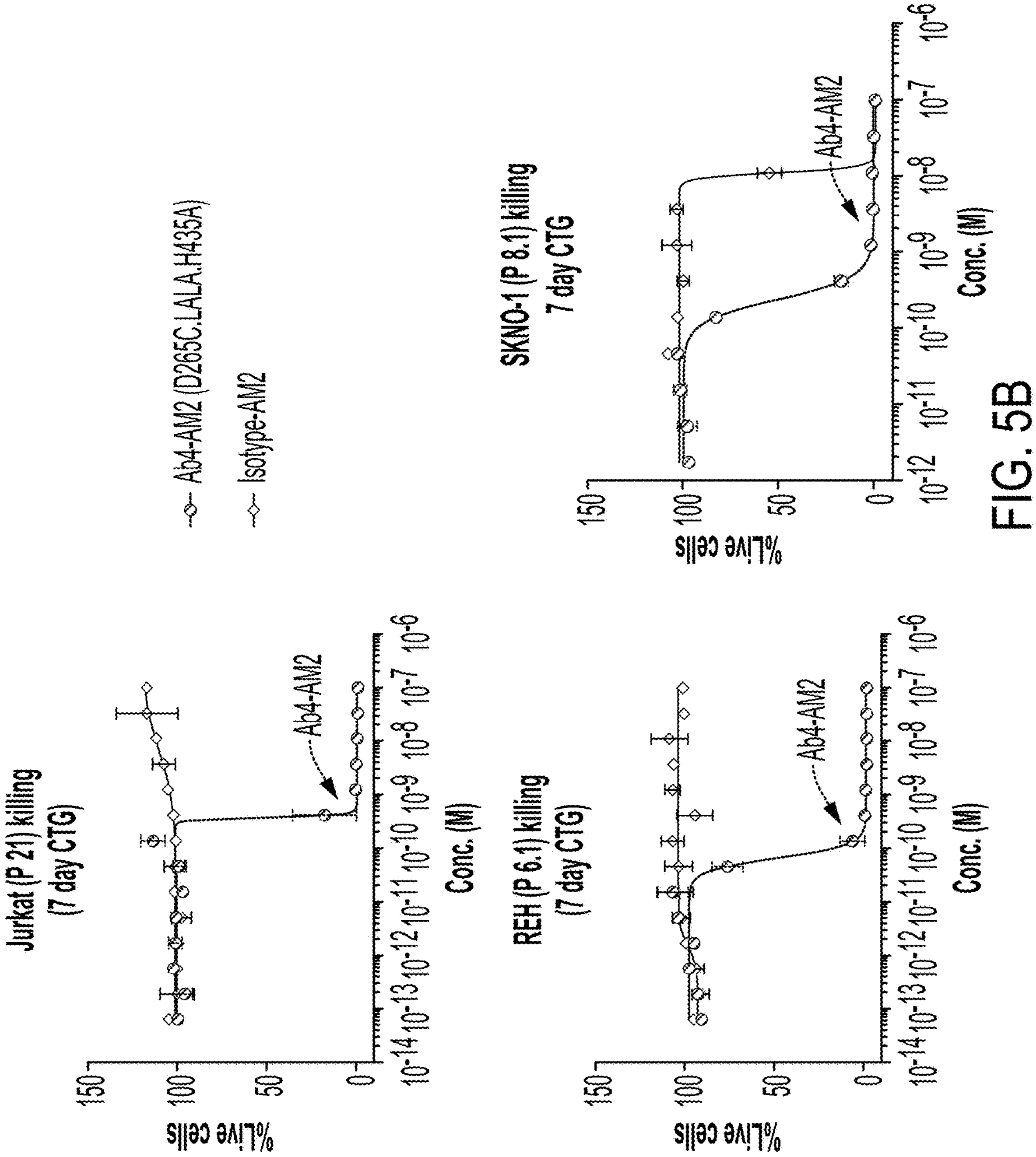

The results described in Tables 4 and 5 and in FIGS. 5A and 5B indicate that each of the tested anti CD45-ADCs were effective at killing CD45 expressing cell lines (e.g., Jurkat, REH-1, or SKNO-1 cells) in vitro.

TABLE 4

In vitro Jurkat, REH, and SKNO-1 cell line killing assay - IC50 values

| ADC | Jurkat IC50 | REH (CD45+) IC50 | SKNO-1 IC50 | REH CD45−/− IC50 |
|---|---|---|---|---|
| Ab5-AM1 D265C.LALA.H435A | 5.8E−10 | 4.3E−11 | 9.10E−11 | N/A |
| Ab4-AM2 D265C.LALA.H435A | 3.80E−10 | 6.6E−11 | 2.378E−10 | — |

TABLE 5

In vitro REH cell line killing assay - IC50 values

| ADC | REH IC50 (M) |
|---|---|
| Ab4-AM2 (D265C.LALA.H435A) | 6.6E−11 |
| Ab4-AM1 (D265C.LALA.H435A) | 2.8E−10 |
| Ab5-AM1 (D265C.LALA.H435A) | 4.3E−11 |
| Ab6-AM1 (D265C.LALA.H435A) | 2.5E−10 |
| Ab3-AM1 (D265C.LALA.H435A) | 4.8E−11 |
| Ab7-AM1 (D265C.LALA.H435A) | 6.9E−11 |
| Ab5-PBD (D265C.LALA.H435A-SG3249) | 2.3E−12 |

Example 8. Analysis of Anti-CD45 Antibody Conjugates Using In Vitro PBMC and HSC Killing Assays Antibody-drug conjugates (ADCs) of anti-CD45 antibodies identified in Examples 1 and 2 (Ab2-Ab7) were assessed for killing of primary human or cynomolgus peripheral blood mononuclear cells (PBMCs) or human hematopoietic stem cells (HSCs) in vitro. The anti-CD45 antibodies, which had a modified Fc region (D265C LALA H435A or D265C.LALA.H435A-SG3249), were each conjugated to one of two amatoxins (amatoxin 1 (AM) or amatoxin 2 (AM2)), or to PBD, to form the ADCs in this study.

PBMCs are 0045 expressing cells consisting of a heterogeneous cell population of lymphocytes (T cells, B cells, Natural Killer cells) and monocytes. For in vitro killing assays using cell lines, the PBMCs were cultured in RPMI 1640 with 10% fetal bovine serum for seven days in the presence of 0045-ADO or the Isotype control-ADO. Cell viability was then measured by Cell-titer Glo assay. Following the PBMC killing assay, the level of cytotoxicity was quantified and IC50s were calculated using GraphPad Prism.

Figure 6A:
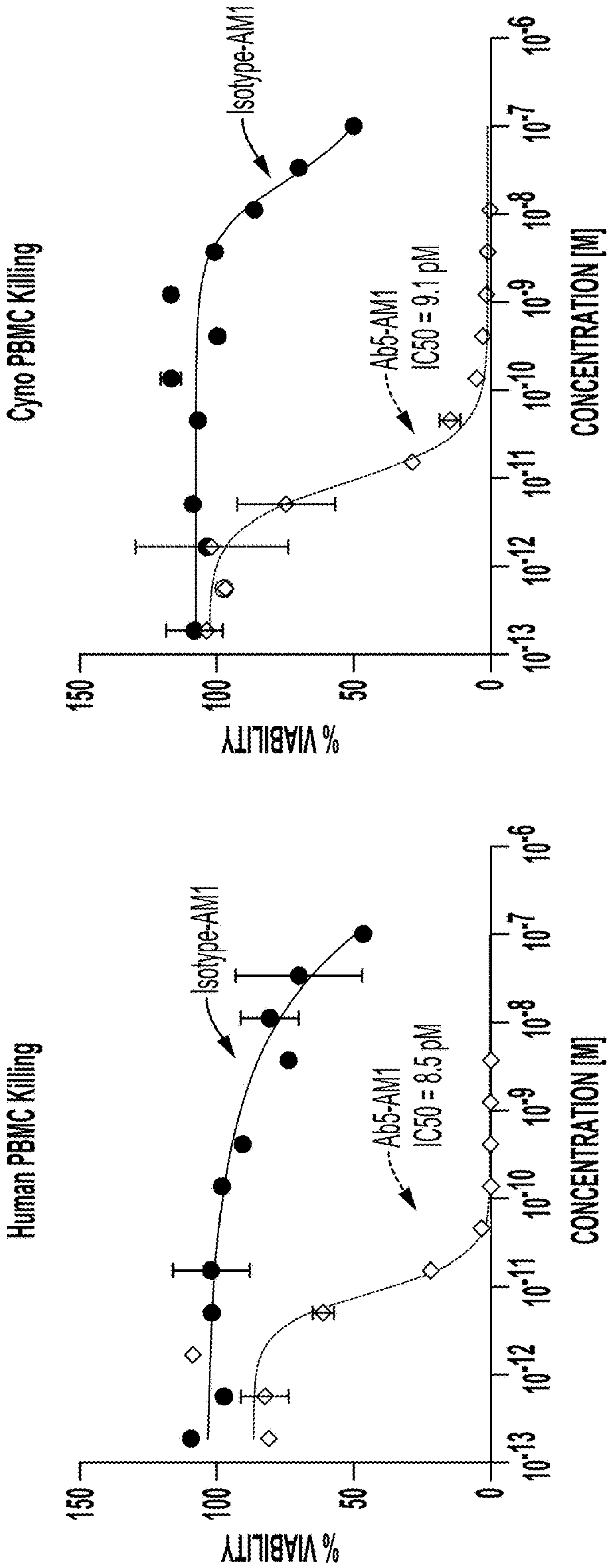
FIGS. 6A-6C graphically depicts the results of in vitro primary cell killing assays showing that anti-CD45 ADCs constructed from Ab2, Ab4, or Ab5 were effective at killing primary human or cynomolgus peripheral blood mononuclear cells (PBMCs) or human hematopoietic stem cells (HSCs) in vitro. Ab2 D265C.LALA.H435A, Ab4 D265C.LALA.H435A, Ab5 D265C.LALA.H435A, Fc variants of Ab2, Ab4, and Ab5, were conjugated to an amatoxin (amatoxin 1 (AM1) or amatoxin 2 (AM2)) to form Ab2-AM2 D265C.LALA.H435A ("Ab2-AM2"), Ab4-AM2 D265C.LALA.H435A ("Ab4-AM2") and Ab5-AM1 D265C.LALA.H435A ("Ab5-AM1").

The results described in FIG. 6A and Table 6 indicate that each of the anti CD45-ADCs were effective at killing human and cynomolgus PBMCs in vitro. Exemplary graphs depicting human and cyno killing for Ab5-AM1 are shown in FIG. 6A and Table 7. Ab5-AM1 exhibited potent killing of primary PBMCs with an $IC_{50}$ of 8.5 pM for human PBMCs and an $IC_{50}$ of 9.1 pm for cyno PBMCs, indicating that human and cyno PBMCs were equally sensitive to Ab5-AM1.

TABLE 6

In vitro cell line killing assay - IC50 values

| Ab1-Derived ADCs | Human PBMC IC50 (M) |
|---|---|
| Ab2-AM2 (D265C LALA H435A) | 5.5E−12 |
| Ab3-AM2 (D265C LALA H435A) | 1.0E−09 |
| Ab4-AM2 (D265C.LALA.H435A) | 2.5E−11 |
| Ab2-AM1 (D265C.LALA.H435A) | 1.1E−11 |

TABLE 6-continued

In vitro cell line killing assay - IC50 values

| Ab1-Derived ADCs | Human PBMC IC50 (M) |
|---|---|
| Ab4-AM1 (D265C.LALA.H435A) | 2.6E−11 |
| Ab5-AM1 (D265C.LALA.H435A) | 8.5E−12 |
| Ab6-AM1 (D265C.LALA.H435A) | 3.0E−11 |
| Ab3-AM1 (D265C.LALA.H435A) | 7.1E−12 |
| Ab7-AM1 (D265C.LALA.H435A) | 3.7E−12 |
| Ab5-PBD (D265C.LALA.H435A-SG3249) | 1.3E−10 |

TABLE 7

In vitro human and cyno PBMC cell killing assay with Ab5-AM1 - IC50 values

| ADC | CD34+CD90+ IC50 | Human PBMCs IC50 | Cyno PBMCs IC50 |
|---|---|---|---|
| Ab5-AM1 D265C LALA H435A | 4.9E−10 | 8.5E−12 | 9.1E−12 |
| Isotype-AM1 D265C LALA H435A | 1.0E−07 | 1.0E−07 | 1.0E−07 |

Figure 6B:
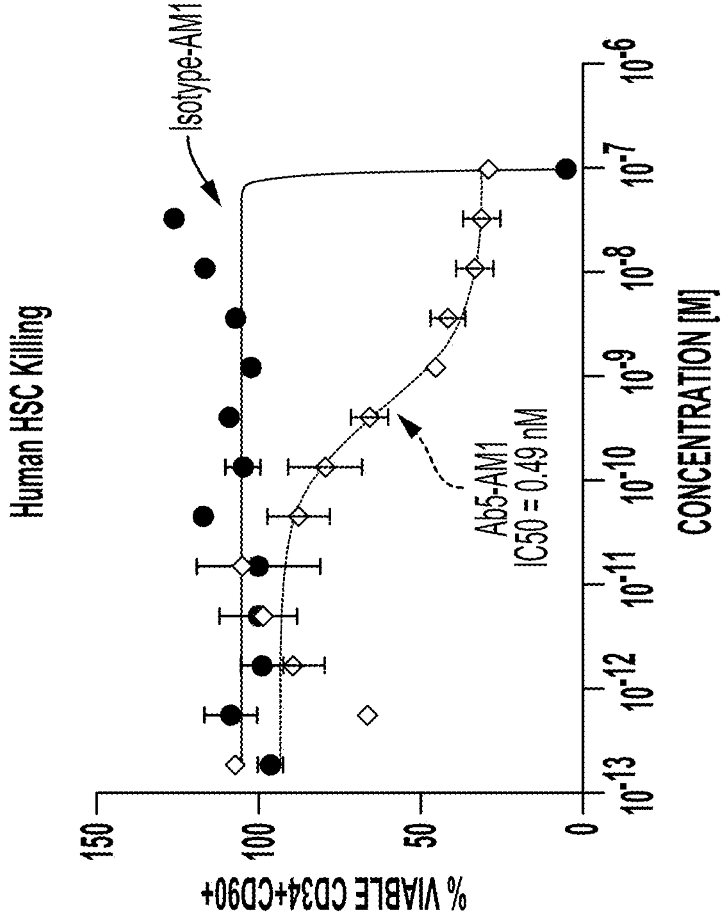
Figure 6C:
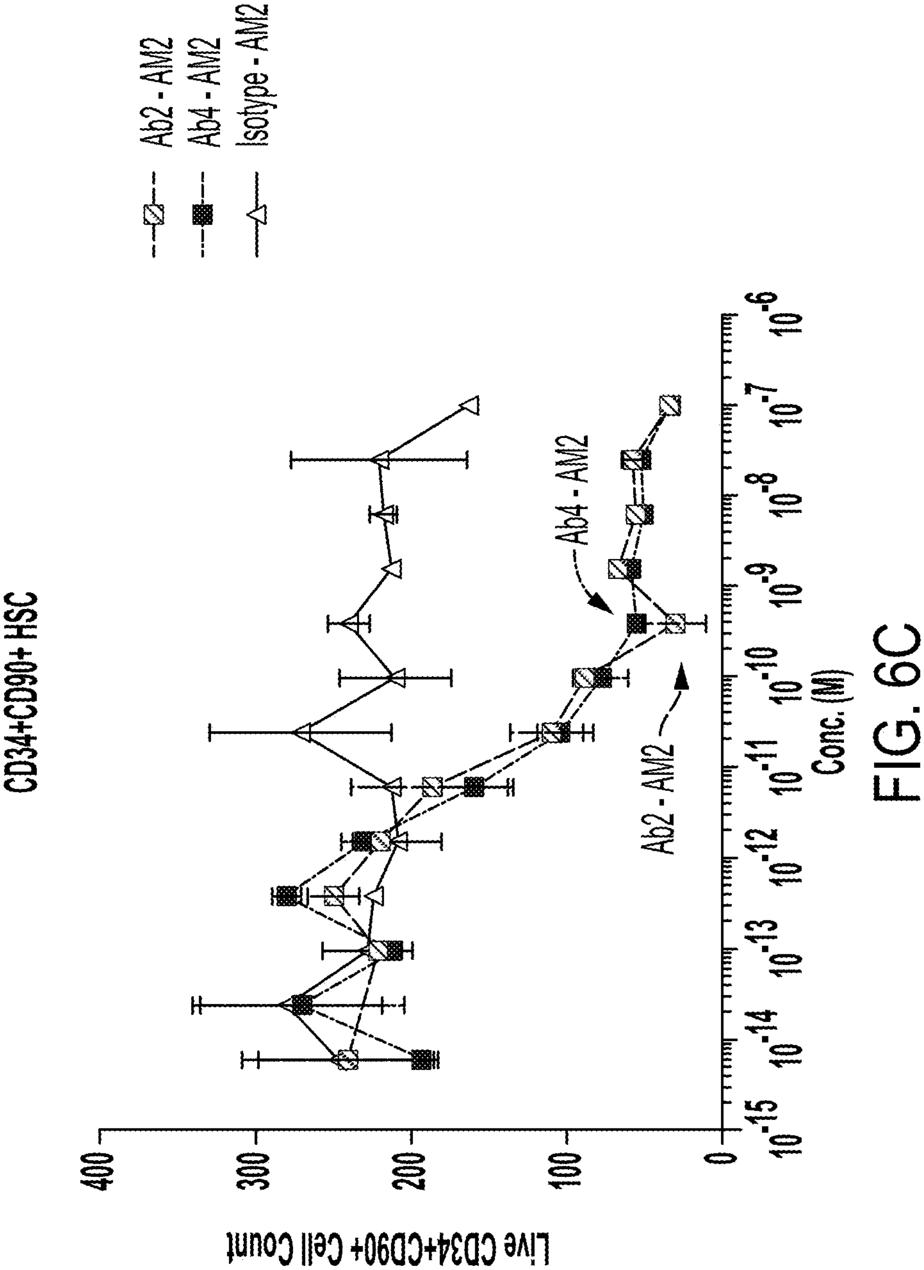

For in vitro killing assays using human HSCs, primary human CD34+ bone marrow cells were cultured for 5 days with Ab2-AM2, Ab4-AM2, Ab5-AM1, or Isotype ADO. Live CD34+CD90+ HSC counts were determined by flow cytometry as a function of antibody concentration. As shown in FIG. 6B, Ab5-AM1 exhibited potent killing of human HSCs with 0.49 nm $IC_{50}$. As shown in FIG. 6C, and summarized in Table 8, Ab2-AM2 and Ab4-AM2 also killed HSCs in vitro.

TABLE 8

In vitro HSC cell killing assay - IC50 values

| ADC | DAR | CD34 CD90 (IC50 pM) |
|---|---|---|
| Ab2-AM2 D265C.LALA.H435A | 1.8 | 14 |
| Ab4-AM2 D265C.LALA.H435A | 1.6 | 9 |
| Isotype-AM2 D265C.H435A | 2 | |

Example 9. Analysis of Anti-CD45 ADC Cell Killing Activity on Stimulated Dividing Vs Non-Stimulated Non-Dividing PBMCs In Vitro An antibody-drug conjugate (ADC) including an anti-CD45 antibody described in Example 1 (Ab2) was assessed for its ability to kill growth stimulated and non-stimulated primary human peripheral blood mononuclear cells (PBMCs) in vitro. For this study, Ab2 having a modified Fc region (D265C LALA H435A) was conjugated to amatoxin 2 (AM2)) to form Ab2-AM2.

Cryopreserved Human PBMCs were thawed and split into two. Half the cells were stimulated with CD3 CD28 Dyna beads at a cell to bead ratio of 2:1 and the other half of cells were not stimulated. Both cells were plated into 384 well plate at 5000 cells/well and treated with ADC for four days, after which cell viability was measured by Cell Titer-Glo.

Figure 7:
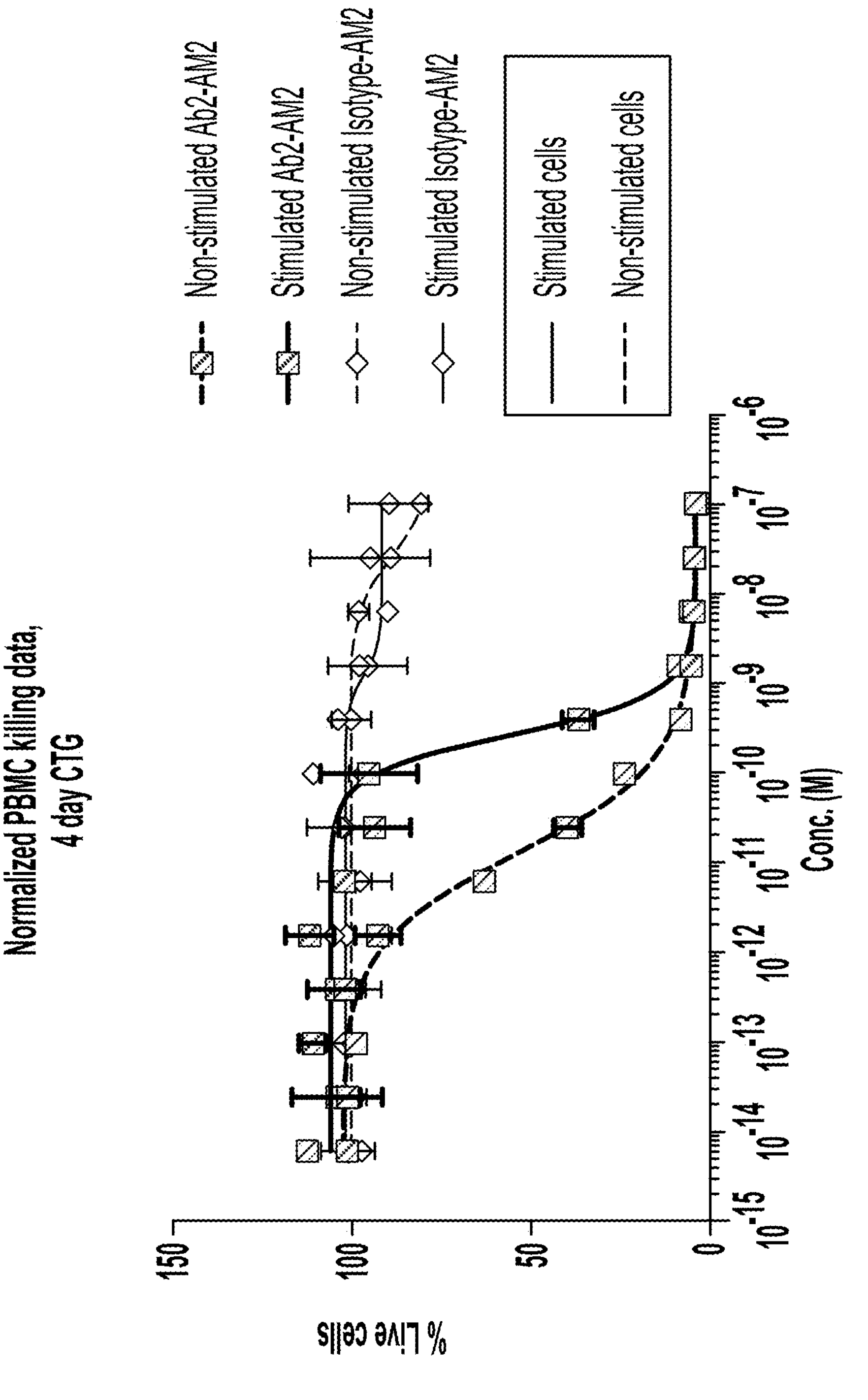
FIG. 7 graphically depicts the results of an in vitro primary cell killing assay showing that an anti-CD45 ADC constructed from Ab2 was effective at killing non-stimulated (non-dividing) and stimulated (dividing) peripheral blood mononuclear cells (PBMCs) in vitro. Ab2 D265C.LALA.H435A, an Fc variant of Ab2, was conjugated to amatoxin 2 (AM2) to form Ab2-AM2 D265C.LALA.H435A ("Ab2-AM2"). Stimulated and non-stimulated PBMCs were cultured for four days in the presence of CD45-AM conjugate (Ab2-AM2) or a control, non-targeting isotype matched-ADC ("Isotype-AM2") and cell viability (y-axis) was measured by Celltiter Glo as a function of antibody concentration (x-axis).

The results described in FIG. 7 indicate the anti CD45-ADC with an amatoxin 2 payload was effective at killing both non-stimulated (non-dividing) and stimulated (dividing) CD45 expressing human PBMCs in vitro. Table 9 below provides additional data quantifying the EC50 values obtained in this cell killing assay.

TABLE 9

In vitro HSC PBMC killing assay (stimulated vs non-stimulated) - IC50 values

| ADC | Unstimulated PBMC-IC50 | Stimulated PBMC-IC50 | Fold difference |
|---|---|---|---|
| Ab2-AM2 D265C LALA H435A | 1.26E−11 | 2.66E−10 | 21 |

Example 10. Analysis of Anti-CD45 ADC Using In Vitro Primary Monocyte-Derived Macrophage Assays An antibody-drug conjugate (ADC) including an anti-CD45 antibody described in Example 1 (Ab6) was assessed for in vitro killing of primary monocyte-derived macrophages. For this study, Ab6 having a modified Fc region (D265C LALA H435A) was conjugated to amatoxin 1 (AM1)) to form Ab6-AM1.

Human PBMCs were plated and differentiated using recombinant M-CSF for 7 days. These cells were then lifted, assessed for macrophage markers, and plated in a 384 flat bottom plate at 5×10^3 cell/well for the cell killing assay. Cells were treated with a 10-point dilution of Ab6-AM1 for six days after which their viability was assessed using Cell Titer Glo.

Figure 8:
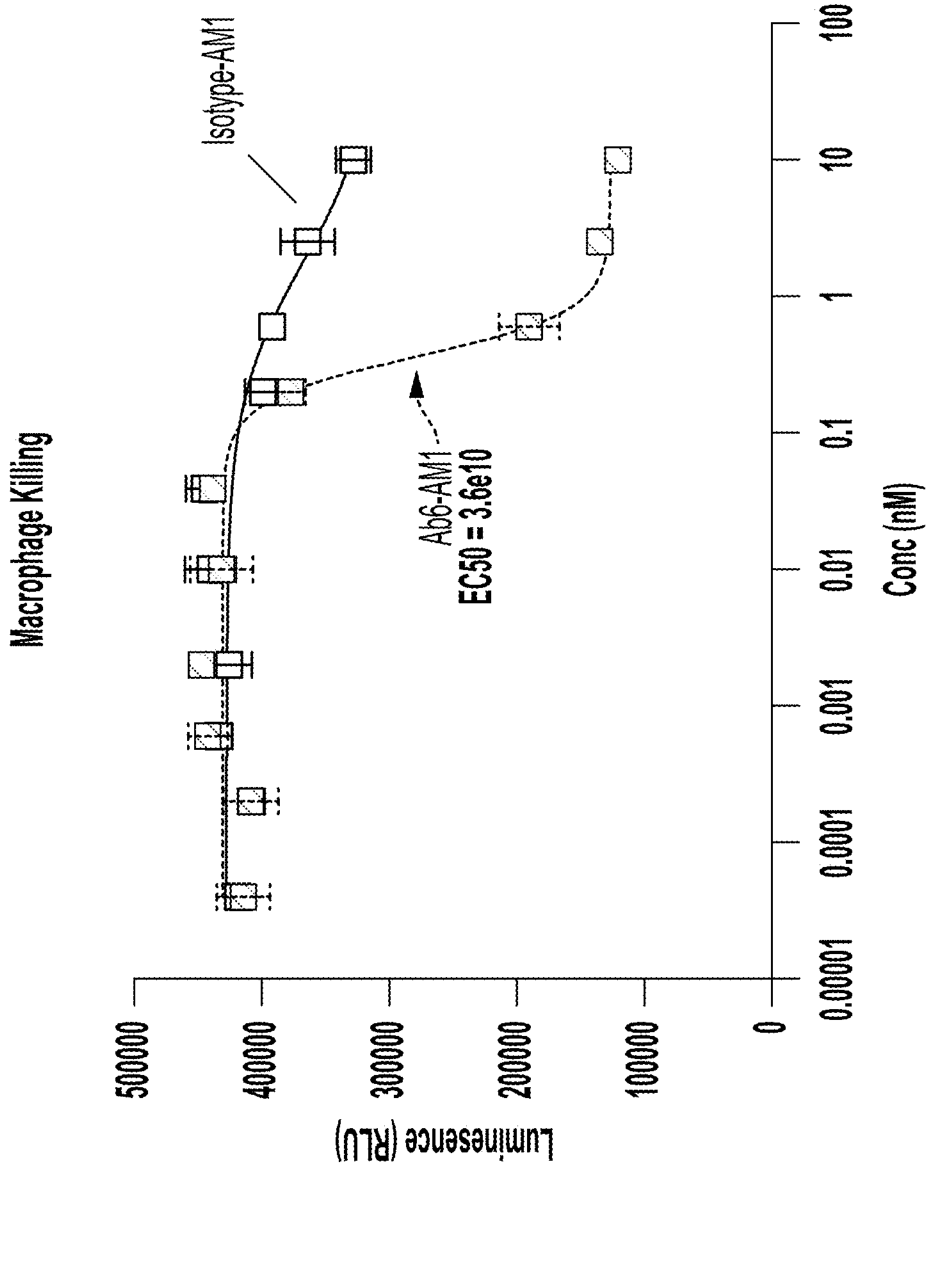
FIG. 8 graphically depicts the results of an in vitro killing assay showing that an anti-CD45 ADC constructed from Ab6 was effective at killing macrophages in vitro. Ab6 D265C.LALA.H435A, an Fc variant of Ab6, was conjugated to amatoxin 1 (AM1) to form Ab6-AM1 D265C.LALA.H435A ("Ab6-AM1"). Macrophages were cultured for six days in the presence of CD45-AM conjugate (Ab6-AM1) or a control, non-targeting isotype matched-ADC ("Isotype-AM1") and cell viability was measured in luminescence (RLU; γ-axis) by Celltiter Glo as a function of antibody concentration (x-axis).

As shown in FIG. 8, human monocyte derived macrophages were sensitive to killing by Ab6-AM1.

Example 11. Analysis of Anti-CD45 Antibody Conjugates Serum Stability Using an In Vitro Cell Killing Assay An antibody-drug conjugate (ADC) including an anti-CD45 antibody described in Examples 1 and 2 (Ab5) was assessed for its stability in serum. For this study, Ab5 was conjugated to amatoxin 1 (AM1) to form the ADC.

The ADC was pre-incubated in human or cynomolgus serum at 37° C. for 0 or 72 hours. After incubating in serum, the ADC was titrated and added to REH cells in growth culture medium. The cells were incubated for 7 days and cell viability was assessed by Cell-Titer-Glo.

Figure 9:
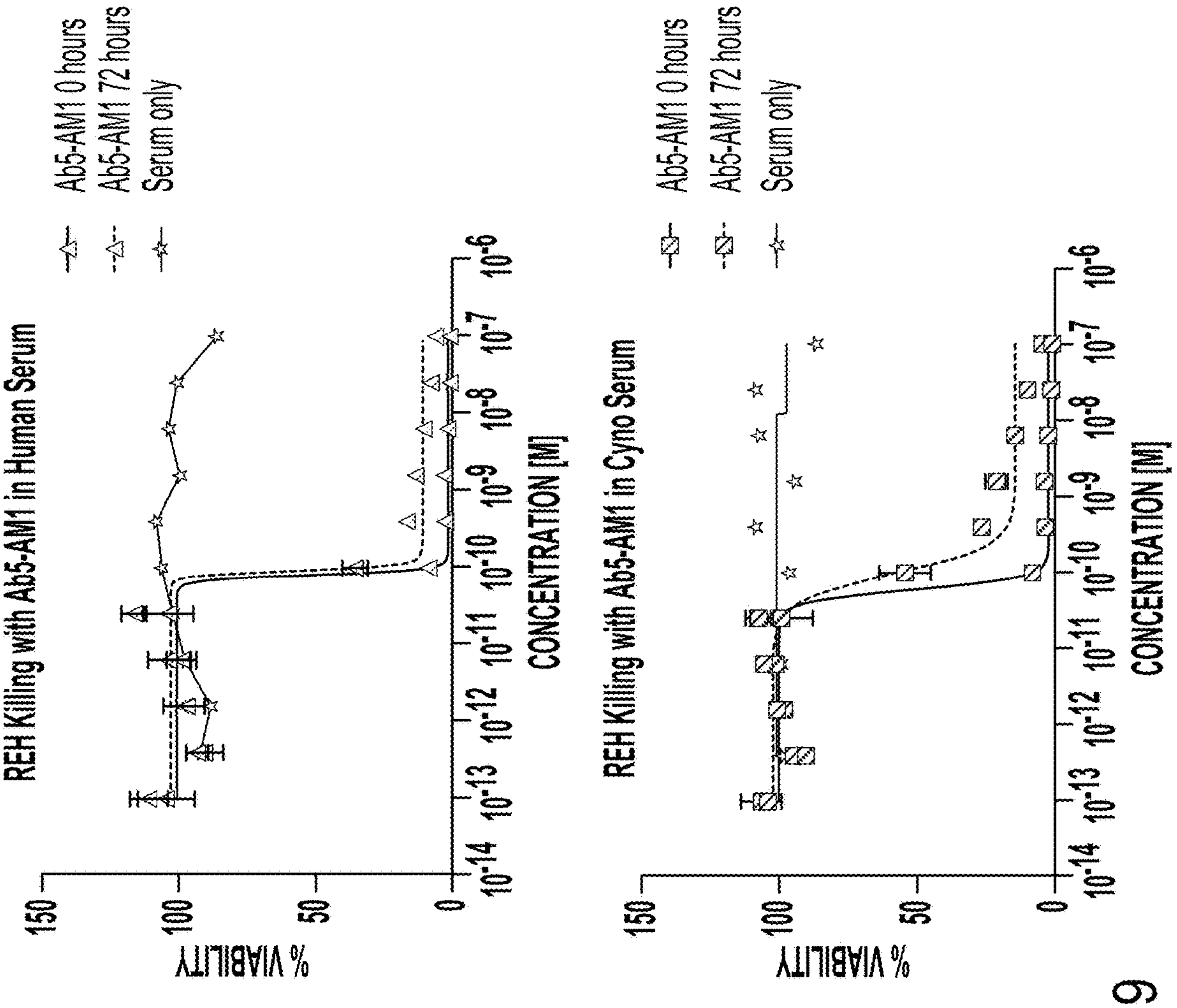
FIG. 9 graphically depicts the results of a serum stability assay assessing stability of an anti-CD45 ADC constructed from Ab5 in human serum (top panel) or cynomolgus ("cyno") serum (bottom panel). Ab5 D265C.LALA.H435A, an Fc variant of Ab5, was conjugated to amatoxin 1 (AM1) to form Ab5-AM1 D265C.LALA.H435A ("Ab5-AM1"). To determine if this ADC is stable in serum, the ADC was pre-incubated in human or cynomolgus (cyno) serum at 37° C. for 0 or 72 hours, after which the ADC was assessed for cell killing of REH cells. Percent cell viability (y-axis) of the REH cells was assessed by Cell-titer Glo as a function of serum-treated ADC concentration (x-axis).

As shown in FIG. 9, Ab5-AM1 demonstrated similar killing after 72 hours incubation in human or cynomolgus serum as compared to 0 hours indicating the ADC is stable in human and cynomolgus serum.

Example 12. In Vivo Hematopoietic Stem Cell (HSC) and Immune Cell Depletion Assay Using Short Half-Life Anti-CD45 ADCs in Humanized NSG Mice Antibody-drug conjugates (ADCs) of select anti-CD45 antibodies identified in Examples 1 and 2 (Ab2, Ab3, Ab5, and Ab7) were assessed for in vivo HSC and immune cell depletion in humanized NSG mice (Jackson Laboratories). In this study, Ab2, Ab3, Ab5, and Ab7 having modifications in the Fc region (i.e., D265C LALA H435A amino acid substitutions) were each conjugated to one of two amatoxins (amatoxin 1 (AM1) or amatoxin 2 (AM2)) to form ADCs (Ab2-AM2, Ab3-AM2, Ab5-AM1, Ab7-AM1). The H435A amino acid substitution in the Fc region was introduced to decrease the half-life of each antibody.

Ab5-AM1 and Ab7-AM1 were administered as a single injection of 1 mg/kg, 3 mg/kg, or 6 mg/kg to the humanized mouse model. Ab2-AM2 (DAR 1.8) and Ab3-AM2 (DAR 2.0) were administered as a single injection of 1 mg/kg, 2 mg/kg, or 3 mg/kg to the humanized mouse model. Bone marrow was collected on day 14 and the absolute number of CD34+ cells was determined by flow cytometry. Blood was also collected on day 7 and 14 and examined by flow cytometry.

Figure 10A:
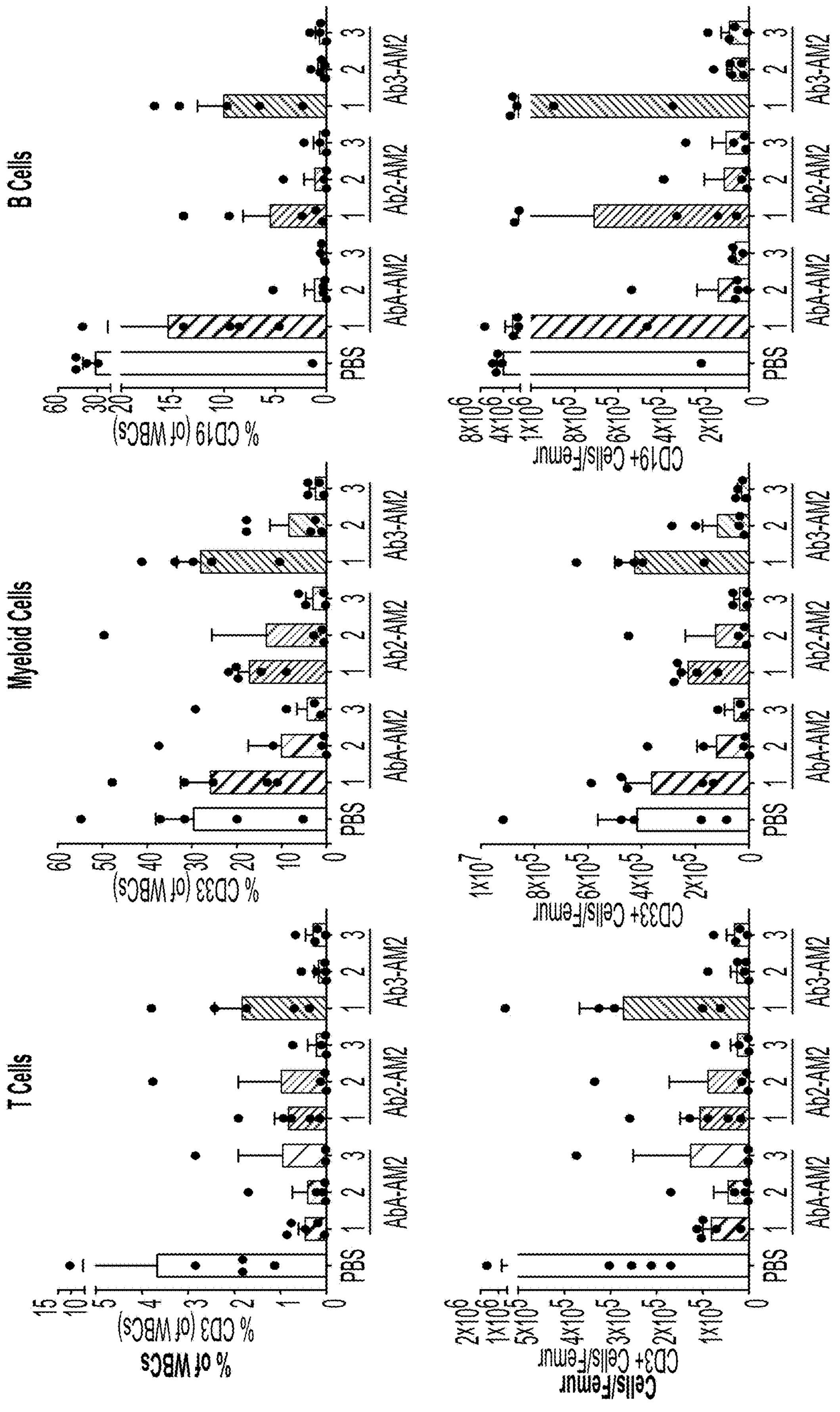
FIGS. 10A-10E graphically depicts the results of an in vivo cell depletion assay showing that short half-life anti-CD45 ADCs constructed from Ab2, Ab3, Ab5, and Ab7 selectively deplete human HSCs and immune cells in humanized NSG mice. Ab2 D265C.LALA.H435A, Ab3 D265C.LALA.H435A, Ab5 D265C.LALA.H435A, and Ab7 D265C.LALA.H435A (Fc variants of Ab2, Ab3, Ab5, and Ab7) were conjugated to amatoxin 1 (AM1) or Amatoxin 2 (AM2) to form Ab2 D265C.LALA.H435A-AM2 ("Ab2-AM2"), Ab3 D265C.LALA.H435A-AM2 ("Ab3-AM2"), Ab5 D265C.LALA.H435A-AM1 ("Ab5-AM1"), and Ab7 D265C.LALA.H435A-AM1 ("Ab7-AM1"). PBS-treated mice were assessed as a control.
Figure 10B:
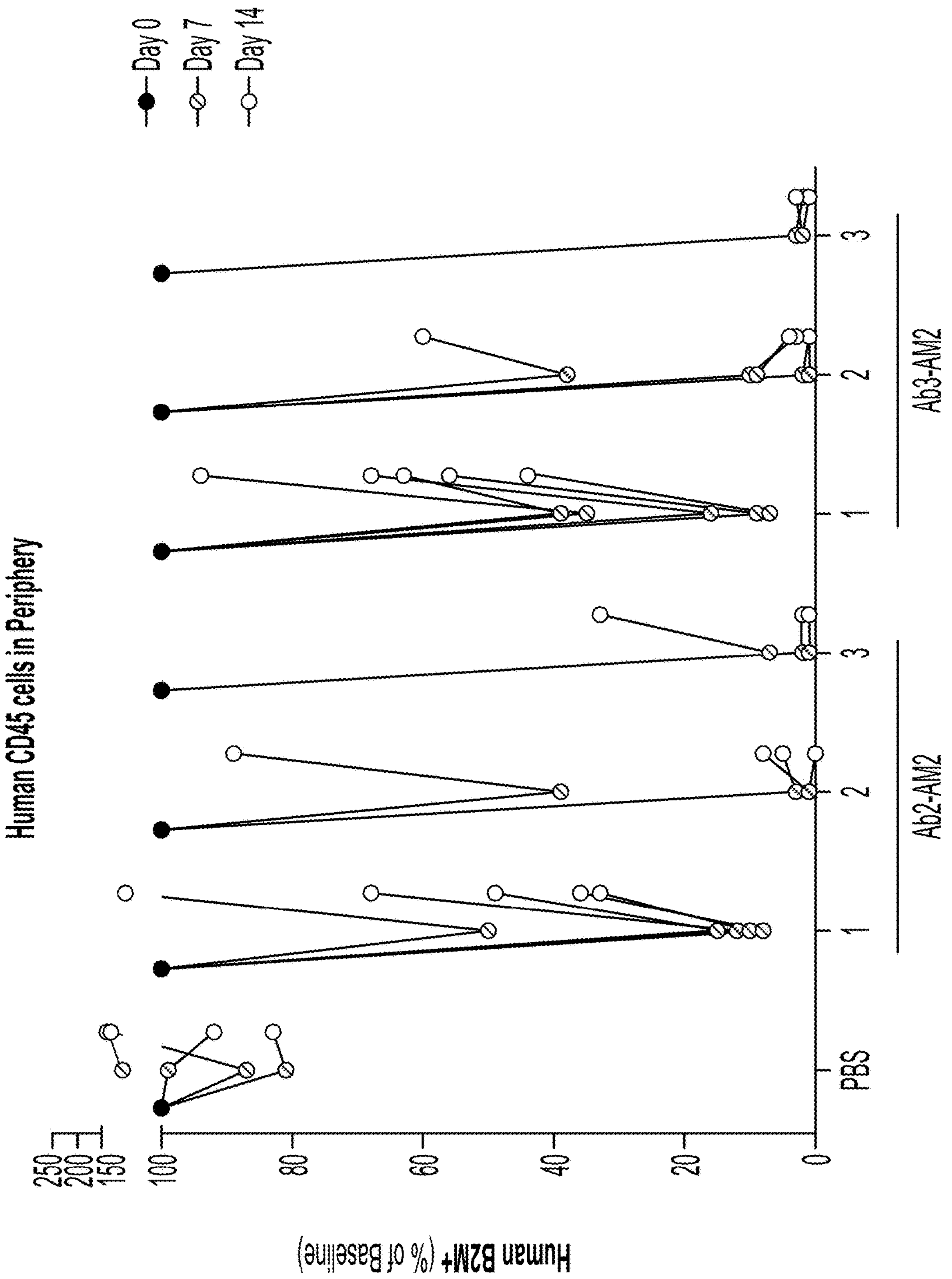
Figure 10C:
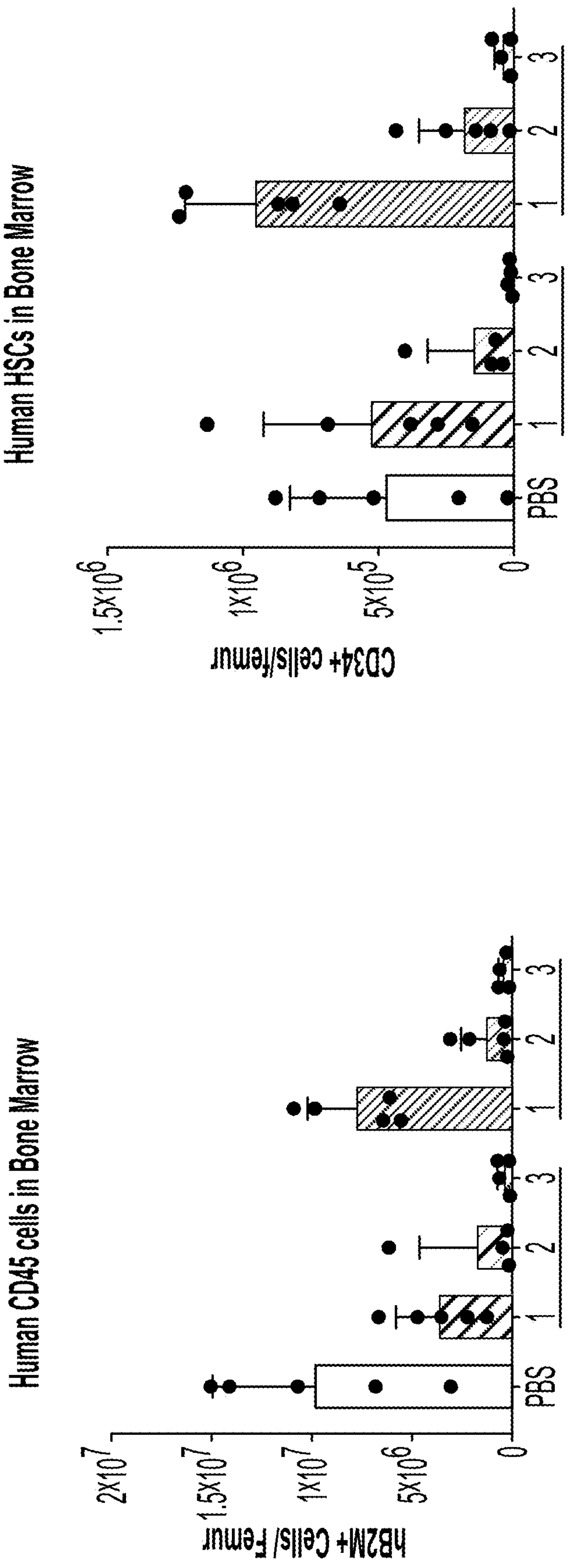
Figure 10D:
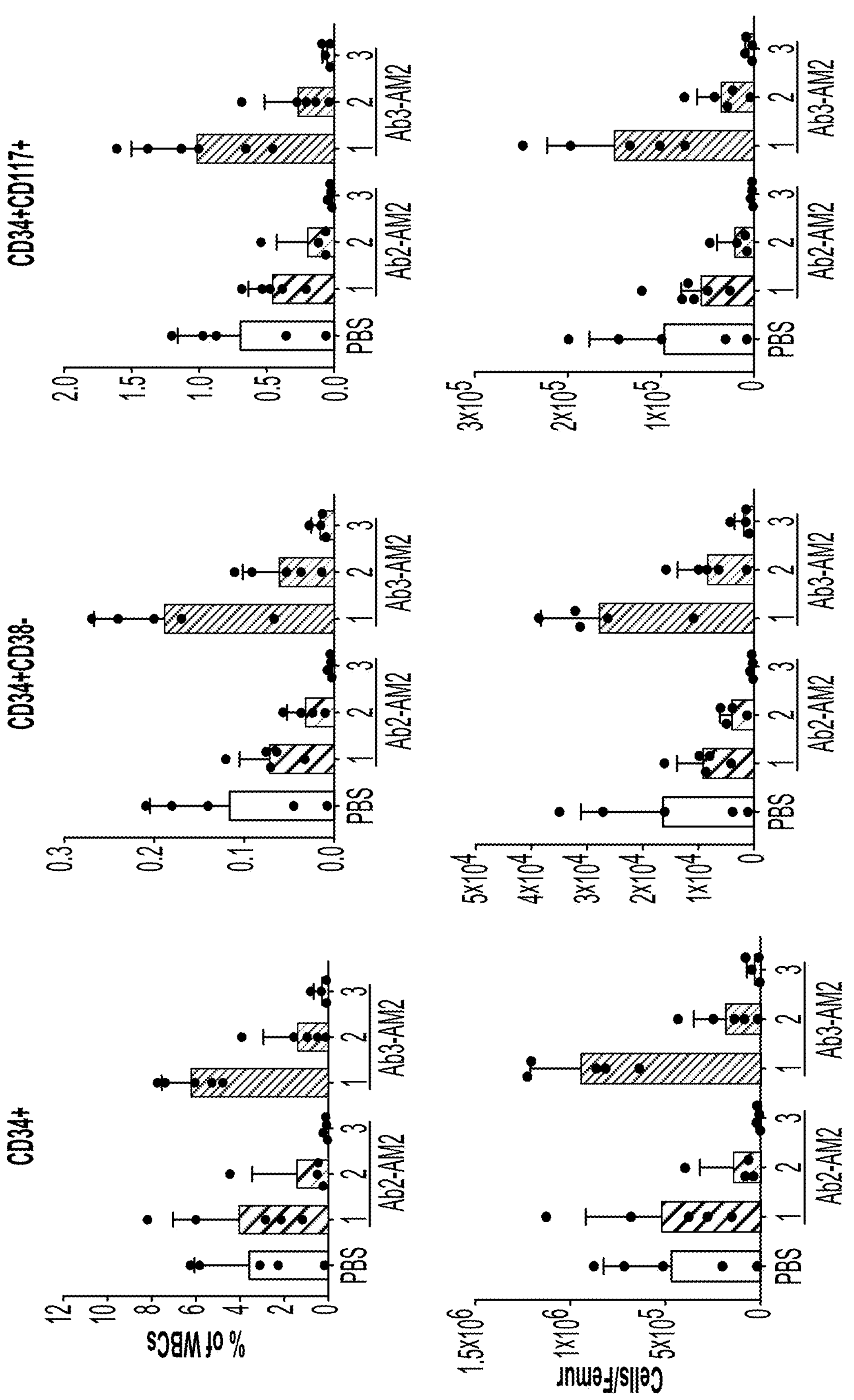
Figure 10E:
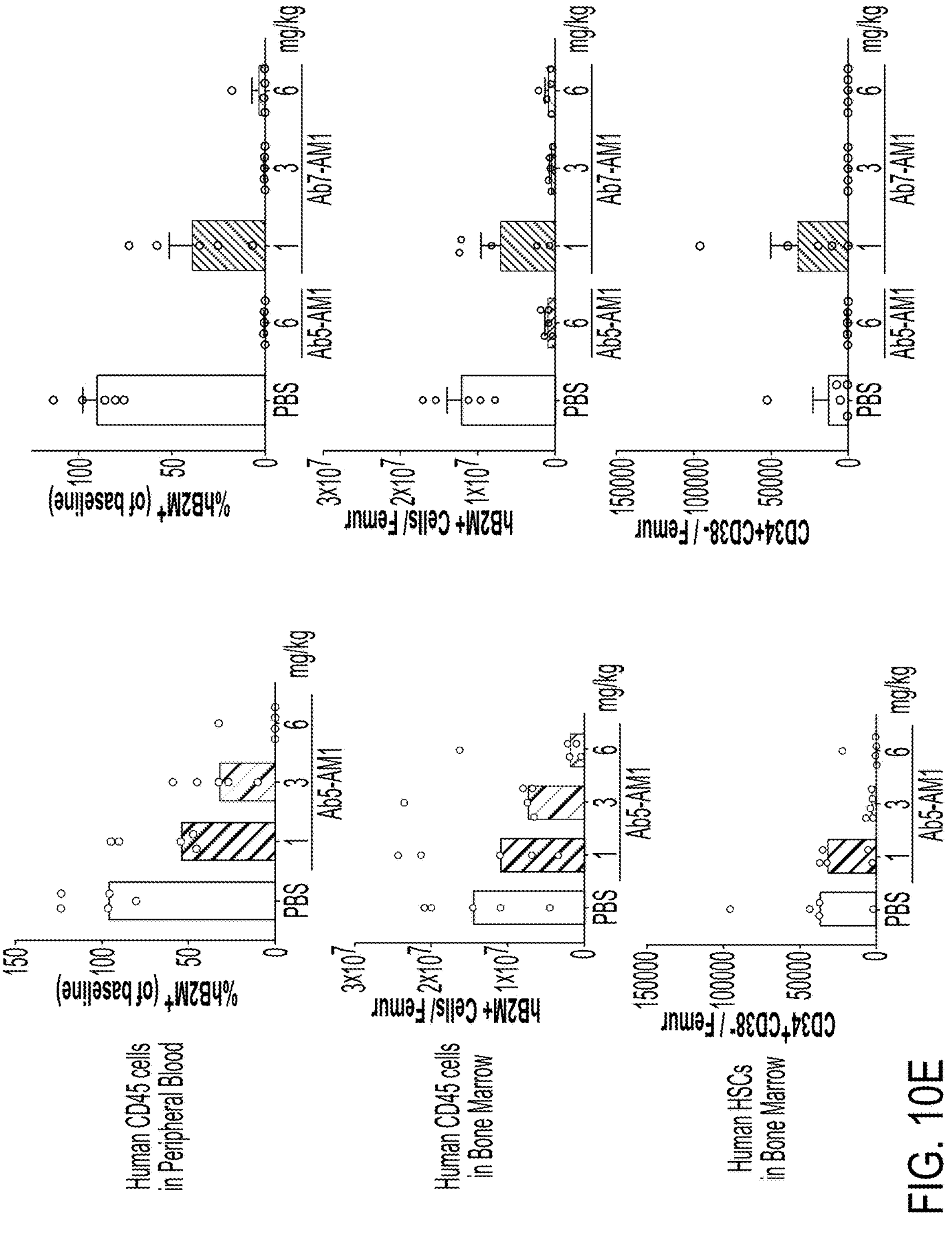

The percentage of human CD3+ T-cells, CD19+ B-cells and CD33+ myeloid cells of treated or control treated mice relative to baseline are shown in FIG. 10A. Humanized NSG mice treated with Ab2-AM2 and Ab3-AM2 showed significant depletion of human CD3+ T-cells, CD19+ B-cells, and CD33+ myeloid cells relative to baseline following a single administration of the treatment regimen (FIG. 10A). These results indicate that the Ab2-AM2 and Ab3-AM2 depleted immune cells (myeloid, T cells, and B cells).

In addition, as shown in FIG. 10B-10E, humanized NSG mice treated with a single injection of 1 mg/kg, 3 mg/kg, or 6 mg/kg of ADCs Ab2-AM2, Ab3-AM2, Ab5-AM1, or Ab7-AM1 showed significant depletion of target human CD45 cells, including human HSCs, in the peripheral blood and bone marrow, 14 days following a single administration of the ADC when compared to the control.

These results indicate that the selected short half-life anti-CD45 ADCs efficiently deplete target human cells in the periphery and bone marrow in a dose-dependent manner.

Example 13: Short Half-Life Anti-CD45-Amatoxin Antibody Drug Conjugates Effectively Deplete Non-Human Primate HSC and Immune Cells In Vivo Antibody-drug conjugates (ADCs) of select anti-CD45 antibodies described in Examples 1 and 2 (Ab4, Ab5, and Ab7) were assessed for in vivo HSC and immune cell depletion in non-human primates (NHP). In this study, Ab4, Ab5, and Ab7 having modifications in the Fc region (i.e., D265C LALA H435A amino acid substitutions in the Fc region) were conjugated to amatoxin 1 (AM1) to form ADCs (Ab4-AM1, Ab5-AM1, Ab7-AM1). The modifications in the Fc region were introduced to decrease the half-life of each antibody.

NHP HSC and immune depletion were evaluated in male cynomolgus monkeys in single ascending doses (3/group). HSC content in the bone marrow, and immune depletion in the peripheral blood and bone marrow was monitored by flow cytometry.

Figure 11A:
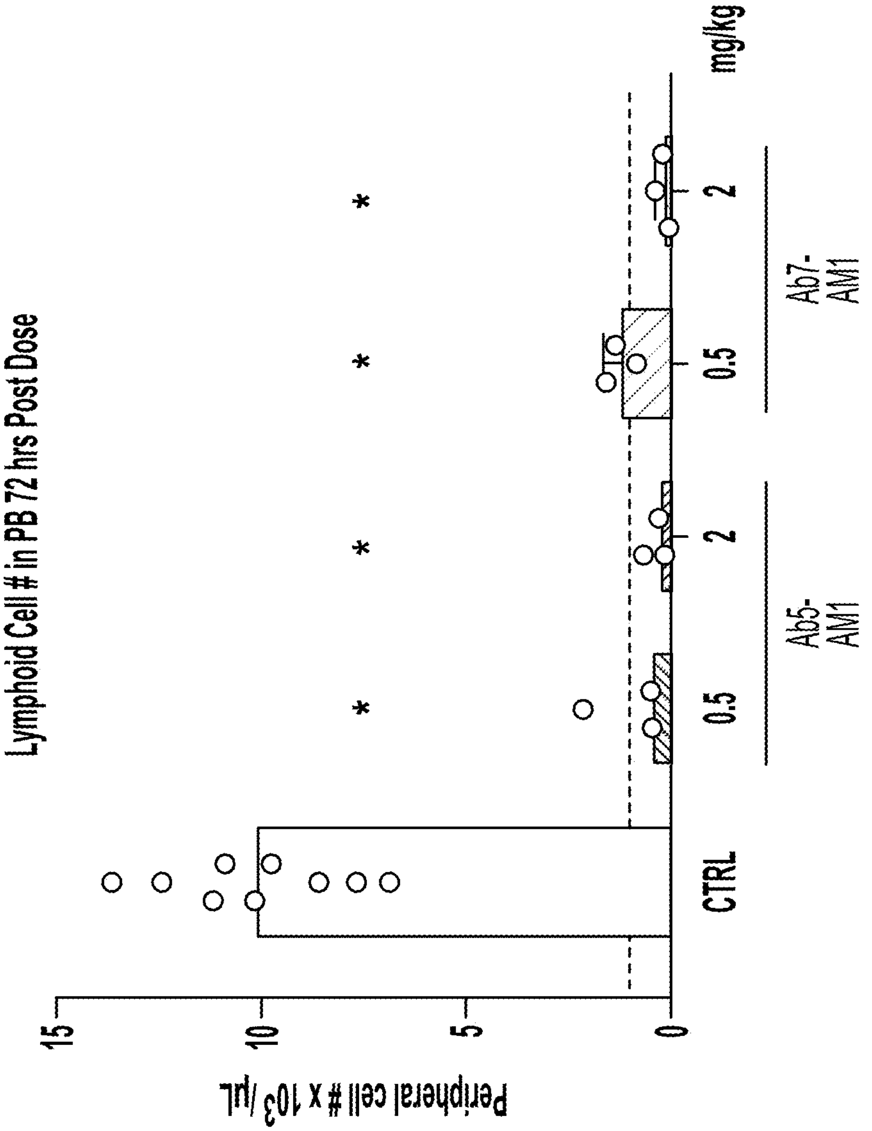
FIGS. 11A and 11B graphically depict the results of an in vivo cell depletion assay showing that short half-life anti-CD45-amatoxin ADCs constructed from Ab4, Ab5, and Ab7 effectively deplete non-human primate HSC and immune cells in vivo. Ab4 D265C.LALA.H435A, Ab5 D265C.LALA.H435A, and Ab7 D265C.LALA.H435A (Fc variants of Ab4, Ab5, and Ab7) were conjugated to amatoxin 1 (AM1) to form Ab4 D265C.LALA.H435A-AM2 ("Ab4-AM1"), Ab5 D265C.LALA.H435A-AM1 ("Ab5-AM1"), and Ab7 D265C.LALA.H435A-AM1("Ab7-AM1").
Figure 11B:
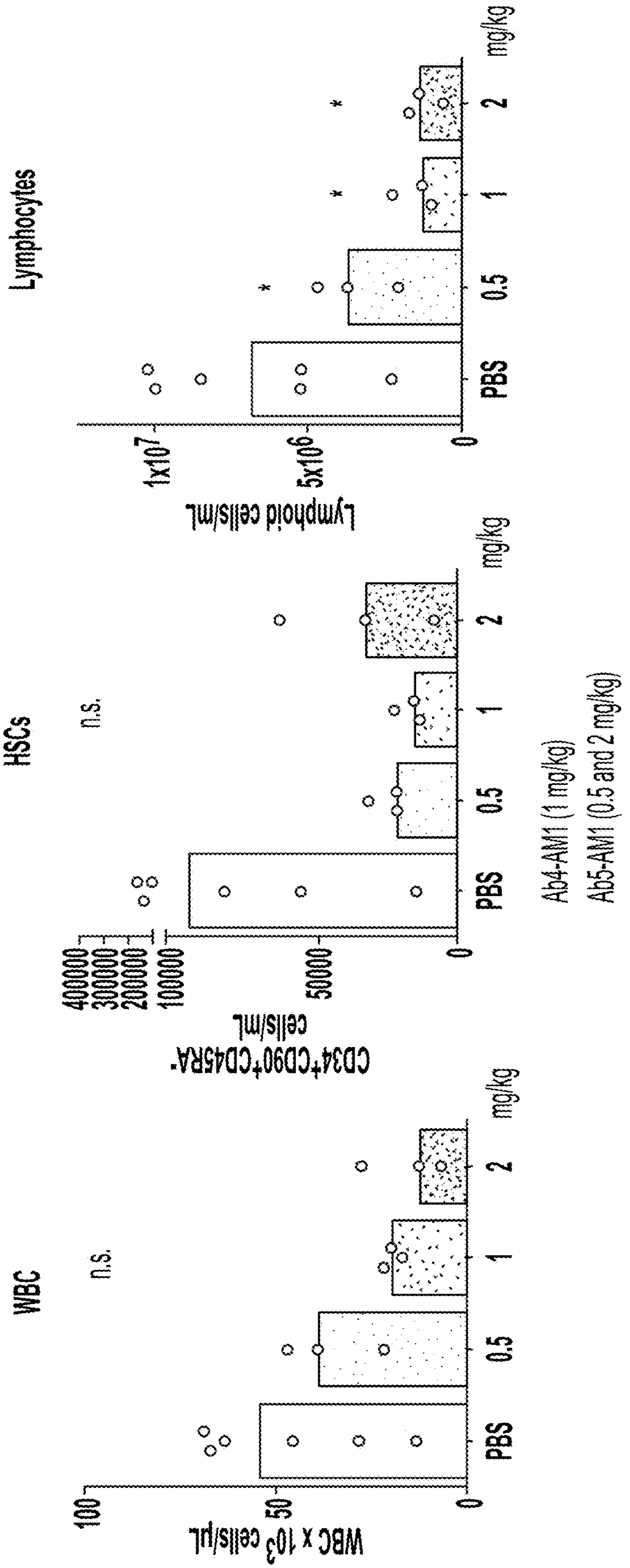

As shown in FIG. 11A, on-target, dose-dependent decreases (>90% depletion) in lymphocytes were observed in the peripheral blood at 72 hours post-dosing anti-CD45 ADCs (Ab5-AM1 and Ab7-AM1 at 0.5 mg/kg or 2 mg/kg). Further, on-target, dose-dependent decreases in WBCs, HSCs, and lymphocytes were observed in the bone marrow at Day 7 post dosing with anti-CD45 ADCs (Ab4-AM1 at 1 mg/kg and Ab5-AM1 at 0.5 and 2 mg/kg; FIG. 11B).

These results indicate that short half-life anti-CD45 ADCs Ab4-AM1, Ab5-AM1, and Ab7-AM1 exhibited potent elimination of NHP HSCs and immune cells in vivo.

Example 14: Pharmacokinetics Analysis and Serum Stability of Short Half-Life Anti-CD45 Antibody Drug Conjugates in NHP The pharmacokinetics of antibody-drug conjugates (ADCs) including an anti-CD45 antibody described in Example 1 (Ab4) was assessed in non-human primates. In this study, Ab4 having modifications in the Fc region (i.e., D265C LALA H435A amino acid substitutions in the Fc region) was conjugated to one of two amatoxins (amatoxin 1 (AM1) or amatoxin 2 (AM2)) to form ADCs (Ab4-AM1, Ab4-AM2). The modifications to the Fc region were introduced to decrease the half-life of the antibody.

A commercially available ELISA kit was adapted to measure plasma drug concentration in male cynomolgus monkeys. Briefly, plates were coated with anti-human IgG capture antibody. Samples and standards (ADCs) were diluted within the dynamic range of the assay in diluent and incubated on the plates. After incubation, plates were incubated with anti-IgG-HRP (to calculate total antibody) or with anti-amatoxin-HRP (to calculate ADC). Finally, the HRP substrate TMB was added followed by a stop solution. The intensity of the color was directly proportional to the amount of bound IgG (to calculate total antibody) or IgG/amatoxin (to calculate ADC).

Figure 12:
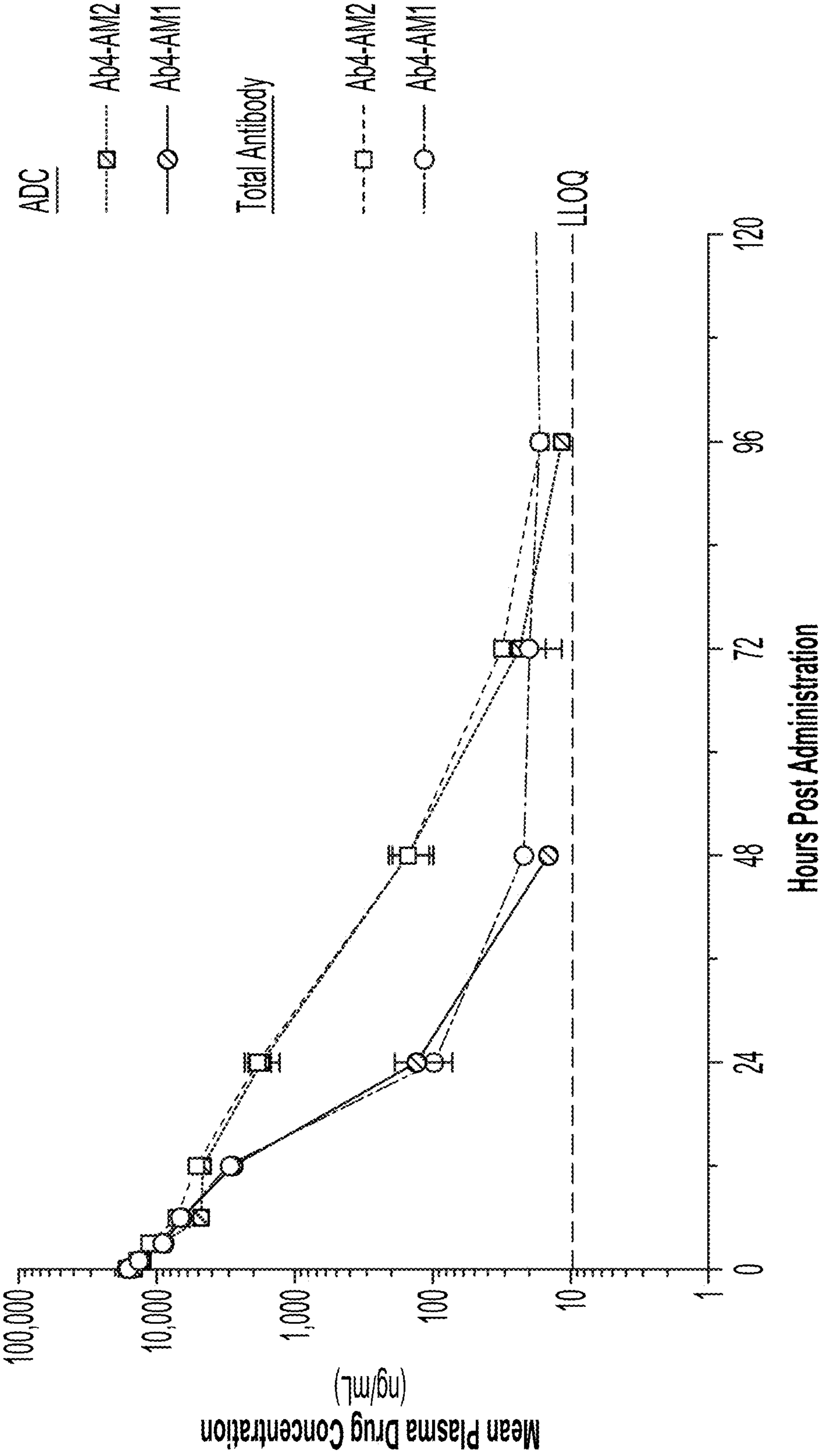
FIG. 12 graphically depicts the results of a pharmacokinetic analysis in cynomolgus macaques of short half-life anti-CD45 ADCs constructed from Ab4. Ab4 D265C.LALA.H435A, an Fc variant of Ab4, was conjugated to Amatoxin 1 (AM1) or Amatoxin 2 (AM2) to form Ab4 D265C.LALA.H435A-AM1 ("Ab4-AM1") and Ab4 D265C.LALA.H435A-AM2 ("Ab4-AM2"). The mean plasma drug concentration (y-axis) of each ADC was monitored overtime (x-axis).

As shown in FIG. 12, the overlay of the anti-amatoxin detection-based PK with the anti-IgG detection-based PK indicated the ADC was serum stable. The results of the pharmacokinetic analysis are further summarized in Table 10. The anti-CD45 ADC was rapidly cleared with a half-life of 3.2-7.4 h, indicating that the ADC had a short-half life in vivo.

TABLE 10

| PK Summary | | | | | | | |
|---|---|---|---|---|---|---|---|
| ADC | Dose (mg/kg) | AUCinf/ Dose (hr*kg*ug/ mL/mg) | Cmax/ Dose (kg*ug/ mL/mg) | Tmax (hr) | Half-life (hr) | CL (mL/hr/ kg) | Vss (mL/ kg) |
| Ab4-AM2 | 1 | 136 | 14.7 | 0.083 | 7.40 | 7.35 | 81.8 |
| Ab4-AM1 | 1 | 96.6 | 16.5 | 0.083 | 3.21 | 10.4 | 54.3 |

Example 15. Preparation of Humanized Anti-CD45 Monoclonal Antibodies

Human CD45 (specifically the extracellular region of human CD45 RO) was used to immunize rats to obtain anti-human CD45 antibodies. Cell lines expressing human CD45RO, human full length CD45 (RABC), cyno RABC and mouse CD45 RABC were created, and binding of 216 antibody clones to CD45 was assessed using flow cytometry.

Octet Bio-Layer Interferometry (BLI) binding experiments were performed to identify cross-reactive mAbs. Clones were selected based on the ability of the antibody to bind human CD45RO and CD45RABC as well as non-human primate (cynomolgus) CD45RABC. Three clones (parent clone A, parent clone B, and parent clone C) were identified as having good cross-reactivity to human and non-human primate CD45 RABC. The sequences of Parent Clones A, B, and C are described in International Publication No. WO 2020/092654 A1 (e.g., see SEQ ID NOs: 1-30 of WO 2020/092654 A1), which is hereby incorporated by reference in its entirety.

Humanization and affinity maturation was employed for each of the three selected cross-reactive mAbs. 13 humanized clones from parent clone A, 11 humanized clones from parent clone B, and 5 humanized clones from parent clone C were obtained.

Figure 13:
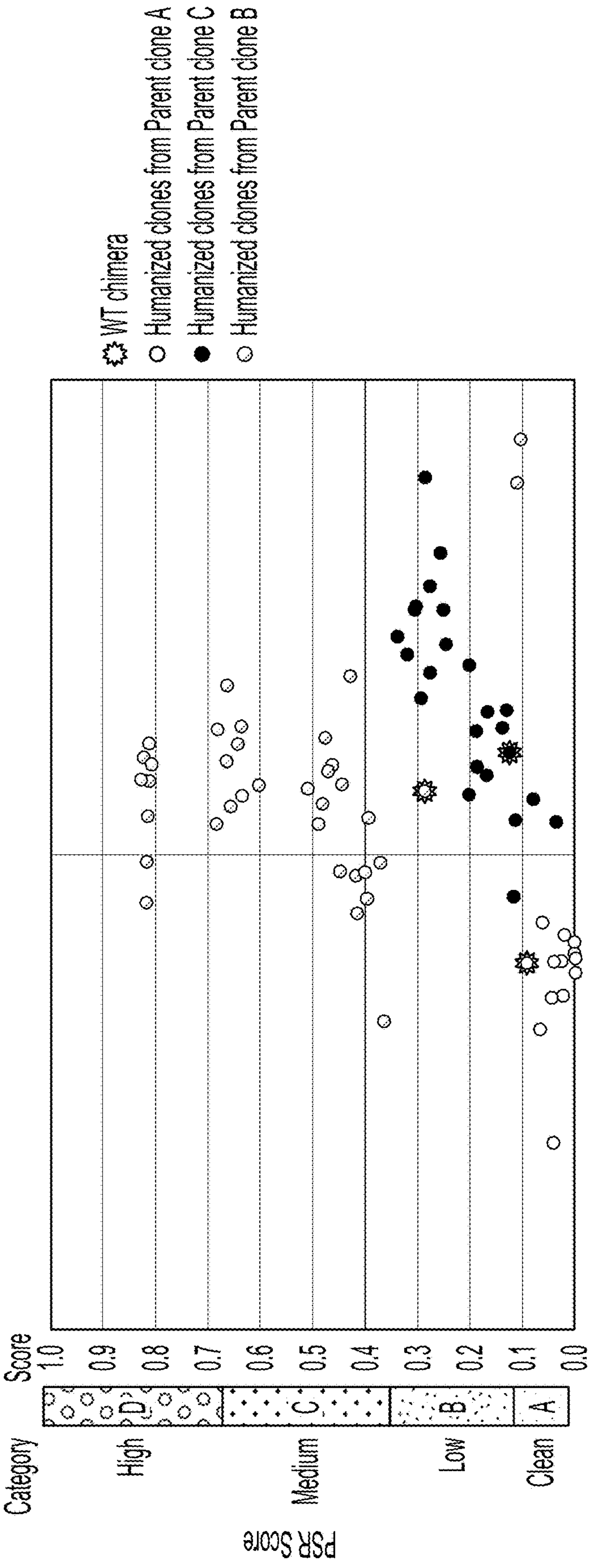
FIG. 13 graphically depicts the results of a polyspecificity reagent (PSR) assay assessing binding of humanized clones derived from Parent Clones A, B, and C of Example 15 to a mixture of membrane and cytosolic proteins.

The humanized and affinity matured clones from parent clones A, B, and C were also tested for non-specific binding to a mixture of membrane and cytosolic proteins using a polyspecificity reagent (PSR) binding assay, in which non-specific binding of biotinylated cell lysate to each antibody was assessed. The results are described in FIG. 13. As shown in FIG. 13, humanized and affinity matured variants of parent clone A had low levels non-specific binding (as evident from the low PSR score). Humanized variants of parent clones B and C generally had higher levels of non-specific binding. However, following affinity maturation, variants were selected that had markedly reduced levels of non-specific binding, comparable to the levels observed with variants of clone A (FIG. 13).

The humanized and affinity matured clones were subsequently expressed as IgG1 antibodies and tested for binding and activity against human CD45 cells. The degree of monovalent binding of AbA, AbB, and AbC to human CD45 RABC, cynomolgus (cyno) CD45 RABC and Rhesus CD45RABC was evaluated by BLI, and binding to human and cynomolgus PBMCs was confirmed by flow cytometry.

From this screening process, 3 humanized IgG1 antibodies were selected based on desired characteristics including cross-reactivity with human and cynomolgus CD45 and low non-specific binding. These antibodies include AbA (humanized and affinity matured variant of parent clone A), AbB (affinity matured variant of parent clone B), and AbC (affinity matured variant of parent clone C). The amino acid sequences of the variable regions and CDR regions of the heavy and light chains of the 3 selected antibodies are provided in Table 27.

Example 16. In Vitro Binding Analysis of Anti-CD45 Antibodies

The humanized and affinity matured anti-CD45 antibodies described in Example 15 (AbA, AbB, and AbC) were studied to determine their binding characteristics with respect to human CD45 and their ability to cross react with cynomolgus (cyno) CD45. To assess the humanized clones for the degree of monovalent binding to human CD45 RABC and cynomolgus CD45 RABC, each of AbA, AbB, and AbC, and the respective parent clones A, B, and C was evaluated by OCTET Biolayer Interferometry (BLI).

Briefly, antibody binding studies were performed at 25° C. in 1×PBS supplemented with 0.1% w/v bovine serum albumin with a PALL FORTEBIO OCTET RED96 using biolayer interferometry (BLI). Each purified antibody was immobilized onto anti-human Fc biosensors (AHQ; PALL FORTEBIO 18-5001) and incubated with 100 nM of purified human or 300 nM of cynomolgus CD45 ectodomain.

The apparent monovalent affinity ($K_D$), apparent association rate ($K_{ON}$), and apparent dissociation rate ($K_{DIS}$ or $K_{OFF}$) were determined by local full fitting with a 1:1 binding model as calculated by FORTEBIO data analysis software version 10. $K_D$, $K_{ON}$, and $K_{DIS}$ for each antibody to purified human or cynomolgus CD45 ectodomain are shown in Table 11. As described in Table 11, binding affinities of humanized clones AbA and AbB were similar to that of the respective parent clones A and B, while humanized clone AbC showed greater than 4-fold improved affinity over the parent clone C. Each of the selected humanized antibodies AbA, AbB, and AbC was able to cross react with human and cynomolgus CD45. In addition, humanized and affinity matured antibody AbB had a significantly improved polyspecific binding score (FIG. 13), indicating that AbB had significantly lower binding to non-specific antigen relative to parent clone B.

TABLE 11

$K_D$, $K_{ON}$, and $K_{DIS}$ of the indicated IgG to human or cynomolgus CD45 ectodomain

| | Human CD45 | | | Cyno CD45 | | |
|---|---|---|---|---|---|---|
| Antibody | KD (M) | $K_{ON}$(1/Ms) | $K_{DIS}$(1/s) | KD (M) | $K_{ON}$(1/Ms) | $K_{DIS}$(1/s) |
| Parent clone A | 2.85E−09 | 5.19E+04 | 1.48E−04 | 2.41E−08 | 1.12E+04 | 2.70E−04 |
| AbA | 3.60E−09 | 5.03E+04 | 1.81E−04 | 3.41E−08 | 9.44E+03 | 3.22E−04 |
| Parent clone B | 5.12E−09 | 4.13E+04 | 2.12E−04 | 2.75E−08 | 1.34E+04 | 3.67E−04 |
| AbB | 5.46E−09 | 4.38E+04 | 2.39E−04 | 5.15E−08 | 8.16E+03 | 4.20E−04 |
| Parent clone C | 1.20E−08 | 3.31E+04 | 3.97E−04 | 1.08E−07 | 9.80E+03 | 1.06E−03 |
| AbC | 2.93E−09 | 5.08E+04 | 1.49E−04 | 2.53E−08 | 1.11E+04 | 2.82E−04 |

Example 17. In Vitro PBMC Cell Binding Activity of Anti-CD45 Antibodies

The humanized and affinity matured anti-CD45 antibodies described in Example 15 (AbA, AbB, AbC) were assessed for binding to CD45-expressing cells. To this end, primary human or cynomolgus (cyno) peripheral blood mononuclear cells (PBMCs) in cell culture media were incubated with titrated doses of the anti-CD45 antibodies overnight at 37° C. Briefly, four concentration points of the anti-CD45 antibodies were used, with highest concentration of 6.25 nM that was titrated 4-fold down to establish a log phase dose response curve. Bound anti-CD45 antibody was detected with fluorescently labeled AF488 anti-human IgG secondary antibody using flow cytometry. IC50s were determined by fitting the data using GRAPHPAD PRISM. An Isotype IgG was used as a control.

Figure 14:
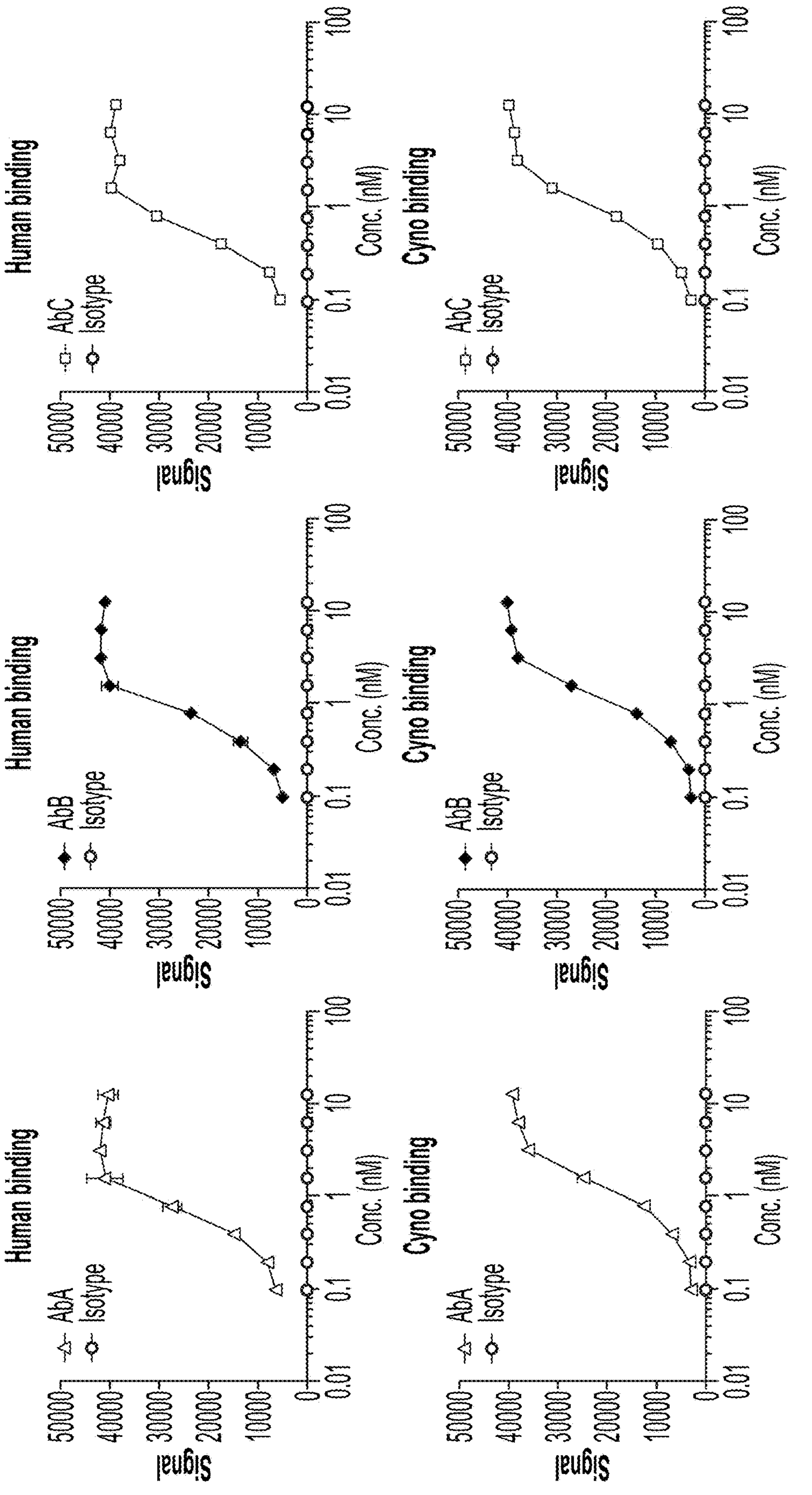
FIG. 14 graphically depicts the results of an in vitro cell binding assay to assess binding of anti-CD45 antibodies AbA, AbB, and AbC (identified in Example 15) to human PBMC cells and cynomolgus ("cyno") PBMC cells.

Using the above method, PBMC binding activity of humanized clones AbA, AbB, and AbC was determined. The results are described in FIG. 14 and Table 12. As described in FIG. 14, compared to the isotype control, humanized clones AbA, AbB, and AbC showed strong binding to both human PBMCs and cyno PBMCs. Also, as described in FIG. 14 and Table 12, AbA, AbB, and AbC bound CD45 at low nM $EC_{50}$ across each cell type, thus demonstrating cross-reactive binding to human and cynomolgus CD45 on live cells. However, an overall higher binding signal was observed in human over cyno PBMCs.

TABLE 12

Binding of humanized clones to human or cynomolgus PBMC

| Antibody clone | Cyno EC50 (nM) | Human EC50 (nM) | Fold Cyno vs Human |
|---|---|---|---|
| AbA | 1.25 | 0.58 | 2.2 |
| AbB | 1.12 | 0.67 | 1.7 |
| AbC | 0.88 | 0.51 | 1.7 |

Next, using the above method, binding of the humanized clones AbA, AbB, and AbC to human and cyno PBMCs was compared to that of the respective parental clones A, B, and C. As shown in Table 13, binding of humanized clones AbA and AbB to human and cyno PBMCs was similar to that of the respective parent clones A and B, while humanized clone AbC showed improvement in binding over the parent clone C.

TABLE 13

Binding of humanized clones and parent chimera to human or cynomolgus PBMC

| Antibody | Human EC50 (nM) | Cyno EC50 (nM) | Fold Cyno v/s Human |
|---|---|---|---|
| Parent clone A | 0.63 | 1.92 | 3.1 |
| AbA | 0.78 | 1.37 | 1.8 |
| Parent clone B | 0.85 | 1.52 | 1.8 |
| AbB | 0.76 | 1.42 | 1.9 |
| Parent clone C | 0.98 | 1.98 | 2.0 |
| AbC | 0.64 | 1.34 | 2.1 |
| Isotype | n/a | n/a | |

Next, using the above method, PBMC binding activity of Fc variants of the humanized clones AbA (i.e., AbA_D265C_LALA_H435A), AbB (i.e., AbB_D265_LALA_H435A), and AbC (i.e., AbC_D265C_LALA_H435A) was determined. These antibodies contain the Fc substitutions 02650, L234A/L235A ("LALA"), and H435A. The results are shown in Table 14. Compared to the isotype control, Fc variants of the humanized clones showed strong binding to human PBMCs and cyno PBMCs. Also, as shown in Table 14, Fc variants of the humanized clones bound 0045 at low nM EC50 across each cell type, thus demonstrating cross-reactive binding to human and cynomolgus 0045 on live cells. However, an overall higher binding signal was observed in human over cyno PBMCs. Thus, the results described in Table 14 indicate that 02650, L234A/L235A (LALA), and H435A modifications do not affect PBMC binding of the humanized clones.

TABLE 14

Binding of Fc variants of humanized clones to human or cynomolgus PBMC

| Antibody | Cyno EC50 (nM) | Human EC50 (nM) | Cyno/Human Ratio |
|---|---|---|---|
| AbA_D265C_LALA_H435A | 3.4 | 2.3 | 1.49 |
| AbB_D265C_LALA_H435A | 2.9 | 2.2 | 1.36 |
| AbC_D265C_LALA_H435A | 3.3 | 2.2 | 1.49 |

Example 18. Epitope Mapping of AbA

The epitope bound by AbA was mapped using crosslinking mass spectrometry. Cross-linking experiments allow direct analysis of non-covalent interaction by High-Mass MALDI mass spectrometry. By mixing a protein sample containing non-covalent interactions with a specially developed cross-linking mixture (Bich et al., *Anal Chem* 82:172-179 (2010)), it is possible to specifically detect non-covalent complex with high-sensitivity, as described in Example 5, above.

In order to determine the epitope of AbA with high resolution, a protein complex was incubated with deuterated cross-linkers and subjected to multi-enzymatic cleavage. The protein complex was an AbA variant antibody (having the same epitope as AbA) bound to human CD45. After enrichment of the cross-linked peptides, the samples were analyzed by high resolution mass spectrometry (nLC-LTQ-Orbitrap MS) and the data generated were analyzed using XQUEST and STAVROX software.

Figure 15:
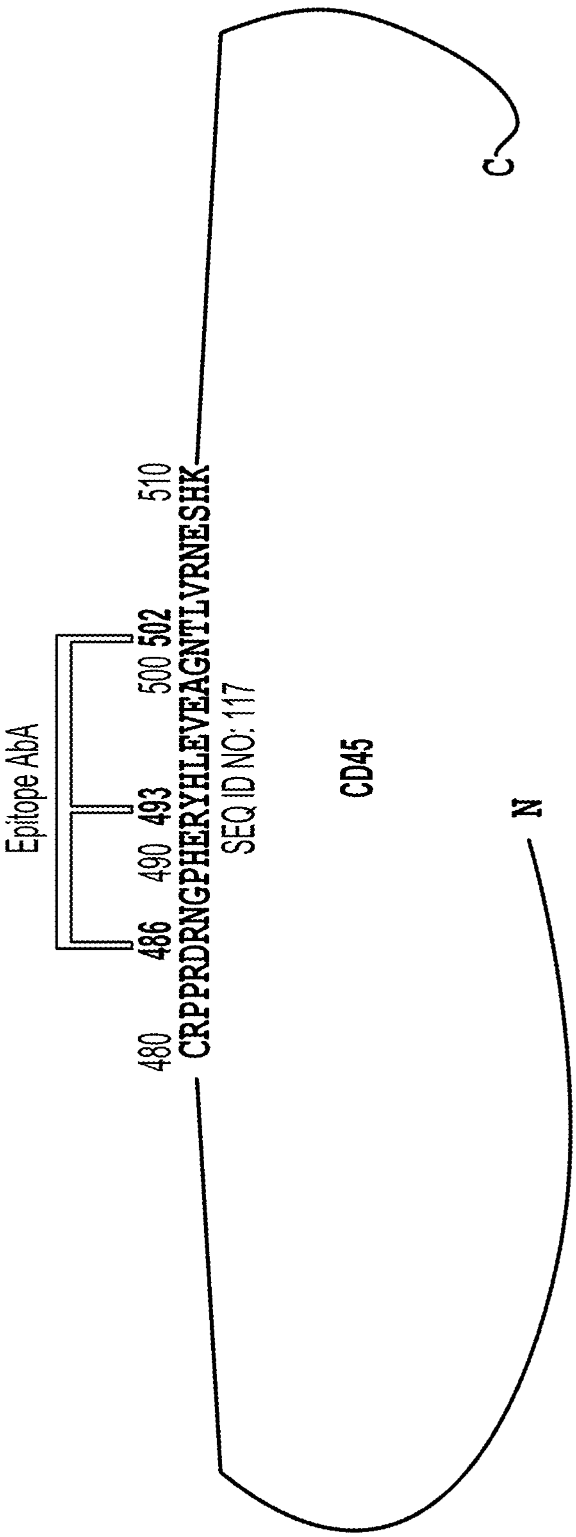
FIG. 15 depicts the results of an CD45 epitope mapping study with the anti-CD45 antibody AbA, identified in Example 15. Depicted is a schematic of the AbA interaction site on CD45, with the amino acid sequence (SEQ ID NO:117) surrounding the AbA epitope notated. Contact residues are highlighted as 486R, 493Y, and 502T, with the residue numbering referring to the human CD45 fragment represented by SEQ ID NO:113.

After Trypsin, Chymotrypsin, ASP-N, Elastase and Thermolysin proteolysis of the protein complex CD45/AbA with deuterated d0d12, the nLC-orbitrap MS/MS analysis indicated that the AbA epitope includes residues in the peptide RNGPHERYHLEVEAGNT (SEQ ID NO:118) and, in particular, interacts with amino acids on human CD45 corresponding to 486R, 493Y, and 502T of SEQ ID NO:113 (fragment of CD45 isoform corresponding to NP_002829.3). These results are illustrated in FIG. 15. FIG. 15 describes the amino acid fragment containing the epitope of AbA, in particular, region RNGPHERYHLEVEAGNT (SEQ ID NO:118).

Based on the present results, AbA interacts with the fibronectin d4 domain of CD45 which is conserved amongst alternatively spliced CD45 isoforms (e.g. RO, RA, RB, RC, RABC, etc.). Residues 493Y and 502T of the AbA epitope are conserved across human, cynomolgus, and rhesus CD45, consistent with the cross-species reactivity of AbA.

Example 19. Internalization of AbA Fc Variant (AbA_D265C_LALA_H435A) ADC

An Fc variant of AbA ("AbA_D265C_LALA_H435A") was conjugated to an amatoxin (AM1) to form an antibody drug conjugate (ADC) ("AbA_D265C_LALA_H435A-AM1"). The internalizing capacity of AbA_D265C_LALA_H435A-AM1 was assessed in an in vitro antibody internalization assay.

For this assay, the anti-CD45 ADC was conjugated to a pHAb dye. Upon internalization, the conjugated antibody/ADC moves to the acidic endosome/lysosome, where the pHAb dye can be detected by flow cytometry in the PE channel, as described above. Using this method, internalization of the AbA_D265C_LALA_H435A amatoxin ADC was assessed in vitro using human CD34+ bone marrow cells.

CD34+ human bone marrow cells were incubated on ice for two hours with a saturating concentration of the ADC for 0, 2, 24, 48, or 72 hours. The level of pHAb (as measured by gMFI) was assessed overtime. At the end of the time course, a fluorophore-labeled anti-IgG molecule was used to assess bound surface human IgG1 (hIgG1) by flow cytometry. An Isotype IgG conjugated to amatoxin 1 (Isotype-AM1), which does not bind human CD34+ cells, was included as a non-internalizing control. As the 0 h time point represents saturated binding of CD45, percent internalized ADC was calculated by comparing the geometric mean fluorescence intensity (gMFI) of the bound surface IgG at each time point to the gMFI of the same ADC at 0 hours. The results are described in FIG. 16.

Figure 16:
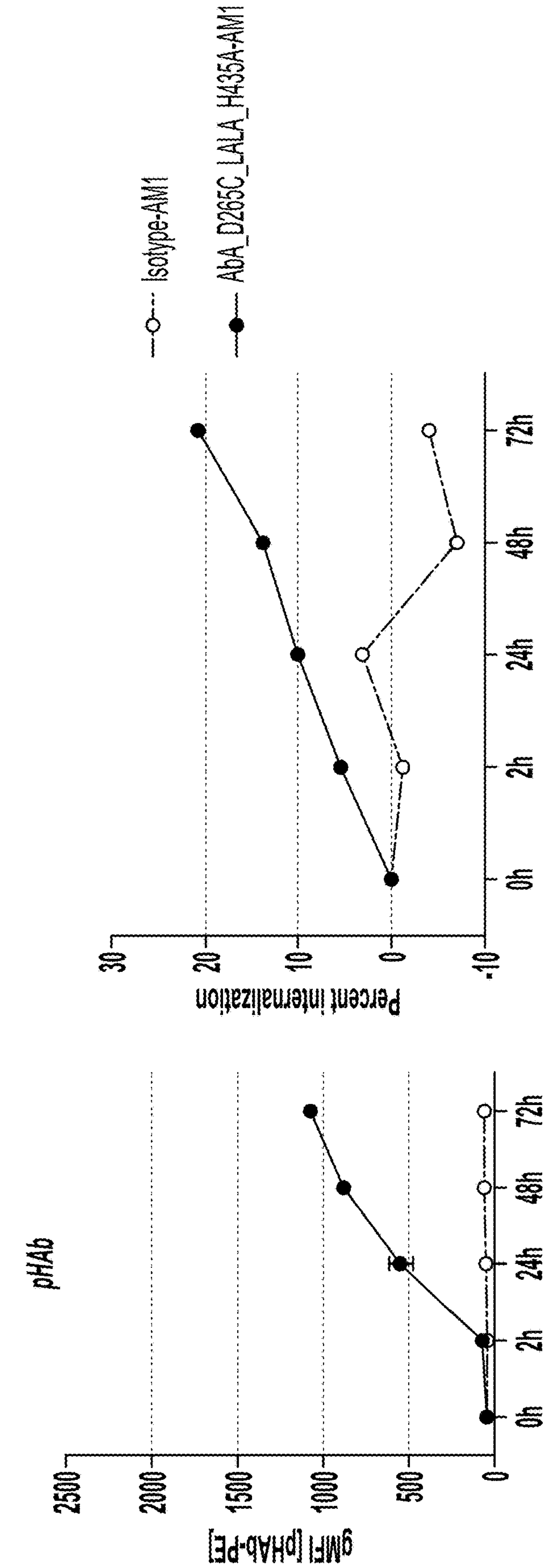
FIG. 16 graphically depicts the results of an in vitro internalization assay assessing internalization of an anti-CD45 antibody-drug conjugate (ADC) constructed from AbA in human CD34+ bone marrow cells. AbA_D265C_LALA_H435A, an Fc variant of AbA was conjugated to an amatoxin (amatoxin 1) to form AbA_D265C_LALA_H435A-AM1, an anti-CD45 ADC. The anti-CD45 ADC was conjugated to a pHAb dye that is water soluble, bright, photo-sensitive, and pH-reactive. Upon internalization, conjugated antibody can move to the acidic endosome/lysosome, where pHAb dye emits at 563 nM and can be detected by flow cytometry. Human bone marrow CD34+ cells were incubated on ice for two hours with a saturating concentration of ADC for 0, 2, 24, 48, or 72 hours. The left panel graphically depicts the level of pHAb over time. A fluorophore-labeled anti-IgG molecule was used to assess bound surface hIgG1 by flow cytometry, from which the percent of surface IgG was calculated overtime, as depicted in the right panel.

As shown in FIG. 16, the level of detected pHAb in the cells increased over time (FIG. 16, left panel), which corresponded to an increase in the percentage of ADC internalization overtime (FIG. 16, right panel). The percent internalization of AbA_D265C_LALA_H435A-AM1 ADC was markedly higher compared to that of the Isotype-AM1, indicating that AbA_D265C_LALA_H435A-AM1 was internalized by human CD34+ bone marrow cells, while the isotype control was not internalized.

Example 20. Analysis of CD45 ADCs Using In Vitro Cell Line Killing Assays

Fc variants of AbA (e.g., AbA_D265C_LALA_H435A, AbA_D265C_LALA_IHH, and AbA_S239C_LALA_IHH) were conjugated to pyrrolobenzodiazepine (PBD) or to one of two amatoxins, i.e., amatoxin 1 (AM1) or amatoxin 2 (AM2) to form the following ADCs: AbA_D265C_LALA_IHH-PBD, AbA_S239C_LALA_IHH-PBD, AbA_D265C_LALA_H435A-AM1, or AbA_D265C_LALA_H435A-AM2. The following example describes in vitro cell killing assays to test the ability of these ADCs to kill CD45-positive cancer cell lines, such as SKNO-1 (acute myeloid leukemia cell line JCRB1170), Jurkat (acute T cell leukemia cell line, ATCC No. TIB-152), and REH-1 (B cell non-Hodgkin's lymphoma cell line, ATCC No. CRL-3004) in vitro.

For the in vitro killing assays using SKNO-1, Jurkat, and REH-1 cell lines, the cells were grown according to ATCC guidelines. More specifically, cells were cultured (in RPMI-1640 (1×) medium supplemented with 10% FBS and 1% Pen-Strep) for seven days in the presence of CD45 ADC (e.g., AbA_D265C_LALA_IHH-PBD, AbA_S239C_LALA_IHH-PBD, AbA_D265C_LALA_H435A-AM1, or AbA_D265C_LALA_H435A-AM2) or the Isotype control-ADC, i.e., IgG1 isotype conjugated to amatoxin ("Isotype-AM") or IgG1 isotype conjugated to PBD ("Isotype-PBD"). Cell viability was then measured by CELL-TITER GLO assay that measures adenosine triphosphate (ATP) content correlating to live cells. The percentage of live cells (y-axis) was measured by CELL-TITER GLO (CTG) as a function of antibody concentration (x-axis). Following the cell line killing assay, the level of cytotoxicity was quantified and IC50s were calculated using GRAPHPAD PRISM. The results are described in Table 15.

As described in Table 15, each of the various anti CD45 ADCs tested was effective at killing CD45 expressing cell lines (i.e., SKNO-1, Jurkat, and REH-1 cell lines) in vitro.

TABLE 15

In vitro cell line killing assays

| | SKNO-1 (Passage 8.1) | | Jurkat | | REH (Passage 6.1) | |
|---|---|---|---|---|---|---|
| ADCs | IC50 | % Efficiency | IC50 | % Efficiency | IC50 | % Efficiency |
| AbA_D265C_LALA_IHH-PBD | 8.185E−10 | 99.0 | 3.60E−10 | 99.8 | 4.20E−11 | 100.0 |
| AbA_S239C_LALA_IHH-PBD | 7.142E−10 | 99.2 | 3.70E−10 | 99.6 | 4.0E−11 | 99.9 |
| Isotype-PBD | 9.624E−09 | 99.5 | 1.20E−08 | 98.9 | 3.80E−09 | 99.8 |
| AbA_D265C_LALA_H435A-AM2 | 6.071E−10 | 98.8 | 4.2E−10 | 99.5 | 1.20E−10 | 99.8 |
| AbA_D265C_LALA_H435A-AM1 | 1.365E−09 | 75.0 | 1.10E−09 | 98.0 | 3.60E−10 | 98.6 |
| Isotype-AM | | | | −17.0 | | −1.7 |
| Blank | | | | −15.3 | | −5.1 |

Example 21. Analysis of CD45 ADCs Using In Vitro PBMC Killing Assays

Antibody-drug conjugates (ADCs) of the humanized anti-CD45 antibodies described in Example 15 were assessed for the ability to kill primary peripheral blood mononuclear cells (PBMCs) in vitro.

An Fc variant of AbA, AbA_D265C_LALA_H435A, was conjugated to amatoxins AM1 or AM2 to form ADCs AbA_D265C LALA H435A-AM1 and AbA_D265C LALA H435A-AM2. The ability of these ADCs to kill primary human or cynomolgus PBMCs was assessed by in vitro PBMC killing assays. PBMCs are CD45 expressing cells consisting of a heterogeneous cell population of lymphocytes (T cells, B cells, Natural Killer cells) and monocytes. For in vitro killing assays using human or cynomolgus PBMCs, the PBMCs were cultured in RPMI-1640 medium with 10% fetal bovine serum for seven days in the presence of the CD45 ADCs, or an Isotype control-ADC, i.e., an antibody of IgG1 isotype conjugated to AM1 ("Isotype-AM1") or IgG1 isotype conjugated to AM2 ("Isotype-AM2"). Cell viability was then measured by CELL-TITER GLO (CTG) assay. Following the PBMC killing assay, the level of cytotoxicity was quantified and IC50s were calculated using GRAPHPAD PRISM. The results are described in FIGS. 17A-17B, Table 16 and Table 17.

Figure 17A:
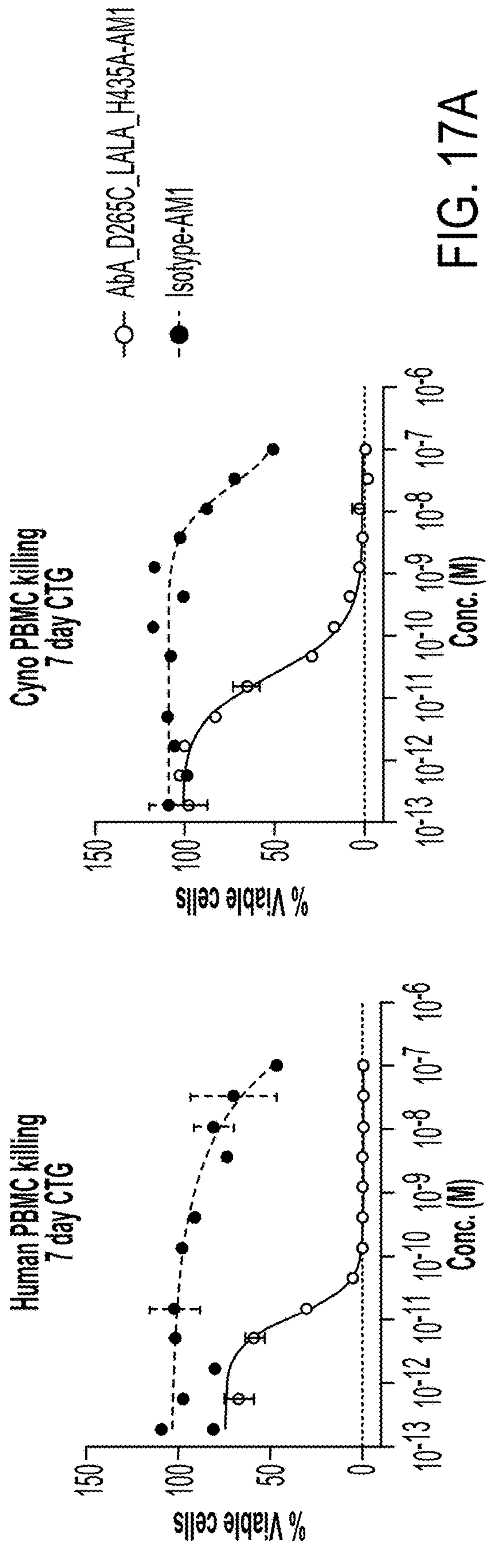
FIGS. 17A and 17B graphically depict the results of in vitro primary cell killing assays showing that anti-CD45 ADCs constructed from AbA were effective at killing primary human or cynomolgus peripheral blood mononuclear cells (PBMCs) in vitro. AbA_D265C_LALA_H435A, an Fc variant of AbA was conjugated to one of two amatoxins, i.e., amatoxin 1 (AM1) or amatoxin 2 (AM2) to form AbA_D265C_LALA_H435A-AM1 or AbA_D265C_LALA_H435A-AM2. Human PBMCs were cultured for seven days in the presence of the indicated CD45-AM conjugate (AbA_D265C_LALA-H435A-AM1 (FIG. 17A) or AbA_D265C_LALA-H435A-AM2 (FIG. 17B)) or a control, non-targeting isotype matched-ADC ("Isotype-AM1" or "Isotype-AM2") and cell viability (y-axis) was measured by Celltiter Glo as a function of antibody concentration (x-axis).
Figure 17B:
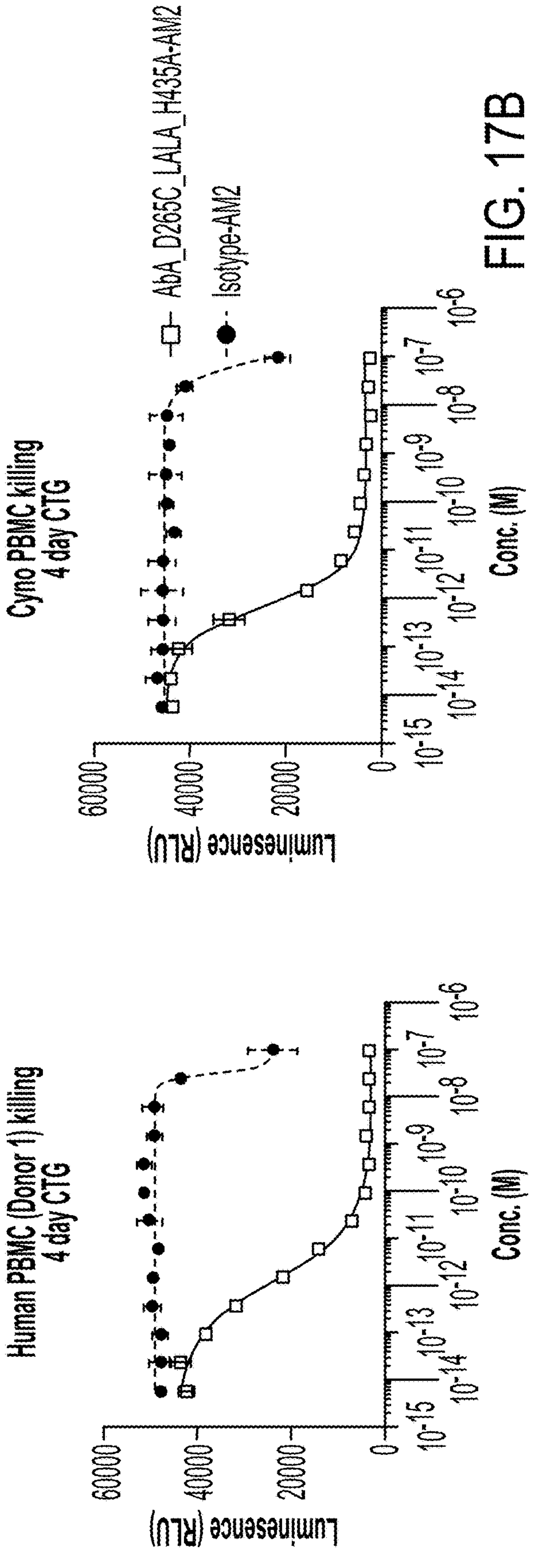

As described in FIGS. 17A-17B, Table 16 and Table 17, each of the AM1-conjugated or AM2-conjugated anti CD45 ADCs were effective at killing human and cynomolgus PBMCs in vitro. Tables 16 and 17 below provide additional data relating to quantification of the cell killing assay. As evident from FIGS. 17A-17B, Table 16 and Table 17, human and cyno PBMCs were equally sensitive to AM1-conjugated CD45 ADCs and AM2-conjugated CD45 ADCs.

TABLE 16

In vitro PBMC killing assays: ADCs conjugated to AM1

| | Human PBMCs | | Cyno PBMCs | |
|---|---|---|---|---|
| ADC | IC50 | % Efficiency | IC50 | % Efficiency |
| AbA_D265C_LALA_H435A-AM1 | 1.2E−11 | 99.0 | 2.3E−11 | 97.4 |
| Isotype-AM1 | | 33.8 | | 29.8 |

TABLE 17

In vitro PBMC killing assays: ADCs conjugated to AM2

| ADC | Cyno PBMC IC50 (M) | Human PBMC IC50 (M) |
|---|---|---|
| AbA_D265C_LALA_H435A-AM2 | 8.0E−13 | 5.0E−13 |
| Isotype-AM2 | 1.0E−7 | 1.0E−7 |

In addition, an Fc variant of AbA was conjugated to PBD (AbA_D265C_LALA_IHH-PBD), and an Fc variant of AbC was conjugated to AM1 (AbC_D265C_LALA_H435A-AM1). The ability of these ADCs, along with the ADCs described in the preceding paragraphs (AbA_D265C_LALA_H435A-AM1 and AbA_D265C_LALA_H435A-AM2) to kill primary human PBMCs and a REH cell line was assessed. The results are provided in Table 18 below.

As described in Table 18, PBD-conjugated ADCs showed higher potency against REH cells, while AM1-conjugated or AM2-conjugated ADCs showed higher potency against PBMCs.

TABLE 18

In vitro cell killing assays: ADCs conjugated to AM1, AM2, or PBD

| Humanized ADCs | Payload | REH IC50 (M) | Human PBMC IC50 (M) |
|---|---|---|---|
| AbA_D265C_LALA_H435A-AM2 | AM2 | 1.6E−10 | 3.3E−11 |
| AbA_D265C_LALA_H435A-AM1 | AM1 | 7.1E−10 | 1.2E−11 |
| AbC_D265C_LALA_H435A-AM1 | AM1 | 4.2E−10 | 6.5E−11 |
| AbA_D265C_LALA_IHH-PBD | PBD | 4.2E−11 | 5.3E−08 |

Next, antibody-drug conjugates (ADCs) of the humanized anti-CD45 antibodies described in Example 15 were tested for the ability to kill growth stimulated and unstimulated primary human PBMCs in vitro. Cryopreserved human PBMCs were thawed and split into two. Half of the cells were stimulated with CD3 CD28 DYNA BEADS at a cell to bead ratio of 2:1 and the other half of cells were left unstimulated. Both stimulated and unstimulated cells were plated into 384 well plate at a concentration of 5000 cells/well and treated with CD45 ADC (AbA_D265C_LALA_H435A-AM2) or Isotype control ADC (Isotype-AM2) at varying concentrations for 4 days, after which cell viability was measured by CELL TITER-GLO (CTG) assay. Following the cell killing assay, the level of cytotoxicity was quantified and IC50s were calculated using GRAPHPAD PRISM. Representative results are described in Table 19.

As described in Table 19, AbA_D265C_LALA_H435A-AM2 was effective at killing both unstimulated (non-dividing) and stimulated (dividing) CD45 expressing human PBMCs in vitro.

TABLE 19

In vitro PBMC killing assays: ADCs conjugated to AM1, PBD, or IGN

| | IC50 | | |
|---|---|---|---|
| CD45 ADC | Unstimulated | Stimulated | Fold difference |
| AbA_D265C_LALA_H435A-AM2 | 1.73E−11 | 5.38E−10 | 31 |

Example 22. Analysis of CD45 ADCs Using In Vitro HSC Killing Assays

Next, antibody-drug conjugates (ADCs) of select anti-CD45 human IgG antibodies described in Example 15 were tested for the ability to kill human hematopoietic stem cells (HSCs) in vitro.

Figure 18:
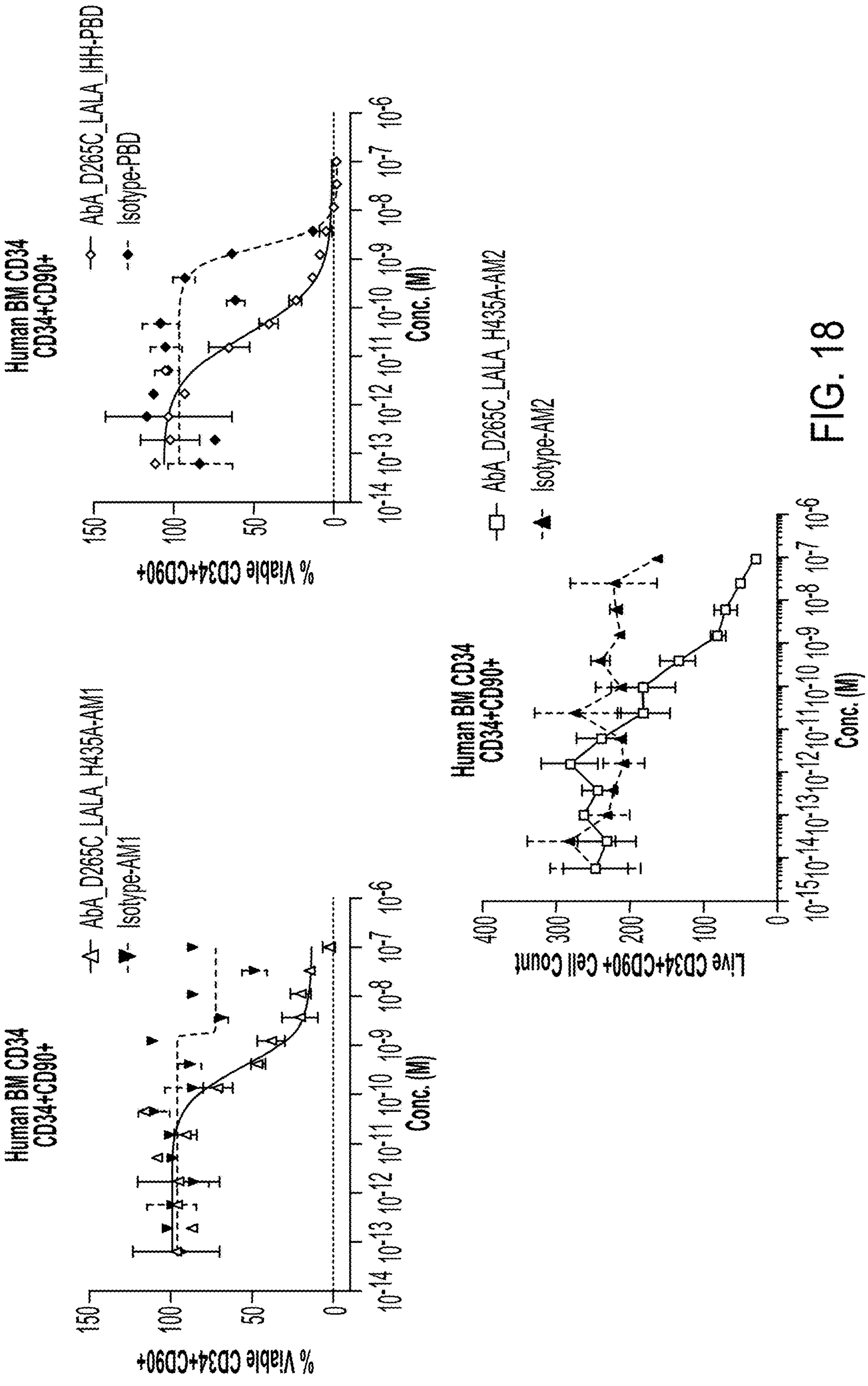
FIG. 18 graphically depict the results of in vitro primary cell killing assays showing that anti-CD45 ADCs constructed from AbA were effective at killing human hematopoietic stem cells (HSCs) in vitro. Fc variants of AbA, AbA_D265C_LALA_H435A and AbA_D265C_LALA_IHH were conjugated to amatoxin 1 (AM1), amatoxin 2 (AM2), or PBD to form AbA_D265C_LALA_H435A-AM1, AbA_D265C_LALA_H435A-AM2, or AbA_D265C_LALA_IHH-PBD. Primary human $CD34^+$ bone marrow cells were cultured for 5 days in the presence of the indicated ADCs (AbA_D265C_LALA_H435A-AM1, and AbA_D265C_LALA_IHH-PBD) or an Isotype control. Live CD34+CD90+ HSC counts (y-axis) were determined by flow cytometry as a function of antibody concentration (x-axis).

Fc variants of AbA were conjugated to AM1, AM2, or PBD to form ADCs AbA_D265C_LALA_H435A-AM1, AbA_D265C_LALA_H435A-AM2, and AbA_D265C_LALA_IHH-PBD, respectively. The ability of these ADCs to kill human bone marrow (BM) HSCs was assessed. CD34+ human BM cells were cultured in SFEM media with SCF, IL-6, FLT3, and TPO for 5 days in presence of the one of the foregoing ADCs, or in the presence of an isotype control-ADC containing an isotype control antibody coupled to AM1 (Isotype-AM1), AM2 ("Isotype-AM2"), or PBD ("Isotype-PBD"). Viability of CD34+CD90+ human BM HSCs was measured by 7-AAD. Following the cell killing assay, the level of cytotoxicity was quantified and IC50 values were calculated using GRAPHPAD PRISM. The results are described in FIG. 18, which provides representative results showing killing of human CD34+CD90+ BM HSCs by AbA ADCs conjugated to AM1, AM2 or PBD. IC50 values are provided in Table 20 and Table 21.

These results confirm that AbA ADCs effectively kill human bone marrow HSCs.

TABLE 20

In vitro BM HSC killing assay: ADCs conjugated to AM1 or PBD

| | CD34+ CD90+ | |
|---|---|---|
| ADC | IC50 | % Efficiency |
| AbA_D265C_LALA_IHH-PBD | 2.94E−11 | 99.5 |
| Isotype-PBD | 1.69E−09 | 99.7 |
| AbA_D265C_LALA_H435A-AM1 | 3.72E−10 | 86.5 |
| Isotype-AM1 | N/A | 25.2 |

TABLE 21

In vitro BM HSC killing assay: ADCs conjugated to AM2

| ADC | DAR | CD34CD90 (IC50 pM) |
|---|---|---|
| AbA_D265C_LALA_H435A-AM2 | 2.2 | 280 |
| Isotype-AM2 | 2 | |

Example 23. Analysis of CD45 ADCs Using In Vitro Primary Monocyte-Derived Macrophage (MDM) Assays Next, an antibody-drug conjugate (ADC) containing an Fc variant of AbA conjugated to AM1 (AbA_D265C_LALA_H435A-AM1) was tested for the ability to kill human monocyte derived macrophages (MDMs) in vitro. Briefly, human PBMCs were plated and differentiated using recombinant M-CSF for 7 days. These cells were then lifted, assessed for macrophage markers, and plated in a 384-well flat bottom plate at a concentration of $5\times10^3$ cell/well for C100 killing assay. The cells were then treated with 10-point dilutions of the CD45 ADC (i.e., AbA_D265C_LALA_H435A-AM1) or Isotype control-ADC, i.e., IgG1 isotype conjugated to amatoxin 1 (“Isotype-AM1”) for 7 days, after which their viability was assessed using CELL TITER GLO (CTG) assay. The results are described in FIG. 19.

Figure 19:
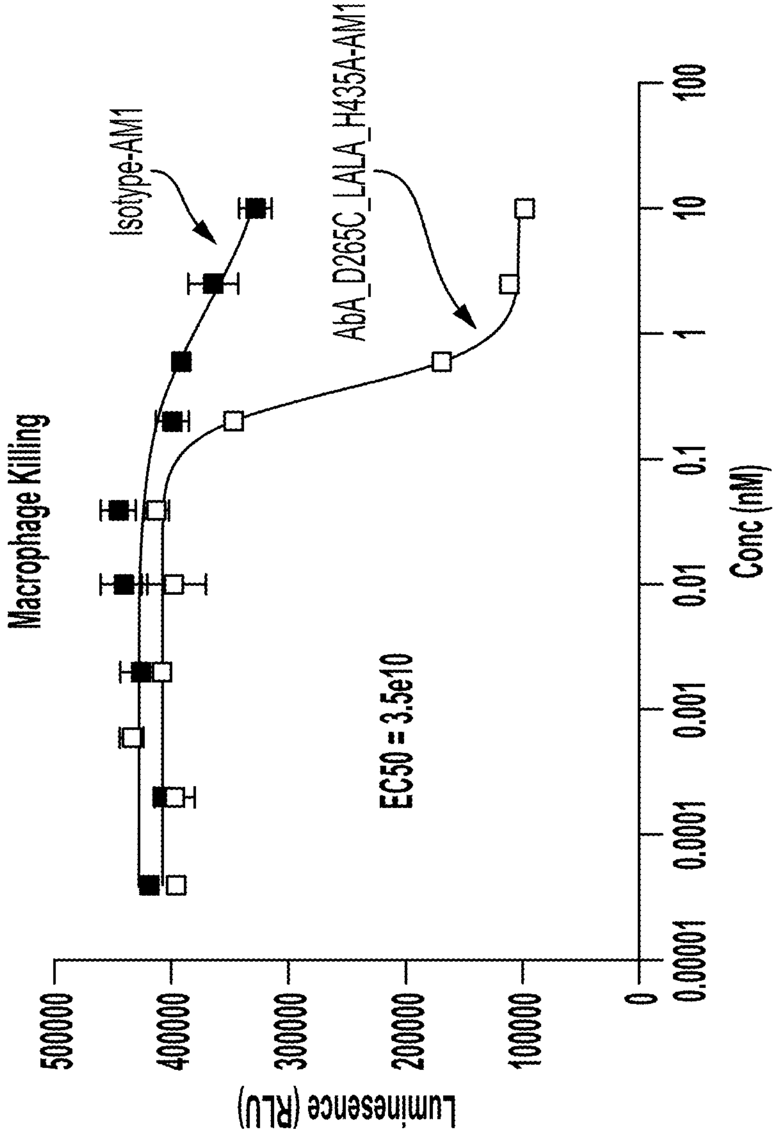
FIG. 19 graphically depicts the results of an in vitro killing assay showing that an anti-CD45 ADC constructed from AbA was effective at killing macrophages in vitro. AbA_D265C_LALA_H435A, an Fc variant of AbA was conjugated to amatoxin 1 (AM1) to form AbA_D265C_LALA_H435A-AM1, a CD45 ADC. Macrophages were cultured for six days in the presence of the ADC (AbA_D265C_LALA_H435A-AM1) or a control, non-targeting isotype matched-ADC ("Isotype-AM1") and cell viability was measured in luminescence (RLU; γ-axis) by Celltiter Glo as a function of antibody concentration (x-axis).

As described in FIG. 19, human MDMs were sensitive to killing by AbA_D265C_LALA_H435A-AM1.

Example 24. In Vivo Efficacy of an Anti-CD45-PBD ADC in a Humanized NSG Mouse Model An anti-CD45 antibody drug conjugate (ADC) comprising an antibody capable of specifically binding human CD45 (AbA) conjugated to a PBD cytotoxin (tesirine) was assessed in this Example (“CD45-PBD”). The anti-CD45 antibody of the ADC included the amino acid substitutions L234A L235A D265C and H435A in the Fc region.

Figure 20:
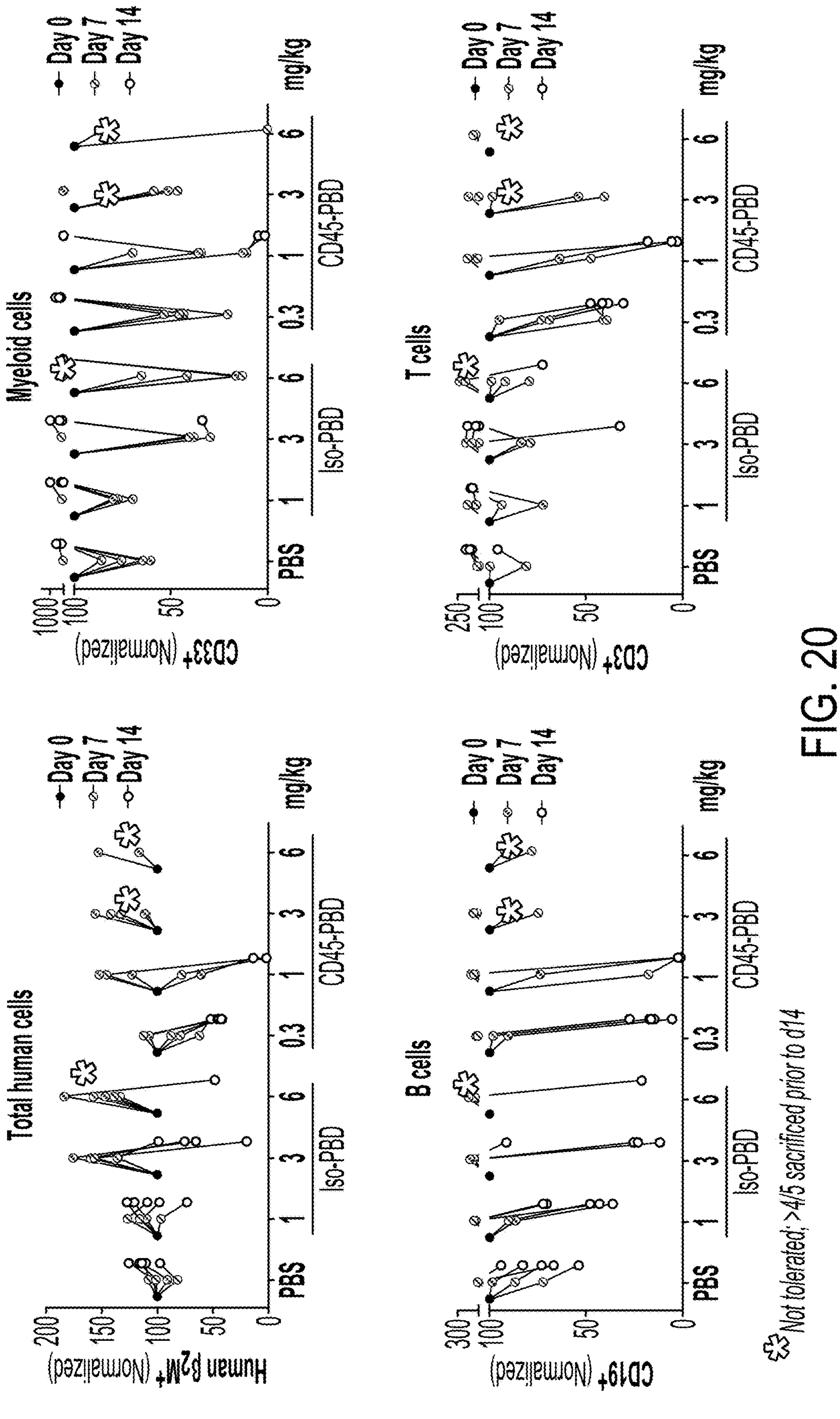
FIG. 20 graphically depicts the results of an in vivo depletion assay in humanized NSG mice treated with an anti-CD45 antibody drug conjugate (AbA-PBD), in which depletion of human cells in peripheral blood was assessed. hNSG mice were administered the indicated single doses of either vehicle (PBS), Isotype control-PBD ("Iso-PBD"), or CD45-PBD (AbA-PBD). Peripheral blood was collected at the indicated time points and evaluated for total human hematopoietic cell content ($h\beta_2M^+$), myeloid cell content ($CD33^+$), B cell content ($CD19^+$), and T cell content ($CD3^+$). The results are presented as percent depletion normalized to baseline.

CD45-PBD was assessed for its ability to deplete peripheral blood lymphocytes, bone marrow (BM) HSCs, or mature single positive (SP) thymocytes in humanized NSG mice (FIG. 20). hNSG mice were administered the indicated single doses of either vehicle (PBS), an isotype control antibody conjugated to PBD (“Iso-PBD”), or CD45-PBD. CD45-PBD was administered to mice at a single dose of 0.3 mg/kg, 1 mg/kg, 3 mg/kg, or 6 mg/kg ADC. Iso-PBD was administered to mice at a single dose of 1 mg/kg, 3 mg/kg, or 6 mg/kg ADC.

Peripheral blood was collected at Day 0, Day 7, and Day 14 and evaluated for total human hematopoietic cell content ($h\beta_2M^+$), myeloid cell content ($CD33^+$), B cell content ($CD19^+$), and T cell content ($CD3^+$). The results from the peripheral blood studies are presented in FIG. 20. These results indicate that dose-dependent depletion of human cells was achieved in peripheral blood at tolerated doses of CD45-PBD. CD45-PBD doses greater than or equal to 3 mg/kg were not tolerated.

Figure 21:
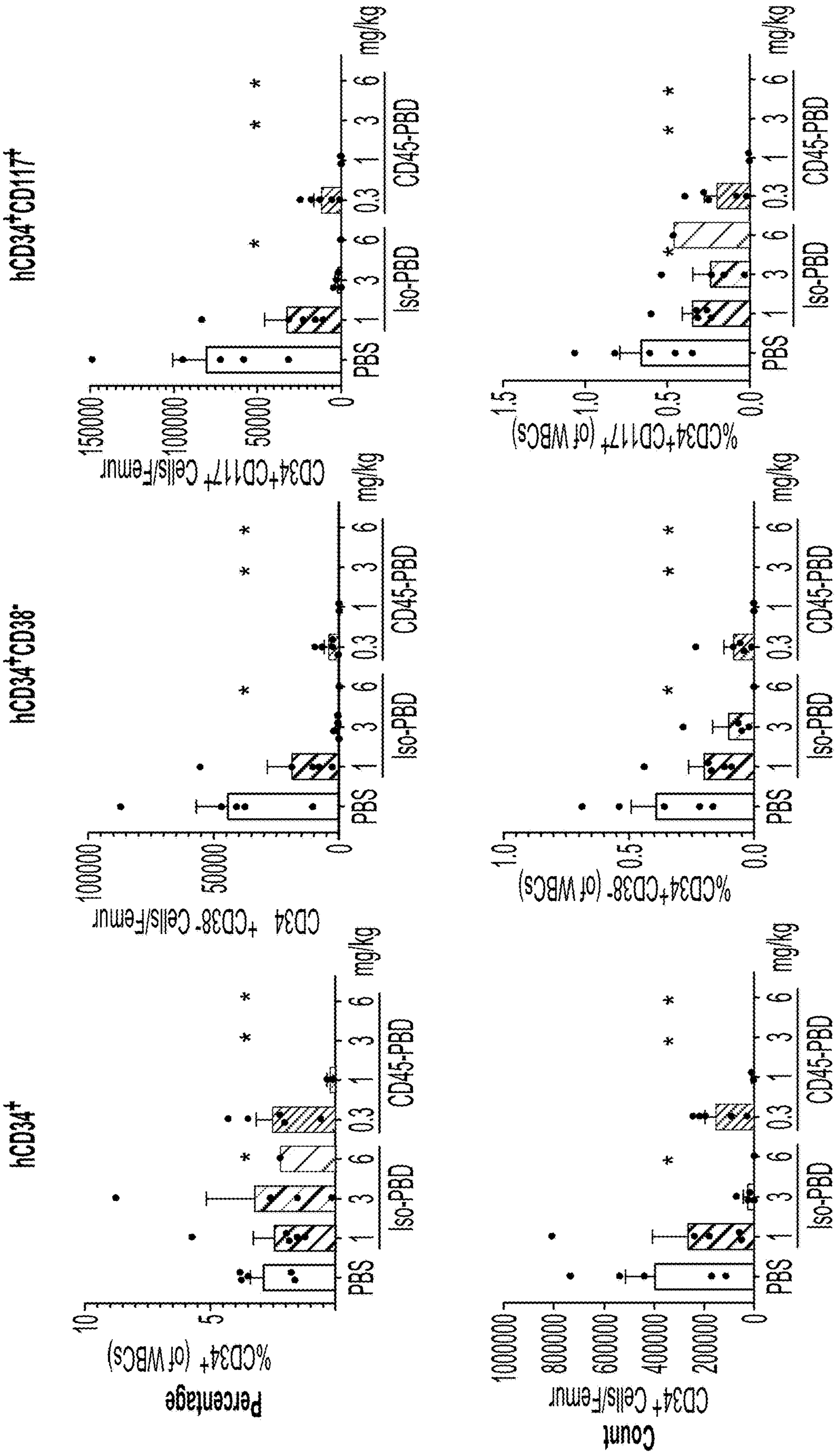
FIG. 21 graphically depicts the results of an in vivo depletion assay in humanized NSG mice treated with an anti-CD45-ADC (AbA-PBD), in which depletion of human cells in bone marrow was assessed. hNSG mice were administered the indicated single doses of either vehicle (PBS), Isotype-PBD, or CD45-PBD (AbA-PBD). BM samples were collected at Day 14 post treatment and evaluated for human progenitor cell/HSC content. The results are presented as percentage of human cells and absolute number/femur.

To assess bone marrow depletion, bone marrow samples were collected from mice at Day 14 post-treatment and evaluated for human progenitor cell/HSC content. The results from the bone marrow studies are described in FIG. 21, and are presented as the percentage of human cells (“Percentage”) or absolute number of cells per femur (“Count”). These results indicated that CD45-PBD mediated targeted, dose-dependent and deep depletion of human progenitor cells and HSCs in the bone marrow after CD45-PBD treatment. Isotype-PBD had significant platform toxicity in bone marrow at elevated doses of 3 mg/kg and 6 mg/kg.

Figure 22:
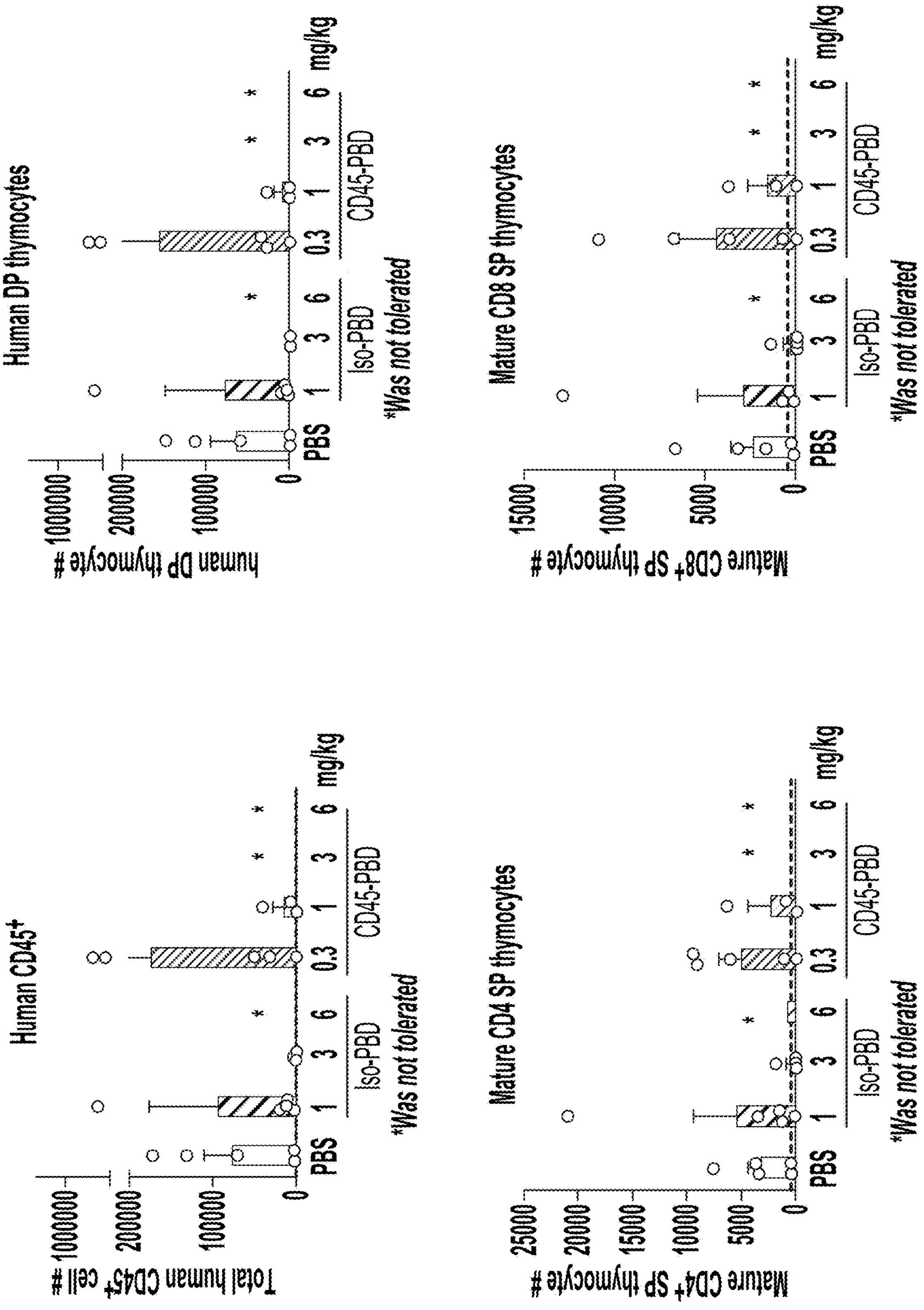
FIG. 22 graphically depicts the results of an in vivo depletion assay in humanized NSG mice treated with an anti-CD45-ADC (AbA-PBD), in which depletion of human CD45+ cells, double-positive (DP) thymocytes, mature $CD4^+$ single-positive (SP) thymocytes, or mature $CD8^+$ single-positive (SP) thymocytes was assessed 14 days post-treatment. hNSG mice were administered the indicated single doses of either vehicle (PBS), Isotype-PBD, or CD45-PBD (AbA-PBD).

Next, depletion of double positive (DP) thymocytes and mature single positive (SP) thymocytes by CD45-PBD was assessed. hNSG mice were randomized and treated with increasing doses of Isotype-PBD, CD45-PBD, or vehicle (PBS). The results of the thymocyte depletion study are shown in FIG. 22. A dose-dependent depletion of human CD45+ cells and human double positive (DP) thymocytes was observed in animals treated with CD45-PBD.

Incomplete targeted depletion of mature CD4 and CD8 SP thymocytes was observed at tolerated doses of CD45-PBD. Depletion of double positive (DP) thymocytes observed at elevated doses of isotype-PBD is consistent with the known platform toxicity of PBD.

Example 25: In Vivo Efficacy of an Anti-CD45-IGN ADC in a Humanized NSG Mouse Model An anti-CD45 antibody drug conjugate (ADC) comprising an antibody capable of specifically binding human CD45 (AbA) conjugated to an IGN cytotoxin (DGN549) was assessed in this Example (“CD45-IGN”). The anti-CD45 antibody of the ADC included the amino acid substitutions L234A L235A D265C and H435A in the Fc region.

hNSG mice were administered single doses of either vehicle (PBS), an isotype control antibody conjugated to IGN (“Iso-IGN”), or CD45-IGN. CD45-IGN was administered to mice at a single dose of 0.3 mg/kg, 1 mg/kg, 3 mg/kg, or 6 mg/kg ADC. Iso-IGN was administered to mice at a single dose of 1 mg/kg, 3 mg/kg, or 6 mg/kg ADC.

Figure 23:
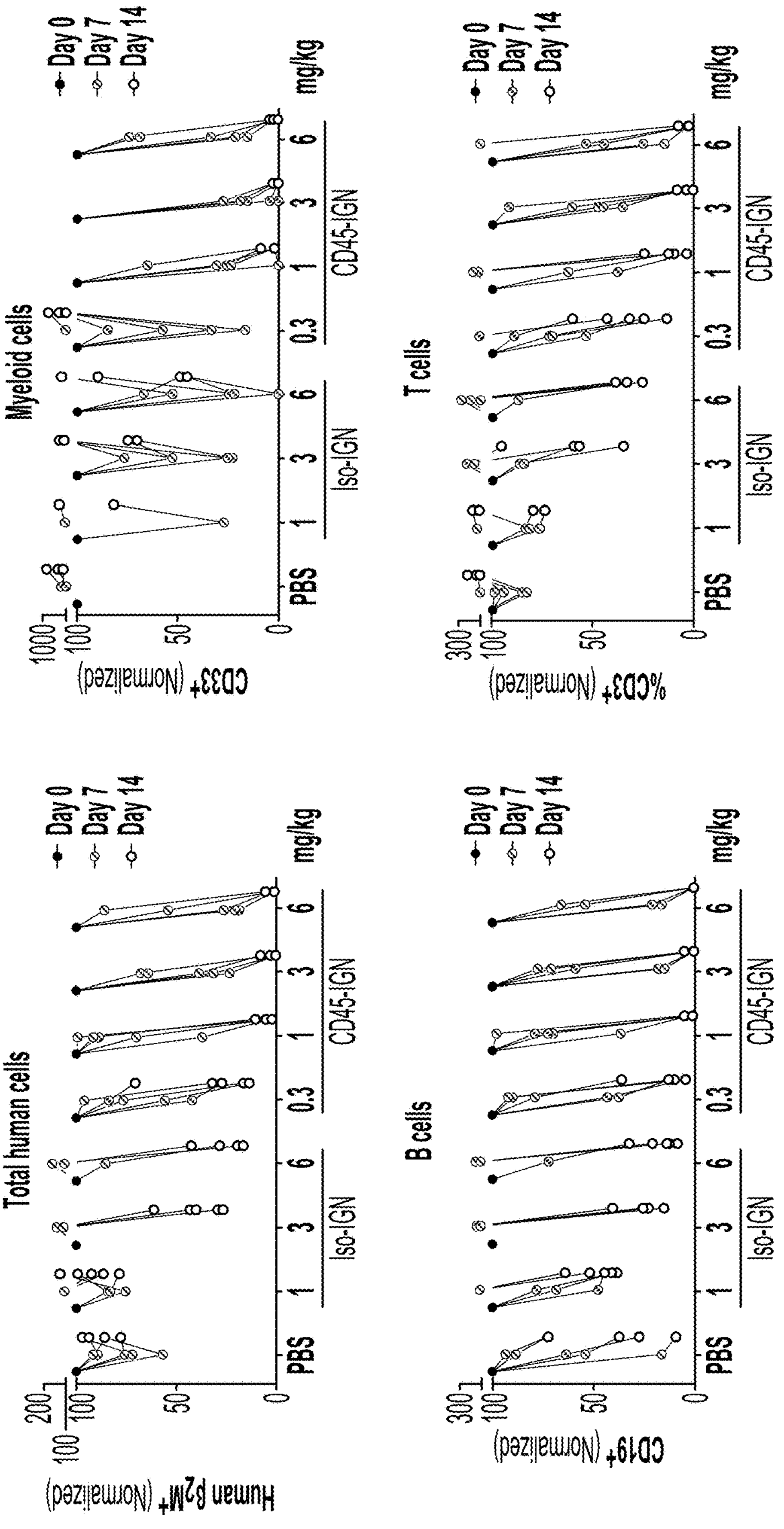
FIG. 23 graphically depicts the results of an in vivo depletion assay in humanized NSG mice treated with an anti-CD45 antibody drug conjugate (AbA-IGN), in which depletion of human cells in peripheral blood was assessed. hNSG mice were administered the indicated single doses of either vehicle (PBS), Isotype control-IGN ("Iso-IGN"), or CD45-IGN (AbA-IGN). Peripheral blood was collected at the indicated time points and evaluated for total human hematopoietic cell content ($h\beta_2M^+$), myeloid cell content ($CD33^+$), B cell content ($CD19^+$), and T cell content ($CD3^+$). The results are presented as percent depletion normalized to baseline.

Peripheral blood was collected at Day 0, Day 7, and Day 14 and evaluated for total human hematopoietic cell content ($h\beta_2M^+$), myeloid cell content ($CD33^+$), B cell content ($CD19^+$), and T cell content ($CD3^+$). The results from the peripheral blood studies are presented in FIG. 23. These results indicate that dose-dependent depletion of human cells was achieved in peripheral blood following administration of a single dose of CD45-IGN. CD45-IGN was well-tolerated at all tested doses.

Figure 24:
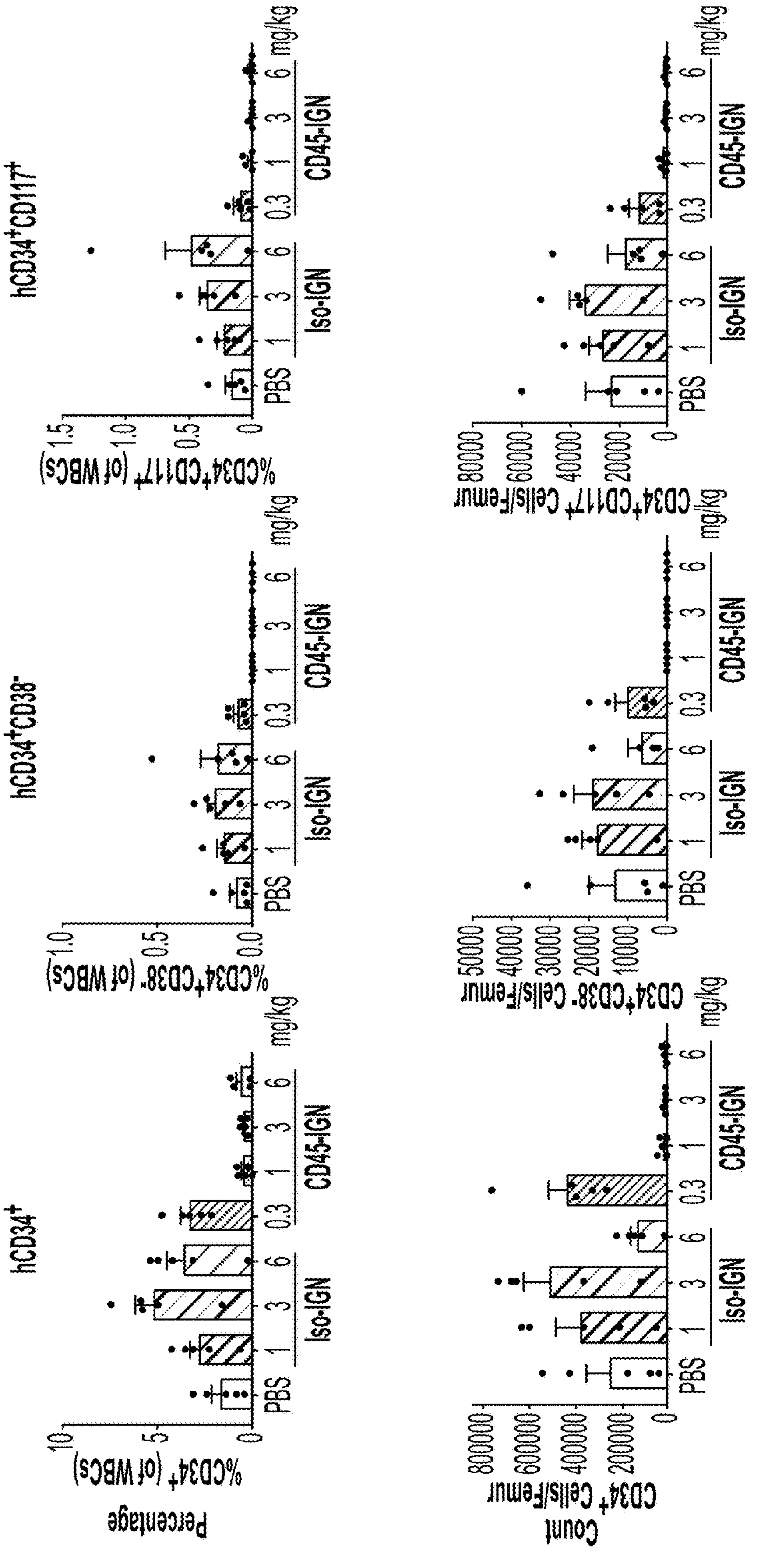
FIG. 24 graphically depicts the results of an in vivo depletion assay in humanized NSG mice treated with CD45-IGN, in which depletion of human cells in bone marrow was assessed. hNSG mice were administered the indicated single doses of either vehicle (PBS), Isotype-IGN, or CD45-IGN. BM samples were collected at Day 14 post treatment and evaluated for human progenitor cell/HSC content. The results are presented as percentage of human cells and absolute number/femur.

Bone marrow depletion was assessed by collection of bone marrow samples from mice at Day 14 post-treatment. Samples were evaluated for human progenitor cell/HSC content. The results from the bone marrow studies are described in FIG. 24, and are presented as the percentage of human cells ("Percentage") or absolute number of cells per femur ("Count"). These results indicated that CD45-IGN mediated targeted, dose-dependent and deep depletion of human progenitor cells and HSCs in the bone marrow after CD45-IGN treatment. Isotype-IGN had no significant effect at any tested dose.

Figure 25:
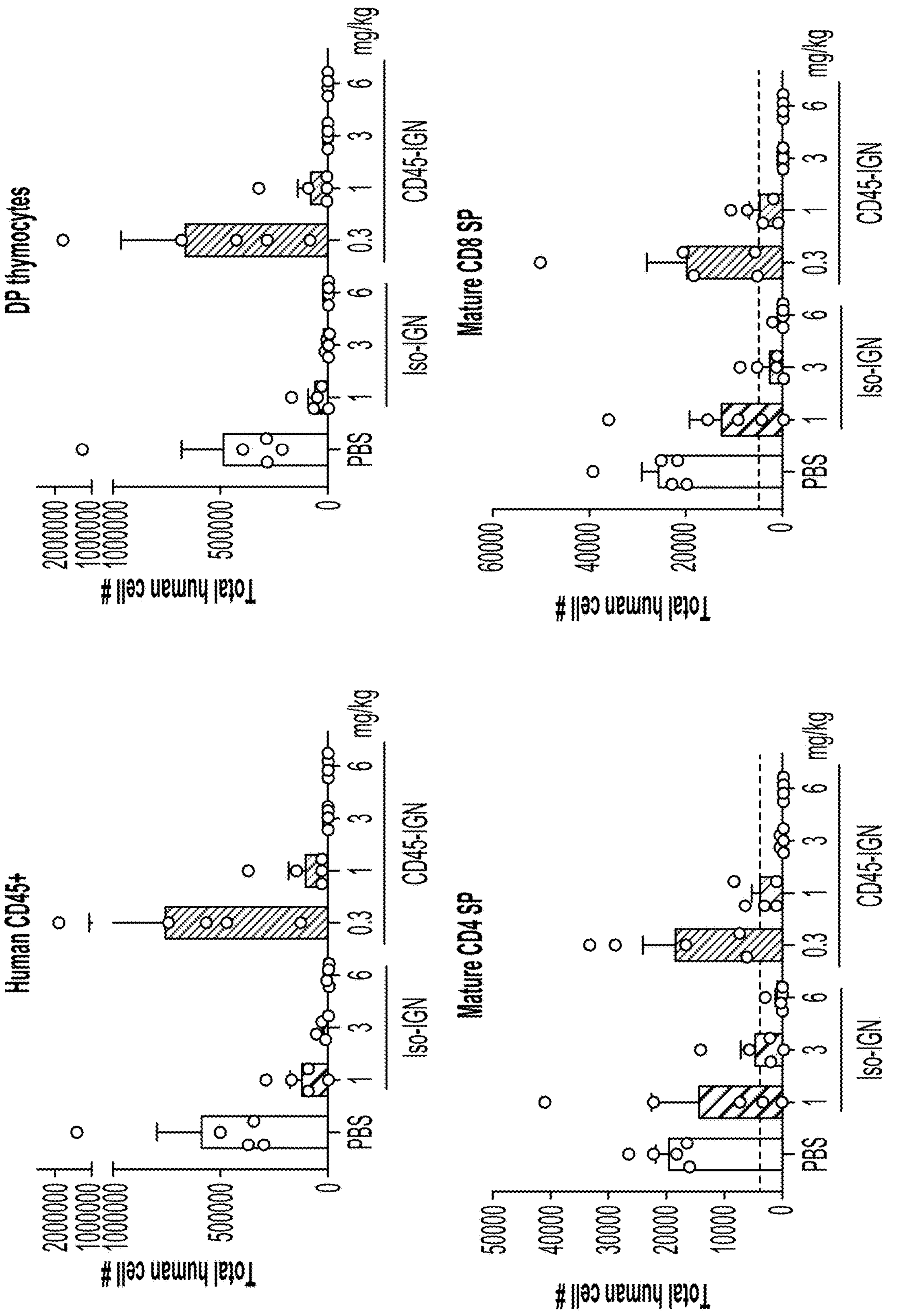
FIG. 25 graphically depicts the results of an in vivo depletion assay in humanized NSG mice treated with AbA-IGN, in which depletion of human CD45+ cells, double-positive (DP) thymocytes, mature $CD4^+$ single-positive (SP) thymocytes, or mature $CD8^+$ single-positive (SP) thymocytes was assessed. hNSG mice were administered the indicated single doses of either vehicle (PBS), Isotype-IGN, or AbA-IGN.

Depletion of double positive (DP) thymocytes and mature single positive (SP) thymocytes by CD45-IGN was also assessed. hNSG mice were randomized and treated with increasing doses of Isotype-IGN, CD45-IGN, or vehicle control (PBS). The results of the thymocyte depletion study are shown in FIG. 25. A dose-dependent depletion of human CD45+ cells and human double positive (DP) thymocytes was observed in animals treated with CD45-IGN. In addition, targeting via CD45-IGN resulted in deeper depletion of CD4 and CD8 SP thymocytes as compared with Isotype-IGN at matched doses, demonstrating that CD45-IGN ADCs achieve robust and targeted depletion of human thymocytes.

Example 26. CD45 ADCs Deplete Non-Human Primate (NHP) HSCs and Immune Cells In Vivo An anti-CD45 antibody drug conjugate (ADC) comprising an antibody capable of specifically binding human CD45 (AbA) was tested for the ability to deplete hematopoietic stem cells (HSCs) and immune cells from non-human primates (NHP) in vivo. An Fc variant of AbA containing a H435A modification in the Fc region to decrease half-life (AbA_D265C_LALA_H435A) was conjugated to amatoxin AM1 or amatoxin AM2 to form CD45 ADCs AbA_D265C_LALA_H435A-AM1 ("CD45 ADC-AM1") and AbA_D265C_LALA_H435A-AM2 ("CD45 ADC-AM2"), respectively. HSC and immune cell depletion efficacy of these CD45 ADCs was tested in NHP in vivo.

Male cynomolgus monkeys were administered a single injection of 1 mg/kg of CD45 ADC-AM1, CD45 ADC-AM2, or vehicle control (PBS). HSC content in the bone marrow, and immune cell depletion in peripheral blood were monitored by flow cytometry at the indicated times. Hematology and clinical chemistries were evaluated throughout the study. The results are described in FIG. 26.

Figure 26:
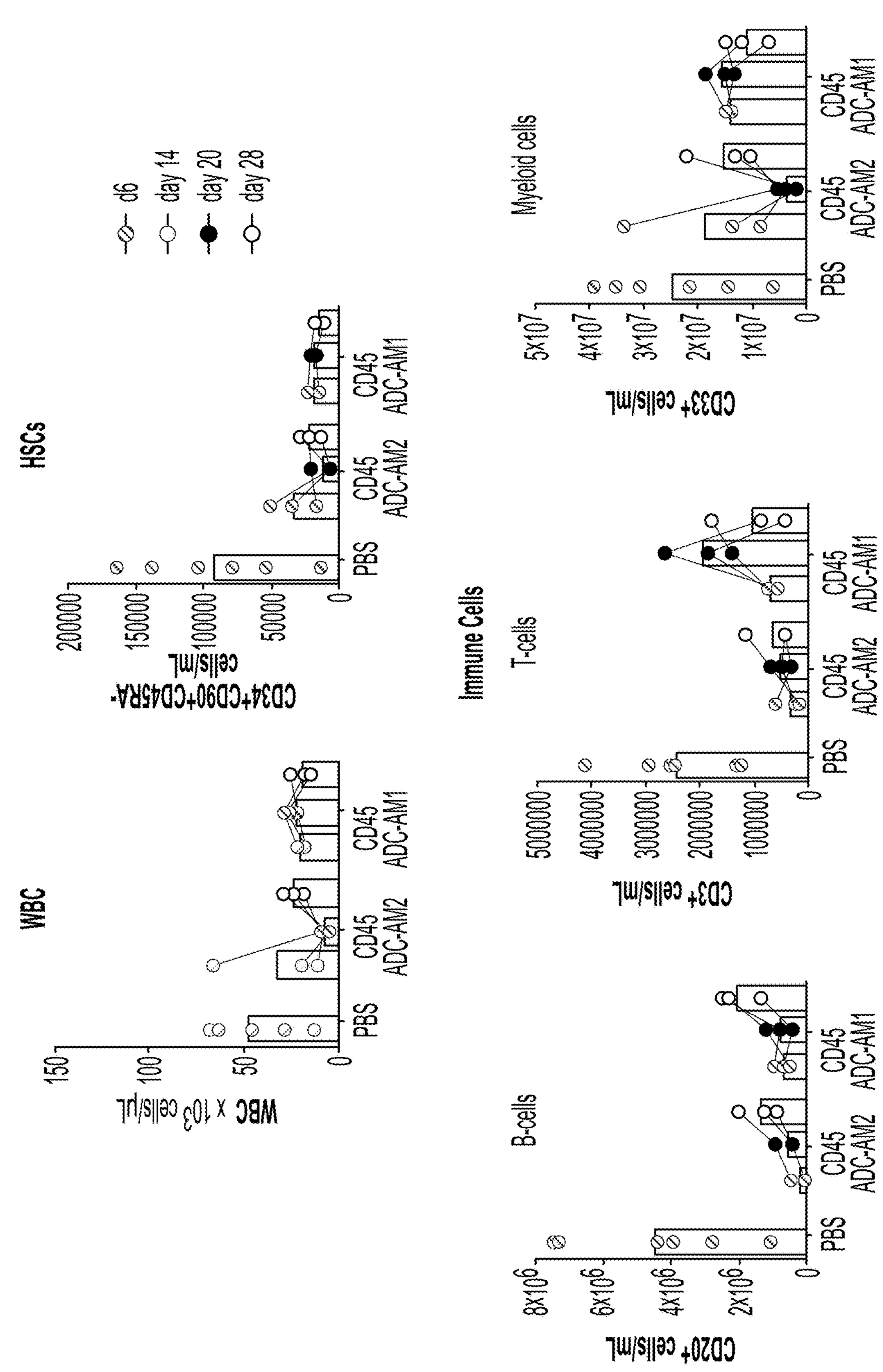
FIG. 26 graphically depict the results of an in vivo cell depletion assay showing that an anti-CD45-amatoxin ADC constructed from AbA effectively depleted non-human primate HSC and immune cells in vivo. AbA_D265C_LALA_H435A, an Fc variant of AbA (modifications in the Fc region were introduced to decrease the half-life) was conjugated to amatoxin 1 (AM1) or amatoxin 2 (AM2) to form AbA_D265C_LALA_H435A-AM1 ("CD45 ADC-AM1") or AbA_D265C_LALA_H435A-AM2 ("CD45 ADC-AM2"). The levels of white blood cells, HSCs, and immune cells (B-cells, T-cells, and Myeloid cells) in the bone marrow of cynomolgus monkeys were measured at the indicated times (Day 6, Day 14, Day 20, and Day 28) post-administration of a single 1 mg/kg injection of the indicated ADCs.

As described in FIG. 26, on-target depletion of WBCs, HSCs, and lymphocytes was observed in BM of NHPs following treatment with the CD45 ADCs. In conclusion, ADCs CD45 ADC-AM1 and CD45 ADC-AM2, containing AbA having modifications in the Fc region to decrease the antibody half-life, exhibited potent elimination of NHP HSCs and immune cells in vivo.

Example 27. Pharmacokinetics Analysis and Serum Stability of CD45 ADC in NHP

ADCs containing anti-CD45 antibody AbA were tested to assess serum stability and pharmacokinetics in non-human primates. A commercially available ELISA kit was adapted to measure plasma drug concentration of CD45 ADC-AM1 and CD45 ADC-AM2 (described in Example 26) in male cynomolgus monkeys.

Figure 27:
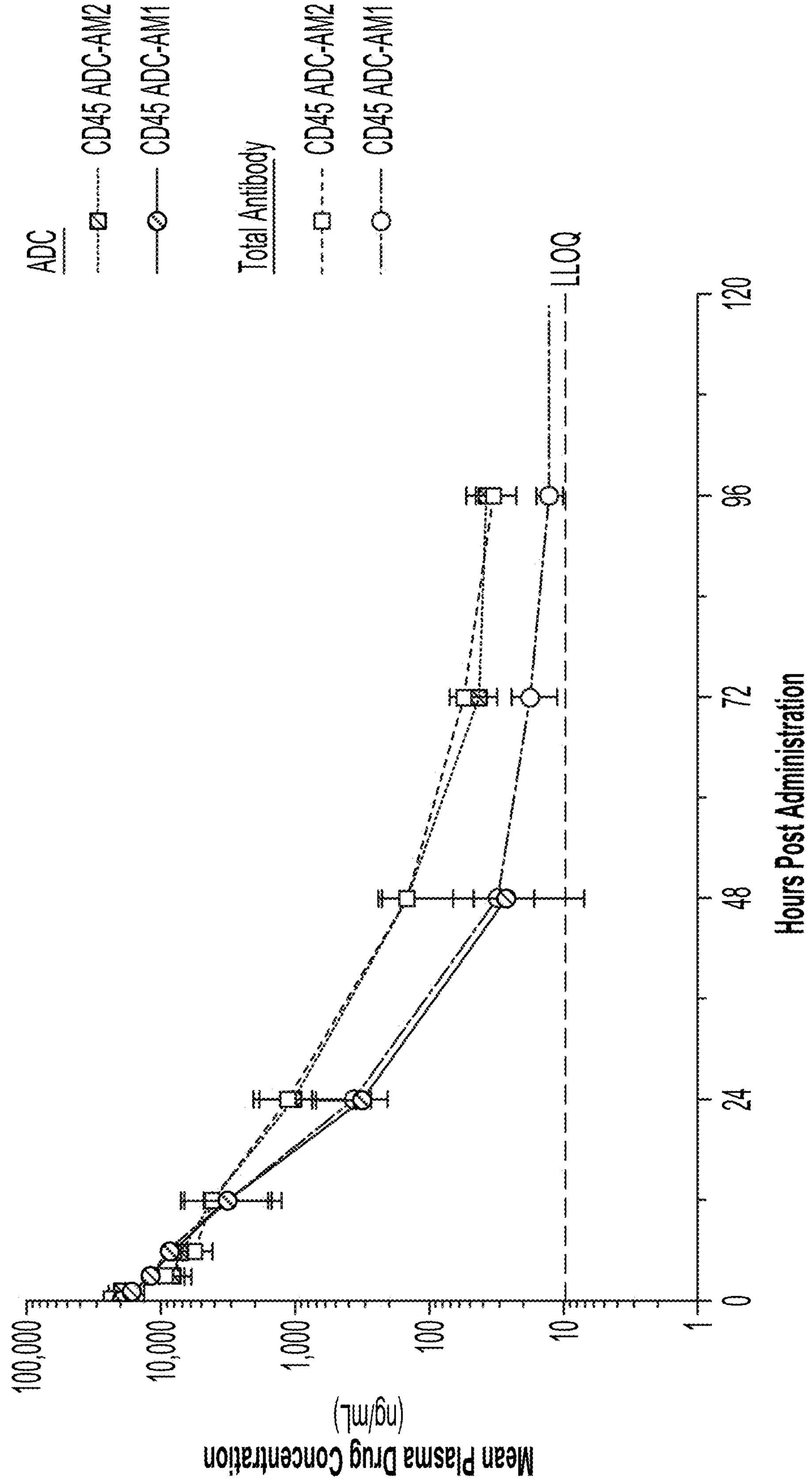
FIG. 27 graphically depicts the results of a pharmacokinetic analysis in cynomolgus macaques of an anti-CD45 ADC constructed from AbA. AbA_D265C_LALA_H435A, an Fc variant of AbA (modifications in the Fc region were introduced to decrease half-life) was conjugated to amatoxin 1 (AM1) or amatoxin 2 (AM2) to form AbA_D265C_LALA_H435A-AM1 ("CD45 ADC-AM1") or AbA_D265C_LALA_H435A-AM2 ("CD45 ADC-AM2"). The mean plasma drug concentration (y-axis) of each ADC was monitored over time (x-axis).

Briefly, ELISA plates were coated with anti-human IgG capture antibody. Plasma samples and standards (CD45 ADCs) were diluted within the dynamic range of the assay in diluent and incubated on the plates. After incubation, plates were incubated with anti-IgG-HRP (to calculate total antibody) or with anti-amatoxin-HRP (to calculate CD45 ADCs). Finally, the HRP substrate TMB was added followed by a stop solution. The intensity of the color was directly proportional to the amount of bound IgG (to calculate total antibody) or IgG/amatoxin (to calculate AM1- or AM2-conjugated CD45 ADC). The results are described in FIG. 27 and Table 22.

The overlay of the anti-amatoxin detection-based PK with the anti-IgG detection-based PK indicates that the ADCs were serum stable in vivo in NHPs. The CD45 ADCs were rapidly cleared with a half-life of 3.79-14.4 h, indicating that the CD45 ADCs had a short-half life in vivo.

TABLE 22

| Mean CD45 ADC PK | | | | | | | |
|---|---|---|---|---|---|---|---|
| ADC | Dose (mg/kg) | AUCinf/ Dose (hr*kg*ug/ mL/mg) | Cmax/ Dose (kg*ug/ mL/mg) | Tmax (hr) | Half-life (hr) | CL (mL/hr/ kg) | Vss (mL/ kg) |
| CD45 ADC-AM2 | 1 | 143 | 22.9 | 0.083 | 14.4 | 8.20 | 76.8 |
| CD45 ADC-AM1 | 1 | 122 | 18.7 | 0.083 | 3.79 | 8.46 | 44.2 |

Example 28. A Single Dose of AbA-AM is Cytoreductive on Patient-Derived Tumors and Extends Survival Beyond Standards of Care in Multiple Pre-Clinical Models of Hematologic Malignancy The targeted antibody drug conjugate (ADC) approach described in this example is designed to improve the safety of current conditioning protocols by specifically depleting CD45+ cells. An anti-human CD45-targeted short half-life ADC comprising AbA conjugated to an amatoxin (AbA-AM1) was used in this study. CD45 may be targeted for allo-HSCT conditioning because it is expressed on all hematopoietic cells (except erythrocytes, plasma cells and platelets), and most hematologic malignancies. Given their targeted specificity, anti-CD45-AM can provide dual benefit to leukemia patients by combining effective conditioning for HSCT with depletion of target-bearing tumor cells.

To demonstrate that AbA-AM has anti-leukemic activity, the ADC was tested in human leukemic xenograft murine models. A panel of models were evaluated to mimic untreated and refractory disease: AML patient derived xenograft (PDX) models (from treatment naïve and relapsed post allogeneic HCT patients; all FLT-3+NPM1+), ALL cells from an immortalized cell line (REH-Luc), and T-ALL patient-derived xenograft (PDX) model (from a patient progressing post DHAP chemotherapy).

AML #1 was derived from a treatment naïve patient (J000106134) and AML #2 was derived from a heavily pre-treated relapsed refectory patient post allogenic HSCT (J000106132), The T-ALL was derived from a patient progressing post DHAP chemotherapy. The cell line-derived ALL was transduced to express firefly luciferase. Cells of each tumor type were systemically inoculated into immune deficient mice (NSG-SGM3, or NSG).

Treatment began when peripheral tumor burden of PDX (n=3-5/group), and CDX mice reached 2-16% blast in the peripheral blood or day 5 post implant for the REH-luc model (n=10/group). Single doses of the anti-CD45-ADC (1, 3, 6, or 10 mg/kg) were compared to vehicle (PBS) or isotype-AM1 (6, or 10 mg/kg), and comparable to clinically validated standard of care regiments of Ara-c (30 mg/kg QDx5, IV), dexamethasone (5 mg/kg Q3Dx9, IP), or doxorubicin (3 mg/kg QWx3, IV). Tumor burden over the course of the study is shown in FIG. 28.

Figure 28:
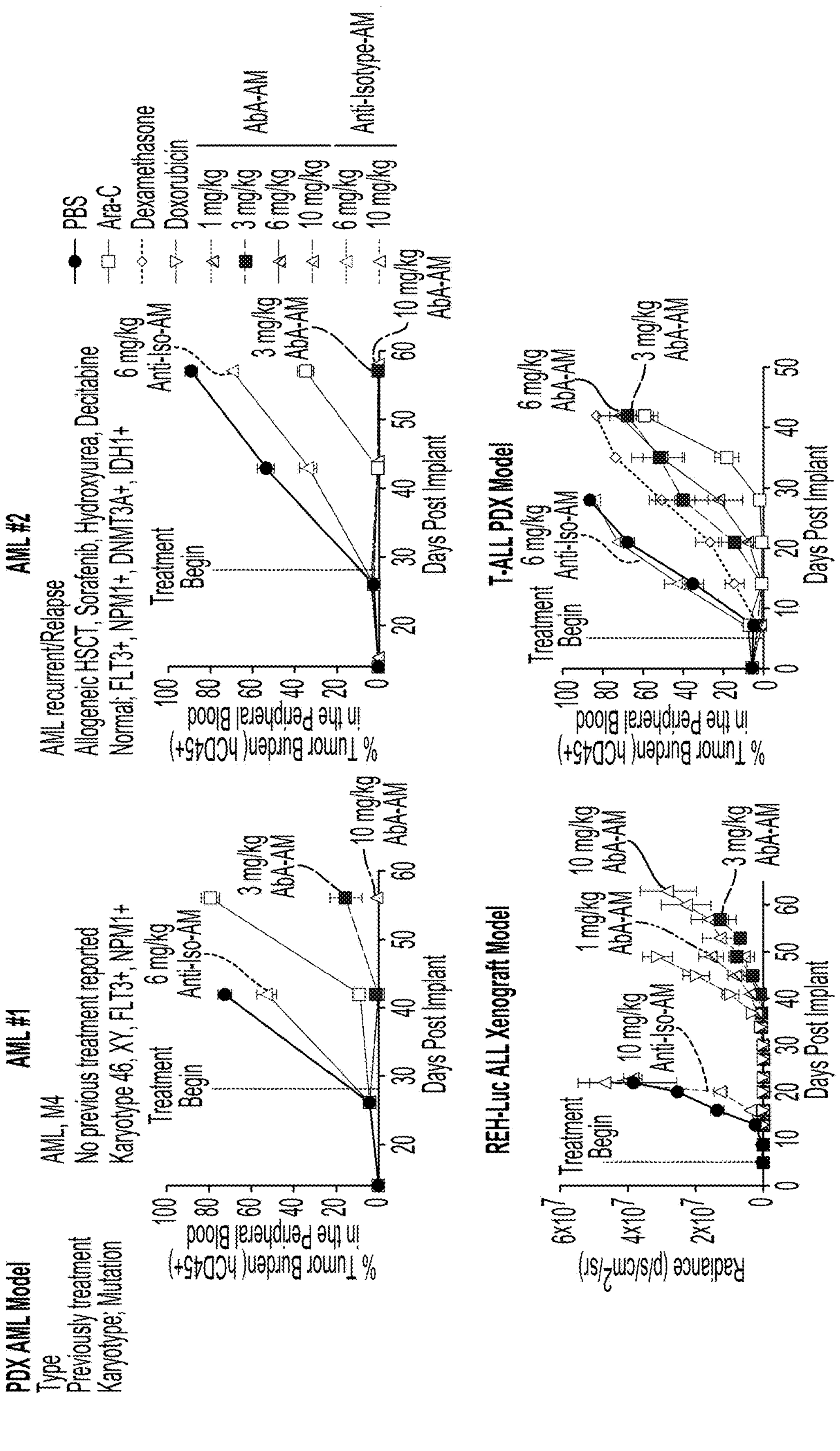
FIG. 28 graphically depicts the results of an in vivo murine study showing that a single dose of AbA-AM ADC is cytoreductive on patient-derived tumors and extends survival beyond standards of care across a panel of models to mimic untreated and refractory disease. Patient derived xenograft (PDX) models of AML [AML #1 (derived from a treatment naïve patient), AML #2 (derived from a heavily pre-treated relapsed refractory patient post allogeneic HSCT)], and T-ALL (derived from a patient progressing post DHAP chemotherapy), along with a cell line derived ALL model of an immortalized cell line (REH-Luc) were systemically inoculated into immune deficient mice (NSG-SGM3, or NSG). Treatment began when peripheral tumor burden of PDX (n=3–5/group), and CDX mice reached 2-16% blast in the peripheral blood or day 5 post implant for the REH-luc model (n=10/group). Single doses of the anti-CD45-ADC (1, 3, 6, or 10 mg/kg) were compared to vehicle (PBS) or isotype-AM (6, or 10 mg/kg), and comparable to clinically validated standard of care regiments of Ara-c (30 mg/kg QDx5, IV), dexamethasone (5 mg/kg Q3Dx9, IP), or doxorubicin (3 mg/kg QWx3, IV). Tumor burden over the course of the study is shown.
Figure 29A:
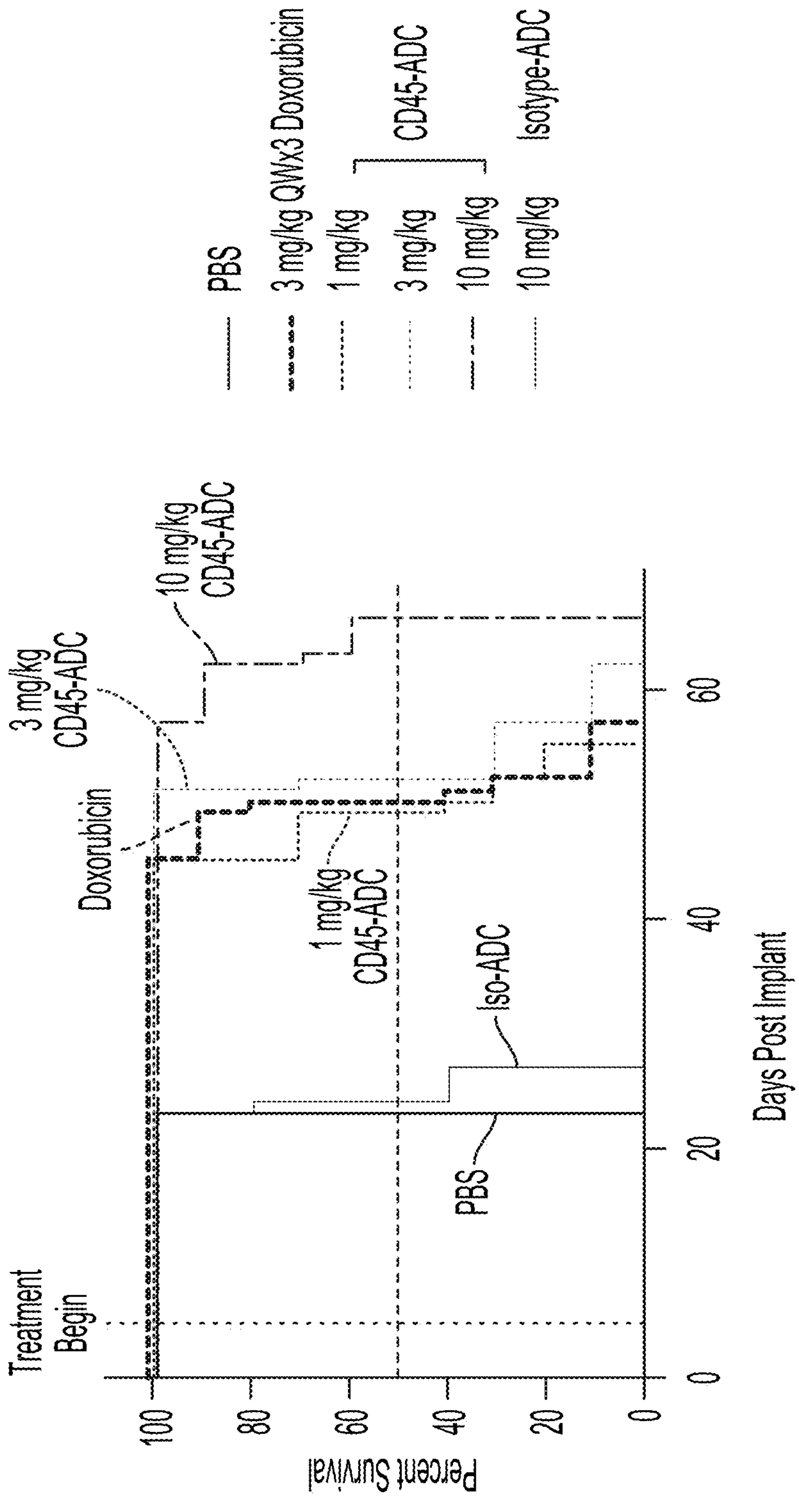
FIGS. 29A-29C graphically depict the results of an in vivo murine study showing that short half-life CD45-ADC (AbA-AM) increases median survival in the REH-Luciferase ALL Xenograft Model.
Figure 29B:
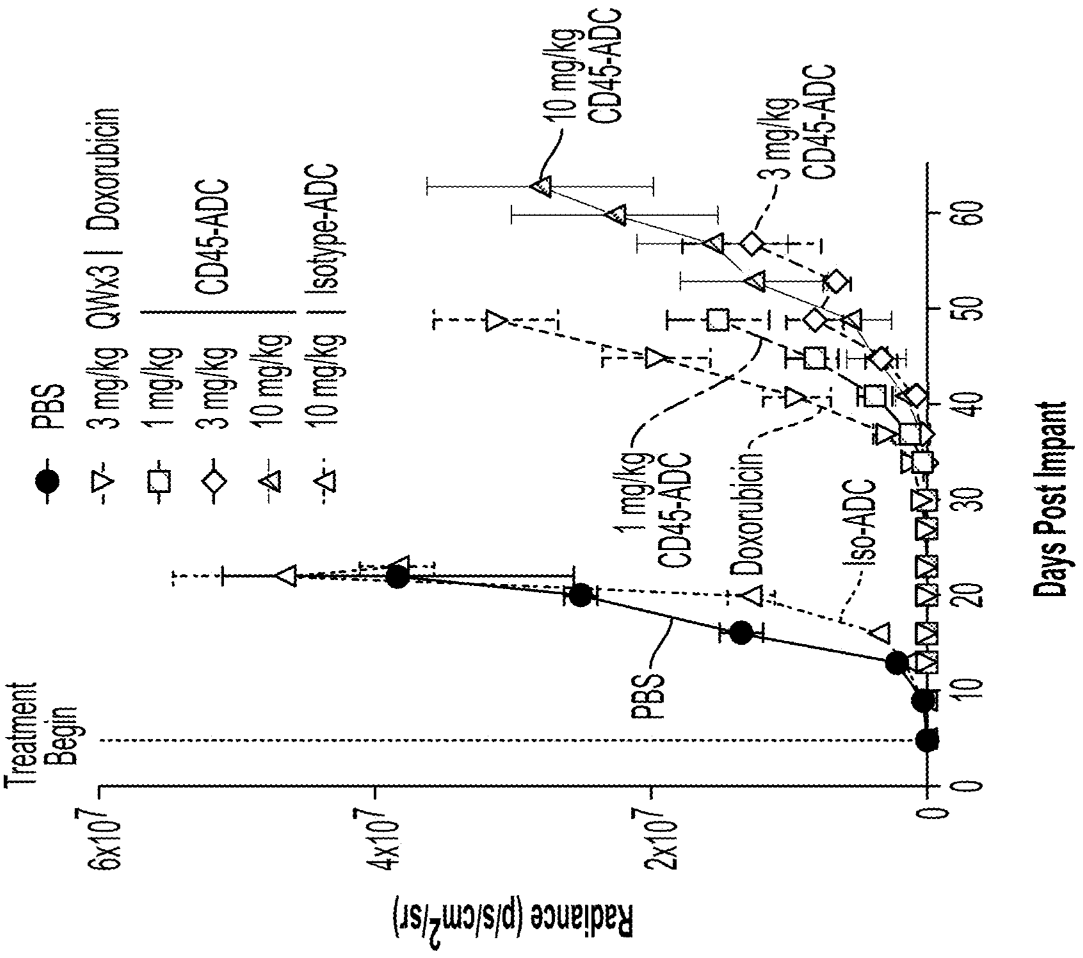
Figure 29C:
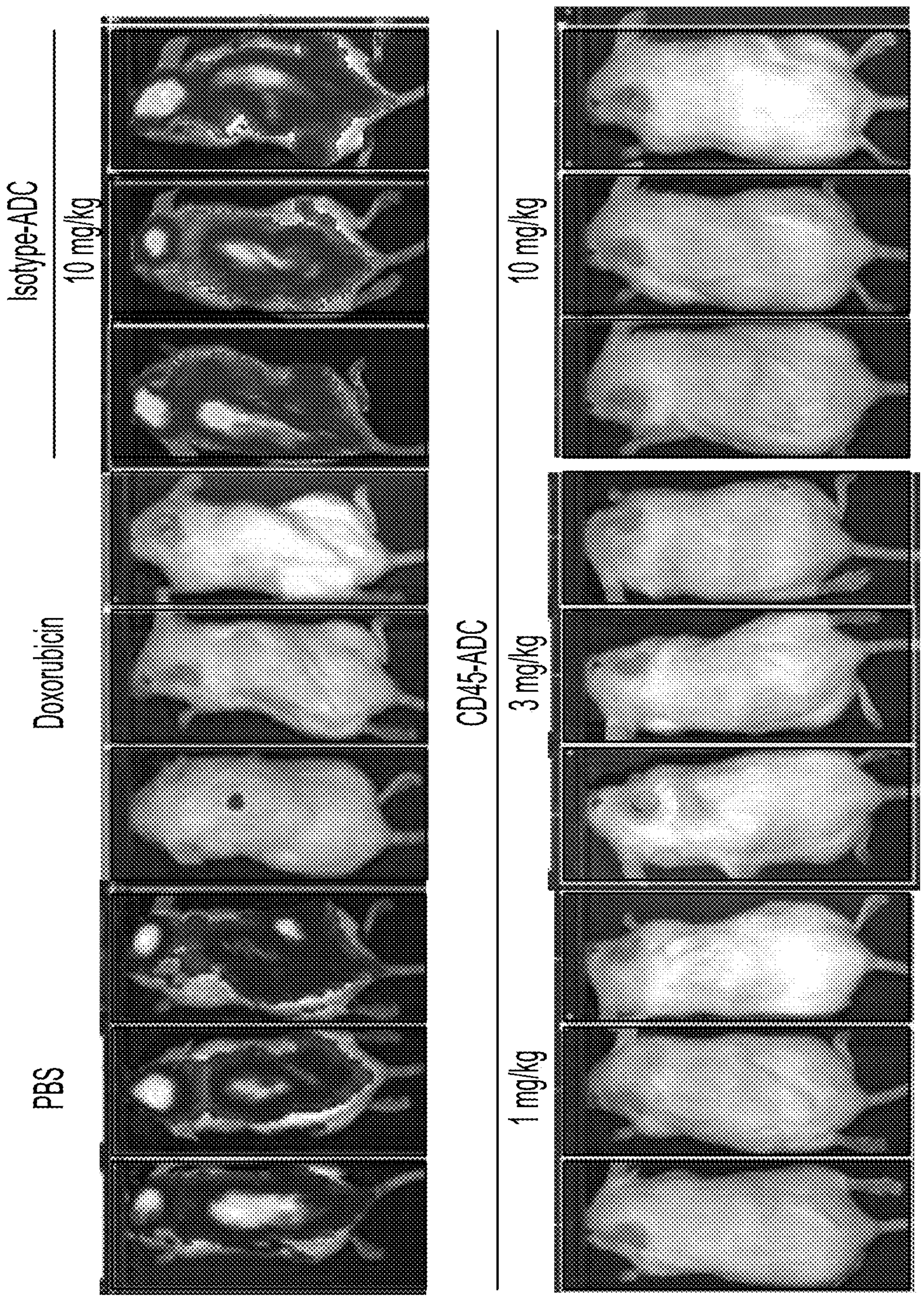

In the REH-Luciferase model cell line derived (CDX) model of human ALL, single doses of AbA-AM1 were well tolerated, and cytoreductive resulting in delayed tumor growth and extended median survival by at least double (2.2-2.8×) compared to vehicle (PBS), isotype-AM1, or standard of care (SoC) doxorubicin (FIG. 28; bottom left panel and FIG. 29B). As shown in FIG. 29A and Table 23, a single injection of AbA-AM1 (1, 3, or 10 mg/kg) on day 5 after ALL inoculation resulted in longer survival by a median of 55-66 days compared to PBS, or Isotype-ADC treated controls, and similar to doxorubicin, which is used clinical as a standard of care treatment for ALL (n=10 mice/group). Bioluminescence signal was measured using the IVIS imaging system (PerkinElmer). Radiance (mean±SEM) was captured over a time course of the study. Representative bioluminescence signal pseudo colored images were captured on day 22-23 post-implantation for all treatment groups, as shown in FIG. 29C.

TABLE 23

Median Survival in REH-Luciferase ALL Xenograft Model

Figure 30A:
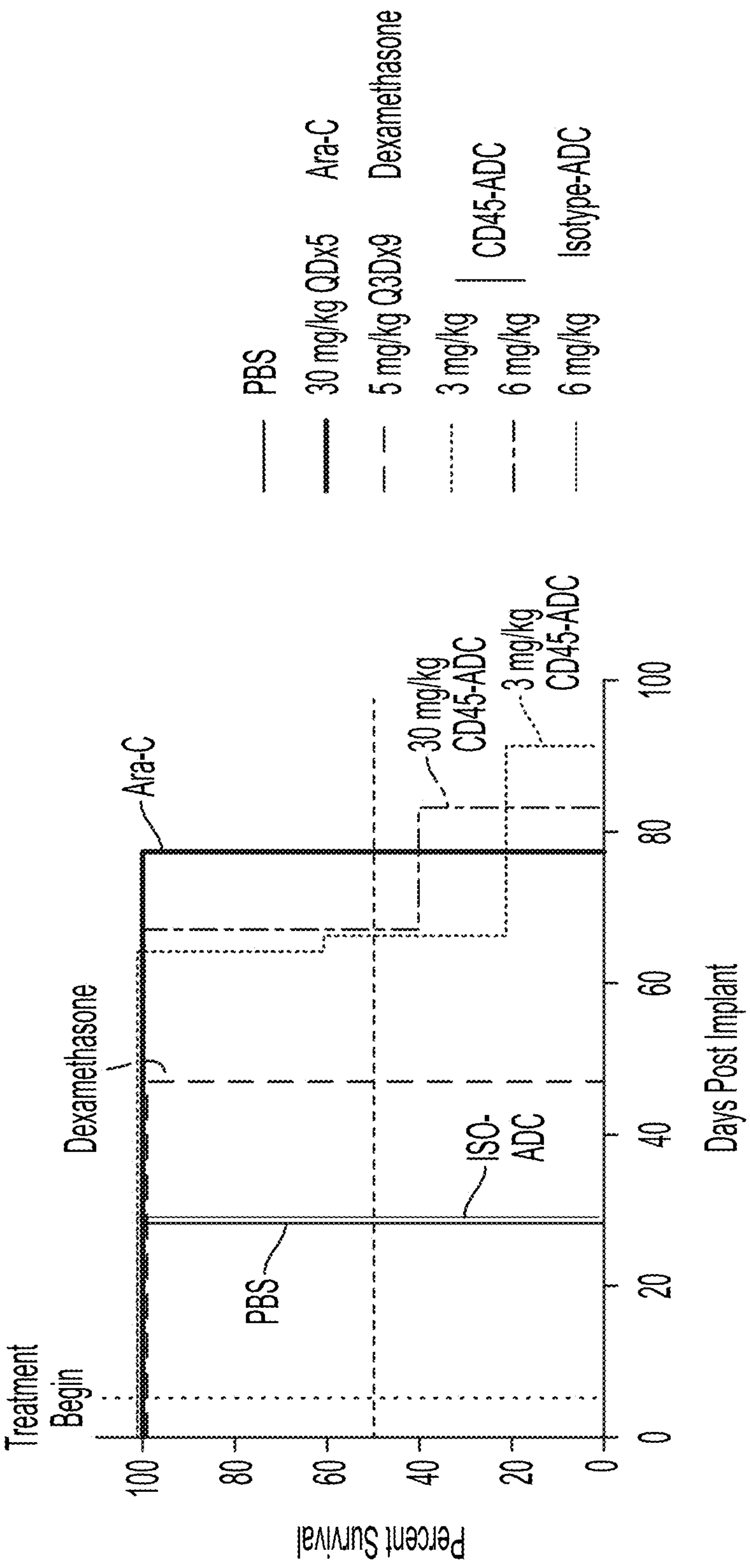
FIGS. 30A and 30B graphically depict the results of an in vivo murine study showing that short half-life CD45-ADC (AbA-AM) decreases Peripheral Leukemia Cells resulting in tumor growth delay in a T-ALL PDX Model.
Figure 30B:
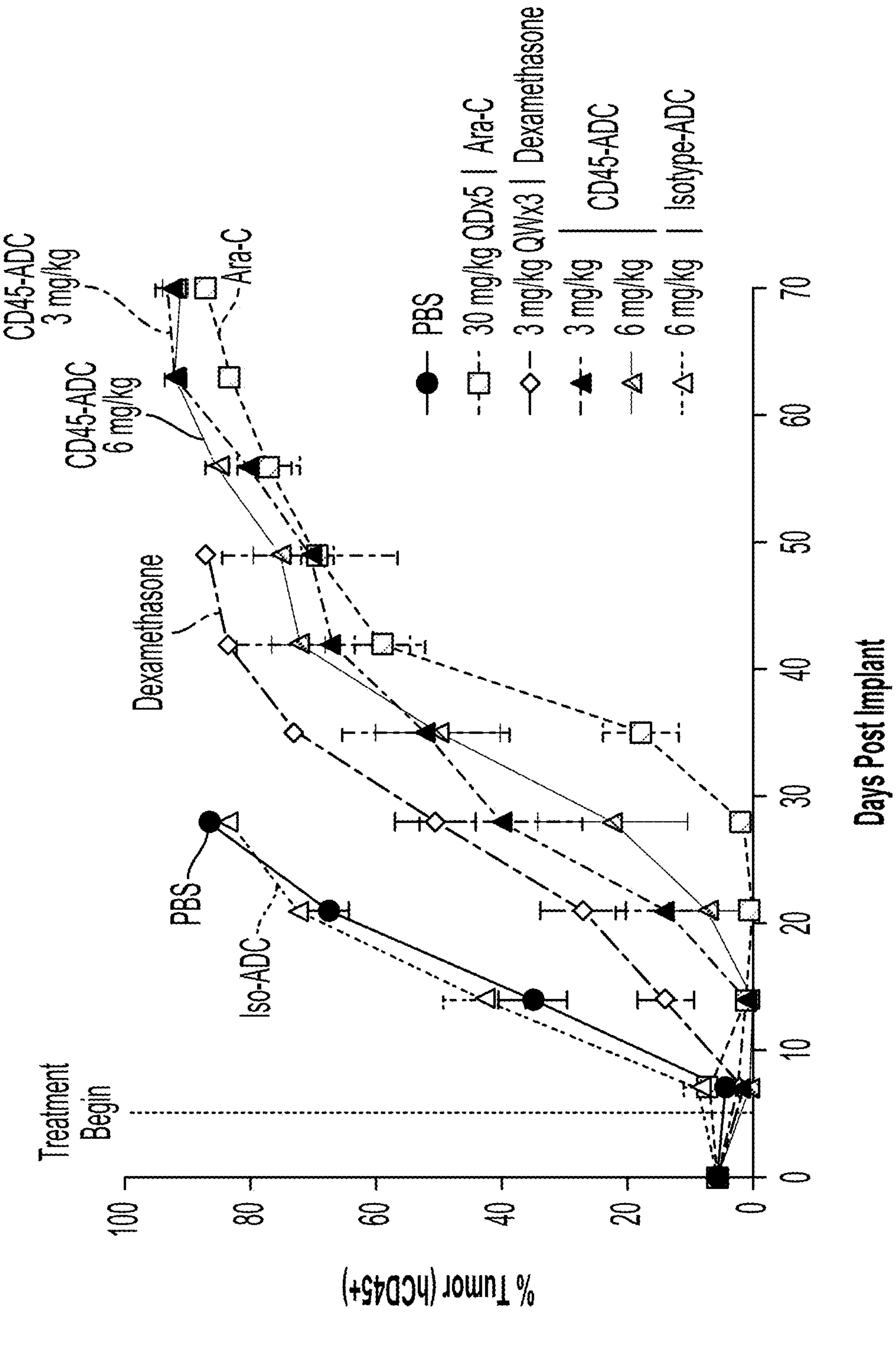

| Treatment Groups | | Median Survival (Days Post Implant) |
|---|---|---|
| PBS | | 23‡ |
| 3 mg/kg QW × 3 Doxorubicin | | 50† |
| 1 mg/kg | CD45-ADC (AbA-AM) | 49† |
| 3 mg/kg | | 52† |
| 10 mg/kg | | 66†‡ |
| 10 mg/kg | Isotype-ADC | 24‡ |

log-rank test
†p ≤ 0.001 compared to PBS or Isotype-ADC;
‡p < 0.05 compared to doxorubicin In the T-ALL patient-derived xenograft (PDX) model, a single injection of short half-life CD45-ADC (AbA-AM1 at 3, or 6 mg/kg) on day 5 after T-ALL inoculation resulted in longer survival by a median of 66-67 days compared to PBS (28 days), or Isotype-ADC (28 days) treated controls, or dexamethasone (47 days, n=5 mice/group; FIG. 30A and Table 24). Further, as shown in FIG. 30B, AbA-AM treatment significantly decreased peripheral tumor burden resulting in delayed tumor growth compared to vehicle, isotype-ADC, and comparable to two clinically validated standards of care (Ara-C, and dexamethasone respectively) in the T-ALL PDX model. These results indicate that treatment with a single dose of a short half-life CD45-ADC decreases peripheral leukemia cells resulting in tumor growth delay and results in a doubling of the median survival.

TABLE 24

Median Survival in T-ALL PDX Model

Figure 31A:
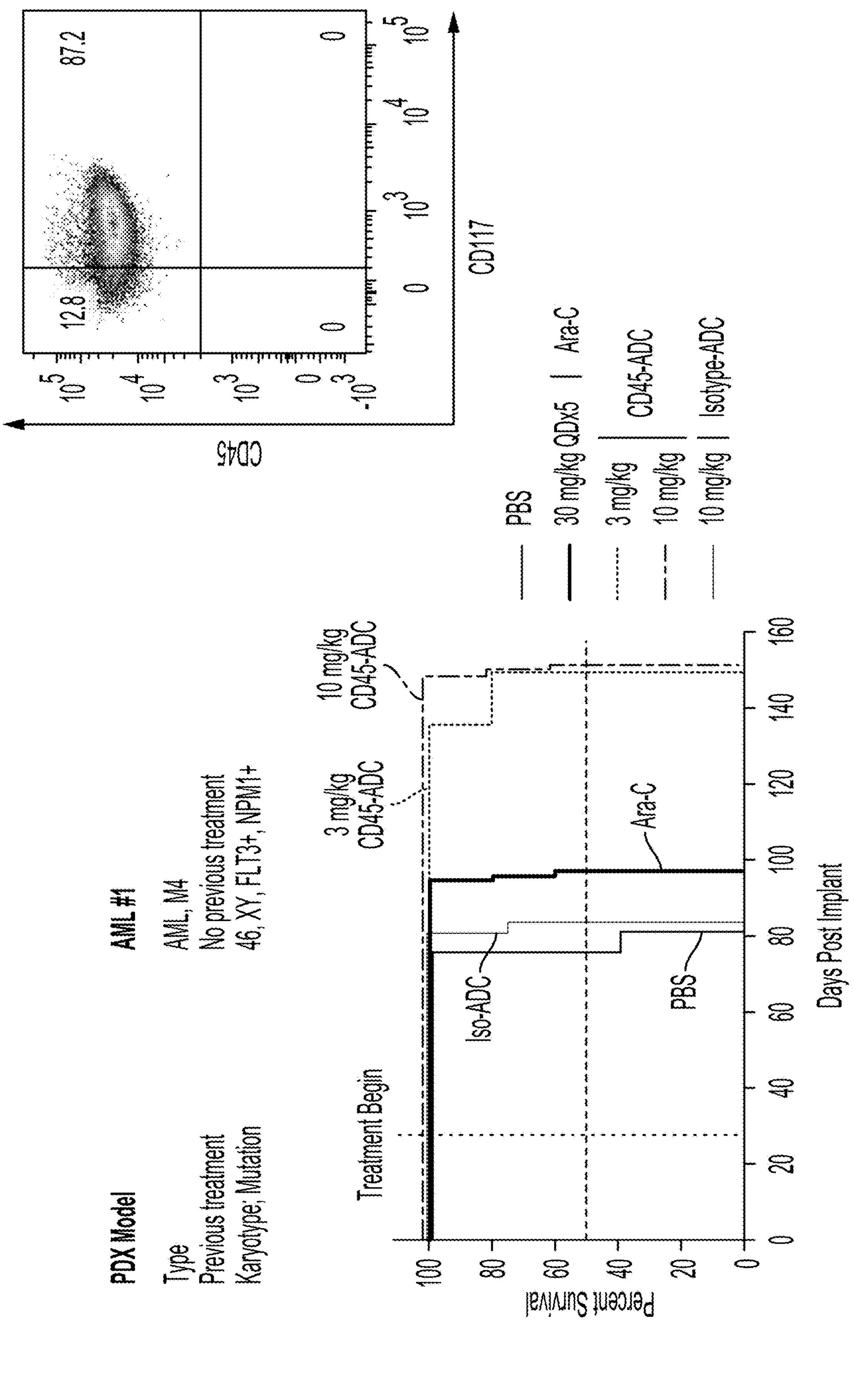
FIGS. 31A-31D graphically depict the results of an in vivo murine study showing that short half-life CD45-DC (AbA-AM) effectively depletes human leukemic cells in two patient derived AML models.
Figure 31B:
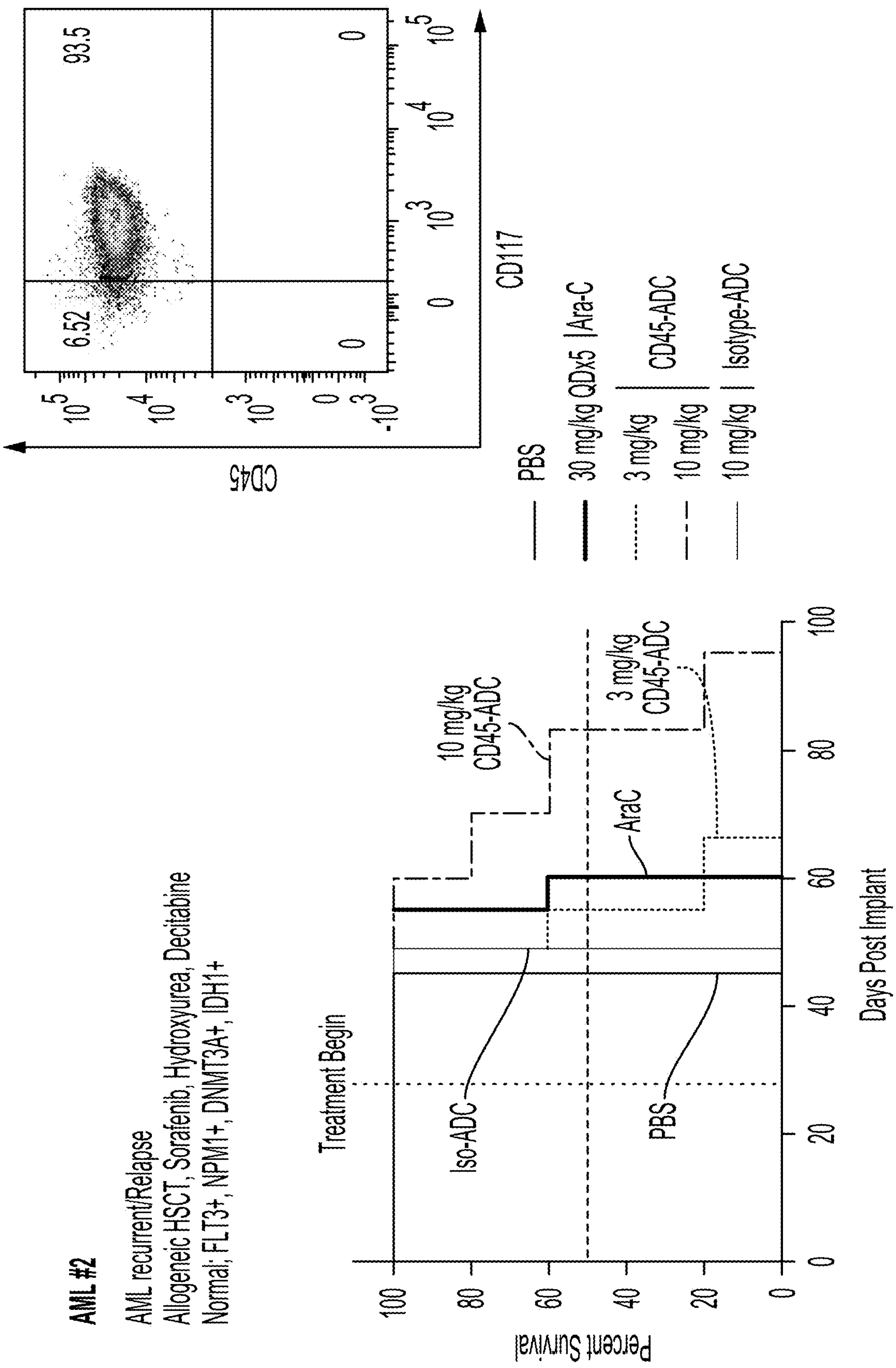
Figure 31C:
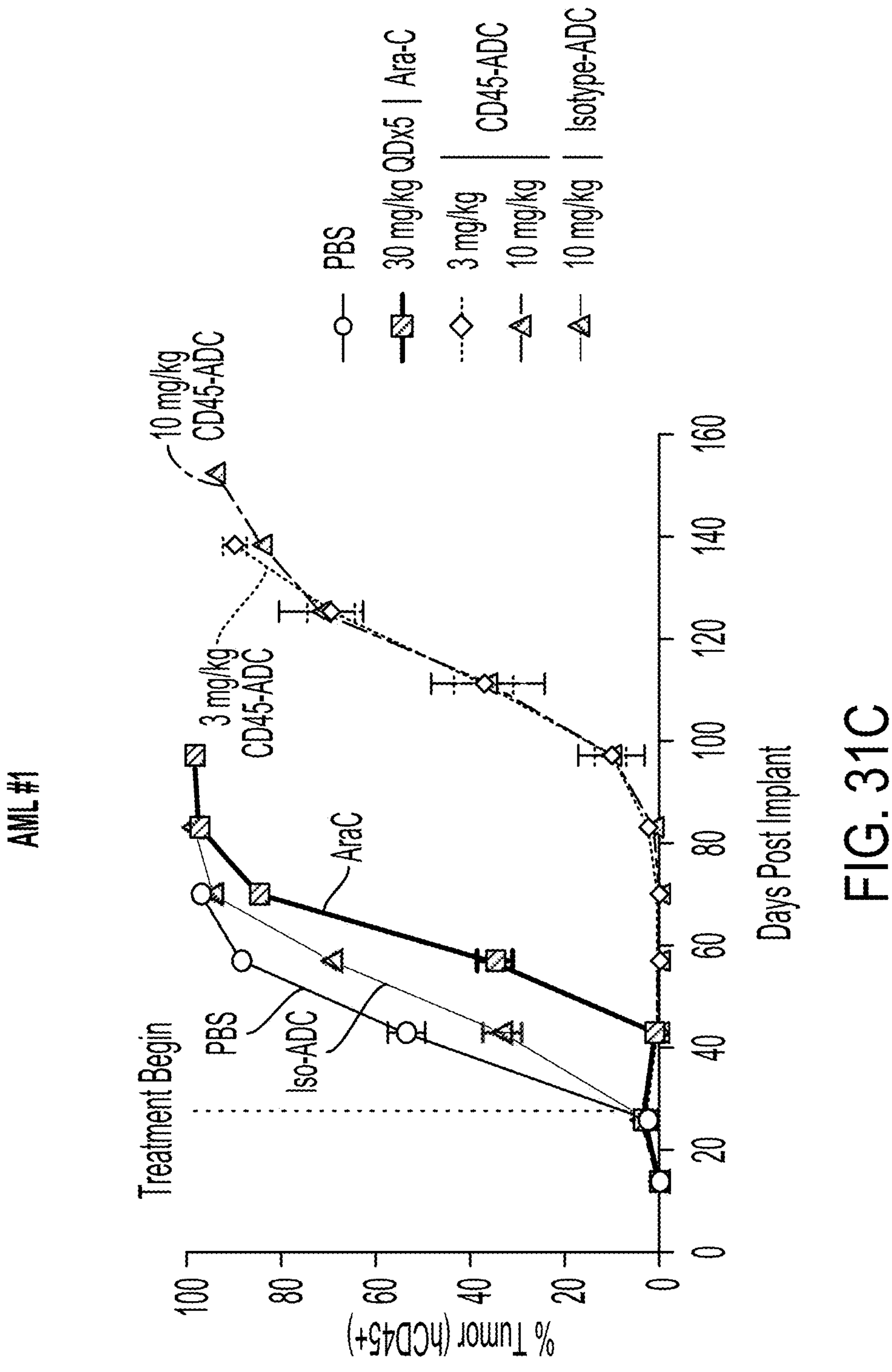
Figure 31D:
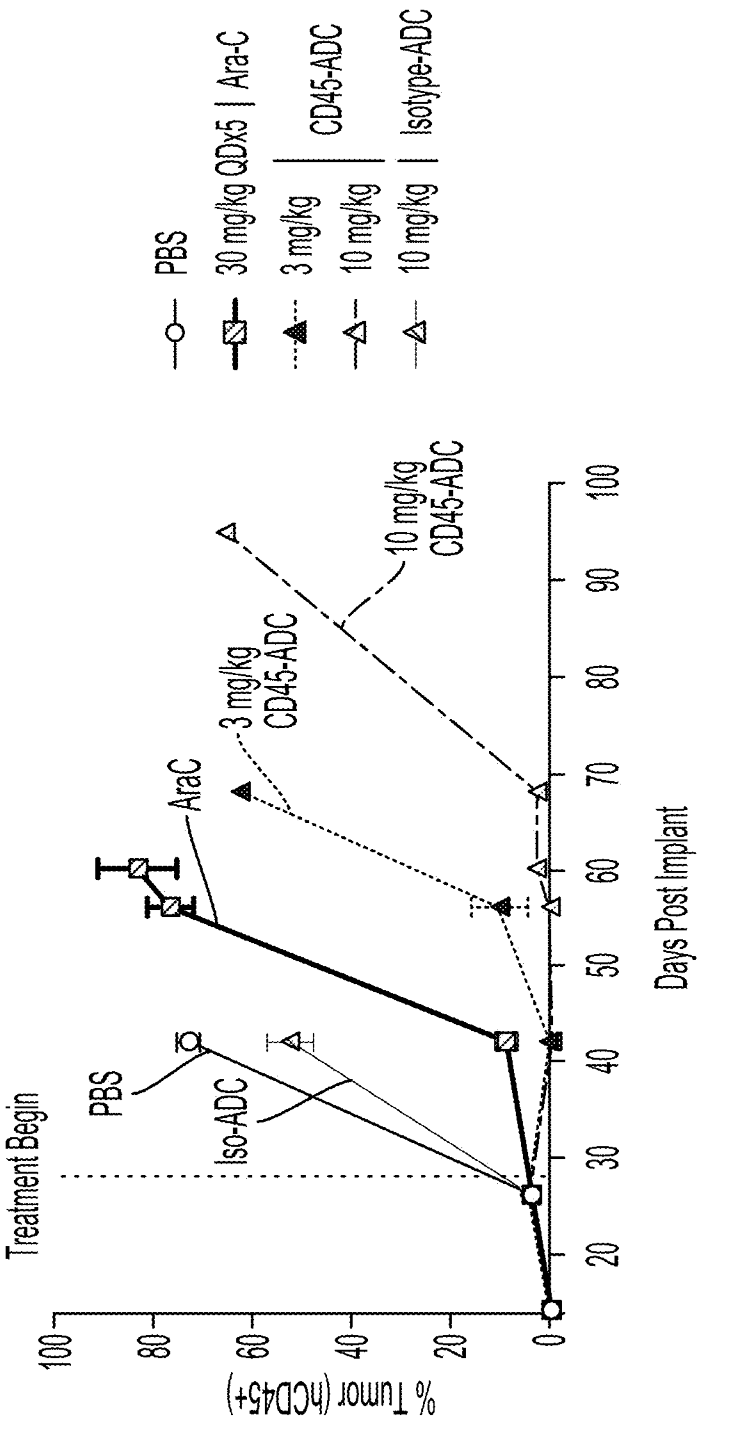

| Treatment Groups | | Median Survival (Days Post Implant) |
|---|---|---|
| PBS | | 28†‡ |
| 30 mg/kg QD × 5 AraC | | 77*† |
| 5 mg/kg Q3D × 9 Dexamethasone | | 47*‡ |
| 3 mg/kg | CD45-ADC (AbA-AM) | 66*† |
| 6 mg/kg | | 67*† |
| 6 mg/kg | Isotype-ADC | 28*†‡ |

log-rank test p ≤ 0.009 compared to
*PBS, or Isotype ADC;
†Dexamethasone;
‡compared to Ara-C In the AML patient derived xenograft (POX) models from treatment naïve and relapsed post allogeneic HOT patients, treatment began when 2-16% blasts were detected in the periphery (n=3-5 mice/group/AML POX model). Mice were treated with a single intravenous dose of anti-human 0045-ADO (AbA-AM), isotype-ADC, or vehicle (PBS). Ara-c was administered intravenously once daily for five consecutive days. As shown in FIGS. 31A and 31B (and Tables 25 and 26), POX AML mice treated with a single intravenous dose of ADO, (anti-CD45-ADC (AbA-AM), Isotype-ADC), vehicle (PBS) resulted in longer survival in recipients of anti-CD45-ADC as compared to PBS controls. Further, as shown in FIGS. 310C and 310D, a single dose of a short half-life 0045-ADO effectively decreases tumor burden of human acute myeloid leukemic cells across the two patient derived xenograft models compared to vehicle (PBS) or isotype-ADC, and was comparable to a clinically validated standard of care regiment (Ara-c).

TABLE 25

Median Survival of PDX Model (AML #1)

| Treatment Groups | | Median Survival (Days Post Implant) |
|---|---|---|
| PBS | | 76‡ |
| 30 mg/kg QDx5 Ara-C | | 97† |
| 3 mg/kg | CD45-ADC | 150†‡ |
| 10 mg/kg | | 151†‡ |
| 10 mg/kg | Isotype-ADC | 84‡ |

Log-rank test
†p ≤ 0.02 compared to PBS or Isotype-ADC;
‡p ≤ 0.005 compared to Ara-C

TABLE 26

Median Survival of PDX Model (AML #2)

| Treatment Groups | | Median Survival (Days Post Implant) |
|---|---|---|
| PBS | | 45‡* |
| 30 mg/kg QD × 5 Ara-C | | 60†‡ |
| 3 mg/kg | CD45-ADC | 55† |
| 10 mg/kg | | 83†‡* |
| 10 mg/kg | Isotype-ADC | 49‡* |

Log-rank test
†p ≤ 0.008 compared to PBS;
‡p ≤ 0.008 compared to isotype ADC;
*p ≤ 0.012 compared to Ara-C.

These results demonstrated that a single dose administration of short half-life 0045-AD (AbA-AM) is well tolerated and capable of reducing tumor burden by potently targeting leukemia cells in multiple xenograft models (ALL, T-All, AML) and significantly prolonging the median survival of established leukemia xenograft models (cell line and patient derived) compared to controls and clinical validated standards of care.

AbA-AM treatment in the POX AML, and T-ALL significantly decreased peripheral tumor burden resulting in delayed tumor growth compared to vehicle, isotype-AM, and comparable to two clinically validated standards of care (Ara-C, and dexamethasone respectively; FIG. 28). As designed for the transplant indication, the ADO had a reduced half-life compared to wild type antibody controls (16 vs 79 h).

These data in humanized murine xenograft models demonstrate that the short half-life AbA-AM ADO is a potent targeted anti-leukemia agent. These non-genotoxic ADCs may be useful in reducing disease burden and inducing durable remissions in patients after transplant particularly those who receive reduced intensity conditioning that are at high risk of relapse.

Sequences referenced throughout this disclosure are provided in Table 27.

TABLE 27

SEQUENCE TABLE

| SEQ ID NO | Description | Sequence |
|---|---|---|
| 1 | Ab1 Heavy Chain Variable Region (CDRs bolded) | QVQLVESGGGLVKPGGSLRLSCAASG**FTFSSYSMN**W<br>VRQAPGKGLEWVS**YISSSSSTIYYADSVKG**RFTISRD<br>NAKNSLYLQMNSLRAEDTAVYYC**ARGGQYYYDSSRY**<br>**GEVAFDI**WGQGTMVTVSS |
| 2 | Ab1-HC CDR1 | FTFSSYSMN |
| 3 | Ab1-HC CDR2 | YISSSSSTIYYADSVKG |
| 4 | Ab1-HC CDR3 | ARGGQYYYDSSRYGEVAFDI |
| 5 | Ab1 Light Chain Variable Region (CDRs bolded) | DIVMTQSPLSLPVTPGEPASISC**RSSQSLLHSNGYNYL**<br>**DWY**LQKPGQSPQLLIY**LGSNRAS**GVPDRFSGSGSGT<br>DFTLKISRVEAEDVGVYYC**MQRRRTPPFT**FGGGTKVE<br>IK |
| 6 | Ab1-LC CDR1 | RSSQSLLHSNGYNYLD |
| 7 | Ab1-LC CDR2 | LGSNRAS |
| 8 | Ab1-LC CDR3 | MQRRRTPPFT |
| 9 | Ab1 Heavy Chain (CDRs in bold; Constant region underlined; D265C.LALA.H435A) | QVQLVESGGGLVKPGGSLRLSCAASG**FTFSSYSMN**W<br>VRQAPGKGLEWVS**YISSSSSTIYYADSVKG**RFTISRD<br>NAKNSLYLQMNSLRAEDTAVYYC**ARGGQYYYDSSRY**<br>**GEVAFDI**WGQGTMVTVSSASTKGPSVFPLAPSSKSTS<br>GGTAALGCLVKDYFPEPVTVSWNSGALTSGVHTFPA<br>VLQSSGLYSLSSVVTVPSSSLGTQTYICNVNHKPSNTK<br>VDKKVEPKSCDKTHTCPPCPAPEAAGGPSVFLFPPKP<br>KDTLMISRTPEVTCVVVCVSHEDPEVKFNWYVDGVEV<br>HNAKTKPREEQYNSTYRVVSVLTVLHQDWLNGKEYK<br>CKVSNKALPAPIEKTISKAKGQPREPQVYTLPPSRDEL<br>TKNQVSLTCLVKGFYPSDIAVEWESNGQPENNYKTTP<br>PVLDSDGSFFLYSKLTVDKSRWQQGNVFSCSVMHEA<br>LHNAYTQKSLSLSPGK |
| 10 | Ab1 Light Chain (CDRs in bold; Constant region underlined) | DIVMTQSPLSLPVTPGEPASISC**RSSQSLLHSNGYNYL**<br>**D**WYLQKPGQSPQLLIY**LGSNRAS**GVPDRFSGSGSGT<br>DFTLKISRVEAEDVGVYYC**MQRRRTPPFT**FGGGTKVE<br>IKRTVAAPSVFIFPPSDEQLKSGTASVVCLLNNFYPRE<br>AKVQWKVDNALQSGNSQESVTEQDSKDSTYSLSSTL<br>TLSKADYEKHKVYACEVTHQGLSSPVTKSFNRGEC |
| 11 | Ab2 Heavy Chain Variable Region (CDRs bolded) | EVQLVESGGGLVQPGGSLRLSCAASG**FTFEAYSMN**W<br>VRQAPGKGLEWVSY**ISLSGATIHYADSVKG**RFTISRD<br>NAKNSLYLQMNSLRAEDTAVYYC**ARGGQYYYDSSDY**<br>**GEVAFDI**WGQGTMVTVSS |
| 12 | Ab2-HC CDR1 | FTFEAYSMN |
| 13 | Ab2-HC CDR2 | YISLSGATIHYADSVKG |
| 14 | Ab2-HC CDR3 | ARGGQYYYDSSDYGEVAFDI |

TABLE 27 -continued

SEQUENCE TABLE

| SEQ ID NO | Description | Sequence |
|---|---|---|
| 15 | Ab2 Light Chain Variable Region (CDRs bolded) | DIVMTQSPLSLPVTPGEPASISC**RSSQSLVSNGYNYL** DWYLQKPGQSPQLLIY**FGSSRAS**GVPDRFSGSGSGT DFTLKISRVEAEDVGVYYC**MQRRRTPWS**FGGGTKVEI K |
| 16 | Ab2-LC CDR1 | RSSQSLVSNGYNYLD |
| 17 | Ab2-LC CDR2 | FGSSRAS |
| 18 | Ab2-LC CDR3 | MQRRRTPWS |
| 19 | Ab2 Heavy Chain (CDRs in bold; Constant region underlined; D265C.LALA.H435A) | EVQLVESGGGLVQPGGSLRLSCAASG**FTFEAYSMN**W VRQAPGKGLEWVS**YISLSGATIHYADSVKG**RFTISRD NAKNSLYLQMNSLRAEDTAVYYC**ARGGQYYYDSSDY GEVAFDI**WGQGTMVTVSSASTKGPSVFPLAPSSKSTS GGTAALGCLVKDYFPEPVTVSWNSGALTSGVHTFPA VLQSSGLYSLSSVVTVPSSSLGTQTYICNVNHKPSNTK VDKKVEPKSCDKTHTCPPCPAPEAAGGPSVFLFPPKP KDTLMISRTPEVTCVVVCVSHEDPEVKFNWYVDGVEV HNAKTKPREEQYNSTYRVVSVLTVLHQDWLNGKEYK CKVSNKALPAPIEKTISKAKGQPREPQVYTLPPSRDEL TKNQVSLTCLVKGFYPSDIAVEWESNGQPENNYKTTP PVLDSDGSFFLYSKLTVDKSRWQQGNVFSCSVMHEA LHNAYTQKSLSLSPGK |
| 20 | Ab2 Light Chain (CDRs in bold; Constant region underlined) | DIVMTQSPLSLPVTPGEPASISC**RSSQSLVSNGYNYL DWY**LQKPGQSPQLLIY**FGSSRAS**GVPDRFSGSGSGT DFTLKISRVEAEDVGVYYC**MQRRRTPWS**FGGGTKVEI KRTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC |
| 21 | Ab3 Heavy Chain Variable Region (CDRs bolded) | QVQLVESGGGLVKPGGSLRLSCAASG**FTFGGYSMN** WVRQAPGKGLEWVS**YISISGATITYADSVKG**RFTISRD NAKNSLYLQMNSLRAEDTAVYYC**ARGGQYYYDSSDY GEVAFDI**WGQGTMVTVSS |
| 22 | Ab3-HC CDR1 | FTFGGYSMN |
| 23 | Ab3-HC CDR2 | YISISGATITYADSVKG |
| 24 | Ab3-HC CDR3 | ARGGQYYYDSSDYGEVAFDI |
| 25 | Ab3 Light Chain Variable Region (CDRs bolded) | DIVMTQSPLSLPVTPGEPASISC**RSSQSLVSNGYNYL DWY**LQKPGQSPQLLIY**FGSSRAS**GVPDRFSGSGSGT DFTLKISRVEAEDVGVYYC**MQRRRTPPFT**FGGGTKVE IK |
| 26 | Ab3-LC CDR1 | RSSQSLVSNGYNYLD |
| 27 | Ab3-LC CDR2 | FGSSRAS |
| 28 | Ab3-LC CDR3 | MQRRRTPPFT |
| 29 | Ab3 Heavy Chain (CDRs in bold; Constant region underlined; D265C.LALA.H435A) | QVQLVESGGGLVKPGGSLRLSCAASG**FTFGGYSMN** WVRQAPGKGLEWVS**YISISGATITYADSVKG**RFTISRD NAKNSLYLQMNSLRAEDTAVYYC**ARGGQYYYDSSDY GEVAFDI**WGQGTMVTVSSASTKGPSVFPLAPSSKSTS GGTAALGCLVKDYFPEPVTVSWNSGALTSGVHTFPA VLQSSGLYSLSSVVTVPSSSLGTQTYICNVNHKPSNTK VDKKVEPKSCDKTHTCPPCPAPEAAGGPSVFLFPPKP KDTLMISRTPEVTCVVVCVSHEDPEVKFNWYVDGVEV HNAKTKPREEQYNSTYRVVSVLTVLHQDWLNGKEYK CKVSNKALPAPIEKTISKAKGQPREPQVYTLPPSRDEL TKNQVSLTCLVKGFYPSDIAVEWESNGQPENNYKTTP PVLDSDGSFFLYSKLTVDKSRWQQGNVFSCSVMHEA LHNAYTQKSLSLSPGK |
| 30 | Ab3 Light Chain (CDRs in bold; Constant region underlined) | DIVMTQSPLSLPVTPGEPASISC**RSSQSLVSNGYNYL** DWYLQKPGQSPQLLIY**FGSSRAS**GVPDRFSGSGSGT DFTLKISRVEAEDVGVYYC**MQRRRTPPFT**FGGGTKVE IKRTVAAPSVFIFPPSDEQLKSGTASVVCLLNNFYPRE AKVQWKVDNALQSGNSQESVTEQDSKDSTYSLSSTL TLSKADYEKHKVYACEVTHQGLSSPVTKSFNRGEC |

TABLE 27 -continued

SEQUENCE TABLE

| SEQ ID NO | Description | Sequence |
|---|---|---|
| 31 | Ab4 Heavy Chain Variable Region (CDRs bolded) | EVQLVESGGGLVQPGGSLRLSCAASG**FTFEAYSMN**W VRQAPGKGLEWVS**YISLSGATIHYADSVKG**RFTISRD NAKNSLYLQMNSLRAEDTAVYYC**ARGGQYYYTSSDY GEVAFDI**WGQGTMVTVSS |
| 32 | Ab4-HC CDR1 | FTFEAYSMN |
| 33 | Ab4-HC CDR2 | YISLSGATIHYADSVKG |
| 34 | Ab4-HC CDR3 | ARGGQYYYTSSDYGEVAFDI |
| 35 | Ab4 Light Chain Variable Region (CDRs bolded) | DIVMTQSPLSLPVTPGEPASISC**RSSQSLVSNGYNYL D**WYLQKPGQSPQLLIY**FGSSRAS**GVPDRFSGSGSGT DFTLKISRVEAEDVGVYYC**MQRRRTPWS**FGGGTKVEI K |
| 36 | Ab4-LC CDR1 | RSSQSLVSNGYNYLD |
| 37 | Ab4-LC CDR2 | FGSSRAS |
| 38 | Ab4-LC CDR3 | MQRRRTPWS |
| 39 | Ab4 Heavy Chain (CDRs in bold; Constant region underlined; D265C.LALA.H435A) | EVQLVESGGGLVQPGGSLRLSCAASG**FTFEAYSMN**W VRQAPGKGLEWVS**YISLSGATIHYADSVKG**RFTISRD NAKNSLYLQMNSLRAEDTAVYYC**ARGGQYYYTSSDY GEVAFDI**WGQGTMVTVSSASTKGPSVFPLAPSSKSTS GGTAALGCLVKDYFPEPVTVSWNSGALTSGVHTFPA VLQSSGLYSLSSVVTVPSSSLGTQTYICNVNHKPSNTK VDKKVEPKSCDKTHTCPPCPAPEAAGGPSVFLFPPKP KDTLMISRTPEVTCVVVCVSHEDPEVKFNWYVDGVEV HNAKTKPREEQYNSTYRVVSVLTVLHQDWLNGKEYK CKVSNKALPAPIEKTISKAKGQPREPQVYTLPPSRDEL TKNQVSLTCLVKGFYPSDIAVEWESNGQPENNYKTTP PVLDSDGSFFLYSKLTVDKSRWQQGNVFSCSVMHEA LHNAYTQKSLSLSPGK |
| 40 | Ab4 Light Chain (CDRs in bold; Constant region underlined) | DIVMTQSPLSLPVTPGEPASISC**RSSQSLVSNGYNYL D**WYLQKPGQSPQLLIY**FGSSRAS**GVPDRFSGSGSGT DFTLKISRVEAEDVGVYYC**MQRRRTPWS**FGGGTKVEI KRTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC |
| 41 | Ab5 Heavy Chain Variable Region (CDRs bolded) | EVQLVESGGGLVQPGGSLRLSCAASG**FTFEAYSMN**W VRQAPGKGLEWVS**YISLSGATIHYADSVKG**RFTISRD NAKNSLYLQMNSLRAEDTAVYYC**ARGGQYYYTSSDY GEVAFDI**WGQGTMVTVSS |
| 42 | Ab5-HC CDR1 | FTFEAYSMN |
| 43 | Ab5-HC CDR2 | YISLSGATIHYADSVKG |
| 44 | Ab5-HC CDR3 | ARGGQYYYTSSDYGEVAFDI |
| 45 | Ab5 Light Chain Variable Region (CDRs bolded) | DIVMTQSPLSLPVTPGEPASISC**RSSQSLVSSGYNYLD** WYLQKPGQSPQLLIY**FGSSRAS**GVPDRFSGSGSGTD FTLKISRVEAEDVGVYYC**MQRRRTPWS**FGGGTKVEIK |
| 46 | Ab5-LC CDR1 | RSSQSLVSSGYNYLD |
| 47 | Ab5-LC CDR2 | FGSSRAS |
| 48 | Ab5-LC CDR3 | MQRRRTPWS |
| 49 | Ab5 Heavy Chain (CDRs in bold; Constant region underlined; D265C.LALA.H435A) | EVQLVESGGGLVQPGGSLRLSCAASG**FTFEAYSMN**W VRQAPGKGLEWVS**YISLSGATIHYADSVKG**RFTISRD NAKNSLYLQMNSLRAEDTAVYYC**ARGGQYYYTSSDY GEVAFDI**WGQGTMVTVSSASTKGPSVFPLAPSSKSTS GGTAALGCLVKDYFPEPVTVSWNSGALTSGVHTFPA VLQSSGLYSLSSVVTVPSSSLGTQTYICNVNHKPSNTK VDKKVEPKSCDKTHTCPPCPAPEAAGGPSVFLFPPKP KDTLMISRTPEVTCVVVCVSHEDPEVKFNWYVDGVEV HNAKTKPREEQYNSTYRVVSVLTVLHQDWLNGKEYK CKVSNKALPAPIEKTISKAKGQPREPQVYTLPPSRDEL |

TABLE 27 -continued

SEQUENCE TABLE

| SEQ ID NO | Description | Sequence |
| --- | --- | --- |
| | | TKNQVSLTCLVKGFYPSDIAVEWESNGQPENNYKTTP PVLDSDGSFFLYSKLTVDKSRWQQGNVFSCSVMHEA LHNAYTQKSLSLSPGK |
| 50 | Ab5 Light Chain (CDRs in bold; Constant region underlined) | DIVMTQSPLSLPVTPGEPASISC**RSSQSLVSSGYNYLD** WYLQKPGQSPQLLIY**FGSSRAS**GVPDRFSGSGSGTD FTLKISRVEAEDVGVYYC**MQRRRTPWS**FGGGTKVEIK RTVAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC |
| 51 | Ab6 Heavy Chain Variable Region (CDRs bolded) | EVQLVESGGGLVQPGGSLRLSCAASG**FTFEAYSMN**W VRQAPGKGLEWVS**YISLSGATIHYADSVKG**RFTISRD NAKNSLYLQMNSLRAEDTAVYYC**ARGGQYYYTSSDY GEVAFDI**WGQGTLVTVSS |
| 52 | Ab6-HC CDR1 | FTFEAYSMN |
| 53 | Ab6-HC CDR2 | YISLSGATIHYADSVKG |
| 54 | Ab6-HC CDR3 | ARGGQYYYTSSDYGEVAFDI |
| 55 | Ab6 Light Chain Variable Region (CDRs bolded) | DIVLTQSPLSLPVTPGEPASISC**RSSQSLVSSGYNYLD** WYLQKPGQSPQLLIY**FGSSRAS**GVPDRFSGSGSGTD FTLKISRVEAEDVGVYYC**MQRRRTPWS**FGGGTKVEIK |
| 56 | Ab6-LC CDR1 | RSSQSLVSSGYNYLD |
| 57 | Ab6-LC CDR2 | FGSSRAS |
| 58 | Ab6-LC CDR3 | MQRRRTPWS |
| 59 | Ab6 Heavy Chain (CDRs in bold; Constant region underlined; D265C.LALA.H435A) | EVQLVESGGGLVQPGGSLRLSCAASG**FTFEAYSMN**W VRQAPGKGLEWVS**YISLSGATIHYADSVKG**RFTISRD NAKNSLYLQMNSLRAEDTAVYYC**ARGGQYYYTSSDY GEVAFDI**WGQGTLVTVSSASTKGPSVFPLAPSSKSTS GGTAALGCLVKDYFPEPVTVSWNSGALTSGVHTFPA VLQSSGLYSLSSVVTVPSSSLGTQTYICNVNHKPSNTK VDKKVEPKSCDKTHTCPPCPAPEAAGGPSVFLFPPKP KDTLMISRTPEVTCVVVCVSHEDPEVKFNWYVDGVEV HNAKTKPREEQYNSTYRVVSVLTVLHQDWLNGKEYK CKVSNKALPAPIEKTISKAKGQPREPQVYTLPPSRDEL TKNQVSLTCLVKGFYPSDIAVEWESNGQPENNYKTTP PVLDSDGSFFLYSKLTVDKSRWQQGNVFSCSVMHEA LHNAYTQKSLSLSPGK |
| 60 | Ab6 Light Chain (CDRs in bold; Constant region underlined) | DIVLTQSPLSLPVTPGEPASISC**RSSQSLVSSGYNYLD** WYLQKPGQSPQLLIY**FGSSRAS**GVPDRFSGSGSGTD FTLKISRVEAEDVGVYYC**MQRRRTPWS**FGGGTKVEIK RTVAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC |
| 61 | Ab7 Heavy Chain Variable Region (CDRs bolded) | QVQLVESGGGLVKPGGSLRLSCAASG**FTFGGYSMN** WVRQAPGKGLEWVS**YISISGATITYADSVKG**RFTISRD NAKNSLYLQMNSLRAEDTAVYYC**ARGGQYYYDSSDY GEVAFDI**WGQGTMVTVSS |
| 62 | Ab7-HC CDR1 | FTFGGYSMN |
| 63 | Ab7-HC CDR2 | YISISGATITYADSVKG |
| 64 | Ab7-HC CDR3 | ARGGQYYYDSSDYGEVAFDI |
| 65 | Ab7 Light Chain Variable Region (CDRs bolded) | DIVMTQSPLSLPVTPGEPASISC**RSSQSLVSSGYNYLD** WYLQKPGQSPQLLIY**FGSSRAS**GVPDRFSGSGSGTD FTLKISRVEAEDVGVYYC**MQRRRTPPFT**FGGGTKVEI K |
| 66 | Ab7-LC CDR1 | RSSQSLVSSGYNYLD |
| 67 | Ab7-LC CDR2 | FGSSRAS |
| 68 | Ab7-LC CDR3 | MQRRRTPPFT |

TABLE 27 -continued

| SEQUENCE TABLE | | |
|---|---|---|
| SEQ ID NO | Description | Sequence |
| 69 | Ab7 Heavy Chain (CDRs in bold; Constant region underlined; D265C.LALA.H435A) | QVQLVESGGGLVKPGGSLRLSCAASG**FTFGGYSMN**<br>WVRQAPGKGLEWVS**YISISGATITYADSVKG**RFTISRD<br>NAKNSLYLQMNSLRAEDTAVYYC**ARGGQYYYDSSDY**<br>**GEVAFDI**WGQGTMVTVSSASTKGPSVFPLAPSSKSTS<br>GGTAALGCLVKDYFPEPVTVSWNSGALTSGVHTFPA<br>VLQSSGLYSLSSVVTVPSSSLGTQTYICNVNHKPSNTK<br>VDKKVEPKSCDKTHTCPPCPAPEAAGGPSVFLFPPKP<br>KDTLMISRTPEVTCVVVCVSHEDPEVKFNWYVDGVEV<br>HNAKTKPREEQYNSTYRVVSVLTVLHQDWLNGKEYK<br>CKVSNKALPAPIEKTISKAKGQPREPQVYTLPPSRDEL<br>TKNQVSLTCLVKGFYPSDIAVEWESNGQPENNYKTTP<br>PVLDSDGSFFLYSKLTVDKSRWQQGNVFSCSVMHEA<br>LHNAYTQKSLSLSPGK |
| 70 | Ab7 Light Chain (CDRs in bold; Constant region underlined) | DIVMTQSPLSLPVTPGEPASISC**RSSQSLVSSGYNYLD**<br>WYLQKPGQSPQLLIY**FGSSRAS**GVPDRFSGSGSGTD<br>FTLKISRVEAEDVGVYYC**MQRRRTPPFT**FGGGTKVEI<br>KRTVAAPSVFIFPPSDEQLKSGTASVVCLLNNFYPREA<br>KVQWKVDNALQSGNSQESVTEQDSKDSTYSLSSTLT<br>LSKADYEKHKVYACEVTHQGLSSPVTKSFNRGEC |
| 71 | AbA Heavy Chain Variable Region (CDRs bolded) | EVQLLESGGGLVQPGGSLRLSCAASG**FTFNNYWMT**<br>WVRQAPGKGLEWVS**SISSSGGSIYYPDRVKG**RFTISR<br>DNSKNTLYLQMNSLRAEDTAVYYC**ARDERWAGAMD**<br>**A**WGQGTTVTVSS |
| 72 | AbA-HC CDR1 | FTFNNYVVMT |
| 73 | AbA-HC CDR2 | SISSSGGSIYYPDRVKG |
| 74 | AbA-HC CDR3 | ARDERWAGAMDA |
| 75 | AbA Light Chain Variable Region (CDRs bolded) | DIQMTQSPSSLSASVGDRVTITC**KASQNINKNLD**WYQ<br>QKPGKAPKLLIY**ETNNLQT**GVPSRFSGSGSGTDFTLTI<br>SSLQPEDFATYYC**YQHNSRFTF**GQGTKLEIK |
| 76 | AbA-LC CDR1 | KASQNINKNLD |
| 77 | AbA-LC CDR2 | ETNNLQT |
| 78 | AbA-LC CDR3 | YQHNSRFT |
| 79 | AbA Heavy Chain (CDRs in bold; Constant region underlined; D265C.LALA.H435A) | EVQLLESGGGLVQPGGSLRLSCAASG**FTFNNYWMT**<br>WVRQAPGKGLEWVS**SISSSGGSIYYPDRVKG**RFTISR<br>DNSKNTLYLQMNSLRAEDTAVYYC**ARDERWAGAMD**<br>**A**WGQGTTVTVSSASTKGPSVFPLAPSSKSTSGGTAA<br>LGCLVKDYFPEPVTVSWNSGALTSGVHTFPAVLQSSG<br>LYSLSSVVTVPSSSLGTQTYICNVNHKPSNTKVDKKVE<br>PKSCDKTHTCPPCPAPEAAGGPSVFLFPPKPKDTLMI<br>SRTPEVTCVVVCVSHEDPEVKFNWYVDGVEVHNAKT<br>KPREEQYNSTYRVVSVLTVLHQDWLNGKEYKCKVSN<br>KALPAPIEKTISKAKGQPREPQVYTLPPSRDELTKNQV<br>SLTCLVKGFYPSDIAVEWESNGQPENNYKTTPPVLDS<br>DGSFFLYSKLTVDKSRWQQGNVFSCSVMHEALHNAY<br>TQKSLSLSPGK |
| 80 | AbA Light Chain (CDRs in bold; Constant region underlined) | DIQMTQSPSSLSASVGDRVTITC**KASQNINKNLD**WYQ<br>QKPGKAPKLLIY**ETNNLQT**GVPSRFSGSGSGTDFTLTI<br>SSLQPEDFATYYC**YQHNSRFT**FGQGTKLEIKRTVAAP<br>SVFIFPPSDEQLKSGTASVVCLLNNFYPREAKVQWKV<br>DNALQSGNSQESVTEQDSKDSTYSLSSTLTLSKADYE<br>KHKVYACEVTHQGLSSPVTKSFNRGEC |
| 81 | AbB Heavy Chain Variable Region (CDRs bolded) | EVQLVESGGGLVQPGGSLRLSCAASG**FTFTNFWMA**<br>WIRQAPGKGLEWVA**SISSSGGSIYYPDSVKD**RFTISR<br>DNSKNTLYLQMNSLRAEDTAVYYC**VKFHHYSGGGDA**<br>WGQGTLVTVSS |
| 82 | AbB-HC CDR1 | FTFTNFWMA |
| 83 | AbB-HC CDR2 | SISSSGGSIYYPDSVKD |
| 84 | AbB-HC CDR3 | VKFHHYSGGGDA |

TABLE 27 -continued

| SEQ ID NO | Description | Sequence |
|---|---|---|
| SEQUENCE TABLE | | |
| 85 | AbB Light Chain Variable Region (CDRs bolded) | DIQMTQSPSSLSASVGDRVTITC**KASQNINKYLD**WYQ QKPGKAPKLLIH**YTNNLHT**GIPSRFSGSGSGTDYTLTI SSLQPEDFATYYC**LQHSSRWT**FGGGTKVEIK |
| 86 | AbB-LC CDR1 | KASQNIN KYLD |
| 87 | AbB-LC CDR2 | YTNNLHT |
| 88 | AbB-LC CDR3 | LQHSSRVVT |
| 89 | AbB Heavy Chain (CDRs in bold; Constant region underlined; D265C.LALA.H435A) | EVQLVESGGGLVQPGGSLRLSCAASG**FTFTNFWMA** WIRQAPGKGLEWVA**SISSSGGSIYYPDSVKD**RFTISR DNSKNTLYLQMNSLRAEDTAVYYC**VKFHHYSGGGDA** WGQGTLVTVSSASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKKVE PKSCDKTHTCPPCPAPEAAGGPSVFLFPPKPKDTLMI SRTPEVTCVVVCVSHEDPEVKFNWYVDGVEVHNAKT KPREEQYNSTYRVVSVLTVLHQDWLNGKEYKCKVSN KALPAPIEKTISKAKGQPREPQVYTLPPSRDELTKNQV SLTCLVKGFYPSDIAVEWESNGQPENNYKTTPPVLDS DGSFFLYSKLTVDKSRWQQGNVFSCSVMHEALHNAY TQKSLSLSPGK |
| 90 | AbB Light Chain (CDRs in bold; Constant region underlined) | DIQMTQSPSSLSASVGDRVTITC**KASQNINKYLD**WYQ QKPGKAPKLLIH**YTNNLHT**GIPSRFSGSGSGTDYTLTI SSLQPEDFATYYC**LQHSSRWT**FGGGTKVEIKRTVAAP SVFIFPPSDEQLKSGTASVVCLLNNFYPREAKVQWKV DNALQSGNSQESVTEQDSKDSTYSLSSTLTLSKADYE KHKVYACEVTHQGLSSPVTKSFNRGEC |
| 91 | AbC Heavy Chain Variable Region (CDRs bolded) | EVQLVESGGGLVQPGGSLRLSCAASG**FTFNNYWMT** WVRQAPGKGLEWVS**SISSSGGSIYYPDSVKD**RFTISR DNAKNSLYLQMNSLRAEDMAVYYC**ARLYYYDGGGD** **A**WGQGTLVTVSS |
| 92 | AbC-HC CDR1 | FTFNNYVVMT |
| 93 | AbC-HC CDR2 | SISSSGGSIYYPDSVKD |
| 94 | AbC-HC CDR3 | ARLYYYDGGGDA |
| 95 | AbC Light Chain Variable Region (CDRs bolded) | GIQMTQSPSSLSASVGDRVTITC**KASQDINKYLD**WYQ QKPGKAPKLLIY**NTNNLHT**GIPSRFSGSGSGTDYTLTI SSLQPEDFATYYC**LQHISRWT**FGGGTKVEIK |
| 96 | AbC-LC CDR1 | KASQDINKYLD |
| 97 | AbC-LC CDR2 | NTNNLHT |
| 98 | AbC-LC CDR3 | LQHISRWT |
| 99 | AbC Heavy Chain (CDRs in bold; Constant region underlined; D265C.LALA.H435A) | EVQLVESGGGLVQPGGSLRLSCAASG**FTFNNYWMT** WVRQAPGKGLEWVS**SISSSGGSIYYPDSVKD**RFTISR DNAKNSLYLQMNSLRAEDMAVYYC**ARLYYYDGGGD** **A**WGQGTLVTVSSASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKKVE PKSCDKTHTCPPCPAPEAAGGPSVFLFPPKPKDTLMI SRTPEVTCVVVCVSHEDPEVKFNWYVDGVEVHNAKT KPREEQYNSTYRVVSVLTVLHQDWLNGKEYKCKVSN KALPAPIEKTISKAKGQPREPQVYTLPPSRDELTKNQV SLTCLVKGFYPSDIAVEWESNGQPENNYKTTPPVLDS DGSFFLYSKLTVDKSRWQQGNVFSCSVMHEALHNAY TQKSLSLSPGK |
| 100 | AbC Light Chain (CDRs in bold; Constant region underlined) | GIQMTQSPSSLSASVGDRVTITC**KASQDINKYLD**WYQ QKPGKAPKLLIY**NTNNLHT**GIPSRFSGSGSGTDYTLTI SSLQPEDFATYYC**LQHISRWT**FGGGTKVEIKRTVAAP SVFIFPPSDEQLKSGTASVVCLLNNFYPREAKVQWKV DNALQSGNSQESVTEQDSKDSTYSLSSTLTLSKADYE KHKVYACEVTHQGLSSPVTKSFNRGEC |

TABLE 27 -continued

SEQUENCE TABLE

| SEQ ID NO | Description | Sequence |
|---|---|---|
| 101 | IgG Light Chain Constant Region | RTVAAPSVFIFPPSDEQLKSGTASVVCLLNNFYP<br>REAKVQWKVDNALQSGNSQESVTEQDSKDSTY<br>SLSSTLTLSKADYEKHKVYACEVTHQGLSSPVTK<br>SFNRGEC |
| 102 | IgG Heavy chain constant region of VVT | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPE**LL**GGPSVFLFPPKPKD<br>TLMISRTPEVTCVVV**D**VSHEDPEVKFNWYVDGV<br>EVHNAKTKPREEQYNSTYRVVSVLTVLHQDWLN<br>GK**E**YKCKVSNKALPAPIEKTISKAKGQPREPQVY<br>TLPPSRDELTKNQVSLTCLVKGFYPSDIAVEWES<br>NGQPENNYKTTPPVLDSDGSFFLYSKLTVDKSR<br>WQQGNVFSCSVMHEALHN**H**YTQKSLSLSPGK |
| 103 | IgG Heavy chain constant region (D265C)* | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVV**C**VSHEDPEVKFNWYVDGV<br>EVHNAKTKPREEQYNSTYRVVSVLTVLHQDWLN<br>GK**E**YKCKVSNKALPAPIEKTISKAKGQPREPQVY<br>TLPPSRDELTKNQVSLTCLVKGFYPSDIAVEWES<br>NGQPENNYKTTPPVLDSDGSFFLYSKLTVDKSR<br>WQQGNVFSCSVMHEALHNHYTQKSLSLSPGK |
| 104 | IgG Heavy chain constant region (L234A/L235A/D265C)* | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPE**AA**GGPSVFLFPPKPKD<br>TLMISRTPEVTCVVV**C**VSHEDPEVKFNWYVDGV<br>EVHNAKTKPREEQYNSTYRVVSVLTVLHQDWLN<br>GK**E**YKCKVSNKALPAPIEKTISKAKGQPREPQVY<br>TLPPSRDELTKNQVSLTCLVKGFYPSDIAVEWES<br>NGQPENNYKTTPPVLDSDGSFFLYSKLTVDKSR<br>WQQGNVFSCSVMHEALHNHYTQKSLSLSPGK |
| 105 | IgG Heavy chain constant region (H435A/D265C)* | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVV**C**VSHEDPEVKFNWYVDGV<br>EVHNAKTKPREEQYNSTYRVVSVLTVLHQDWLN<br>GK**E**YKCKVSNKALPAPIEKTISKAKGQPREPQVY<br>TLPPSRDELTKNQVSLTCLVKGFYPSDIAVEWES<br>NGQPENNYKTTPPVLDSDGSFFLYSKLTVDKSR<br>WQQGNVFSCSVMHEALHN**A**YTQKSLSLSPGK |
| 106 | IgG Heavy chain constant region (L234A/L235A/H435A/ D265C)* | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPE**AA**GGPSVFLFPPKPKD<br>TLMISRTPEVTCVVV**C**VSHEDPEVKFNWYVDGV<br>EVHNAKTKPREEQYNSTYRVVSVLTVLHQDWLN<br>GKEYKCKVSNKALPAPIEKTISKAKGQPREPQVY<br>TLPPSRDELTKNQVSLTCLVKGFYPSDIAVEWES<br>NGQPENNYKTTPPVLDSDGSFFLYSKLTVDKSR<br>WQQGNVFSCSVMHEALHN**A**YTQKSLSLSPGK |
| 107 | Human CD45RA Isoform (Uniprot Accession No: P08575-8) | MTMYLWLKLLAFGFAFLDTEVFVTGQSPTPSPTGLTT<br>AKMPSVPLSSDPLPTHTTAFSPASTFERENDFSETTTS<br>LSPDNTSTQVSPDSLDNASAFNTTDAYLNASETTTLSP<br>SGSAVISTTTIATTPSKPTCDEKYANITVDYLYNKETKL<br>FTAKLNVNENVECGNNTCTNNEVHNLTECKNASVSIS<br>HNSCTAPDKTLILDVPPGVEKFQLHDCTQVEKADTTIC<br>LKWKNIETFTCDTQNITYRFQCGNMIFDNKEIKLENLE<br>PEHEYKCDSEILYNNHKFTNASKIIKTDFGSPGEPQIIF<br>CRSEAAHQGVITWNPPQRSFHNFTLCYIKETEKDCLN<br>LDKNLIKYDLQNLKPYTKYVLSLHAYIIAKVQRNGSAAM<br>CHFTTKSAPPSQVWNMTVSMTSDNSMHVKCRPPRD<br>RNGPHERYHLEVEAGNTLVRNESHKNCDFRVKDLQY<br>STDYTFKAYFHNGDYPGEPFILHHSTSYNSKALIAFLA<br>FLIIVTSIALLVVLYKIYDLHKKRSCNLDEQQELVERDDE |

TABLE 27 -continued

| SEQUENCE TABLE | | |
|---|---|---|
| SEQ ID NO | Description | Sequence |
| | | KQLMNVEPIHADILLETYKRKIADEGRLFLAEFQSIPRV FSKFPIKEARKPFNQNKNRYVDILPYDYNRVELSEING DAGSNYINASYIDGFKEPRKYIAAQGPRDETVDDFWR MIWEQKATVIVMVTRCEEGNRNKCAEYWPSMEEGTR AFGDVVVKINQHKRCPDYIIQKLNIVNKKEKATGREVT HIQFTSWPDHGVPEDPHLLLKLRRRVNAFSNFFSGPIV VHCSAGVGRTGTYIGIDAMLEGLEAENKVDVYGYVVK LRRQRCLMVQVEAQYILIHQALVEYNQFGETEVNLSEL HPYLHNMKKRDPPSEPSPLEAEFQRLPSYRSWRTQHI GNQEENKSKNRNSNVIPYDYNRVPLKHELEMSKESE HDSDESSDDDSDSEEPSKYINASFIMSYWKPEVMIAA QGPLKETIGDFWQMIFQRKVKVIVMLTELKHGDQEICA QYWGEGKQTYGDIEVDLKDTDKSSTYTLRVFELRHSK RKDSRTVYQYQYTNWSVEQLPAEPKELISMIQVVKQK LPQKNSSEGNKHHKSTPLLIHCRDGSQQTGIFCALLNL LESAETEEVVDIFQVVKALRKARPGMVSTFEQYQFLY DVIASTYPAQNGQVKKNNHQEDKIEFDNEVDKVKQDA NCVNPLGAPEKLPEAKEQAEGSEPTSGTEGPEHSVN GPASPALNQGS |
| 108 | Human CD45RO Isoform (NCBI Accession No: NP_563578.2) | MTMYLWLKLLAFGFAFLDTEVFVTGQSPTPSPTDAYL NASETTTLSPSGSAVISTTTIATTPSKPTCDEKYANITV DYLYNKETKLFTAKLNVNENVECGNNTCTNNEVHNLT ECKNASVSISHNSCTAPDKTLILDVPPGVEKFQLHDCT QVEKADTTICLKWKNIETFTCDTQNITYRFQCGNMIFD NKEIKLENLEPEHEYKCDSEILYNNHKFTNASKIIKTDF GSPGEPQIIFCRSEAAHQGVITWNPPQRSFHNFTLCYI KETEKDCLNLDKNLIKYDLQNLKPYTKYVLSLHAYIIAK VQRNGSAAMCHFTTKSAPPSQVWNMTVSMTSDNSM HVKCRPPRDRNGPHERYHLEVEAGNTLVRNESHKNC DFRVKDLQYSTDYTFKAYFHNGDYPGEPFILHHSTSY NSKALIAFLAFLIIVTSIALLVVLYKIYDLHKKRSCNLDEQ QELVERDDEKQLMNVEPIHADILLETYKRKIADEGRLF LAEFQSIPRVFSKFPIKEARKPFNQNKNRYVDILPYDY NRVELSEINGDAGSNYINASYIDGFKEPRKYIAAQGPR DETVDDFWRMIWEQKATVIVMVTRCEEGNRNKCAEY WPSMEEGTRAFGDVVVKINQHKRCPDYIIQKLNIVNKK EKATGREVTHIQFTSWPDHGVPEDPHLLLKLRRRVNA FSNFFSGPIVVHCSAGVGRTGTYIGIDAMLEGLEAENK VDVYGYVVKLRRQRCLMVQVEAQYILIHQALVEYNQF GETEVNLSELHPYLHNMKKRDPPSEPSPLEAEFQRLP SYRSWRTQHIGNQEENKSKNRNSNVIPYDYNRVPLK HELEMSKESEHDSDESSDDDSDSEEPSKYINASFIMS YWKPEVMIAAQGPLKETIGDFWQMIFQRKVKVIVMLT ELKHGDQEICAQYWGEGKQTYGDIEVDLKDTDKSSTY TLRVFELRHSKRKDSRTVYQYQYTNWSVEQLPAEPK ELISMIQVVKQKLPQKNSSEGNKHHKSTPLLIHCRDGS QQTGIFCALLNLLESAETEEVVDIFQVVKALRKARPGM VSTFEQYQFLYDVIASTYPAQNGQVKKNNHQEDKIEF DNEVDKVKQDANCVNPLGAPEKLPEAKEQAEGSEPT SGTEGPEHSVNGPASPALNQGS |
| 109 | Human CD45RB Isoform (NCBI Accession No: XP_006711537.1) | MTMYLWLKLLAFGFAFLDTEVFVTGQSPTPSPTGVSS VQTPHLPTHADSQTPSAGTDTQTFSGSAANAKLNPTP GSNAISDAYLNASETTTLSPSGSAVISTTTIATTPSKPT CDEKYANITVDYLYNKETKLFTAKLNVNENVECGNNT CTNNEVHNLTECKNASVSISHNSCTAPDKTLILDVPPG VEKFQLHDCTQVEKADTTICLKWKNIETFTCDTQNITY RFQCGNMIFDNKEIKLENLEPEHEYKCDSEILYNNHKF TNASKIIKTDFGSPGEPQIIFCRSEAAHQGVITWNPPQ RSFHNFTLCYIKETEKDCLNLDKNLIKYDLQNLKPYTKY VLSLHAYIIAKVQRNGSAAMCHFTTKSAPPSQVWNMT VSMTSDNSMHVKCRPPRDRNGPHERYHLEVEAGNTL VRNESHKNCDFRVKDLQYSTDYTFKAYFHNGDYPGE PFILHHSTSYNSKALIAFLAFLIIVTSIALLVVLYKIYDLHK KRSCNLDEQQELVERDDEKQLMNVEPIHADILLETYK RKIADEGRLFLAEFQSIPRVFSKFPIKEARKPFNQNKN RYVDILPYDYNRVELSEINGDAGSNYINASYIDGFKEP RKYIAAQGPRDETVDDFWRMIWEQKATVIVMVTRCEE GNRNKCAEYWPSMEEGTRAFGDVVVKINQHKRCPDY IIQKLNIVNKKEKATGREVTHIQFTSWPDHGVPEDPHL LLKLRRRVNAFSNFFSGPIVVHCSAGVGRTGTYIGIDA MLEGLEAENKVDVYGYVVKLRRQRCLMVQVEAQYILI HQALVEYNQFGETEVNLSELHPYLHNMKKRDPPSEP SPLEAEFQRLPSYRSWRTQHIGNQEENKSKNRNSNVI |

TABLE 27 -continued

SEQUENCE TABLE

| SEQ ID NO | Description | Sequence |
|---|---|---|
| | | PYDYNRVPLKHELEMSKESEHDSDESSDDDSDSEEP SKYINASFIMSYWKPEVMIAAQGPLKETIGDFWQMIFQ RKVKVIVMLTELKHGDQEICAQYWGEGKQTYGDIEVD LKDTDKSSTYTLRVFELRHSKRKDSRTVYQYQYTNWS VEQLPAEPKELISMIQVVKQKLPQKNSSEGNKHHKST PLLIHCRDGSQQTGIFCALLNLLESAETEEVVDIFQVVK ALRKARPGMVSTFEQYQFLYDVIASTYPAQNGQVKKN NHQEDKIEFDNEVDKVKQDANCVNPLGAPEKLPEAKE QAEGSEPTSGTEGPEHSVNGPASPALNQGS |
| 110 | Human CD45RAB Isoform (NCBI Accession No: XP_006711535.1) | MTMYLWLKLLAFGFAFLDTEVFVTGQSPTPSPTGLTT AKMPSVPLSSDPLPTHTTAFSPASTFERENDFSETTTS LSPDNTSTQVSPDSLDNASAFNTTGVSSVQTPHLPTH ADSQTPSAGTDTQTFSGSAANAKLNPTPGSNAISDAY LNASETTTLSPSGSAVISTTTIATTPSKPTCDEKYANIT VDYLYNKETKLFTAKLNVNENVECGNNTCTNNEVHNL TECKNASVSISHNSCTAPDKTLILDVPPGVEKFQLHDC TQVEKADTTICLKWKNIETFTCDTQNITYRFQCGNMIF DNKEIKLENLEPEHEYKCDSEILYNNHKFTNASKIIKTD FGSPGEPQIIFCRSEAAHQGVITWNPPQRSFHNFTLC YIKETEKDCLNLDKNLIKYDLQNLKPYTKYVLSLHAYIIA KVQRNGSAAMCHFTTKSAPPSQVWNMTVSMTSDNS MHVKCRPPRDRNGPHERYHLEVEAGNTLVRNESHKN CDFRVKDLQYSTDYTFKAYFHNGDYPGEPFILHHSTS YNSKALIAFLAFLIIVTSIALLVVLYKIYDLHKKRSCNLDE QQELVERDDEKQLMNVEPIHADILLETYKRKIADEGRL FLAEFQSIPRVFSKFPIKEARKPFNQNKNRYVDILPYDY NRVELSEINGDAGSNYINASYIDGFKEPRKYIAAQGPR DETVDDFWRMIWEQKATVIVMVTRCEEGNRNKCAEY WPSMEEGTRAFGDVVVKINQHKRCPDYIIQKLNIVNKK EKATGREVTHIQFTSWPDHGVPEDPHLLLKLRRRVNA FSNFFSGPIVVHCSAGVGRTGTYIGIDAMLEGLEAENK VDVYGYVVKLRRQRCLMVQVEAQYILIHQALVEYNQF GETEVNLSELHPYLHNMKKRDPPSEPSPLEAEFQRLP SYRSWRTQHIGNQEENKSKNRNSNVIPYDYNRVPLK HELEMSKESEHDSDESSDDDSDSEEPSKYINASFIMS YWKPEVMIAAQGPLKETIGDFWQMIFQRKVKVIVMLT ELKHGDQEICAQYWGEGKQTYGDIEVDLKDTDKSSTY TLRVFELRHSKRKDSRTVYQYQYTNWSVEQLPAEPK ELISMIQVVKQKLPQKNSSEGNKHHKSTPLLIHCRDGS QQTGIFCALLNLLESAETEEVVDIFQVVKALRKARPGM VSTFEQYQFLYDVIASTYPAQNGQVKKNNHQEDKIEF DNEVDKVKQDANCVNPLGAPEKLPEAKEQAEGSEPT SGTEGPEHSVNGPASPALNQGS |
| 111 | Human CD45RBC Isoform (NCBI Accession No: XP_006711536.1) | MTMYLWLKLLAFGFAFLDTEVFVTGQSPTPSPTGVSS VQTPHLPTHADSQTPSAGTDTQTFSGSAANAKLNPTP GSNAISDVPGERSTASTFPTDPVSPLTTTLSLAHHSSA ALPARTSNTTITANTSDAYLNASETTTLSPSGSAVISTT TIATTPSKPTCDEKYANITVDYLYNKETKLFTAKLNVNE NVECGNNTCTNNEVHNLTECKNASVSISHNSCTAPDK TLILDVPPGVEKFQLHDCTQVEKADTTICLKWKNIETFT CDTQNITYRFQCGNMIFDNKEIKLENLEPEHEYKCDSE ILYNNHKFTNASKIIKTDFGSPGEPQIIFCRSEAAHQGVI TWNPPQRSFHNFTLCYIKETEKDCLNLDKNLIKYDLQN LKPYTKYVLSLHAYIIAKVQRNGSAAMCHFTTKSAPPS QVWNMTVSMTSDNSMHVKCRPPRDRNGPHERYHLE VEAGNTLVRNESHKNCDFRVKDLQYSTDYTFKAYFHN GDYPGEPFILHHSTSYNSKALIAFLAFLIIVTSIALLVVLY KIYDLHKKRSCNLDEQQELVERDDEKQLMNVEPIHADI LLETYKRKIADEGRLFLAEFQSIPRVFSKFPIKEARKPF NQNKNRYVDILPYDYNRVELSEINGDAGSNYINASYID GFKEPRKYIAAQGPRDETVDDFWRMIWEQKATVIVMV TRCEEGNRNKCAEYWPSMEEGTRAFGDVVVKINQHK RCPDYIIQKLNIVNKKEKATGREVTHIQFTSWPDHGVP EDPHLLLKLRRRVNAFSNFFSGPIVVHCSAGVGRTGT YIGIDAMLEGLEAENKVDVYGYVVKLRRQRCLMVQVE AQYILIHQALVEYNQFGETEVNLSELHPYLHNMKKRDP PSEPSPLEAEFQRLPSYRSWRTQHIGNQEENKSKNR NSNVIPYDYNRVPLKHELEMSKESEHDSDESSDDDSD SEEPSKYINASFIMSYWKPEVMIAAQGPLKETIGDFWQ MIFQRKVKVIVMLTELKHGDQEICAQYWGEGKQTYGD IEVDLKDTDKSSTYTLRVFELRHSKRKDSRTVYQYQYT NWSVEQLPAEPKELISMIQVVKQKLPQKNSSEGNKHH KSTPLLIHCRDGSQQTGIFCALLNLLESAETEEVVDIFQ |

TABLE 27 -continued

SEQUENCE TABLE

| SEQ ID NO | Description | Sequence |
|---|---|---|
| | | VVKALRKARPGMVSTFEQYQFLYDVIASTYPAQNGQV KKNNHQEDKIEFDNEVDKVKQDANCVNPLGAPEKLPE AKEQAEGSEPTSGTEGPEHSVNGPASPALNQGS |
| 112 | Human CD45RABC Isoform (NCBI Accession No. NP_002829.3) | MTMYLWLKLLAFGFAFLDTEVFVTGQSPTPSPTGLTT AKMPSVPLSSDPLPTHTTAFSPASTFERENDFSETTS LSPDNTSTQVSPDSLDNASAFNTTGVSSVQTPHLPTH ADSQTPSAGTDTQTFSGSAANAKLNPTPGSNAISDVP GERSTASTFPTDPVSPLTTTLSLAHHSSAALPARTSNT TITANTSDAYLNASETTTLSPSGSAVISTTTIATTPSKPT CDEKYANITVDYLYNKETKLFTAKLNVNENVECGNNT CTNNEVHNLTECKNASVSISHNSCTAPDKTLILDVPPG VEKFQLHDCTQVEKADTTICLKWKNIETFTCDTQNITY RFQCGNMIFDNKEIKLENLEPEHEYKCDSEILYNNHKF TNASKIIKTDFGSPGEPQIIFCRSEAAHQGVITWNPPQ RSFHNFTLCYIKETEKDCLNLDKNLIKYDLQNLKPYTKY VLSLHAYIIAKVQRNGSAAMCHFTTKSAPPSQVWNMT VSMTSDNSMHVKCRPPRDRNGPHERYHLEVEAGNTL VRNESHKNCDFRVKDLQYSTDYTFKAYFHNGDYPGE PFILHHSTSYNSKALIAFLAFLIIVTSIALLVVLYKIYDLHK KRSCNLDEQQELVERDDEKQLMNVEPIHADILLETYK RKIADEGRLFLAEFQSIPRVFSKFPIKEARKPFNQNKN RYVDILPYDYNRVELSEINGDAGSNYINASYIDGFKEP RKYIAAQGPRDETVDDFWRMIWEQKATVIVMVTRCEE GNRNKCAEYWPSMEEGTRAFGDVVVKINQHKRCPDY IIQKLNIVNKKEKATGREVTHIQFTSWPDHGVPEDPHL LLKLRRRVNAFSNFFSGPIVVHCSAGVGRTGTYIGIDA MLEGLEAENKVDVYGYVVKLRRQRCLMVQVEAQYILI HQALVEYNQFGETEVNLSELHPYLHNMKKRDPPSEP SPLEAEFQRLPSYRSWRTQHIGNQEENKSKNRNSNVI PYDYNRVPLKHELEMSKESEHDSDESSDDDSDSEEP SKYINASFIMSYWKPEVMIAAQGPLKETIGDFWQMIFQ RKVKVIVMLTELKHGDQEICAQYWGEGKQTYGDIEVD LKDTDKSSTYTLRVFELRHSKRKDSRTVYQYQYTNWS VEQLPAEPKELISMIQVVKQKLPQKNSSEGNKHHKST PLLIHCRDGSQQTGIFCALLNLLESAETEEVVDIFQVVK ALRKARPGMVSTFEQYQFLYDVIASTYPAQNGQVKKN NHQEDKIEFDNEVDKVKQDANCVNPLGAPEKLPEAKE QAEGSEPTSGTEGPEHSVNGPASPALNQGS |
| 113 | Human CD45RABC Antigen (Fragment of Human CD45RABC Isoform) | QSPTPSPTGLTTAKMPSVPLSSDPLPTHTTAFSPASTF ERENDFSETTTSLSPDNTSTQVSPDSLDNASAFNTTG VSSVQTPHLPTHADSQTPSAGTDTQTFSGSAANAKLN PTPGSNAISDVPGERSTASTFPTDPVSPLTTTLSLAHH SSAALPARTSNTTITANTSDAYLNASETTTLSPSGSAVI STTTIATTPSKPTCDEKYANITVDYLYNKETKLFTAKLN VNENVECGNNTCTNNEVHNLTECKNASVSISHNSCTA PDKTLILDVPPGVEKFQLHDCTQVEKADTTICLKWKNI ETFTCDTQNITYRFQCGNMIFDNKEIKLENLEPEHEYK CDSEILYNNHKFTNASKIIKTDFGSPGEPQIIFCRSEAA HQGVITWNPPQRSFHNFTLCYIKETEKDCLNLDKNLIK YDLQNLKPYTKYVLSLHAYIIAKVQRNGSAAMCHFTTK SAPPSQVWNMTVSMTSDNSMHVKCRPPRDRNGPHE RYHLEVEAGNTLVRNESHKNCDFRVKDLQYSTDYTFK AYFHNGDYPGEPFILHHSTSYNSK |
| 114 | CD45 Fragment 1 | TEKDCLNLDKNLIKYDLQNLK |
| 115 | CD45 Fragment 2 | CYIKETEKDCLNLDKNLIKYDLQNLKPYTKY |
| 116 | CD45 Fragment 3 | RPPRDRNGPHERYHLEVEAGNTLVRNESH |
| 117 | CD45 Fragment 4 | CRPPRDRNGPHERYHLEVEAGNTLVRNESHK |
| 118 | CD45 Fragments | RNGPHERYHLEVEAGNT |
| 119 | Consensus Sequence of variable heavy chain CDR1 (Abs 1-7) | FTF(S/E/G)(S/NG)YSMN |
| 120 | Consensus Sequence of variable heavy chain CDR2 (Abs 1-7) | YIS(S/L/DS(S/G)(S/A)TI(Y/H/T)YYADSVKG |

TABLE 27 -continued

SEQUENCE TABLE

| SEQ ID NO | Description | Sequence |
| --- | --- | --- |
| 121 | Consensus Sequence of variable heavy chain CDR3 (Abs 1-7) | ARGGQYYY(D/T)SS(R/D)YGEVAFDI |
| 122 | Consensus Sequence of variable light chain CDR1 (Abs 1-7) | RSSQSLL(H/-)SNGYNYLD |
| 123 | onsensus Sequence of variable light chain CDR2 (Abs 1-7) | (L/F)GS(N/S)RAS |
| 124 | Consensus Sequence of variable light chain CDR3 (Abs 1-7) | MQRRRTP(P/VV)(F/S)(T/F) |
| 125 | Ab1 Heavy Chain Variable Region (Nucleic Acid) | CAGGTGCAGCTGGTGGAGTCTGGGGGAGGCTTGG TCAAGCCTGGAGGGTCCCTGAGACTCTCCTGTGCA GCCTCTGGATTCACCTTCAGTAGCTATAGCATGAAC TGGGTCCGCCAGGCTCCAGGGAAGGGGCTGGAGT GGGTTTCATACATTAGTAGTAGTAGTAGTACCATAT ACTACGCAGACTCTGTGAAGGGCCGATTCACCATC TCCAGAGACAATGCCAAGAACTCACTGTATCTGCAA ATGAACAGCCTGAGAGCTGAGGACACGGCGGTGTA CTACTGCGCCAGAGGTGGACAATACTACTACGACA GCAGCAGATACGGTGAGGTAGCATTCGACATATGG GGTCAGGGTACAATGGTCACCGTCTCCTCA |
| 126 | Ab1 Light Chain Variable Region (Nucleic Acid) | GATATTGTGATGACTCAGTCTCCACTCTCCCTGCCC GTCACCCCTGGAGAGCCGGCCTCCATCTCCTGCAG GTCTAGTCAGAGCCTCCTGCATAGTAATGGATACAA CTATTTGGATTGGTACCTGCAGAAGCCAGGGCAGT CTCCACAGCTCCTGATCTATTTGGGTTCTAATCGGG CCTCCGGGGTCCCTGACAGGTTCAGTGGCAGTGGA TCAGGCACAGATTTTACACTGAAAATCAGCAGAGTG GAGGCTGAGGATGTTGGGGTTTATTACTGCATGCA GAGAAGACGCACTCCTCCTTTCACTTTTGGCGGAG GGACCAAGGTTGAGATCAAA |
| 127 | Ab2 Heavy Chain Variable Region (Nucleic Acid) | GAAGTGCAGCTTGTGGAGTCCGGTGGCGGACTGGT CCAGCCGGGCGGATCTCTGAGACTTTCGTGTGCCG CCTCGGGATTCACCTTCGAAGCGTATTCCATGAACT GGGTCAGACAGGCCCCCGGAAAGGGCCTGGAATG GGTGTCGTACATTAGCCTGTCGGGGGCCACCATCC ATTACGCCGATAGCGTGAAGGGCCGGTTCACAATC TCCCGGGACAACGCCAAGAACTCCCTCTACCTCCA AATGAACAGCCTGCGCGCTGAGGACACTGCTGTGT ACTATTGCGCGAGGGGTGGCCAGTACTACTACGAC TCAAGCGACTACGGCGAAGTGGCATTCGATATCTG GGGACAGGGGACCATGGTCACCGTCAGCTCC |
| 128 | Ab2 Light Chain Variable Region (Nucleic Acid) | GATATCGTGATGACACAGTCCCCTCTGTCCCTCCCT GTGACCCCCGGAGAACCAGCCTCTATTTCCTGCCG GTCCTCCCAATCCCTGGTGTCCAACGGTTATAACTA CCTGGATTGGTACTTGCAAAAGCCCGGACAGAGCC CCCAGCTGCTCATCTACTTCGGAAGCTCACGCGCG AGCGGGGTGCCGGATAGGTTTTCGGGATCCGGAA GCGGCACCGACTTCACGCTGAAGATCTCGAGAGTC GAGGCCGAGGACGTGGGCGTGTACTACTGTATGCA GCGGCGGCGCACCCCCTGGTCCTTCGGCGGCGGA ACTAAGGTCGAGATCAAG |
| 129 | Ab3 Heavy Chain Variable Region (Nucleic Acid) | CAAGTGCAGCTTGTGGAGTCCGGTGGCGGACTGGT CAAGCCGGGCGGATCTCTGAGACTTTCGTGTGCCG CCTCGGGATTCACCTTCGGCGGATATTCCATGAACT GGGTCAGACAGGCCCCCGGAAAGGGCCTGGAATG GGTGTCGTACATTAGCATCTCGGGGGCCACCATCA CTTACGCCGATAGCGTGAAGGGCCGGTTCACAATC TCCCGGGACAACGCCAAGAACTCCCTCTACCTCCA AATGAACAGCCTGCGCGCTGAGGACACTGCTGTGT ACTATTGCGCGAGGGGTGGCCAGTACTACTACGAC TCAAGCGACTACGGCGAAGTGGCATTCGATATCTG GGGACAGGGGACCATGGTCACCGTCAGCTCC |

TABLE 27 -continued

SEQUENCE TABLE

| SEQ ID NO | Description | Sequence |
|---|---|---|
| 130 | Ab3 Light Chain Variable Region (Nucleic Acid) | GATATCGTGATGACACAGTCCCCTCTGTCCCTCCCT<br>GTGACCCCCGGAGAACCAGCCTCTATTTCCTGCCG<br>GTCCTCCCAATCCCTGGTGTCCAACGGTTATAACTA<br>CCTGGATTGGTACTTGCAAAAGCCCGGACAGAGCC<br>CCCAGCTGCTCATCTACTTCGGAAGCTCACGCGCG<br>AGCGGGGTGCCGGATAGGTTTTCGGGATCCGGAA<br>GCGGCACCGACTTCACGCTGAAGATCTCGAGAGTC<br>GAGGCCGAGGACGTGGGCGTGTACTACTGTATGCA<br>GCGGCGGCGCACCCCGCCCTTCACCTTCGGCGGC<br>GGAACTAAGGTCGAGATCAAG |
| 131 | Ab4 Heavy Chain Variable Region (Nucleic Acid) | GAAGTGCAGCTTGTGGAGTCCGGTGGCGGACTGGT<br>CCAGCCGGGCGGATCTCTGAGACTTTCGTGTGCCG<br>CCTCGGGATTCACCTTCGAAGCGTATTCCATGAACT<br>GGGTCAGACAGGCCCCCGGAAAGGGCCTGGAATG<br>GGTGTCGTACATTAGCCTGTCGGGGGCCACCATCC<br>ATTACGCCGATAGCGTGAAGGGCCGGTTCACAATC<br>TCCCGGGACAACGCCAAGAACTCCCTCTACCTCCA<br>AATGAACAGCCTGCGCGCTGAGGACACTGCTGTGT<br>ACTATTGCGCGAGGGGTGGCCAGTACTACTACACC<br>TCAAGCGACTACGGCGAAGTGGCATTCGATATCTG<br>GGGACAGGGGACCATGGTCACCGTCAGCTCC |
| 132 | Ab4 Light Chain Variable Region (Nucleic Acid) | GATATCGTGATGACACAGTCCCCTCTGTCCCTCCCT<br>GTGACCCCCGGAGAACCAGCCTCTATTTCCTGCCG<br>GTCCTCCCAATCCCTGGTGTCCAACGGTTATAACTA<br>CCTGGATTGGTACTTGCAAAAGCCCGGACAGAGCC<br>CCCAGCTGCTCATCTACTTCGGAAGCTCACGCGCG<br>AGCGGGGTGCCGGATAGGTTTTCGGGATCCGGAA<br>GCGGCACCGACTTCACGCTGAAGATCTCGAGAGTC<br>GAGGCCGAGGACGTGGGCGTGTACTACTGTATGCA<br>GCGGCGGCGCACCCCCTGGTCCTTCGGCGGCGGA<br>ACTAAGGTCGAGATCAAG |
| 133 | Ab5 Heavy Chain Variable Region (Nucleic Acid) | GAAGTGCAGCTTGTGGAGTCCGGTGGCGGACTGGT<br>CCAGCCGGGCGGATCTCTGAGACTTTCGTGTGCCG<br>CCTCGGGATTCACCTTCGAAGCGTATTCCATGAACT<br>GGGTCAGACAGGCCCCCGGAAAGGGCCTGGAATG<br>GGTGTCGTACATTAGCCTGTCGGGGGCCACCATCC<br>ATTACGCCGATAGCGTGAAGGGCCGGTTCACAATC<br>TCCCGGGACAACGCCAAGAACTCCCTCTACCTCCA<br>AATGAACAGCCTGCGCGCTGAGGACACTGCTGTGT<br>ACTATTGCGCGAGGGGTGGCCAGTACTACTACACC<br>TCAAGCGACTACGGCGAAGTGGCATTCGATATCTG<br>GGGACAGGGGACCATGGTCACCGTCAGCTCC |
| 134 | Ab5 Light Chain Variable Region (Nucleic Acid) | GATATCGTGATGACACAGTCCCCTCTGTCCCTCCCT<br>GTGACCCCCGGAGAACCAGCCTCTATTTCCTGCCG<br>GTCCTCCCAATCCCTGGTGTCCTCGGGTTATAACTA<br>CCTGGATTGGTACTTGCAAAAGCCCGGACAGAGCC<br>CCCAGCTGCTCATCTACTTCGGAAGCTCACGCGCG<br>AGCGGGGTGCCGGATAGGTTTTCGGGATCCGGAA<br>GCGGCACCGACTTCACGCTGAAGATCTCGAGAGTC<br>GAGGCCGAGGACGTGGGCGTGTACTACTGTATGCA<br>GCGGCGGCGCACCCCCTGGTCCTTCGGCGGCGGA<br>ACTAAGGTCGAGATCAAG |
| 135 | Ab6 Heavy Chain Variable Region (Nucleic Acid) | GAGGTGCAGCTGGTCGAAAGCGGAGGAGGGCTGG<br>TGCAGCCTGGAGGATCCCTGCGGCTCTCATGTGCC<br>GCCTCCGGCTTTACCTTCGAAGCCTACTCCATGAAC<br>TGGGTCAGACAGGCTCCCGGGAAGGGACTGGAAT<br>GGGTCAGCTACATTTCGCTGTCCGGAGCCACCATC<br>CACTACGCTGACTCAGTTAAGGGACGCTTCACCATC<br>TCCCGGGATAATGCAAAGAACTCCCTGTACCTCCAA<br>ATGAATTCACTGAGGGCCGAGGACACTGCCGTGTA<br>CTACTGCGCCCGGGGAGGTCAATACTATTACACCT<br>CCTCCGACTACGGCGAAGTGGCCTTCGATATCTGG<br>GGCCAAGGAACCCTCGTGACTGTCTCCTCC |
| 136 | Ab6 Light Chain Variable Region (Nucleic Acid) | GACATCGTGCTGACCCAGTCACCGCTTTCCTTGCC<br>CGTGACTCCTGGGGAACCGGCCTCCATTTCGTGCC<br>GGTCCAGCCAGTCCCTGGTGTCCTCCGGCTACAAT<br>TACCTGGATTGGTACCTCCAAAAGCCCGGACAGTC<br>CCCACAACTGCTCATCTACTTCGGGAGCTCAAGGG<br>CCTCAGGAGTGCCGGATCGCTTCTCGGGTTCCGGA |

TABLE 27 -continued

| SEQ ID NO | Description | Sequence |
|---|---|---|
| | | AGCGGGACTGACTTCACTCTGAAAATCAGCCGCGT GGAAGCAGAGGACGTGGGCGTGTACTACTGCATGC AGCGCAGGAGAACCCCCTGGTCCTTTGGCGGTGGA ACGAAGGTCGAAATCAAG |
| 137 | Ab7 Heavy Chain Variable Region (Nucleic Acid) | CAAGTGCAGCTTGTGGAGTCCGGTGGCGGACTGGT CAAGCCGGGCGGATCTCTGAGACTTTCGTGTGCCG CCTCGGGATTCACCTTCGGCGGATATTCCATGAACT GGGTCAGACAGGCCCCCGGAAAGGGCCTGGAATG GGTGTCGTACATTAGCATCTCGGGGGCCACCATCA CTTACGCCGATAGCGTGAAGGGCCGGTTCACAATC TCCCGGGACAACGCCAAGAACTCCCTCTACCTCCA AATGAACAGCCTGCGCGCTGAGGACACTGCTGTGT ACTATTGCGCGAGGGGTGGCCAGTACTACTACGAC TCAAGCGACTACGGCGAAGTGGCATTCGATATCTG GGGACAGGGGACCATGGTCACCGTCAGCTCC |
| 138 | Ab7 Light Chain Variable Region (Nucleic Acid) | GATATCGTGATGACACAGTCCCCTCTGTCCCTCCCT GTGACCCCCGGAGAACCAGCCTCTATTTCCTGCCG GTCCTCCCAATCCCTGGTGTCCTCCGGTTATAACTA CCTGGATTGGTACTTGCAAAAGCCCGGACAGAGCC CCCAGCTGCTCATCTACTTCGGAAGCTCACGCGCG AGCGGGGTGCCGGATAGGTTTTCGGGATCCGGAA GCGGCACCGACTTCACGCTGAAGATCTCGAGAGTC GAGGCCGAGGACGTGGGCGTGTACTACTGTATGCA GCGGCGGCGCACCCCGCCCTTCACCTTCGGCGGC GGAACTAAGGTCGAGATCAAG |
| 139 | AbA Heavy Chain Variable Region (Nucleic Acid) | GAAGTGCAGCTTCTGGAGTCCGGTGGCGGACTGGT CCAGCCGGGCGGATCTCTGAGACTTTCGTGTGCCG CCTCGGGATTCACCTTCAACAACTATTGGATGACCT GGGTCAGACAGGCCCCCGGAAAGGGCCTGGAATG GGTGTCGTCAATTAGCTCCTCGGGGGGATCCATCT ACTACCCTGATCGCGTGAAGGGCCGGTTCACAATC TCCCGGGACAACAGCAAGAACACCCTCTACCTCCA AATGAACAGCCTGCGCGCTGAGGACACTGCTGTGT ACTATTGCGCGAGGGACGAGAGATGGGCCGGCGC AATGGATGCCTGGGGACAGGGGACCACCGTCACC GTCAGCTCC |
| 140 | AbA Light Chain Variable Region (Nucleic Acid) | GATATTCAGATGACCCAGTCCCCATCATCCCTGTCC GCCTCCGTGGGCGACCGCGTGACGATCACTTGCAA AGCCAGCCAGAATATCAACAAGAACCTGGATTGGTA CCAACAGAAGCCGGGGAAGGCCCCTAAGCTGCTGA TCTACGAAACCAACAACTTGCAAACTGGCGTGCCGT CAAGGTTCAGCGGTTCCGGGTCGGGCACCGACTTC ACCCTGACCATTTCCTCGCTGCAACCCGAGGACTT CGCGACCTACTACTGCTATCAGCACAACAGCCGGT TCACCTTCGGACAGGGCACCAAGCTCGAGATCAAG |
| 141 | AbB Heavy Chain Variable Region (Nucleic Acid) | GAAGTGCAGCTCGTGGAGTCGGGTGGAGGCCTTGT GCAACCGGGAGGATCCCTGCGGCTCTCCTGCGCC GCATCAGGCTTCACGTTCACCAACTTTTGGATGGCC TGGATTAGACAGGCACCGGGGAAGGGACTGGAATG GGTGGCGTCCATTAGCTCGTCCGGAGGATCCATCT ACTATCCTGACTCAGTGAAGGACAGGTTTACCATCT CCCGGGACAACAGCAAGAACACTCTGTACCTCCAA ATGAACTCGCTGCGCGCCGAGGACACCGCCGTGTA CTACTGCGTGAAGTTCCATCACTACTCCGGCGGAG GAGATGCCTGGGGACAGGGTACTCTCGTGACTGTG TCGTCC |
| 142 | AbB Light Chain Variable Region (Nucleic Acid) | GACATCCAGATGACCCAGAGCCCCTCCTCCCTGTC CGCGTCTGTGGGCGACCGCGTGACCATTACGTGCA AAGCTTCCCAGAACATTAACAAGTACCTGGATTGGT ACCAGCAGAAGCCTGGAAAGGCCCCCAAGCTGTTG ATCCACTACACAAACAACCTCCACACTGGTATCCCG TCCCGGTTCTCGGGGTCCGGATCGGGAACTGACTA CACCCTGACCATCAGCAGCCTGCAGCCTGAAGATT TCGCCACCTATTACTGCCTGCAACACTCCTCGCGCT GGACCTTCGGCGGGGGTACTAAGGTCGAGATCAAG |
| 143 | AbC Heavy Chain Variable Region (Nucleic Acid) | GAAGTGCAGCTCGTGGAGTCGGGTGGAGGCCTTGT GCAACCGGGAGGATCCCTGCGGCTCTCCTGCGCC GCATCAGGCTTCACGTTCAACAACTACTGGATGACT |

TABLE 27 -continued

SEQUENCE TABLE

| SEQ ID NO | Description | Sequence |
|---|---|---|
| | | TGGGTCAGACAGGCACCGGGGAAGGGACTGGAAT<br>GGGTGTCCAGCATTAGCTCGTCCGGAGGATCCATC<br>TACTATCCGGACTCAGTGAAGGACAGGTTTACCATC<br>TCCCGGGACAACGCAAAGAACTCCCTGTACCTCCA<br>AATGAACTCGCTGCGCGCCGAGGACATGGCCGTGT<br>ACTACTGCGCGAGGCTGTACTACTACGATGGGGGG<br>GGCGATGCCTGGGGACAGGGAACCCTAGTGACTGT<br>GTCGTCC |
| 144 | AbC Light Chain Variable Region (Nucleic Acid) | GGAATCCAGATGACACAGAGCCCGTCTAGCCTGTC<br>AGCATCCGTGGGGGACAGGGTCACCATCACCTGTA<br>AAGCCAGCCAGGATATTAACAAGTACCTGGACTGG<br>TACCAGCAGAAGCCCGGGAAGGCCCCGAAGCTCCT<br>GATCTACAACACCAACAACTTGCACACCGGAATTCC<br>GTCCCGCTTTTCGGGATCGGGATCCGGGACCGATT<br>ACACCCTGACTATCTCCTCCCTGCAACCCGAGGAC<br>TTCGCCACTTACTATTGCCTCCAACACATTTCCCGG<br>TGGACTTTCGGCGGCGGCACCAAGGTCGAGATCAA<br>G |
| 145 | Cynomolgus monkey CD45 | MTMCLWLKLLAFVFAFLDTEVFVTGQGSTLSPTGRRT<br>TKMPSVPLSSDPLPTHTTAFSPASISERENDFSETTPS<br>LSSDNTSTQVSPDSLDNASAFNTTGVSSALTPHLPTH<br>ADSQTPSTGTDTQTPSGSAANTTLSPTPRSNDISDVP<br>GERSTASTFPTDPISPLATTLIPARNSSAALPARTSNTT<br>ITANTSVSYLNASETTTPSPSGSTVISTPTIATTTSKPTC<br>AEKYATIPVDYLYNNKTKLFTAKLNVNENVECTNNNHT<br>HNICTNNEVLNLPECKEMNVFVSHNSCTDRHKELKLD<br>VPPEVEKFQLDDCTPDVEANTTICLKWKIIETFACDKS<br>KITYRFQCGNKTYNKEGIYLENLEPEYEYKCDSEILYN<br>NHKYINITKLIKTDFGIPGQPQNVVCRHEDAHQGVITW<br>NPPQRSFHNFTLCYVNKPAKKCLILDKHLTTYHLQNLK<br>PYTNYSLSLHAYIIAKVQRNGTAATCNFTTESAPPSQV<br>QNMIVSTSDNSMHVKCEVPRDVNGPTGLYHLEVEAG<br>NTLVRNLSQSKCDFSVNNLQYSTYYNLKAYYHNGKYS<br>GEPVILRESTSYNSKALIAFLAFLIIVTSIALLVVLYKIYDL<br>HKKRSCNLDEQQELVERDDEKQLMNVEPIHADILLET<br>YKRKIADEGRLFLAEFQSIPRVFSKFPIKEARKPFNQN<br>KNRYVDILPYDYNRVELSEINGDAGSNYINASYIDGFK<br>EPRKYIAAQGPRDETVDDFWRMIWEQKATVIVMVTRC<br>EEGNRNKCAEYWPSMEEGTRAFGDIVVKINQHKRCP<br>DYIIQKLNIVNKKEKATGREVTHIQFTSWPDHGVPEDP<br>HLLLKLRRRVNAFSNFFSGPIVVHCSAGVGRTGTYIGI<br>DAMLEGLEAENKVDVYGYVVKLRRQRCLMVQVEAQY<br>ILIHQALVEYNQFGETEVNLSELHPYLHNMKKRDPPSE<br>PSPLEAEFQRLPSYRSWRTQHIGNQEENKNKNRNSN<br>VIPYDYNRVPLKHELEMSKESDHDSDESSDDDSDSEE<br>PSKYINASFIMSYWKPEVMIAAQGPLKETIGDFWQMIF<br>QRKVKVIVMLTELKHGDQEICAQYWGEGKQTYGDIEV<br>DMKDTNKSSTYTLRVFELRHSKRKDSRTVYQYQYTN<br>WSVEQLPAEPKELVSLIQVLKEKLPQKNFSEGNKHHK<br>STPLLIHCRDGSQQTGIFCALLNLLESAETEEVVDIFQV<br>VKALRKARPGMVSTFEQYQFLYDIIASTYPAQNGQVK<br>KNNHQEDKIEFDNEVDKVKQDANCVNPLGATEKLPEA<br>KEQATGSEPTSGTEGPEHSVNGPASPALNQGS |
| 146 | Rhesus macaque CD45 | MTMCLWLKLLAFVFAFLDTEVFVTGQGSTLSPTGRRT<br>TKMPSVPLSSDPLPTHTTAFSPASISERENDFSETTPS<br>LSSDNTSTHVSPDSLDNASAFNTTGVSSALTPHLPTH<br>ADSQTPSTGTDTQTPSGSAANTTLSPTPRSNDISDVP<br>GERSTASTFPTDPISPLATTLIPARNSSAALPARTSNTT<br>ITANTSVSYLNASETTTPSPSGSTVISTPTIATTTSKPTC<br>AEKYATIPVDYLYNNKTKLFTAKLNVNENVECTNNNHT<br>HNICTNNEVLNLPECKEMNVFVSHNSCTDRHKELKLD<br>VPPEVEKFQLDDCTPDVEANTTICLKWKIIETFACDKS<br>KITYRFQCGNKTYNKEGIYLENLEPEYEYKCDSEILYN<br>NHKYINITKLIKTDFGIPGQPQNVVCRHEDAHQGVITW<br>NPPQRSFHNFTLCYVSKTAKKCLSLDKHLTTYHLQNL<br>KPYTNYSLSLHAYIIAKVQRNGTAATCNFTTESAPPSQ<br>VQNMIVSTSDNSMRVKCEAPRDVNGPTELYLLEVEAG<br>NTLVRNLSQSECDFSVNNLQYSTYYNLKAYYHNGKYS<br>GEPVILRESTSYNSKALIAFLAFLIIVTSIALLVVLYKIYDL<br>HKKRSCNLDEQQELVERDDEKQLMNVEPIHADILLET<br>YKRKIADEGRLFLAEFQSIPRVFSKFPIKEARKPFNQN<br>KNRYVDILPYDYNRVELSEINGDAGSNYINASYIDGFK<br>EPRKYIAAQGPRDETVDDFWRMIWEQKATVIVMVTRC |

TABLE 27 -continued

| SEQUENCE TABLE | | |
|---|---|---|
| SEQ ID NO | Description | Sequence |
| | | EEGNRNKCAEYWPSMEEGTRAFGDVVVKINQHKRCP DYIIQKLNIVNKKEKATGREVTHIQFTSWPDHGVPEDP HLLLKLRRRVNAFSNFFSGPIVVHCSAGVGRTGTYIGI DAMLEGLEAENKVDVYGYVVKLRRQRCLMVQVEAQY ILIHQALVEYNQFGETEVNLSELHPYLHNMKKRDPPSE PSPLEAEFQRLPSYRSWRTQHIGNQEENKNKNRNSN VIPYDYNRVPLKHELEMSKESDHDSDESSDDDSDSEE PSKYINASFIMSYWKPEVMIAAQGPLKETIGDFWQMIF QRKVKVIVMLTELKHGDQEICAQYWGEGKQTYGDIEV DMKDTNKSSTYTLRVFELRHSKRKDSRTVYQYQYTN WSVEQLPAEPKELVSLIQVLKEKLPQKNSSEGNKHHK STPLLIHCRDGSQQTGIFCALLNLLESAETEEVVDIFQV VKALRKARPGMVSTFEQYQFLYDIIASTYPAQNGQVK KNNHQEDKIEFDNEVDKVKQDANCVNPLGATEKLPEA KEQATGSEPTSGTEGPEHSVNGPASPALNQGS |
| 147 | Shiga-like toxin 1 subunit A (SLT-1A) | KEFTLDFSTAKTYVDSLNVIRSAIGTPLQTISSGGTSLL MIDSGSGDNLFAVDVRGIDPEEGRFNNLRLIVERNNLY VTGFVNRTNNVFYRFADFSHVTFPGTTAVTLSGDSSY TTLQRVAGISRTGMQINRHSLTTSYLDLMSHSGTSLTQ SVARAMLRFVTVTAEALRFRQIQRGFRTTLDDLSGRS YVMTAEDVDLTLNWGRLSSVLPDYHGQDSVRVGRIS FGSINAILGSVALILNCHHHASRVARMASDEFPSMCPA DGRVRGITHNKILWDSSTLGAILMRRTISS |
| 148 | Shiga toxin subunit A (StxA) | KEFTLDFSTAKTYVDSLNVIRSAIGTPLQTISSGGTSLL MIDSGTGDNLFAVDVRGIDPEEGRFNNLRLIVERNNLY VTGFVNRTNNVFYRFADFSHVTFPGTTAVTLSGDSSY TTLQRVAGISRTGMQINRHSLTTSYLDLMSHSGTSLTQ SVARAMLRFVTVTAEALRFRQIQRGFRTTLDDLSGRS YVMTAEDVDLTLNWGRLSSVLPDYHGQDSVRVGRIS FGSINAILGSVALILNCHHHASRVARMASDEFPSMCPA DGRVRGITHNKILWDSSTLGAILMRRTISS |
| 149 | Shiga-like toxin 2 subunit A (SLT-2A) | DEFTVDFSSQKSYVDSLNSIRSAISTPLGNISQGGVSV SVINHVLGGNYISLNVRGLDPYSERFNHLRLIMERNNL YVAGFINTETNIFYRFSDFSHISVPDVITVSMTTDSSYS SLQRIADLERTGMQIGRHSLVGSYLDLMEFRGRSMTR ASSRAMLRFVTVIAEALRFRQIQRGFRPALSEASPLYT MTAQDVDLTLNWGRISNVLPEYRGEEGVRIGRISFNS LSAILGSVAVILNCHSTGSYSVRSVSQKQKTECQIVGD RAAIKVNNVLWEANTIAALLNRKPQDLTEPNQ |
| 150 | Ab2 Heavy Chain Variable Region (Alternate Nucleic Acid Sequence) | GAGGTGCAGCTGGTGGAGTCTGGGGGAGGCTTGG TACAGCCTGGGGGGTCCCTGAGACTCTCCTGTGCA GCCTCTGGATTCACCTTCGAAGCATATAGCATGAAC TGGGTCCGCCAGGCTCCAGGGAAGGGGCTGGAGT GGGTTTCATACATTAGTCTCAGTGGTGCCACCATAC ACTACGCAGACTCTGTGAAGGGCCGATTCACCATC TCCAGGGACAACGCCAAGAACTCACTGTATCTGCA AATGAACAGCCTGAGAGCCGAGGACACGGCGGTGT ATTACTGCGCCAGAGGTGGACAATACTACTACGACA GCAGTGATTACGGTGAGGTAGCATTCGACATATGG GGTCAGGGTACAATGGTCACCGTCTCCTCA |
| 151 | Ab2 Light Chain Variable Region (Alternate Nucleic Acid Sequence) | GATATTGTGATGACTCAGTCTCCACTCTCCCTGCCC GTCACCCCTGGAGAGCCGGCCTCCATCTCCTGCAG GTCTAGTCAGAGCCTGGTCAGTAATGGATACAACTA TTTGGATTGGTACCTGCAGAAGCCAGGGCAGTCTC CACAGCTCCTGATCTATTTCGGTTCTTCCCGGGCCT CCGGGGTCCCTGACAGGTTCAGTGGCAGTGGATCA GGCACAGATTTTACACTGAAAATCAGCAGAGTGGA GGCTGAGGATGTTGGGGTTTATTACTGCATGCAGA GAAGACGCACTCCTTGGTCTTTTGGCGGAGGGACC AAGGTTGAGATCAAA |
| 152 | Ab3 Heavy Chain Variable Region (Alternate Nucleic Acid Sequence) | CAGGTGCAGCTGGTGGAGTCTGGGGGAGGCTTGG TCAAGCCTGGAGGGTCCCTGAGACTCTCCTGTGCA CGCTCTGGATTCACCTTCGGAGGATATAGCATGAAC TGGGTCCGCCAGGCTCCAGGGAAGGGGCTGGAGT GGGTTTCATACATTAGTATCAGTGGTGCCACCATAA CCTACGCAGACTCTGTGAAGGGCCGATTCACCATC TCCAGGGACAACGCCAAGAACTCACTGTATCTGCA AATGAACAGCCTGAGAGCCGAGGACACGGCGGTGT ACTACTGCGCCAGAGGTGGACAATACTACTACGAC |

TABLE 27 -continued

SEQUENCE TABLE

| SEQ ID NO | Description | Sequence |
|---|---|---|
| | | AGCAGCGATTATGGTGAGGTAGCATTCGACATATG GGGTCAGGGTACAATGGTCACCGTCTCCTCA |
| 153 | Ab3 Light Chain Variable Region (Alternate Nucleic Acid Sequence) | GATATTGTGATGACTCAGTCTCCACTCTCCCTGCCC GTCACCCCTGGAGAGCCGGCCTCCATCTCCTGCAG GTCTAGTCAGAGCCTGGTCAGTAATGGATACAACTA TTTGGATTGGTACCTGCAGAAGCCAGGGCAGTCTC CACAGCTCCTGATCTATTTCGGTTCTTCCCGGGCCT CCGGGGTCCCTGACAGGTTCAGTGGCAGTGGATCA GGCACAGATTTTACACTGAAAATCAGCAGAGTGGA GGCTGAGGATGTTGGGGTTTATTACTGCATGCAGA GAAGACGCACTCCTCCTTTCACTTTTGGCGGAGGG ACCAAGGTTGAGATCAAA |
| 154 | Ab4 Heavy Chain Variable Region (Alternate Nucleic Acid Sequence) | GAGGTGCAGCTGGTGGAGTCTGGGGGAGGCTTGG TACAGCCTGGGGGGTCCCTGAGACTCTCCTGTGCA CGCTCTGGATTCACCTTCGAAGCATATAGCATGAAC TGGGTCCGCCAGGCTCCAGGGAAGGGGCTGGAGT GGGTTTCATACATTAGTCTCAGTGGTGCCACCATAC ACTACGCAGACTCTGTGAAGGGCCGATTCACCATC TCCAGGGACAACGCCAAGAACTCACTGTATCTGCA AATGAACAGCCTGAGAGCCGAGGACACGGCGGTGT ATTACTGCGCCAGAGGTGGACAATACTACTACACGA GCAGTGATTACGGTGAGGTAGCATTCGACATATGG GGTCAGGGTACAATGGTCACCGTCTCCTCA |
| 155 | Ab4 Light Chain Variable Region (Alternate Nucleic Acid Sequence) | GATATTGTGATGACTCAGTCTCCACTCTCCCTGCCC GTCACCCCTGGAGAGCCGGCCTCCATCTCCTGCAG GTCTAGTCAGAGCCTGGTCAGTAATGGATACAACTA TTTGGATTGGTACCTGCAGAAGCCAGGGCAGTCTC CACAGCTCCTGATCTATTTCGGTTCTTCCCGGGCCT CCGGGGTCCCTGACAGGTTCAGTGGCAGTGGATCA GGCACAGATTTTACACTGAAAATCAGCAGAGTGGA GGCTGAGGATGTTGGGGTTTATTACTGCATGCAGA GAAGACGCACTCCTTGGTCTTTTGGCGGAGGGACC AAGGTTGAGATCAAA |
| 156 | AbA Heavy Chain Variable Region (Alternate Nucleic Acid Sequence) | GAGGTGCAGCTGTTGGAGTCTGGGGGAGGCTTGG TACAGCCTGGCGGGTCCCTGAGACTCTCCTGTGCA CGCTCTGGATTCACCTTTAATAATTATTGGATGACAT GGGTCCGCCAGGCTCCAGGGAAGGGGCTGGAGTG GGTCTCATCTATTAGTTCCAGTGGTGGTAGCATTTA CTACCCCGACAGGGTGAAGGGCCGGTTCACCATCT CCAGAGACAATTCCAAGAACACGCTGTATCTGCAAA TGAACAGCCTGAGAGCCGAGGACACGGCGGTGTA CTACTGCGCAAGAGACGAGAGATGGGCAGGTGCTA TGGATGCCTGGGGGCAAGGGACCACGGTCACCGT CTCCTCA |
| 157 | AbA Light Chain Variable Region (Alternate Nucleic Acid Sequence) | GACATCCAGATGACCCAGTCTCCATCCTCCCTGTCT GCATCTGTAGGAGACAGAGTCACCATCACTTGCAA GG CAAGTCAGAATATTAACAAGAATTTAGACTGGTA TCAGCAGAAACCAGGGAAAGCCCCTAAGCTCCTGA TCTATGAGACGAATAATTGCAAACAGGGGTCCCAT CAAGGTTCAGTGGCAGTGGATCTGGGACAGATTTC ACTCTCACCATCAGCAGTCTGCAACCTGAAGATTTT GCAACTTACTACTGTTATCAGCATAATTCTAGATTTA CTTTTGGCCAGGGGACCAAGCTGGAGATCAAA |
| 158 | AbB Heavy Chain Variable Region (Alternate Nucleic Acid Sequence) | GAGGTGCAGCTGGTGGAGTCTGGGGGAGGCTTGG TACAGCCTGGAGGGTCCCTGAGACTCTCCTGTGCA GCCTCTGGATTCACCTTTACCAATTTTTGGATGGCG TGGATCCGCCAGGCTCCAGGGAAGGGGCTGGAGT GGGTCGCAAGTATTAGTTCAAGTGGTGGTAGCATCT ACTACCCTGACTCCGTGAAGGACCGGTTCACCATC TCCAGAGACAATTCCAAGAACACGCTGTATCTGCAA ATGAACAGCCTGAGAGCCGAGGACACGGCGGTGTA CTACTGCGTCAAGTTTCACCACTATTCAGGCGGCG GCGATGCTTGGGGCCAAGGGACCCTGGTCACCGT CTCCTCA |
| 159 | AbB Light Chain Variable Region (Alternate Nucleic Acid Sequence) | GACATCCAGATGACCCAGTCTCCATCCTCCCTGTCT GCATCTGTAGGAGACAGAGTCACCATCACTTGCAAA GCAAGTCAGAATATTAACAAGTATTTAGATTGGTATC AGCAGAAACCAGGGAAAGCCCCTAAGCTCCTGATC |

TABLE 27 -continued

SEQUENCE TABLE

| SEQ ID NO | Description | Sequence |
|---|---|---|
| | | CATTACACTAACAACTTGCACACCGGGATTCCATCA AGGTTCAGTGGCAGTGGATCTGGGACAGATTATAC TCTCACCATCAGCAGTCTGCAACCTGAAGATTTTGC AACTTACTACTGTCTGCAGCACAGTTCCAGATGGAC ATTCGGCGGAGGGACCAAGGTGGAGATCAAA |
| 160 | AbC Heavy Chain Variable Region (Alternate Nucleic Acid Sequence) | GAGGTGCAGCTGGTGGAGTCTGGGGGAGGCTTGG TACAGCCTGGAGGGTCCCTGAGACTCTCCTGTGCA GCCTCTGGATTCACCTTCAATAACTATTGGATGACG TGGGTCCGCCAGGCTCCAGGGAAGGGGCTGGAGT GGGTTTCATCCATTAGTAGTAGTGGCGGTAGTATAT ACTACCCTGACTCTGTGAAGGATCGATTCACCATCT CCAGAGACAATGCCAAGAACTCACTGTATCTGCAAA TGAACAGCCTGAGAGCTGAGGACATGGCGGTGTAC TACTGCGCCAGGTTGTACTACTACGACGGGGGAGG GGATGCGTGGGGCCAAGGAACCCTGGTCACCGTCT CCTCA |
| 161 | AbC Light Chain Variable Region (Alternate Nucleic Acid Sequence) | GGCATCCAGATGACCCAGTCTCCATCCTCCCTGTCT GCATCTGTAGGAGACAGAGTCACCATCACTTGCAA GGCGAGTCAGGACATTAATAAGTATTTAGATTGGTA TCAGCAGAAACCAGGGAAAGCCCCTAAGCTCCTGA TCTACAATACAAACAATTTGCATACAGGGATCCCAT CAAGGTTCAGTGGAAGTGGATCTGGGACAGATTAT ACTCTTACCATCAGCAGCCTGCAGCCTGAAGATTTT GCAACATATTACTGTCTTCAACACATATCTAGATGG ACGTTCGGCGGAGGGACCAAGGTGGAGATCAAA |

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A method of depleting a population of CD45+ cells in a human patient in need thereof, the method comprising administering to the patient an effective amount of an antibody drug conjugate (ADC);

wherein the human patient has a hematological cancer and is in need of a hematopoietic stem cell transplant, wherein the ADC comprises an anti-CD45 antibody, or an antigen-binding portion thereof, conjugated to a cytotoxin via a linker, wherein the cytotoxin is a DNA alkylating agent, and wherein the anti-CD45 antibody, or antigen-binding portion thereof comprises a heavy chain comprising a CDR1 domain comprising the amino acid sequence as set forth in SEQ ID NO: 42, a CDR2 domain comprising the amino acid sequence as set forth in SEQ ID NO:43, and a CDR3 domain comprising the amino acid sequence as set forth in SEQ ID NO:44; and a light chain comprising a CDR1 domain comprising the amino acid sequence as set forth in SEQ ID NO: 46, a CDR2 domain comprising the amino acid sequence as set forth in SEQ ID NO:47; and a CDR3 domain comprising the amino acid sequence as set forth in SEQ ID NO:48.

2. The method of claim 1, wherein the CD45+ cells are depleted from the bone marrow of the patient and/or from the peripheral blood of the patient.

3. The method of claim 1, further comprising administering to the patient a transplant comprising hematopoietic stem cells.

4. A method of treating a human patient having a hematological cancer, the method comprising (a) administering to a human patient an antibody drug conjugate (ADC), in an amount sufficient to deplete a population of CD45+ cells in the patient, wherein the human patient has a hematological cancer; and (b) subsequently administering to the patient a transplant comprising hematopoietic stem cells, wherein the ADC comprises an anti-CD45 antibody, or an antigen-binding portion thereof, conjugated to a cytotoxin via a linker, wherein the cytotoxin is a DNA alkylating agent, and wherein the anti-CD45 antibody, or antigen-binding portion thereof comprises a heavy chain comprising a CDR1 domain comprising the amino acid sequence as set forth in SEQ ID NO: 42, a CDR2 domain comprising the amino acid sequence as set forth in SEQ ID NO:43, and a CDR3 domain comprising the amino acid sequence as set forth in SEQ ID NO:44; and a light chain comprising a CDR1 domain comprising the amino acid sequence as set forth in SEQ ID NO: 46, a CDR2 domain comprising the amino acid sequence as set forth in SEQ ID NO:47; and a CDR3 domain comprising the amino acid sequence as set forth in SEQ ID NO:48.

5. The method of claim 4, wherein the transplant is allogeneic or autologous; or wherein the transplant comprising hematopoietic stem cells is administered to the patient after the concentration of the ADC has substantially cleared from the blood of the patient.

6. The method of claim 1, wherein the hematological cancer is acute myeloid leukemia, acute lymphoid leukemia, chronic myeloid leukemia, chronic lymphoid leukemia, or multiple myeloma.

7. The method of claim 1, wherein the heavy chain comprises a variable region comprising an amino acid sequence as set forth in SEQ ID NO: 41, and wherein the light chain comprises a variable region comprising an amino acid sequence as set forth in SEQ ID NO: 45.

8. The method of claim 1, wherein the heavy chain comprises an amino acid sequence as set forth in SEQ ID NO: 49, and the light chain comprises an amino acid sequence as set forth in SEQ ID NO: 50.

9. The method of claim 1, wherein the heavy chain comprises an amino acid sequence as set forth in SEQ ID NO: 106, and the light chain comprises an amino acid sequence as set forth in SEQ ID NO: 101.

10. The method of claim 1, wherein the cytotoxin is an indolinobenzodiazepine or an indolinobenzodiazepine pseudodimer.

11. The method of claim 1, wherein the cytotoxin has a structure represented by:

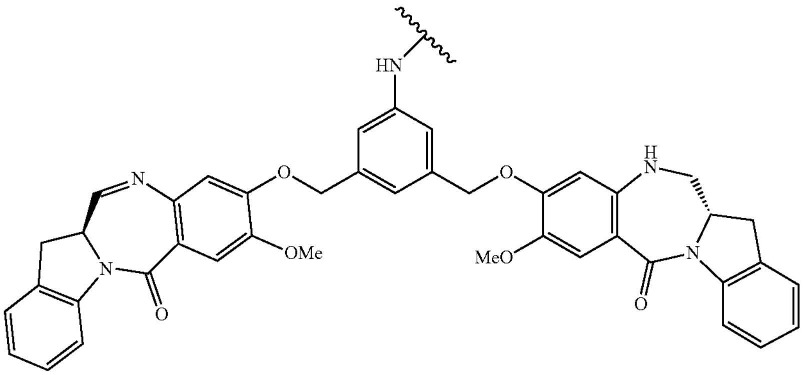 [SMILES: *Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
, wherein the wavy line indicates the point of covalent attachment to the linker of the ADC.

12. The method of claim 4, wherein the heavy chain comprises a variable region comprising an amino acid sequence as set forth in SEQ ID NO: 41, and wherein the light chain comprises a variable region comprising an amino acid sequence as set forth in SEQ ID NO: 45.

13. The method of claim 4, wherein the heavy chain comprises an amino acid sequence as set forth in SEQ ID NO: 49, and the light chain comprises an amino acid sequence as set forth in SEQ ID NO: 50.

14. The method of claim 4, wherein the heavy chain comprises an amino acid sequence as set forth in SEQ ID NO: 106, and the light chain comprises an amino acid sequence as set forth in SEQ ID NO: 101.

15. The method of claim 4, wherein the cytotoxin is an indolinobenzodiazepine or an indolinobenzodiazepine pseudodimer.

16. The method of claim 4, wherein the cytotoxin has a structure represented by:

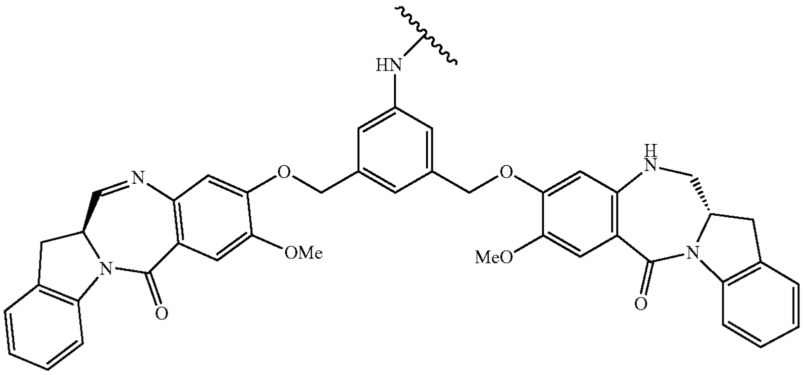
, wherein the wavy line indicates the point of covalent attachment to the linker of the ADC.

17. A method of depleting a population of CD45+ cells in a human patient in need thereof, the method comprising administering to the patient an effective amount of an antibody drug conjugate (ADC), wherein the human patient has acute myeloid leukemia (AML) and is in need of a hematopoietic stem cell transplant, wherein the ADC comprises an anti-CD45 antibody, or an antigen-binding portion thereof, conjugated to a DNA alkylating agent via a linker, and wherein the anti-CD45 antibody, or antigen-binding portion thereof, comprises a heavy chain comprising a CDR1 domain comprising the amino acid sequence as set forth in SEQ ID NO: 42, a CDR2 domain comprising the amino acid sequence as set forth in SEQ ID NO:43, and a CDR3 domain comprising the amino acid sequence as set forth in SEQ ID NO:44; and a light chain comprising a CDR1 domain comprising the amino acid sequence as set forth in SEQ ID NO: 46, a CDR2 domain comprising the amino acid sequence as set forth in SEQ ID NO:47; and a CDR3 domain comprising the amino acid sequence as set forth in SEQ ID NO:48.

18. The method of claim 17, wherein the heavy chain comprises a variable region comprising an amino acid sequence as set forth in SEQ ID NO: 41, and wherein the light chain comprises a variable region comprising an amino acid sequence as set forth in SEQ ID NO: 45.

19. The method of claim 17, wherein the heavy chain comprises an amino acid sequence as set forth in SEQ ID NO: 49, and the light chain comprises an amino acid sequence as set forth in SEQ ID NO: 50.

20. The method of claim 17, wherein the heavy chain comprises an amino acid sequence as set forth in SEQ ID NO: 106, and the light chain comprises an amino acid sequence as set forth in SEQ ID NO: 101.

21. The method of claim 17, further comprising administering to the patient a transplant comprising hematopoietic stem cells.

* * * * *